(12) United States Patent
Hung et al.

(10) Patent No.: US 12,398,121 B2
(45) Date of Patent: Aug. 26, 2025

(54) ANTI-CANCER NUCLEAR HORMONE RECEPTOR-TARGETING COMPOUNDS

(71) Applicant: Nuvation Bio Inc., New York, NY (US)

(72) Inventors: David Hung, New York, NY (US); Son Minh Pham, San Francisco, CA (US); Sarvajit Chakravarty, Edmond, OK (US); Jiyun Chen, San Francisco, CA (US); Jayakanth Kankanala, Saint Paul, MN (US); Anup Barde, Noida (IN); Anjan Kumar Nayak, Noida (IN)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 18/058,220

(22) Filed: Nov. 22, 2022

(65) Prior Publication Data

US 2023/0122310 A1 Apr. 20, 2023

Related U.S. Application Data

(63) Continuation of application No. 16/412,319, filed on May 14, 2019, now abandoned.

(60) Provisional application No. 62/671,382, filed on May 14, 2018.

(51) Int. Cl.
| | |
|---|---|
| C07D 491/22 | (2006.01) |
| A61K 9/00 | (2006.01) |
| A61K 31/4745 | (2006.01) |
| A61P 35/00 | (2006.01) |
| C07D 401/14 | (2006.01) |
| C07D 403/10 | (2006.01) |
| C07D 403/14 | (2006.01) |
| C07D 413/14 | (2006.01) |
| C07D 417/14 | (2006.01) |
| C07D 451/02 | (2006.01) |
| C07D 471/04 | (2006.01) |
| C07D 487/04 | (2006.01) |
| C07D 491/048 | (2006.01) |
| C07D 498/04 | (2006.01) |
| C07D 519/00 | (2006.01) |
| C07J 43/00 | (2006.01) |
| A61K 45/06 | (2006.01) |

(52) U.S. Cl.
CPC .......... *C07D 403/14* (2013.01); *A61K 9/0053* (2013.01); *A61P 35/00* (2018.01); *C07D 401/14* (2013.01); *C07D 403/10* (2013.01); *C07D 413/14* (2013.01); *C07D 417/14* (2013.01); *C07D 451/02* (2013.01); *C07D 471/04* (2013.01); *C07D 487/04* (2013.01); *C07D 491/048* (2013.01); *C07D 498/04* (2013.01); *C07D 519/00* (2013.01); *C07J 43/003* (2013.01); *A61K 45/06* (2013.01)

(58) Field of Classification Search
CPC ................ C07D 491/22; C07D 519/00; A61K 31/4745; A61P 35/00
See application file for complete search history.

(56) References Cited

U.S. PATENT DOCUMENTS

| | | | |
|---|---|---|---|
| 4,636,505 | A | 1/1987 | Tucker |
| 6,074,625 | A | 6/2000 | Hawthorne et al. |
| 6,462,038 | B1 | 10/2002 | Higuchi et al. |
| 6,777,427 | B2 | 8/2004 | Miyakawa et al. |
| 7,037,919 | B1 | 5/2006 | Hanada et al. |
| 7,038,041 | B2 | 5/2006 | Ray et al. |
| 7,220,730 | B2 | 5/2007 | Baranowska-kortylewicz et al. |
| 7,449,464 | B2 | 11/2008 | Martin et al. |
| 7,981,889 | B2 | 7/2011 | Barr et al. |
| 8,012,976 | B2 | 9/2011 | Wang |
| 8,129,380 | B2 | 3/2012 | Menear et al. |
| 8,252,802 | B2 | 8/2012 | Foote et al. |
| 8,629,167 | B2 | 1/2014 | Miller |
| 8,785,501 | B2 | 7/2014 | Witt-enderby et al. |
| 8,871,765 | B2 | 10/2014 | Shrivastava |
| 9,056,140 | B2 | 6/2015 | Stoloff et al. |
| 9,963,433 | B2 | 5/2018 | Qin |
| 10,300,143 | B2 | 5/2019 | Sengupta et al. |
| 10,723,717 | B2 | 7/2020 | Crew et al. |
| 10,730,870 | B2 | 8/2020 | Crew et al. |
| 11,034,669 | B2 | 6/2021 | Chakravarty et al. |
| 11,292,782 | B2 | 4/2022 | Chakravarty et al. |
| 11,826,430 | B2 | 11/2023 | Hung et al. |
| 11,952,349 | B2 | 4/2024 | Pham |
| 12,006,314 | B2 | 6/2024 | Hung |
| 2003/0059465 | A1 | 3/2003 | Unger et al. |
| 2005/0059663 | A1 | 3/2005 | Martin et al. |
| 2005/0069495 | A1 | 3/2005 | Baranowska-kortylewicz et al. |

(Continued)

FOREIGN PATENT DOCUMENTS

| | | |
|---|---|---|
| CN | 101948500 A | 1/2011 |
| CN | 101967172 A | 2/2011 |

(Continued)

OTHER PUBLICATIONS

Ahmed, N. et al. (2007). "Synthesis, Characterization, and Estrogen Receptor Binding Affinity of Flavone-, Indole-, and Furan-Estradiol Conjugates," Bioorganic & Medicinal Chemistry Letters 17:3212-3216.

Beretta, G.L. et al. (2019). "Androgen Receptor-Directed Molecular Conjugates for Targeting Prostate Cancer," Frontiers in Chemistry 7(369):1-8.

Berge, S.M. et al. (Jan. 1977). "Pharmaceuticals Salts," J. Pharmaceutical Sciences 66(1):1-19.

Bertrand, B. et al. (2018). "A Gold(III) Pincer Ligand Scaffold for the Synthesis of Binuclear and Bioconjugated Complexes: Synthesis and Anticancer Potential," Chemistry—A European Journal 24(14):3613-3622.

(Continued)

*Primary Examiner* — Bruck Kifle
(74) *Attorney, Agent, or Firm* — MORRISON & FOERSTER LLP

(57) ABSTRACT

The disclosure relates to anti-cancer compounds derived from nuclear steroid receptor binders, to products containing the same, as well as to methods of their use and preparation.

12 Claims, No Drawings

(56) References Cited

U.S. PATENT DOCUMENTS

| | | |
|---|---|---|
| 2005/0096381 A1 | 5/2005 | Kohen et al. |
| 2005/0227919 A1 | 10/2005 | Ashworth et al. |
| 2005/0245485 A1 | 11/2005 | Lanter et al. |
| 2005/0250741 A1 | 11/2005 | Lanter et al. |
| 2005/0277660 A1 | 12/2005 | Miyakawa |
| 2005/0277681 A1 | 12/2005 | Hanney et al. |
| 2006/0063819 A1 | 3/2006 | Lanter et al. |
| 2006/0128737 A1 | 6/2006 | Miyakawa et al. |
| 2006/0142387 A1 | 6/2006 | Cadilla et al. |
| 2006/0148893 A1 | 7/2006 | Blanc et al. |
| 2006/0160845 A1 | 7/2006 | Schlienger et al. |
| 2006/0211756 A1 | 9/2006 | Zhang et al. |
| 2008/0200469 A1 | 8/2008 | Martin et al. |
| 2009/0257999 A1 | 10/2009 | Fink |
| 2010/0003192 A1 | 1/2010 | Sherman et al. |
| 2011/0028420 A1 | 2/2011 | Boulares et al. |
| 2011/0053923 A1 | 3/2011 | Foote et al. |
| 2011/0104074 A1 | 5/2011 | Kakar |
| 2011/0305631 A1 | 12/2011 | Govindan et al. |
| 2012/0046461 A1 | 2/2012 | Hanson |
| 2012/0083514 A1 | 4/2012 | Prevost |
| 2012/0208497 A1 | 8/2012 | Moeller et al. |
| 2013/0156698 A1 | 6/2013 | Zhou et al. |
| 2013/0309170 A1 | 11/2013 | Reiner et al. |
| 2014/0080905 A1 | 3/2014 | Dalton et al. |
| 2015/0110742 A1 | 4/2015 | Spiegel et al. |
| 2015/0284416 A1 | 10/2015 | Zhao |
| 2015/0322155 A1 | 11/2015 | Zhao |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2017/0008904 A1 | 1/2017 | Crew et al. |
| 2017/0217903 A1 | 8/2017 | Qin et al. |
| 2017/0233365 A1 | 8/2017 | Hilderbrand et al. |
| 2017/0319543 A1 | 11/2017 | Ashworth et al. |
| 2017/0327469 A1 | 11/2017 | Crew et al. |
| 2018/0052180 A1 | 2/2018 | Jose et al. |
| 2018/0099940 A1 | 4/2018 | Crew et al. |
| 2018/0215731 A1 | 8/2018 | Crew et al. |
| 2018/0228907 A1 | 8/2018 | Crew et al. |
| 2018/0346461 A1 | 12/2018 | Crew et al. |
| 2019/0111010 A1 | 4/2019 | Narayanan et al. |
| 2019/0337938 A1 | 11/2019 | Lu |
| 2019/0365904 A1 | 12/2019 | Low et al. |
| 2019/0375732 A1 | 12/2019 | Hung et al. |
| 2020/0055825 A1 | 2/2020 | Crew et al. |
| 2020/0155689 A1 | 5/2020 | Crew et al. |
| 2020/0155690 A1 | 5/2020 | Crew et al. |
| 2020/0172480 A1 | 6/2020 | Zhao et al. |
| 2020/0199098 A1 | 6/2020 | Chakravarty et al. |
| 2020/0239433 A1 | 7/2020 | Chakravarty et al. |
| 2020/0281955 A1 | 9/2020 | Xu et al. |
| 2020/0297725 A1 | 9/2020 | Crews et al. |
| 2020/0360523 A1 | 11/2020 | Hung et al. |
| 2020/0392131 A1 | 12/2020 | Crew et al. |
| 2021/0214316 A1 | 7/2021 | Pham et al. |
| 2022/0340587 A1 | 10/2022 | Hung et al. |
| 2022/0380364 A1 | 12/2022 | Hung et al. |
| 2023/0122310 A1 | 4/2023 | Hung et al. |
| 2024/0181066 A1 | 6/2024 | Hung |

FOREIGN PATENT DOCUMENTS

| | | |
|---|---|---|
| CN | 101967173 A | 2/2011 |
| CN | 102492009 A | 6/2012 |
| CN | 102492010 A | 6/2012 |
| CN | 102516347 A | 6/2012 |
| CN | 102532237 A | 7/2012 |
| CN | 104292290 A | 1/2015 |
| CN | 105315294 A | 2/2016 |
| CN | 107266520 A | 10/2017 |
| CN | 107286166 A | 10/2017 |
| EP | 0699754 A1 | 3/1996 |
| EP | 0705903 A1 | 4/1996 |
| JP | 5934986 B2 | 6/2016 |
| JP | 2017071567 A | 4/2017 |
| WO | 199010638 A1 | 9/1990 |
| WO | 199600090 A1 | 1/1996 |
| WO | 199613613 A1 | 5/1996 |
| WO | 199700071 A1 | 1/1997 |
| WO | 200127086 A1 | 4/2001 |
| WO | 200224638 A1 | 3/2002 |
| WO | 2003034987 A2 | 5/2003 |
| WO | 2003079965 A2 | 10/2003 |
| WO | 2003101995 A2 | 12/2003 |
| WO | 2004000816 A1 | 12/2003 |
| WO | 2004013104 A1 | 2/2004 |
| WO | 2004035736 A2 | 4/2004 |
| WO | 2004041277 A1 | 5/2004 |
| WO | 2004080976 A1 | 9/2004 |
| WO | 2004093807 A2 | 11/2004 |
| WO | 2004113309 A1 | 12/2004 |
| WO | 2005000795 A2 | 1/2005 |
| WO | 2005034856 A2 | 4/2005 |
| WO | 2005085185 A1 | 9/2005 |
| WO | 2005086974 A2 | 9/2005 |
| WO | 2005108351 A1 | 11/2005 |
| WO | 2005115361 A2 | 12/2005 |
| WO | 2005118612 A1 | 12/2005 |
| WO | 2006044707 A1 | 4/2006 |
| WO | 2006060108 A1 | 6/2006 |
| WO | 2006124447 A2 | 11/2006 |
| WO | 2006133216 A2 | 12/2006 |
| WO | 2007002181 A2 | 1/2007 |
| WO | 2007035927 A2 | 3/2007 |
| WO | 2007057909 A1 | 5/2007 |
| WO | 2008090379 A1 | 7/2008 |
| WO | 2009005839 A2 | 1/2009 |
| WO | 2009029375 A1 | 3/2009 |
| WO | 2009114459 A2 | 9/2009 |
| WO | 2009155431 A1 | 12/2009 |
| WO | 2010085747 A1 | 7/2010 |
| WO | 2010108251 A2 | 9/2010 |
| WO | 2011079245 A1 | 6/2011 |
| WO | 2011130697 A2 | 10/2011 |
| WO | 2012014221 A1 | 2/2012 |
| WO | 2012037410 A2 | 3/2012 |
| WO | 2012050868 A1 | 4/2012 |
| WO | 2012074840 A2 | 6/2012 |
| WO | 2012123820 A1 | 9/2012 |
| WO | 2012134446 A1 | 10/2012 |
| WO | 2013028495 A1 | 2/2013 |
| WO | 2013106643 A2 | 7/2013 |
| WO | 2013170147 A1 | 11/2013 |
| WO | 2014011220 A2 | 1/2014 |
| WO | 2014080251 A1 | 5/2014 |
| WO | 2014108452 A1 | 7/2014 |
| WO | 2014191726 A1 | 12/2014 |
| WO | 2014201026 A2 | 12/2014 |
| WO | 2015038649 A1 | 3/2015 |
| WO | 2015095755 A1 | 6/2015 |
| WO | 2015134464 A2 | 9/2015 |
| WO | 2015143004 A1 | 9/2015 |
| WO | 2015151078 A2 | 10/2015 |
| WO | 2015151080 A2 | 10/2015 |
| WO | 2015151081 A2 | 10/2015 |
| WO | 2015155753 A2 | 10/2015 |
| WO | 2016059622 A2 | 4/2016 |
| WO | 2016077505 A2 | 5/2016 |
| WO | 2016097072 A1 | 6/2016 |
| WO | 2016118666 A1 | 7/2016 |
| WO | 2016149668 A1 | 9/2016 |
| WO | 2016196337 A1 | 12/2016 |
| WO | 2016197032 A1 | 12/2016 |
| WO | 2016197114 A1 | 12/2016 |
| WO | 2017011590 A1 | 1/2017 |
| WO | 2017059139 A1 | 4/2017 |
| WO | 2017075495 A1 | 5/2017 |
| WO | 2017136688 A1 | 8/2017 |
| WO | 2017170564 A1 | 10/2017 |
| WO | 2017199042 A1 | 11/2017 |
| WO | 2017214491 A1 | 12/2017 |
| WO | 2017216279 A1 | 12/2017 |
| WO | 2018019793 A1 | 2/2018 |

(56) References Cited

FOREIGN PATENT DOCUMENTS

| | | | |
|---|---|---|---|
| WO | 2018038680 A1 | 3/2018 |
| WO | 2018071606 A1 | 4/2018 |
| WO | 2018111990 A1 | 6/2018 |
| WO | 2018130124 A1 | 7/2018 |
| WO | 2018156815 A1 | 8/2018 |
| WO | 2018185526 A1 | 10/2018 |
| WO | 2018234636 A1 | 12/2018 |
| WO | 2019023553 A1 | 1/2019 |
| WO | 2019100973 A1 | 5/2019 |
| WO | 2019111010 A1 | 6/2019 |
| WO | 2019123367 A1 | 6/2019 |
| WO | 2019199634 A1 | 10/2019 |
| WO | 2019199816 A1 | 10/2019 |
| WO | 2019222272 A1 | 11/2019 |
| WO | 2019241231 A1 | 12/2019 |
| WO | 2020023851 A1 | 1/2020 |
| WO | 2020113088 A1 | 6/2020 |
| WO | 2020113094 A1 | 6/2020 |
| WO | 2020232119 A1 | 11/2020 |
| WO | 2020257998 A1 | 12/2020 |
| WO | 2021013735 A1 | 1/2021 |
| WO | 2021055705 A1 | 3/2021 |
| WO | 2021097046 A1 | 5/2021 |
| WO | 2021127443 A1 | 6/2021 |
| WO | 2021212638 A1 | 10/2021 |
| WO | 2022035818 A2 | 2/2022 |
| WO | 2022040635 A1 | 2/2022 |
| WO | 2022087125 A1 | 4/2022 |
| WO | 2022098544 A1 | 5/2022 |
| WO | 2022204184 A1 | 9/2022 |
| WO | 2022228387 A1 | 11/2022 |
| WO | 2022235585 A1 | 11/2022 |

OTHER PUBLICATIONS

Biersack, B. et al. (2009). "Metallodrug Conjugates with Steroids and Selective Estrogen Receptor Modulators (SERM)," Current Medicinal Chemistry 16:2324-2337.

Borsari, C. et al. (2020). "Designing Chimeric Molecules for Drug Discovery by Leveraging Chemical Biology," Journal of Medicinal Chemistry 63(5):1908-1928.

Brix, H.P. et al. (1990). "Androgen-Linked Alkylating Agents: Biological Activity in Methylnitrosourea-Induced Rat Mammary Carcinoma," Journal of Cancer Research and Clinical Oncology 116:538-549.

Burke, P.J. et al. (2004). "Design, Synthesis, and Biological Evaluation of Doxorubicin-Formaldehyde Conjugates Targeted to Breast Cancer Cells," Journal of Medicinal Chemistry 47(5):1193-1206.

Chekler, E.L.P. (Mar. 27, 2014, e-pub. Feb. 17, 2014). "1-(2-Hydroxy-2-methyl-3-phenoxypropanoyl) indoline-4-carbonitrile Derivatives as Potent and Tissue Selective Androgen Receptor Modulators," J. Med. Chem. 57(6):2462-2471.

Cheng, C.J. et al. (2015). "MicroRNA Silencing for Cancer Therapy Targeted to The Tumour Microenvironment," Nature 518(7537):107-110.

Cogan, P.S. et al. (2004). "Studies of Targeting and Intracellular Trafficking of an Anti-Androgen Doxorubicin-Formaldehyde Conjugate in PC-3 Prostate Cancer Cells Bearing Androgen Receptor-GFP Chimera," Journal of Medicinal Chemistry 47(23):5690-5699.

Dao, K.-L. et al. (Apr. 18, 2012). "Design, Synthesis, and Initial Biological Evaluation of a Steroidal Anti-estrogen-Doxorubicin Bioconjugate for Targeting Estrogen Receptor-Positive Breast Cancer Cells," Bioconjugate Chemistry 23(4):785-795, 25 pages.

Dao, K.-L. et al. (Oct. 5, 2012). "Targeting the Estrogen Receptor using Steroid-Therapeutic Drug Conjugates (Hybrids)," Bioconjugate Chemistry 23(11):2139-2158.

Dawicki-McKenna, J.M. et al. (Dec. 3, 2015). "PARP-1 Activation Requires Local Unfolding of an Autoinhibitory Domain," Molecular Cell 60(5):755-768.

Delfosse, V. et al. (2015, e-pub. Dec. 15, 2014). "A Structural Perspective on Nuclear Receptors as Targets of Environmental Compounds," Acta Pharmacologica Sinica 36:88-101.

Devraj, R. et al. (1996). "Design, Synthesis, and Biological Evaluation of Ellipticine-Estradiol Conjugates," Journal of Medicinal Chemistry 39(17):3367-3374.

Ding, S. et al. (2013). "Design of a Platinum-Acridine-Endoxifen Conjugate Targeted at Hormone-Dependent Breast Cancer," Chemical Communications 49(24):2415-2417.

Dizio, J.P. et al. (1991). "Progestin-Rhenium Complexes: Metal-Labeled Steroids with High Receptor Binding Affinity, Potential Receptor-Directed Agents for Diagnostic Imaging or Therapy," Bioconjugate Chemistry 2(5):353-366.

Extended European Search Report, dated Oct. 5, 2023, for European Patent Application No. 20806178.8, 27 pages.

French, A.N. et al. (1993). "A Synthesis of 7α-Substituted Estradiols: Synthesis and Biological Evaluation of a 7α-Pentyl-Substituted Bodi Py Fluorescent Conjugate and a Fluorine-18-Labeled 7α-Pentylestradiol Analog," Steroids 58(4):157-169.

Fröhlich, T. et al. (Oct. 19, 2018). "Synthesis of Artemisinin-Estrogen Hybrids Highly Active Against HCMV, P. falciparum, and Cervical and Breast Cancer," ACS Medicinal Chemistry Letters 9(11):1128-1133.

George, A. et al. (2018, e-pub. Feb. 16, 2018). "Design, Synthesis, and Evaluation of the Antiproliferative Activity of Hydantoin-Derived Antiandrogen-Genistein Conjugates," Bioorganic & Medicinal Chemistry 26(8):1481-1487.

Gillmore, A.T. et al. (Nov. 14, 2012). "Multikilogram Scale-Up of a Reductive Alkylation Route to a Novel PARP Inhibitor," Org. Process Res. Dev. 16(12):1897-1904.

Gryder, B.E. et al (Jun. 20, 2013). "Histone Deacetylase Inhibitors Equipped with Estrogen Receptor Modulation Activity," Journal of Medicinal Chemistry 56(14):5782-5796.

Gryder, B.E. et al. (Sep. 4, 2013). "Selectively Targeting Prostate Cancer with Antiandrogen Equipped Histone Deacetylase Inhibitors," ACS Chemical Biology 8(11):2550-2560.

Guo, C. et al. (Sep. 21, 2011). "Discovery of Aryloxy Tetramethylcyclobutanes as Novel Androgen Receptor Antagonists," J. Medicinal Chemistry 54:7693-7704.

Hanson, R.N. et al. (2012). "Convergent Synthesis of a Steroidal Antiestrogen-Mitomycin C Hybrid Using "Click" Chemistry," Organic & Biomolecular Chemistry 10(42):8501-8508.

Hasan, M. et al. (2019). "Pharmacological, Mechanistic, and Pharmacokinetic Assessment of Novel Melatonin-Tamoxifen Drug Conjugates as Breast Cancer Drugs," Molecular Pharmacology 96(2):272-296.

He, H. et al. (2009, e-pub. Dec. 31, 2006). "Synthesis and Characterization of Nonsteroidal-Linked M(C0)3+(M=99mTc, Re) Compounds Based on the Androgen Receptor Targeting Molecule Flutamide," Bioconjugate Chemistry 20(1):78-86.

Hendricks, J.A. et al. (2013, e-pub. Apr. 4, 2013). "Synthesis and Preliminary Evaluation Steroidal Antiestrogen-Geldanamycin Conjugates," 23(12):3635-3639.

Hillier, S.M. et al. (Apr. 2006). "DNA Adducts Formed by a Novel Antitumor Agent 11β-dichloro in vitro and in vivo," Molecular Cancer Therapies 5(4):977-984.

Hu, W. et al. (2018). "A Study on Platinum(IV) Species Containing an Estrogen Receptor Modulator to Reverse Tamoxifen Resistance of Breast Cancer," Metallomics 10(2):346-359.

Hughes-Davies, L. et al. (Nov. 26, 2003). "EMSY Links the BRCA2 Pathway to Sporadic Breast and Ovarian Cancer," Cell 115:523-535.

Huxley, M. et al. (2010). "An Androgenic Steroid Delivery Vector That Imparts Activity to a Non-Conventional Platinum(II) Metallo-Drug," Dalton Trans. 39:11353-11364.

Hödl, C. et al. (2009, e-pub. Feb. 13, 2009). "Syntheses and Antigestagenic Activity of Mifepristone Derivatives," Journal of Medicinal Chemistry 52(5):1268-1274.

International Preliminary Report on Patentability, issued May 17, 2022, for PCT Application No. PCT/US2020/060165, filed Nov. 12, 2020, 9 pages.

International Preliminary Report on Patentability, issued Nov. 16, 2021, for PCT Application No. PCT/US2020/032672, filed May 13, 2020, 8 pages.

International Preliminary Report on Patentability, Issued Nov. 17, 2021, for PCT/US2019/032295, filed May 14, 2019, 7 pages.

(56) References Cited

OTHER PUBLICATIONS

International Preliminary Report on Patentability, issued Oct. 24, 2023, for PCT Application No. PCT/US2022/027334, filed May 2, 2022, 9 pages.
International Preliminary Report on Patentability, issued Sep. 12, 2023, for PCT Application No. PCT/US2022/021390, filed Mar. 22, 2022, 9 pages.
International Search Report and Written Opinion, dated May 11, 2022, regarding Application No. PCT/US2022/021390, filed Mar. 22, 2022, 12 pages.
International Search Report and Written Opinion, mailed Aug. 22, 2022, PCT Application No. PCT/US2022/027334, filed May 2, 2022, 14 pages.
International Search Report and Written Opinion, mailed Sep. 30, 2019, for PCT/US2019/32295, filed May 14, 2019, 10 pages.
International Search Report and Written Opinion, mailed Mar. 15, 2021 for PCT/US2020/060165, filed Nov. 12, 2020, 13 pages.
International Search Report and Written Opinion, Sep. 28, 2020 for PCT/US2020/032672, filed May 13, 2020, 11 pages.
Ishiki, N. et al., (1997)."Biological Properties of Conjugates of Mitomycin C with Estradiol Benzoate and Estradiol: A147 Their Stability Characteristics in Biological Media and Their Binding Abilities to Estrogen Receptor," Biological and Pharmaceutical Bulletin 20(10):1096-1102.
Jadhavar, P.S. et al. (Nov. 1, 2016, e-pub. Oct. 4, 2016). "Targeting Prostate Cancer with Compounds Possessing Dual Activity as Androgen Receptor Antagonists and HDAC6 Inhibitors," Bioorg. Med. Chem. Letter 26:5222-5228.
Janatová, M. et al. (2003). "Detection of the Most Frequent Mutations in BRCA1 Gene on Polyacrylamide Gels Containing Spreadex Polymer NAB," Neoplasma 50(4):246-250.
Jasin, M. (2002). "Homologous Repair of DNA Damage and Tumorigenesis:The BRCA Connection," Oncogene 21(58):8981-8993.
Jones, G.B. et al. (1996). "Target Directed Enediyne Prodrugs: Cytotoxic Estrogen Conjugates," Tetrahedron Letters 37(21):3643-3646.
Jones, G.B. et al. (2001). "Target-Directed Enediynes: Designed Estramycins," The Journal of Organic Chemistry 66(11):3688-3695.
Jurášek, M. et al. (2017, e-pub. Aug. 17, 2016). "Trilobolide-Steroid Hybrids: Synthesis, Cytotoxic and Antimycobacterial Activity," Steroids 117:97-104.
Kamal, A. et al. (2011, e-pub. Mar. 12, 2011). "Synthesis and Biological Evaluation of Estradiol Linked Pyrrolo [2,1-c]-[1,4] Benzodiazepine A151 (PBD) Conjugates as Potential Anticancer Agents," Bioorganic & Medicinal Chemistry 19(8):2565-2581.
Kasiotis, K.M. et al. (2011). "Synthesis and Biological Evaluation of Novel Daunorubicin-Estrogen Conjugates," Steroids 66(10):785-791.
Katzenellenbogen, J.A. (2005). "Designing Effective Hybrid Toxins," Chemistry & Biology 12(7):719-724.
Keely, N.O. et al. (2009). "Targeting Tumors Using Estrogen Receptor Ligand Conjugates," Current Cancer Drug Targets 9(3):370-380.
Keely, N.O. et al. (2012). "Design, Synthesis and Biochemical Evaluation of Estrogen Receptor Ligand Conjugates as Tumour Targeting Agents," Letters in Drug Design & Discovery 9(3):295-304.
Keely, N.O. et al. (2016). "Design, Synthesis and Biochemical Evaluation of Novel Selective Estrogen Receptor Ligand Conjugates Incorporating an Endoxifen-Combretastatin Hybrid Scaffold," Biomedicines 4(3):1-34.
Kelly, P.M. et al. (Aug. 31, 2017). "Novel Selective Estrogen Receptor Ligand Conjugates Incorporating Endoxifen-Combretastatin and Cyclofenil-Combretastatin Hybrid Scaffolds: Synthesis and Biochemical Evaluation," Molecules 22(9):1-50.
Khan, E.H. et al. (2003). "Synthesis and Biological Activities of Phthalocyanine-Estradiol Conjugates," Bioorganic & Medicinal Chemistry Letters 13(7):1287-1290.
Khanna, K.K. et al. (Mar. 2001). "DNA Double-Strand Breaks: Signaling, Repair and the Cancer Connection," Nat. Genet. 27(3):247-254.
Koseki, Y. et al. (2019). "Influence of Hydrolysis Susceptibility and Hydrophobicity of SN-38 Nano-Prodrugs on Their Anticancer Activity," Bulletin of the Chemical Society of Japan 92(8):1305-1313.
Kreis, W. et al. (1997). "Unique Synergism or Antagonism of Combinations of Chemotherapeutic and Hormonal Agents in Human Prostate Cancer Cell Lines," British Journal of Urology 79(2):196-202.
Kronenberger, T. et al. (Jun. 3, 2015). "Chapter 5—Nuclear Receptor Modulators—Current Approaches and Future Perspectives," in Drug Discovery and Development—From Molecules to Medicine, pp. 107-130.
Levine, P.M. et al. (Jun. 17, 2014). "Targeting the Androgen Receptor with Steroid Conjugates: Miniperspective," Journal of Medicinal Chemistry 57(20):8224-8237.
Li, X. et al. (Mar. 24, 2014). "Synthesis and Biological Activity of Some Bile Acid-Based Camptothecin Analogues," Molecules 19(3):3761-3776.
Liu, C. et al. (2004, e-pub. Nov. 21, 2003). "Design, Synthesis, and Bioactivities of Steroid-Linked Taxol Analogues as Potential Targeted Drugs for Prostate and Breast Cancer," Journal of Natural Products 67(2):152-159.
Lowder, L. et al. (2016). "Testosterone Conjugated DNA Methylating Agents Targeted to Prostate Cancer Cells," SERMACS-695, 68th Southeastern Regional Meeting of the American Chemistry Society, Meeting Abstract AN:2016:1708008, 2 pages.
Lv, G. et al. (2019). "Enhancement of Therapeutic Effect in Breast Cancer With a Steroid-Conjugated Ruthenium Complex," New Journal of Chemistry 43(8):3419-3427.
Marchal, E. et al. (2015). "Synthesis of Prodigiosene-Estrogen Conjugates: Optimization of Protecting Group Strategies and Anticancer Properties," Canadian Journal of Chemistry 93(5):526-535.
Marquis, J.C. et al. (Jul. 2005). "Disruption of Gene Expression and Induction of Apoptosis in Prostate Cancer Cells by A168 a DNA-Damaging Agent Tethered to an Androgen Receptor Ligand," Chemistry & Biology 12(7):779-787.
Menear, K.A. et al. (Oct. 23, 2008, e-pub. Sep. 19, 2008). "4-[3-(4-Cyclopropanecarbonylpiperazine-1-Carbonyl)-4-Fluorobenzyl]-2H-Phthalazin-1-One: A Novel Bioavailable Inhibitor of Poly(ADP-Ribose) Polymerase-1," J. Med. Chem. 51(20):6581-6591.
Mitra, K. et al. (2002, e-pub. Feb. 8, 2002). "A Rationally Designed Genotoxin that Selectively Destroys Estrogen Receptor-Positive Breast Cancer Cells," Journal of the American Chemical Society 124(9):1862-1863.
Morioka, M. et al. (2010). "Design, Synthesis, and Biological Evaluation of Novel Estradiol-Bisphosphonate A170 Conjugates as Bone-Specific Estrogens," Bioorganic & Medicinal Chemistry 18(3):1143-1148.
Mortensen, D.S. et al. (Jul. 23, 2015, e-pub. Jun. 23, 2015). "Optimization of a Series of Triazole Containing Mammalian Target of Rapamycin (mTOR) Kinase Inhibitors and the Discovery of CC-115," J. Med. Chem. 58(14):5599-5608.
Murai, J. et al. (Nov. 1, 2012, e-pub. Nov. 1, 2013). "Differential Trapping of PARP1 and PARP2 by Clinical PARP Inhibitors," Cancer Research 72(21):5588-5599, 22 pages.
Narayanan, R. et al. (2008). "Selective Androgen Receptor Modulators in Preclinical and Clinical Development," Nuclear Receptor Signaling 6(1):1-26.
Neuhausen, S.L. et al. (1992). "Mutation Testing of Early-Onset Breast Cancer Genes BRCA1 and BRCA2," Genet. Test 1(2):75-83.
Ning, W. et al. (Jul. 27, 2018). "Novel Hybrid Conjugates with Dual Suppression of Estrogenic and Inflammatory Activites Display Significantly Improved Potency Agains Breast Cancer," J. of Medicinal Chemistry 61:8115-8173.
O'Connor, M.J .et al. (Nov. 19, 2015). "Targeting the DNA Damage Response in Cancer," Molecular Cell 60(4):547-560.
Ota, Y. et al. (2016). "Targeting Cancer with PCPA-Drug Conjugates: LSD1 Inhibition-Triggered Release of 4-Hydroxytamoxifen," Angewandte Chemie International Edition 55:16115-16118.

(56) References Cited

OTHER PUBLICATIONS

Palermo, A.F. et al. (2018). "Incorporation of Histone Deacetylase Inhibitory Activity Into the Core of Tamoxifen—A New Hybrid Design Paradigm," Bioorganic & Medicinal Chemistry 26(15):4428-4440.
Patel, H.K. et al. (2014). "A Chimeric SERM-Histone Deacetylase Inhibitor Approach to Breast Cancer Therapy," ChemMedChem 9(3):602-613.
Peng, K.-W. et al. (Dec. 18, 2009). "Selective Estrogen Receptor Modulator Delivery of Quinone Warheads to DNA Triggering Apoptosis in Breast Cancer Cells," ACS Chemical Biology 4(12):1039-1049, 21 pages.
Powell, M. et al. (2015). "Cyano-Nilutamide Conjugates with a DNA Minor Groove Methylating Agent for Selective Destruction of Prostate Cancer Cells," 67th Southeast/71st Southwest Joint Regional Meeting of the American Chemical Society, 2015, SERMACS-SWRM-317, Meetina Abstract, 1 page.
Premnauth, G. et al. (2019). "Reactive Oxygen Species (ROS)-Dependent Release of an Anticancer Drug From a Targeting Peptide," Chemical Abstracts , 1 page.
PubChem (2005). CID-2375, created date: Mar. 25, 2005, 63 pages.
PubChem (2006). CID-11297720, created date Oct. 26, 2006, 9 pages.
Qin, X. et al. (Apr. 18, 2018). "Theranostic Pt(IV) Conjugate with Target Selectivity for Androgen Receptor," Inorganic Chemistry 57(9):5019-5029.
Radice, P. (Sep. 2002). "Mutations of BRCA Genes in Hereditary Breast and Ovarian Cancer," J. Exp. Clin. Cancer Res. 21(Suppl. 3):9-12.
Ragozin, E. et al. (2016, e-pub. Dec. 11, 2015). "Biolabile Peptidyl Delivery Systems Toward Sequential Drug Release," Biopolymers 106(1):119-132.
Rapozzi, V. et al. (Jun. 24, 2015). "Androgen Receptor Targeted Conjugate for Bimodal Photodynamic Therapy of Prostate Cancer in Vitro," Bioconjugate Chemistry 26(8):1662-1671.
Rink, S.M. et al. (Dec. 1996). "Synthesis and Biological Activity of DNA Damaging Agents That Form Decoy Binding Sites for A185 the Estrogen Receptor," Proceedings of the National Academy of Sciences 93(26):15063-15068.
Sadler, S. et al. (2011, e-pub. Jun. 1, 2011). "Internalization of a C17α-alkynylestradiol-Porphyrin Conjugate Into Estrogen A186 Receptor Positive MCF-7 Breast Cancer Cells," Bioorganic & Medicinal Chemistry Letters 21(15):4638-4641.
Saha, P. et al. (2012, e-pub. Jul. 16, 2012). "Design, Synthesis, Cytocidal Activity and Estrogen Receptor a Affinity of Doxorubicin A187 Conjugates At 16α-Position of Estrogen for Site-Specific Treatment of Estrogen Receptor Positive Breast Cancer," Steroids 77(11):1113-1122.
Sanchez-Cano, C. et al.(2010)., "Conjugation of Testosterone Modifies the Interaction of Mono-Functional Cationic A188 Platinum (II) Complexes with DNA, Causing Significant Alterations to the DNA Helix," Dalton Transactions 39(47):11365-11374.
Sharifi, N. et al. (Aug. 2007). "A Bifunctional Colchicinoid that Binds to the Androgen Receptor," Molecular Cancer Therapeutics 6(8):2328-2336.
Sharma, U. et al. (2004). "Design, Synthesis, and Evaluation of Estradiol-Linked Genotoxicants as Anti-Cancer Agents," Bioorganic & Medicinal Chemistry Letters 14(14):3829-3833.
Shen, L-Q. et al. (2013). "Synthesis and Anti-tumor Activity of Novel Steroidal Conjugates of Campothecin," Chinese Journal of New Drugs 22(5):585-589. English Abstract.
Shi, Q. et al. (2012, e-pub. May 15, 2012). "Antitumor Agents 290. Design, Synthesis, and Biological Evaluation of New LNCaP and PC-3 Cytotoxic Curcumin Analogs Conjugated with Anti-Androgens," Bioorganic & Medicinal Chemistry 20(13):4020-4031.
Shibata, N. et al. (Jun. 8, 2018). "Development of Protein Degradation Inducers of Androgen Receptor by Conjugation of Androgen Receptor Ligands and Inhibitor of Apoptosis Protein Ligands," Journal of Medicinal Chemistry 61(2):543-575.
Steffen, J.D. et al. (Dec. 2013). "Structural Implications for Selective Targeting of PARPs," Frontiers in Oncology 3(301):1-14.
Sundaram, S. et al. (2009, e-pub. Jun. 9, 2009). "Luteinizing Hormone-Releasing Hormone Receptor-Targeted Deslorelin-Docetaxel Conjugate Enhances Efficacy of Docetaxel in Prostate Cancer Therapy," Molecular Cancer Therapeutics 1655-1665.
Suzuki, A. et al. (2007). "Target-Selective Degradation of Proteins by a Light-Activated 2-Phenylquinoline-Estradiol Hybrid," Chemical Communications pp. 4260-4262.
Swamy, N. et al. (2002). "An Estradiol-Porphyrin Conjugate Selectively Localizes Into Estrogen Receptor-Positive Breast Cancer Cells," Bioorganic & Medicinal Chemistry 10:3237-3243.
Tang, C. et al. (May 20, 2015). "Novel Bioactive Hybrid Compound Dual Targeting Estrogen Receptor and Histone Deacetylase for the Treatment of Breast Cancer," Journal of Medicinal Chemistry 58(11):4550-4572.
Teutsch, G. et al. (Jan. 1994). "Synthesis of a Fluorescent Steroid Derivative with High Affinities for the Glucocorticoid and Progesterone Receptors," Steroids 59(1):22-26.
Tikhe, J.G. et al. (2004, e-pub. Sep. 29, 2004). "Design, Synthesis, and Evaluation of 3,4-Dihydro-2H-[1,4]diazepino[6, 7, 1-hi]indol-1-ones as Inhibitors of Poly(ADP-Ribose) Polymerase," Journal of Medicinal Chemistry 47:5467-5481.
Tutt, A. et al. (Dec. 2002). "The Relationship Between the Roles of BRCA Genes in DNA Repair and Cancer Predisposition," Trends Mol. Med. 8(12):571-576.
Wang, B. et al. (Dec. 10, 2016). "Discovery and Characterization of (8S,9R)-5-Fluoro-8-(4-fluorophenyl)-9-(1-methyl-1 H-1,2,4-triazol-5-yl)-2, 7,8, 9-tetrohydro-3H-pyrido[4,3,2-de ]phthalazi n-3-one (BMN 673, Talazoparib ), a Novel, Highly Potent, and Orally Efficacious Poly(ADP-ribose) Polymerase-1/2 Inhibitor, as an Anticancer Agent," Journal of Medicinal Chemistry 59:335-357.
Wang, F.-Z. et al. (2014, e-pub. Jun. 14, 2014). "The Checkpoint 1 Kinase Inhibitor LY2603618 Induces Cell Cycle Arrest, DNA Damage Response and Autophagy in Cancer Cells," Apoptosis 19(9):1389-1398.
Weinstain, R. et al. (Apr. 20, 2013). "Fluorescent Ligand for Human Progesterone Receptor Imaging in Live Cells," Bioconjugate Chemistry 24:766-771.
Wood, R.D. et al. (Feb. 16, 2001). "Human DNA Repair Genes," Science 291:1284-1289.
Zeinyeh, W. et al. (2012, e-pub. Jul. 31, 2012). "Progesterone-Adenine Hybrids as Bivalent Inhibitors of P-Glycoprotein-Mediated Multidrug Efflux: Design, Synthesis, Characterization and Biological Evaluation," Steroids 77(12):1177-1191.
Zhang, F.-L. et al. (2019). "Tamoxifen-Zinc(II) Phthalocyanine Conjugates for Target-Based Photodynamic Therapy and Hormone Therapy," Journal of Porphyrins and Phthalocyanines 23(10):1073-1083.
Zhang, Y. et al. (Aug. 22, 2016). "Antagonizing the Androgen Receptor with a Biomimetic Acyltransferase," ACS Chemical Biology 11(10):2797-2802.
Zhuang, C. et al. (Feb. 1, 2019, e-pub. Dec. 16, 2018). "Small Molecule-Drug Conjugates: A Novel Strategy for Cancer-Targeted Treatment," European Journal of Medicinal Chemistry 163:883-895.
Zolottsev, V.A. et al. (2018). "Conjugates of 17-Substituted Testosterone and Epitestosterone with Pyropheophorbide a Differing in the Length of Linkers," Steroids 138:82-90.

ANTI-CANCER NUCLEAR HORMONE RECEPTOR-TARGETING COMPOUNDS

CROSS REFERENCE TO RELATED APPLICATIONS

This application is a continuation of U.S. application Ser. No. 16/412,319, filed May 14, 2019, which claims the benefit under 35 U.S.C. § 119 (e) of U.S. Provisional Application 62/671,382, filed on May 14, 2018, both of which are hereby incorporated by reference in their entirety.

BACKGROUND

The disclosure relates to anti-cancer compounds derived from nuclear receptor binders, such as nuclear steroid receptor binders, to products containing the same, as well as to methods of their use and preparation.

PARP inhibitors are pharmacologic agents that prevent DNA repair leading to the death of cells and hence tumor growth inhibition. This mechanism of preventing cell growth leads to significant anti tumor activity in tumors with BRCA1, BRCA2 and PALB2 mutations, as these proteins are important for the repair of double strand DNA breaks by the homologous recombinant repair (HRR) pathway. Normal cells that are not dividing as fast as tumors and do not carry mutated BRCA1 or BRCA2 still have the HRR pathway intact which allows them to survive in the face of PARP inhibition. In addition to the catalytic inhibition of PARP, researchers at the National Cancer Institute in 2012 discovered an additional mechanism that drives the toxic effect of PARP inhibitors in tumor cells. Their observation that in addition to the blockade of the enzymatic activity of PARP, certain PARP inhibitors have the ability to localize PARP proteins to sites of DNA damage, correlated with the cytotoxicity of these inhibitors. This mode of action, called "PARP trapping" is an additional mechanism by which this class of pharmacologic agents works in the preventing tumor growth and survival (Murai, et al. Cancer Research (2012) 72(21): 5588-99). Inhibitors of PARP enzymes (such as olaparib, rucaparib, niraparib, and talzoparib) have been approved for the treatment of breast cancer in patients with BRCA mutations, and ovarian cancer. There are several others (e.g., velaparib) that are in clinical testing for breast, prostate and ovarian cancers. The use of PARP inhibitors is not without side effects, and one of the major road blocks to the long-term use of PARP inhibitors is the rapid and dose dependent development of neutropenia. This requires dosing holidays and/or dose reductions in clinical practice, which compromise the ability to achieve maximal efficacy.

SUMMARY

Provided herein are compounds comprising at least one nuclear payload and at least one nuclear receptor-targeting epitope. Compounds described herein are designed to bind nuclear receptors within the cell and allow the compound, with its nuclear payload, to accumulate in the nucleus.

Also provided herein are compounds comprising at least one nuclear payload and at least one nuclear steroid receptor-targeting epitope. Compounds described herein are designed to bind nuclear steroid receptors within the cell (e.g., the androgen receptor in the cytosol) and allow the compound, with its nuclear payload, to accumulate in the nucleus. This approach allows for compounds to have cell-type selectivity, not merely improved potency, and possibly a higher therapeutic index.

Further, the compounds described herein offer targeted delivery of a nuclear payload. The compounds both target and localize within tumor tissue. The transport of the compound, which comprises at least one nuclear receptor-targeting epitope, such as a nuclear steroid receptor-targeting epitope, covalently attached to at least one nuclear payload, to the nucleus allows for accumulation of the nuclear payload in the nucleus, enhancing tumor cell death. By doing so, compounds described in this disclosure may exhibit superior efficacy. In addition, the compounds described in this disclosure will, by accumulating preferentially in the of nuclear receptor positive cells, such as steroid receptor positive cells, spare cells that do not express the specific nuclear steroid receptor, and therefore reduce side effects.

In certain embodiments, provided is a compound comprising at least one nuclear payload and at least one nuclear receptor-targeting epitope. In certain embodiments, when the compound comprises one nuclear payload and one nuclear receptor-targeting epitope, the nuclear receptor-targeting epitope is not a peptide, protein, nanoparticle or antibody. In certain embodiments, when the compound comprises one nuclear payload and one nuclear receptor-targeting epitope, where the nuclear receptor-targeting epitope is an androgen receptor-targeting epitope or an estrogen receptor-targeting epitope, the nuclear payload is not doxorubicin, or an analog thereof. In certain embodiments, when the compound comprises one nuclear payload and one nuclear receptor-targeting epitope, where the nuclear receptor-targeting epitope is an androgen receptor-targeting epitope or an estrogen receptor-targeting epitope, the nuclear payload is not a hydroxamic acid which binds histone deacetylase (HDAC).

In certain embodiments, provided is a compound comprising at least one nuclear payload and at least one nuclear receptor-targeting epitope; provided that when the compound comprises one nuclear payload and one nuclear receptor-targeting epitope:

the nuclear receptor-targeting epitope is not a peptide, protein, nanoparticle or antibody; and when the nuclear receptor-targeting epitope is an androgen receptor-targeting epitope or an estrogen receptor-targeting epitope, the nuclear payload is not doxorubicin, or an analog thereof, and is not a hydroxamic acid which binds histone deacetylase (HDAC).

In certain embodiments, provided is a compound comprising at least one nuclear payload which binds to a catalytic domain of poly(ADP-ribose) polymerase (PARP) and at least one nuclear receptor-targeting epitope. In certain embodiments, the at least one nuclear receptor-targeting epitope is a nuclear steroid receptor-targeting epitope.

In certain embodiments, provided is a compound comprising at least one nuclear payload which binds to a poly(ADP-ribose) polymerase (PARP) (e.g., PARP-1 and/or PARP-2) and at least one nuclear receptor-targeting epitope. In certain embodiments, provided is a compound comprising at least one nuclear payload which binds to a poly(ADP-ribose) polymerase (PARP) (e.g., PARP-1 and/or PARP-2) and at least one estrogen receptor-targeting epitope, glucocorticoid receptor-targeting epitope, progesterone receptor-targeting epitope or androgen receptor-targeting epitope.

In certain embodiments, provided is a compound comprising at least one nuclear payload which binds to poly (ADP-ribose) polymerase (PARP) (e.g., PARP-1 and/or PARP-2) and at least one nuclear receptor-targeting epitope derived from an androgen receptor agonist, an androgen receptor antagonist, a selective androgen-receptor modulator (SARM), an estrogen receptor agonist, an estrogen receptor antagonist, a selective estrogen receptor modulator (SERM), a selective estrogen receptor modulator (SERM), a glucocorticoid receptor agonist, a glucocorticoid receptor antagonist, a selective glucocorticoid receptor modulator (SGRM), a progesterone receptor antagonist, a progesterone receptor agonist, a selective progesterone receptor modulator (SPRM), or a combination thereof.

In certain embodiments, provided is a compound comprising at least one nuclear payload which binds to poly (ADP-ribose) polymerase (PARP) (e.g., PARP-1 and/or PARP-2) and at least one nuclear steroid receptor-targeting epitope derived from an androgen receptor agonist, an androgen receptor antagonist, a selective androgen-receptor modulator (SARM), an estrogen receptor agonist, an estrogen receptor antagonist, a progesterone receptor antagonist, a progesterone receptor agonist, a selective progesterone receptor modulator (SPRM), or a combination thereof.

In certain embodiments, provided is a compound comprising at least one nuclear payload which binds to a poly(ADP-ribose) polymerase (PARP) (e.g., PARP-1 and/or PARP-2) and at least one nuclear receptor-targeting epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof.

Also provided is a compound of Formula I or II, or a stereoisomer, mixture of stereoisomers, hydrate, solvate, isotopically enriched analog or pharmaceutically acceptable salt thereof:

$$A\text{-}(L\text{-}B)_m \quad \text{I}$$

$$A\text{-}L\text{-}(B)_m \quad \text{II}$$

wherein:

A is a nuclear payload;

m is 1, 2 or 3;

each B is independently a nuclear receptor-targeting epitope; and each L is independently a covalent bond or a linking moiety.

In certain embodiments of Formula I or II, when m is 1, the nuclear receptor-targeting epitope is not a peptide, protein, nanoparticle or antibody. In certain embodiments of Formula I or II, when m is 1, and B is an androgen receptor-targeting epitope or an estrogen receptor-targeting epitope, then A is not doxorubicin, or an analog thereof. In certain embodiments of Formula I or II, when m is 1, and B is an androgen receptor-targeting epitope or an estrogen receptor-targeting epitope, then A is not a hydroxamic acid which binds histone deacetylase (HDAC).

Also provided is compound of Formula III, IV, V or VI, or stereoisomer, mixture of stereoisomers, hydrate, solvate, isotopically enriched analog or pharmaceutically acceptable salt thereof:

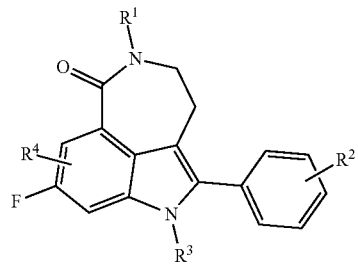

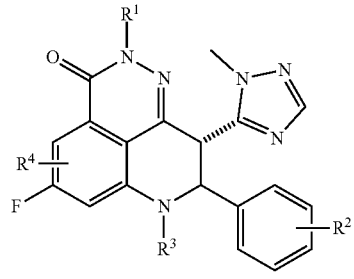

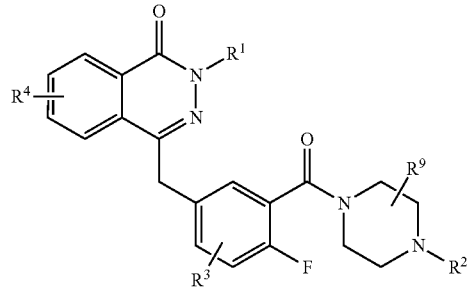

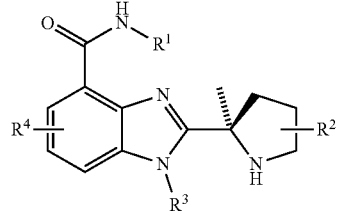

wherein:

each $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more (e.g., 1 to 5, or 1 to 3) $R^{10}$ as valency permits;

m is 1, 2, or 3;

each L is independently a covalent bond or a linking moiety;

each B is independently a nuclear receptor-targeting epitope;

each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR⁷C(=O)NR⁷R⁸, —S(=O)₁₋₂R⁷, —S(=O)₁₋₂NR⁷R⁸, —NR⁷S(=O)₁₋₂R⁸, —NR⁷S(=O)₁₋₂NR⁷R⁸, —NR⁷C(=O)R⁸, —NR⁷C(=O)OR⁸ or —C=NOR⁷, wherein each alkyl, alkenyl, alkynyl, cycloalkyl, heterocyclyl, aryl and heteroaryl of R¹⁰ are independently optionally substituted with one or more (e.g., 1 to 5, or 1 to 3) halo or $C_{1-12}$ alkyl optionally substituted by oxo, halo, hydroxyl or amino as valency permits;

each R⁵ and R⁶ is independently hydrogen, deuterium, $C_{1-12}$ alkyl or $C_{3-12}$ cycloalkyl, optionally substituted with oxo, halo, hydroxyl or amino as valency permits; or R⁵ and R⁶ are taken together with the atoms to which they are attached to form heterocyclyl optionally substituted by halo or $C_{1-12}$ alkyl optionally substituted by oxo, halo, hydroxyl or amino;

each R⁷ and R⁸ is independently hydrogen, deuterium or $C_{1-12}$ alkyl optionally substituted with oxo, halo, hydroxyl or amino as valency permits; or R⁷ and R⁸ are taken together with the atoms to which they are attached to form heterocyclyl optionally substituted by halo or $C_{1-12}$ alkyl optionally substituted by oxo, halo, hydroxyl or amino; and R⁹ is hydrogen or R²;

provided that at least one R¹, R², R³ and R⁴ is -L-(B)$_m$.

Also provided is compound of Formula IIIA, IV, VA or VI, or stereoisomer, mixture of stereoisomers, hydrate, solvate, isotopically enriched analog or pharmaceutically acceptable salt thereof:

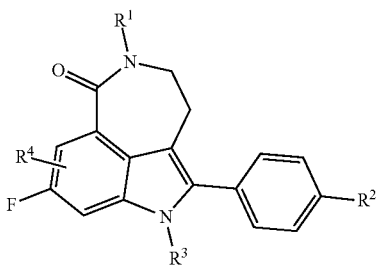

IIIA

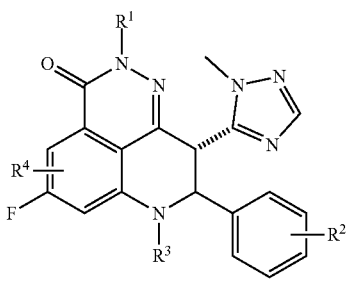

IV

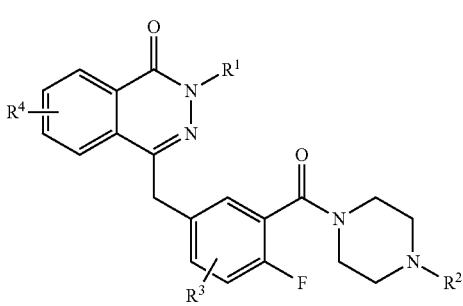

VA

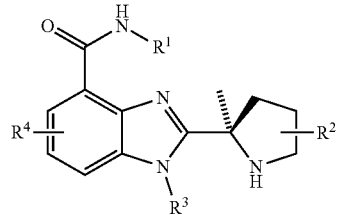

VI wherein:

each of R¹, R², R³ and R⁴ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R⁵, —C(=O)OR⁵, —OC(=O)R⁵, —C(=O)NR⁵R⁶, —NR⁵C(=O)R⁶, —S(=O)₁₋₂R⁵, —S(=O)₁₋₂NR⁵R⁶, —NR⁵S(=O)₁₋₂R⁶ or —C=NOR⁵, wherein each alkyl, alkenyl, alkynyl, cycloalkyl, heterocyclyl, aryl and heteroaryl of R¹, R², R³ and R⁴ are independently optionally substituted with one or more (e.g., 1 to 5, or 1 to 3) R¹⁰ as valency permits;

m is 1, 2, or 3;

each L is independently a covalent bond or a linking moiety;

each B is independently a nuclear receptor-targeting epitope;

each R¹⁰ is independently halo, cyano, nitro, —OR⁷, —SR⁷, —SF₅, —NR⁷R⁸, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R⁷, —C(=O)OR⁷, —OC(=O)R⁷, —OC(=O)R⁷, —C(=O)NR⁷R⁸, —OC(=O)NR⁷R⁸, —NR⁷C(=O)NR⁷R⁸, —S(=O)₁₋₂R⁷, —S(=O)₁₋₂NR⁷R⁸, —NR⁷S(=O)₁₋₂R⁸, —NR⁷S(=O)₁₋₂NR⁷R⁸, —NR⁷C(=O)R⁸, —NR⁷C(=O)OR⁸ or —C=NOR⁷, wherein each alkyl, alkenyl, alkynyl, cycloalkyl, heterocyclyl, aryl and heteroaryl of R¹⁰ are independently optionally substituted with one or more (e.g., 1 to 5, or 1 to 3) halo or $C_{1-12}$ alkyl optionally substituted by oxo, halo, hydroxyl or amino as valency permits;

each R⁵ and R⁶ is independently hydrogen, deuterium, $C_{1-12}$ alkyl or $C_{3-12}$ cycloalkyl, optionally substituted with oxo, halo, hydroxyl or amino as valency permits; or R⁵ and R⁶ are taken together with the atoms to which they are attached to form heterocyclyl optionally substituted by halo or $C_{1-12}$ alkyl optionally substituted by oxo, halo, hydroxyl or amino; and each R⁷ and R⁸ is independently hydrogen, deuterium or $C_{1-12}$ alkyl optionally substituted with oxo, halo, hydroxyl or amino as valency permits; or R⁷ and R⁸ are taken together with the atoms to which they are attached to form heterocyclyl optionally substituted by halo or $C_{1-12}$ alkyl optionally substituted by oxo, halo, hydroxyl or amino;

provided that at least one of R¹, R², R³ and R⁴ is -L-(B)$_m$.

Also provided is compound of Formula IIIB, IVA, VB or VIA, or stereoisomer, mixture of stereoisomers, hydrate, solvate, isotopically enriched analog or pharmaceutically acceptable salt thereof:

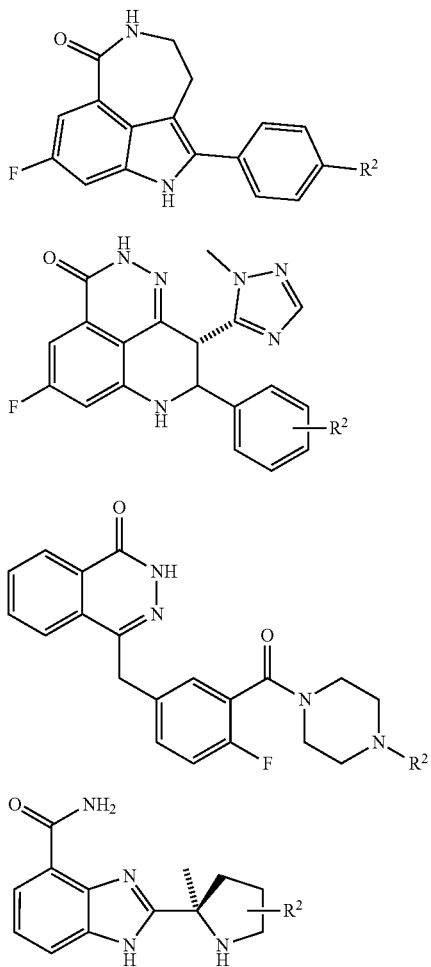

wherein:

m is 1, 2, or 3;

L is a covalent bond or a linking moiety; and each B is independently a nuclear receptor-targeting epitope.

Also provided is a compound of Table 1, or stereoisomer, mixture of stereoisomers, hydrate, solvate, isotopically enriched analog or pharmaceutically acceptable salt thereof.

Also provided is a composition comprising a compound as described herein or stereoisomer, mixture of stereoisomers, hydrate, solvate, isotopically enriched analog or pharmaceutically acceptable salt thereof, and a pharmaceutically acceptable excipient.

Also provided is a method of treating or preventing cancer, comprising administering an effective amount of a compound or composition as described herein to an individual in need thereof. The cancer can be a blood cancer, lung cancer, breast cancer, fallopian tube cancer, brain cancer, head and neck cancer, esophageal cancer, ovarian cancer, pancreatic cancer, peritoneal cancer, prostate cancer or skin cancer, such as, but not limited to, liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma.

Also provided is a method of treating or preventing bladder cancer, breast cancer, fallopian tube cancer, ovarian cancer, prostate cancer, peritoneal cancer, testicular cancer, endometrial cancer, or uterine cancer, comprising administering an effective amount of a compound or composition as described herein, or a pharmaceutically acceptable salt or solvate thereof, to an individual in need thereof.

Also provided is a method of treating or preventing cancer, comprising administering an effective amount of a compound, or a pharmaceutically acceptable salt or solvate thereof, comprising at least one nuclear payload and at least one nuclear receptor-targeting epitope comprising testosterone, a testosterone ester (e.g., testosterone enanthate, propionate, cypionate, etc., or an analog thereof), enobosarm, BMS-564929, PS178990, LGD-4033 (ligandrol), LGD-2941, AC-262,356, JNJ-28330835, JNJ-37654032, JNJ-26146900, LGD-2226, LGD-3303, LGD-121071, LG-120907, S-40503, S-23, RAD-140, acctothiolutamide, andarine (S-4), LG-121071, TFM-4AS-1, YK-11, MK-0773 (PF-05314882), GSK2849466, GSK2881078, GSK8698, GSK4336, ACP-105, TT701, LY2452473, a 1-(2-hydroxy-2-methyl-3-phenoxypropanoyl)-indoline-4-carbonitrile-derivative (J Med Chem. 2014, 57(6), 2462-71), anordrin, bazedoxifene, broparestrol (Acnestrol), clomifene (Clomid), cyclofenil (Sexovid), lasofoxifene (Fablyn), ormeloxifene (Centron, Novex, Novex-DS, Sevista), ospemifene (Osphena, deaminohydroxytoremifene), raloxifene (Evista), tamoxifen (Nolvadex), toremifene (Fareston; 4-chlorotamoxifen), acolbifene, afimoxifene (4-hydroxytamoxifen; metabolite of tamoxifen), elacestrant, enclomifene ((E)-clomifene), endoxifen (4-hydroxy-N-desmethyltamoxifen; metabolite of tamoxifen), zuclomifene ((Z)-clomifene), bazedoifene, arzoxifene, brilanestrant, clomifenoxide (clomiphene N-oxide; metabolite of clomifene), droloxifene (3-hydroxytamoxifen), etacstil, fispemifene, GW-7604 (4-hydroxyetacstil), idoxifene (pyrrolidino-4-iodotamoxifen), levormeloxifene ((L)-ormeloxifene), miproxifene, nafoxidine, nitromifene (CI-628), panomifene, pipendoxifene (ERA-923), trioxifene, keoxifene, LY117018, onapristone, fareston (toremifine citrate), zindoxifene (D-16726), fulvestrant, ARN-810, GW5638, GW7604, ulipristal acetate, asoprisnil (J867), mifepristone, telapristone (CDB-4124, Proellex, Progenta), or an analog thereof. In certain embodiments, the nuclear payload comprises a PARP inhibitor.

Also provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. In certain embodiments, the cancer is prostate, breast, triple negative breast cancer, bladder, or liver cancer. In certain embodiments, the androgen receptor-targeting epitope comprises an androgen receptor agonist, a selective androgen-receptor modulator (SARM), an androgen receptor antagonist, a selective estrogen receptor modulator (SERM), an estrogen receptor antagonist, a progestin, or an estrogen. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, darolutamide, or an analog thereof. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, or an analog thereof. In certain embodiments, the nuclear payload comprises a PARP inhibitor.

Also provided is a method of treating or preventing an estrogen and/or progesterone receptor overexpressing cancer, comprising administering an effective amount of a compound, or a pharmaceutically acceptable salt or solvate thereof, comprising at least one nuclear payload and at least one estrogen and/or progesterone receptor-targeting epitope to an individual in need thereof. In certain embodiments, the cancer is breast, uterine, or ovarian cancer. In certain embodiments, the nuclear payload comprises a PARP inhibitor.

Also provided is a method of treating or preventing a glucocorticoid receptor overexpressing cancer, comprising administering an effective amount of a compound, or a pharmaceutically acceptable salt or solvate thereof, comprising at least one nuclear payload and at least one glucocorticoid receptor-targeting epitope to an individual in need thereof. In certain embodiments, the cancer is prostate, breast, uterine, or ovarian cancer. In certain embodiments, the nuclear payload comprises a PARP inhibitor.

Also provided is a method of treating or preventing cancer, comprising administering an effective amount of a compound or composition as described herein, or a pharmaceutically acceptable salt or solvate thereof, in combination with an additional chemotherapeutic agent, to an individual in need thereof.

Also provided is a method for the treatment or prevention of a condition which can be ameliorated by inhibition of PARP in an individual in need thereof, the method comprising administering to the individual an effective amount of a compound or composition of any preceding claim or a pharmaceutically acceptable salt thereof.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

The term "about" refers to a variation of ±1%, ±3%, ±5%, or ±10% of the value specified. For example, "about 50" can in some embodiments includes a range of from 45 to 55. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. Also, the singular forms "a" and "the" include plural references unless the context clearly dictates otherwise. Thus, e.g., reference to "the compound" includes a plurality of such compounds and reference to "the assay" includes reference to one or more compounds and equivalents thereof known to those skilled in the art.

"Alkyl" refers to an unbranched or branched saturated hydrocarbon chain. As used herein, alkyl has 1 to 10 carbon atoms (i.e., $C_{1-10}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —$S(O)_2$—, and the like. As used herein, heteroalkyl includes 1 to 8 carbon atoms, or 1 to 4 carbon atoms; and 1 to 3 heteroatoms, 1 to 2 heteroatoms, or 1 heteroatom.

"Alkoxy" refers to the group "—O-alkyl".

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2 dimethylbutoxy.

"Alkoxyalkyl" refers to the group "alkyl-O-alkyl".

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more awl groups are fused with a heterocyclyl, the resulting ring system is heterocyclyl.

"Cycloalkyl" refers to a saturated or partially unsaturated cyclic alkyl group having a single ring or multiple rings including fused, bridged and Spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Further, the term cycloalkyl is intended to encompass any non-aromatic ring which may be fused to an awl ring, regardless of the attachment to the remainder of the molecule. Still further, cycloalkyl also includes "spirocycloalkyl" when there are two positions for substitution on the same carbon atom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with awl as defined above.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. The term "heterocyclyl" also includes "spiroheterocyclyl" when there are two positions for substitution on the same carbon atom.

"Alkylene" refers to a divalent alkyl group as defined above. As used herein, alkylene has 1 to 10 carbon atoms (i.e., $C_{1-10}$ alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene).

"Heteroalkylene" refers to an alkylene group in which one or more of the carbon atoms (and any associated hydrogen atoms) are each independently replaced with the same or different heteroatomic group. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —S(O)$_2$—, and the like. As used herein, heteroalkylene includes 1 to 8 carbon atoms, or 1 to 4 carbon atoms; and 1 to 3 heteroatoms, 1 to 2 heteroatoms, or 1 heteroatom.

"Alkenylene" refers to an alkylene group containing at least one carbon-carbon double bond and having from 2 to 8 carbon atoms (i.e., $C_{2-8}$ alkenylene), 2 to 6 carbon atoms (i.e., $C_{2-6}$ alkenylene), or 2 to 4 carbon atoms (i.e., $C_{2-4}$ alkenylene).

"Heteroalkenylene" refers to a heteroalkylene group containing at least one carbon-carbon double bond and having from 2 to 8 carbon atoms, 2 to 6 carbon atoms, or 2 to 4 carbon atoms; and 1 to 3 heteroatoms, 1 to 2 heteroatoms, or 1 heteroatom. The term "heteroalkynyl" also includes those groups having one triple bond and one double bond.

"Alkynylene" refers to an alkylene group containing at least one carbon-carbon triple bond and having from 2 to 8 carbon atoms (i.e., $C_{2-8}$ alkynylene), 2 to 6 carbon atoms (i.e., $C_{2-6}$ alkynylene), or 2 to 4 carbon atoms (i.e., $C_{2-4}$ alkynylene). The term "alkynyl" also includes those groups having one triple bond and one double bond.

"Heteroalkynylene" refers to a heteroalkylene group containing at least one carbon-carbon triple bond and having from 2 to 8 carbon atoms, 2 to 6 carbon atoms, or 2 to 4 carbon atoms; and 1 to 3 heteroatoms, 1 to 2 heteroatoms, or 1 heteroatom. The term "heteroalkynyl" also includes those groups having one triple bond and one double bond.

"Cycloalkylene" refers to a divalent saturated or partially unsaturated cyclic alkyl group having a single ring or multiple rings including fused, bridged, and spiro ring systems. The term "cycloalkylene" includes cycloalkenylene groups (i.e. the cyclic group having at least one double bond). As used herein, cycloalkenylene has from 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl).

"Heterocycloalkylene" refers to a cycloalkylene group in which one or more of the carbon atoms (and any associated hydrogen atoms) are each independently replaced with the same or different heteroatomic group. By way of example, 1, 2 or 3 carbon atoms may be independently replaced with the same or different heteroatomic group. Heteroatomic groups include, but are not limited to, —NH—, —O—, —S—, —S(O)—, —S(O)$_2$—, and the like. As used herein, heterocycloalkylene includes 1 to 9 carbon atoms, or 1 to 4 carbon atoms; and 1 to 3 heteroatoms, 1 to 2 heteroatoms, or 1 heteroatom.

"Oxo" refers to =O.

"Halogen" or "halo" includes fluoro, chloro, bromo, and iodo.

The terms "optional" or "optionally" means that the subsequently described event or circumstance may or may not occur. The term "optionally substituted" refers to any one or more hydrogen atoms on the designated atom or group may or may not be replaced by a moiety other than hydrogen.

Provided are also are stereoisomers, mixture of stereoisomers, tautomers, hydrates, solvates, isotopically enriched analog, and pharmaceutically acceptable salts of the compounds described herein.

The compounds disclosed herein, or their pharmaceutically acceptable salts, may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another and "diastereomers," which refers to stereoisomers that have at least two asymmetric atoms, but which are not mirror-images of each other. Thus, all stereoisomers (for example, geometric isomers, optical isomers and the like) of the present compounds (including those of the salts, solvates and hydrates of the compounds), such as those which may exist due to asymmetric carbons on various substituents, including enantiomeric forms (which may exist even in the absence of asymmetric carbons), rotameric forms, atropisomers, and diastereomeric forms, are contemplated.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1) may be atropisomers and are considered as part of this disclosure. Stereoisomers can also be separated by use of chiral HPLC.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Any compound or structure given herein, is also intended to represent unlabeled forms as well as isotopically labeled forms of the compounds. These forms of compounds may also be referred to as an "isotopically enriched analog." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Such compounds may exhibit increased resistance to metabolism and are thus useful for increasing the half-life of any compound when administered to a mammal, particularly a human. Such compounds are synthesized by means well known in the art, for example by employing starting materials in which one or more hydrogens have been replaced by deuterium.

Certain compounds disclosed herein contain one or more ionizable groups (groups from which a proton can be removed (e.g., —COOH) or added (e.g., amines) or which can be quaternized (e.g., amines)). All possible ionic forms of such molecules and salts thereof are intended to be included individually in the disclosure herein. With regard to salts of the compounds described herein, one of ordinary skill in the art can select from among a wide variety of available counterions those that are appropriate. In specific applications, the selection of a given anion or cation for preparation of a salt may result in increased or decreased solubility of that salt.

As used herein, the term "non-biocleavable linking moiety" is intended to refer to a linking moiety which is not readily hydrolyzed under physiological conditions. As used herein, the term "biocleavable linking moiety" is intended to refer to a linking moiety which is readily hydrolyzed under physiological conditions. In certain embodiments, at least one linking moiety is hydrolyzed under intracellular conditions (e.g., low pH).

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

The phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this disclosure.

"Chemotherapeutic agent" refers to any substance capable of reducing or preventing the growth, proliferation, or spread of a cancer cell, a population of cancer cells, tumor, or other malignant tissue. The term is intended also to encompass radiotherapy, or any antitumor or anticancer agent.

As used herein, "treatment" or "treating" is an approach for obtaining a beneficial or desired result, such as a clinical result. For purposes of this disclosure, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the disclosure or a pharmaceutically acceptable salt thereof is accompanied by no or fewer side effects than are associated with currently available therapies for the disease or condition and/or improves the quality of life of the individual.

The terms "inhibit," "inhibiting," and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the disclosure alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the disclosure which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, the term "agonist" refers to a compound, the presence of which results in a biological activity of a protein that is the same as the biological activity resulting from the presence of a naturally occurring ligand for the protein, such as, for example, PARP.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" or "inhibitor" refers to a compound, the presence of which results in a decrease in the magnitude of a biological activity of a protein. In certain embodiments, the presence of an antagonist results in complete inhibition of a biological activity of a protein, such as, for example, the enzyme poly(ADP-ribose) polymerase (PARP).

As used herein, the $IC_{50}$ refers to an amount, concentration or dosage of a particular test compound that achieves a 50% inhibition of a maximal response, such as modulation of PARP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer," as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid)), prostate, skin (melanoma) or hematological tumors (such as the leukemias).

The term "carrier," as used herein, refers to relatively nontoxic chemical compounds or agents that facilitate the incorporation of a compound into cells or tissues.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, J. Pharm. Sci. 1977 January; 66(1):1-19. Pharmaceutically acceptable salts can be prepared in situ in the manufacturing process, or by separately reacting a purified compound of the disclosure in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (directly compressible), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

Provided herein are compounds comprising at least one nuclear payload and at least one nuclear receptor-targeting epitope. The compounds described herein are capable of targeting the nucleus of a cell by recognition and binding of a nuclear receptor-targeting epitope to the respective binding site and delivering the nuclear payload to the nucleus of the cell. The nuclear payload then is capable of binding to one or more target sites within the nucleus and/or disrupting one or more cellular processes, causing the cell to die. In certain embodiments, the nuclear payload is bonded to the nuclear receptor-targeting epitope(s) via a linking moiety. In certain embodiments, the linking moiety provides a single or mono-linkage, meaning that the linker is only conjugated to one atom of each of the payload and the epitope.

The compounds described herein can comprise more than one nuclear receptor-targeting epitope. The epitopes can be the same or different, such that the compounds are directed to one or more cellular targets, in addition to the nucleus.

Accordingly, provided is a compound of Formula I, or stereoisomer, mixture of stereoisomers, hydrate, solvate, isotopically enriched analog or pharmaceutically acceptable salt thereof:

A-(L-B)$_m$     I wherein:
A is a nuclear payload;
m is 1, 2 or 3;
each B is independently a nuclear receptor-targeting epitope; and
each L is independently a covalent bond or a linking moiety.

In certain embodiments, one or more nuclear receptor-targeting epitopes are bonded to a nuclear payload via a single linking moiety. Accordingly, also provided is a compound of Formula II, or stereoisomer, mixture of stereoisomers, hydrate, solvate, isotopically enriched analog or pharmaceutically acceptable salt thereof:

A-L-(B)$_m$     II wherein:
A is a nuclear payload;
m is 1, 2 or 3;
each B is independently a nuclear receptor-targeting epitope; and
L is a linking moiety.

In certain embodiments, the nuclear receptor-targeting epitope of Formula I or II is a nuclear hormone receptor-targeting epitope. In certain embodiments, the nuclear receptor-targeting epitope of Formula I or II is a nuclear steroid receptor-targeting epitope.

Also provided is a compound of Formula I or Formula II, or stereoisomer, mixture of stereoisomers, hydrate, solvate, isotopically enriched analog or pharmaceutically acceptable salt thereof:

A-(L-B)$_m$     I

A-L-(B)$_m$     II wherein:
A is a nuclear payload;
m is 1, 2 or 3;
each B is independently a nuclear receptor-targeting epitope derived from estrogen, estetrol, estriol, estrone, progesterone, enobosarm, bicalutamide, apalutamide, testosterone, dihydrotestosterone, testosterone, 19-nortestosterone, progesterone, andarine, cortisol, prednisone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, ulipristal acetate, asoprisnil (J867), mifepristone, telapristone (CDB-4124, Proellex, Progenta), or an analog thereof; and each L is independently a covalent bond or a linking moiety.

Also provided is a compound of Formula I, or stereoisomer, mixture of stereoisomers, hydrate, solvate, isotopically enriched analog or pharmaceutically acceptable salt thereof:

A-(L-B)$_m$     I wherein:
A is a nuclear payload which binds to poly(ADP-ribose) polymerase-1 (PARP-1) and/or poly(ADP-ribose) polymerase PARP-2);
m is 1, 2 or 3;

each B is independently a nuclear receptor-targeting epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof; and
each L is independently a covalent bond or a linking moiety.

Also provided is a compound of Formula II, or stereoisomer, mixture of stereoisomers, hydrate, solvate, isotopically enriched analog or pharmaceutically acceptable salt thereof:

A-L-(B)$_m$     II wherein:
A is a nuclear payload which binds to poly(ADP-ribose) polymerase-1 (PARP-1) and/or poly(ADP-ribose) polymerase PARP-2);
m is 1, 2 or 3;
each B is independently a nuclear receptor-targeting epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof; and
each L is independently a covalent bond or a linking moiety.

The "linking moiety" of any compounds described herein can be biocleavable (e.g., acid labile) or non-biocleavable. Linking moieties can be linear, branched, saturated, unsaturated, all-carbon or heteroatomic. Linking moieties can also contain one or more rings that are fused, saturated, unsaturated, as well as be all-carbon or heteroatomic. In certain embodiments, the linking moiety is a non-biocleavable linking moiety. In certain embodiments, the linking moiety is a biocleavable linking moiety. In certain embodiments, a nuclear payload is bonded to one nuclear steroid receptor-targeting epitope via a non-biocleavable linking moiety and one or more nuclear steroid receptor-targeting epitope(s) via a biocleavable linking moiety. In certain embodiments, the biocleavable linking moiety is an acid-labile linking moiety. In some embodiments, the linking moiety comprises a hydrazone linkage.

It is contemplated that any linking moiety can be used in the compounds described herein, provided that it does not significantly interfere with or disrupt the desired binding of the nuclear payload or the nuclear receptor-targeting epitope. In some embodiments, the linking moiety is alkylene, heteroalkylene, alkenylene, heteroalkenylene, alkynylene, heteroalkynylene, arylene, heteroarylene, cycloalkylene or heterocycloalkylene; wherein each alkylene, heteroalkylene, alkenylene, heteroalkenylene, alkynylene, heteroalkynylene, may optionally comprise an arylene, heteroarylene, cycloalkylene or heterocycloalkylene; and further wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl.

In certain embodiments, the linking moiety is of the formula:

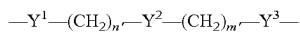

wherein:

each of $Y^1$, $Y^2$, and $Y^3$ are independently a $-NR^{11}-$, $-O-$, $-S(O)_{0-2}-$, $-NR^{11}C(O)-$, $-C(O)NR^{11}-$, $-NR^{11}S(O)_2-$, $-S(O)_2NR^{11}-$, $-CR^{12}=N-NR^{11}-$, $-NR^{11}-N=CR^{12}-$, $-C(O)-$, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently $C_{1-4}$ alkyl, $C_{1-4}$ haloalkyl, aryl, heteroaryl, cycloalkyl or heterocyclyl;

each $R^{12}$ is independently $C_{1-4}$ alkyl, $C_{1-4}$ haloalkyl, aryl, heteroaryl, cycloalkyl or heterocyclyl; and n' and m' are each independently 0, 1, 2, 3, 4, 5, 6, 7, or 8.

Also provided is a compound of Formula IA, or stereoisomer, mixture of stereoisomers, hydrate, solvate, isotopically enriched analog or pharmaceutically acceptable salt thereof:

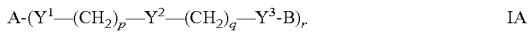

A-(Y$^1$—(CH$_2$)$_p$—Y$^2$—(CH$_2$)$_q$—Y$^3$-B)$_r$    IA wherein:

A is a nuclear payload which binds to poly(ADP-ribose) polymerase-1 (PARP-1) and/or poly(ADP-ribose) polymerase PARP-2);

r is 1, 2 or 3;

each B is independently a nuclear receptor-targeting epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof; and each of $Y^1$, $Y^2$, and $Y^3$ are independently a bond, $-NR^{11}-$, $-O-$, $-S(O)_{0-2}-$, $-NR^{11}C(O)-$, $-C(O)NR^{11}-$, $-NR^{11}S(O)_2-$, $-S(O)_2NR^{11}-$, $-CR^{12}=N-NR^{11}-$, $-NR^{11}-N=CR^{12}-$, $-C(O)-$, arylene, heteroarylene, cycloalkylene, or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently $C_{1-4}$ alkyl, $C_{1-4}$ haloalkyl, aryl, heteroaryl, cycloalkyl or heterocyclyl;

each $R^{12}$ is independently $C_{1-4}$ alkyl, $C_{1-4}$ haloalkyl, aryl, heteroaryl, cycloalkyl or heterocyclyl; and p and q are each independently 0, 1, 2, 3, 4, 5, 6, 7, or 8.

Also provided is a compound of Formula IIA, or stereoisomer, mixture of stereoisomers, hydrate, solvate, isotopically enriched analog or pharmaceutically acceptable salt thereof:

A-Y$^1$—(CH$_2$)$_p$—Y$^2$—(CH$_2$)$_q$—Y$^3$-(B)$_r$    IIA wherein:

A is a nuclear payload which binds to poly(ADP-ribose) polymerase-1 (PARP-1) and/or poly(ADP-ribose) polymerase PARP-2);

r is 1, 2 or 3;

each B is independently a nuclear receptor-targeting epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof; and each of $Y^1$, $Y^2$, and $Y^3$ are independently a bond, $-NR^{11}-$, $-O-$, $-S(O)_{0-2}-$, $-NR^{11}C(O)-$, $-C(O)NR^{11}$, $-NR^{11}S(O)_2-$, $-S(O)_2NR^{11}-$, $-CR^{12}=N-NR^{11}-$, $-NR^{11}-N=CR^{12}-$, $-C(O)$-arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently $C_{1-4}$ alkyl, $C_{1-4}$ haloalkyl, aryl, heteroaryl, cycloalkyl or heterocyclyl; each $R^{12}$ is independently $C_{1-4}$ alkyl, $C_{1-4}$ haloalkyl, aryl, heteroaryl, cycloalkyl or heterocyclyl; and p and q are each independently 0, 1, 2, 3, 4, 5, 6, 7, or 8.

In certain embodiments, the linking moiety is not a bond.

In certain embodiments, each $R^{11}$ is independently hydrogen, $C_{1-4}$ alkyl, $C_{1-4}$ haloalkyl, aryl, heteroaryl, cycloalkyl or heterocyclyl; and each $R^{12}$ is independently hydrogen, $C_{1-4}$ alkyl, $C_{1-4}$ haloalkyl, aryl, heteroaryl, cycloalkyl or heterocyclyl.

In certain embodiments, the linking moiety is of the formula:

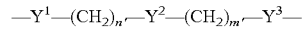

—Y$^1$—(CH$_2$)$_{n'}$—Y$^2$—(CH$_2$)$_{m'}$—Y$^3$— wherein:

each of $Y^1$, $Y^2$, and $Y^3$ are independently a $-NR^{11}-$, $-O-$, $-S(O)_{0-2}-$, $-NR^{11}C(O)-$, $-C(O)NR^{11}-$, $-NR^{11}S(O)_2-$, $-S(O)_2NR^{11}-$, $-CR^{12}=N-NR^{11}-$, $-NR^{11}-N=CR^{12}-$, $-C(O)-$, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently hydrogen, $C_{1-4}$ alkyl, $C_{1-4}$ haloalkyl, aryl, heteroaryl, cycloalkyl or heterocyclyl;

each $R^{12}$ is independently hydrogen, $C_{1-4}$ alkyl, $C_{1-4}$ haloalkyl, aryl, heteroaryl, cycloalkyl or heterocyclyl; and n' and m' are each independently 0, 1, 2, 3, 4, 5, 6, 7, or 8.

Also provided is a compound of Formula I or II, or a stereoisomer, mixture of stereoisomers, hydrate, solvate, isotopically enriched analog or pharmaceutically acceptable salt thereof:

A-(L-B)$_m$    I

A-L-(B)$_m$    II wherein:

A is a nuclear payload;

m is 1, 2 or 3;

each B is independently a nuclear receptor-targeting epitope; and each L is independently a covalent bond or a linking moiety.

Also provided is a compound of Formula I or II, or a stereoisomer, mixture of stereoisomers, hydrate, solvate, isotopically enriched analog or pharmaceutically acceptable salt thereof:

A-(L-B)$_m$  I

A-L-(B)$_m$  II wherein:

A is a nuclear payload;

m is 1, 2 or 3;

each B is independently a nuclear steroid receptor-targeting epitope; and each L is independently a covalent bond or a linking moiety.

In certain embodiments of any Formula or subformula disclosed herein (e.g., Formula I or II), when m is 1, then the nuclear receptor-targeting epitope is not a peptide, protein, nanoparticle or antibody. In certain embodiments of any Formula or subformula disclosed herein (e.g., Formula I or II), when m is 1, and B is an androgen receptor-targeting epitope, then A is not doxorubicin, or an analog thereof. In certain embodiments of any Formula or subformula disclosed herein (e.g., Formula I or II), when m is 1, and B is an androgen receptor-targeting epitope, then A is not a hydroxamic acid which binds histone deacetylase (HDAC). In certain embodiments of any Formula or subformula disclosed herein (e.g., Formula I or II), when in is 1, and B is an estrogen receptor-targeting epitope, then A is not doxorubicin, or an analog thereof. In certain embodiments of any Formula or subformula disclosed herein (e.g., Formula I or II), when m is 1, and B is an estrogen receptor-targeting epitope, then A is not a hydroxamic acid which binds histone deacetylase (HDAC).

Also provided is compound of Formula III, IV, V or VI, or stereoisomer, mixture of stereoisomers, hydrate, solvate, isotopically enriched analog or pharmaceutically acceptable salt thereof:

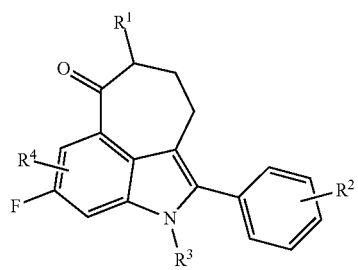

III

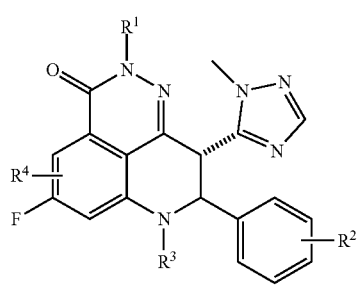

IV

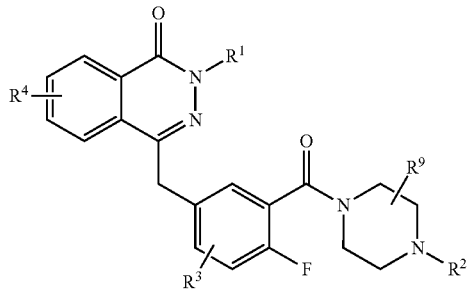

V

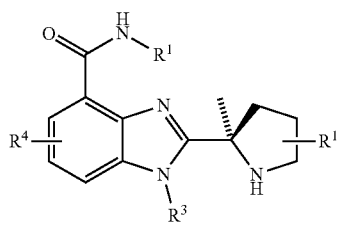

VI wherein:

each $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)$R^5$, —C(=O)O$R^5$, —OC(=O)$R^5$, —C(=O)N$R^5R^6$, —N$R^5$C(=O)$R^6$, —S(=O)$_{1-2}R^5$, —S(=O)$_{1-2}$N$R^5R^6$, —N$R^5$S(=O)$_{1-2}R^6$ or —C=NO$R^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more (e.g., 1 to 5, or 1 to 3) $R^{10}$ as valency permits;

m is 1, 2, or 3;

each L is independently a covalent bond or a linking moiety;

each B is independently a nuclear receptor-targeting epitope;

each $R^{10}$ is independently halo, cyano, nitro, —O$R^7$, —S$R^7$, —SF$_5$, —N$R^7R^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)$R^7$, —C(=O)O$R^7$, —OC(=O)O$R^7$, —OC(=O)$R^7$, —C(=O)N$R^7R^8$, —OC(=O)N$R^7R^8$, —N$R^7$C(=O)N$R^7R^8$, —S(=O)$_{1-2}R^7$, —S(=O)$_{1-2}$N$R^7R^8$, —N$R^7$S(=O)$_{1-2}R^8$, —N$R^7$S(=O)$_{1-2}$N$R^7R^8$, —N$R^7$C(=O)$R^8$, —N$R^7$C(=O)O$R^8$ or —C=NO$R^7$, wherein each alkyl, alkenyl, alkynyl, cycloalkyl, heterocyclyl, aryl and heteroaryl of $R^{10}$ are independently optionally substituted with one or more (e.g., 1 to 5, or 1 to 3) halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{5-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino;

each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino; and $R^9$ is hydrogen or $R^2$;

provided that at least one $R^1$, $R^2$, $R^3$ and $R^4$ is -L-(B)$_m$.

Also provided is compound of Formula IIIA, IV, VA or VI, or stereoisomer, mixture of stereoisomers, hydrate, solvate, isotopically enriched analog or pharmaceutically acceptable salt thereof:

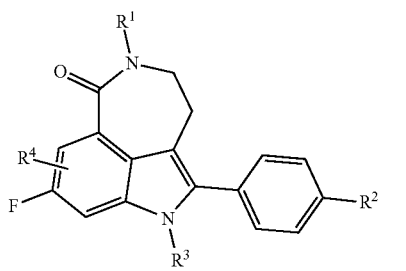

IIIA

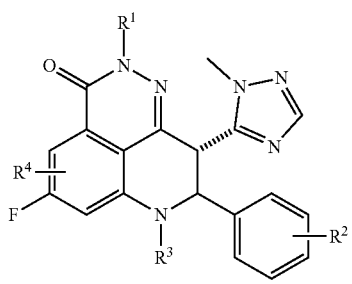

IV

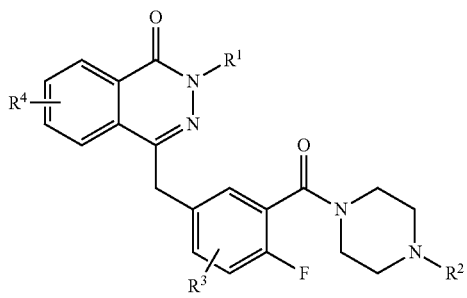

VA

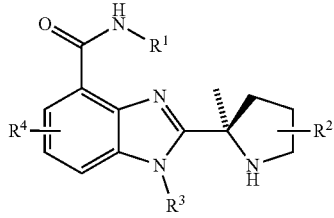

VI wherein:
each of $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more (e.g., 1 to 5, or 1 to 3) $R^{10}$ as valency permits;
m is 1, 2, or 3;
each L is independently a covalent bond or a linking moiety;
each B is independently a nuclear receptor-targeting epitope;

each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^7$, —NR$^7$S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of $R^{10}$ are independently optionally substituted with one or more (e.g., 1 to 5, or 1 to 3) halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$, $R^3$ and $R^4$ is -L-(B)$_m$.

Also provided is compound of Formula IIIB, IVA, VB or VIA, or stereoisomer, mixture of stereoisomers, hydrate, solvate, isotopically enriched analog or pharmaceutically acceptable salt thereof:

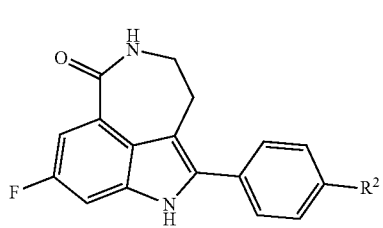

IIIB

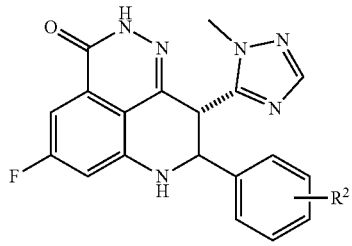

IVA

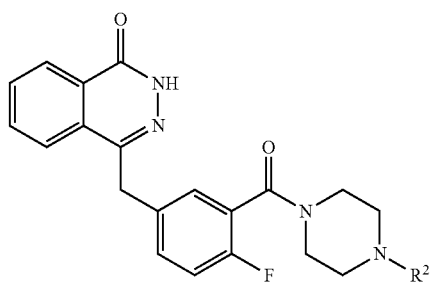

VB

-continued

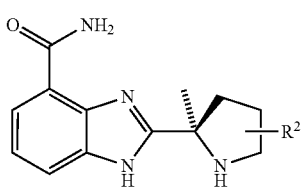

VIA wherein:
R² is -L-(B)ₘ;
m is 1, 2, or 3;
L is a covalent bond or a linking moiety; and
each B is independently a nuclear receptor-targeting epitope.

Also provided is compound of Formula III', IV', V' or VI', or stereoisomer, mixture of stereoisomers, hydrate, solvate, isotopically enriched analog or pharmaceutically acceptable salt thereof:

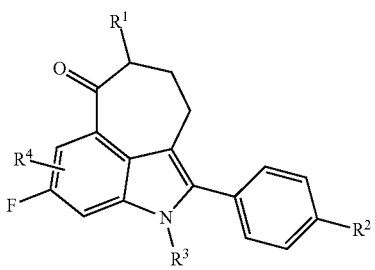

III'

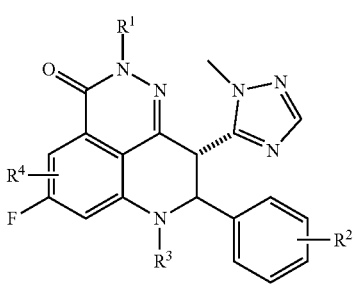

IV'

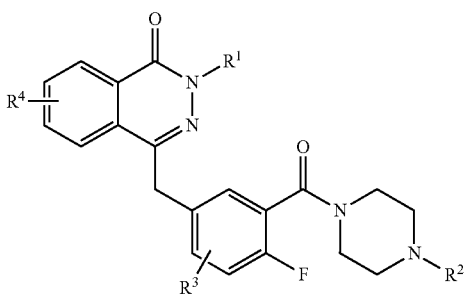

V'

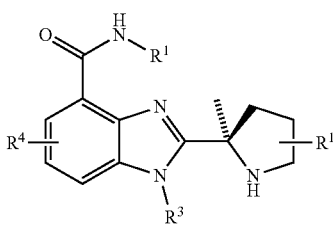

VI' wherein:
each of $R^1$, $R^2$, $R^3$ and $R^4$ is independently -L-(B)ₘ, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R⁵, —C(=O)OR⁵, —OC(=O)R⁵, —C(=O)NR⁵R⁶, —NR⁵C(=O)R⁶, —S(=O)$_{1-2}$R⁵, —S(=O)$_{1-2}$NR⁵R⁶, —NR⁵S(=O)$_{1-2}$R⁶ or —C=NOR⁵, wherein each alkyl, alkenyl, alkynyl, cycloalkyl, heterocyclyl, aryl and heteroaryl of $R^1$, $R^2$, $R^3$ and $R^4$ are independently optionally substituted with one or more (e.g., 1 to 5, or 1 to 3) $R^{10}$ as valency permits;

m is 1, 2, or 3;

each L is independently a covalent bond or a linking moiety;

each B is independently a nuclear steroid receptor-targeting epitope;

each $R^{10}$ is independently halo, cyano, nitro, —OR⁷, —SR⁷, —SF₅, —NR⁷R⁸, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R⁷, —C(=O)OR⁷, —OC(=O)R⁷, —OC(=O)R⁷, —C(=O)NR⁷R⁸, —OC(=O)NR⁷R⁸, —NR⁷C(=O)NR⁷R⁸, —S(=O)$_{1-2}$R⁷, —S(=O)$_{1-2}$NR⁷R⁸, —NR⁷S(=O)$_{1-2}$R⁸, —NR⁷S(=O)$_{1-2}$NR⁷R⁸, —NR⁷C(=O)R⁸, —NR⁷C(=O)OR⁸ or —C=NOR⁷, wherein each alkyl, alkenyl, alkynyl, cycloalkyl, heterocyclyl, aryl and heteroaryl of $R^{10}$ are independently optionally substituted with one or more (e.g., 1 to 5, or 1 to 3) halo or $C_{1-12}$ alkyl optionally substituted by oxo, halo, hydroxyl or amino as valency permits; and each $R^5$ and $R^6$ is independently hydrogen, deuterium or $C_{1-12}$ alkyl optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$, $R^3$ and $R^4$ is -L-(B)ₘ.

Also provided is compound of Formula IIIA', IVA', VA' or VIA', or stereoisomer, mixture of stereoisomers, hydrate, solvate, isotopically enriched analog or pharmaceutically acceptable salt thereof:

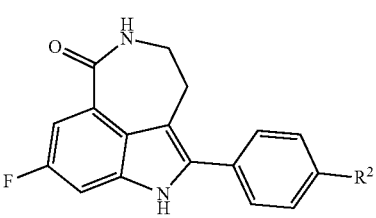

IIIA'

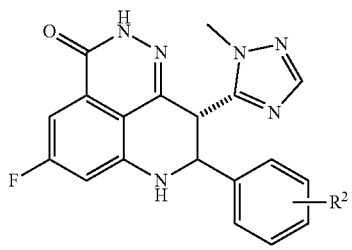

IVA'

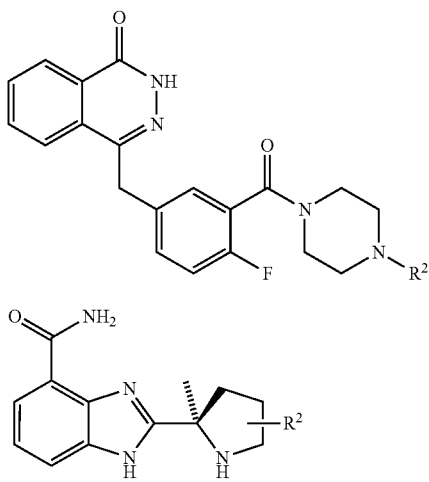

VA'

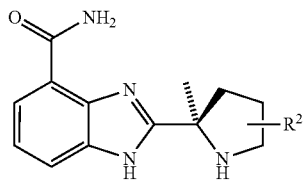

VIA' wherein:
R² is -L-(B)$_m$;
m is 1, 2, or 3;
L is a covalent bond or a linking moiety; and
each B is independently a nuclear steroid receptor-targeting epitope.

Nuclear Payloads

The nuclear payloads as used herein are generally capable of binding to any site which is involved in a cellular process important for the development of cancer, or cellular replication. In certain embodiments, the nuclear payload binds to the target site within the nucleus and disrupts one or more cellular processes, causing the cell to die. Target sites within the nucleus include, but are not limited to, a sub-nuclear compartment (e.g., promyelocytic leukemia nuclear body (PML NB), nucleolus), a protein-protein interaction within the nucleus (e.g., hypoxia-inducible factor 1α (HIF-1α), FKBP25) or modifications of the chromatin structure. In certain embodiments, the nuclear payload targets a protein involved in the DNA damage repair process, such as, but not limited to, poly(ADP-ribose) polymerase (PARP), DNA-dependent protein kinase (DNA-PK), myelin transcription factor 1 (MYT1), p53, melanocyte-stimulating hormone (MSH), mutL homolog (MLH), ERCC1, apurinic/apyrimidinic endonuclease 1 (APE1), topoisomerase I (Topo I), topoisomerase II (Topo II), Wee1, checkpoint kinase1 (Chk1), checkpoint kinase2 (Chk2), ataxia telangiectasia (ATR), or ataxia-telangiectasia mutated (ATM).

In certain embodiments, the nuclear payload comprises olaparib (AZD-2281), Olaparib TOPARP-A, rucaparib (AG014699, PF-01367338), niraparib, talazoparib (BMN-673), veliparib (ABT-888), CEP 9722, E7016, BGB-290, 3-aminobenzamide, methoxyamine, CC-115, MSC2490484A, AZD6738, VX-970, AZD0156, GDC-0575, MK-8776, LY2606368, AZD1775, belotecan, CRLX101, irinotecan, LMP 400, LMP 776, NKTR-102, topotecan, doxorubicin, epirubicin, etoposide, idarubicin, mitoxantrone, teniposide, or an analog thereof. In certain embodiments, the nuclear payload comprises AZD-1775 (MK-1775, Adavosertib), SCH900776 (MK-8776), AZD0156, M6620 (VX-970, VE-822, Berzosertib), AZD6738, or CC-115, or an analog thereof. In certain embodiments, the nuclear payload comprises a combination of CC-115 with an additional nuclear payload. In certain embodiments, the nuclear payload comprises CC-115 and the compound comprises enzalutamide or an analog thereof.

The analogs are derived from the known nuclear payloads named herein and are modified to be conjugated to at least one nuclear receptor-targeting epitope, optionally via a linking moiety. The analogs, even after modification to arrive at the compounds described herein, maintain biological activity, which is comparable to that observed in the original, unmodified nuclear payload. In certain embodiments, the analogs exhibit a binding activity or inhibition which is at least about 98%, about 95%, about 90%, about 85%, about 80%, about 75%, about 70%, about 65%, about 60%, about 55%, or about 50% of that observed in the original, unmodified nuclear payload.

In certain embodiments, the terms "modified" and "derived from" as used in reference to a nuclear payload, means that at most, one non-hydrogen atom of the original, unmodified nuclear payload (i.e., a known nuclear payload) is replaced by a covalent bond linking at least one nuclear receptor-targeting epitope(s), optionally via a linking moiety. In certain embodiments, the terms "modified" and "derived from" as used in reference to a nuclear payload, means that at most, only one hydrogen atom of the original, unmodified nuclear payload (i.e., a known nuclear payload) is replaced by a covalent bond linking at least one nuclear receptor-targeting epitope(s), optionally via a linking moiety. In certain embodiments, one hydrogen atom bound to a heteroatom (e.g., N, O, or S) of the original, unmodified nuclear payload (i.e., a known nuclear payload) is replaced by a covalent bond linking at least one nuclear receptor-targeting epitope(s), optionally via a linking moiety.

In certain embodiments, the nuclear payload binds to an epigenetic target, such as histone deacetylase (HDAC) (e.g., vorinostat, romidepsin (Istodax), chidamide, panobinostat (Farydak), belinostat (PXD101), panobinostat (LBH589), valproic acid (as Mg valproate), mocctinostat (MGCD0103), abexinostat (PCI-24781), entinostat (MS-275), SB939, resminostat (4SC-201), givinostat (ITF2357), quisinostat (JNJ-26481585), HBI-8000, kevetrin, CUDC-101, AR-42, CHR-2845, CHR-3996, 4SC-202, CG200745, ACY-1215, ME-344, sulforaphane, etc., or an analog thereof), enhancer of zeste homolog 2 (EZH2) (e.g., tazemetostat, MAK638, CPI-1205), DS-3201b, etc., or an analog thereof), histone acetyl transferase (HAT) (e.g., anacardic acid, MG149, C646, etc., or an analog thereof), methyltransferase (e.g., S-adenosyl methionine, etc., or an analog thereof), a bromodomain (e.g., JQ1, I-BET 151 (GSK1210151A), I-BET 762 (GSK525762), OTX-015, TEN-010, CPI-203, CPI-0610, olinone, LY294002, or an analog thereof), and the like.

Any known nuclear payload which targets proteins one or more cellular processes can be used as the nuclear payload of the compounds described herein. Small molecule nuclear payloads (i.e., molecular weight of less than about 1,000 g/mol) are contemplated to be especially useful in the compounds described herein (e.g., tripazamine, chetomin, rapamycin, PARP inhibitors, etc.).

In certain embodiments, the compound comprises at least one nuclear payload which binds to poly(ADP-ribose) polymerase (PARP) and are referred to herein as "PARP inhibitors." PARP inhibitors are cytotoxic agents that prevent such DNA repair leading to the death of cells and tumor growth inhibition. In certain embodiments, the PARP is human PARP, and comprises PARP-1 and/or PARP-2, or a variant thereof. In certain embodiments, the nuclear payload is capable of blocking the enzymatic activity of PARP and/or localizing PARP proteins to sites of DNA damage (i.e., "PARP trapping"). Accordingly, in certain embodiments, the nuclear payload binds to PARP and induces an allosteric conformational change in the enzyme.

In certain embodiments, the nuclear payload binds to the PARP-1 catalytic domain. In certain embodiments, the nuclear payload binds to the PARP-2 catalytic domain. In certain embodiments, the nuclear payload binds to a conserved HYE motif. In certain embodiments, the nuclear payload binds to the nicotinamide-binding pocket in the PARP protein.

In one embodiment, the nuclear payload is an analog of a known PARP inhibitor. Exemplary PARP inhibitors which can be used as nuclear payloads in the compounds described herein include, but are not limited to olaparib (AZD-2281), olaparib TOPARP-A, rucaparib (AG014699, PF-01367338), niraparib, talazoparib (BMN-673), veliparib (ABT-888), CEP 9722, E7016, BGB-290, and 3-aminobenzamide, or an analog thereof.

The PARP inhibitor analogs are derived from PARP inhibitors and are modified to be conjugated to at least one nuclear steroid receptor-targeting epitope, optionally via a linking moiety. The PARP inhibitor analogs, even after modification to arrive at the compounds described herein, maintain biological activity which is comparable to that observed in the original, unmodified PARP inhibitor. In certain embodiments, the PARP inhibitor analogs maintain the ability to inhibit PARP. In certain embodiments, the PARP inhibitor analogs exhibit a binding activity which is at least about 98%, about 95%, about 90%, about 85%, about 80%, about 75%, about 70%, about 65%, about 60%, about 55%, or about 50% of that observed in the original, unmodified PARP inhibitor. In certain embodiments, the compound as described herein is binds to a poly(ADP-ribose) polymerase (PARP) (e.g., PARP-1 and/or PARP-2) with an $IC_{50}$ of less than about 500 nM, or less than about 400 nM, or less than about 350 nM, or less than about 300 nM, or less than about 200 nM, or less than about 100 nM, or less than about 50 nM.

In certain embodiments, the nuclear payload (e.g., PARP inhibitor analog) comprises one or more moieties capable of having a binding interaction with G863, Y907, S904, A898, K903, E988, Y896, and/or Y889 of PARP-1. In certain embodiments, the nuclear payload (e.g., PARP inhibitor analog) comprises one or more moieties capable of having a binding interaction with Y889, Y896, H862, G863, S904, Y907, K903, E988, and/or M890 of PARP-1. In certain embodiments, the nuclear payload (e.g., PARP inhibitor analog) comprises one or more moieties capable of having a binding interaction with Y896, Q763, G863, S904, Y907, K903, and/or E988 of PARP-1. In certain embodiments, the nuclear payload (e.g., PARP inhibitor analog) comprises one or more positively charged moieties (e.g., amino group) which interact with the side chains of Q763, D766, and/or Y896 of PARP-1. In certain embodiments, the nuclear payload (e.g., PARP inhibitor analog) comprises one or more moieties capable of having a binding interaction with E322, D326, I425, S417, H415, E545, and/or Y449 of PARP-2.

In certain embodiments, the nuclear payload comprises rucaparib (AG014699, PF-01367338), or an analog thereof (i.e., rucaparib-containing analogs). Accordingly, provided is a compound of Formula III, or stereoisomer, mixture of stereoisomers, hydrate, solvate, isotopically enriched analog or pharmaceutically acceptable salt thereof:

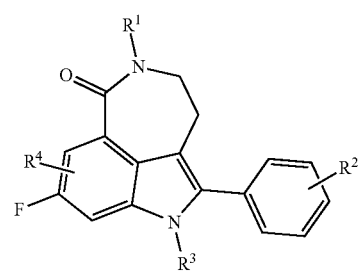

III wherein:
each of $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more $R^{10}$ as valency permits;

m is 1, 2, or 3;

each L is independently a covalent bond or a linking moiety;

each B is independently a nuclear receptor-targeting epitope;

each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)R$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR'S(=O)$_{1-2}$R$^8$, —NR'S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$, $R^3$ and $R^4$ is -L-(B)$_m$.

In certain embodiments, m is 1. In certain embodiments, m is 2. In certain embodiments, only one of $R^1$, $R^2$, $R^3$ and $R^4$ is -L-(B)$_m$.

In certain embodiments, provided is a compound of Formula IIIA, or stereoisomer, mixture of stereoisomers, hydrate, solvate, isotopically enriched analog or pharmaceutically acceptable salt thereof:

IIIA

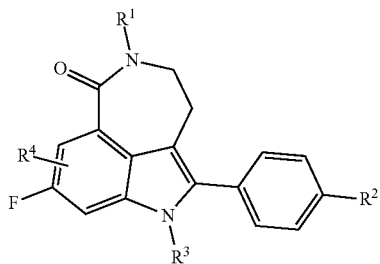

wherein:
each of $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more $R^{10}$ as valency permits;
m is 1, 2, or 3;
each L is independently a covalent bond or a linking moiety;
each B is independently a nuclear receptor-targeting epitope;
each $R^{16}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^8$, —NR$^7$S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and
each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and
each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;
provided that at least one of $R^1$, $R^2$, $R^3$ and $R^4$ is -L-(B)$_m$.

In certain embodiments, provided is a compound of Formula IIIB, or stereoisomer, mixture of stereoisomers, hydrate, solvate, isotopically enriched analog or pharmaceutically acceptable salt thereof:

IIIB

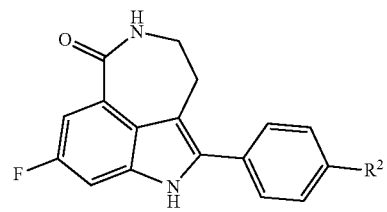

wherein:
$R^2$ is -L-(B)$_m$;
m is 1, 2, or 3;
L is a covalent bond or a linking moiety; and
each B is independently a nuclear receptor-targeting epitope.

In certain embodiments of Formula III, IIIA and IIIB, the nuclear receptor-targeting epitope is a nuclear steroid receptor-targeting epitope. In certain embodiments of Formula III, IIIA and IIIB, m is 1. In certain embodiments of Formula III, IIIA and IIIB, m is 2. In certain embodiments of Formula III and IIIA, only one of $R^1$, $R^2$, $R^3$ and $R^4$ is -L-(B)$_m$.

In certain embodiments, the nuclear payload is derived from talazoparib (BMN-673), or an analog thereof (i.e., talazoparib-containing analogs). Accordingly, provided is a compound of Formula IV, or stereoisomer, mixture of stereoisomers, hydrate, solvate, isotopically enriched analog or pharmaceutically acceptable salt thereof:

IV

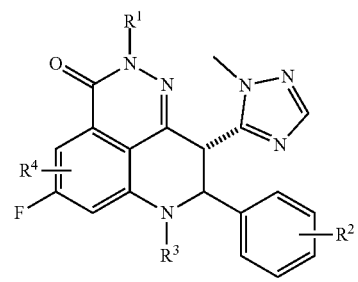

wherein:
each of $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more $R^{10}$ as valency permits;
m is 1, 2, or 3;
each L is independently a covalent bond or a linking moiety;
each B is independently a nuclear receptor-targeting epitope;
each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^8$, —NR$^7$S(=O)$_{1-2}$NR$^7$R$^8$, —NR⁷C(=O)R⁸, —NR⁷C(=O)OR⁸ or —C=NOR⁷, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$, $R^3$ and $R^4$ is -L-(B)$_m$.

In certain embodiments, provided is a compound of Formula IVA, or stereoisomer, mixture of stereoisomers, hydrate, solvate, isotopically enriched analog or pharmaceutically acceptable salt thereof:

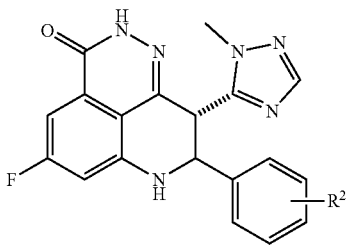

IVA m is 1, 2, or 3;
L is a covalent bond or a linking moiety; and
each B is independently a nuclear receptor-targeting epitope.

In certain embodiments, provided is a compound of Formula IVB, or stereoisomer, mixture of stereoisomers, hydrate, solvate, isotopically enriched analog or pharmaceutically acceptable salt thereof:

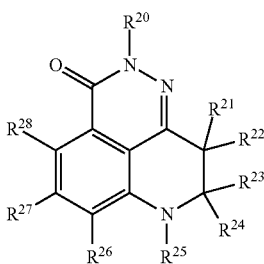

IVB wherein:
$R^{21}$ and $R^{23}$ are each independently selected from hydrogen, halo, hydroxyl, $C_{1-12}$ alkyl, $C_{3-10}$ cycloalkyl, $C_{1-12}$ alkoxy, $C_{1-12}$ alkoxyalkyl; wherein each alkyl, cycloalkyl, alkoxy, alkoxyalkyl are independently optionally substituted with at least one substituent selected from cyano, halo, hydroxyl, nitro, $C_{1-12}$ alkyl, and $C_{3-10}$ cycloalkyl, wherein $R^{23}$ is not hydroxyl;

$R^{22}$ and $R^{24}$ are each independently hydrogen, $C_{1-12}$ alkyl, $C_{2-12}$ alkenyl, $C_{2-12}$ alkynyl, $C_{1-12}$ alkoxy, C(=O)R⁵⁰, —C(=O)OR⁵⁰, —C(=O)N(R⁵⁰)₂, —S(=O)₀₋₂R⁵⁰, —S(=O)₁₋₂N(R⁵⁰)₂, —NR⁵⁰S(=O)₁₋₂R⁵⁰, $C_{3-10}$ cycloalkyl, aryl, heterocyclyl, or heteroaryl, wherein each $C_{1-12}$ alkyl, $C_{2-12}$ alkenyl, $C_{2-12}$ alkynyl, $C_{1-12}$ alkoxy, $C_{3-10}$ cycloalkyl, aryl, heterocyclyl, or heteroaryl may be independently optionally substituted with 1, 2, or 3 $R^{29}$;

$R^{20}$ and $R^{25}$ are each independently selected from the group consisting of hydrogen, $C_{1-12}$ alkyl, $C_{3-10}$ cycloalkyl, $C_{1-12}$ alkoxyalkyl, $C_{1-12}$ haloalkyl, $C_{1-12}$ alkyl-OH and $C_{1-12}$ alkyl-NR⁵¹R⁵²;

$R^{26}$, $R^{27}$, and $R^{28}$ are each independently selected from the group consisting of hydrogen, halo, cyano, nitro, amino, hydroxyl, $C_{1-12}$ alkyl, $C_{2-12}$ alkenyl, $C_{2-12}$ alkynyl, $C_{1-12}$ alkoxy, $C_{3-10}$ cycloalkyl, C(=O)-alkyl, —C(=O)-alkoxy, haloalkoxy, haloalkyl, heteroalkyl; wherein each alkyl, alkenyl, alkynyl, cycloalkyl, heterocyclyl, aryl and heteroaryl of $R^{10}$ are independently optionally substituted with one or more halo, hydroxyl, or $C_{1-12}$ alkyl optionally substituted by oxo, halo, hydroxyl or amino as valency permits;

each $R^{29}$ is selected from hydroxyl, halo, cyano, nitro, —OR⁵¹, —SR⁵¹, —SF₅, —NR⁵¹R⁵², $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R⁵¹, —C(=O)OR⁵¹, —OC(=O)OR⁵¹, —OC(=O)R⁵¹, —C(=O)NR⁵¹R⁵², —OC(=O)NR⁵¹R⁵², —NR⁵¹C(=O)NR⁵¹R⁵², —S(=O)₁₋₂R⁵¹, —S(=O)₁₋₂NR⁵¹R⁵², —NR⁵¹S(=O)₁₋₂R⁵², —NR⁵¹S(=O)₁₋₂NR⁵¹R⁵², —NR⁵¹C(=O)R⁵², —NR⁵¹C(=O)OR⁵² or —C=NOR⁵¹, wherein each alkyl, alkenyl, alkynyl, cycloalkyl, heterocyclyl, aryl and heteroaryl of $R^{29}$ are independently optionally substituted with one or more halo or $C_{1-12}$ alkyl optionally substituted by oxo, halo, hydroxyl or amino as valency permits;

each $R^{50}$ is independently hydrogen, $C_{1-12}$ alkyl, $C_{2-12}$ alkenyl, $C_{2-12}$ alkynyl, $C_{3-10}$ cycloalkyl, aryl, heterocyclyl, or heteroaryl, wherein each alkyl, alkenyl, alkynyl, cycloalkyl, heterocyclyl, aryl and heteroaryl of $R^{50}$ are independently optionally substituted with one or more halo or $C_{1-12}$ alkyl optionally substituted by oxo, halo, hydroxyl or amino as valency permits; and each $R^{51}$ and $R^{52}$ is independently hydrogen, $C_{1-12}$ alkyl, $C_{2-12}$ alkenyl, $C_{2-12}$ alkynyl, $C_{3-10}$ cycloalkyl, heterocyclyl, aryl, or heteroaryl, wherein each alkyl, alkenyl, alkynyl, cycloalkyl, heterocyclyl, aryl and heteroaryl of $R^{51}$ and $R^{52}$ are optionally substituted with oxo, halo, hydroxyl or amino as valency permits; or $R^{51}$ and $R^{52}$ are taken together with the atoms to which they are attached to form heterocyclyl optionally substituted by halo or $C_{1-12}$ alkyl optionally substituted by oxo, halo, hydroxyl or amino;

provided at least one $R^{22}$ or $R^{24}$ comprises a -L-(B)$_m$ group bonded thereto, wherein each L is independently a covalent bond or a linking moiety, each B is independently a nuclear receptor-targeting epitope, and m is 1, 2 or 3.

In the compounds of Formula VIB, at least one $R^{22}$ or $R^{24}$ comprises a substituent having a -L-(B)$_m$ group bonded thereto. As such, it should be understood that the -L-(B)$_m$ group is not bound directly to the tricyclic core.

In certain embodiments of Formula IV, IVA and IVB the nuclear receptor-targeting epitope is a nuclear steroid receptor-targeting epitope. In certain embodiments of Formula IV, IVA and IVB, m is 1. In certain embodiments of Formula IV, IVA and IVB, m is 2. In certain embodiments of Formula IV, only one of $R^1$, $R^2$, $R^3$ and $R^4$ is -L-(B)$_m$.

In certain embodiments, the nuclear payload is derived from olaparib (AZD-2281), or an analog thereof (i.e., olaparib-containing analogs). In certain embodiments, the compound is of Formula V, or stereoisomer, mixture of stereoisomers, hydrate, solvate, isotopically enriched analog or pharmaceutically acceptable salt thereof:

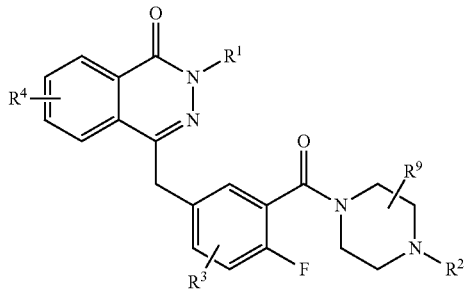

V wherein:
each $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more $R^{10}$ as valency permits;
m is 1, 2, or 3;
each L is independently a covalent bond or a linking moiety;
each B is independently a nuclear receptor-targeting epitope;
each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^8$, —NR$^7$S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and
each $R^5$ and $R^6$ is independently hydrogen, deuterium, $C_{1-12}$ alkyl or $C_{5-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino;
each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;
$R^9$ is hydrogen or $R^2$; and
provided that at least one $R^1$, $R^2$, $R^3$ and $R^4$ is -L-(B)$_m$.

In certain embodiments, provided is a compound of Formula VA, or stereoisomer, mixture of stereoisomers, hydrate, solvate, isotopically enriched analog or pharmaceutically acceptable salt thereof:

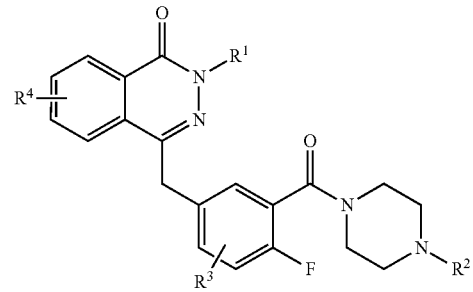

VA wherein:
each of $R^1$, $R^2$, $R^3$ and $R^4$ is independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of $R^1$, $R^2$, $R^3$ and $R^4$ are independently optionally substituted with one or more $R^{10}$ as valency permits;
m is 1, 2, or 3;
each L is independently a covalent bond or a linking moiety;
each B is independently a nuclear receptor-targeting epitope;
each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^8$, —NR$^7$S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and
each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and
each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;
provided that at least one of $R^1$, $R^2$, $R^3$ and $R^4$ is -L-(B)$_m$.

In certain embodiments, provided is a compound of Formula VB, or stereoisomer, mixture of stereoisomers, hydrate, solvate, isotopically enriched analog or pharmaceutically acceptable salt thereof:

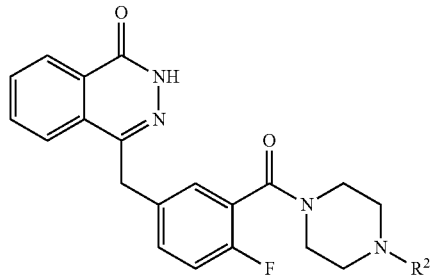

VB wherein:
R² is -L-(B)$_m$;
m is 1, 2, or 3;
L is a covalent bond or a linking moiety; and
each B is independently a nuclear receptor-targeting epitope.

In certain embodiments, provided is a compound of Formula VC, or stereoisomer, mixture of stereoisomers, hydrate, solvate, isotopically enriched analog or pharmaceutically acceptable salt thereof:

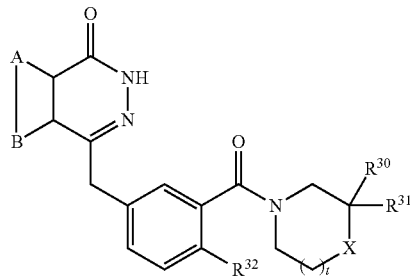

VC wherein:
A and B together represent an optionally substituted, fused aromatic ring:
R³⁰ and R³¹ are independently hydrogen or C$_{1-12}$ alkyl, or when X is —CR³³R³⁴, R³⁰, R³¹, R³³ and R³⁴ together with the carbon atoms to which they are attached, may form an optionally substituted fused aromatic ring;
R³² is hydrogen or halo;
X is —NR³³ or —CR³³R³⁴; where if X is —NR³³ then t is 1 or 2; and if X is —CR³³R³⁴ then t is 1;
R³³ is hydrogen, optionally substituted C$_{1-12}$ alkyl, aryl, heterocyclyl, —C(=O)R⁵⁰, —C(=O)OR⁵⁰, —C(=O)N(R⁵⁰)₂, —S(=O)$_{0-2}$R⁵⁰, —S(=O)$_{1-2}$N(R⁵⁰)₂, —NR⁵⁰S(=O)$_{1-2}$R⁵⁰;
R³⁴ is hydrogen, hydroxyl, or amino;
or R³³ and R³⁴ may together form a C$_{3-10}$ cycloalkyl or heterocyclyl group; and
each R⁵⁰ is independently hydrogen, C$_{1-12}$ alkyl, C$_{2-12}$ alkenyl, C$_{2-12}$ alkynyl, C$_{3-10}$ cycloalkyl, aryl, heterocyclyl, or heteroaryl, wherein each alkyl, alkenyl, alkynyl, cycloalkyl, aryl and heteroaryl of R⁵⁰ are independently optionally substituted with one or more halo or C$_{1-12}$ alkyl optionally substituted by oxo, halo, hydroxyl or amino as valency permits;
provided at least one R³⁰, R³¹, R³³ or R³⁴ group comprises a -L-(B)$_m$ group bonded thereto, wherein each L is independently a covalent bond or a linking moiety, each B is independently a nuclear receptor-targeting epitope, and m is 1, 2 or 3.

In certain embodiments of Formula V, VA, VB, and VC, the nuclear receptor-targeting epitope is a nuclear steroid receptor-targeting epitope. In certain embodiments of Formula V, VA, VB, and VC, m is 1. In certain embodiments of Formula V, VA, VB, and VC, m is 2. In certain embodiments of Formula V and VA, only one of R¹, R², R³ and R⁴ is -L-(B)$_m$.

In certain embodiments, the nuclear payload is derived from veliparib (ABT-888), or an analog thereof (i.e., veliparib-containing analogs). Also provided is a compound of Formula VI, or stereoisomer, mixture of stereoisomers, hydrate, solvate, isotopically enriched analog or pharmaceutically acceptable salt thereof:

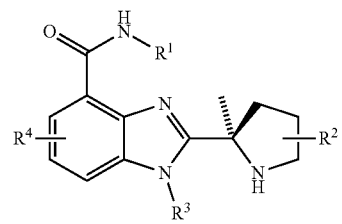

VI wherein:
each of R¹, R², R³ and R⁴ is independently -L-(B)$_m$, hydrogen, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R⁵, —C(=O)OR⁵, —OC(=O)R⁵, —C(=O)NR⁵R⁶, —NR⁵C(=O)R⁶, —S(=O)$_{1-2}$R⁵, —S(=O)$_{1-2}$NR⁵R⁶, —NR⁵S(=O)$_{1-2}$R⁶ or —C=NOR⁵, wherein each alkyl, alkenyl, alkynyl, cycloalkyl, heterocyclyl, aryl and heteroaryl of R¹, R², R³ and R⁴ are independently optionally substituted with one or more R¹⁰ as valency permits;
m is 1, 2, or 3;
each L is independently a covalent bond or a linking moiety;
each B is independently a nuclear receptor-targeting epitope;
each R¹⁰ is independently halo, cyano, nitro, —OR⁷, —SR⁷, —SF₅, —NR⁷R⁸, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R⁷, —C(=O)OR⁷, —OC(=O)R⁷, —OC(=O)R⁷, —C(=O)NR⁷R⁸, —OC(=O)NR⁷R⁸, —NR⁷C(=O)NR⁷R⁸, —S(=O)$_{1-2}$R⁷, —S(=O)$_{1-2}$NR'R⁸, —NR⁷S(=O)$_{1-2}$R⁸, —NR⁷S(=O)$_{1-2}$NR⁷R⁸, —NR⁷C(=O)R⁸, —NR⁷C(=O)OR⁸ or —C=NOR⁷, wherein each alkyl, alkenyl, alkynyl, cycloalkyl, heterocyclyl, aryl and heteroaryl of R¹⁰ are independently optionally substituted with one or more halo or C$_{1-12}$ alkyl optionally substituted by oxo, halo, hydroxyl or amino as valency permits; and
each R⁵ and R⁶ is independently hydrogen, deuterium, C$_{1-12}$ alkyl or C$_{3-12}$ cycloalkyl, optionally substituted with oxo, halo, hydroxyl or amino as valency permits;
or R⁵ and R⁶ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$, $R^3$ and $R^4$ is -L-(B)$_m$.

In certain embodiments, provided is a compound of Formula VIA, or stereoisomer, mixture of stereoisomers, hydrate, solvate, isotopically enriched analog or pharmaceutically acceptable salt thereof:

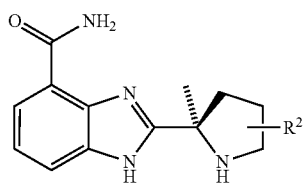

VIA wherein:
$R^2$ is -L-(B)$_m$;
m is 1, 2, or 3;
L is a covalent bond or a linking moiety; and
each B is independently a nuclear receptor-targeting epitope.

In certain embodiments of Formula VI and VIA, the nuclear receptor-targeting epitope is a nuclear steroid receptor-targeting epitope. In certain embodiments of Formula VI and VIA, m is 1. In certain embodiments of Formula VI and VIA, m is 2. In certain embodiments of Formula V, only one of $R^1$, $R^2$, $R^3$ and $R^4$ is -L-(B)$_m$.

In certain embodiments, the nuclear payload comprises CC-115 or an analog thereof (CC-115-containing analogs). Also provided is a compound of Formula VII or stereoisomer, mixture of stereoisomers, hydrate, solvate, isotopically enriched analog or pharmaceutically acceptable salt thereof:

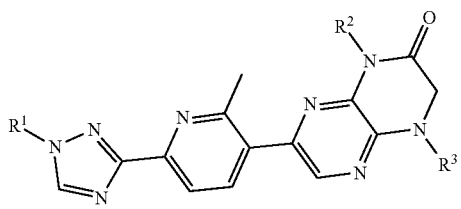

VII each of $R^1$, $R^2$ and $R^3$ are independently -L-(B)$_m$, hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^5$, —C(=O)OR$^5$, —OC(=O)R$^5$, —C(=O)NR$^5$R$^6$, —NR$^5$C(=O)R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of R$^1$, R$^2$ and R$^3$ are independently optionally substituted with one or more R$^{10}$ as valency permits;

each L is independently a covalent bond or a linking moiety;

each B is independently a nuclear receptor-targeting epitope;

each $R^{10}$ is independently halo, cyano, nitro, —OR$^7$, —SR$^7$, —SF$_5$, —NR$^7$R$^8$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)R$^7$, —C(=O)OR$^7$, —OC(=O)OR$^7$, —OC(=O)R$^7$, —C(=O)NR$^7$R$^8$, —OC(=O)NR$^7$R$^8$, —NR$^7$C(=O)NR$^7$R$^8$, —S(=O)$_{1-2}$R$^7$, —S(=O)$_{1-2}$NR$^7$R$^8$, —NR$^7$S(=O)$_{1-2}$R$^8$, —NR$^7$S(=O)$_{1-2}$NR$^7$R$^8$, —NR$^7$C(=O)R$^8$, —NR$^7$C(=O)OR$^8$ or —C=NOR$^7$, wherein each alkyl, alkenyl, alkynyl, cycloalkyl, heterocyclyl, aryl and heteroaryl of R$^{10}$ are independently optionally substituted with one or more halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino; and each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino;

provided that at least one of $R^1$, $R^2$ and $R^3$ is -L-(B)$_m$.

In certain embodiments, provided is a compound of Formula VIIA, or stereoisomer, mixture of stereoisomers, hydrate, solvate, isotopically enriched analog or pharmaceutically acceptable salt thereof:

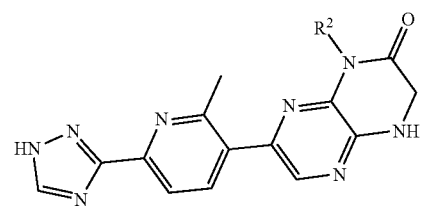

VIIA wherein:
$R^2$ is -L-(B)$_m$;
m is 1, 2, or 3;
L is a covalent bond or a linking moiety; and
each B is independently a nuclear receptor-targeting epitope.

In certain embodiments of Formula VII and VIIA, the nuclear receptor-targeting epitope is a nuclear steroid receptor-targeting epitope. In certain embodiments of Formula VII and VIIA, m is 1. In certain embodiments of Formula VII and VILA, m is 2. In certain embodiments of Formula VII, only one of $R^1$, $R^2$, $R^3$ and $R^4$ is -L-(B)$_m$.

In certain embodiments of a Formula disclosed herein, each $R^5$ and $R^6$ is independently hydrogen, deuterium, or $C_{1-12}$ alkyl optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino.

In certain embodiments, the nuclear payload binds DNA-dependent protein kinase (DNA-PK). In certain embodiments, the nuclear payload is an inhibitor of DNA-dependent protein kinase (DNA-PK). In certain embodiments, the nuclear payload is derived from AZD-1775 (MK-1775, Adavosertib), SCH900776 (MK-8776), AZD0156, M6620 (VX-970, VE-822, Berzosertib), AZD6738, or CC-115, or an analog thereof. In certain embodiments, provided is a compound of formula:

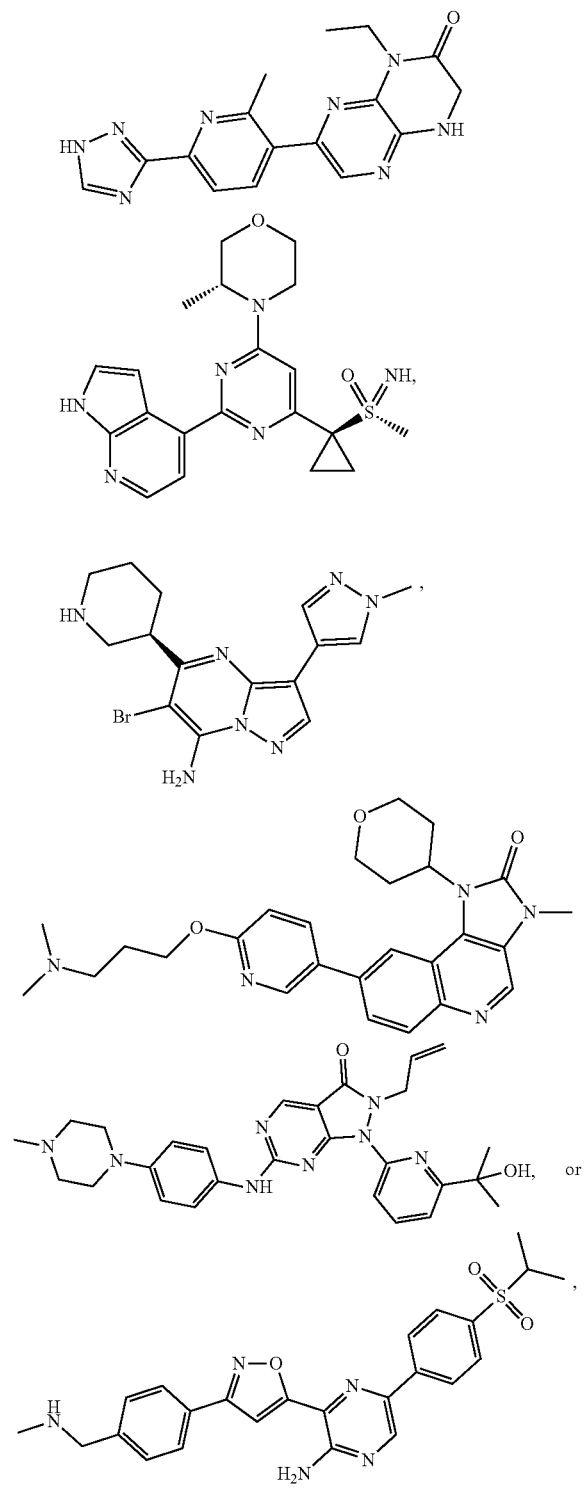

wherein one hydrogen atom is replaced by -L-(B)$_m$;
wherein
m is 1, 2, or 3;
L is a covalent bond or a linking moiety; and
each B is independently a nuclear receptor-targeting epitope.

In certain embodiments, the hydrogen atom replaced by -L-(B)$_m$ is on a heteroatom. In certain embodiments, the hydrogen atom replaced by -L-(B)$_m$ is on a nitrogen. In certain embodiments, the hydrogen atom replaced by -L-(B)$_m$ is on an oxygen. In certain embodiments, the hydrogen atom replaced by -L-(B)$_m$ is on a carbon. In certain embodiments, the nuclear receptor-targeting epitope is a nuclear steroid receptor-targeting epitope. In certain embodiments, m is 1. In certain embodiments, m is 2.

In certain embodiments, provided is a compound of Formula:

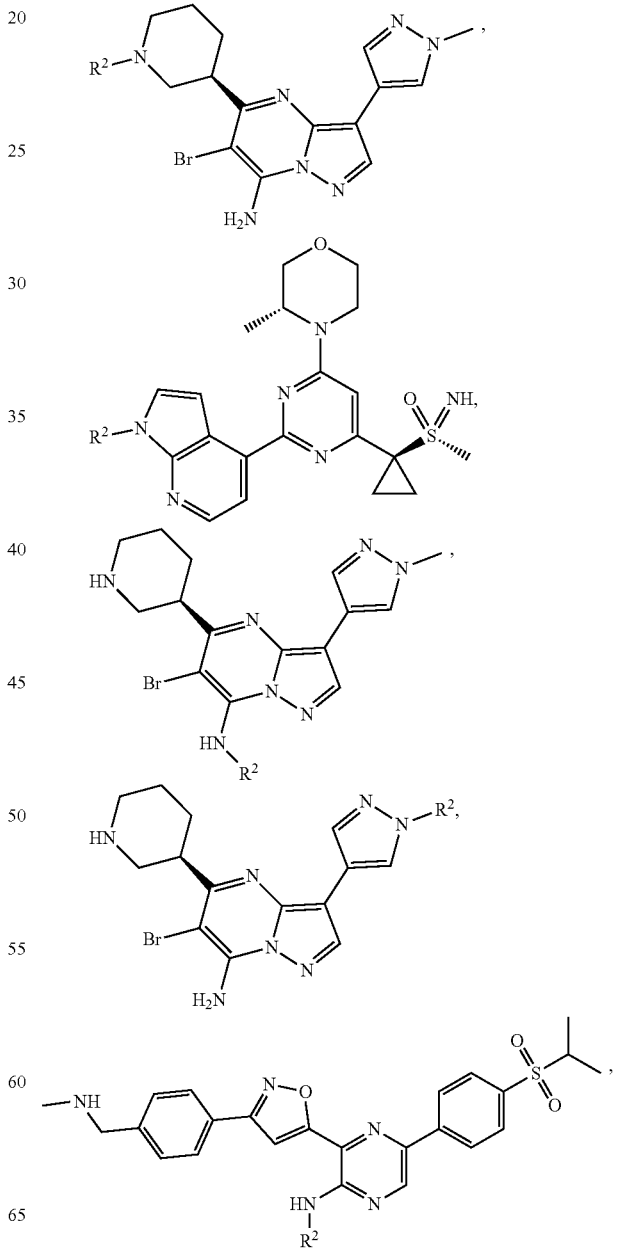

-continued

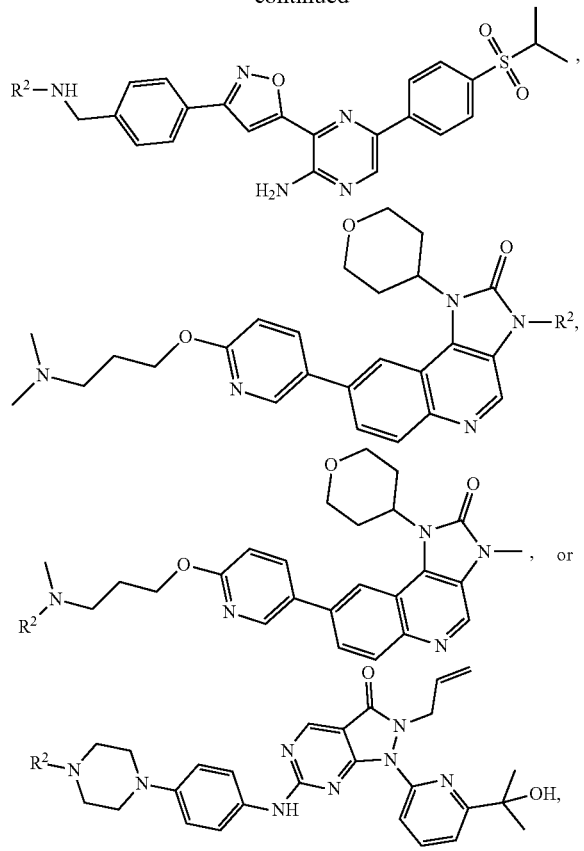

wherein:
R² is -L-(B)ₘ;
m is 1, 2, or 3;
L is a covalent bond or a linking moiety; and
each B is independently a nuclear receptor-targeting epitope.

In certain embodiments of any compound, Formula or embodiment disclosed herein, the nuclear receptor-targeting epitope is a nuclear steroid receptor-targeting epitope. In certain embodiments, m is 1. In certain embodiments, m is 2.

Nuclear Receptor-Targeting Epitopes

As used herein, "nuclear receptor-targeting epitope" refers to the portion of the compound described herein (e.g., the "B" moiety of Formula I or Formula II) which portion is derived from a nuclear targeting agent as disclosed herein and interacts with a ligand-binding domain of the target nuclear receptor, i.e., the portion of the compound which drives a ligand-binding interaction. The nuclear receptor-targeting epitope serves to associate the compound with a target nuclear receptor, e.g. a nuclear steroid receptor, facilitate the localization of compound to nuclear steroid receptor-expressing cells, and translocate the nuclear payload from the cytosol to nucleus, allowing the compound to accumulate in the nucleus. The level of accumulation can be controlled by selecting the appropriate nuclear receptor-targeting epitope. For example, the compounds described herein can accumulate in the nucleus to varying degrees, high in the case of a full agonist (e.g., dihydrotestosterone (DHT)), moderate in the case of a partial agonist (e.g., bicalutamide), and low, in the case of antagonists (e.g., enzalutamide), through nuclear translocation of the nuclear steroid receptor which happens, following epitope binding to the receptor.

The steroid receptor target can be any steroid receptor, including, but not limited to, those which are over-expressed on cancer cells. In certain embodiments, at least one nuclear steroid receptor-targeting epitope is capable of binding to a ligand binding domain of a nuclear steroid receptor, such as a ligand binding domain on an estrogen receptor, glucocorticoid receptor, progesterone receptor or androgen receptor.

Exemplary nuclear steroid receptor-targeting epitopes include those derived from an androgen receptor agonist, an androgen receptor antagonist, a selective androgen-receptor modulator (SARM), an estrogen receptor agonist, an estrogen receptor antagonist, a selective estrogen receptor modulator (SERM), a glucocorticoid receptor antagonist, a glucocorticoid receptor agonist, a selective glucocorticoid receptor modulator (SGRM), a progesterone receptor antagonist, a progesterone receptor agonist, a selective progesterone receptor modulator (SPRM), or a combination thereof. The nuclear steroid receptor-targeting epitopes are typically capable of binding to a nuclear steroid receptor with an $IC_{50}$ of less than about 500 nM, or less than about 400 nM, or less than about 300 nM, or less than about 200 nM, or less than about 100 nM, or with an $EC_{50}$ of less than about 1 μM, or less than about 900 nM, or less than about 800 nM, or less than about 700 nM, or less than about 600 nM, or less than about 500 nM, or less than about 400 nM, or less than about 3400 nM, or less than about 200 nM, or less than about 100 nM.

In certain embodiments, the nuclear steroid receptor-targeting epitope is an agonist at the androgen receptor. In certain embodiments, the nuclear steroid receptor-targeting epitope is an antagonist at the androgen receptor.

In certain embodiments, the nuclear steroid receptor-targeting epitope is steroidal (e.g., dihydrotestosterone). In certain embodiments, the nuclear steroid receptor-targeting epitope is non-steroidal (e.g., enzalutamide, apalutamide and bicalutamide).

The analogs are derived from the known nuclear steroid receptor-targeting epitope described herein and are modified to be conjugated to at least one nuclear steroid payload, optionally via a linking moiety. The analogs, even after modification to arrive at the compounds described herein, maintain biological activity, which is comparable to that observed in the original, unmodified nuclear steroid receptor-targeting epitope. In certain embodiments, the analogs exhibit a binding activity or inhibition which is at least about 98%, about 95%, about 90%, about 85%, about 80%, about 75%, about 70%, about 65%, about 60%, about 55%, or about 50% of that observed in the original, unmodified nuclear steroid receptor-targeting epitope.

In certain embodiments, the analogs are derived from a known nuclear receptor-targeting epitope, such as a known nuclear steroid receptor-targeting epitope. In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. Exemplary non-hydrogen atoms include, but are not limited to, —CH₃, —OH, =O, and —NHS. In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. In certain embodiments, one hydrogen atom bound to a heteroatom (e.g., N, O, or S) of the original, unmodified nuclear receptor-targeting compound (i.e., a known nuclear steroid receptor-targeting compound) is replaced by a covalent bond to the nuclear payload, optionally via a linking moiety.

In certain embodiments, the nuclear steroid receptor-targeting epitope is an androgen receptor-targeting epitope. As used herein, the term "androgen receptor-targeting epitope" is intended to refer to the portion of the compound which binds to an androgen receptor agonist or androgen receptor antagonist (including partial androgen receptor agonists or partial androgen receptor antagonists) and which is capable of shuttling a compound from the cytoplasm into the nucleus of a cell. The "androgen receptor" (AR), also known as NR3C4 (nuclear receptor subfamily 3, group C, member 4), is a type of nuclear receptor that, when activated by binding an androgen receptor binder (e.g., an androgenic hormone such as testosterone, or dihydrotestosterone) in the cytoplasm, is capable of translocating the androgenic hormone into the nucleus.

Exemplary androgen receptor-targeting epitopes which can be used in the compounds described herein include, but are not limited to, an androgen receptor agonist, a selective androgen-receptor modulator (SARM) (e.g., enobosarm), an androgen receptor antagonist (e.g., bicalutamide, flutamide, nilutamide, or enzalutamide), a selective estrogen receptor modulator (SERM) (e.g., tamoxifen, toremifene, or raloxifene), an estrogen receptor antagonist (e.g., fulvestrant), a progestin (e.g., megestrol acetate), an estrogen (e.g., estramustine), ketoconazole, abiraterone, darolutamide, or an analog thereof.

In certain embodiments, the nuclear steroid receptor-targeting epitope is a selective androgen receptor modulator (SARM). In certain embodiments, the compound comprises at least one nuclear steroid receptor-targeting epitope independently comprises an epitope derived from testosterone, a testosterone ester (e.g., testosterone enanthate, propionate, cypionate, etc., or an analog thereof), enobosarm, BMS-564929, PS178990, LGD-4033 (ligandrol), LGD-2941, AC-262,356, JNJ-28330835, JNJ-37654032, JNJ-26146900, LGD-2226, LGD-3303, LGD-121071, LG-120907, S-40503, S-23, RAD-140, acetothiolutamide, andarine (S-4), LG-121071, TFM-4AS-1, YK-11, MK-0773 (PF-05314882), GSK2849466, GSK2881078, GSK8698, GSK4336, ACP-10.5, TT701, LY24.52473, 1-(2-hydroxy-2-methyl-3-phenoxypropanoyl)-indoline-4-carbonitrile-derivatives (J Med Chem. 2014, 57(6), 2462-71), or an analog thereof.

In certain embodiments, a single atom on the nuclear receptor-targeting epitope as disclosed herein is replaced for attachment to the remainder of the compound (e.g., the moiety A-L- of Formula I and Formula II). In certain embodiments, a halogen atom on a nuclear receptor-targeting epitope disclosed herein is replaced for attachment to the remainder of the compound. In certain embodiments, a hydrogen atom on a nuclear receptor-targeting epitope disclosed herein is replaced for attachment to the remainder of the compound. In certain embodiments, the hydrogen atom is on a heteroatom. In certain embodiments, the hydrogen atom is on a nitrogen. In certain embodiments, the hydrogen atom is on an oxygen. In certain embodiments, the hydrogen atom is on a carbon.

In certain embodiments, the moiety -B of Formula I or Formula II comprises at least one nuclear receptor-targeting epitope derived from:

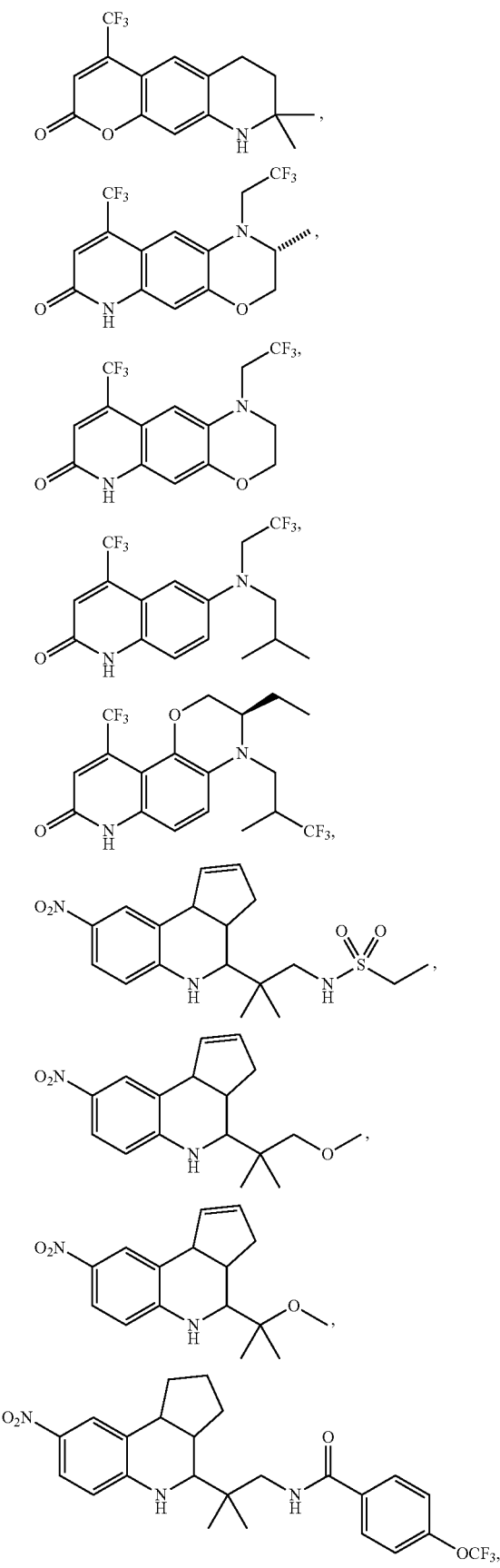

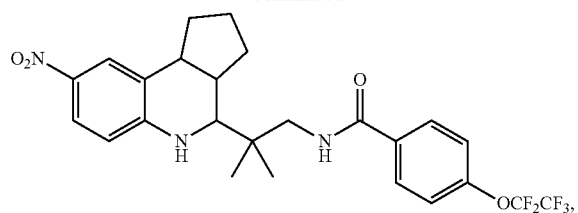
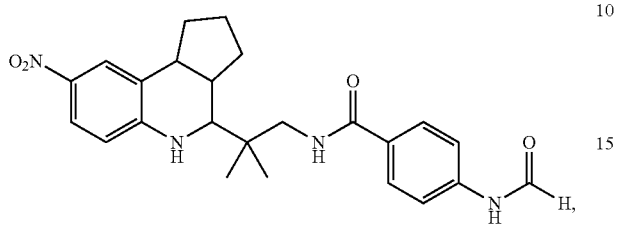
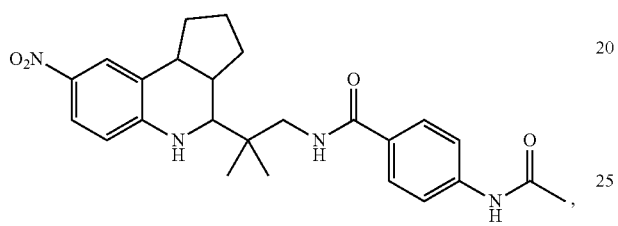
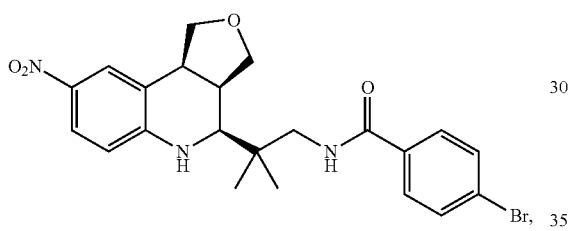
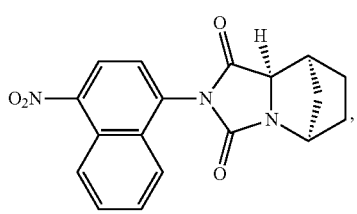
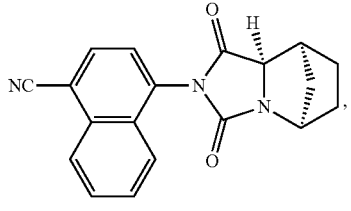
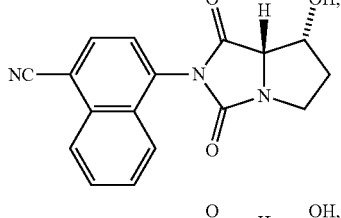
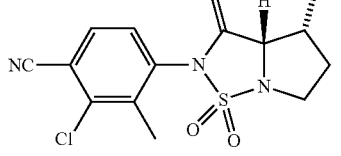
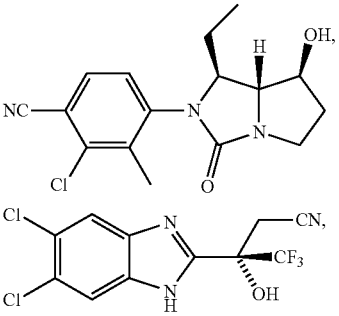
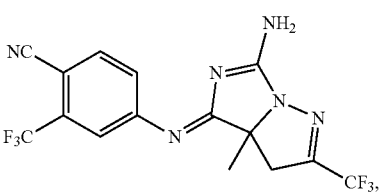
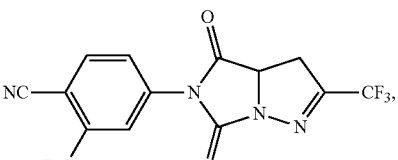
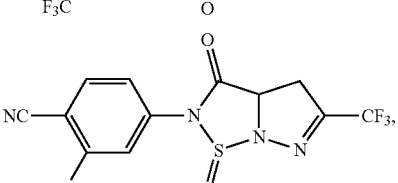
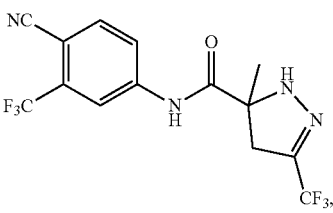
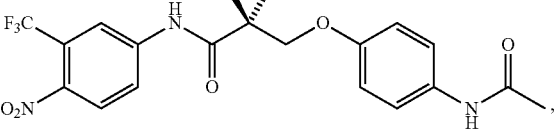
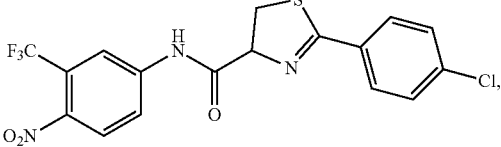
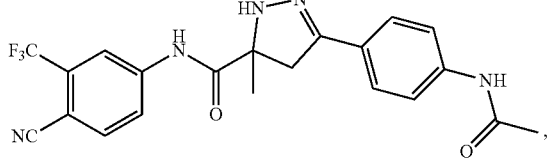

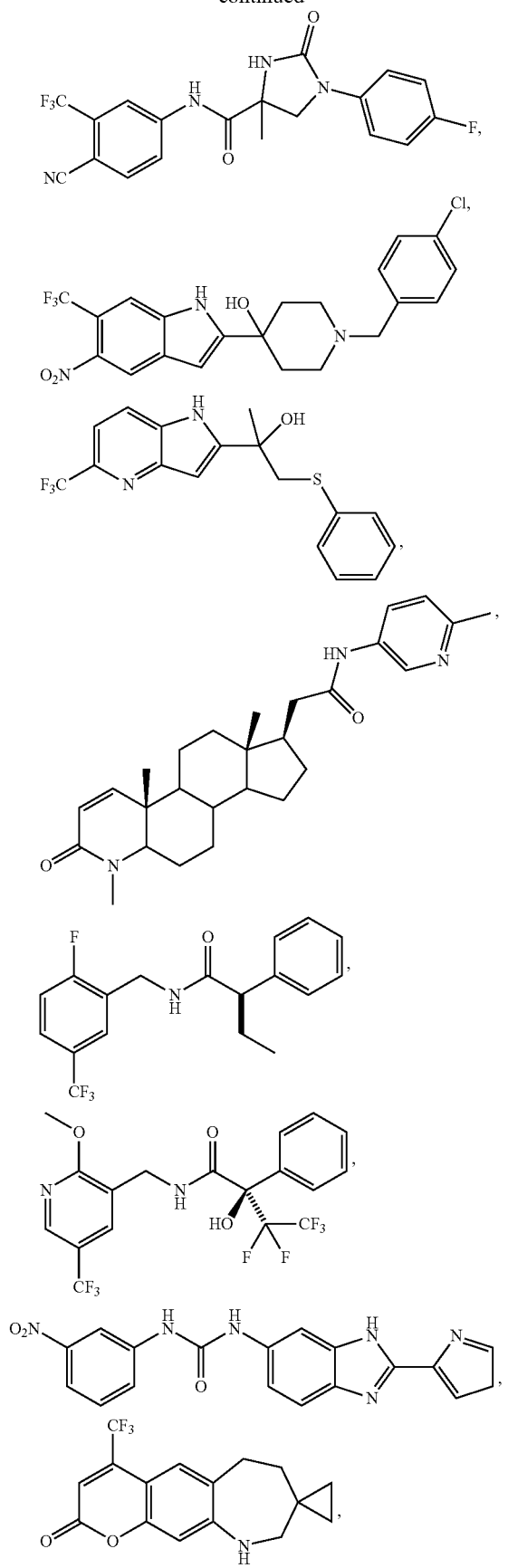
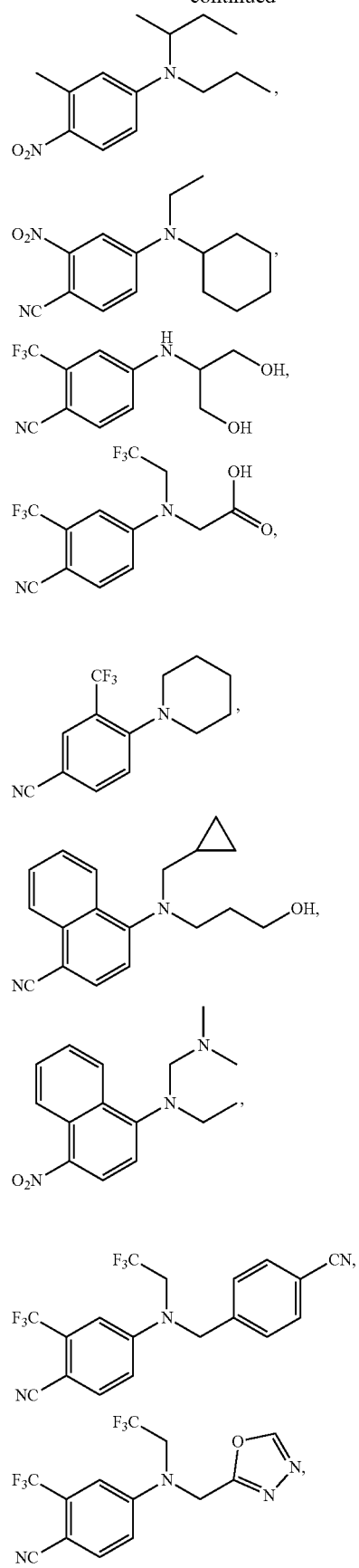

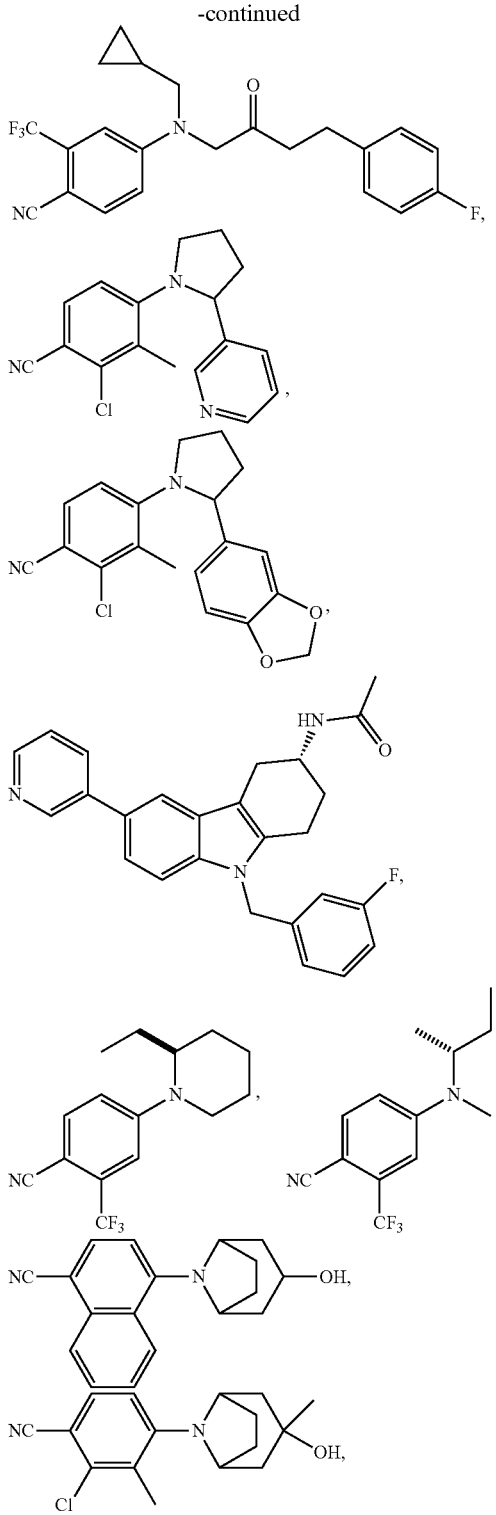

or a stereoisomer or a mixture of stereoisomers thereof or an analog thereof.

These and other selective androgen receptor modulator (SARMs) which can be used as a nuclear steroid receptor-targeting epitope in the compounds described herein can be found in U.S. Pat. Nos. 6,462,038, 6,777,427, WO2001/027086, WO2004/013104, WO2004/000816, WO2004/0113309, US2006/0211756, US2006/0063819, US2005/245485, US2005/250741, US2005/277681, WO2006/060108, WO2004/041277, WO2003/034987, US2006/0148893, US2006/0142387, WO2005/000795, WO2005/085185, WO2006/133216, WO2006/044707, WO2006/124447, WO2007/002181, WO2005/108351, WO2005/115361, and US2006/0160845.

In certain embodiments, the nuclear steroid receptor-targeting epitope is a selective estrogen receptor modulator (SERM). In certain embodiments, the compound comprises at least one nuclear steroid receptor-targeting epitope independently comprises an epitope derived from anordrin, bazedoxifene, broparestrol (Acnestrol), clomifene (Clomid), cyclofenil (Sexovid), lasofoxifene (Fablyn), ormeloxifene (Centron, Novex, Novex-DS, Sevista), ospemifene (Osphena, deaminohydroxytoremifene), raloxifene (Evista), tamoxifen (Nolvadex), toremifene (Fareston; 4-chlorotamoxifen), acolbifene, afimoxifene (4-hydroxytamoxifen; metabolite of tamoxifen), elacestrant, enclomifene ((E)-clomifene), endoxifen (4-hydroxy-N-desmethyltamoxifen; metabolite of tamoxifen), zuclomifene ((Z)-clomifene), bazedoifene, arzoxifene, brilanestrant, clomifenoxide (clomiphene N-oxide; metabolite of clomifene), droloxifene (3-hydroxytamoxifen), etacstil, fispemifene, GW-7604 (4-hydroxyetacstil), idoxifene (pyrrolidino-4-iodotamoxifen), levormeloxifene ((L)-ormeloxifene), miproxifene, nafoxidine, nitromifene (CI-628), panomifene, pipendoxifene (ERA-923), trioxifene, keoxifene, LY117018, onapristone, fareston (toremifine citrate) or zindoxifene (D-16726), or an analog thereof.

In certain embodiments, the SERM is classified structurally as a triphenylethylene (tamoxifen, clomifene, toremifene, droloxifene, idoxifene, ospemifene, fispemifene, afimoxifene, etc., or an analog thereof), a benzothiophene (raloxifene, arzoxifene, etc., or an analog thereof), an indole (bazedoxifene, zindoxifene, pipendoxifene, etc., or an analog thereof), a tetrahydronaphthalene (lasofoxifene, nafoxidine, etc., or an analog thereof), or a benzopyran (acolbifene, ormeloxifene, levormeloxifene, etc., or an analog thereof).

In certain embodiments, the nuclear steroid receptor-targeting epitope is a selective estrogen receptor downregulator (SERD). In certain embodiments, the compound comprises at least one nuclear steroid receptor-targeting epitope independently comprises an epitope derived from fulvestrant, ARN-810, GW5638, or GW7604.

In certain embodiments, the nuclear steroid receptor-targeting epitope is a selective progesterone receptor modulator (SPRM). In certain embodiments, the compound comprises at least one nuclear steroid receptor-targeting epitope independently comprises an epitope derived from ulipristal acetate, asoprisnil (J867), mifepristone, telapristone (CDB-4124, Proellex, Progenta), or an analog thereof.

In certain embodiments, the compound comprises at least one nuclear steroid receptor-targeting epitope independently comprises an epitope derived from estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof.

In certain embodiments, at least one nuclear steroid receptor-targeting epitope is an androgen receptor-targeting epitope, and comprises:

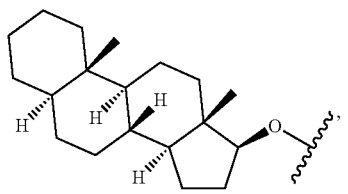
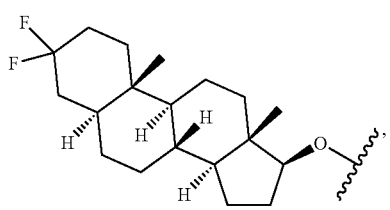
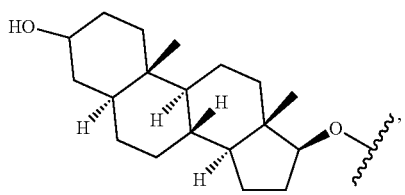
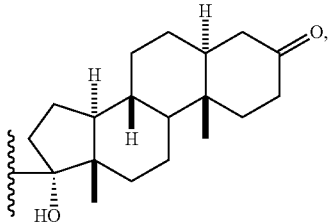
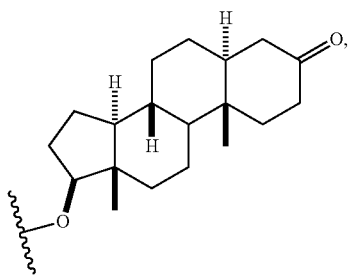
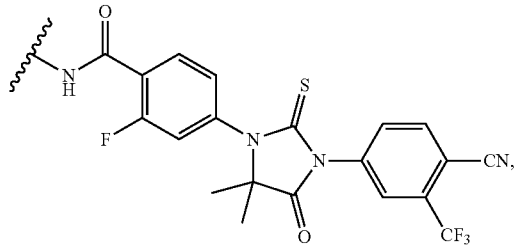
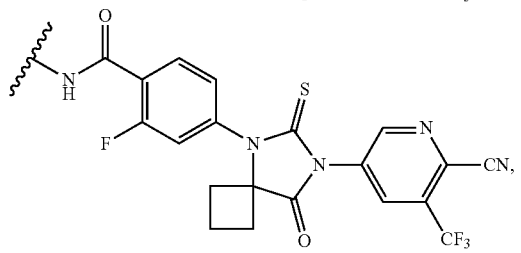
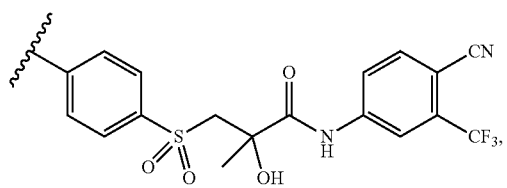
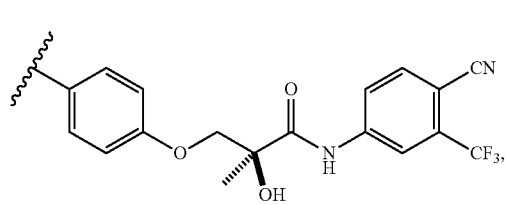
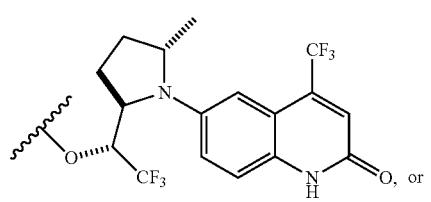
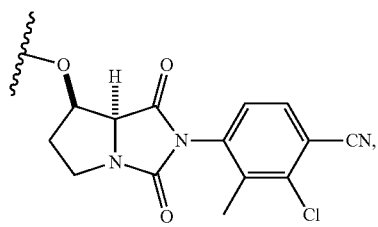
or a stereoisomer or a mixture of stereoisomers thereof or an analog thereof, where the wavy line indicates the point of attachment to the linking moiety or nuclear payload.
In certain embodiments, at least one nuclear steroid receptor-targeting epitope is an estrogen receptor-targeting epitope, and comprises:
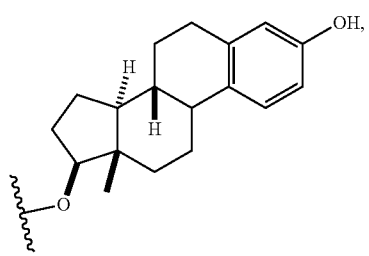
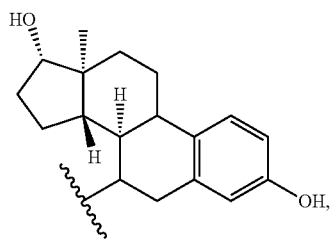

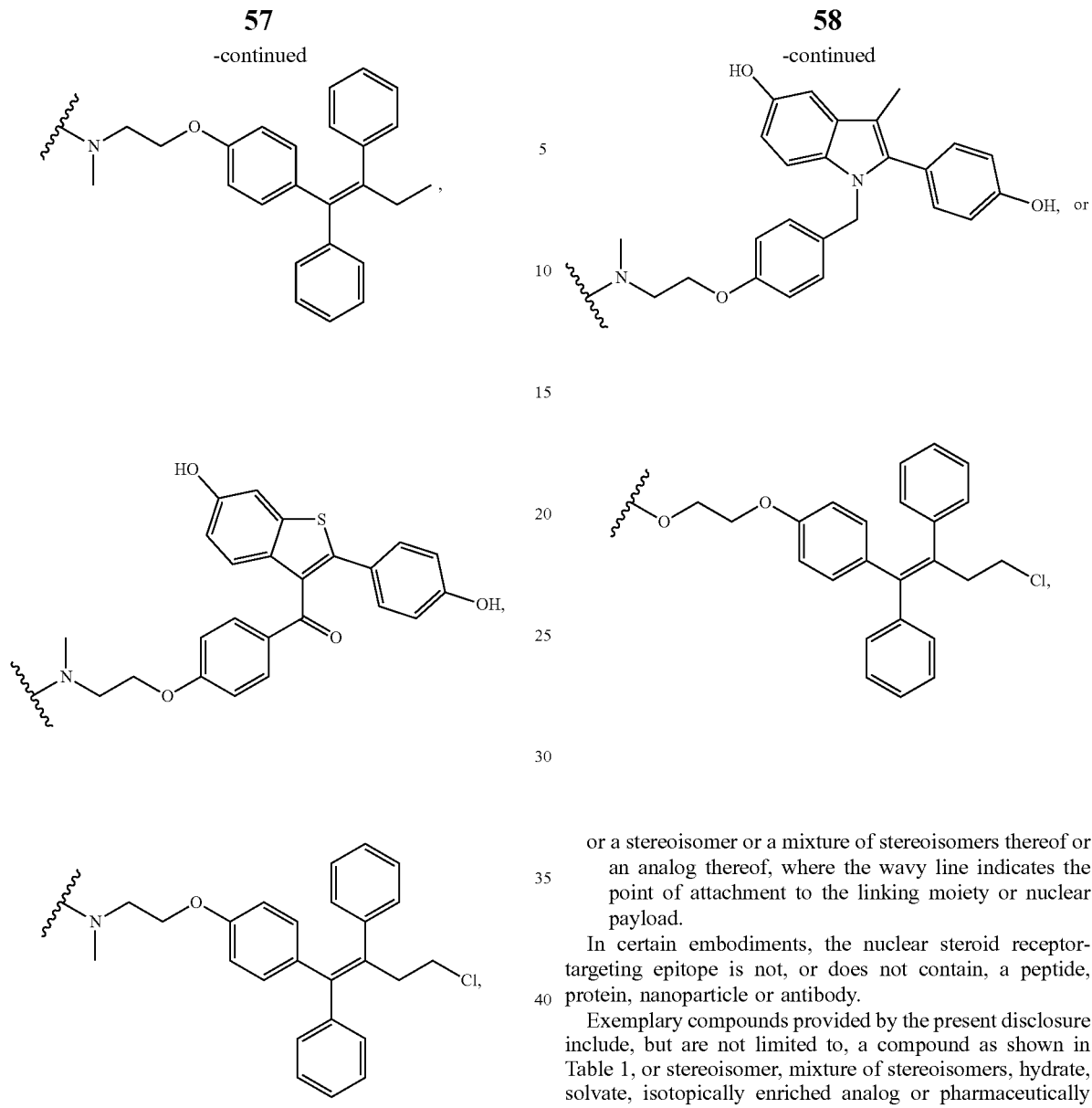

or a stereoisomer or a mixture of stereoisomers thereof or an analog thereof, where the wavy line indicates the point of attachment to the linking moiety or nuclear payload.

In certain embodiments, the nuclear steroid receptor-targeting epitope is not, or does not contain, a peptide, protein, nanoparticle or antibody.

Exemplary compounds provided by the present disclosure include, but are not limited to, a compound as shown in Table 1, or stereoisomer, mixture of stereoisomers, hydrate, solvate, isotopically enriched analog or pharmaceutically acceptable salt thereof.

TABLE 1

| No. | Structure |
|---|---|
| 1.1 | 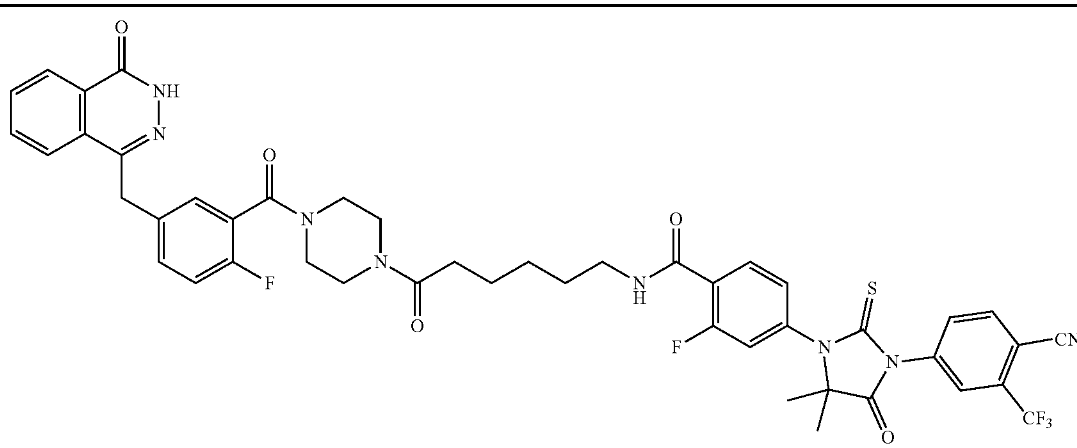 |

TABLE 1-continued

| No. | Structure |
| --- | --- |
| 1.2 | 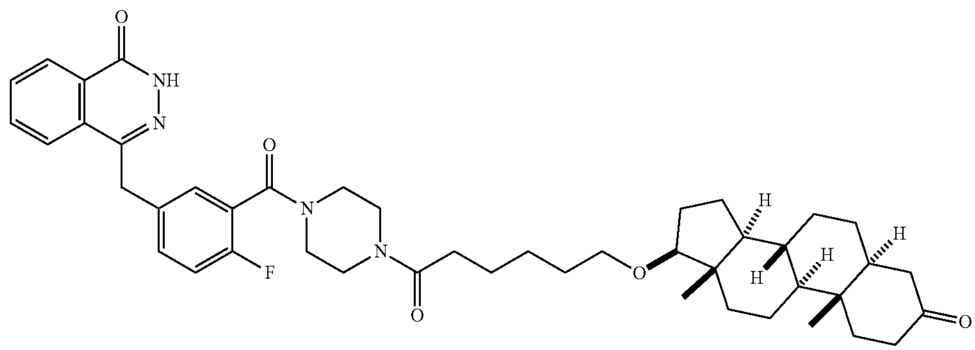 |
| 1.3 | 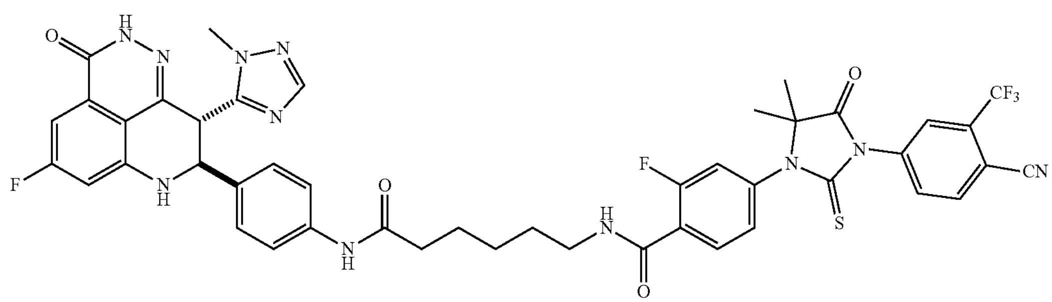 [SMILES: Cn1ncnc1[C@H]1c2n[nH]c(=O)c3cc(F)cc(c23)N[C@@H]1c1ccc(NC(=O)CCCCCNC(=O)c2ccc(N3C(=S)N(c4ccc(C#N)c(C(F)(F)F)c4)C(=O)C3(C)C)cc2F)cc1] |
| ent. 1.3 | 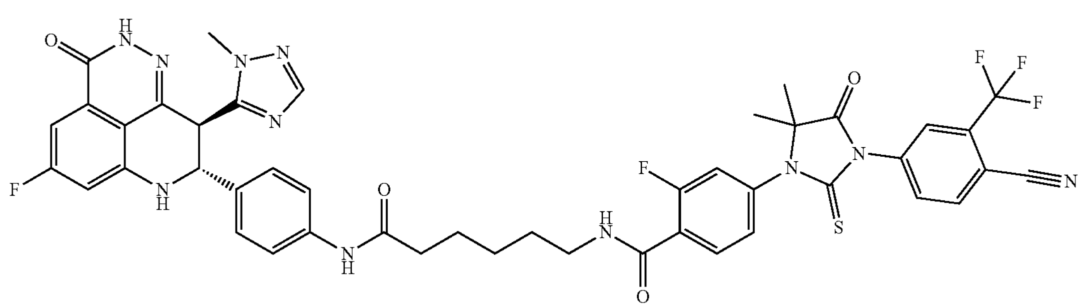 [SMILES: Cn1ncnc1[C@@H]1c2n[nH]c(=O)c3cc(F)cc(c23)N[C@H]1c1ccc(NC(=O)CCCCCNC(=O)c2ccc(N3C(=S)N(c4ccc(C#N)c(C(F)(F)F)c4)C(=O)C3(C)C)cc2F)cc1] |
| 1.4 | 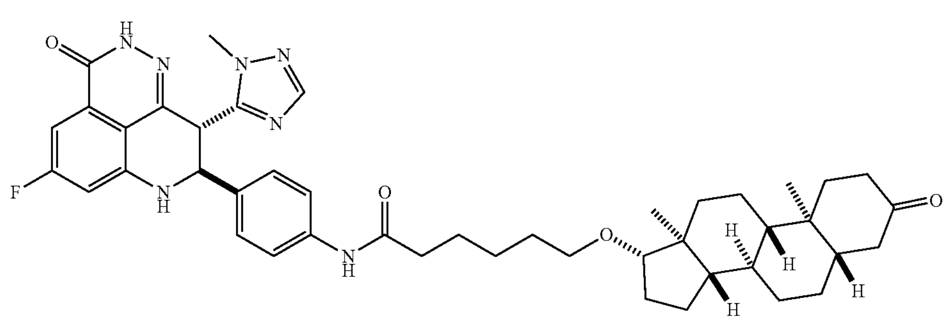 |

TABLE 1-continued

| No. | Structure |
|---|---|
| 1.5 | 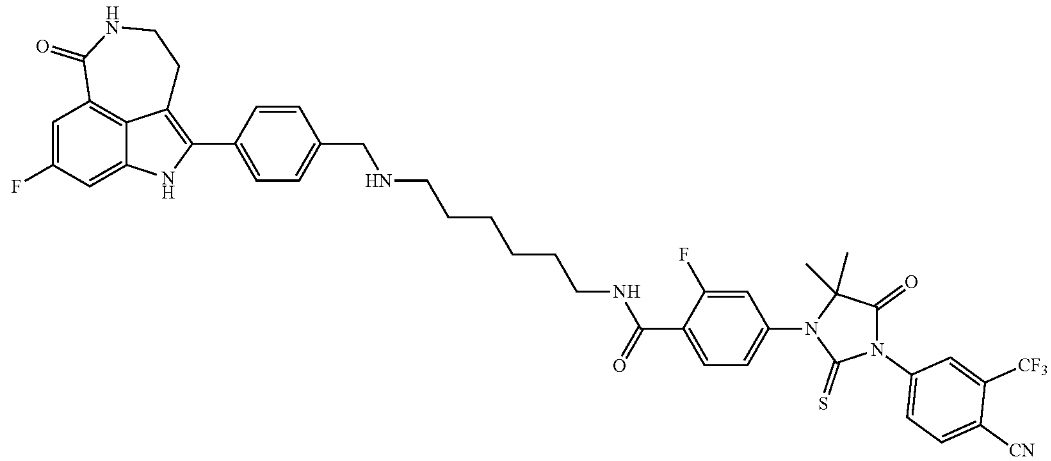 [SMILES: CC1(C)C(=O)N(c2ccc(C#N)c(C(F)(F)F)c2)C(=S)N1c1ccc(C(=O)NCCCCCCNCc2ccc(-c3[nH]c4cc(F)cc5c4c3CCNC5=O)cc2)c(F)c1] |
| 1.6 | 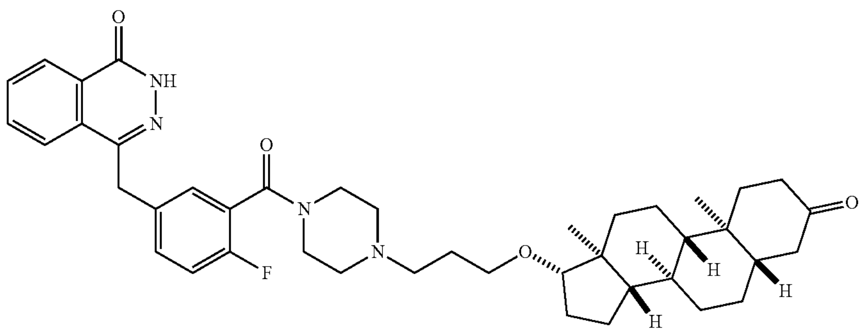 |
| 1.7 | 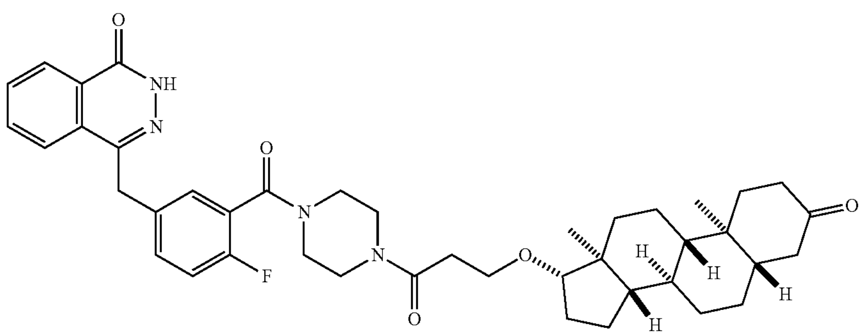 |
| 1.8 | 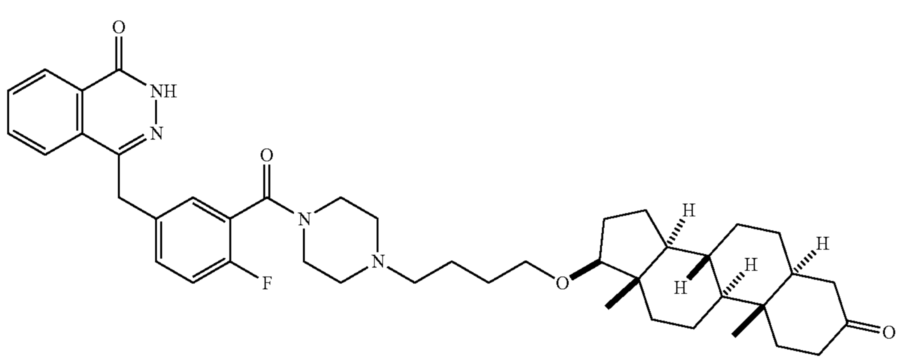 |

TABLE 1-continued

| No. | Structure |
|---|---|
| 1.9 | 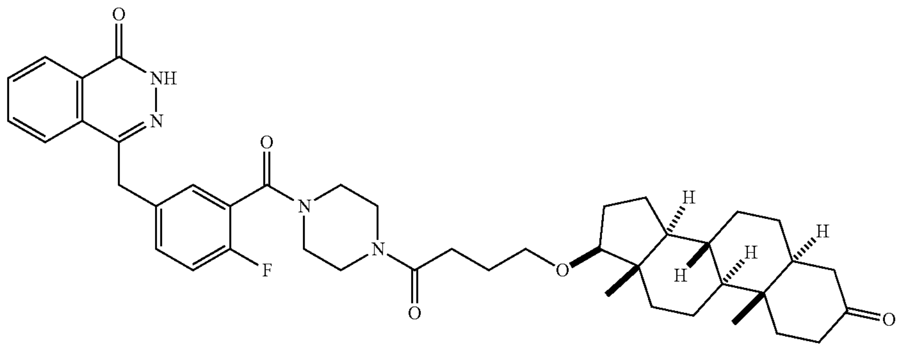 |
| 1.10 | 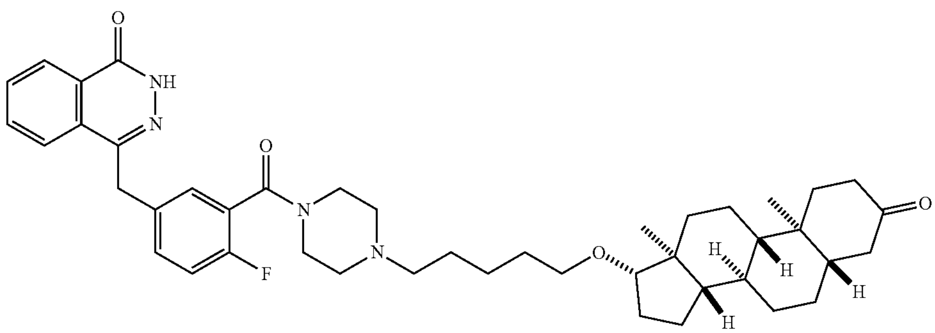 |
| 1.11 | 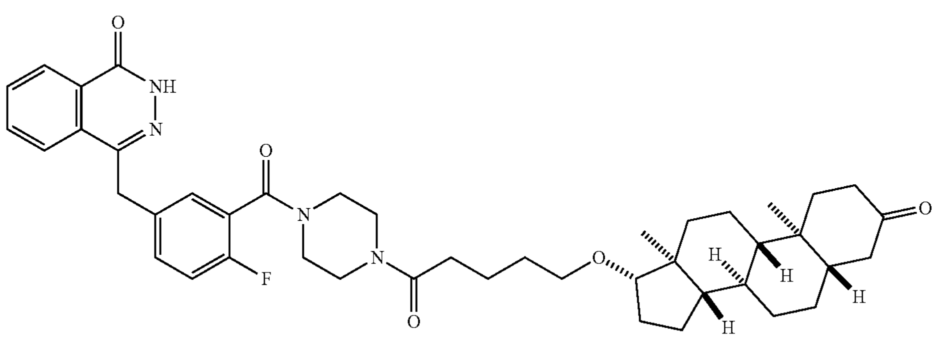 |
| 1.12 | 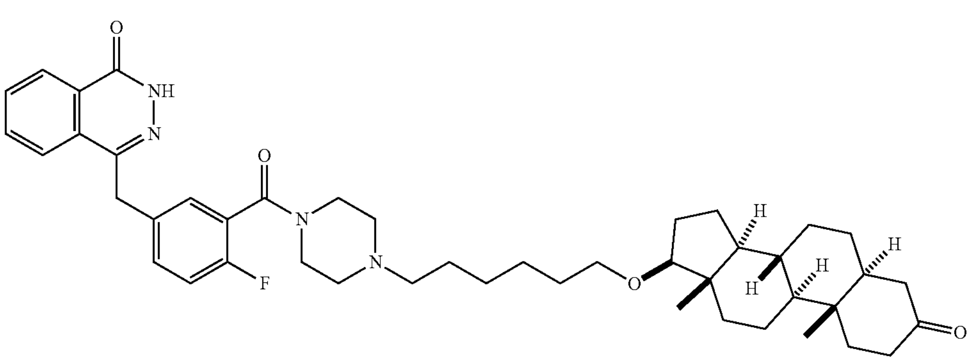 |

TABLE 1-continued

| No. | Structure |
| --- | --- |
| 1.13 | 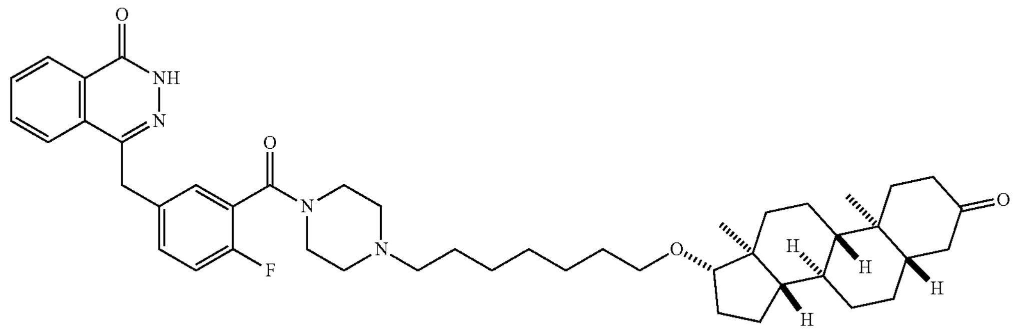 |
| 1.14 | 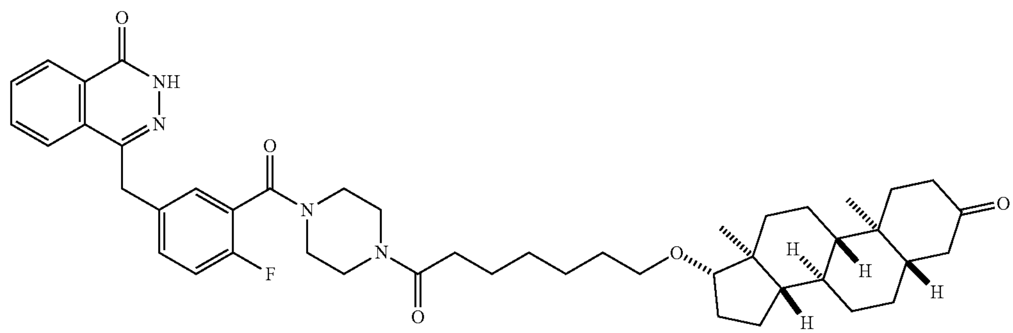 |
| 1.15 | 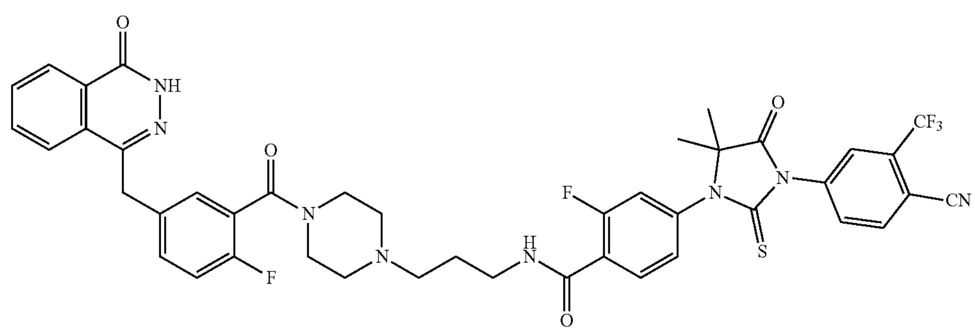 [SMILES: CC1(C)C(=O)N(c2ccc(C#N)c(C(F)(F)F)c2)C(=S)N1c1ccc(C(=O)NCCCN2CCN(C(=O)c3cc(Cc4n[nH]c(=O)c5ccccc45)ccc3F)CC2)c(F)c1] |
| 1.16 | 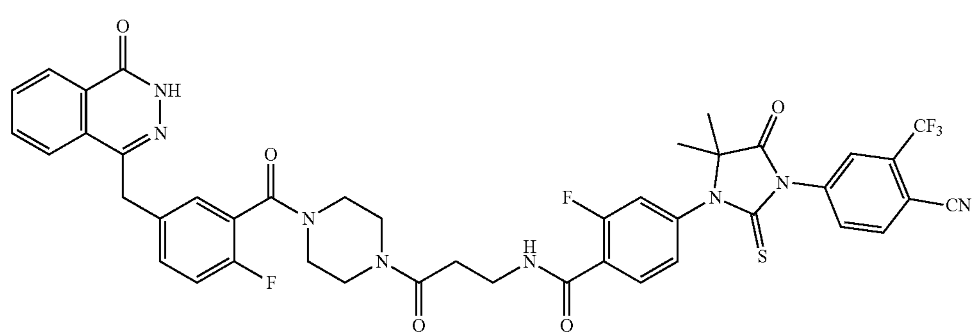 [SMILES: CC1(C)C(=O)N(c2ccc(C#N)c(C(F)(F)F)c2)C(=S)N1c1ccc(C(=O)NCCC(=O)N2CCN(C(=O)c3cc(Cc4n[nH]c(=O)c5ccccc45)ccc3F)CC2)c(F)c1] |

TABLE 1-continued

| No. | Structure |
|---|---|
| 1.17 | 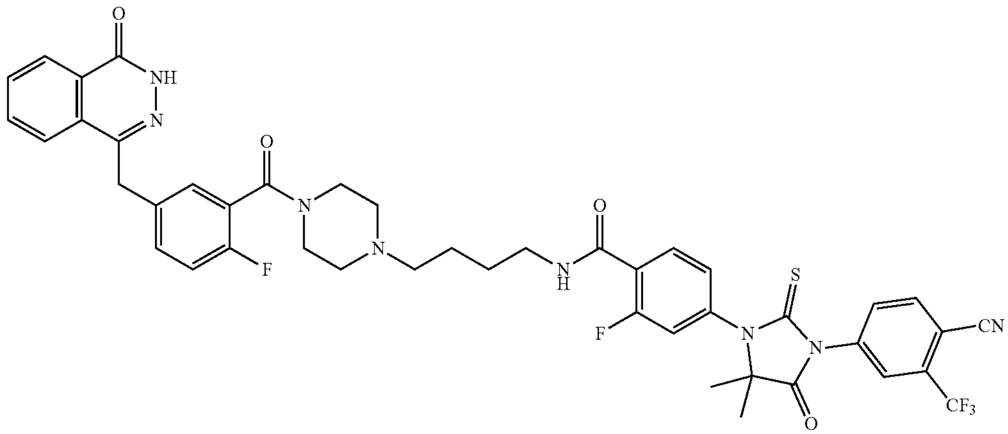 [SMILES: CC1(C)C(=O)N(c2ccc(C#N)c(C(F)(F)F)c2)C(=S)N1c1ccc(C(=O)NCCCCN2CCN(C(=O)c3cc(Cc4n[nH]c(=O)c5ccccc45)ccc3F)CC2)c(F)c1] |
| 1.18 | 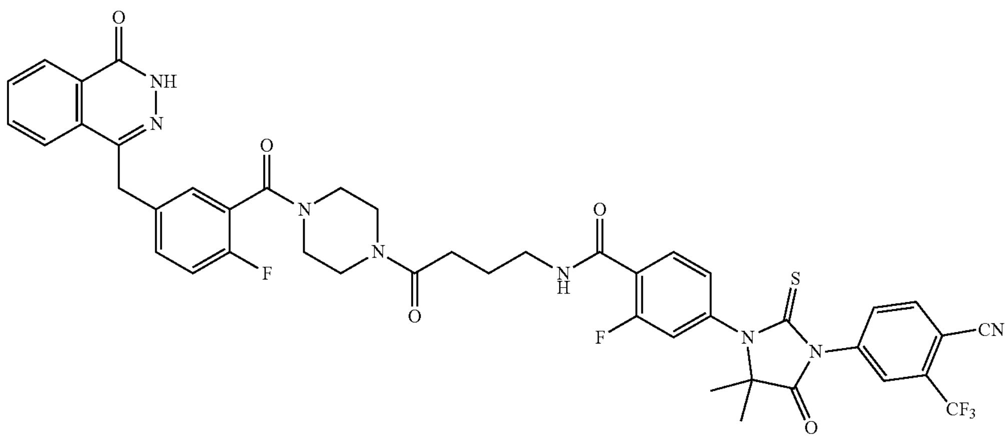 [SMILES: CC1(C)C(=O)N(c2ccc(C#N)c(C(F)(F)F)c2)C(=S)N1c1ccc(C(=O)NCCCC(=O)N2CCN(C(=O)c3cc(Cc4n[nH]c(=O)c5ccccc45)ccc3F)CC2)c(F)c1] |
| 1.19 | 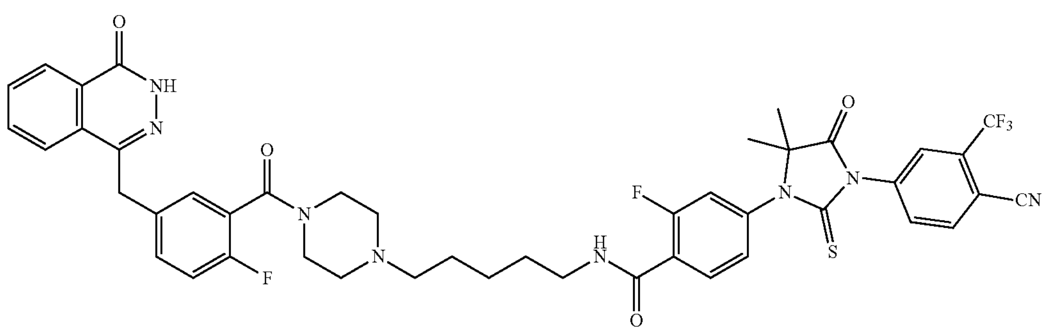 [SMILES: CC1(C)C(=O)N(c2ccc(C#N)c(C(F)(F)F)c2)C(=S)N1c1ccc(C(=O)NCCCCCN2CCN(C(=O)c3cc(Cc4n[nH]c(=O)c5ccccc45)ccc3F)CC2)c(F)c1] |
| 1.20 | 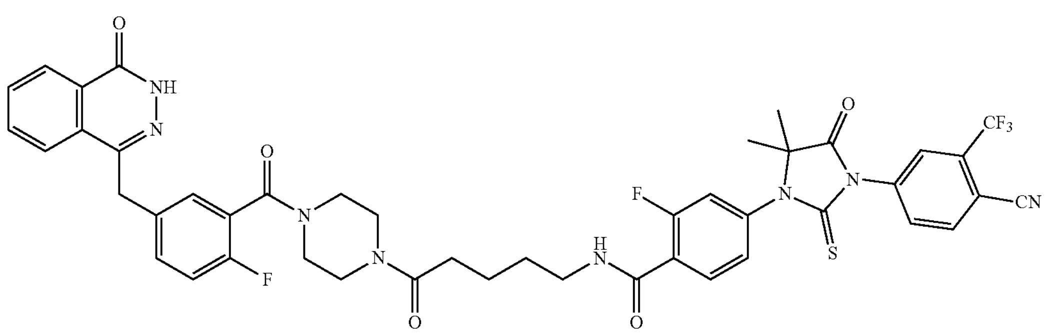 [SMILES: CC1(C)C(=O)N(c2ccc(C#N)c(C(F)(F)F)c2)C(=S)N1c1ccc(C(=O)NCCCCC(=O)N2CCN(C(=O)c3cc(Cc4n[nH]c(=O)c5ccccc45)ccc3F)CC2)c(F)c1] |

TABLE 1-continued

| No. | Structure |
|---|---|
| 1.21 | 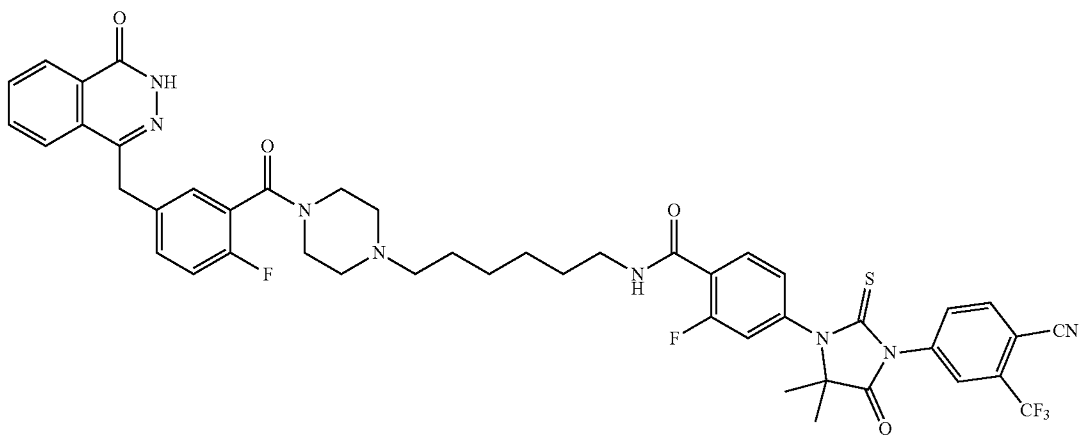 [SMILES: CC1(C)C(=O)N(c2ccc(C#N)c(C(F)(F)F)c2)C(=S)N1c1ccc(C(=O)NCCCCCCN2CCN(C(=O)c3cc(Cc4n[nH]c(=O)c5ccccc45)ccc3F)CC2)c(F)c1] |
| 1.22 | 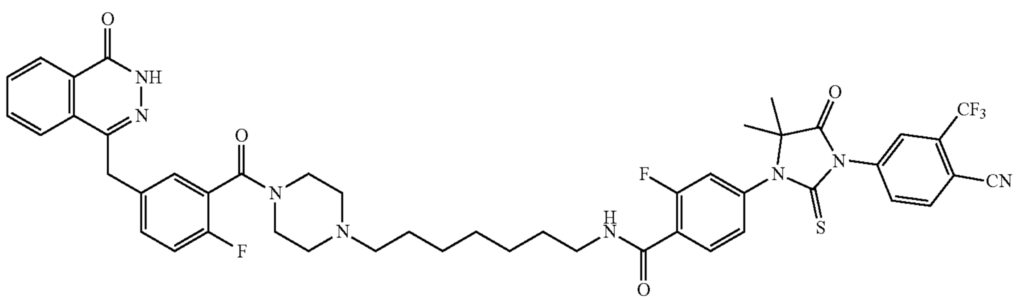 [SMILES: CC1(C)C(=O)N(c2ccc(C#N)c(C(F)(F)F)c2)C(=S)N1c1ccc(C(=O)NCCCCCCCN2CCN(C(=O)c3cc(Cc4n[nH]c(=O)c5ccccc45)ccc3F)CC2)c(F)c1] |
| 1.23 | 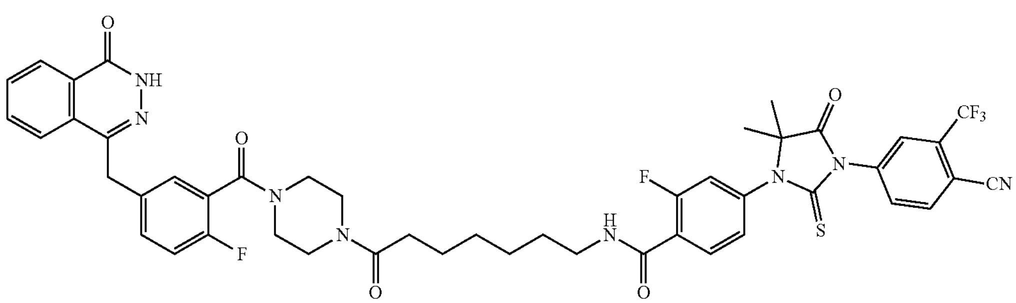 [SMILES: CC1(C)C(=O)N(c2ccc(C#N)c(C(F)(F)F)c2)C(=S)N1c1ccc(C(=O)NCCCCCCC(=O)N2CCN(C(=O)c3cc(Cc4n[nH]c(=O)c5ccccc45)ccc3F)CC2)c(F)c1] |
| 1.24 | 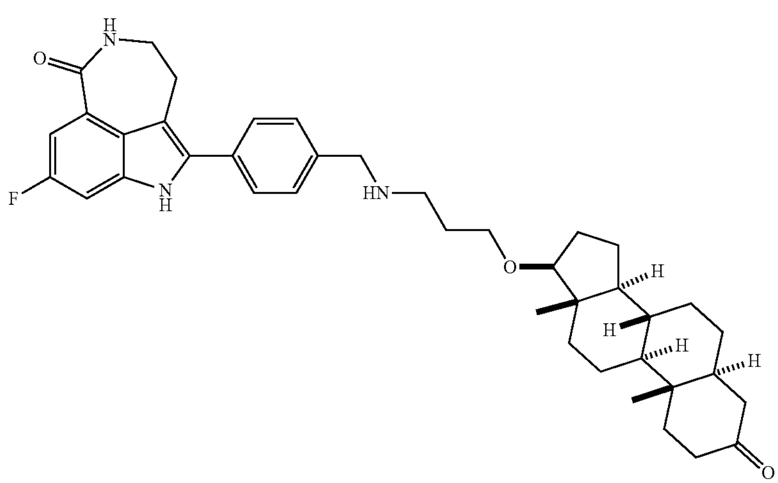 |

TABLE 1-continued
| No. | Structure |
|---|---|
| 1.25 | 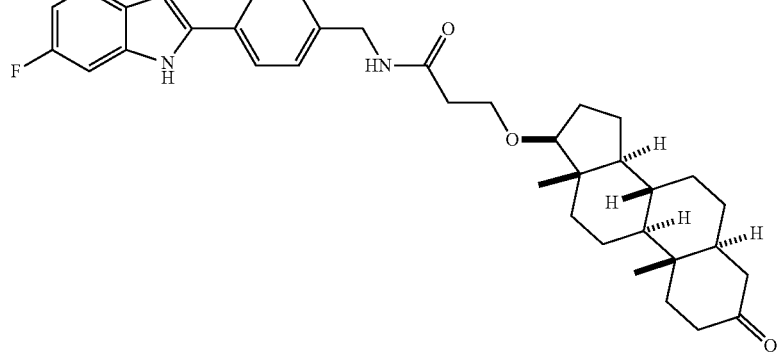 |
| 1.26 | 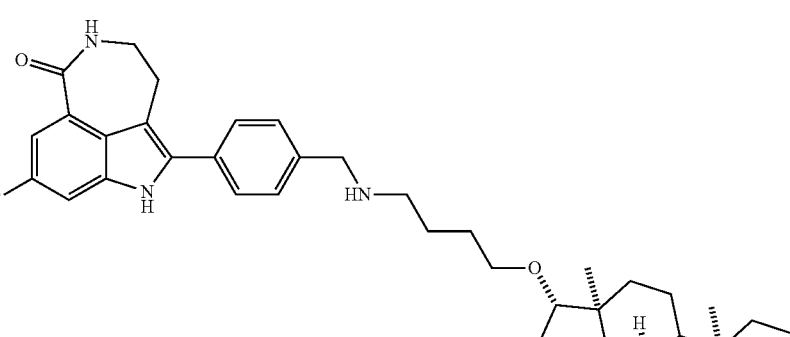 |
| 1.27 | 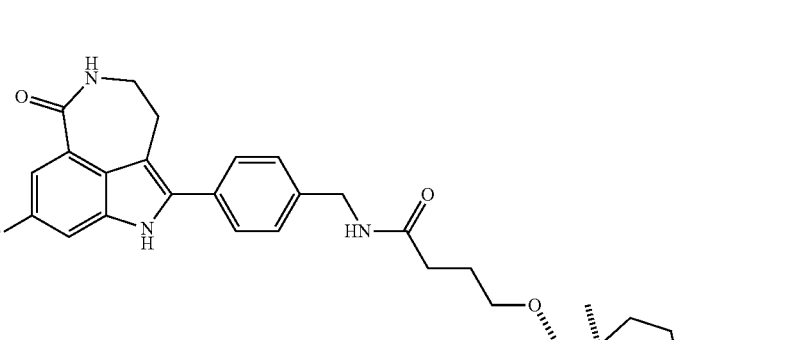 |

TABLE 1-continued
| No. | Structure |
|---|---|
| 1.28 | 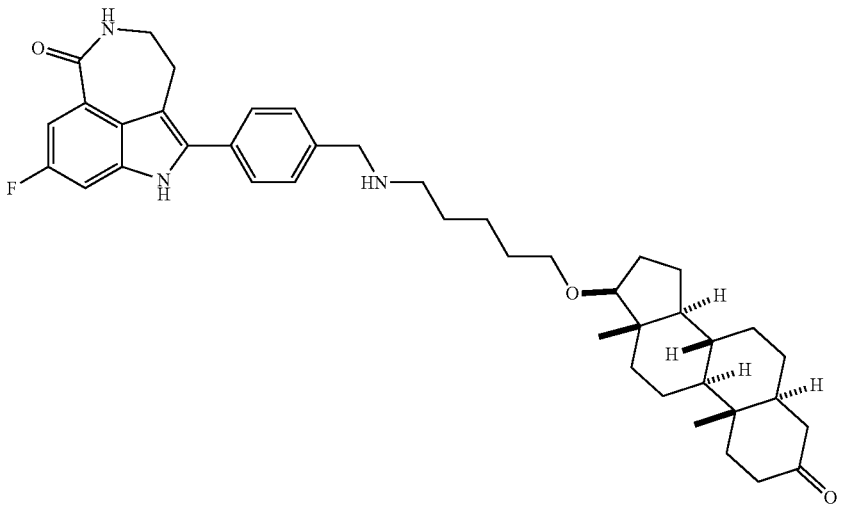 |
| 1.29 | 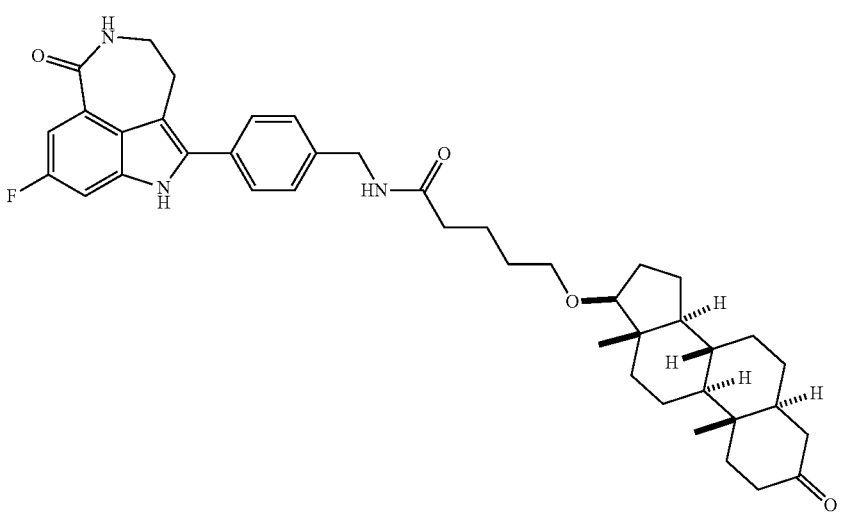 |
| 1.30 | 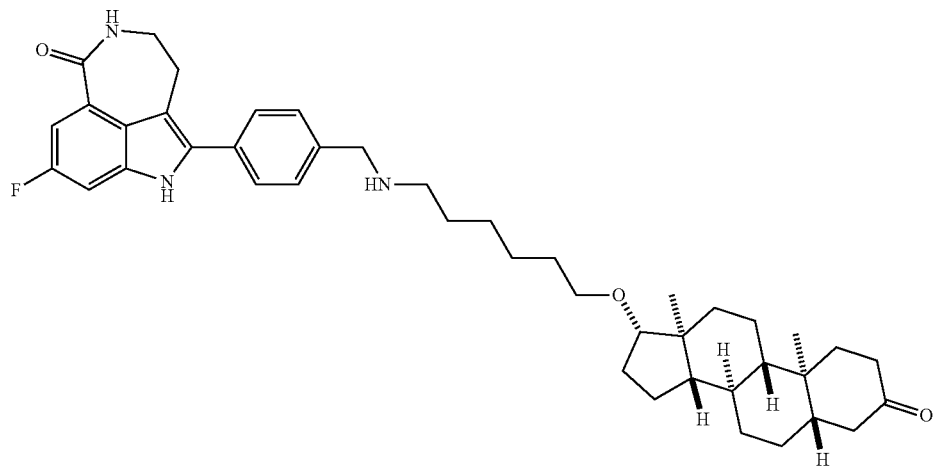 |

TABLE 1-continued
| No. | Structure |
|---|---|
| 1.31 | 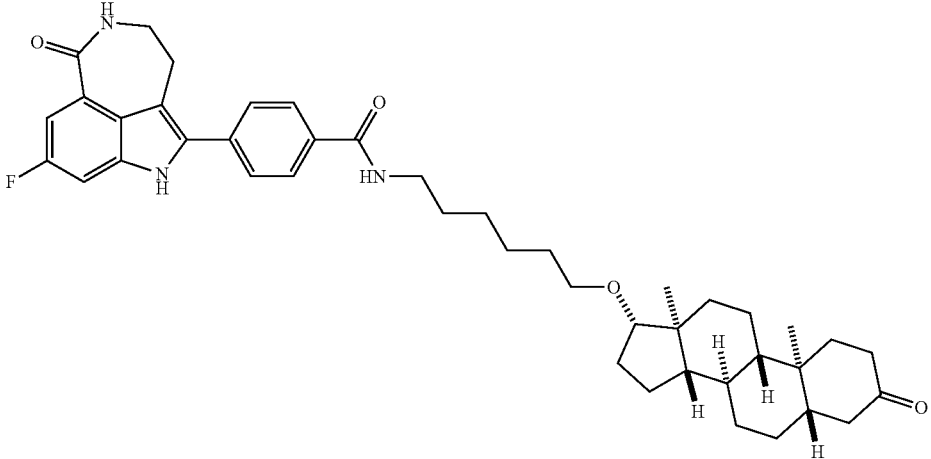 |
| 1.32 | 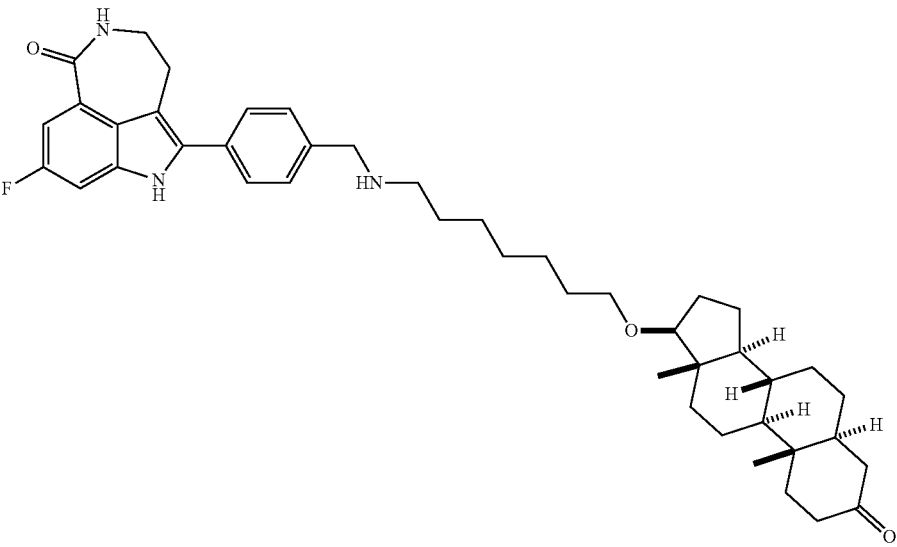 |
| 1.33 | 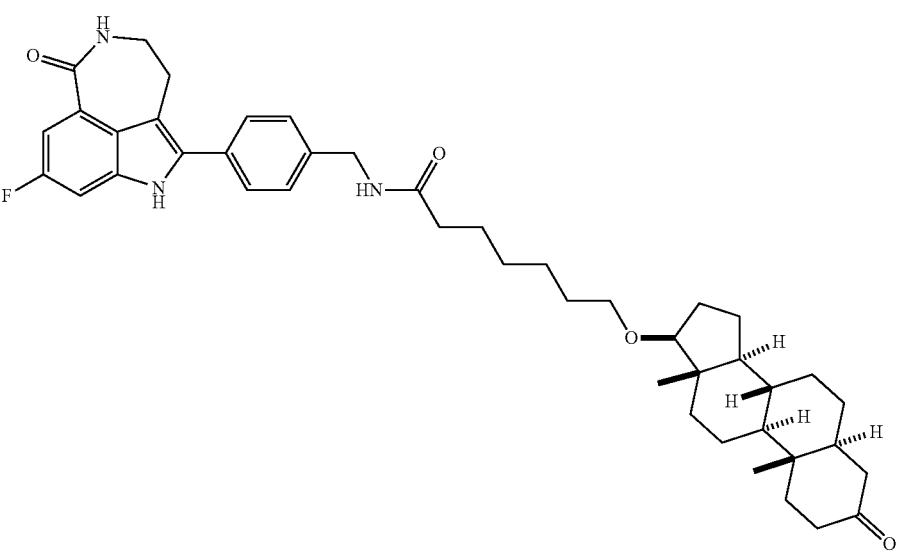 |

TABLE 1-continued

| No. | Structure |
|---|---|
| 1.34 | 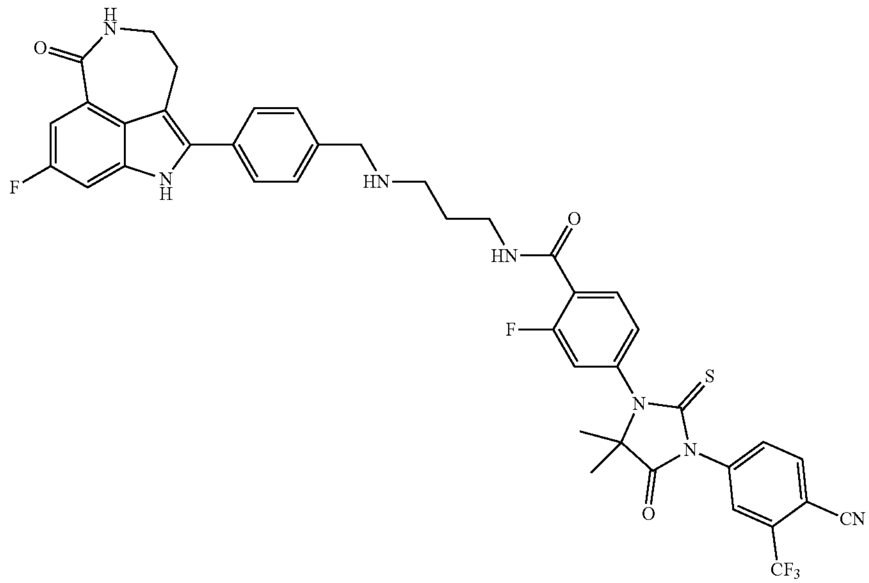 [SMILES: CC1(C)C(=O)N(c2ccc(C#N)c(C(F)(F)F)c2)C(=S)N1c1ccc(C(=O)NCCCNCc2ccc(-c3[nH]c4cc(F)cc5c4c3CCNC5=O)cc2)c(F)c1] |
| 1.35 | 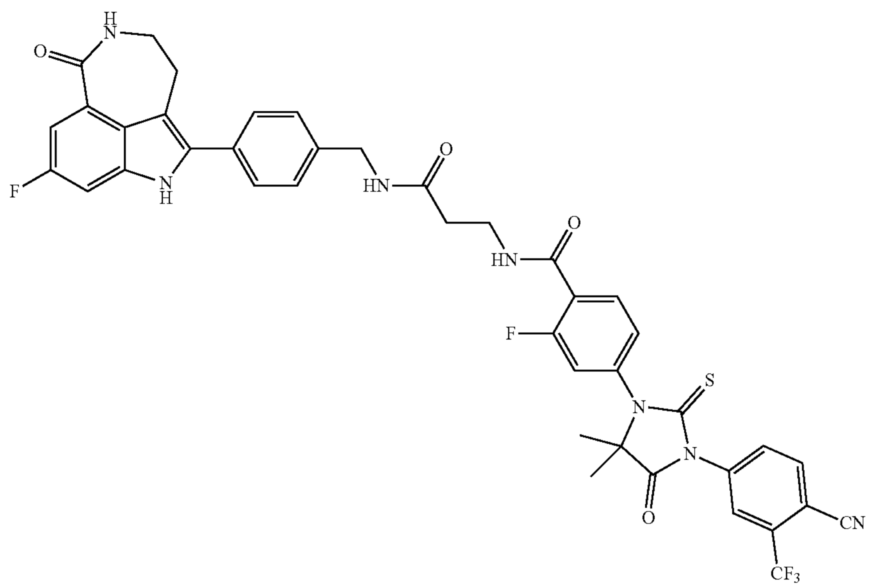 [SMILES: CC1(C)C(=O)N(c2ccc(C#N)c(C(F)(F)F)c2)C(=S)N1c1ccc(C(=O)NCCC(=O)NCc2ccc(-c3[nH]c4cc(F)cc5c4c3CCNC5=O)cc2)c(F)c1] |
| 1.36 | 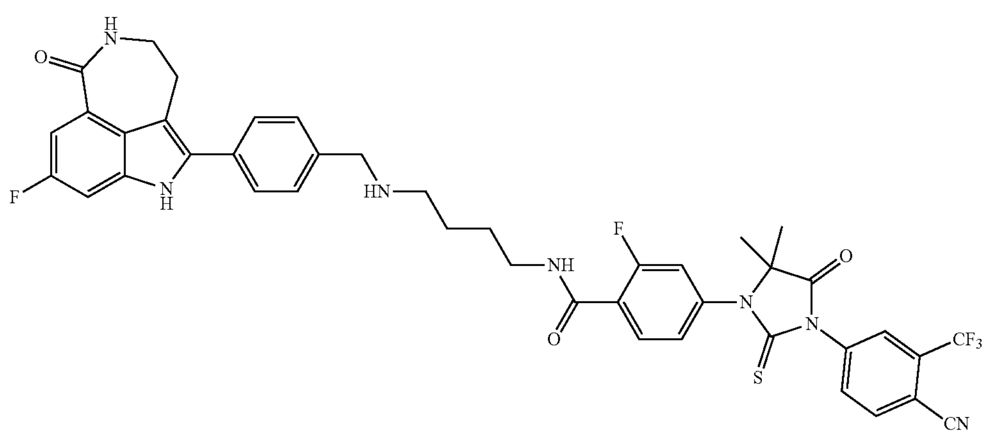 [SMILES: CC1(C)C(=O)N(c2ccc(C#N)c(C(F)(F)F)c2)C(=S)N1c1ccc(C(=O)NCCCCNCc2ccc(-c3[nH]c4cc(F)cc5c4c3CCNC5=O)cc2)c(F)c1] |

TABLE 1-continued
| No. | Structure |
|---|---|
| 1.37 | 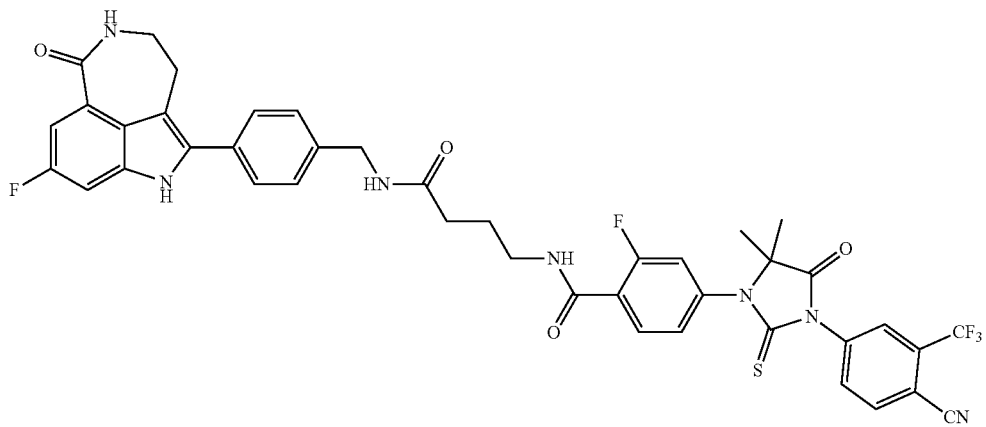 [SMILES: CC1(C)C(=O)N(c2ccc(C#N)c(C(F)(F)F)c2)C(=S)N1c1ccc(C(=O)NCCCC(=O)NCc2ccc(-c3[nH]c4cc(F)cc5c4c3CCNC5=O)cc2)c(F)c1] |
| 1.38 | 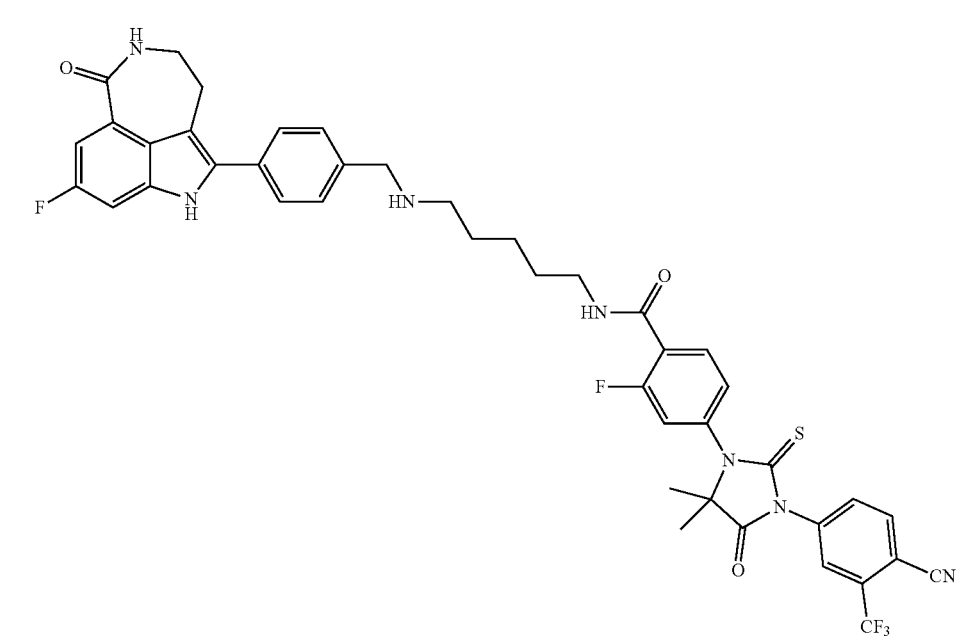 [SMILES: CC1(C)C(=O)N(c2ccc(C#N)c(C(F)(F)F)c2)C(=S)N1c1ccc(C(=O)NCCCCCNCc2ccc(-c3[nH]c4cc(F)cc5c4c3CCNC5=O)cc2)c(F)c1] |

TABLE 1-continued
| No. | Structure |
|---|---|
| 1.39 | 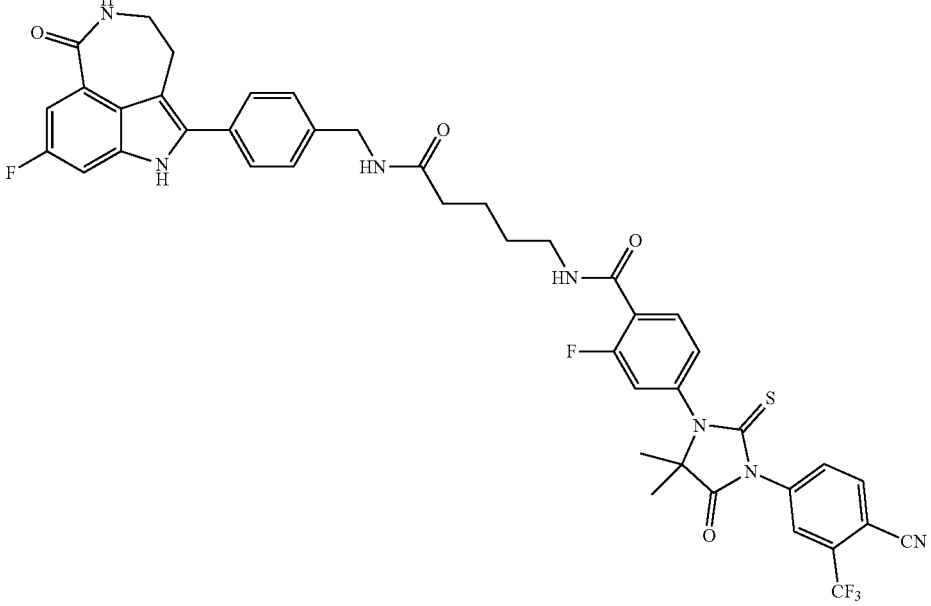 |
| 1.40 | 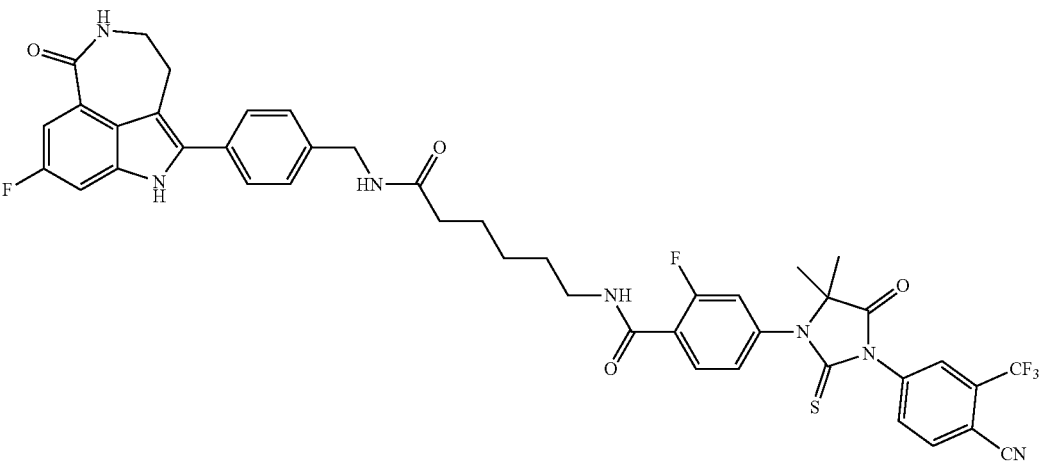 [SMILES: CC1(C)C(=O)N(c2ccc(C#N)c(C(F)(F)F)c2)C(=S)N1c1ccc(C(=O)NCCCCCC(=O)NCc2ccc(-c3[nH]c4cc(F)cc5c4c3CCNC5=O)cc2)c(F)c1] |

TABLE 1-continued

| No. | Structure |
|---|---|
| 1.41 | 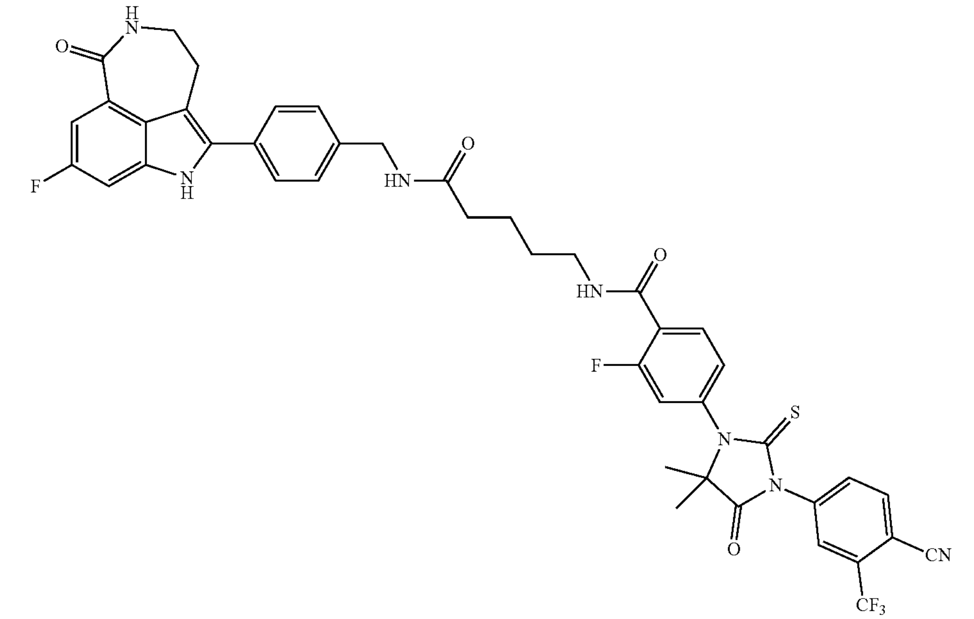 [SMILES: CC1(C)C(=O)N(c2ccc(C#N)c(C(F)(F)F)c2)C(=S)N1c1ccc(C(=O)NCCCCC(=O)NCc2ccc(-c3[nH]c4cc(F)cc5c4c3CCNC5=O)cc2)c(F)c1] |
| 1.42 | 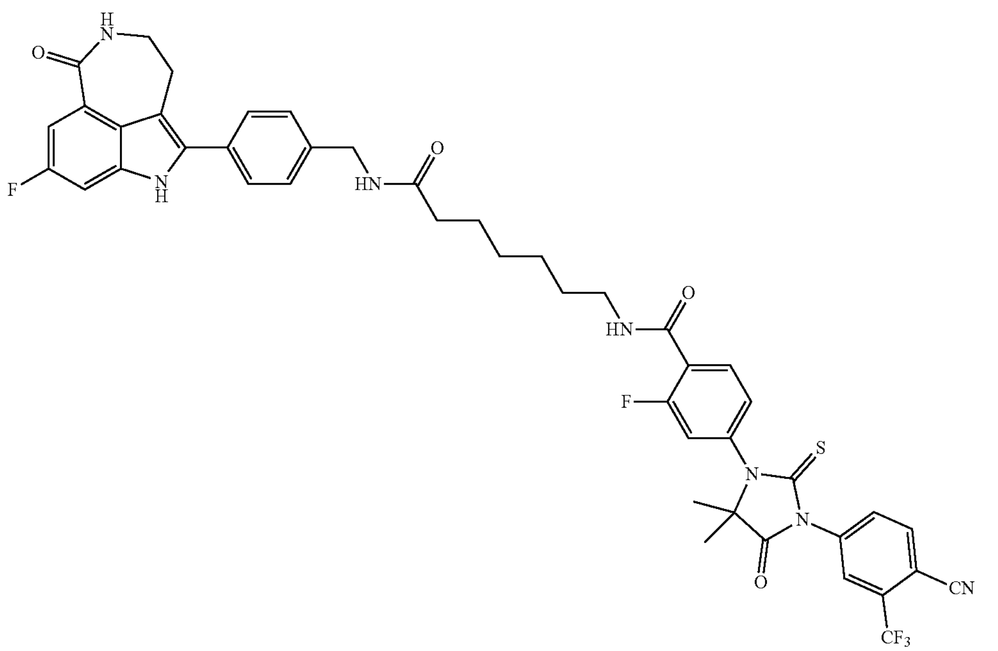 [SMILES: CC1(C)C(=O)N(c2ccc(C#N)c(C(F)(F)F)c2)C(=S)N1c1ccc(C(=O)NCCCCCCC(=O)NCc2ccc(-c3[nH]c4cc(F)cc5c4c3CCNC5=O)cc2)c(F)c1] |
| 1.43 | 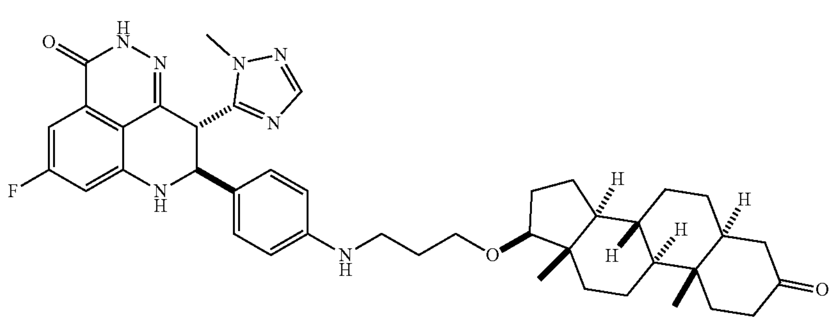 |

TABLE 1-continued

| No. | Structure |
|---|---|
| 1.44 | 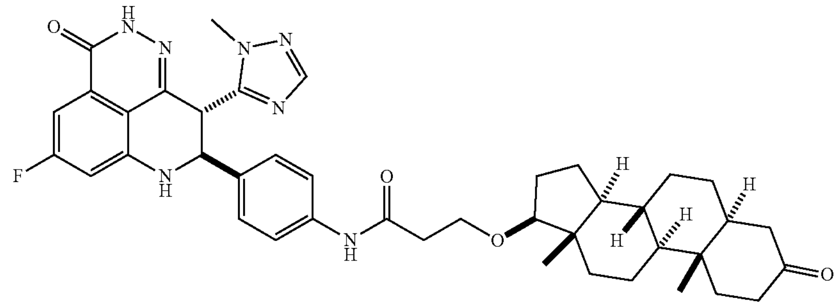 |
| 1.45 | 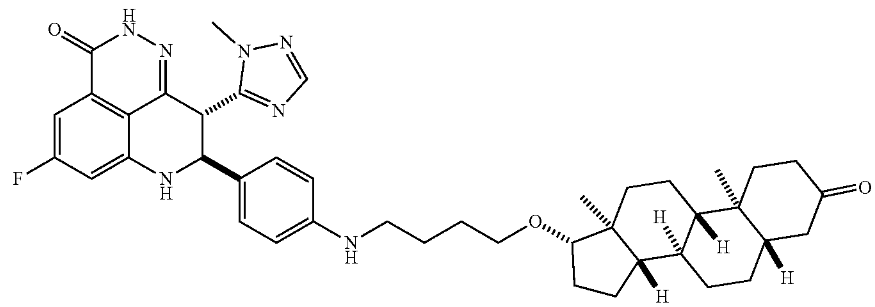 |
| 1.46 | 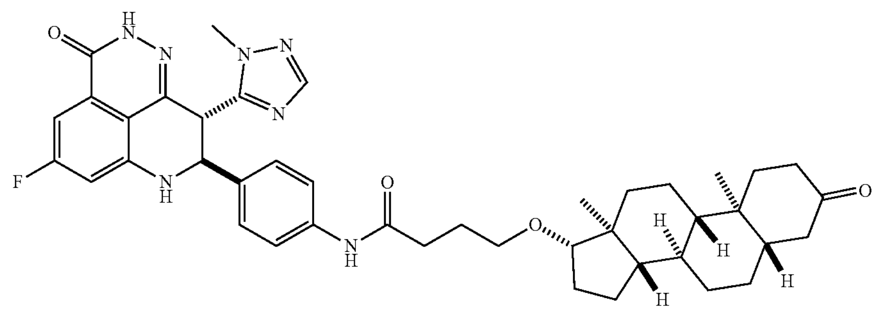 |
| 1.47 | 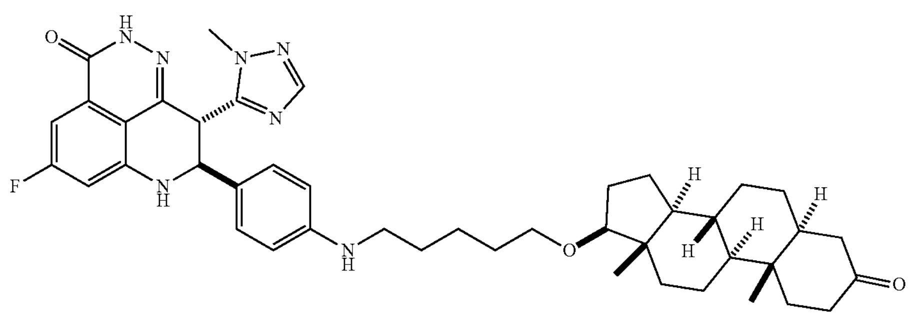 |
| 1.48 | 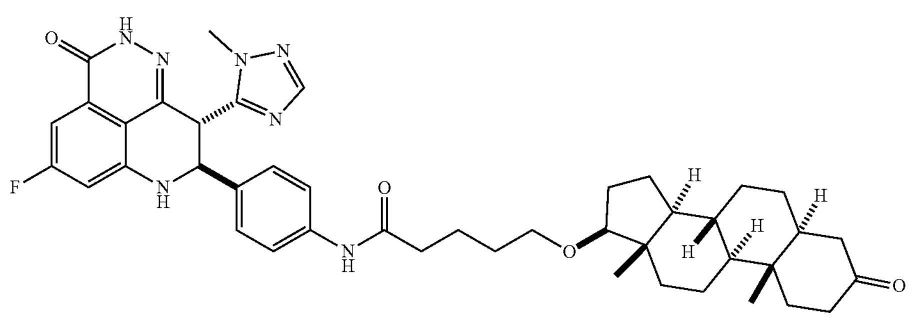 |

TABLE 1-continued
| No. | Structure |
|---|---|
| 1.49 | 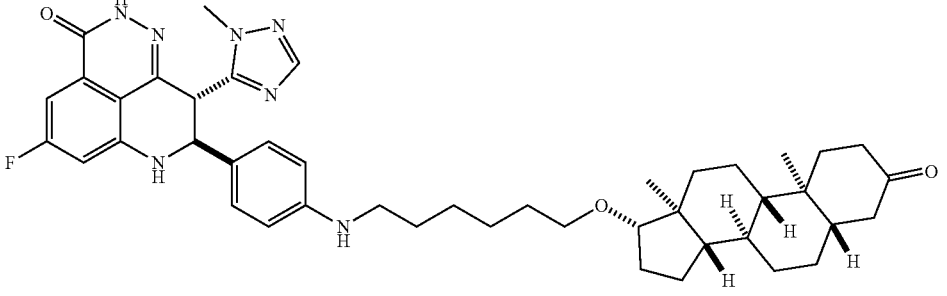 |
| 1.50 | 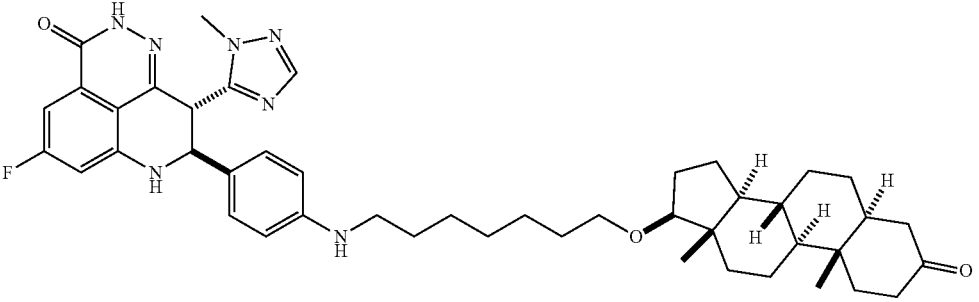 |
| 1.51 | 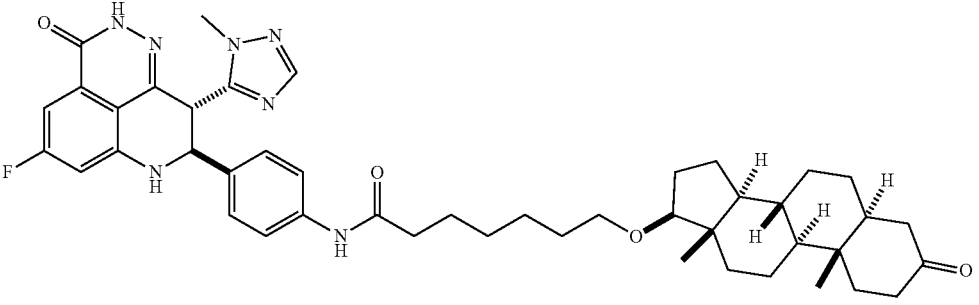 |
| 1.52 | 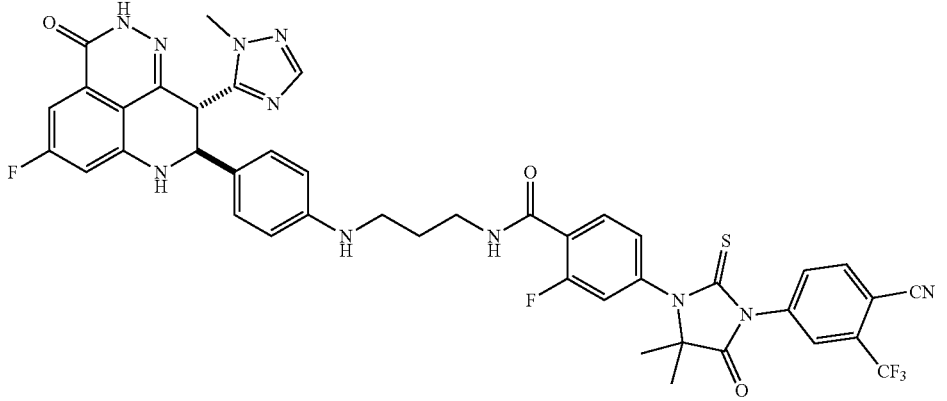 [SMILES: Cn1ncnc1[C@H]1c2n[nH]c(=O)c3cc(F)cc(c23)N[C@@H]1c1ccc(NCCCNC(=O)c2ccc(N3C(=S)N(c4ccc(C#N)c(C(F)(F)F)c4)C(=O)C3(C)C)cc2F)cc1] |

TABLE 1-continued

| No. | Structure |
|---|---|
| 1.53 | 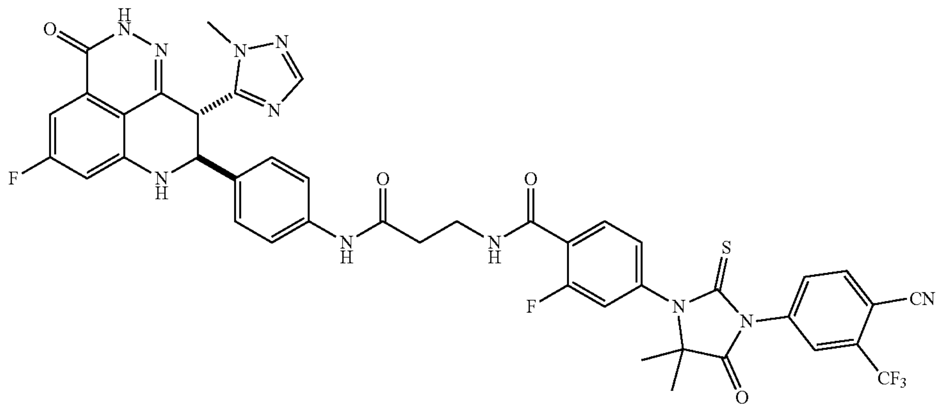 [SMILES: Cn1ncnc1[C@H]1c2n[nH]c(=O)c3cc(F)cc(c23)N[C@@H]1c1ccc(NC(=O)CCNC(=O)c2ccc(N3C(=S)N(c4ccc(C#N)c(C(F)(F)F)c4)C(=O)C3(C)C)cc2F)cc1] |
| 1.54 | 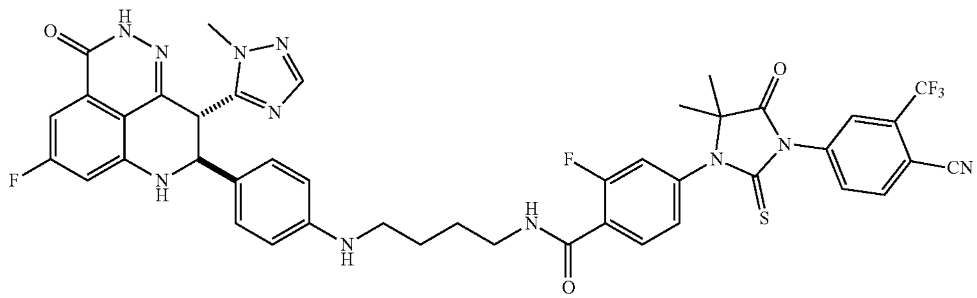 [SMILES: Cn1ncnc1[C@H]1c2n[nH]c(=O)c3cc(F)cc(c23)N[C@@H]1c1ccc(NCCCCNC(=O)c2ccc(N3C(=S)N(c4ccc(C#N)c(C(F)(F)F)c4)C(=O)C3(C)C)cc2F)cc1] |
| 1.55 | 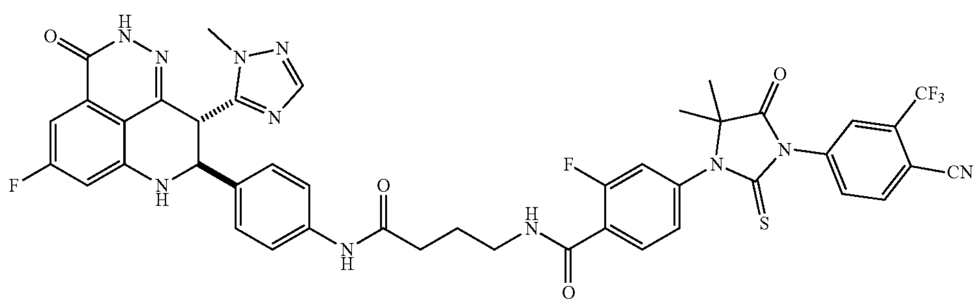 [SMILES: Cn1ncnc1[C@H]1c2n[nH]c(=O)c3cc(F)cc(c23)N[C@@H]1c1ccc(NC(=O)CCCNC(=O)c2ccc(N3C(=S)N(c4ccc(C#N)c(C(F)(F)F)c4)C(=O)C3(C)C)cc2F)cc1] |
| 1.56 | 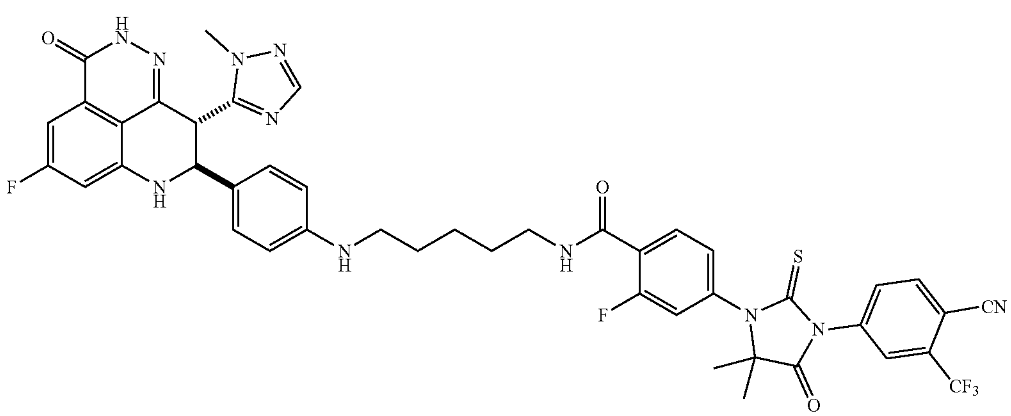 [SMILES: Cn1ncnc1[C@H]1c2n[nH]c(=O)c3cc(F)cc(c23)N[C@@H]1c1ccc(NCCCCCNC(=O)c2ccc(N3C(=S)N(c4ccc(C#N)c(C(F)(F)F)c4)C(=O)C3(C)C)cc2F)cc1] |

TABLE 1-continued

| No. | Structure |
|---|---|
| 1.57 | 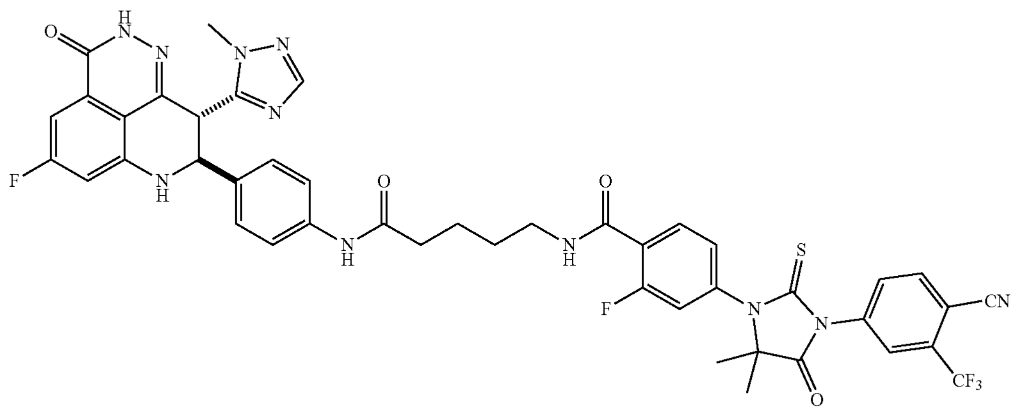 [SMILES: Cn1ncnc1[C@H]1c2n[nH]c(=O)c3cc(F)cc(c23)N[C@@H]1c1ccc(NC(=O)CCCCNC(=O)c2ccc(N3C(=S)N(c4ccc(C#N)c(C(F)(F)F)c4)C(=O)C3(C)C)cc2F)cc1] |
| 1.58 | 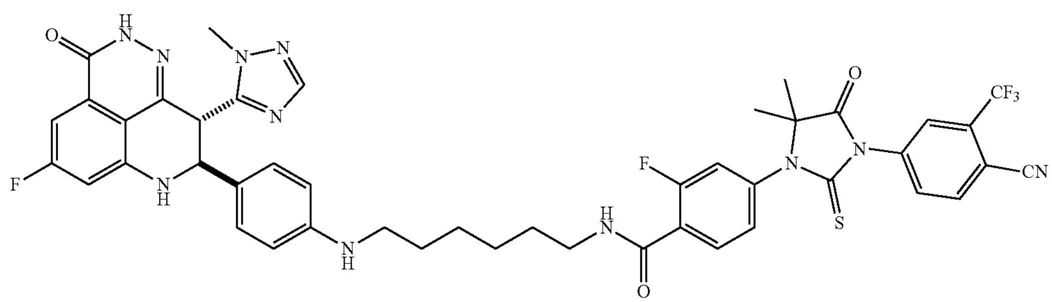 [SMILES: Cn1ncnc1[C@H]1c2n[nH]c(=O)c3cc(F)cc(c23)N[C@@H]1c1ccc(NCCCCCCNC(=O)c2ccc(N3C(=S)N(c4ccc(C#N)c(C(F)(F)F)c4)C(=O)C3(C)C)cc2F)cc1] |
| 1.59 | 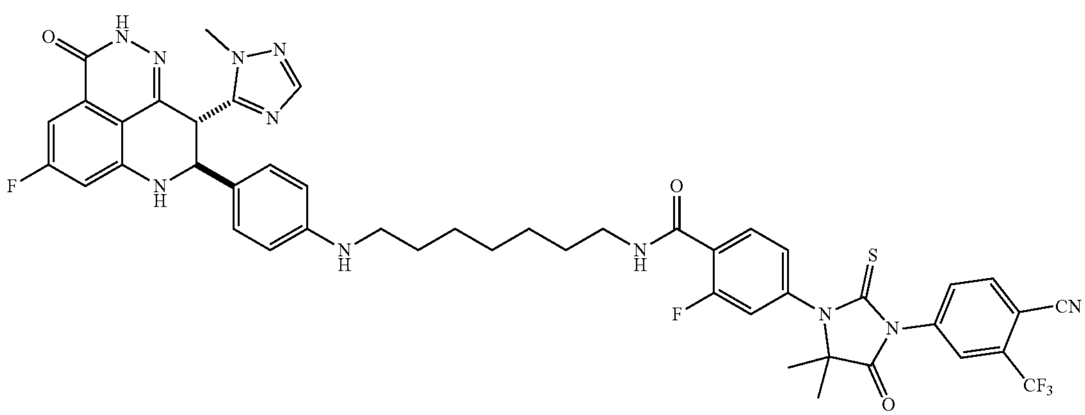 [SMILES: Cn1ncnc1[C@H]1c2n[nH]c(=O)c3cc(F)cc(c23)N[C@@H]1c1ccc(NCCCCCCCNC(=O)c2ccc(N3C(=S)N(c4ccc(C#N)c(C(F)(F)F)c4)C(=O)C3(C)C)cc2F)cc1] |
| 1.60 | 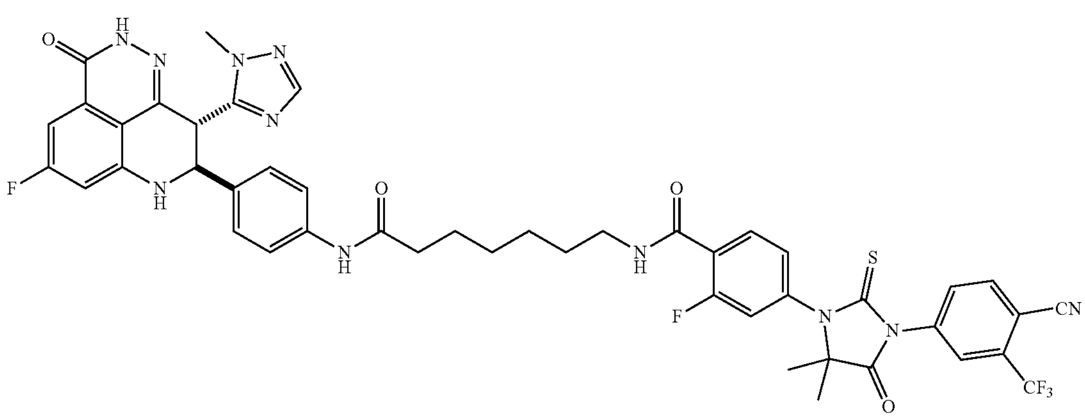 [SMILES: Cn1ncnc1[C@H]1c2n[nH]c(=O)c3cc(F)cc(c23)N[C@@H]1c1ccc(NC(=O)CCCCCCNC(=O)c2ccc(N3C(=S)N(c4ccc(C#N)c(C(F)(F)F)c4)C(=O)C3(C)C)cc2F)cc1] |

TABLE 1-continued
| No. | Structure |
|---|---|
| 1.61 | 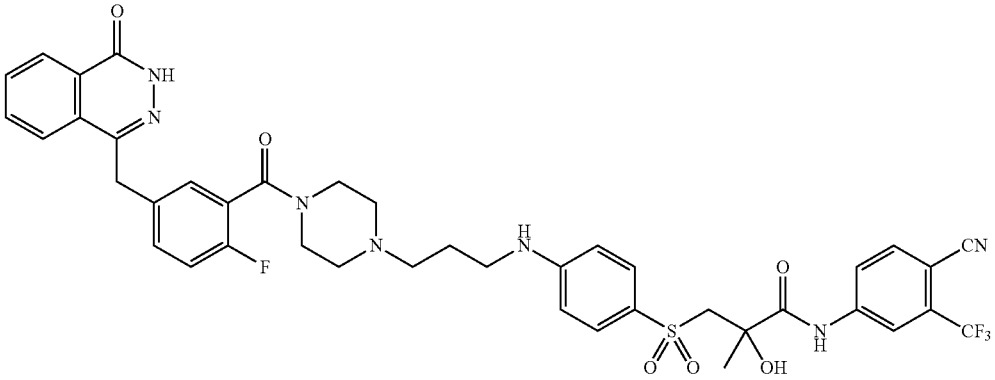 [SMILES: CC(O)(CS(=O)(=O)c1ccc(NCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.62 | 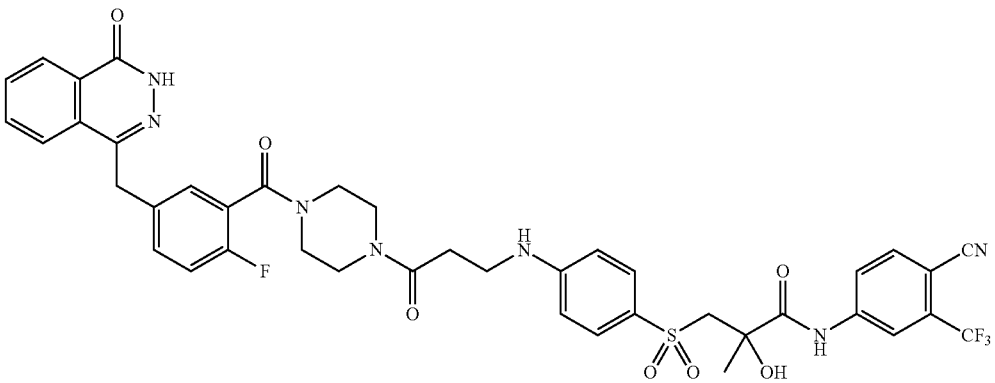 [SMILES: CC(O)(CS(=O)(=O)c1ccc(NCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.63 | 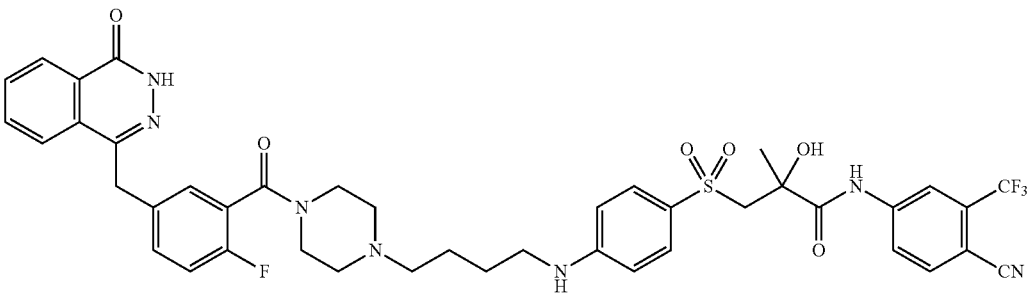 [SMILES: CC(O)(CS(=O)(=O)c1ccc(NCCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.64 | 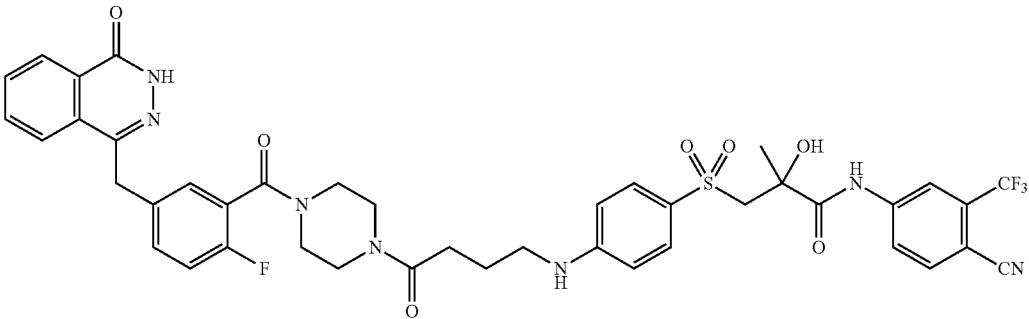 [SMILES: CC(O)(CS(=O)(=O)c1ccc(NCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.65 | 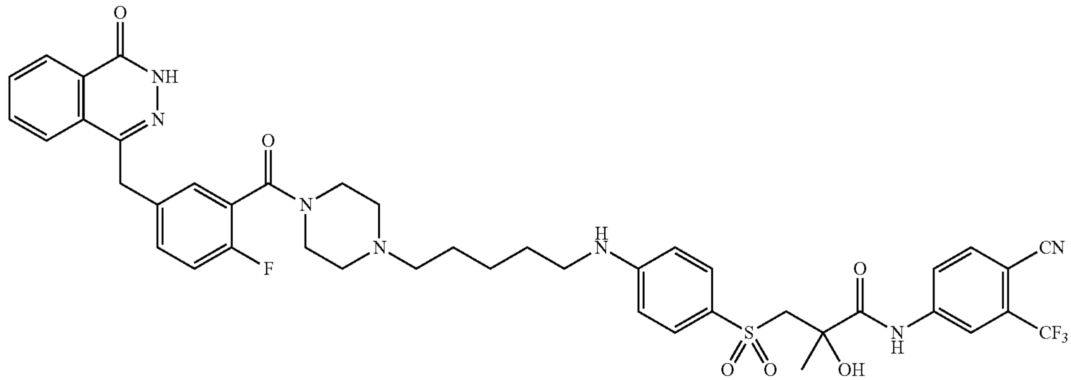 [SMILES: CC(O)(CS(=O)(=O)c1ccc(NCCCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.66 | 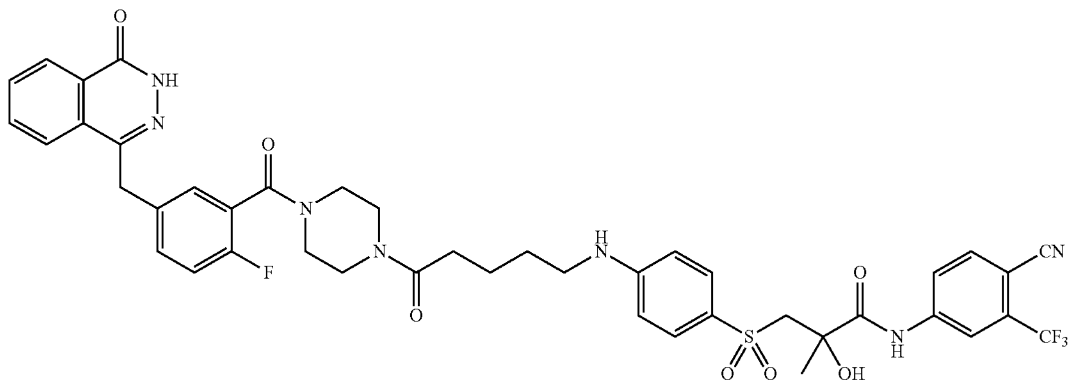 [SMILES: CC(O)(CS(=O)(=O)c1ccc(NCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.67 | 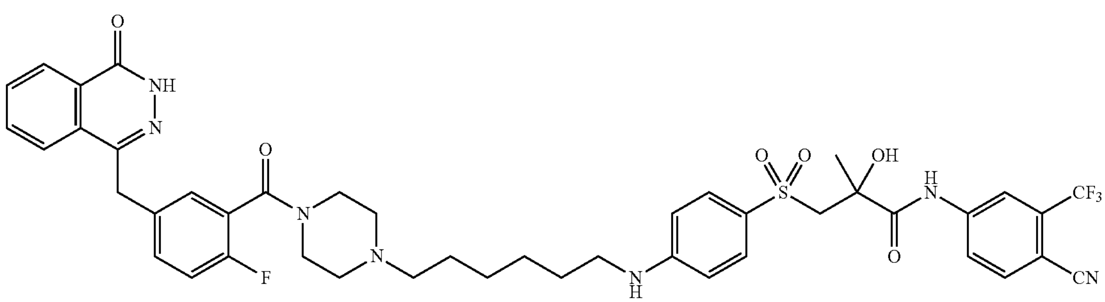 [SMILES: CC(O)(CS(=O)(=O)c1ccc(NCCCCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.68 | 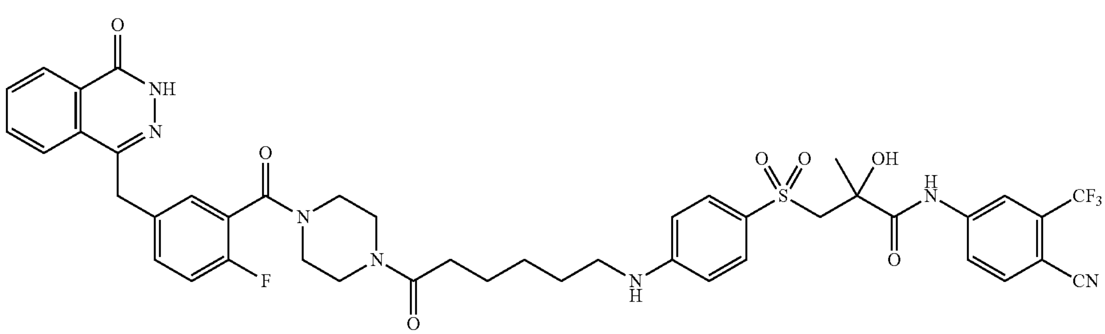 [SMILES: CC(O)(CS(=O)(=O)c1ccc(NCCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued
| No. | Structure |
|---|---|
| 1.69 | 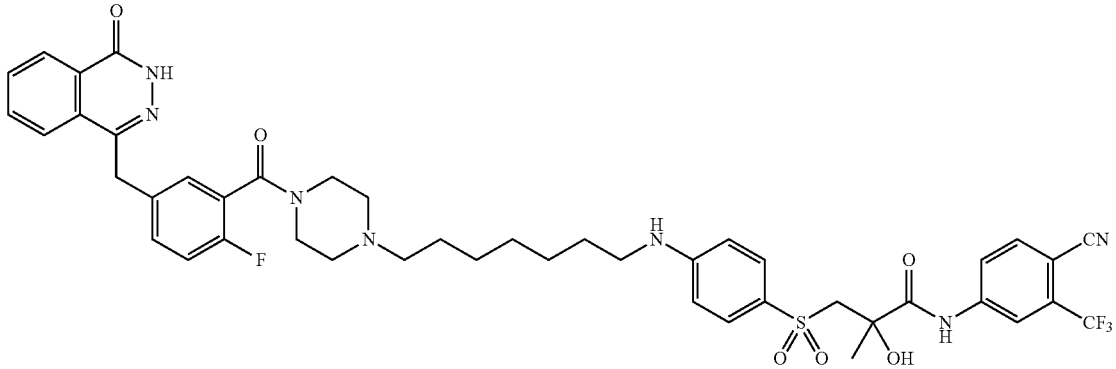 [SMILES: CC(O)(CS(=O)(=O)c1ccc(NCCCCCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.70 | 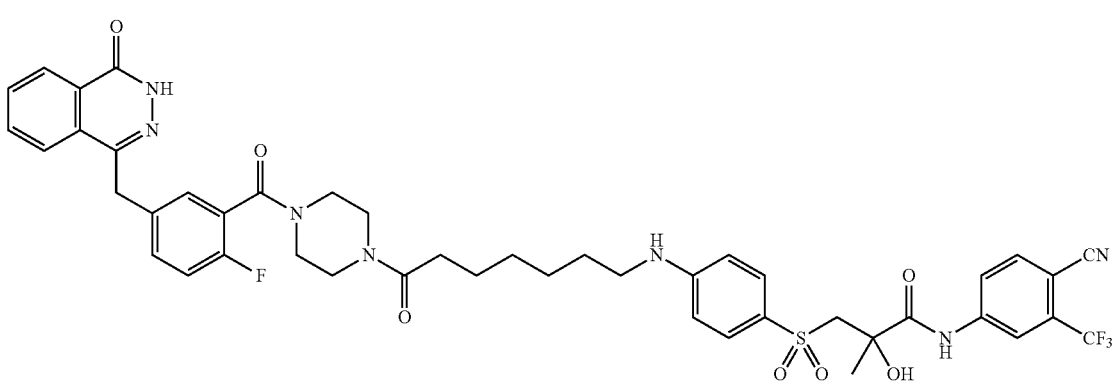 [SMILES: CC(O)(CS(=O)(=O)c1ccc(NCCCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.71 | 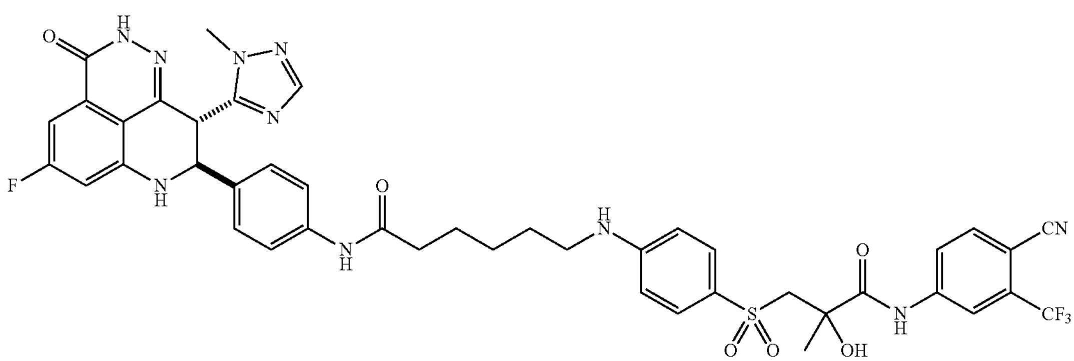 [SMILES: Cn1ncnc1[C@H]1c2n[nH]c(=O)c3cc(F)cc(c23)N[C@@H]1c1ccc(NC(=O)CCCCCNc2ccc(S(=O)(=O)CC(C)(O)C(=O)Nc3ccc(C#N)c(C(F)(F)F)c3)cc2)cc1] |
| 1.72 | 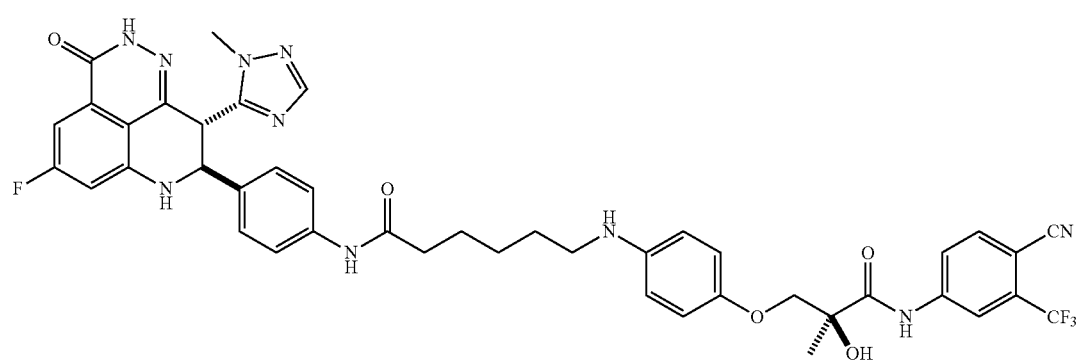 [SMILES: Cn1ncnc1[C@H]1c2n[nH]c(=O)c3cc(F)cc(c23)N[C@@H]1c1ccc(NC(=O)CCCCCNc2ccc(OC[C@](C)(O)C(=O)Nc3ccc(C#N)c(C(F)(F)F)c3)cc2)cc1] |

TABLE 1-continued

| No. | Structure |
|---|---|
| 1.73 | 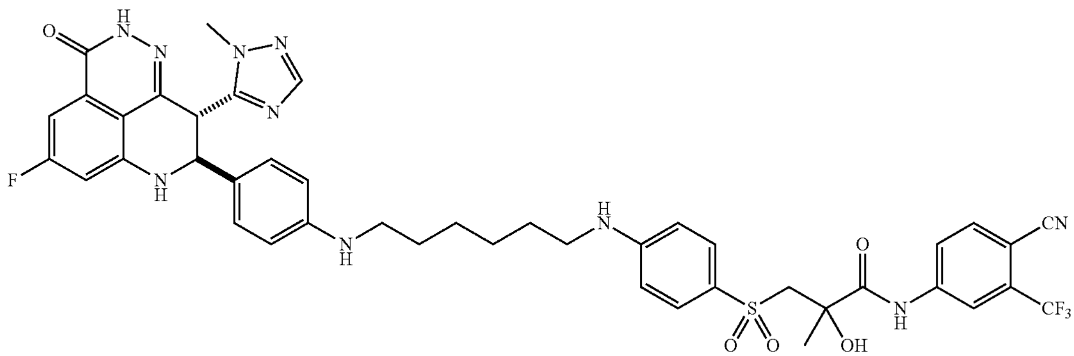 [SMILES: Cn1ncnc1[C@H]1c2n[nH]c(=O)c3cc(F)cc(c23)N[C@@H]1c1ccc(NCCCCCCNc2ccc(S(=O)(=O)CC(C)(O)C(=O)Nc3ccc(C#N)c(C(F)(F)F)c3)cc2)cc1] |
| 1.74 | 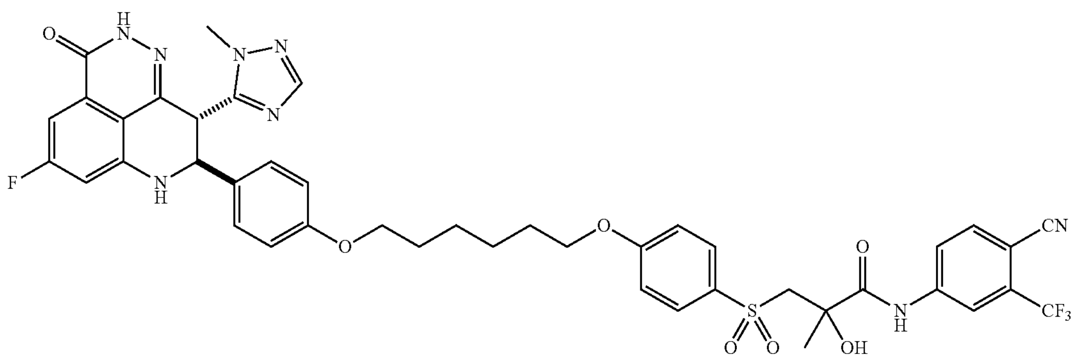 [SMILES: Cn1ncnc1[C@H]1c2n[nH]c(=O)c3cc(F)cc(c23)N[C@@H]1c1ccc(OCCCCCCOc2ccc(S(=O)(=O)CC(C)(O)C(=O)Nc3ccc(C#N)c(C(F)(F)F)c3)cc2)cc1] |
| 1.75 | 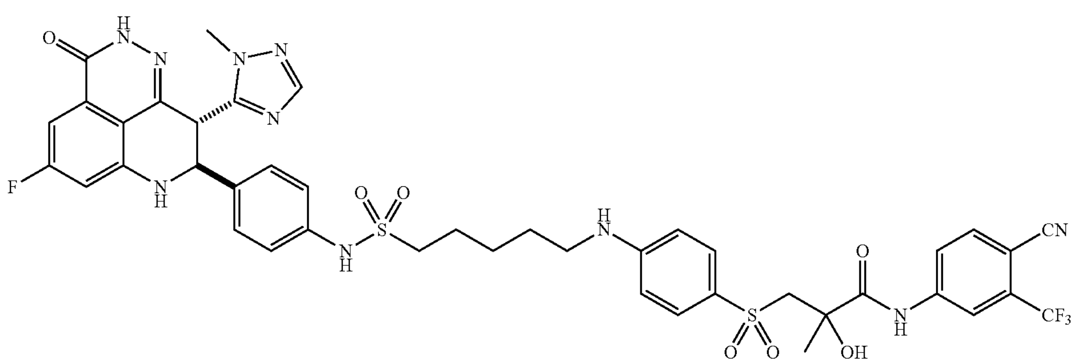 [SMILES: Cn1ncnc1[C@H]1c2n[nH]c(=O)c3cc(F)cc(c23)N[C@@H]1c1ccc(NS(=O)(=O)CCCCCNc2ccc(S(=O)(=O)CC(C)(O)C(=O)Nc3ccc(C#N)c(C(F)(F)F)c3)cc2)cc1] |
| 1.76 | 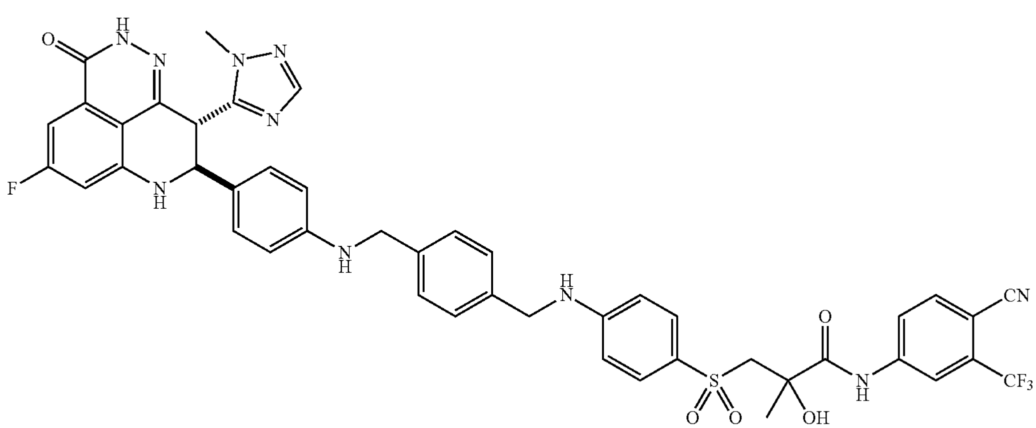 [SMILES: Cn1ncnc1[C@H]1c2n[nH]c(=O)c3cc(F)cc(c23)N[C@@H]1c1ccc(NCc2ccc(CNc3ccc(S(=O)(=O)CC(C)(O)C(=O)Nc4ccc(C#N)c(C(F)(F)F)c4)cc3)cc2)cc1] |

TABLE 1-continued
| No. | Structure |
|---|---|
| 1.77 | 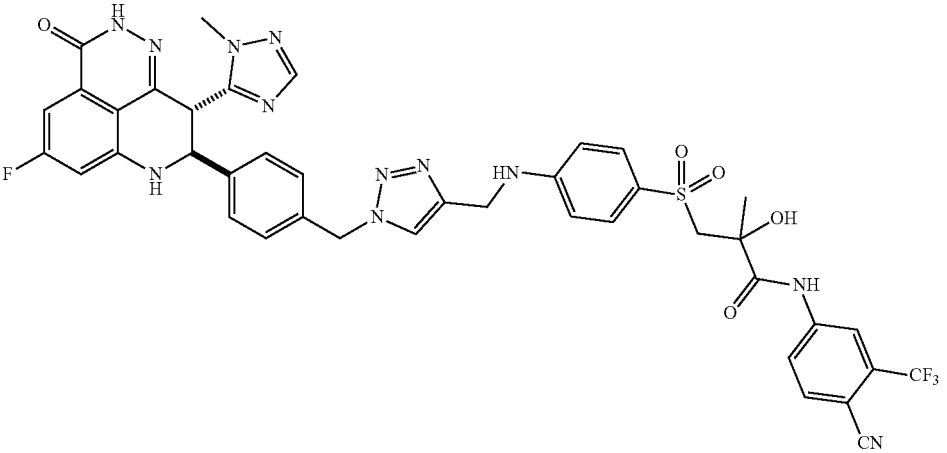 [SMILES: Cn1ncnc1[C@H]1c2n[nH]c(=O)c3cc(F)cc(c23)N[C@@H]1c1ccc(Cn2cc(CNc3ccc(S(=O)(=O)CC(C)(O)C(=O)Nc4ccc(C#N)c(C(F)(F)F)c4)cc3)nn2)cc1] |
| 1.78 | 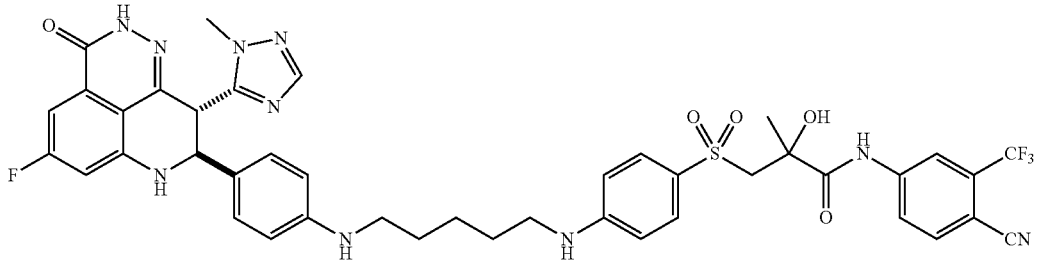 [SMILES: Cn1ncnc1[C@H]1c2n[nH]c(=O)c3cc(F)cc(c23)N[C@@H]1c1ccc(NCCCCCNc2ccc(S(=O)(=O)CC(C)(O)C(=O)Nc3ccc(C#N)c(C(F)(F)F)c3)cc2)cc1] |
| 1.79 | 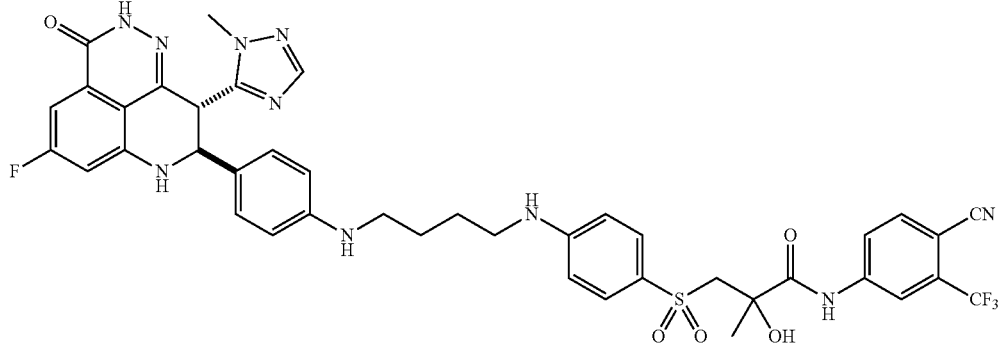 [SMILES: Cn1ncnc1[C@H]1c2n[nH]c(=O)c3cc(F)cc(c23)N[C@@H]1c1ccc(NCCCCNc2ccc(S(=O)(=O)CC(C)(O)C(=O)Nc3ccc(C#N)c(C(F)(F)F)c3)cc2)cc1] |
| 1.80 | 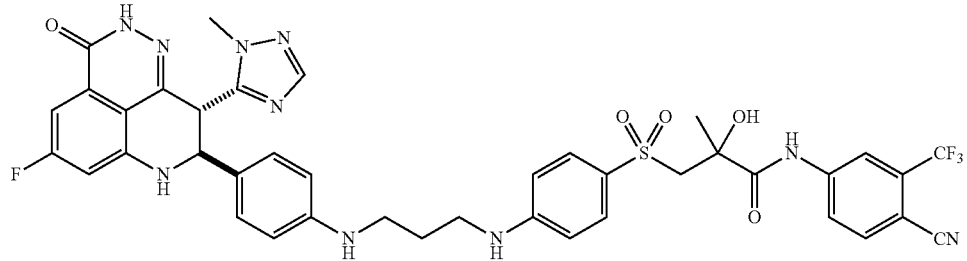 [SMILES: Cn1ncnc1[C@H]1c2n[nH]c(=O)c3cc(F)cc(c23)N[C@@H]1c1ccc(NCCCNc2ccc(S(=O)(=O)CC(C)(O)C(=O)Nc3ccc(C#N)c(C(F)(F)F)c3)cc2)cc1] |

TABLE 1-continued

| No. | Structure |
|---|---|
| 1.81 | 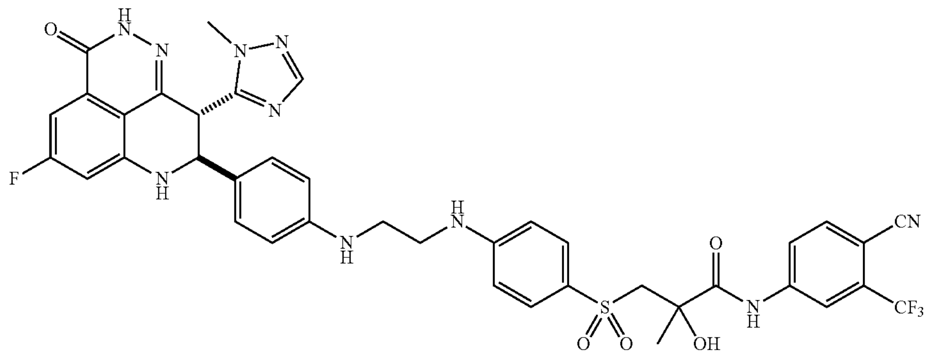 [SMILES: Cn1ncnc1[C@H]1c2n[nH]c(=O)c3cc(F)cc(c23)N[C@@H]1c1ccc(NCCNc2ccc(S(=O)(=O)CC(C)(O)C(=O)Nc3ccc(C#N)c(C(F)(F)F)c3)cc2)cc1] |
| 1.82 | 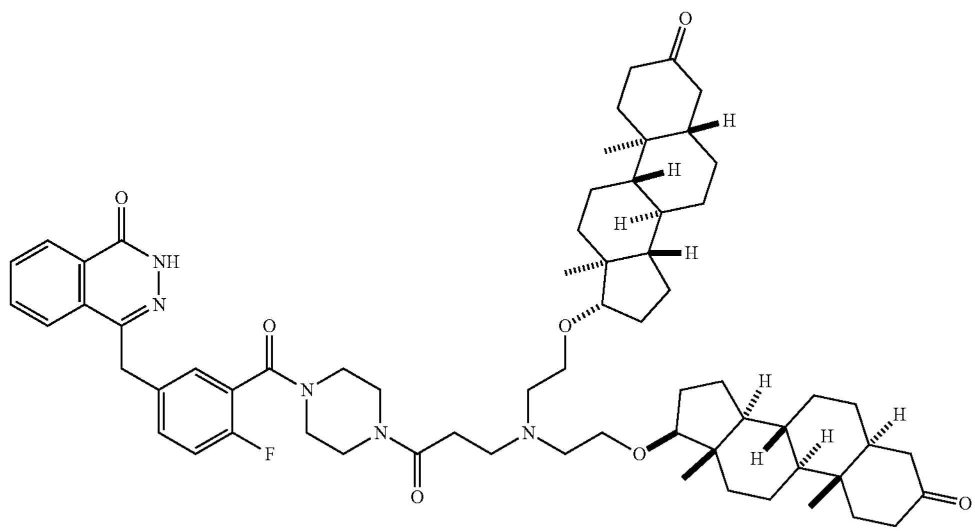 |
| 1.83 | 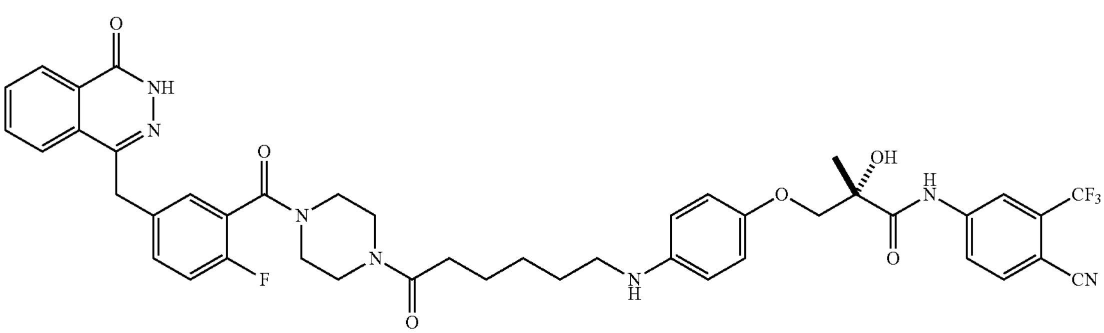 [SMILES: C[C@](O)(COc1ccc(NCCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.84 | 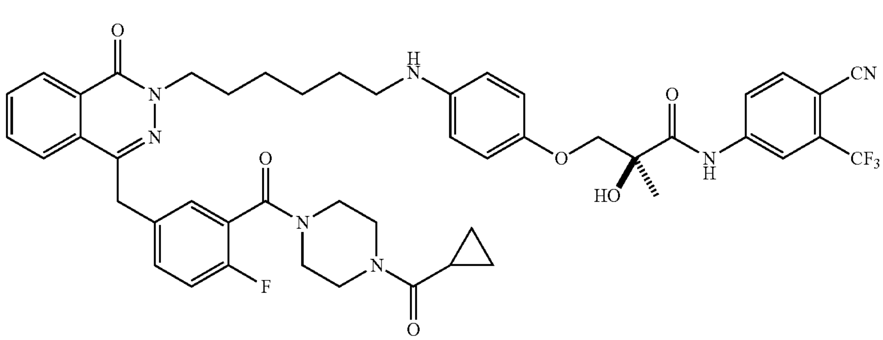 [SMILES: C[C@](O)(COc1ccc(NCCCCCCn2nc(Cc3ccc(F)c(C(=O)N4CCN(C(=O)C5CC5)CC4)c3)c3ccccc3c2=O)cc1)C(=O)Nc1ccc(C#N)c(C(F)(F)F)c1] |

TABLE 1-continued

| No. | Structure |
|---|---|
| 1.85 | 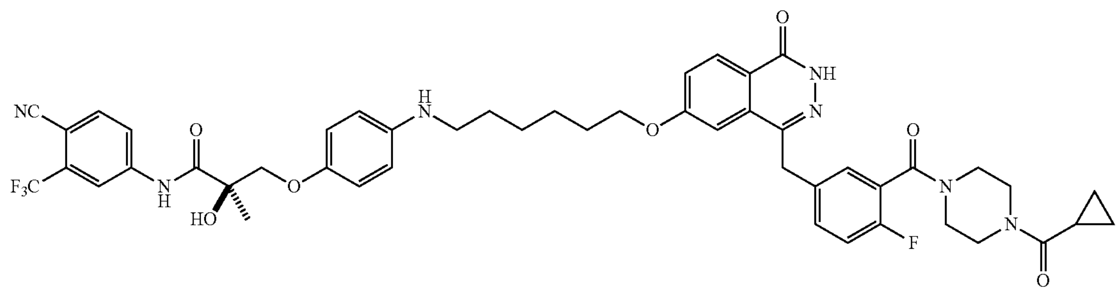 [SMILES: C[C@@](O)(COc1ccc(NCCCCCCOc2ccc3c(=O)[nH]nc(Cc4ccc(F)c(C(=O)N5CCN(C(=O)C6CC6)CC5)c4)c3c2)cc1)C(=O)Nc1ccc(C#N)c(C(F)(F)F)c1] |
| 1.86 | 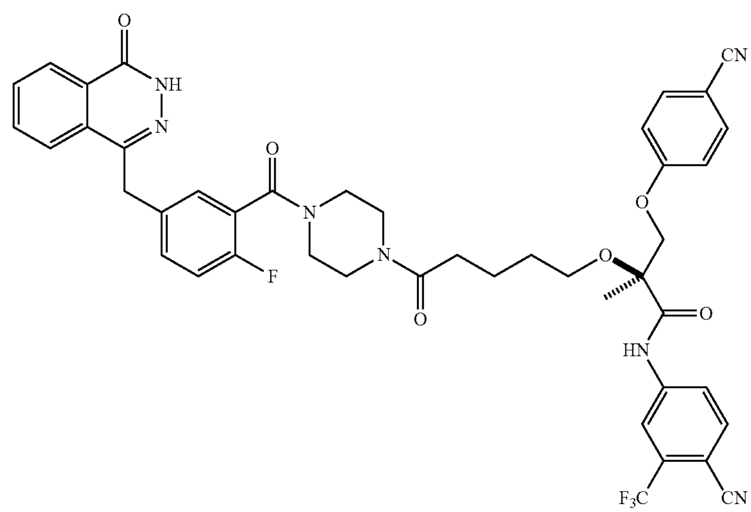 [SMILES: C[C@@](COc1ccc(C#N)cc1)(OCCCCC(=O)N1CCN(C(=O)c2cc(Cc3n[nH]c(=O)c4ccccc34)ccc2F)CC1)C(=O)Nc1ccc(C#N)c(C(F)(F)F)c1] |
| 1.87 | 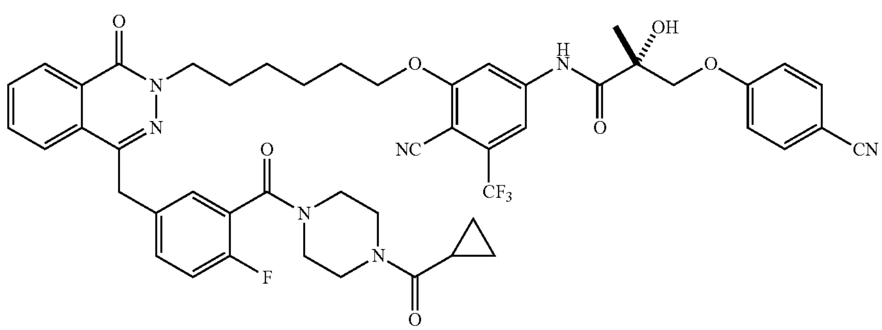 [SMILES: C[C@@](O)(COc1ccc(C#N)cc1)C(=O)Nc1cc(OCCCCCCn2nc(Cc3ccc(F)c(C(=O)N4CCN(C(=O)C5CC5)CC4)c3)c3ccccc3c2=O)c(C#N)c(C(F)(F)F)c1] |
| 1.88 | 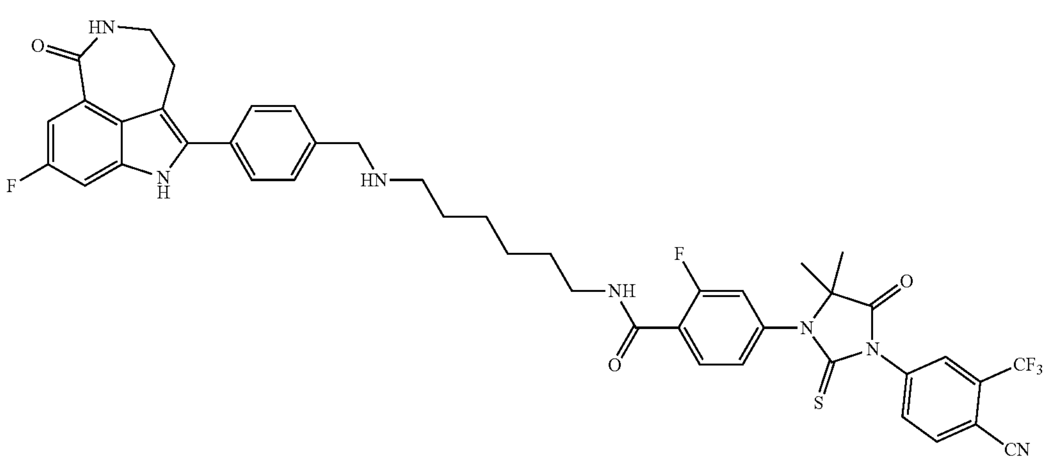 [SMILES: CC1(C)C(=O)N(c2ccc(C#N)c(C(F)(F)F)c2)C(=S)N1c1ccc(C(=O)NCCCCCCNCc2ccc(-c3[nH]c4cc(F)cc5c4c3CCNC5=O)cc2)c(F)c1] |

TABLE 1-continued

| No. | Structure |
|-----|-----------|
| 1.89 | 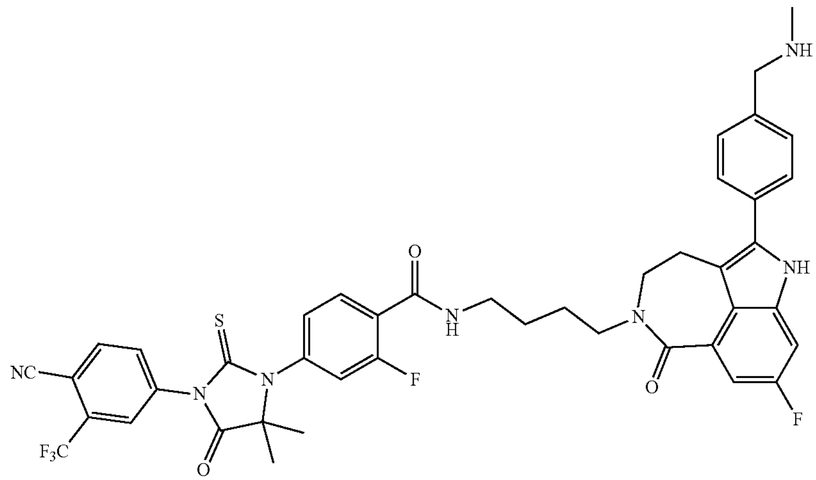 [SMILES: CNCc1ccc(-c2[nH]c3cc(F)cc4c3c2CCN(CCCCNC(=O)c2ccc(N3C(=S)N(c5ccc(C#N)c(C(F)(F)F)c5)C(=O)C3(C)C)cc2F)C4=O)cc1] |
| 1.90 | 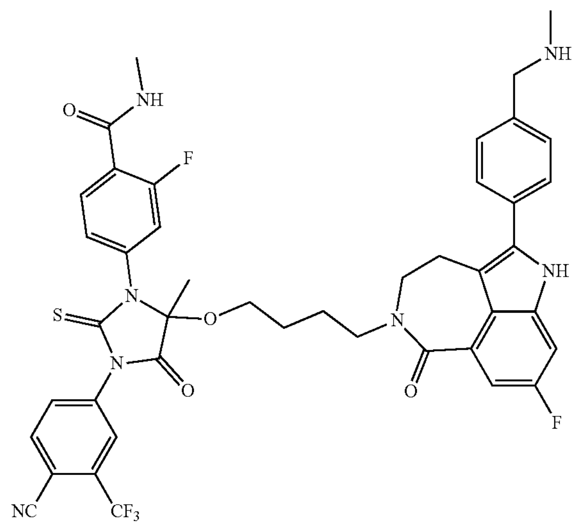 [SMILES: CNCc1ccc(-c2[nH]c3cc(F)cc4c3c2CCN(CCCCOC2(C)C(=O)N(c3ccc(C#N)c(C(F)(F)F)c3)C(=S)N2c2ccc(C(=O)NC)c(F)c2)C4=O)cc1] |
| 1.91 | 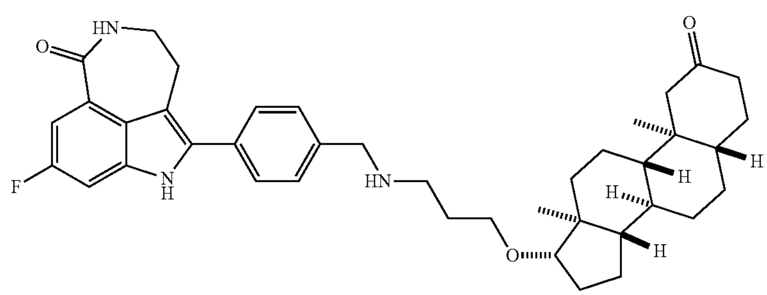 |
| 1.92 | 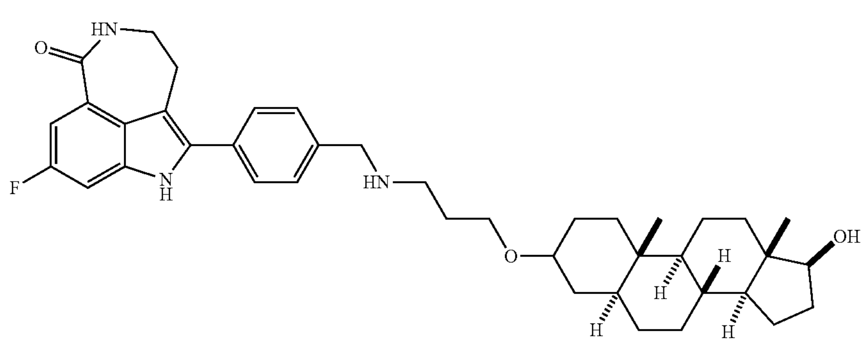 |

TABLE 1-continued

| No. | Structure |
| --- | --- |
| 1.93 | 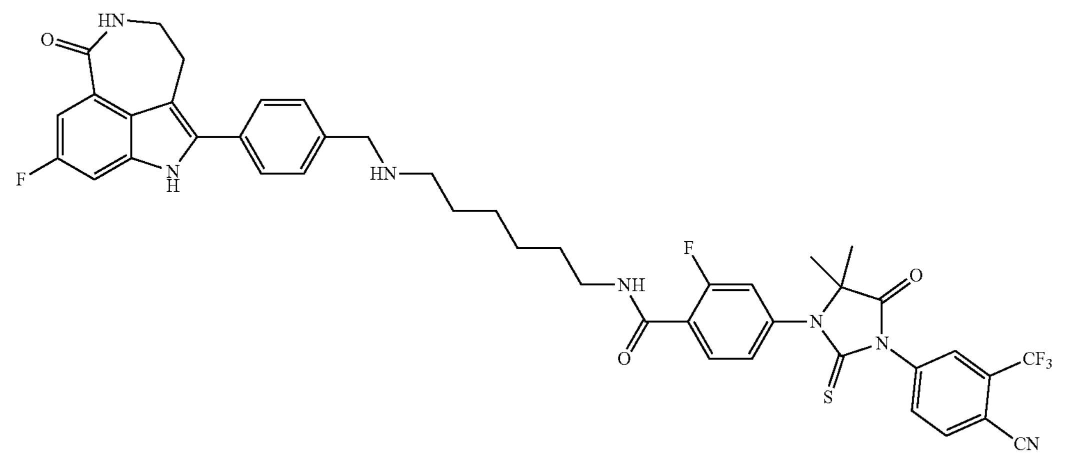 [SMILES: CC1(C)C(=O)N(c2ccc(C#N)c(C(F)(F)F)c2)C(=S)N1c1ccc(C(=O)NCCCCCCNCc2ccc(-c3[nH]c4cc(F)cc5c4c3CCNC5=O)cc2)c(F)c1] |
| 1.94 | 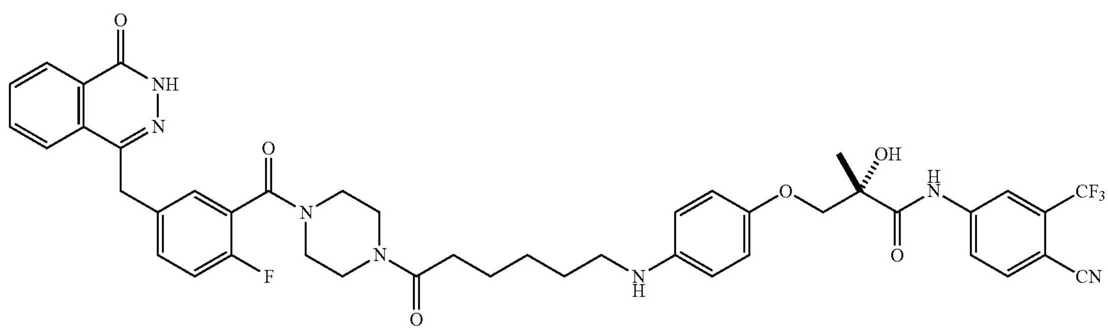 [SMILES: C[C@](O)(COc1ccc(NCCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.95 | 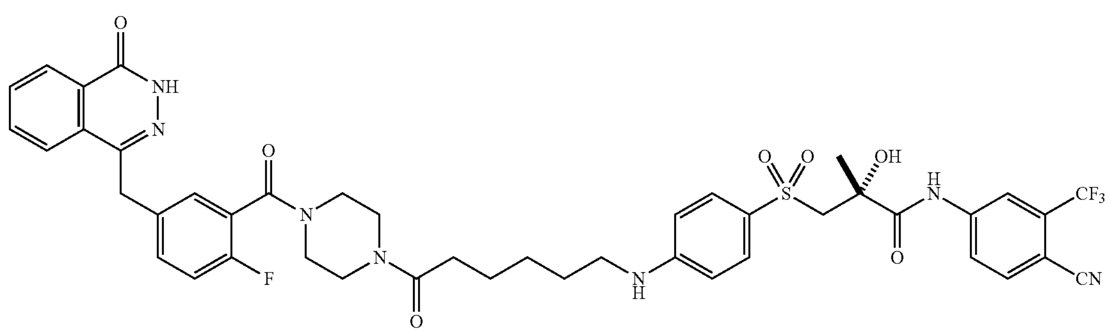 [SMILES: C[C@](O)(CS(=O)(=O)c1ccc(NCCCCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.96 | 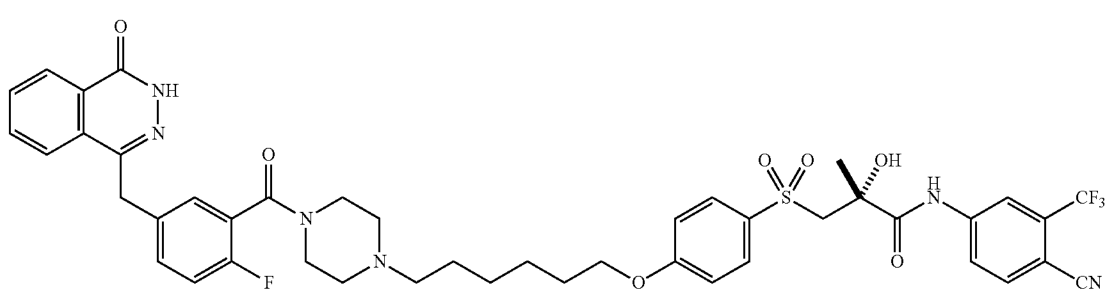 [SMILES: C[C@](O)(CS(=O)(=O)c1ccc(OCCCCCCN2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.97 | 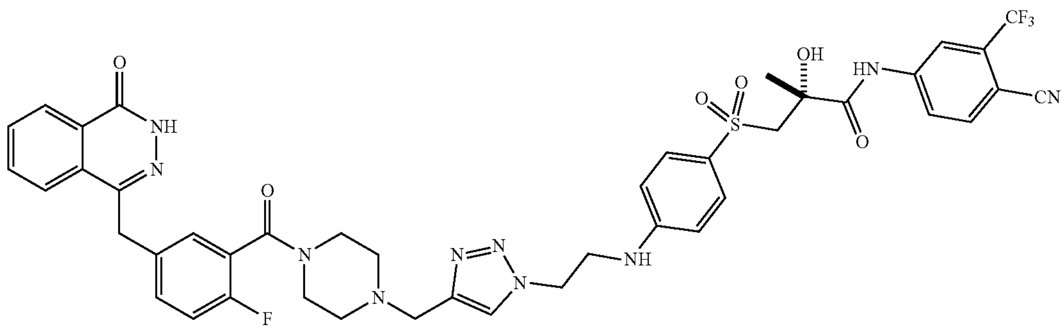 [SMILES: C[C@](O)(CS(=O)(=O)c1ccc(NCCn2cc(CN3CCN(C(=O)c4cc(Cc5n[nH]c(=O)c6ccccc56)ccc4F)CC3)nn2)cc1)C(=O)Nc1ccc(C#N)c(C(F)(F)F)c1] |
| 1.98 | 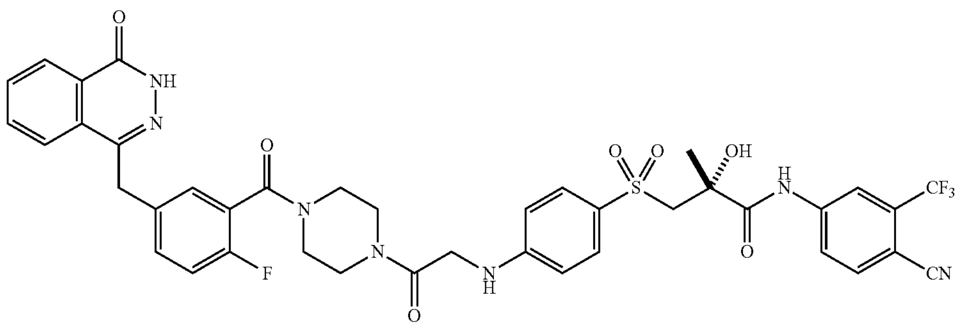 [SMILES: C[C@](O)(CS(=O)(=O)c1ccc(NCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.99 | 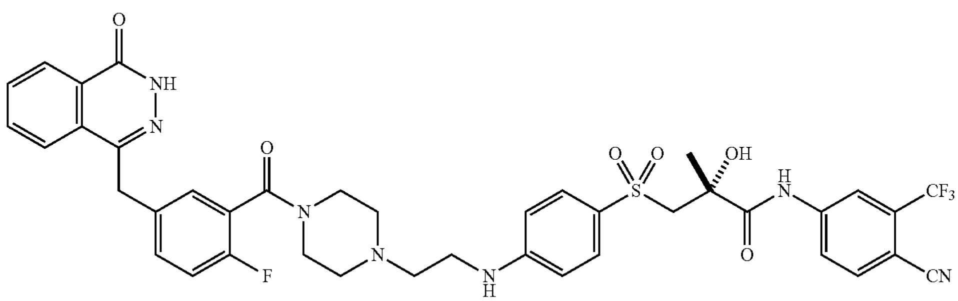 [SMILES: C[C@](O)(CS(=O)(=O)c1ccc(NCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.101 | 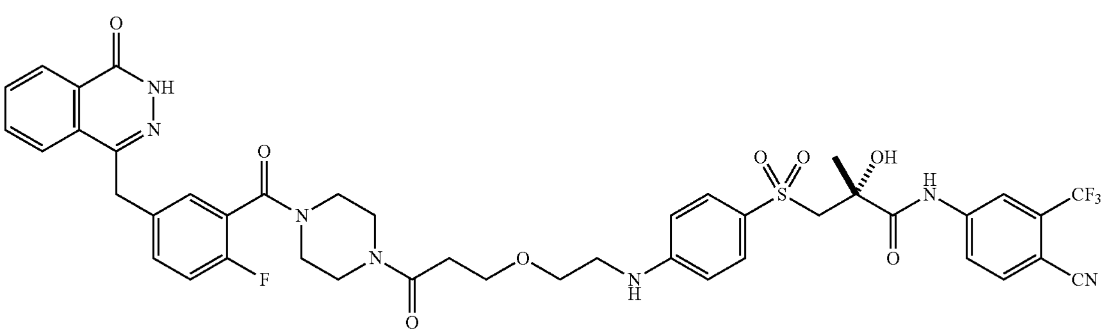 [SMILES: C[C@](O)(CS(=O)(=O)c1ccc(NCCOCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.102 | 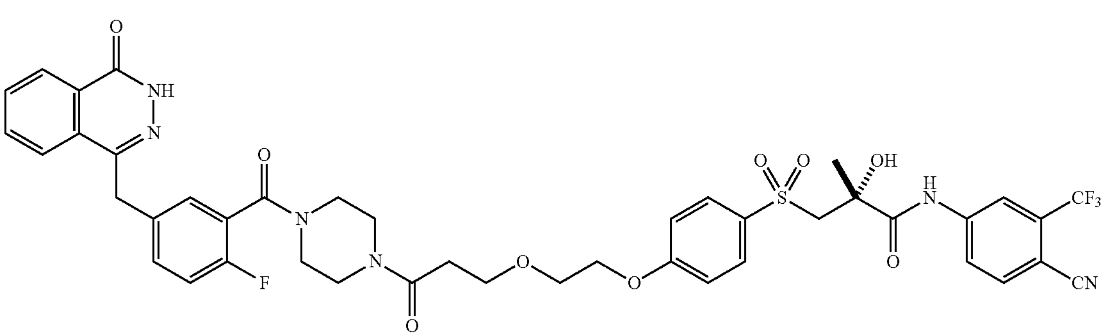 [SMILES: C[C@](O)(CS(=O)(=O)c1ccc(OCCOCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.103 | 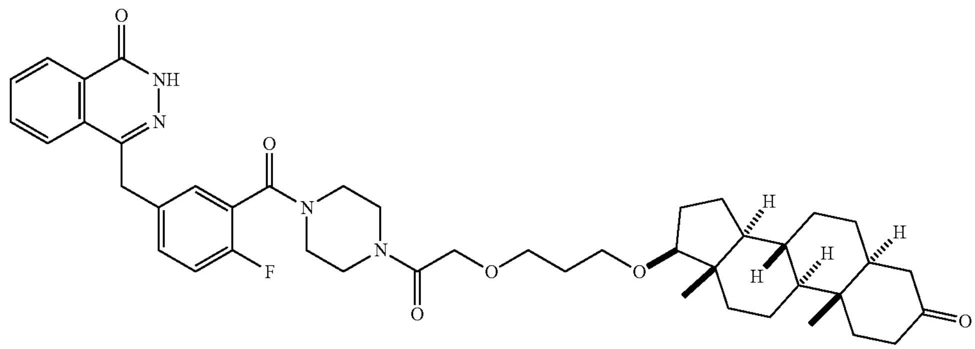 |
| 1.104 | 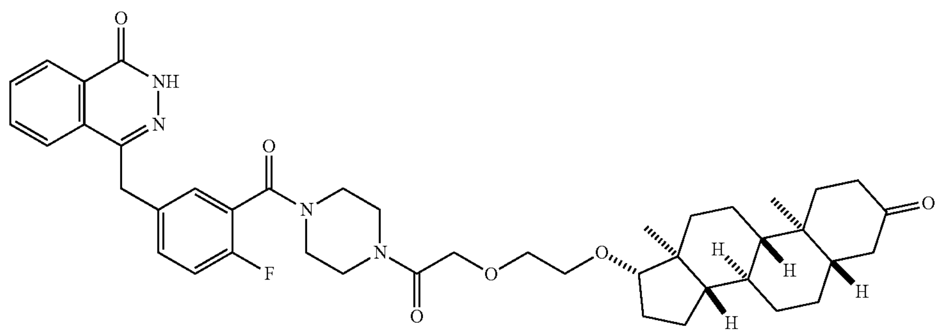 |
| 1.105 | 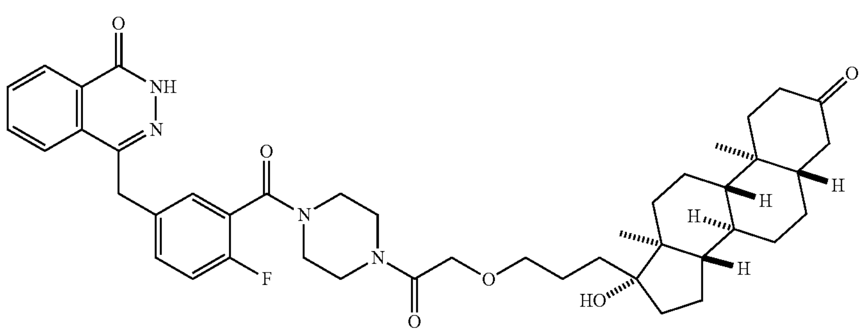 |
| 1.106 | 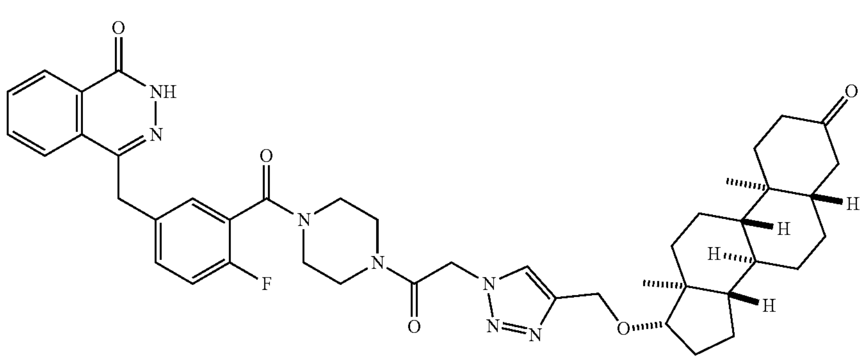 |

TABLE 1-continued

| No. | Structure |
|---|---|
| 1.107 | 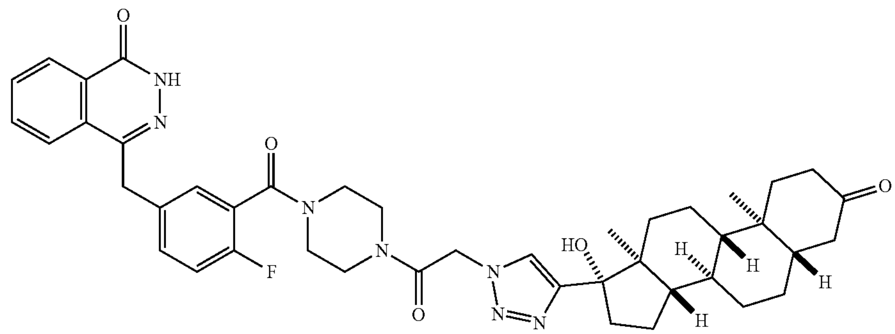 |
| 1.108 | 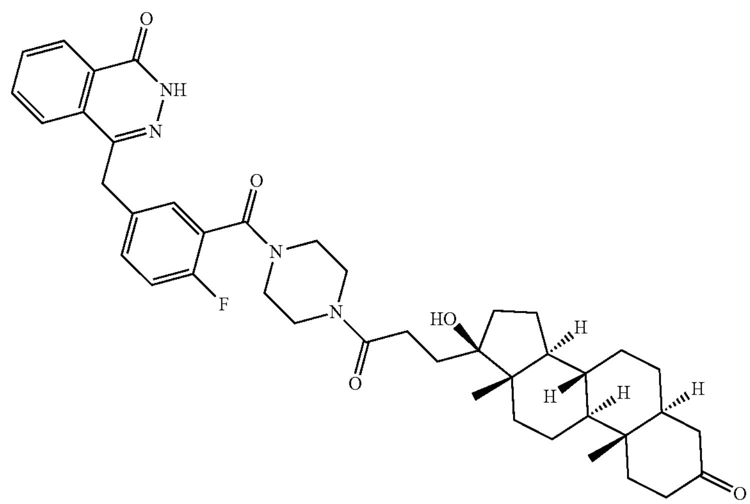 |
| 1.109 | 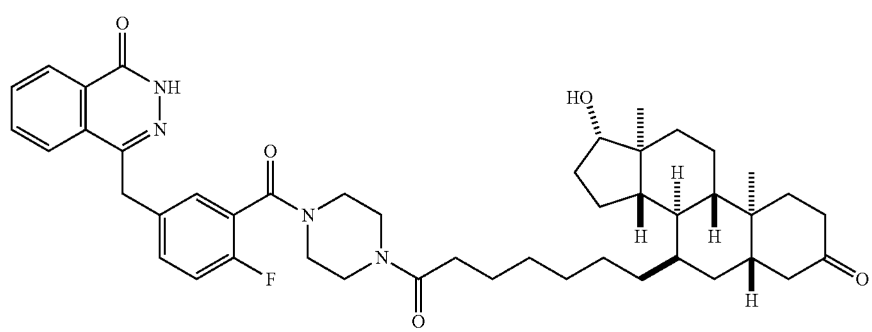 |
| 1.110 | 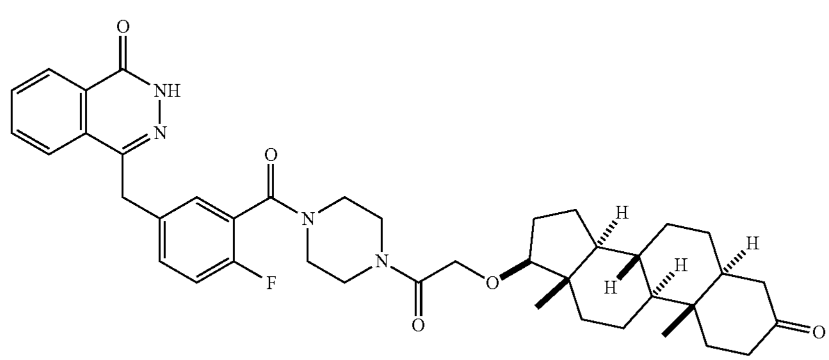 |

TABLE 1-continued

| No. | Structure |
| --- | --- |
| 1.111 | 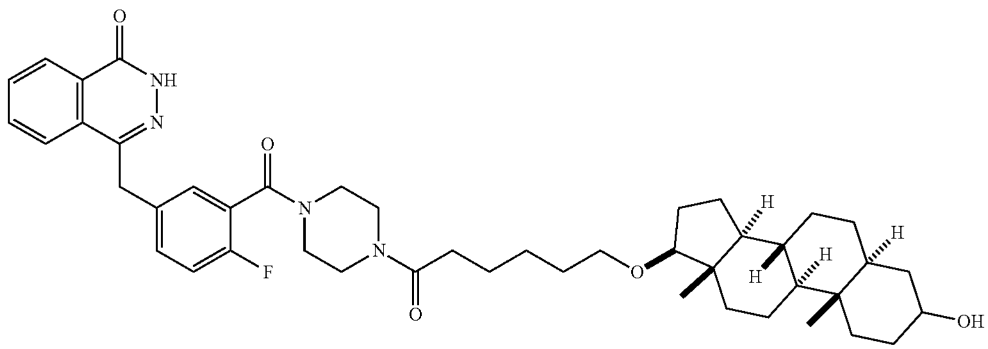 |
| 1.112 | 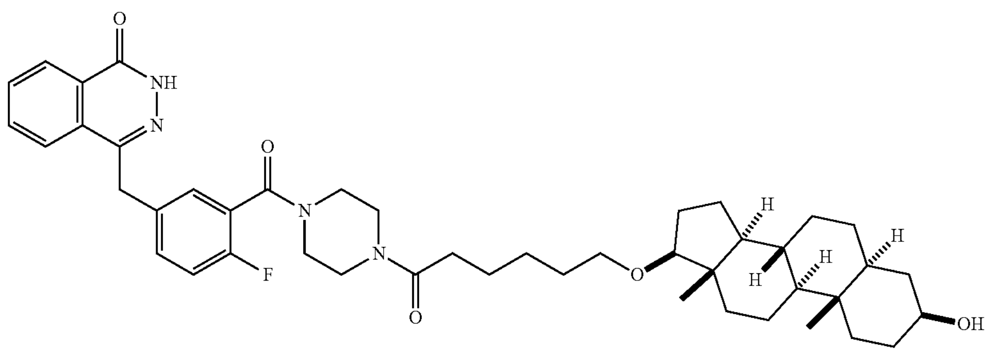 |
| 1.113 | 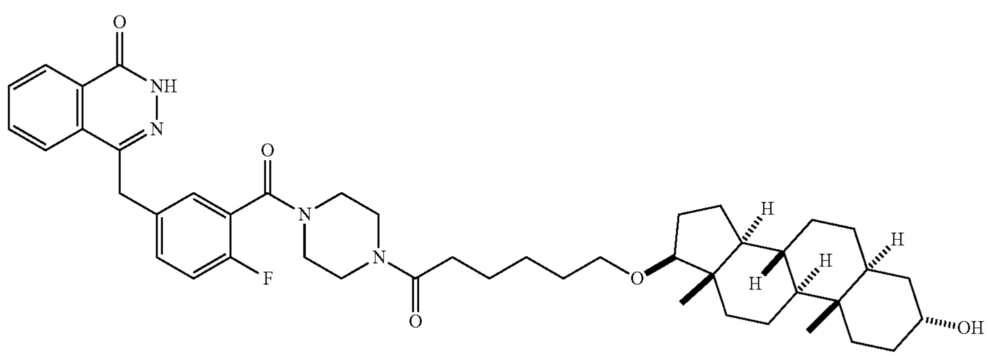 |
| 1.114 | 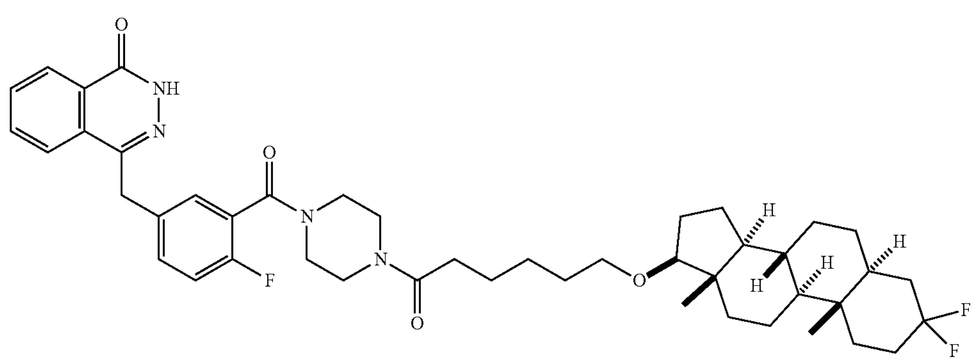 |

TABLE 1-continued

| No. | Structure |
| --- | --- |
| 1.115 | 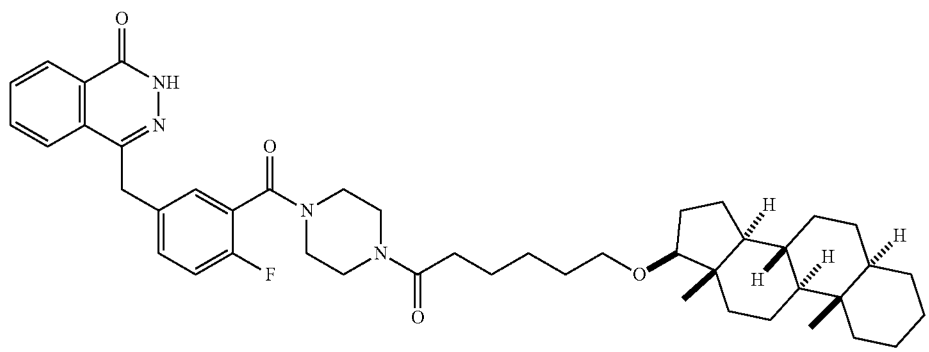 |
| 1.116 | 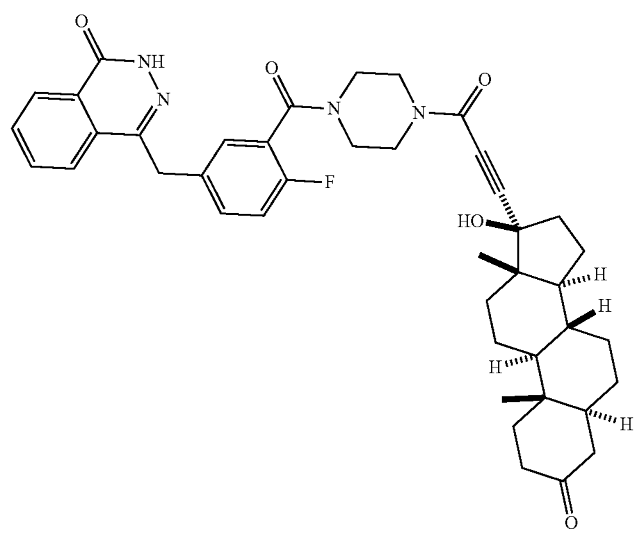 |
| 1.117 | 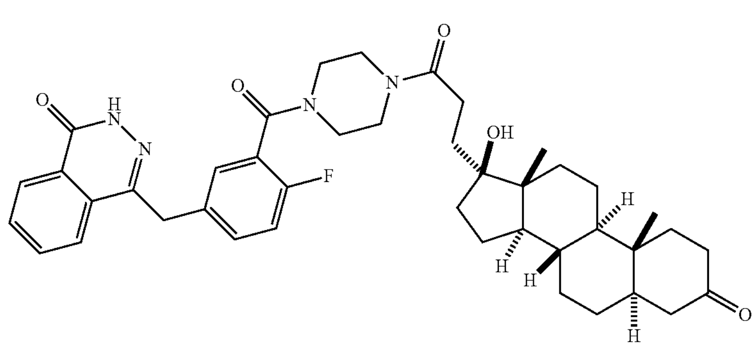 |

TABLE 1-continued

| No. | Structure |
|---|---|
| 1.118 | 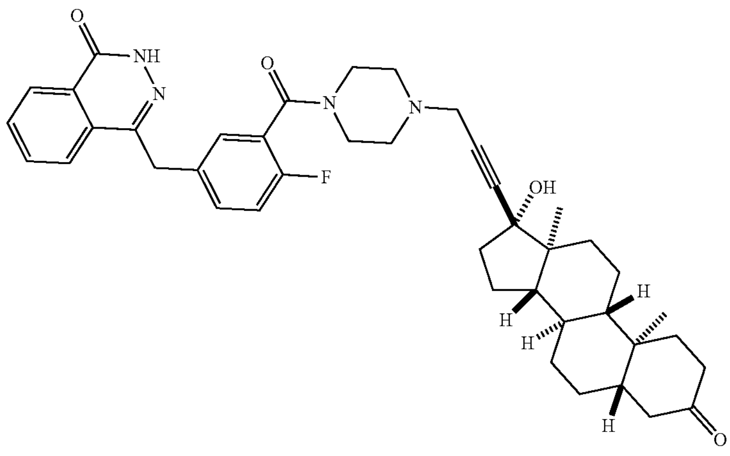 |
| 1.119 | 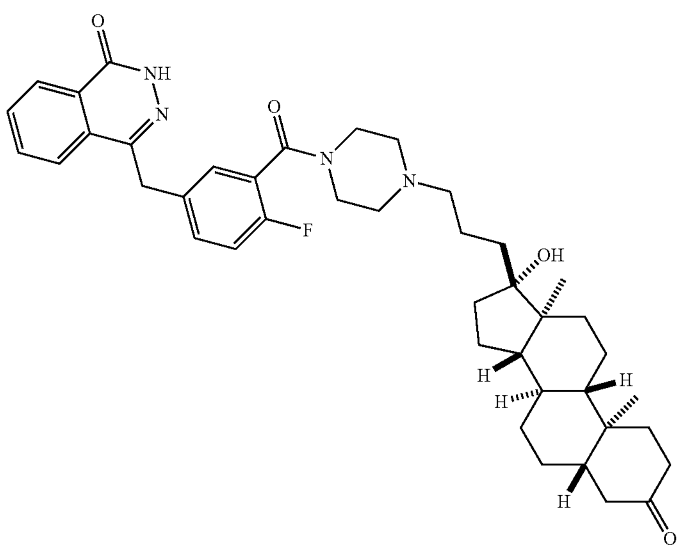 |
| 1.120 | 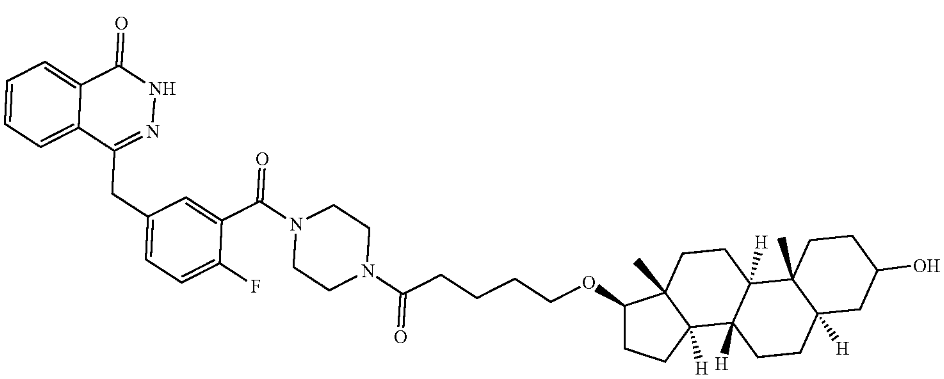 [SMILES: C[C@@]12CCC(O)C[C@H]1CC[C@H]1[C@H]2CC[C@]2(C)[C@@H]1CC[C@H]2OCCCCC(=O)N1CCN(C(=O)c2cc(Cc3n[nH]c(=O)c4ccccc34)ccc2F)CC1] |
| 1.121 | 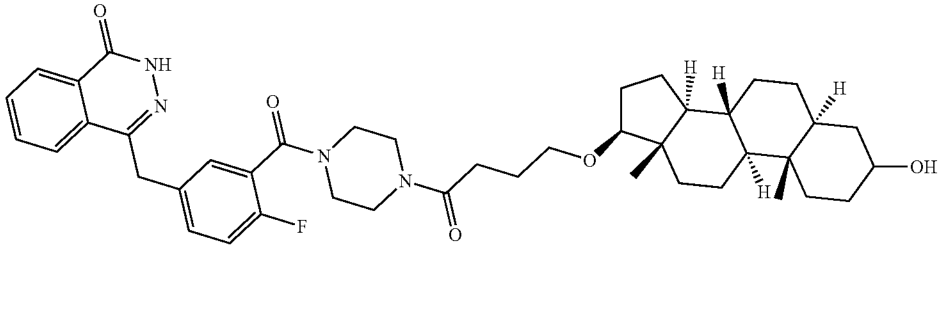 [SMILES: C[C@]12CCC(O)C[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |

TABLE 1-continued

| No. | Structure |
|---|---|
| 1.122 | 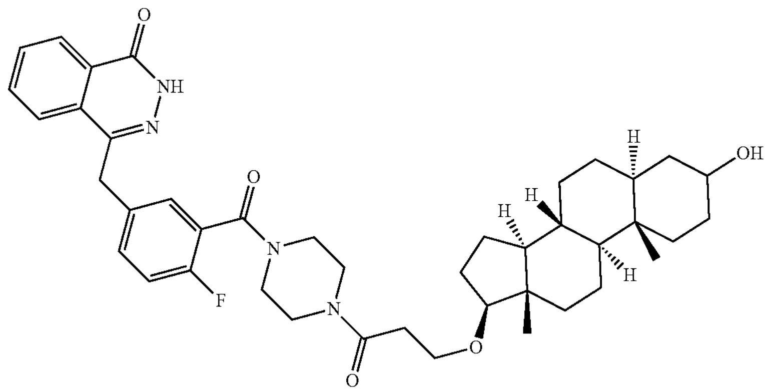 [SMILES: C[C@]12CCC(O)C[C@@H]1CC[C@@H]1[C@@H]2CC[C@]2(C)[C@@H](OCCC(=O)N3CCN(C(=O)c4cc(Cc5n[nH]c(=O)c6ccccc56)ccc4F)CC3)CC[C@@H]12] |
| 1.123 | 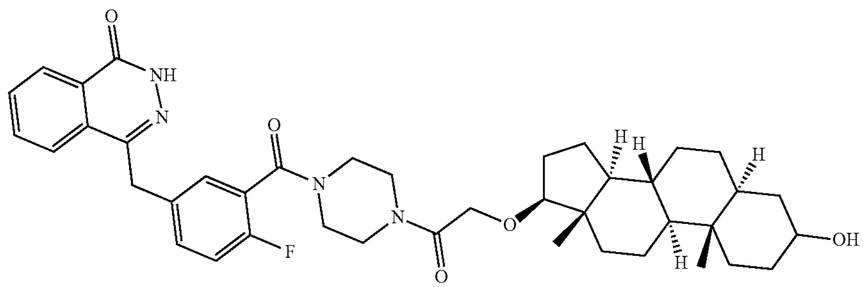 [SMILES: C[C@]12CCC(O)C[C@@H]1CC[C@@H]1[C@@H]2CC[C@]2(C)[C@@H](OCC(=O)N3CCN(C(=O)c4cc(Cc5n[nH]c(=O)c6ccccc56)ccc4F)CC3)CC[C@@H]12] |
| 1.124 | 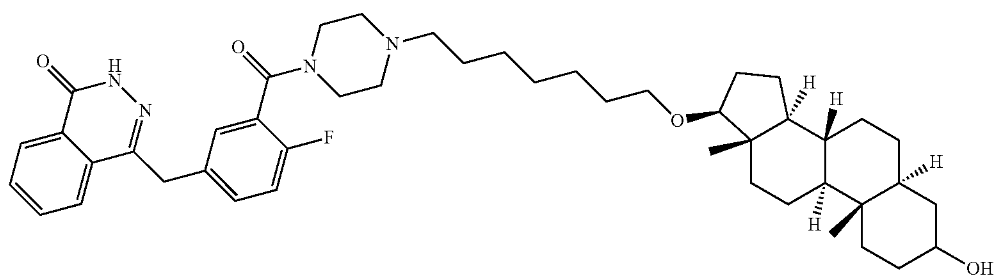 [SMILES: C[C@]12CCC(O)C[C@@H]1CC[C@@H]1[C@@H]2CC[C@]2(C)[C@@H](OCCCCCCCN3CCN(C(=O)c4cc(Cc5n[nH]c(=O)c6ccccc56)ccc4F)CC3)CC[C@@H]12] |
| 1.125 | 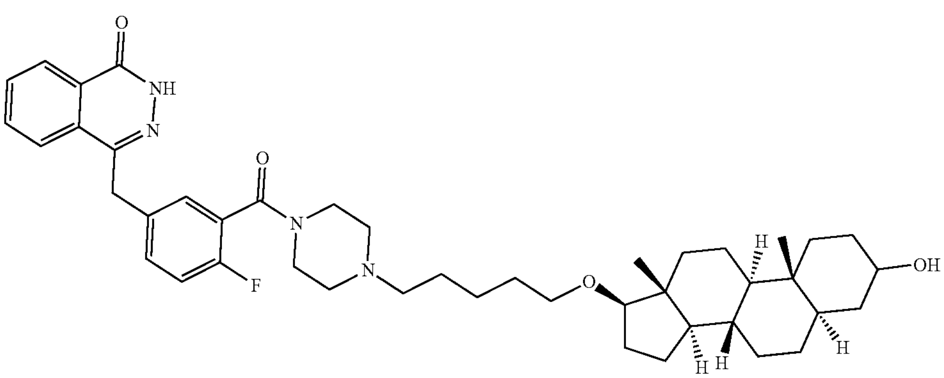 [SMILES: C[C@@]12CCC(O)C[C@H]1CC[C@H]1[C@H]2CC[C@]2(C)[C@@H]1CC[C@H]2OCCCCCN1CCN(C(=O)c2cc(Cc3n[nH]c(=O)c4ccccc34)ccc2F)CC1] |
| 1.126 | 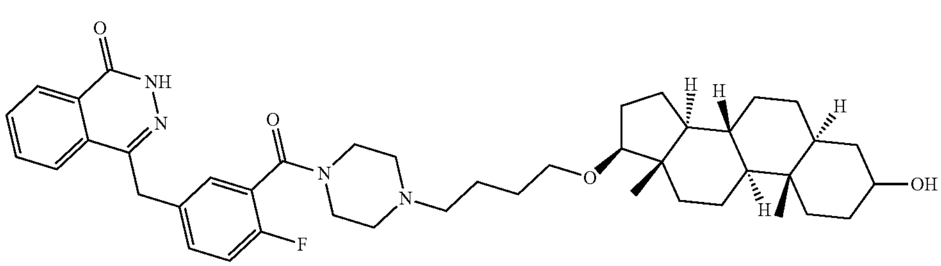 [SMILES: C[C@]12CCC(O)C[C@@H]1CC[C@@H]1[C@@H]2CC[C@]2(C)[C@@H](OCCCCN3CCN(C(=O)c4cc(Cc5n[nH]c(=O)c6ccccc56)ccc4F)CC3)CC[C@@H]12] |

TABLE 1-continued
| No. | Structure |
|---|---|
| 1.127 | 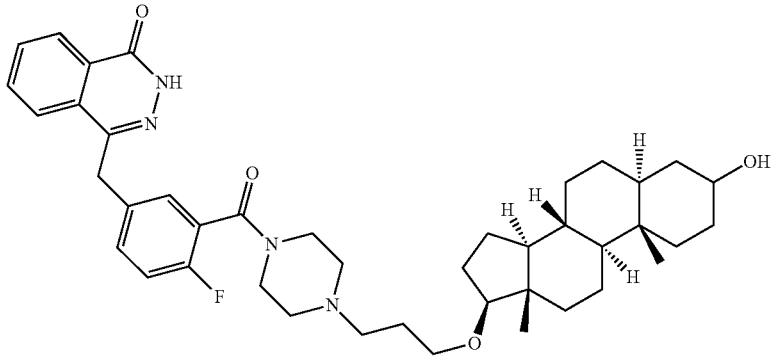 [SMILES: C[C@]12CCC(O)C[C@@H]1CC[C@@H]1[C@@H]2CC[C@]2(C)[C@@H](OCCCN3CCN(C(=O)c4cc(Cc5n[nH]c(=O)c6ccccc56)ccc4F)CC3)CC[C@@H]12] |
| 1.128 | 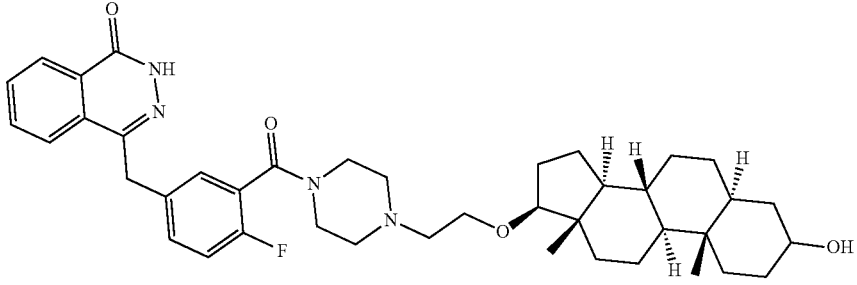 [SMILES: C[C@]12CCC(O)C[C@@H]1CC[C@@H]1[C@@H]2CC[C@]2(C)[C@@H](OCCN3CCN(C(=O)c4cc(Cc5n[nH]c(=O)c6ccccc56)ccc4F)CC3)CC[C@@H]12] |
| 1.129 | 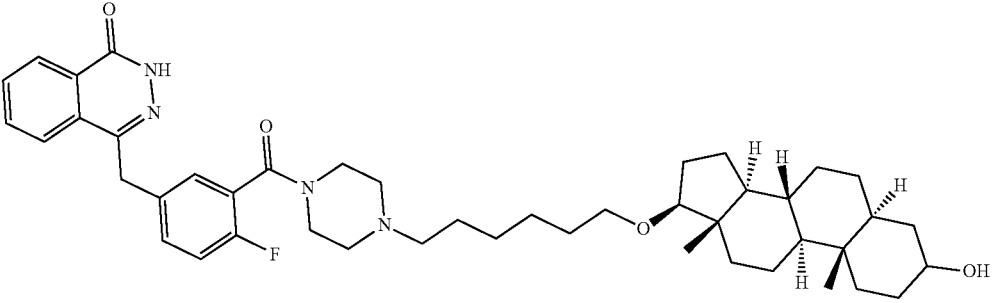 [SMILES: C[C@]12CCC(O)C[C@@H]1CC[C@@H]1[C@@H]2CC[C@]2(C)[C@@H](OCCCCCCN3CCN(C(=O)c4cc(Cc5n[nH]c(=O)c6ccccc56)ccc4F)CC3)CC[C@@H]12] |
| 1.130 | 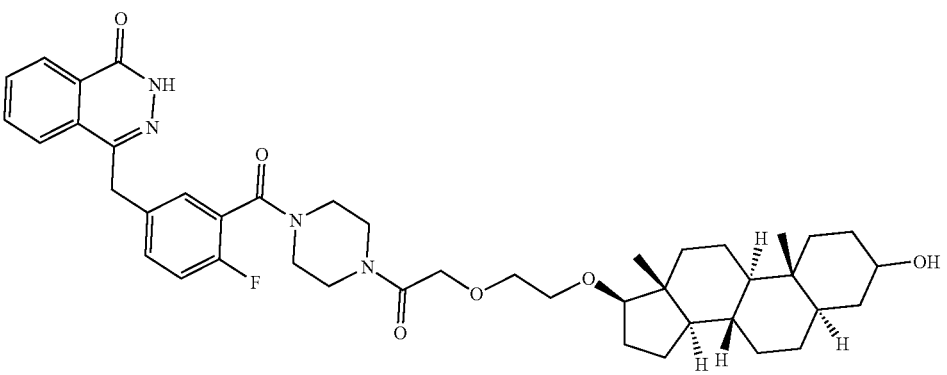 [SMILES: C[C@@]12CCC(O)C[C@H]1CC[C@H]1[C@H]2CC[C@]2(C)[C@@H]1CC[C@H]2OCCOCC(=O)N1CCN(C(=O)c2cc(Cc3n[nH]c(=O)c4ccccc34)ccc2F)CC1] |

TABLE 1-continued

| No. | Structure |
| --- | --- |
| 1.131 | 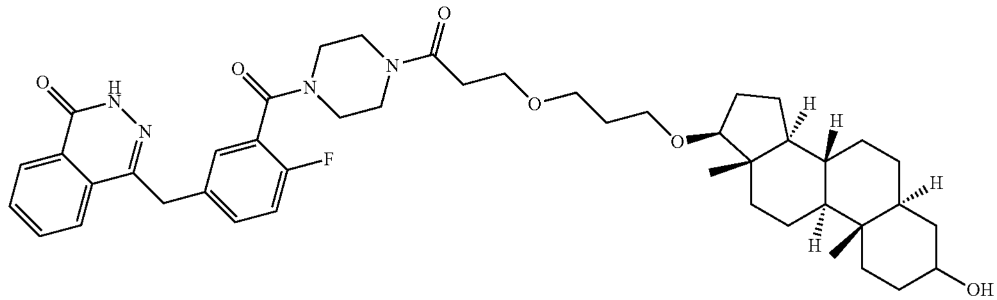 [SMILES: C[C@]12CCC(O)C[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.132 | 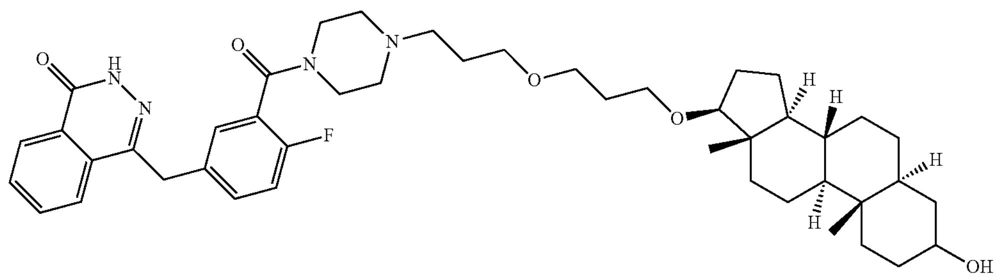 [SMILES: C[C@]12CCC(O)C[C@@H]1CC[C@@H]1[C@@H]2CC[C@]2(C)[C@@H](OCCCOCCCN3CCN(C(=O)c4cc(Cc5n[nH]c(=O)c6ccccc56)ccc4F)CC3)CC[C@@H]12] |
| 1.133 | 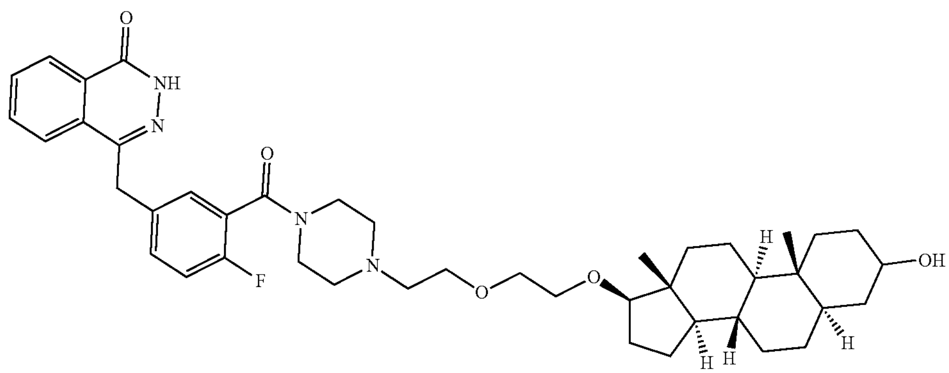 |
| 1.134 | 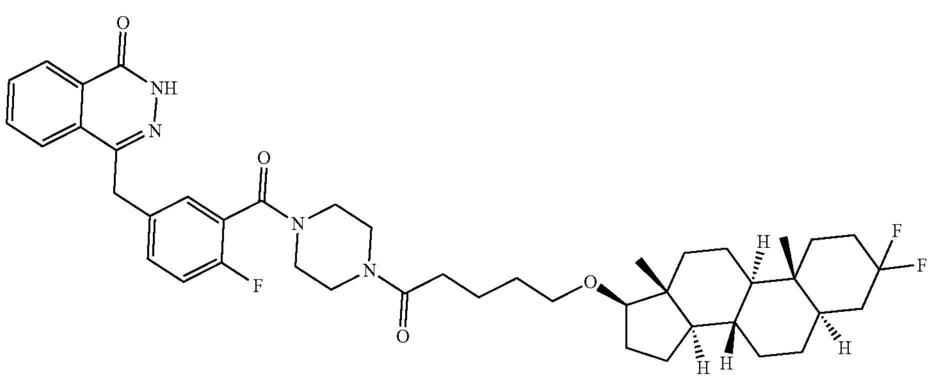 [SMILES: C[C@@]12CCC(F)(F)C[C@H]1CC[C@H]1[C@H]2CC[C@]2(C)[C@@H]1CC[C@H]2OCCCCC(=O)N1CCN(C(=O)c2cc(Cc3n[nH]c(=O)c4ccccc34)ccc2F)CC1] |
| 1.135 | 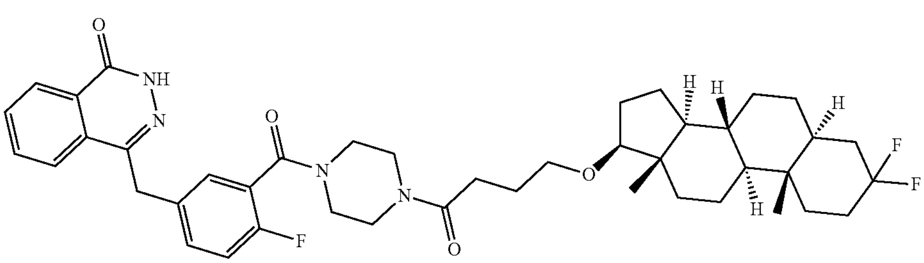 [SMILES: C[C@]12CCC(F)(F)C[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |

TABLE 1-continued

| No. | Structure |
|---|---|
| 1.136 | 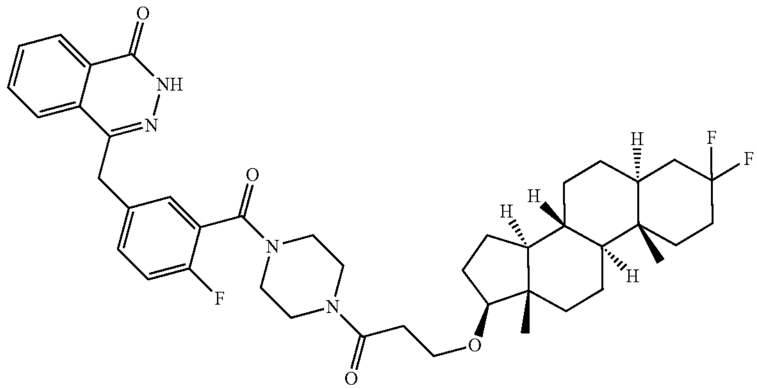 [SMILES: C[C@]12CCC(F)(F)C[C@@H]1CC[C@@H]1[C@@H]2CC[C@]2(C)[C@@H](OCCC(=O)N3CCN(C(=O)c4cc(Cc5n[nH]c(=O)c6ccccc56)ccc4F)CC3)CC[C@@H]12] |
| 1.137 | 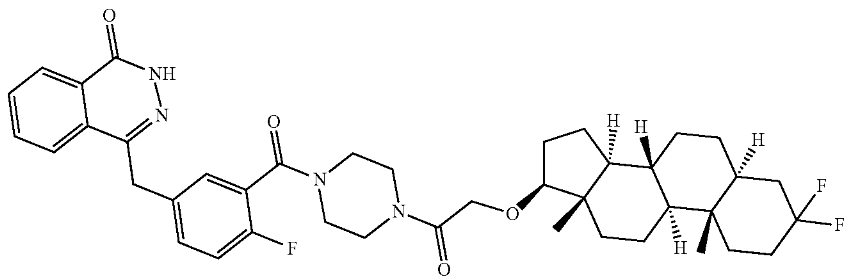 [SMILES: C[C@]12CCC(F)(F)C[C@@H]1CC[C@@H]1[C@@H]2CC[C@]2(C)[C@@H](OCC(=O)N3CCN(C(=O)c4cc(Cc5n[nH]c(=O)c6ccccc56)ccc4F)CC3)CC[C@@H]12] |
| 1.138 | 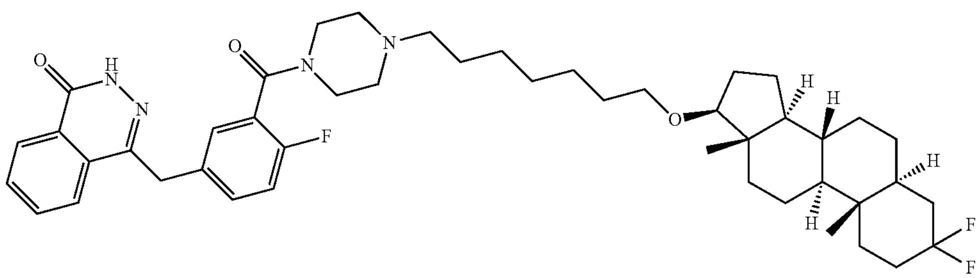 [SMILES: C[C@]12CCC(F)(F)C[C@@H]1CC[C@@H]1[C@@H]2CC[C@]2(C)[C@@H](OCCCCCCCN3CCN(C(=O)c4cc(Cc5n[nH]c(=O)c6ccccc56)ccc4F)CC3)CC[C@@H]12] |
| 1.139 | 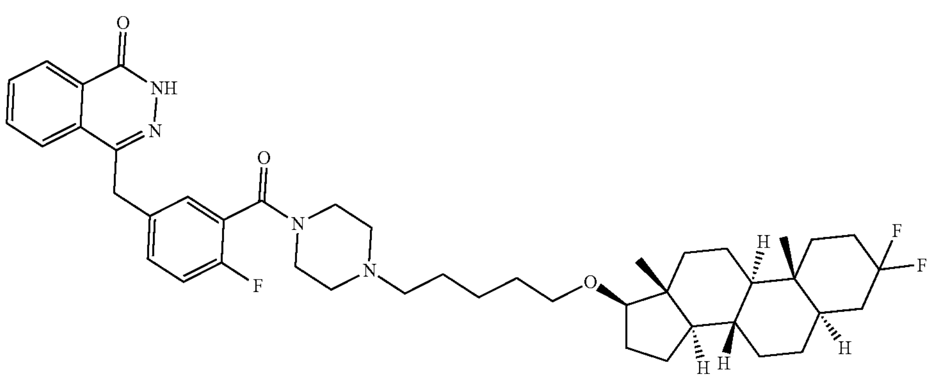 [SMILES: C[C@@]12CCC(F)(F)C[C@H]1CC[C@H]1[C@H]2CC[C@]2(C)[C@@H]1CC[C@H]2OCCCCCN1CCN(C(=O)c2cc(Cc3n[nH]c(=O)c4ccccc34)ccc2F)CC1] |
| 1.140 | 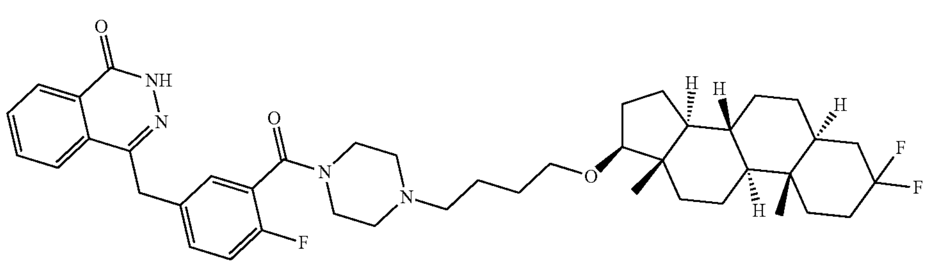 [SMILES: C[C@]12CCC(F)(F)C[C@@H]1CC[C@@H]1[C@@H]2CC[C@]2(C)[C@@H](OCCCCN3CCN(C(=O)c4cc(Cc5n[nH]c(=O)c6ccccc56)ccc4F)CC3)CC[C@@H]12] |

TABLE 1-continued
| No. | Structure |
|---|---|
| 1.141 | 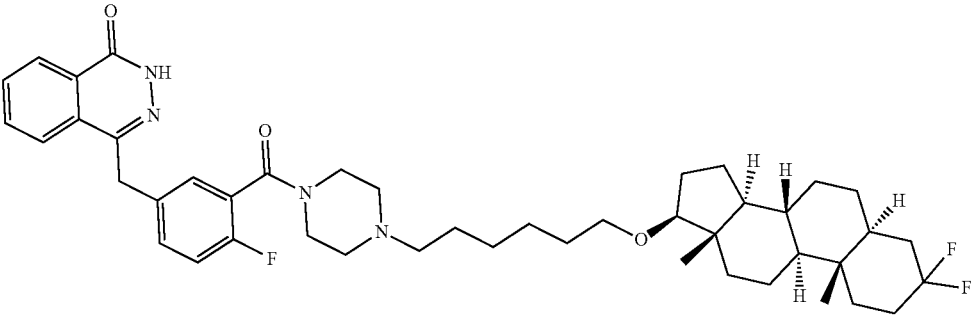 [SMILES: C[C@]12CCC(F)(F)C[C@@H]1CC[C@@H]1[C@@H]2CC[C@]2(C)[C@@H](OCCCCCCN3CCN(C(=O)c4cc(Cc5n[nH]c(=O)c6ccccc56)ccc4F)CC3)CC[C@@H]12] |
| 1.142 | 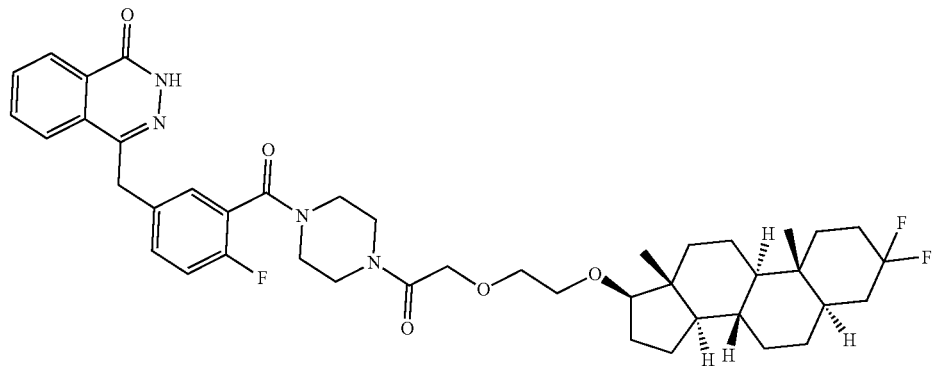 [SMILES: C[C@@]12CCC(F)(F)C[C@H]1CC[C@H]1[C@H]2CC[C@]2(C)[C@@H]1CC[C@H]2OCCOCC(=O)N1CCN(C(=O)c2cc(Cc3n[nH]c(=O)c4ccccc34)ccc2F)CC1] |
| 1.143 | 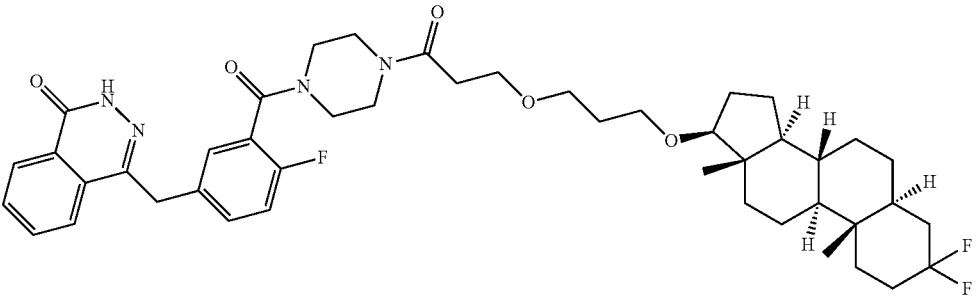 [SMILES: C[C@]12CCC(F)(F)C[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.144 | 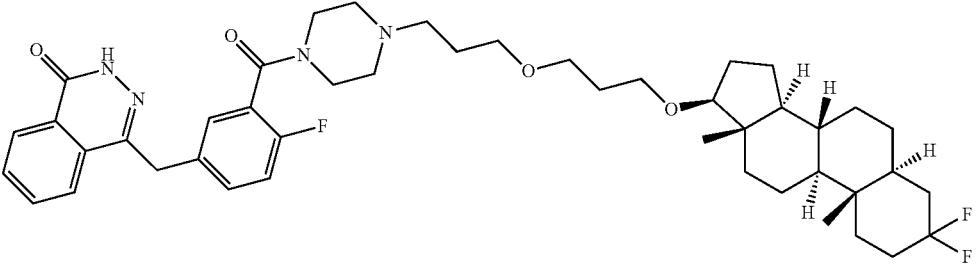 [SMILES: C[C@]12CCC(F)(F)C[C@@H]1CC[C@@H]1[C@@H]2CC[C@]2(C)[C@@H](OCCCOCCCN3CCN(C(=O)c4cc(Cc5n[nH]c(=O)c6ccccc56)ccc4F)CC3)CC[C@@H]12] |

TABLE 1-continued

| No. | Structure |
|---|---|
| 1.145 | 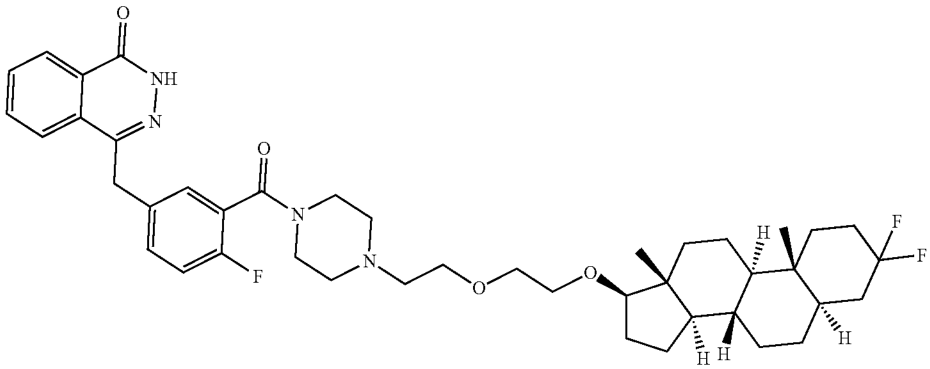 [SMILES: C[C@@]12CCC(F)(F)C[C@H]1CC[C@H]1[C@H]2CC[C@]2(C)[C@@H]1CC[C@H]2OCCOCCN1CCN(C(=O)c2cc(Cc3n[nH]c(=O)c4ccccc34)ccc2F)CC1] |
| 1.146 | 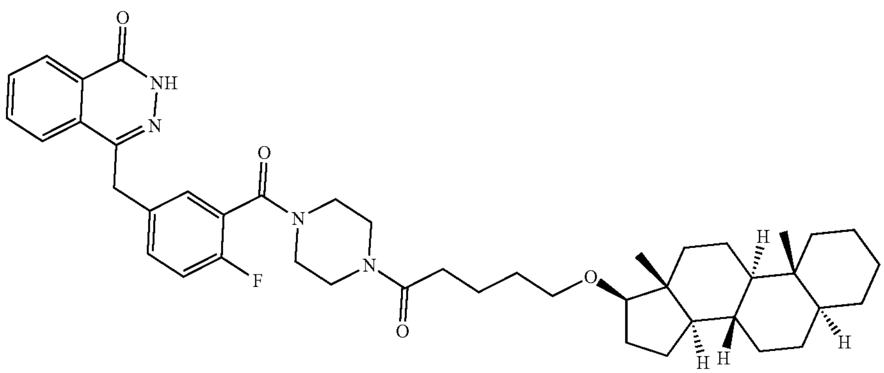 [SMILES: C[C@@]12CCCC[C@H]1CC[C@H]1[C@H]2CC[C@]2(C)[C@@H]1CC[C@H]2OCCCCC(=O)N1CCN(C(=O)c2cc(Cc3n[nH]c(=O)c4ccccc34)ccc2F)CC1] |
| 1.147 | 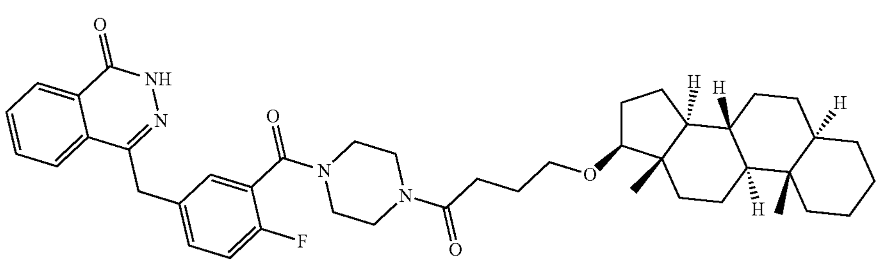 [SMILES: C[C@]12CCCC[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |
| 1.148 | 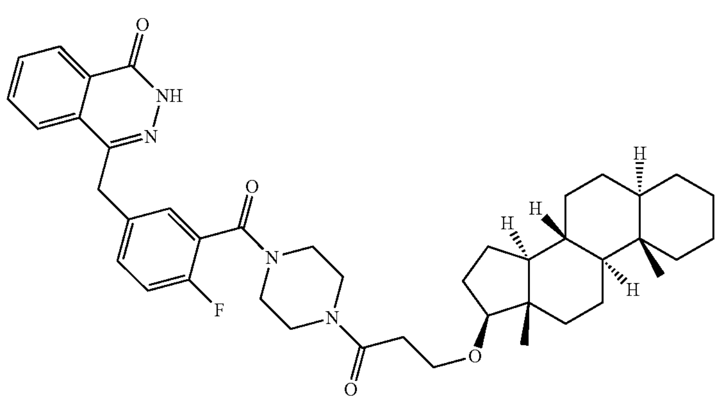 [SMILES: C[C@]12CCCC[C@@H]1CC[C@@H]1[C@@H]2CC[C@]2(C)[C@@H](OCCC(=O)N3CCN(C(=O)c4cc(Cc5n[nH]c(=O)c6ccccc56)ccc4F)CC3)CC[C@@H]12] |

TABLE 1-continued

| No. | Structure |
|---|---|
| 1.149 | 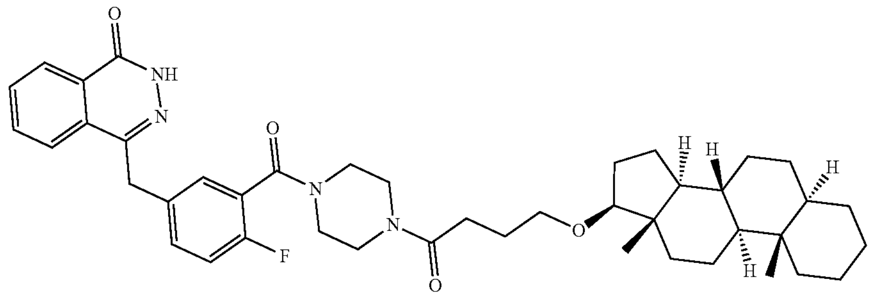 [SMILES: C[C@]12CCCC[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |
| 1.150 | 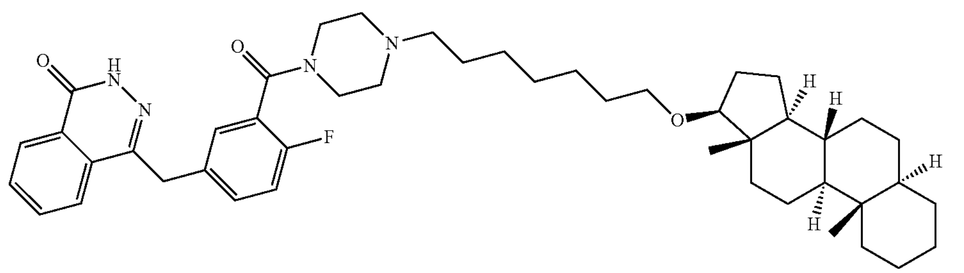 [SMILES: C[C@]12CCCC[C@@H]1CC[C@@H]1[C@@H]2CC[C@]2(C)[C@@H](OCCCCCCCN3CCN(C(=O)c4cc(Cc5n[nH]c(=O)c6ccccc56)ccc4F)CC3)CC[C@@H]12] |
| 1.151 | 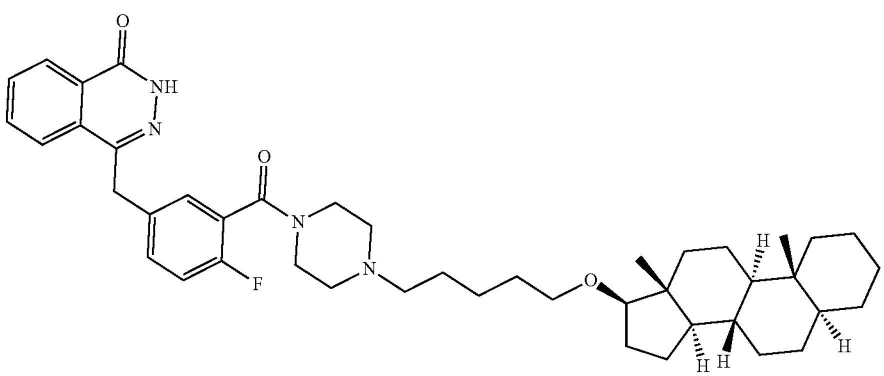 [SMILES: C[C@@]12CCCC[C@H]1CC[C@H]1[C@H]2CC[C@]2(C)[C@@H]1CC[C@H]2OCCCCCN1CCN(C(=O)c2cc(Cc3n[nH]c(=O)c4ccccc34)ccc2F)CC1] |
| 1.152 | 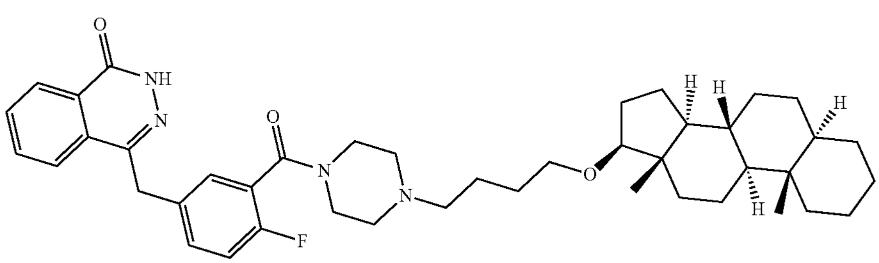 [SMILES: C[C@]12CCCC[C@@H]1CC[C@@H]1[C@@H]2CC[C@]2(C)[C@@H](OCCCCN3CCN(C(=O)c4cc(Cc5n[nH]c(=O)c6ccccc56)ccc4F)CC3)CC[C@@H]12] |
| 1.153 | 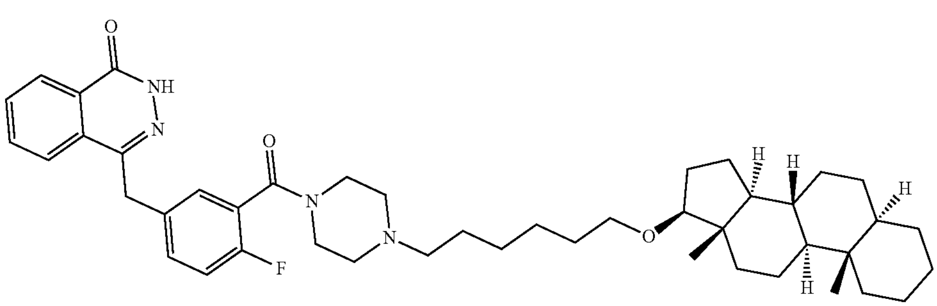 [SMILES: C[C@]12CCCC[C@@H]1CC[C@@H]1[C@@H]2CC[C@]2(C)[C@@H](OCCCCCCN3CCN(C(=O)c4cc(Cc5n[nH]c(=O)c6ccccc56)ccc4F)CC3)CC[C@@H]12] |

TABLE 1-continued

| No. | Structure |
|---|---|
| 1.154 | 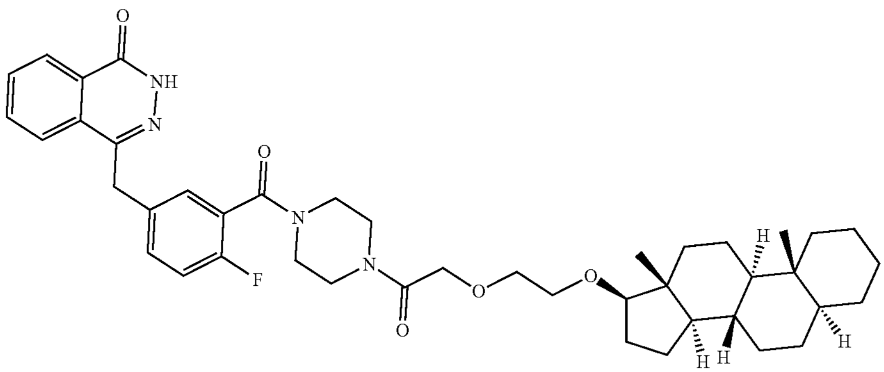 |
| 1.155 | 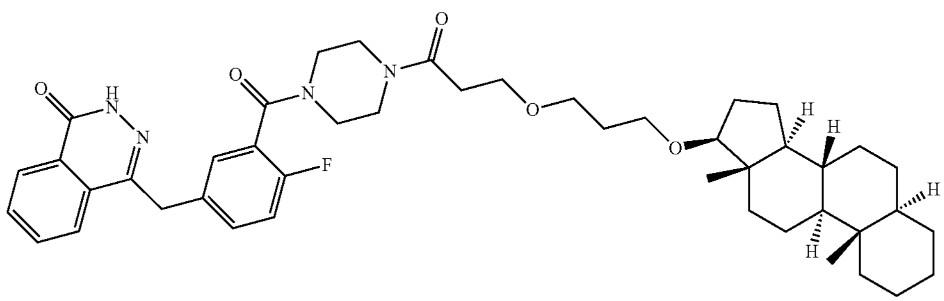 [SMILES: C[C@]12CCCC[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.156 | 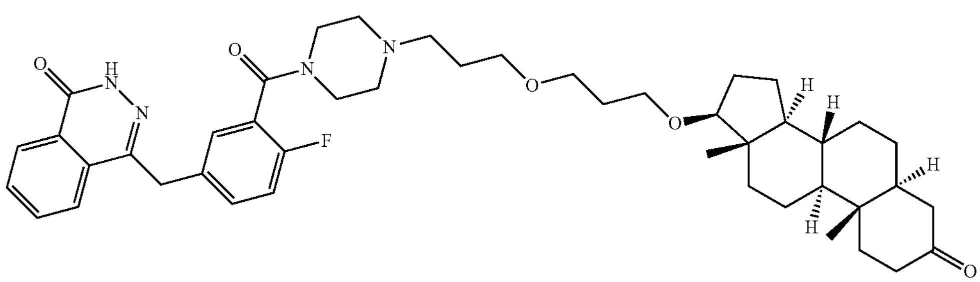 [SMILES: C[C@]12CCC(=O)C[C@@H]1CC[C@@H]1[C@@H]2CC[C@]2(C)[C@@H](OCCCOCCCN3CCN(C(=O)c4cc(Cc5n[nH]c(=O)c6ccccc56)ccc4F)CC3)CC[C@@H]12] |
| 1.157 | 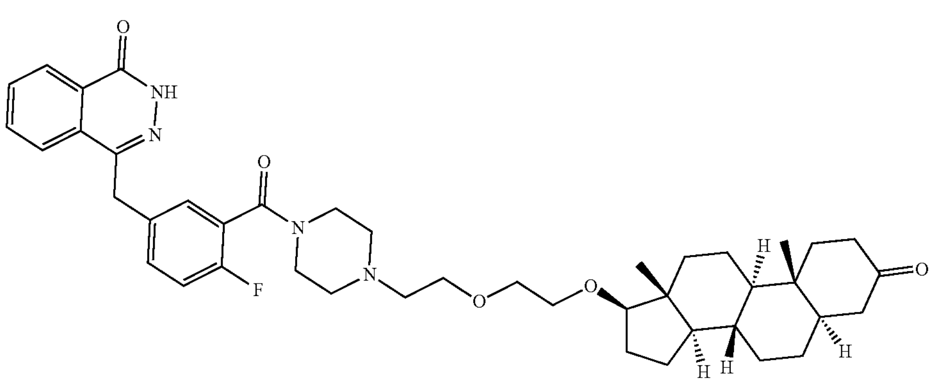 [SMILES: C[C@@]12CCC(=O)C[C@H]1CC[C@H]1[C@H]2CC[C@]2(C)[C@@H]1CC[C@H]2OCCOCCN1CCN(C(=O)c2cc(Cc3n[nH]c(=O)c4ccccc34)ccc2F)CC1] |

TABLE 1-continued

| No. | Structure |
|---|---|
| 1.158 | 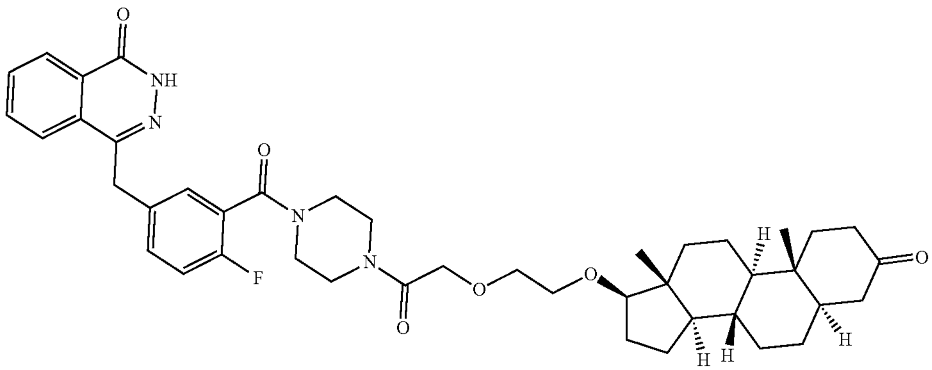 [SMILES: C[C@@]12CCC(=O)C[C@H]1CC[C@H]1[C@H]2CC[C@]2(C)[C@@H]1CC[C@H]2OCCOCC(=O)N1CCN(C(=O)c2cc(Cc3n[nH]c(=O)c4ccccc34)ccc2F)CC1] |
| 1.159 | 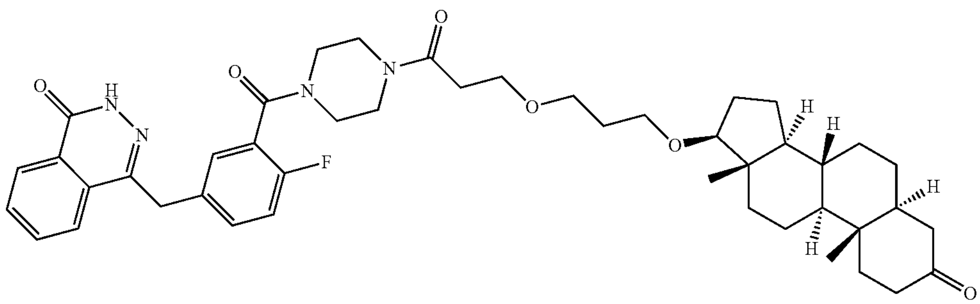 [SMILES: C[C@]12CCC(=O)C[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.160 | 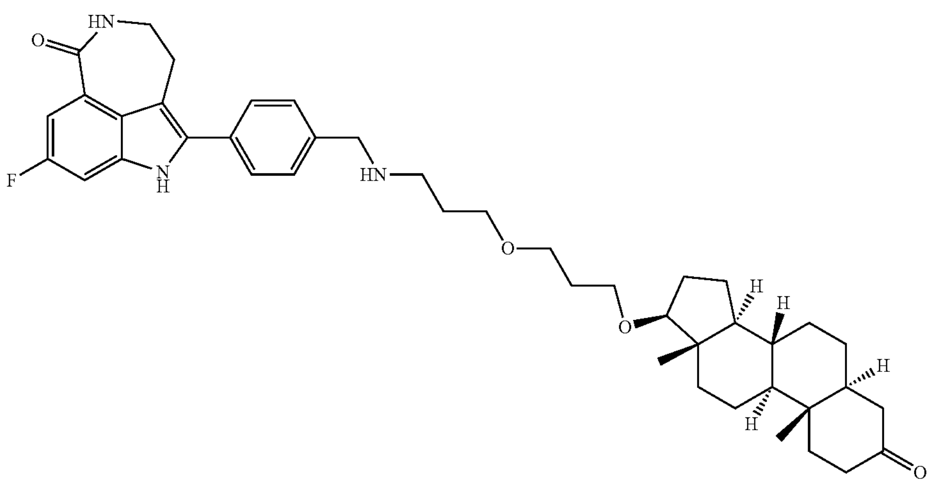 [SMILES: C[C@]12CCC(=O)C[C@@H]1CC[C@@H]1[C@@H]2CC[C@]2(C)[C@@H](OCCCOCCCNCc3ccc(-c4[nH]c5cc(F)cc6c5c4CCNC6=O)cc3)CC[C@@H]12] |
| 1.161 | 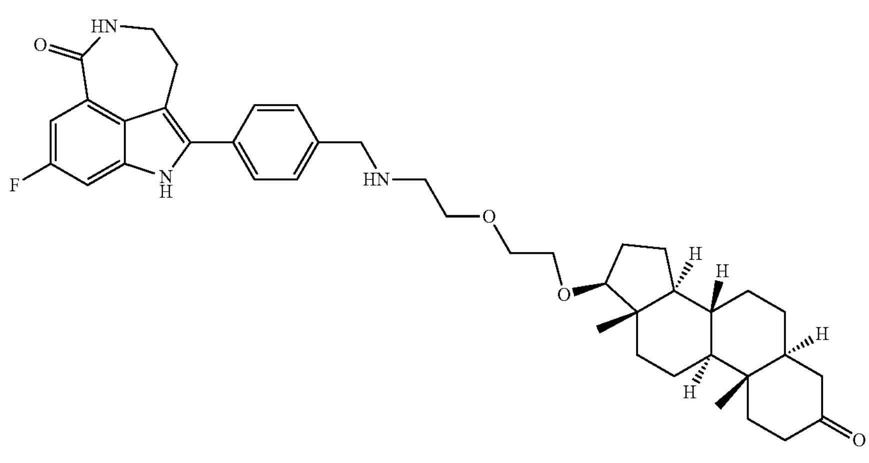 [SMILES: C[C@]12CCC(=O)C[C@@H]1CC[C@@H]1[C@@H]2CC[C@]2(C)[C@@H](OCCOCCNCc3ccc(-c4[nH]c5cc(F)cc6c5c4CCNC6=O)cc3)CC[C@@H]12] |

TABLE 1-continued
| No. | Structure |
|---|---|
| 1.162 | 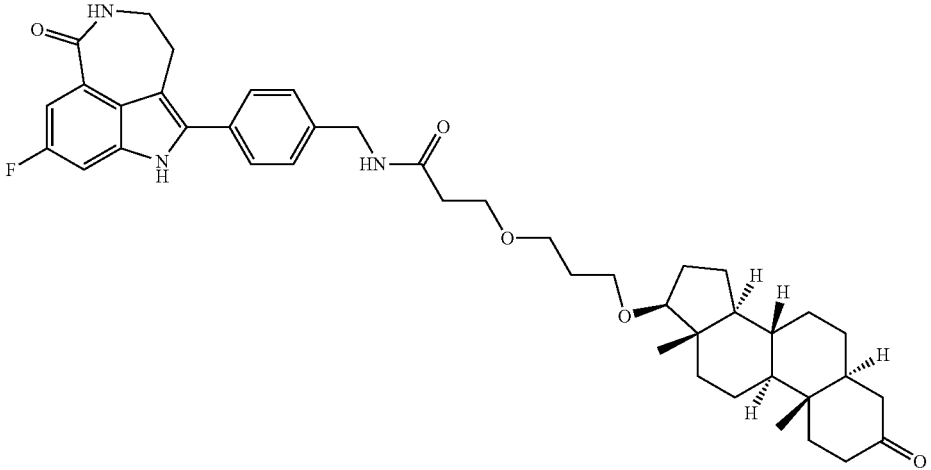 [SMILES: C[C@]12CCC(=O)C[C@@H]1CC[C@@H]1[C@@H]2CC[C@]2(C)[C@@H](OCCCOCCC(=O)NCc3ccc(-c4[nH]c5cc(F)cc6c5c4CCNC6=O)cc3)CC[C@@H]12] |
| 1.163 | 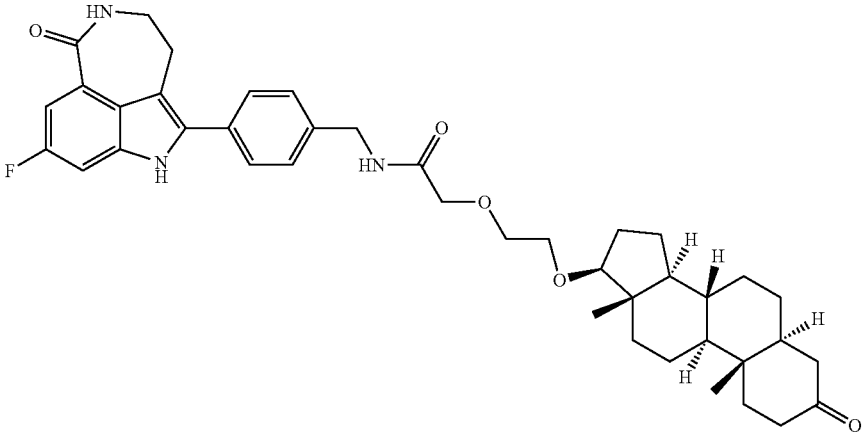 [SMILES: C[C@]12CCC(=O)C[C@@H]1CC[C@@H]1[C@@H]2CC[C@]2(C)[C@@H](OCCOCC(=O)NCc3ccc(-c4[nH]c5cc(F)cc6c5c4CCNC6=O)cc3)CC[C@@H]12] |
| 1.164 | 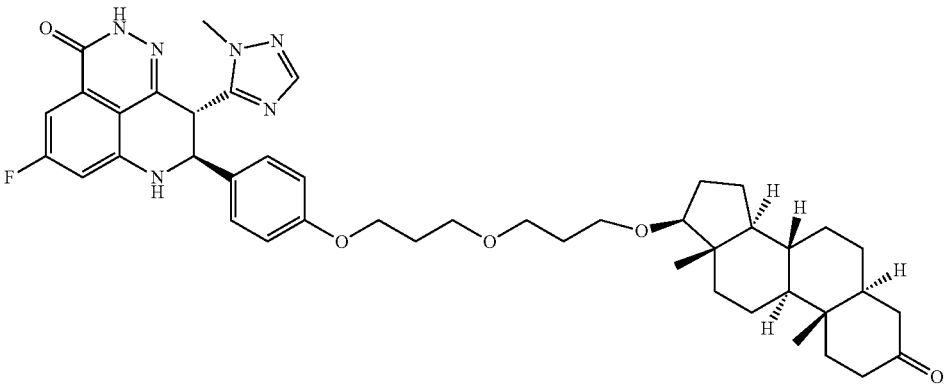 [SMILES: Cn1ncnc1[C@H]1c2n[nH]c(=O)c3cc(F)cc(c23)N[C@@H]1c1ccc(OCCCOCCCO[C@H]2CC[C@H]3[C@@H]4CC[C@H]5CC(=O)CC[C@]5(C)[C@H]4CC[C@]23C)cc1] |

TABLE 1-continued

| No. | Structure |
|---|---|
| 1.165 | 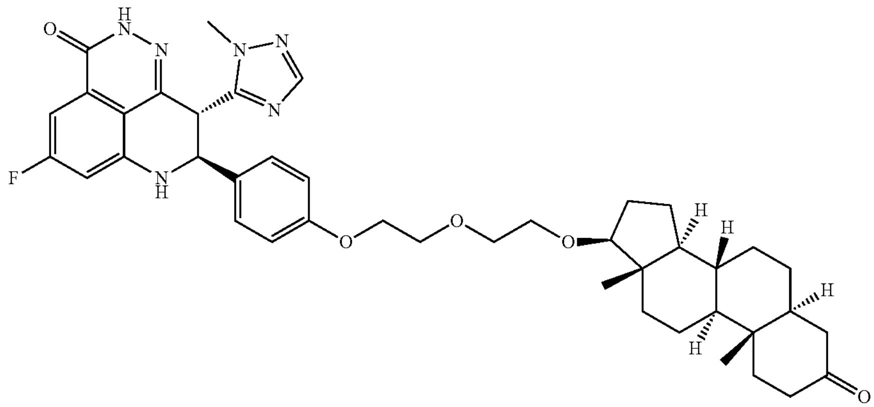 [SMILES: Cn1ncnc1[C@H]1c2n[nH]c(=O)c3cc(F)cc(c23)N[C@@H]1c1ccc(OCCOCCO[C@H]2CC[C@H]3[C@@H]4CC[C@H]5CC(=O)CC[C@]5(C)[C@H]4CC[C@]23C)cc1] |
| 1.166 | 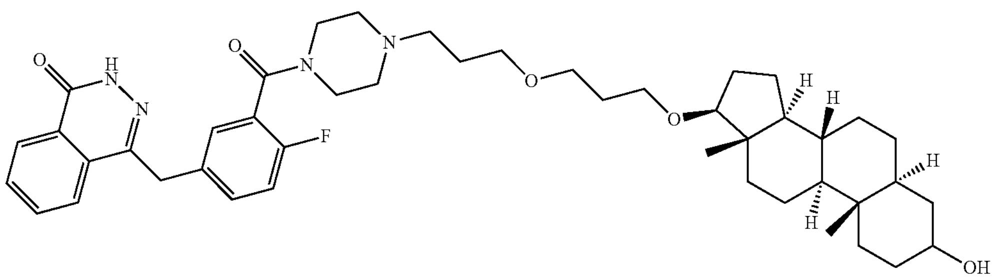 [SMILES: C[C@]12CCC(O)C[C@@H]1CC[C@@H]1[C@@H]2CC[C@]2(C)[C@@H](OCCCOCCCN3CCN(C(=O)c4cc(Cc5n[nH]c(=O)c6ccccc56)ccc4F)CC3)CC[C@@H]12] |
| 1.167 | 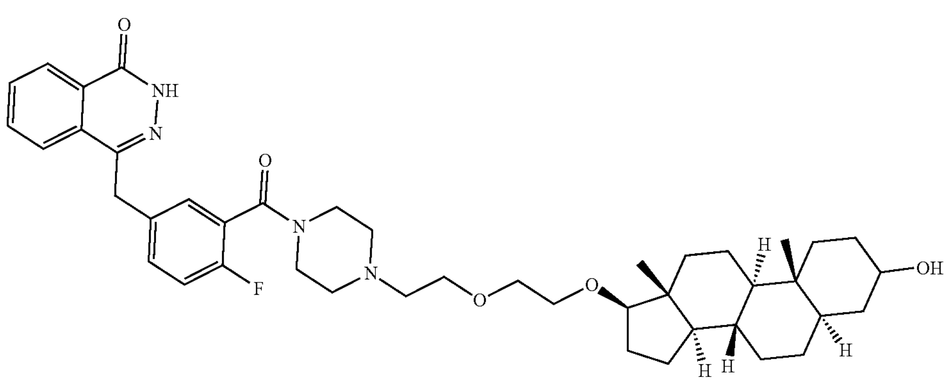 [SMILES: C[C@@]12CCC(O)C[C@H]1CC[C@H]1[C@H]2CC[C@]2(C)[C@@H]1CC[C@H]2OCCOCCN1CCN(C(=O)c2cc(Cc3n[nH]c(=O)c4ccccc34)ccc2F)CC1] |
| 1.168 | 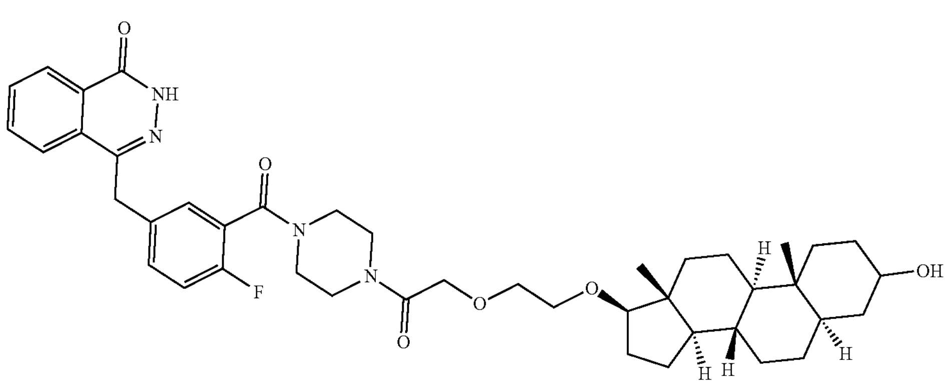 |

TABLE 1-continued

| No. | Structure |
|---|---|
| 1.169 | 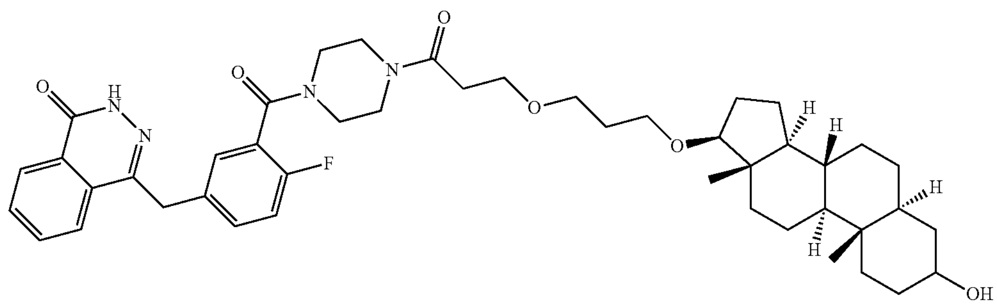 [SMILES: C[C@]12CCC(O)C[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.170 | 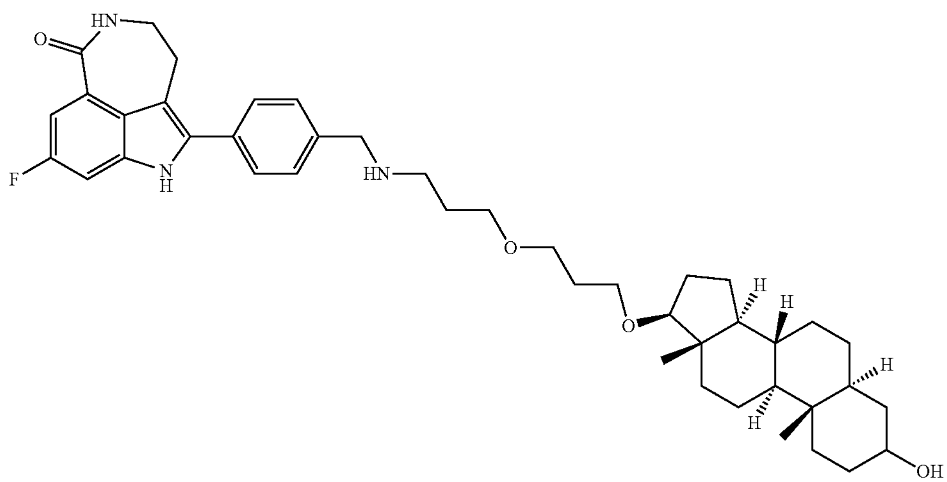 [SMILES: C[C@]12CCC(O)C[C@@H]1CC[C@@H]1[C@@H]2CC[C@]2(C)[C@@H](OCCCOCCCNCc3ccc(-c4[nH]c5cc(F)cc6c5c4CCNC6=O)cc3)CC[C@@H]12] |
| 1.171 | 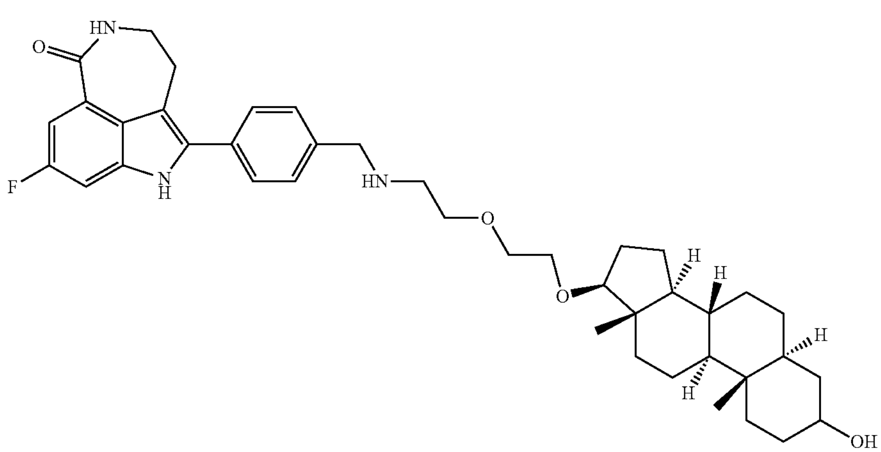 [SMILES: C[C@]12CCC(O)C[C@@H]1CC[C@@H]1[C@@H]2CC[C@]2(C)[C@@H](OCCOCCNCc3ccc(-c4[nH]c5cc(F)cc6c5c4CCNC6=O)cc3)CC[C@@H]12] |

TABLE 1-continued
| No. | Structure |
|---|---|
| 1.172 | 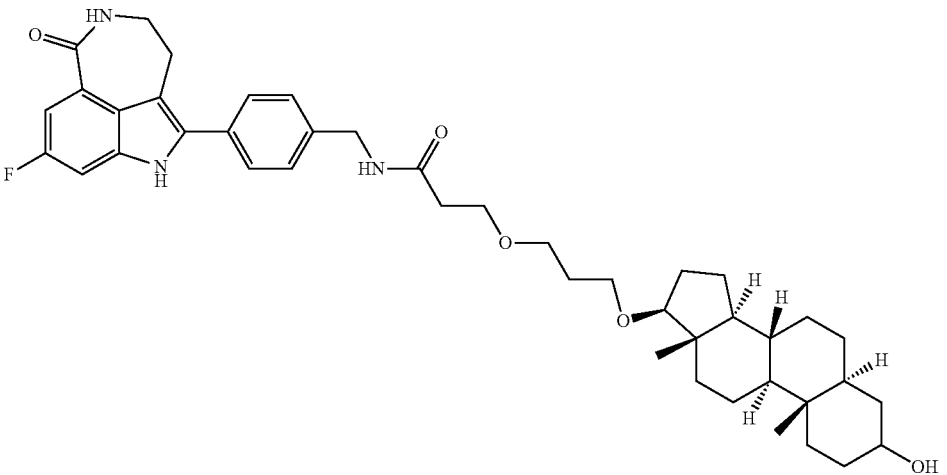 [SMILES: C[C@]12CCC(O)C[C@@H]1CC[C@@H]1[C@@H]2CC[C@]2(C)[C@@H](OCCCOCCC(=O)NCc3ccc(-c4[nH]c5cc(F)cc6c5c4CCNC6=O)cc3)CC[C@@H]12] |
| 1.173 | 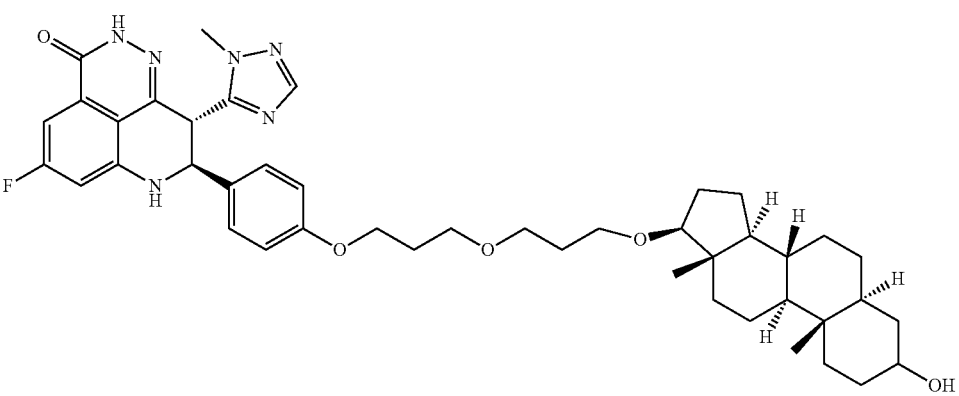 [SMILES: Cn1ncnc1[C@H]1c2n[nH]c(=O)c3cc(F)cc(c23)N[C@@H]1c1ccc(OCCCOCCCO[C@H]2CC[C@H]3[C@@H]4CC[C@H]5CC(O)CC[C@]5(C)[C@H]4CC[C@]23C)cc1] |
| 1.174 | 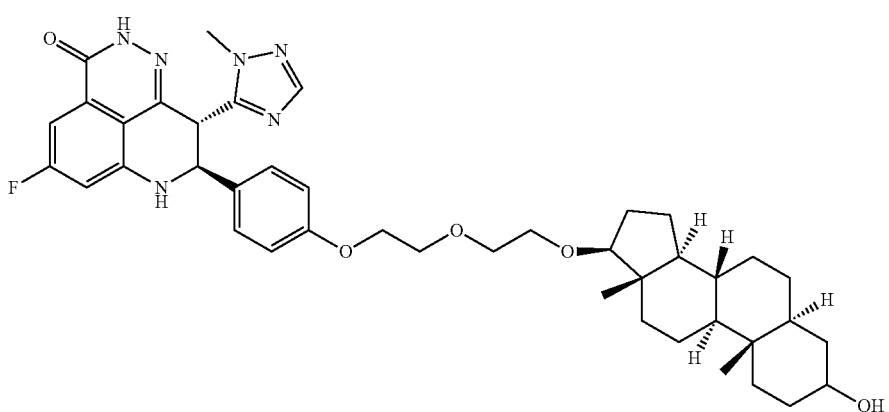 [SMILES: Cn1ncnc1[C@H]1c2n[nH]c(=O)c3cc(F)cc(c23)N[C@@H]1c1ccc(OCCOCCO[C@H]2CC[C@H]3[C@@H]4CC[C@H]5CC(O)CC[C@]5(C)[C@H]4CC[C@]23C)cc1] |

TABLE 1-continued

| No. | Structure |
|---|---|
| 1.175 | 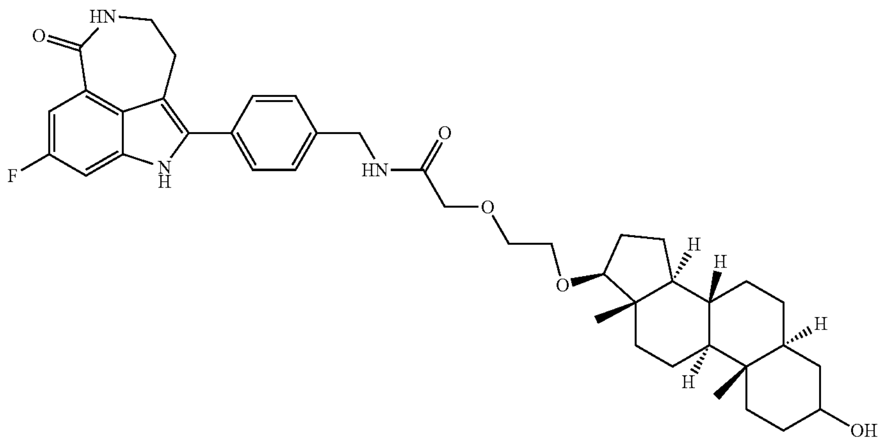 [SMILES: C[C@]12CCC(O)C[C@@H]1CC[C@@H]1[C@@H]2CC[C@]2(C)[C@@H](OCCOCC(=O)NCc3ccc(-c4[nH]c5cc(F)cc6c5c4CCNC6=O)cc3)CC[C@@H]12] |
| 1.176 | 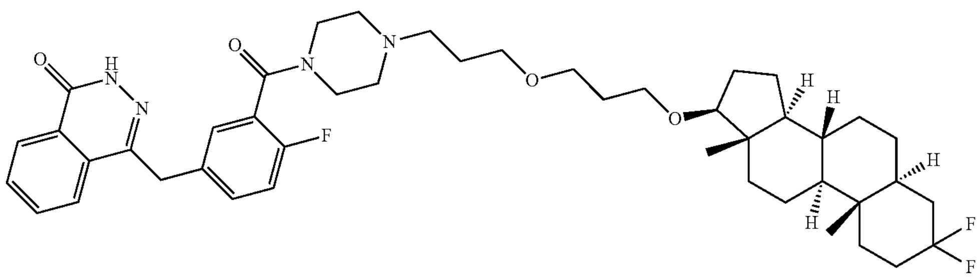 [SMILES: C[C@]12CCC(F)(F)C[C@@H]1CC[C@@H]1[C@@H]2CC[C@]2(C)[C@@H](OCCCOCCCN3CCN(C(=O)c4cc(Cc5n[nH]c(=O)c6ccccc56)ccc4F)CC3)CC[C@@H]12] |
| 1.177 | 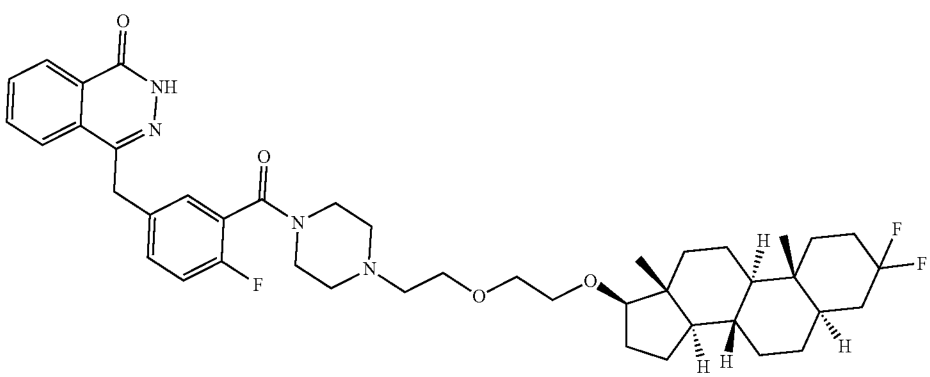 |
| 1.178 | 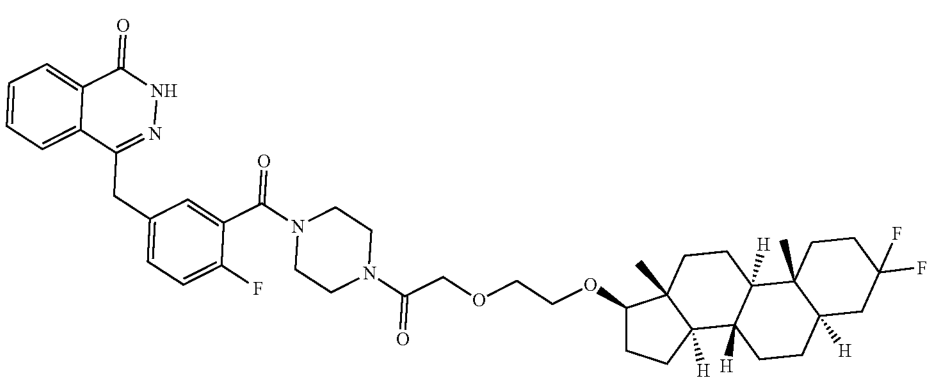 |

TABLE 1-continued
| No. | Structure |
|---|---|
| 1.179 | 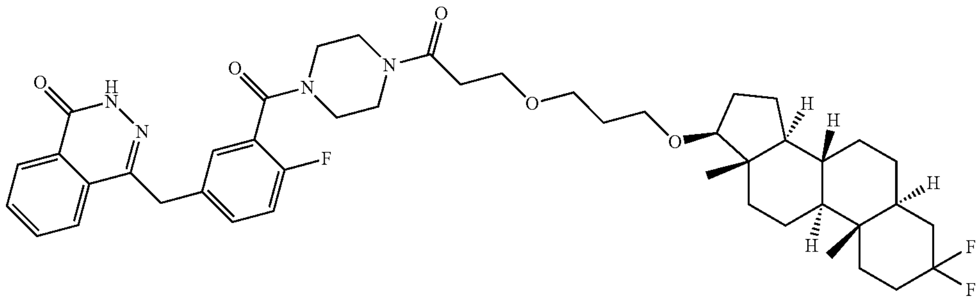 [SMILES: C[C@]12CCC(F)(F)C[C@@H]1CC[C@@H]1[C@@H]2CC[C@]2(C)[C@@H](OCCCOCCC(=O)N3CCN(C(=O)c4cc(Cc5n[nH]c(=O)c6ccccc56)ccc4F)CC3)CC[C@@H]12] |
| 1.180 | 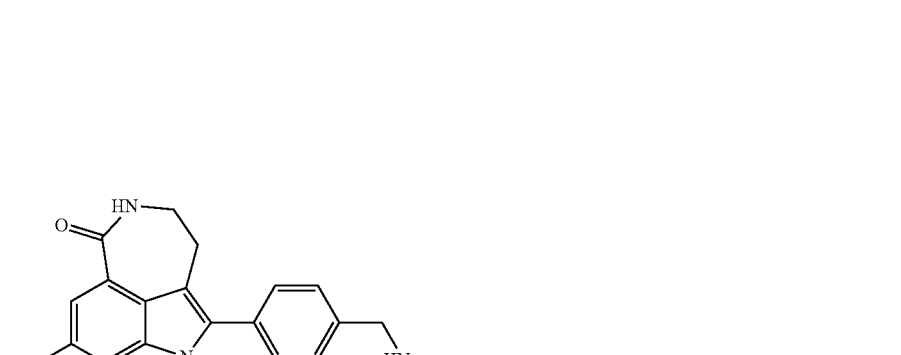 |
| 1.181 | 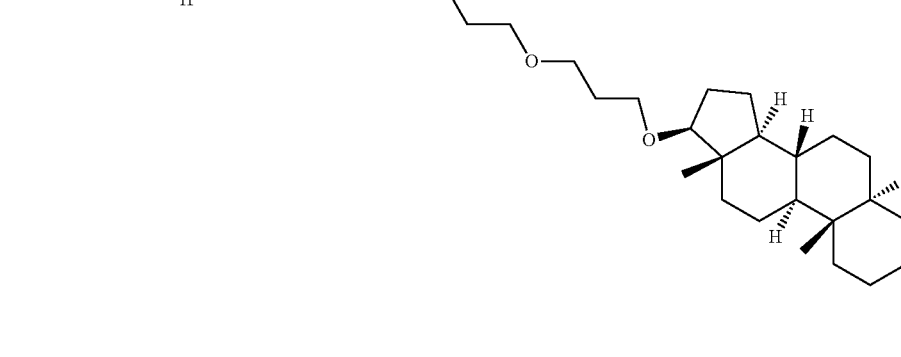 |

TABLE 1-continued

| No. | Structure |
|---|---|
| 1.182 | 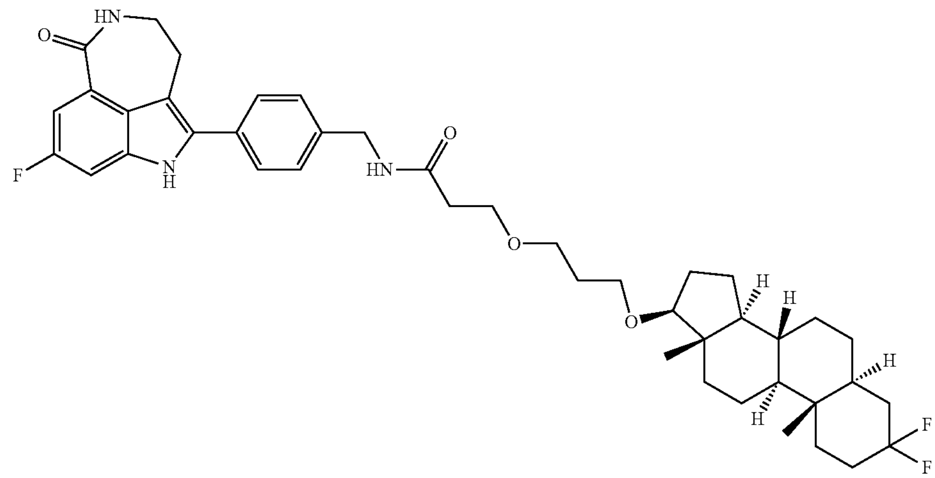 [SMILES: C[C@]12CCC(F)(F)C[C@@H]1CC[C@@H]1[C@@H]2CC[C@]2(C)[C@@H](OCCCOCCC(=O)NCc3ccc(-c4[nH]c5cc(F)cc6c5c4CCNC6=O)cc3)CC[C@@H]12] |
| 1.183 | 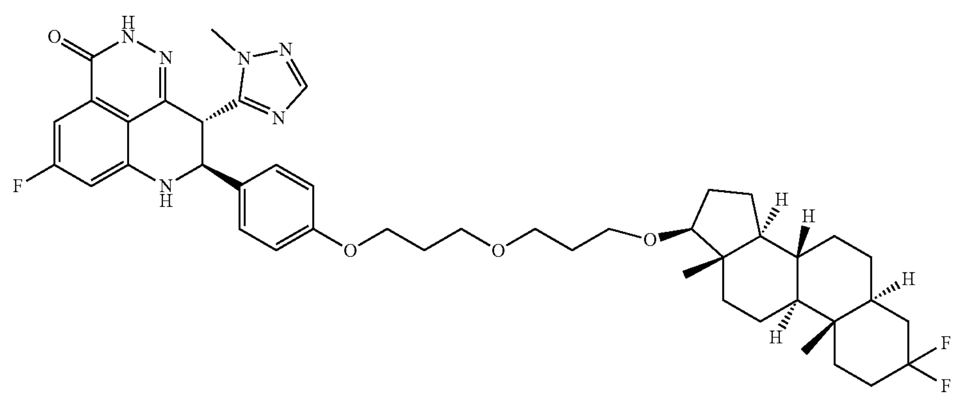 [SMILES: Cn1ncnc1[C@H]1c2n[nH]c(=O)c3cc(F)cc(c23)N[C@@H]1c1ccc(OCCCOCCCO[C@H]2CC[C@H]3[C@@H]4CC[C@H]5CC(F)(F)CC[C@]5(C)[C@H]4CC[C@]23C)cc1] |
| 1.184 | 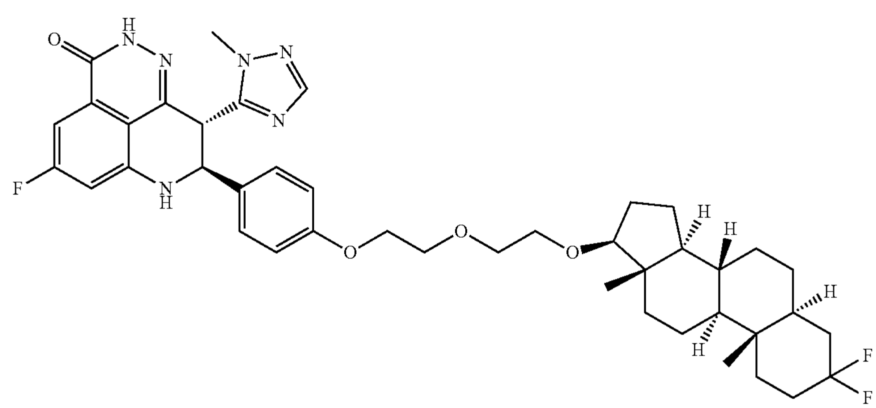 [SMILES: Cn1ncnc1[C@H]1c2n[nH]c(=O)c3cc(F)cc(c23)N[C@@H]1c1ccc(OCCOCCO[C@H]2CC[C@H]3[C@@H]4CC[C@H]5CC(F)(F)CC[C@]5(C)[C@H]4CC[C@]23C)cc1] |

TABLE 1-continued

| No. | Structure |
|---|---|
| 1.185 | 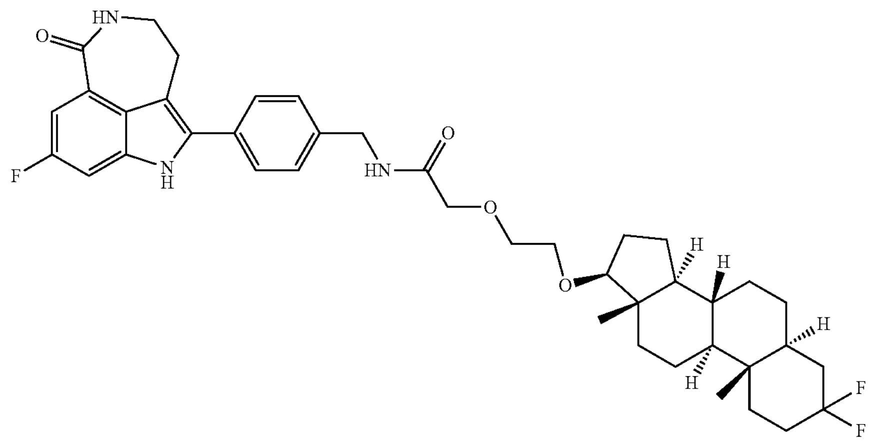 [SMILES: C[C@]12CCC(F)(F)C[C@@H]1CC[C@@H]1[C@@H]2CC[C@]2(C)[C@@H](OCCOCC(=O)NCc3ccc(-c4[nH]c5cc(F)cc6c5c4CCNC6=O)cc3)CC[C@@H]12] |
| 1.186 | 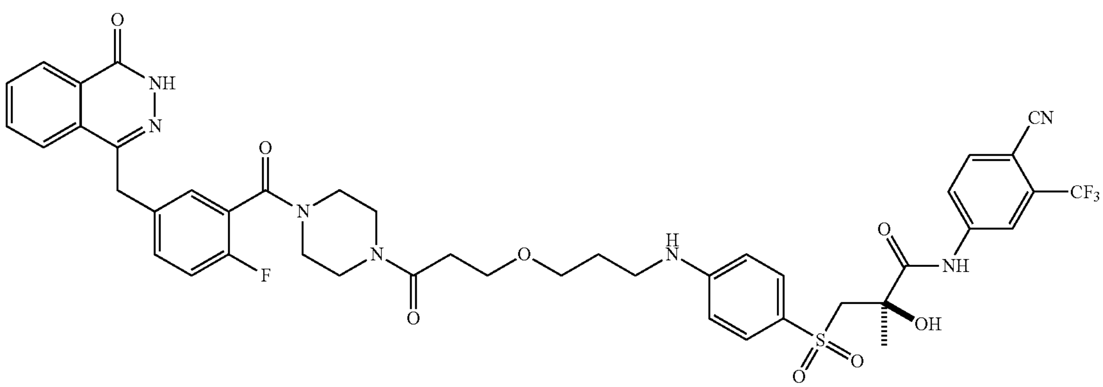 [SMILES: C[C@](O)(CS(=O)(=O)c1ccc(NCCCOCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.187 | 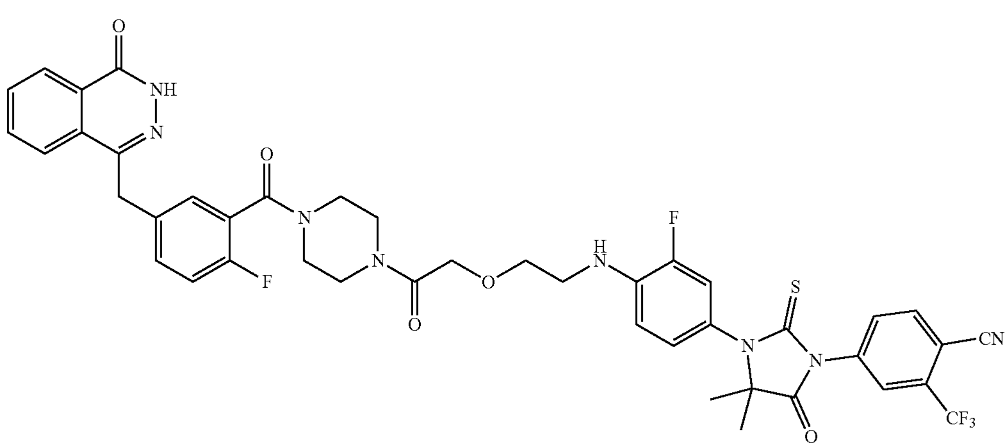 [SMILES: CC1(C)C(=O)N(c2ccc(C#N)c(C(F)(F)F)c2)C(=S)N1c1ccc(NCCOCC(=O)N2CCN(C(=O)c3cc(Cc4n[nH]c(=O)c5ccccc45)ccc3F)CC2)c(F)c1] |

TABLE 1-continued
| No. | Structure |
|---|---|
| 1.188 | 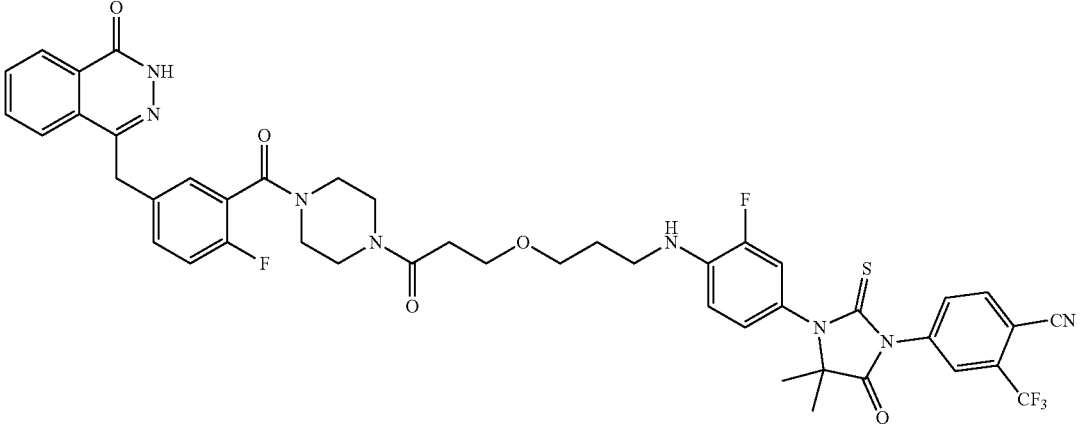 [SMILES: CC1(C)C(=O)N(c2ccc(C#N)c(C(F)(F)F)c2)C(=S)N1c1ccc(NCCCOCCC(=O)N2CCN(C(=O)c3cc(Cc4n[nH]c(=O)c5ccccc45)ccc3F)CC2)c(F)c1] |
| 1.189 | 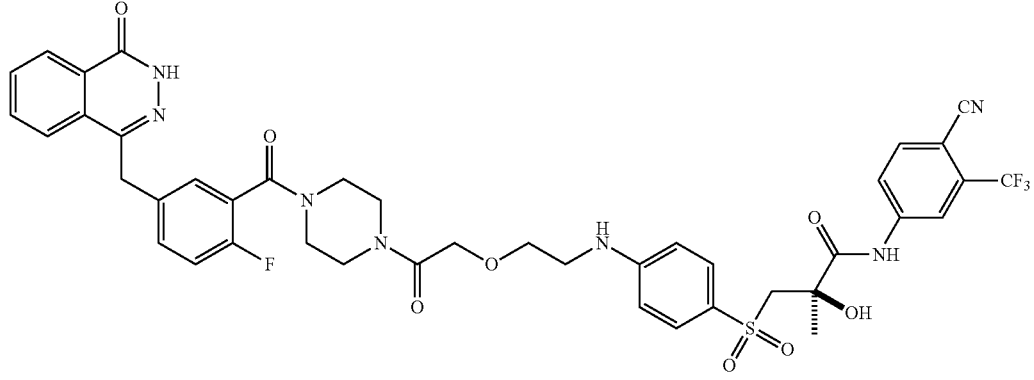 [SMILES: C[C@](O)(CS(=O)(=O)c1ccc(NCCOCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |
| 1.190 | 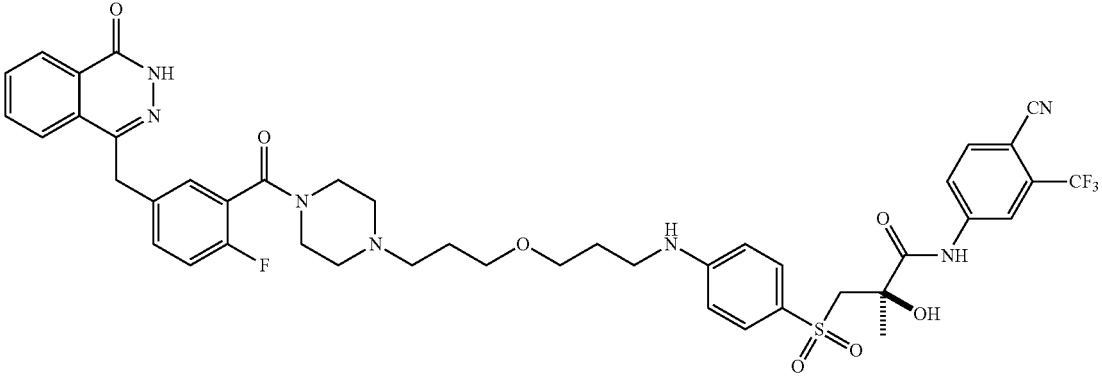 [SMILES: C[C@](O)(CS(=O)(=O)c1ccc(NCCCOCCCN2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.191 | 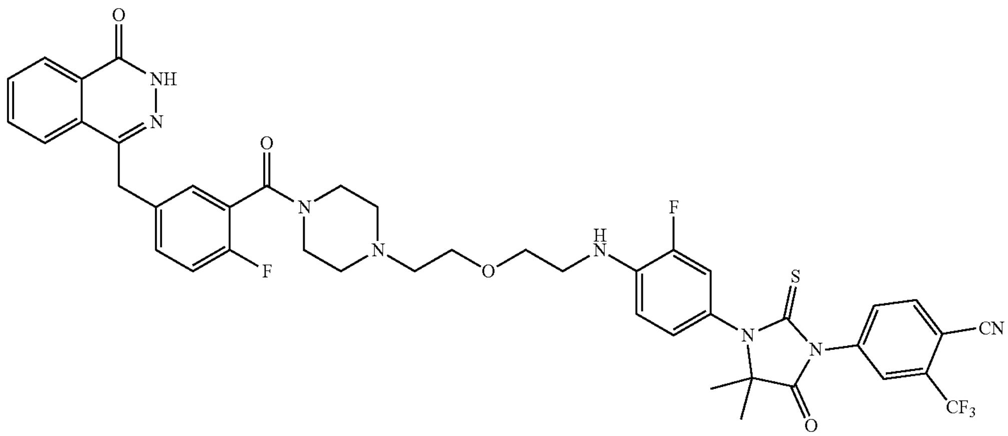 |
| 1.192 | 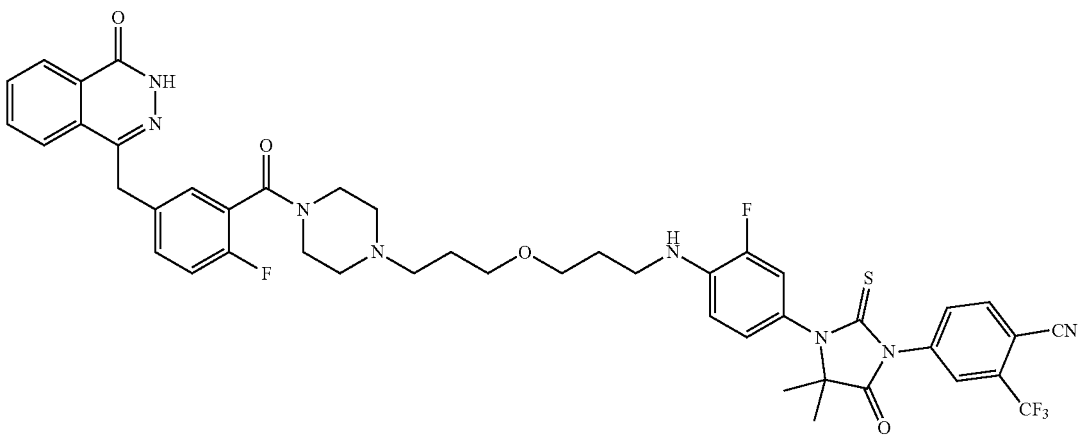 [SMILES: CC1(C)C(=O)N(c2ccc(C#N)c(C(F)(F)F)c2)C(=S)N1c1ccc(NCCCOCCCN2CCN(C(=O)c3cc(Cc4n[nH]c(=O)c5ccccc45)ccc3F)CC2)c(F)c1] |
| 1.193 | 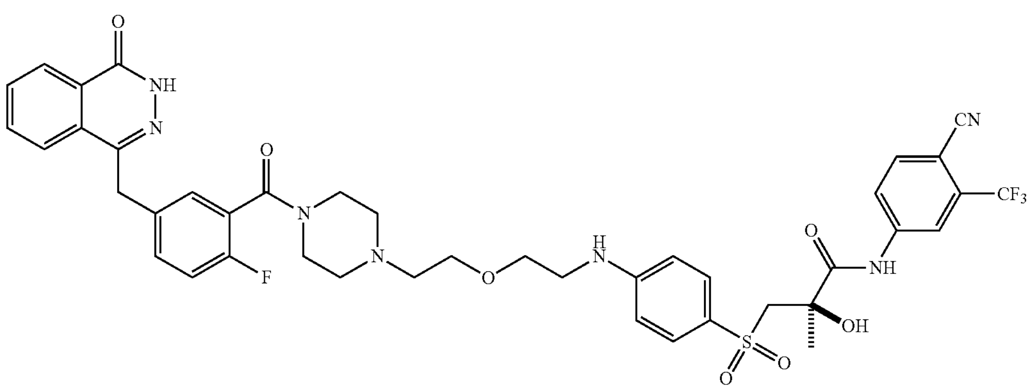 [SMILES: C[C@](O)(CS(=O)(=O)c1ccc(NCCOCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.194 | 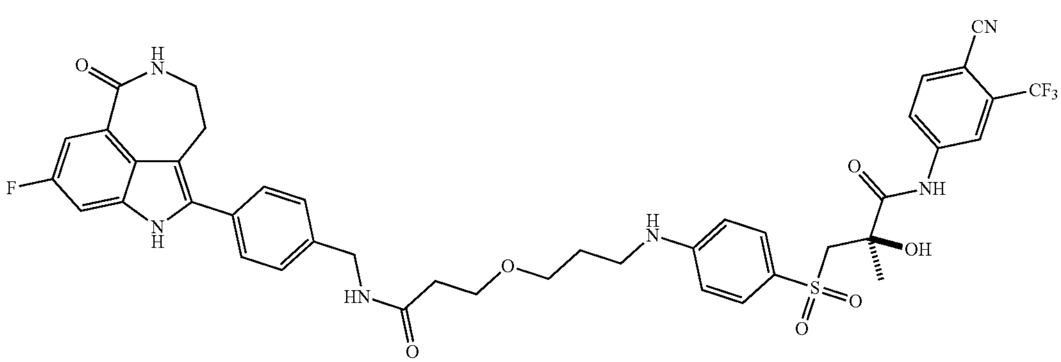 [SMILES: C[C@](O)(CS(=O)(=O)c1ccc(NCCCOCCC(=O)NCc2ccc(-c3[nH]c4cc(F)cc5c4c3CCNC5=O)cc2)cc1)C(=O)Nc1ccc(C#N)c(C(F)(F)F)c1] |

TABLE 1-continued

| No. | Structure |
|---|---|
| 1.195 | 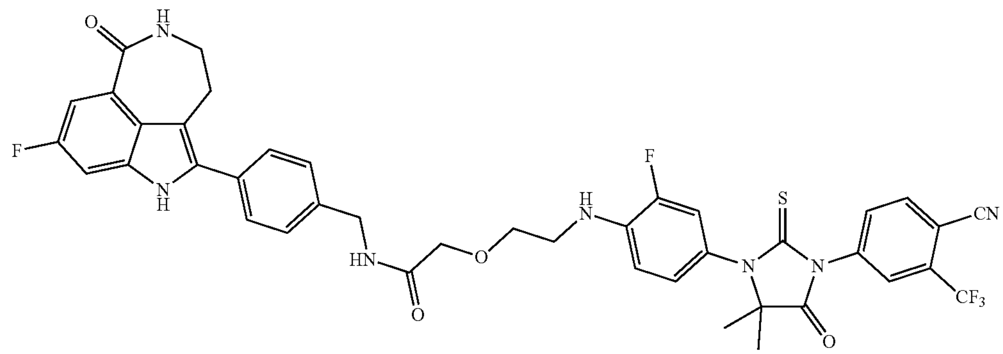 [SMILES: CC1(C)C(=O)N(c2ccc(C#N)c(C(F)(F)F)c2)C(=S)N1c1ccc(NCCOCC(=O)NCc2ccc(-c3[nH]c4cc(F)cc5c4c3CCNC5=O)cc2)c(F)c1] |
| 1.196 | 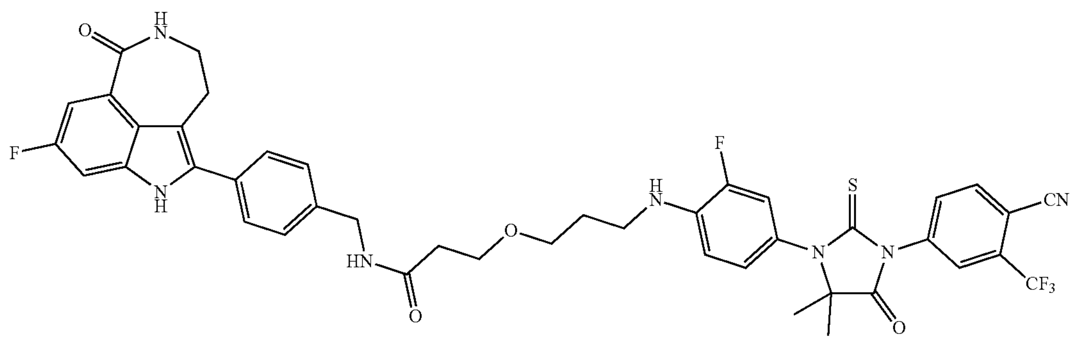 [SMILES: CC1(C)C(=O)N(c2ccc(C#N)c(C(F)(F)F)c2)C(=S)N1c1ccc(NCCCOCCC(=O)NCc2ccc(-c3[nH]c4cc(F)cc5c4c3CCNC5=O)cc2)c(F)c1] |
| 1.197 | 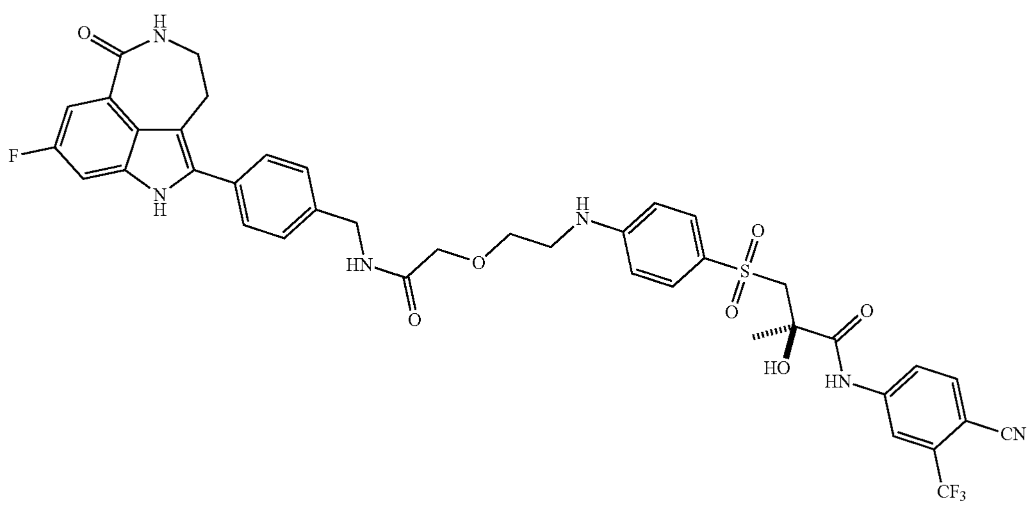 [SMILES: C[C@](O)(CS(=O)(=O)c1ccc(NCCOCC(=O)NCc2ccc(-c3[nH]c4cc(F)cc5c4c3CCNC5=O)cc2)cc1)C(=O)Nc1ccc(C#N)c(C(F)(F)F)c1] |
| 1.198 | 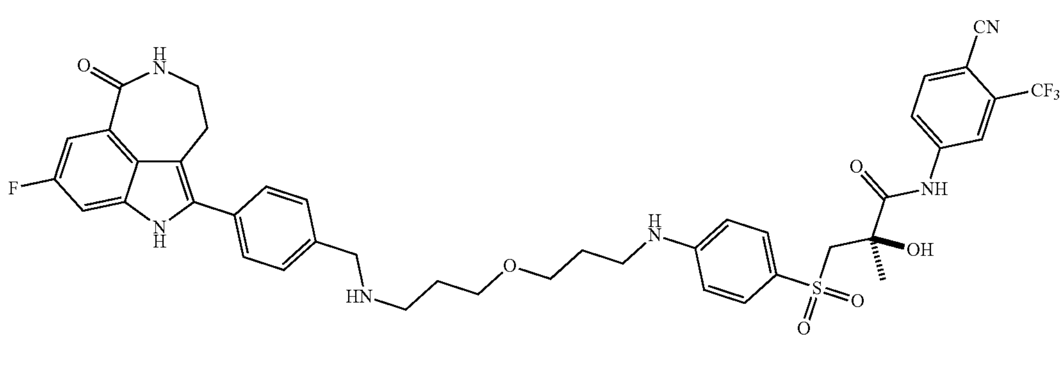 [SMILES: C[C@](O)(CS(=O)(=O)c1ccc(NCCCOCCCNCc2ccc(-c3[nH]c4cc(F)cc5c4c3CCNC5=O)cc2)cc1)C(=O)Nc1ccc(C#N)c(C(F)(F)F)c1] |

TABLE 1-continued

| No. | Structure |
|---|---|
| 1.199 | 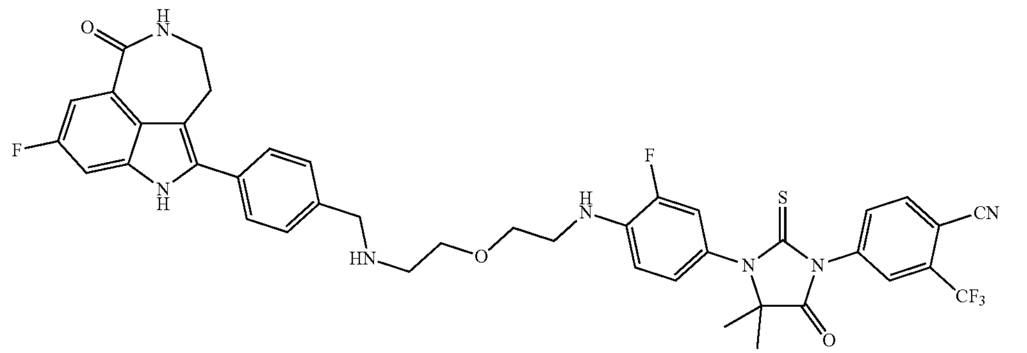 [SMILES: CC1(C)C(=O)N(c2ccc(C#N)c(C(F)(F)F)c2)C(=S)N1c1ccc(NCCOCCNCc2ccc(-c3[nH]c4cc(F)cc5c4c3CCNC5=O)cc2)c(F)c1] |
| 1.200 | 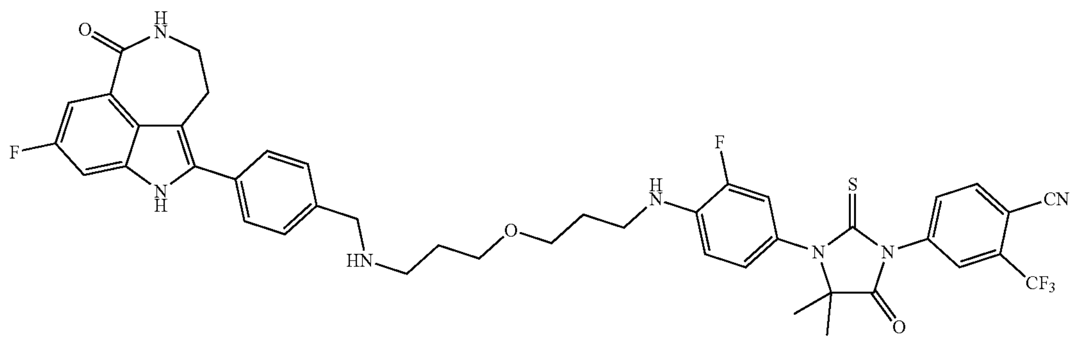 [SMILES: CC1(C)C(=O)N(c2ccc(C#N)c(C(F)(F)F)c2)C(=S)N1c1ccc(NCCCOCCCNCc2ccc(-c3[nH]c4cc(F)cc5c4c3CCNC5=O)cc2)c(F)c1] |
| 1.201 | 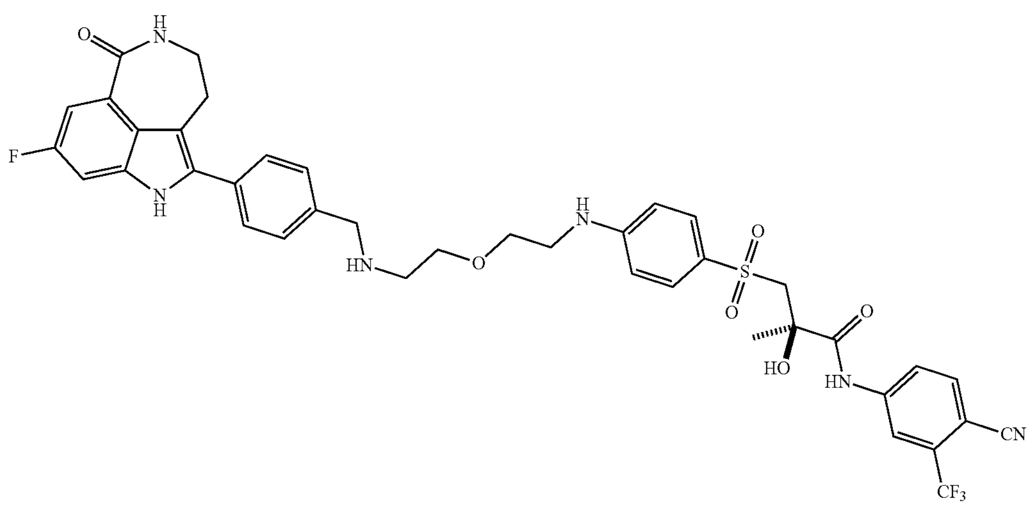 [SMILES: C[C@](O)(CS(=O)(=O)c1ccc(NCCOCCNCc2ccc(-c3[nH]c4cc(F)cc5c4c3CCNC5=O)cc2)cc1)C(=O)Nc1ccc(C#N)c(C(F)(F)F)c1] |
| 1.202 | 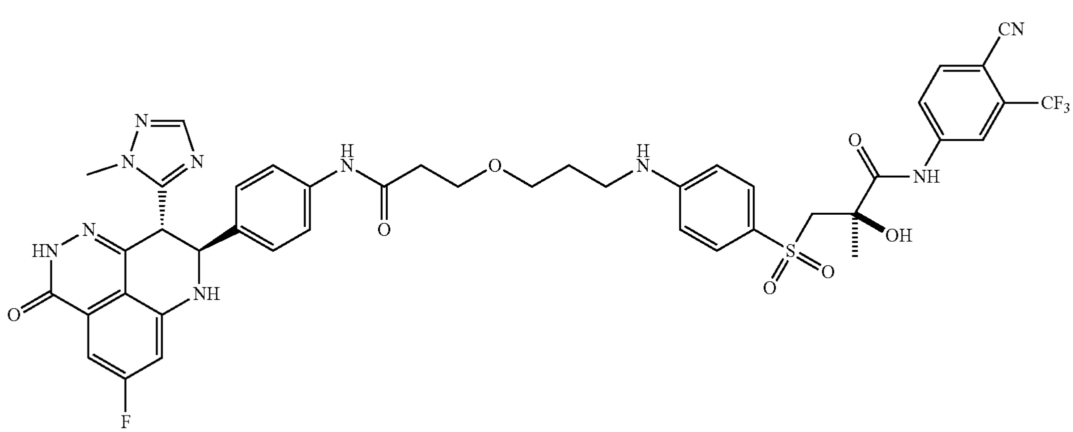 [SMILES: Cn1ncnc1[C@H]1c2n[nH]c(=O)c3cc(F)cc(c23)N[C@@H]1c1ccc(NC(=O)CCOCCCNc2ccc(S(=O)(=O)C[C@](C)(O)C(=O)Nc3ccc(C#N)c(C(F)(F)F)c3)cc2)cc1] |

TABLE 1-continued
| No. | Structure |
|---|---|
| 1.203 | 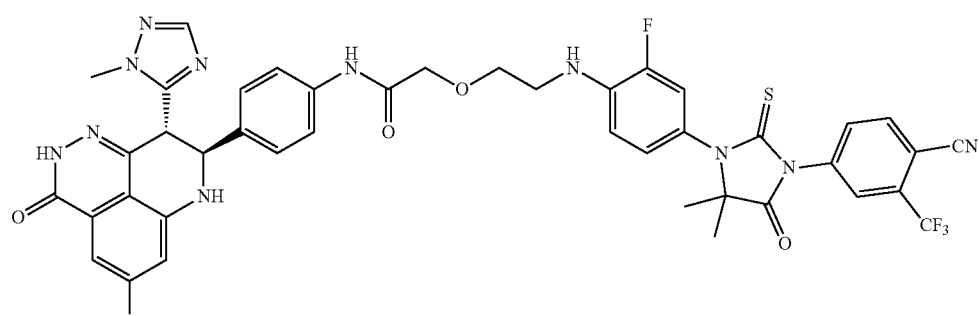 |
| 1.204 | 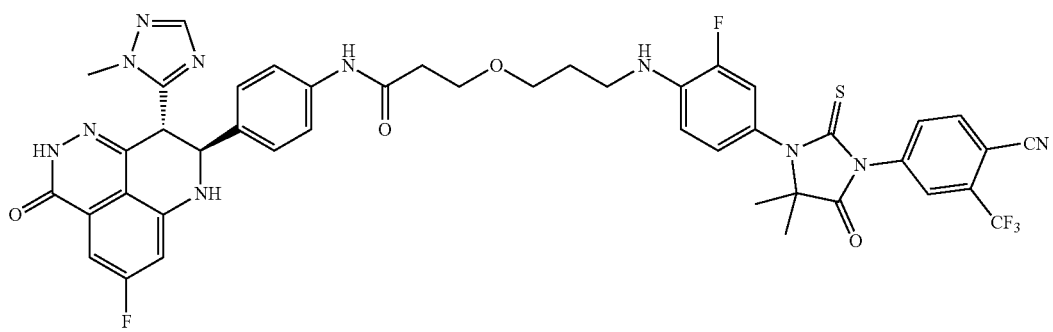 |
| 1.205 | 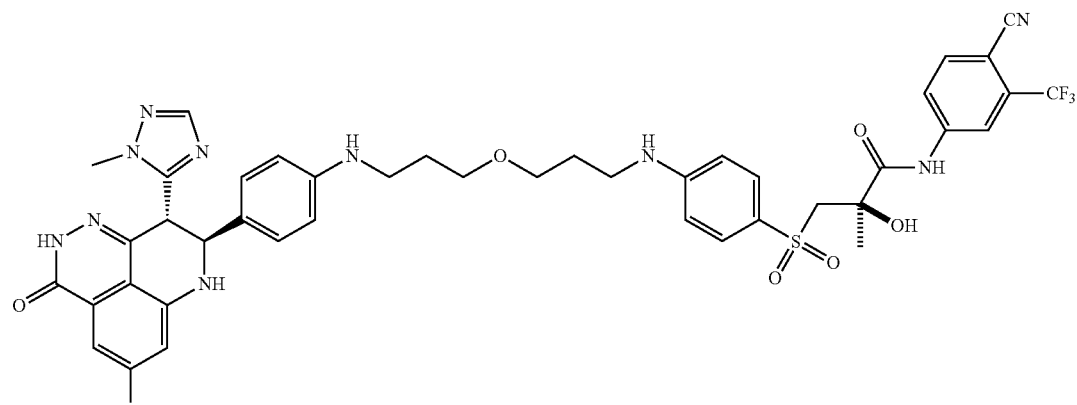 |
| 1.206 | 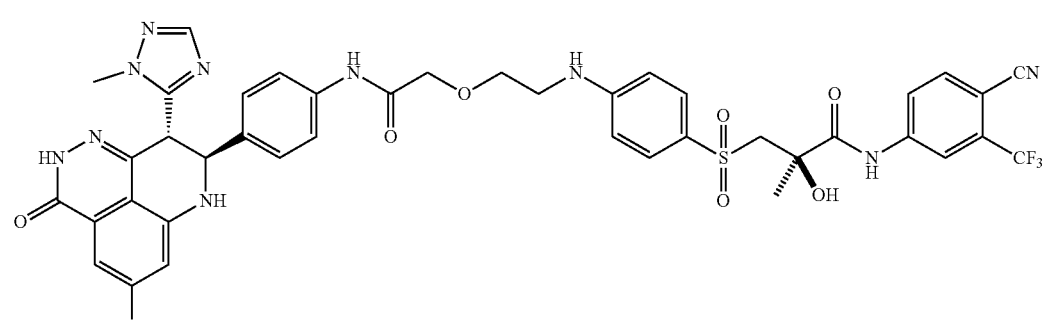 |

TABLE 1-continued

| No. | Structure |
|---|---|
| 1.207 | 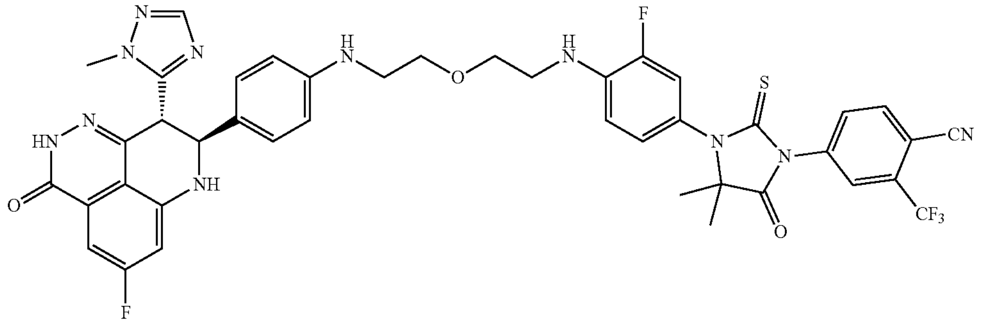 [SMILES: Cn1ncnc1[C@H]1c2n[nH]c(=O)c3cc(F)cc(c23)N[C@@H]1c1ccc(NCCOCCNc2ccc(N3C(=S)N(c4ccc(C#N)c(C(F)(F)F)c4)C(=O)C3(C)C)cc2F)cc1] |
| 1.208 | 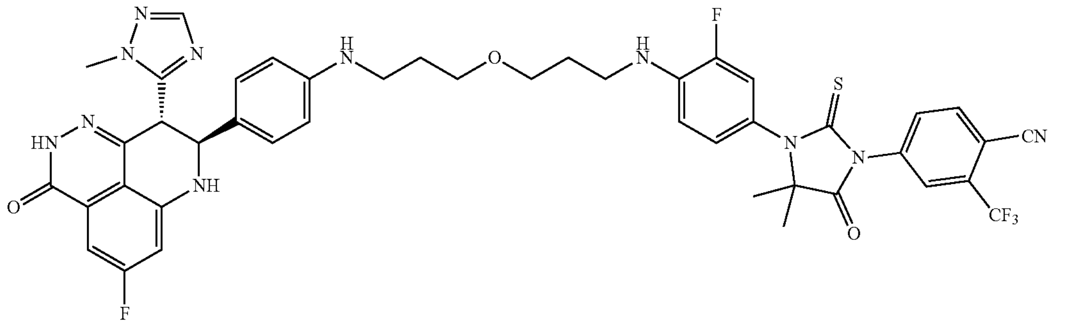 [SMILES: Cn1ncnc1[C@H]1c2n[nH]c(=O)c3cc(F)cc(c23)N[C@@H]1c1ccc(NCCCOCCCNc2ccc(N3C(=S)N(c4ccc(C#N)c(C(F)(F)F)c4)C(=O)C3(C)C)cc2F)cc1] |
| 1.209 | 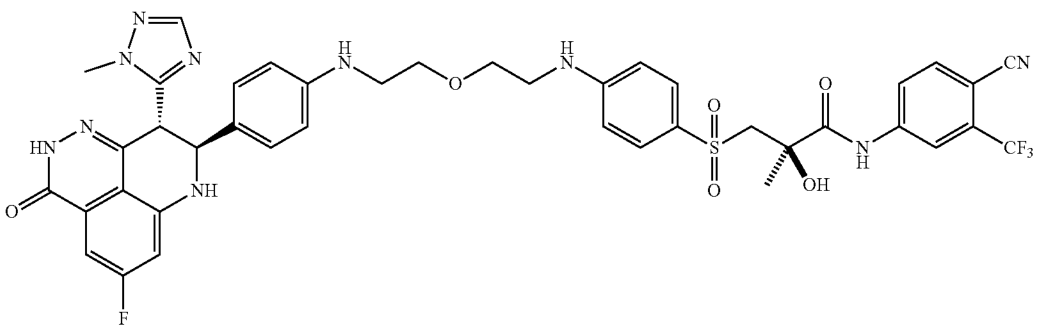 [SMILES: Cn1ncnc1[C@H]1c2n[nH]c(=O)c3cc(F)cc(c23)N[C@@H]1c1ccc(NCCOCCNc2ccc(S(=O)(=O)C[C@](C)(O)C(=O)Nc3ccc(C#N)c(C(F)(F)F)c3)cc2)cc1] |
| 1.210 | 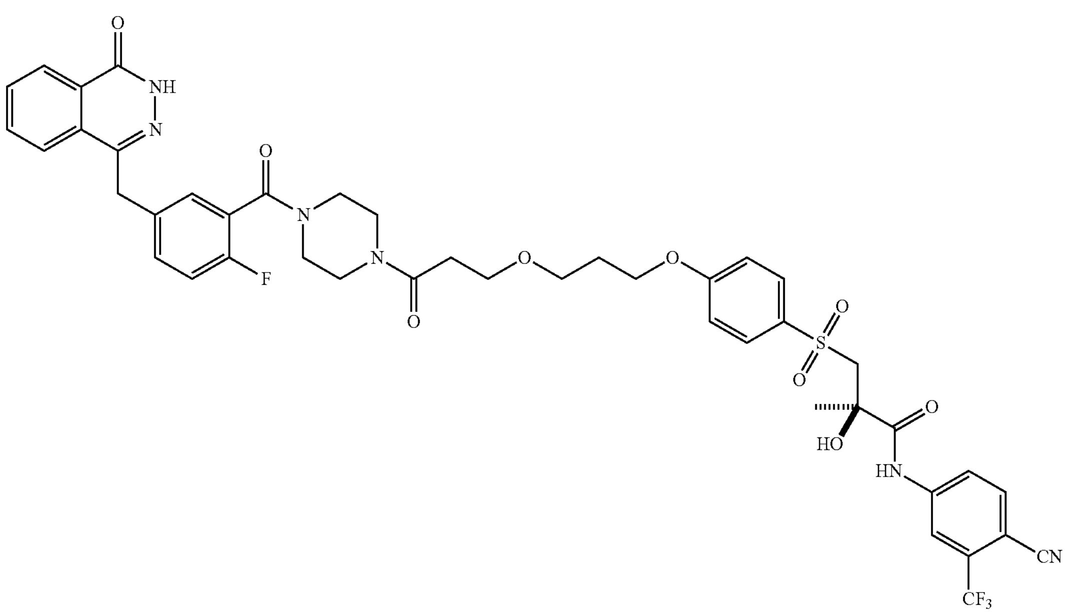 [SMILES: C[C@](O)(CS(=O)(=O)c1ccc(OCCCOCCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.211 | 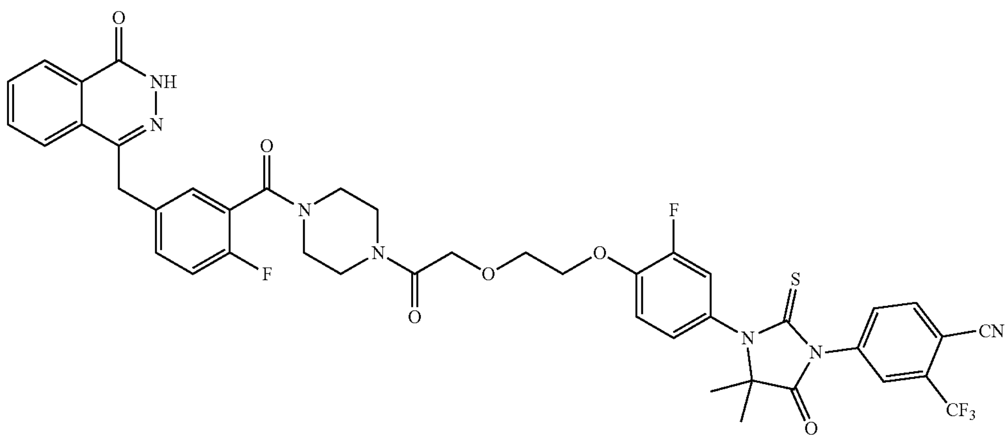 [SMILES: CC1(C)C(=O)N(c2ccc(C#N)c(C(F)(F)F)c2)C(=S)N1c1ccc(OCCOCC(=O)N2CCN(C(=O)c3cc(Cc4n[nH]c(=O)c5ccccc45)ccc3F)CC2)c(F)c1] |
| 1.212 | 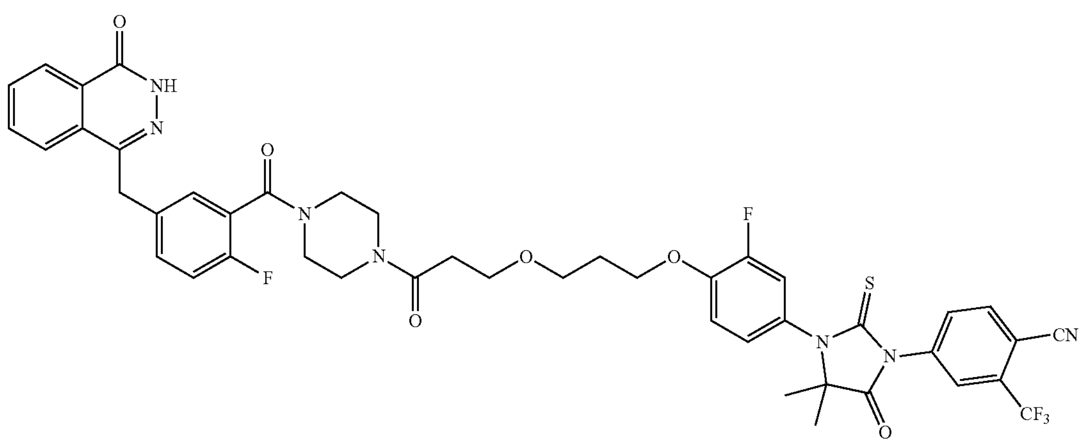 [SMILES: CC1(C)C(=O)N(c2ccc(C#N)c(C(F)(F)F)c2)C(=S)N1c1ccc(OCCCOCCC(=O)N2CCN(C(=O)c3cc(Cc4n[nH]c(=O)c5ccccc45)ccc3F)CC2)c(F)c1] |
| 1.213 | 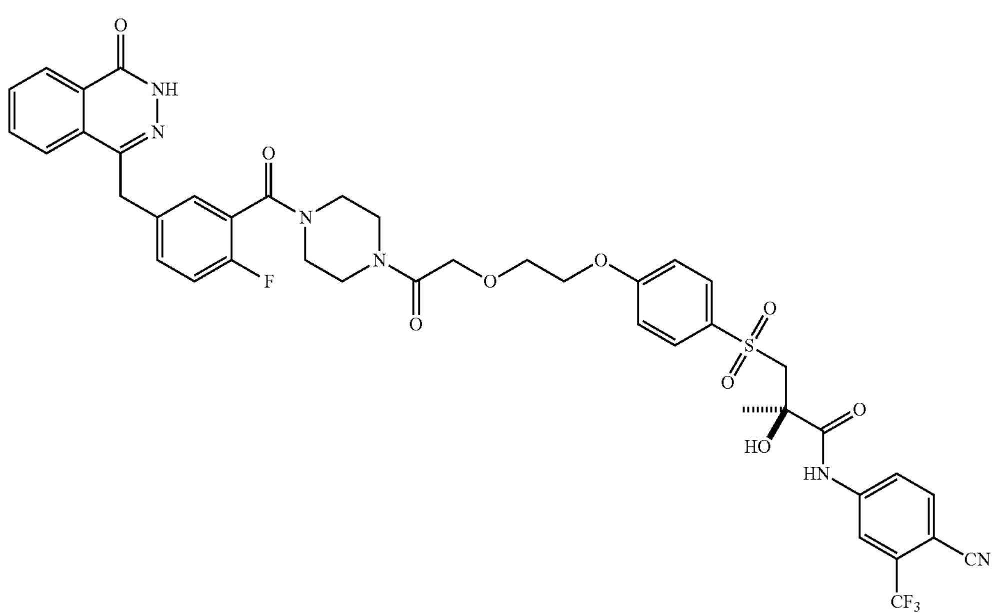 [SMILES: C[C@](O)(CS(=O)(=O)c1ccc(OCCOCC(=O)N2CCN(C(=O)c3cc(Cc4n[nH]c(=O)c5ccccc45)ccc3F)CC2)cc1)C(=O)Nc1ccc(C#N)c(C(F)(F)F)c1] |

TABLE 1-continued

| No. | Structure |
|---|---|
| 1.214 | 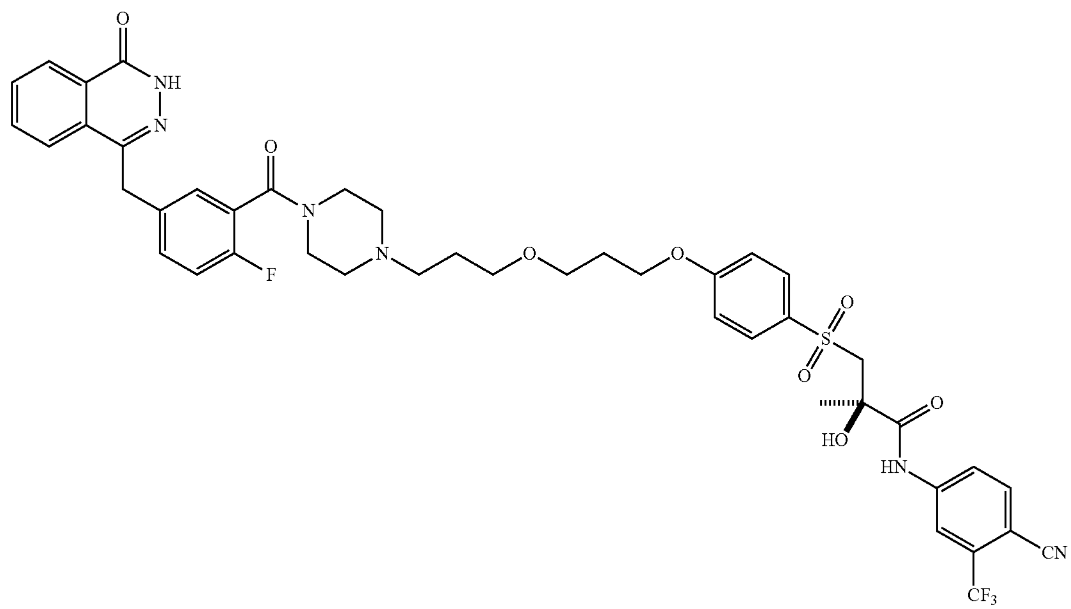 [SMILES: C[C@](O)(CS(=O)(=O)c1ccc(OCCCOCCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.215 | 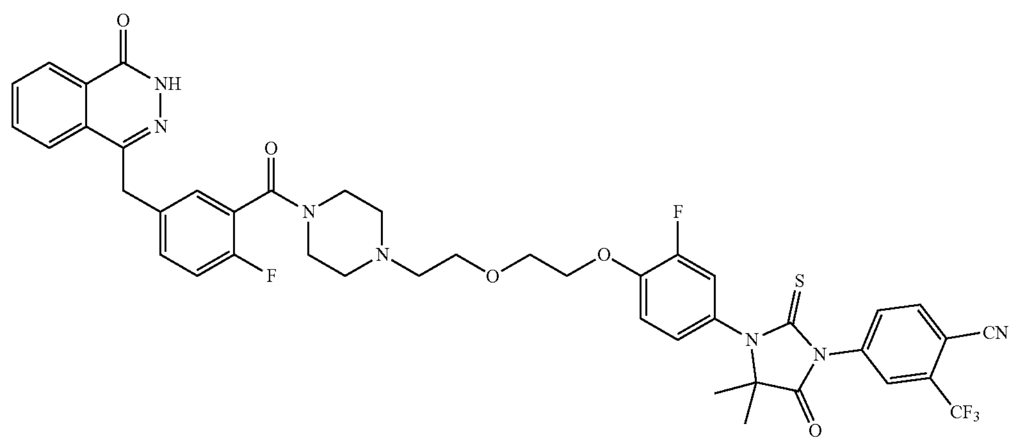 [SMILES: CC1(C)C(=O)N(c2ccc(C#N)c(C(F)(F)F)c2)C(=S)N1c1ccc(OCCOCCN2CCN(C(=O)c3cc(Cc4n[nH]c(=O)c5ccccc45)ccc3F)CC2)c(F)c1] |
| 1.216 | 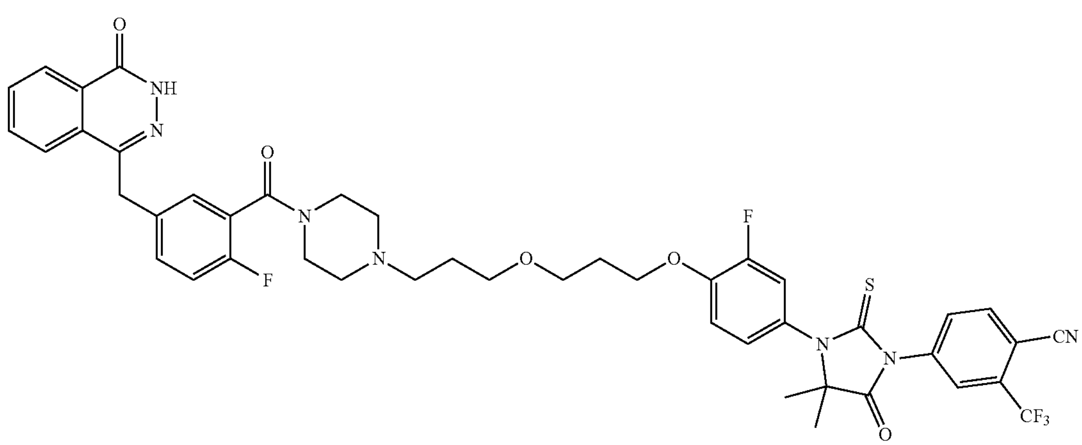 [SMILES: CC1(C)C(=O)N(c2ccc(C#N)c(C(F)(F)F)c2)C(=S)N1c1ccc(OCCCOCCCN2CCN(C(=O)c3cc(Cc4n[nH]c(=O)c5ccccc45)ccc3F)CC2)c(F)c1] |

TABLE 1-continued

| No. | Structure |
|---|---|
| 1.217 | 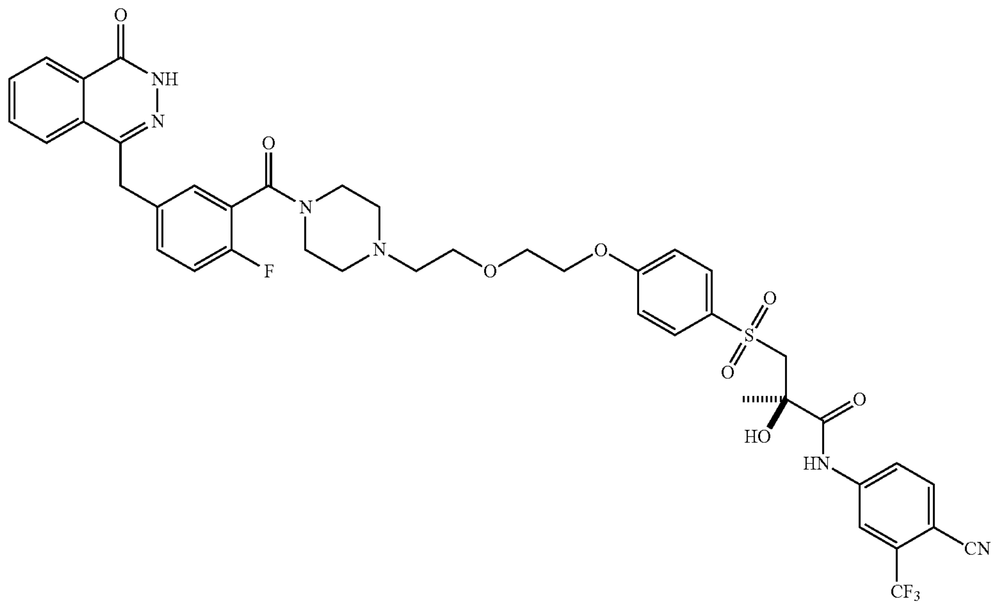 [SMILES: C[C@](O)(CS(=O)(=O)c1ccc(OCCOCCN2CCN(C(=O)c3cc(Cc4n[nH]c(=O)c5ccccc45)ccc3F)CC2)cc1)C(=O)Nc1ccc(C#N)c(C(F)(F)F)c1] |
| 1.218 | 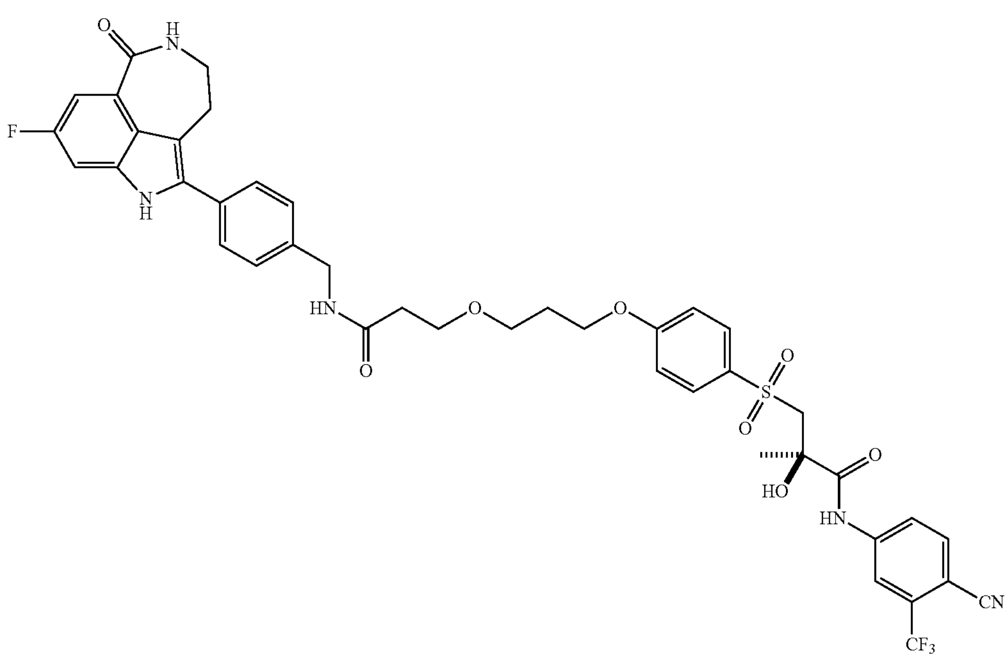 [SMILES: C[C@](O)(CS(=O)(=O)c1ccc(OCCCOCCC(=O)NCc2ccc(-c3[nH]c4cc(F)cc5c4c3CCNC5=O)cc2)cc1)C(=O)Nc1ccc(C#N)c(C(F)(F)F)c1] |

TABLE 1-continued
| No. | Structure |
|---|---|
| 1.219 | 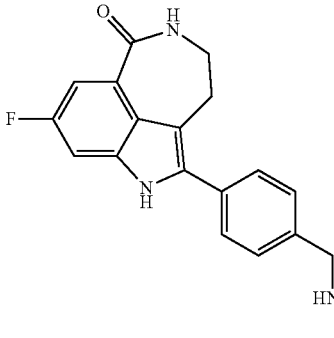 |
| 1.220 | 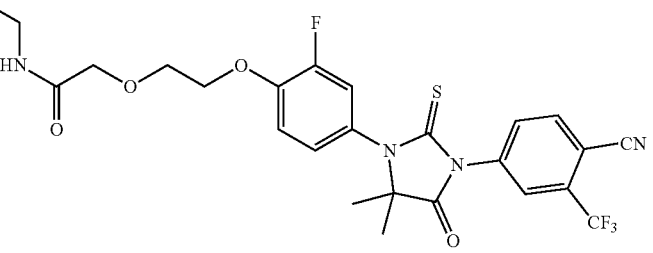 |
| 1.221 | 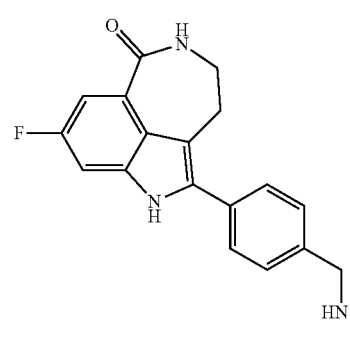 |

TABLE 1-continued

| No. | Structure |
|---|---|
| 1.222 | 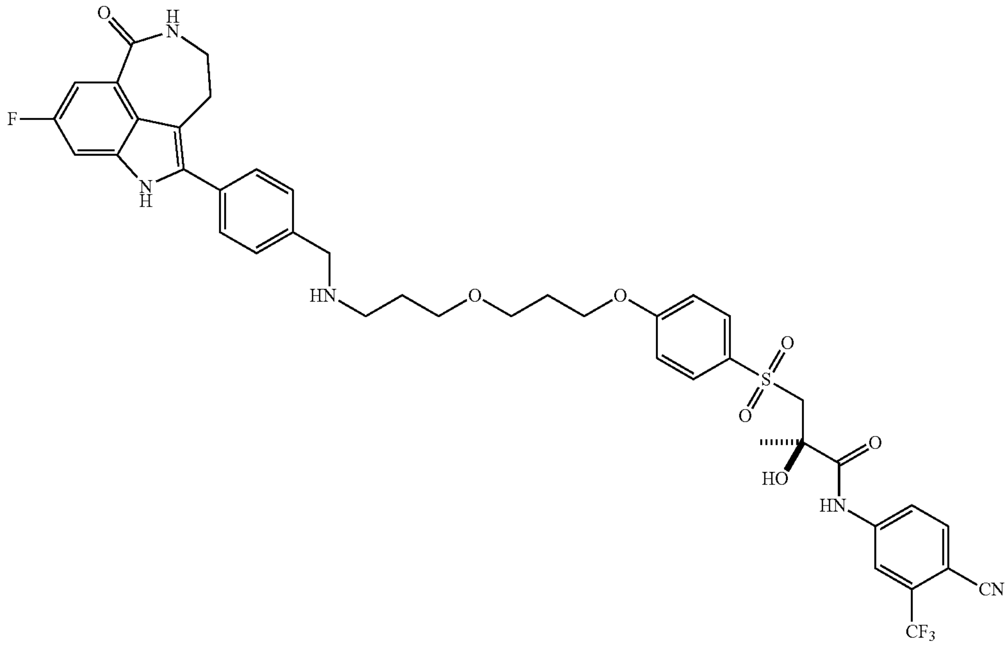 [SMILES: C[C@](O)(CS(=O)(=O)c1ccc(OCCCOCCCNCc2ccc(-c3[nH]c4cc(F)cc5c4c3CCNC5=O)cc2)cc1)C(=O)Nc1ccc(C#N)c(C(F)(F)F)c1] |
| 1.223 | 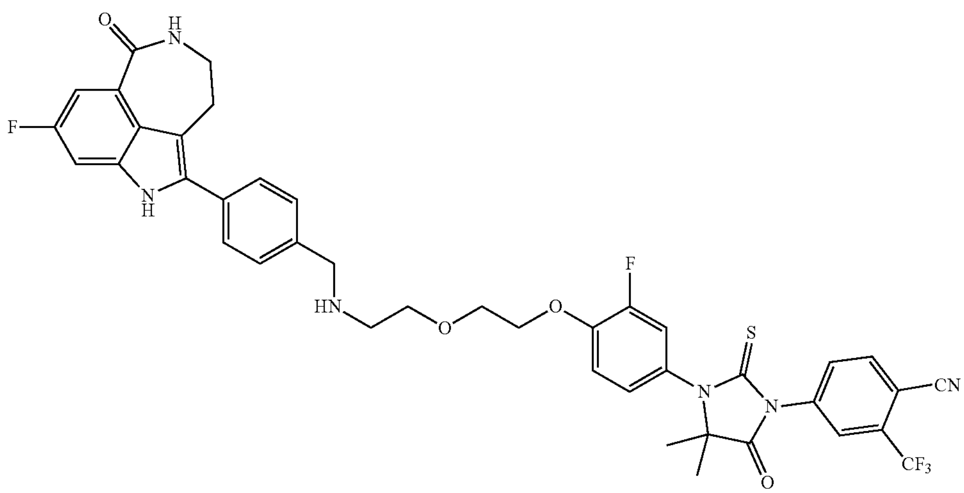 [SMILES: CC1(C)C(=O)N(c2ccc(C#N)c(C(F)(F)F)c2)C(=S)N1c1ccc(OCCOCCNCc2ccc(-c3[nH]c4cc(F)cc5c4c3CCNC5=O)cc2)c(F)c1] |
| 1.224 | 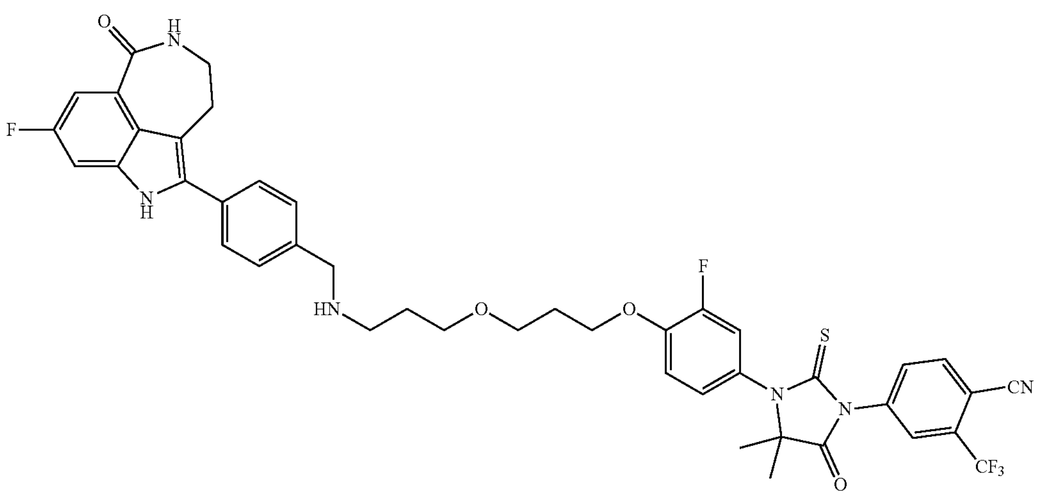 [SMILES: CC1(C)C(=O)N(c2ccc(C#N)c(C(F)(F)F)c2)C(=S)N1c1ccc(OCCCOCCCNCc2ccc(-c3[nH]c4cc(F)cc5c4c3CCNC5=O)cc2)c(F)c1] |

TABLE 1-continued
| No. | Structure |
|---|---|
| 1.225 | 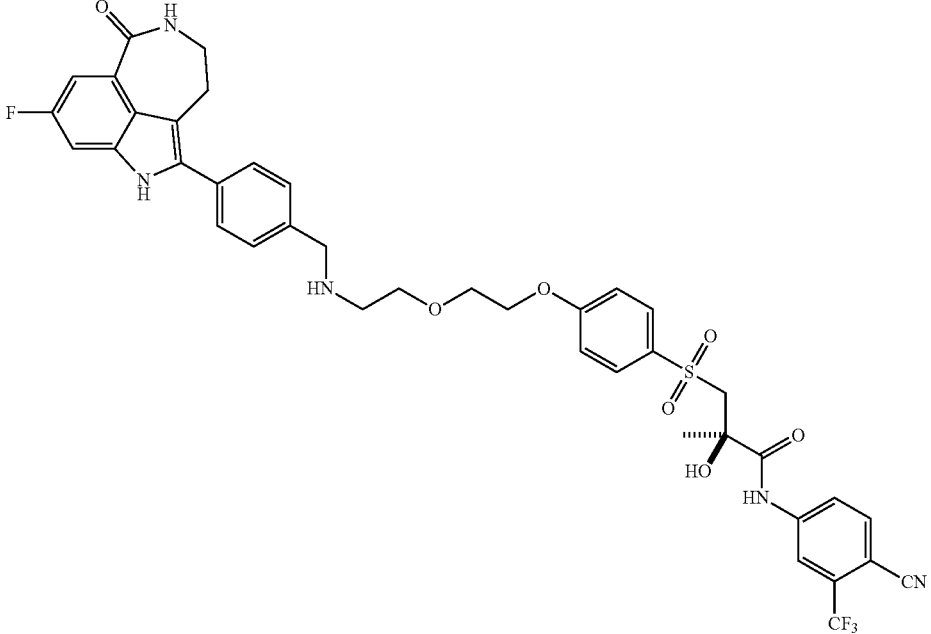 [SMILES: C[C@](O)(CS(=O)(=O)c1ccc(OCCOCCNCc2ccc(-c3[nH]c4cc(F)cc5c4c3CCNC5=O)cc2)cc1)C(=O)Nc1ccc(C#N)c(C(F)(F)F)c1] |
| 1.226 | 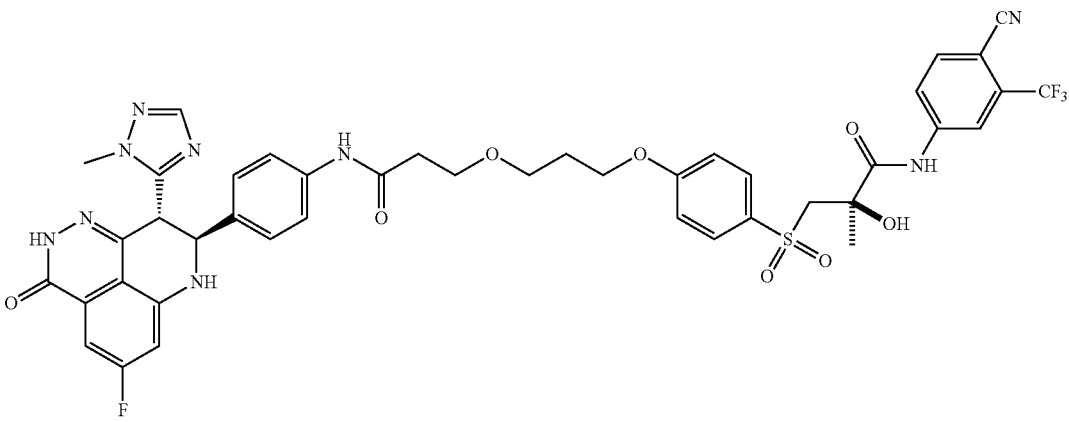 [SMILES: Cn1ncnc1[C@H]1c2n[nH]c(=O)c3cc(F)cc(c23)N[C@@H]1c1ccc(NC(=O)CCOCCCOc2ccc(S(=O)(=O)C[C@](C)(O)C(=O)Nc3ccc(C#N)c(C(F)(F)F)c3)cc2)cc1] |
| 1.227 | 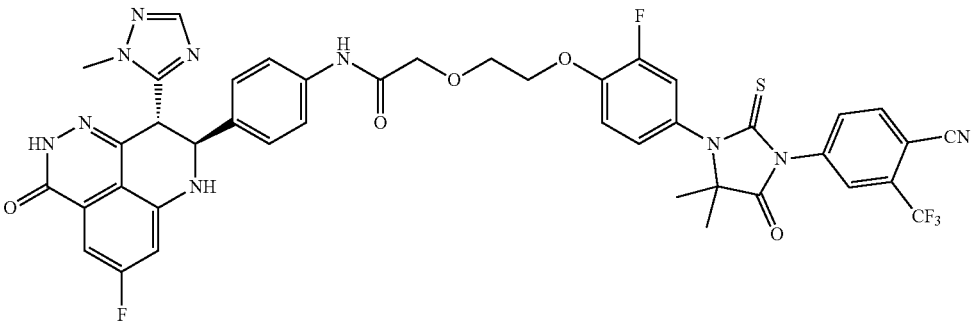 [SMILES: Cn1ncnc1[C@H]1c2n[nH]c(=O)c3cc(F)cc(c23)N[C@@H]1c1ccc(NC(=O)COCCOc2ccc(N3C(=S)N(c4ccc(C#N)c(C(F)(F)F)c4)C(=O)C3(C)C)cc2F)cc1] |

TABLE 1-continued

| No. | Structure |
|---|---|
| 1.228 | 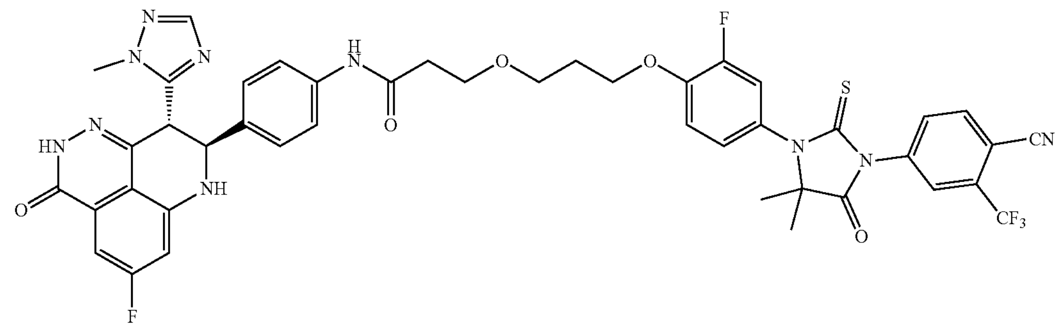 [SMILES: Cn1ncnc1[C@H]1c2n[nH]c(=O)c3cc(F)cc(c23)N[C@@H]1c1ccc(NC(=O)CCOCCCOc2ccc(N3C(=S)N(c4ccc(C#N)c(C(F)(F)F)c4)C(=O)C3(C)C)cc2F)cc1] |
| 1.229 | 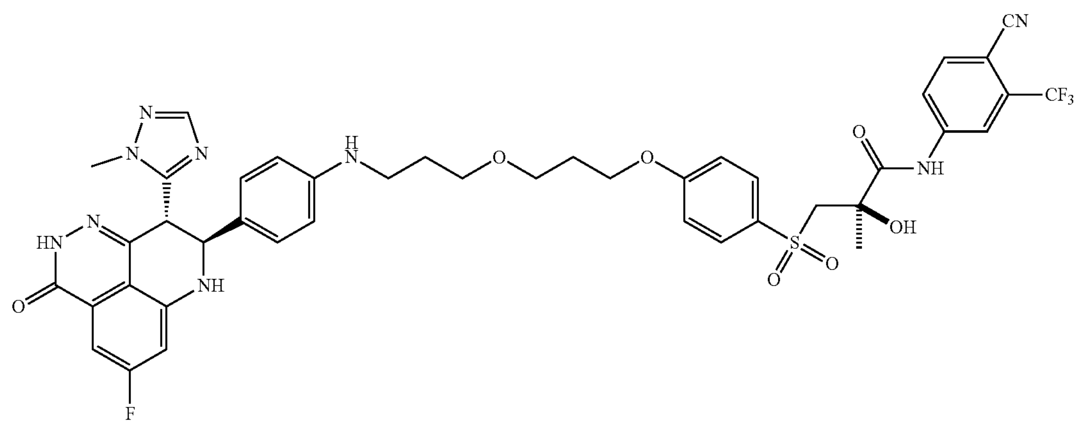 [SMILES: Cn1ncnc1[C@H]1c2n[nH]c(=O)c3cc(F)cc(c23)N[C@@H]1c1ccc(NCCCOCCCOc2ccc(S(=O)(=O)C[C@](C)(O)C(=O)Nc3ccc(C#N)c(C(F)(F)F)c3)cc2)cc1] |
| 1.230 | 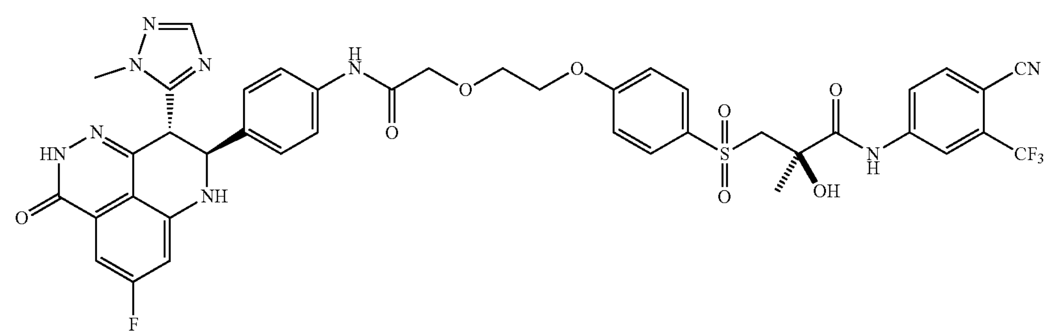 [SMILES: Cn1ncnc1[C@H]1c2n[nH]c(=O)c3cc(F)cc(c23)N[C@@H]1c1ccc(NC(=O)COCCOc2ccc(S(=O)(=O)C[C@](C)(O)C(=O)Nc3ccc(C#N)c(C(F)(F)F)c3)cc2)cc1] |
| 1.231 | 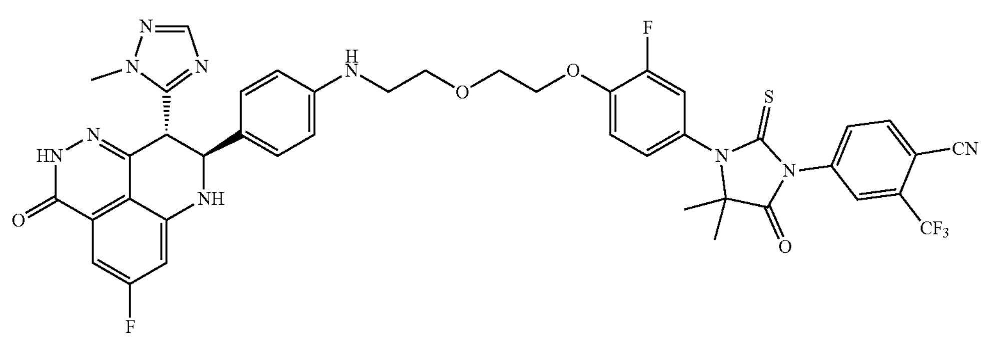 [SMILES: Cn1ncnc1[C@H]1c2n[nH]c(=O)c3cc(F)cc(c23)N[C@@H]1c1ccc(NCCOCCOc2ccc(N3C(=S)N(c4ccc(C#N)c(C(F)(F)F)c4)C(=O)C3(C)C)cc2F)cc1] |

TABLE 1-continued
| No. | Structure |
|---|---|
| 1.232 | 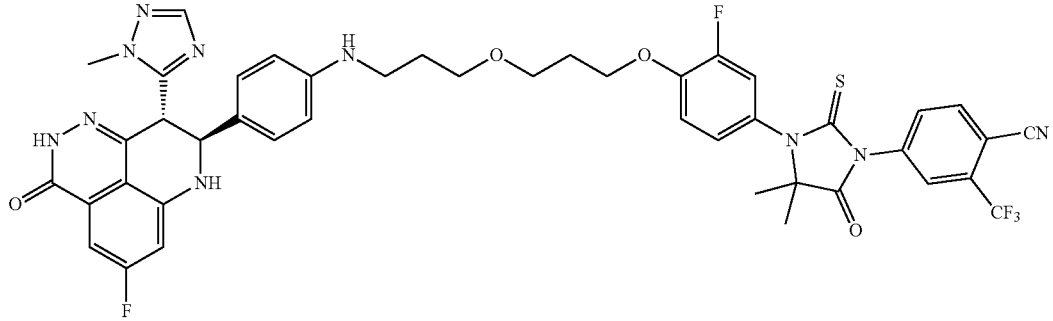 [SMILES: Cn1ncnc1[C@H]1c2n[nH]c(=O)c3cc(F)cc(c23)N[C@@H]1c1ccc(NCCCOCCCOc2ccc(N3C(=S)N(c4ccc(C#N)c(C(F)(F)F)c4)C(=O)C3(C)C)cc2F)cc1] |
| 1.233 | 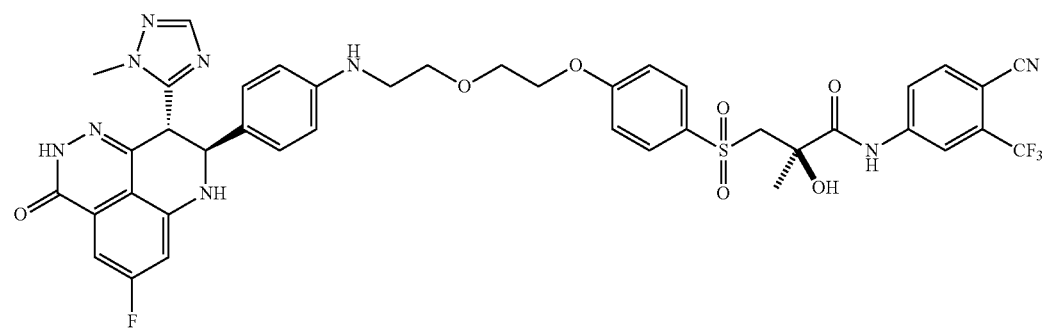 [SMILES: Cn1ncnc1[C@H]1c2n[nH]c(=O)c3cc(F)cc(c23)N[C@@H]1c1ccc(NCCOCCOc2ccc(S(=O)(=O)C[C@](C)(O)C(=O)Nc3ccc(C#N)c(C(F)(F)F)c3)cc2)cc1] |
| 1.234 | 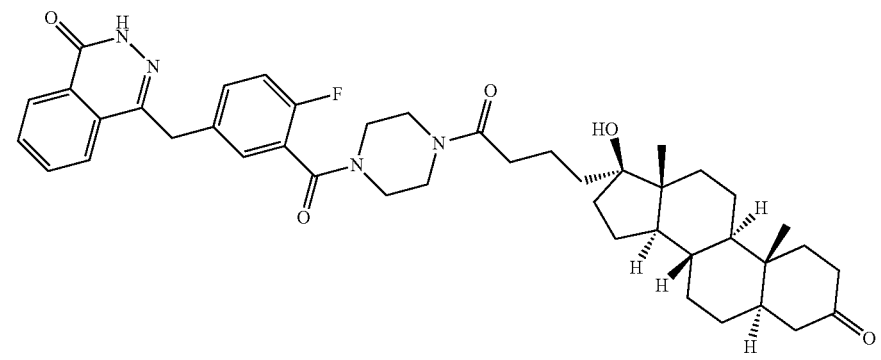 [SMILES: C[C@@]12CCC(=O)C[C@H]1CC[C@H]1[C@H]2CC[C@]2(C)[C@@H]1CC[C@]2(O)CCCC(=O)N1CCN(C(=O)c2cc(Cc3n[nH]c(=O)c4ccccc34)ccc2F)CC1] |
| 1.235 | 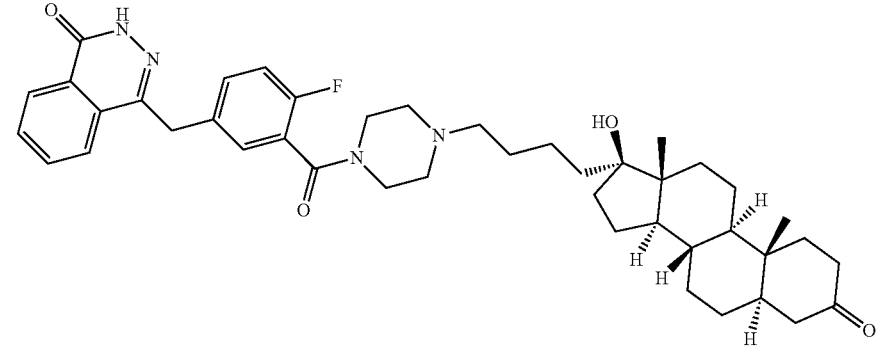 [SMILES: C[C@@]12CCC(=O)C[C@H]1CC[C@H]1[C@H]2CC[C@]2(C)[C@@H]1CC[C@]2(O)CCCCN1CCN(C(=O)c2cc(Cc3n[nH]c(=O)c4ccccc34)ccc2F)CC1] |

TABLE 1-continued

| No. | Structure |
|---|---|
| 1.236 | 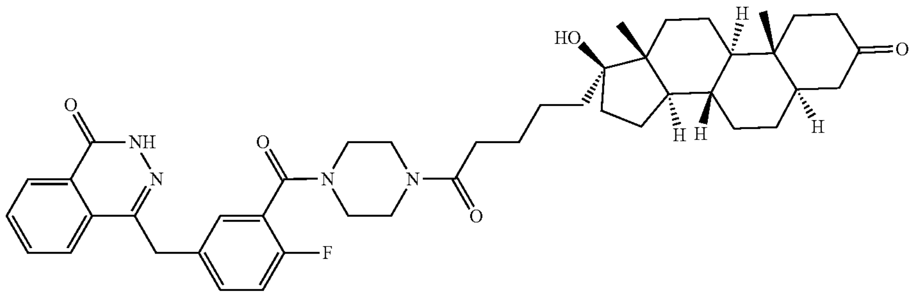 [SMILES: C[C@@]12CCC(=O)C[C@H]1CC[C@H]1[C@H]2CC[C@]2(C)[C@@H]1CC[C@]2(O)CCCCC(=O)N1CCN(C(=O)c2cc(Cc3n[nH]c(=O)c4ccccc34)ccc2F)CC1] |
| 1.237 | 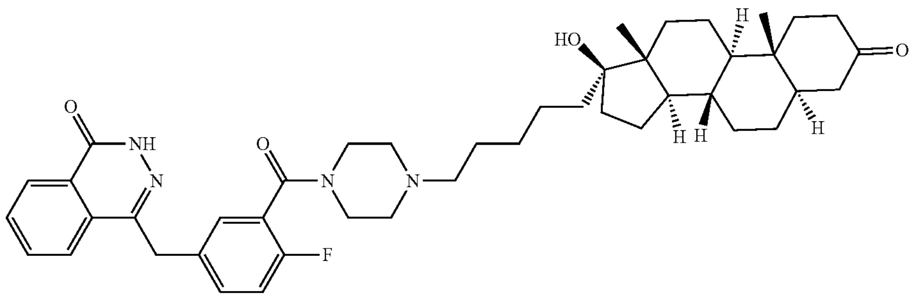 [SMILES: C[C@@]12CCC(=O)C[C@H]1CC[C@H]1[C@H]2CC[C@]2(C)[C@@H]1CC[C@]2(O)CCCCCN1CCN(C(=O)c2cc(Cc3n[nH]c(=O)c4ccccc34)ccc2F)CC1] |
| 1.238 | 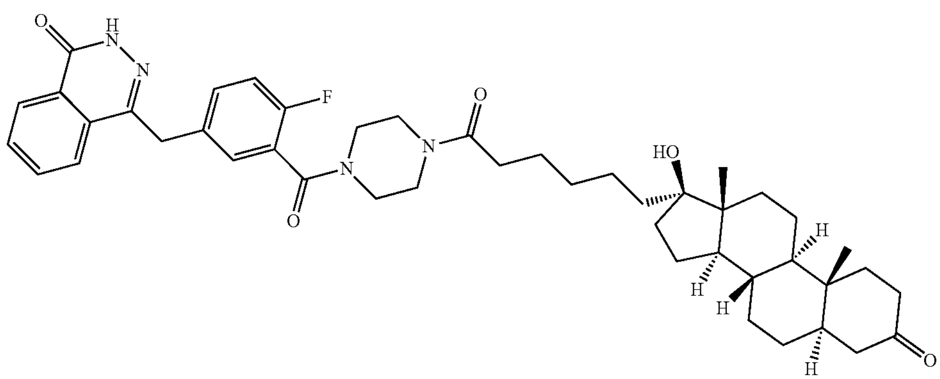 [SMILES: C[C@@]12CCC(=O)C[C@H]1CC[C@H]1[C@H]2CC[C@]2(C)[C@@H]1CC[C@]2(O)CCCCCC(=O)N1CCN(C(=O)c2cc(Cc3n[nH]c(=O)c4ccccc34)ccc2F)CC1] |
| 1.239 | 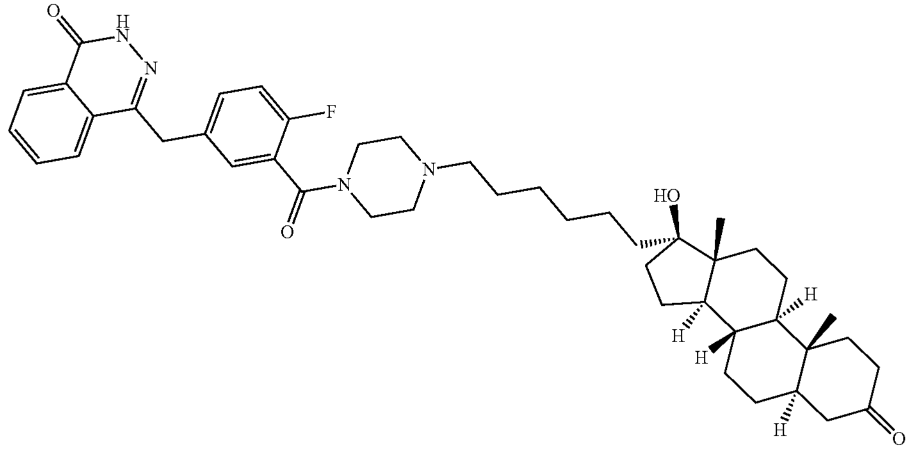 [SMILES: C[C@@]12CCC(=O)C[C@H]1CC[C@H]1[C@H]2CC[C@]2(C)[C@@H]1CC[C@]2(O)CCCCCCN1CCN(C(=O)c2cc(Cc3n[nH]c(=O)c4ccccc34)ccc2F)CC1] |

TABLE 1-continued

| No. | Structure |
|---|---|
| 1.240 | 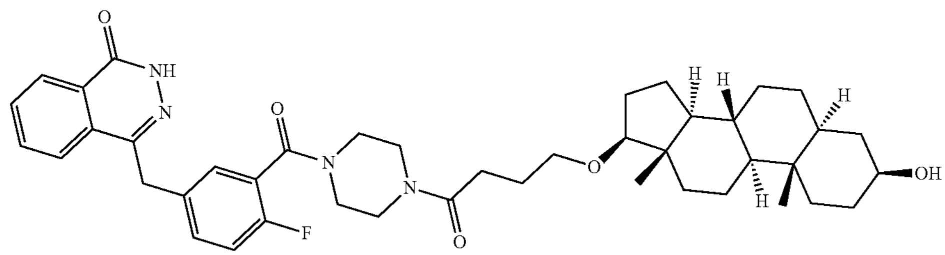 [SMILES: C[C@]12CC[C@H](O)C[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |
| 1.241 | 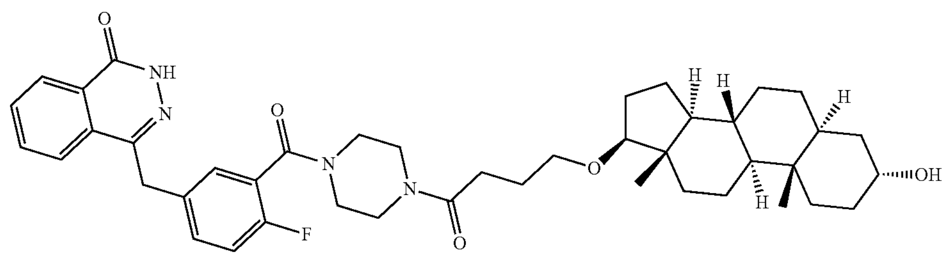 [SMILES: C[C@]12CC[C@@H](O)C[C@@H]1CC[C@@H]1[C@@H]2CC[C@]2(C)[C@@H](OCCCC(=O)N3CCN(C(=O)c4cc(Cc5n[nH]c(=O)c6ccccc56)ccc4F)CC3)CC[C@@H]12] |
| 1.242 | 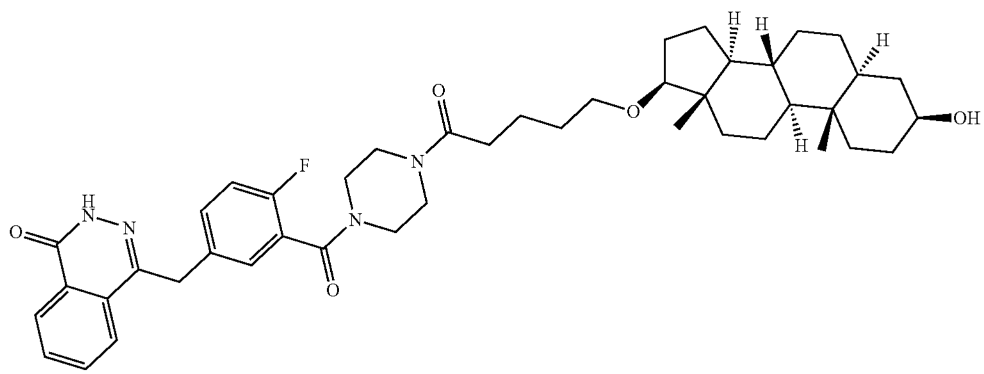 [SMILES: C[C@]12CC[C@H](O)C[C@@H]1CC[C@@H]1[C@@H]2CC[C@]2(C)[C@@H](OCCCCC(=O)N3CCN(C(=O)c4cc(Cc5n[nH]c(=O)c6ccccc56)ccc4F)CC3)CC[C@@H]12] |
| 1.243 | 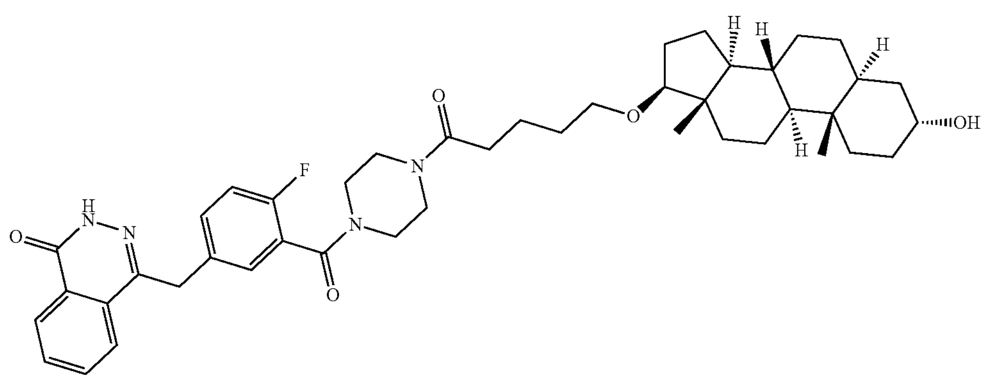 [SMILES: C[C@]12CC[C@@H](O)C[C@@H]1CC[C@@H]1[C@@H]2CC[C@]2(C)[C@@H](OCCCCC(=O)N3CCN(C(=O)c4cc(Cc5n[nH]c(=O)c6ccccc56)ccc4F)CC3)CC[C@@H]12] |
| 1.244 | 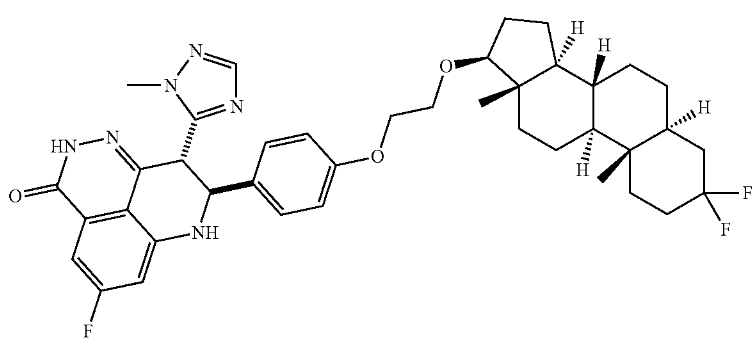 |

TABLE 1-continued

| No. | Structure |
|---|---|
| 1.245 | 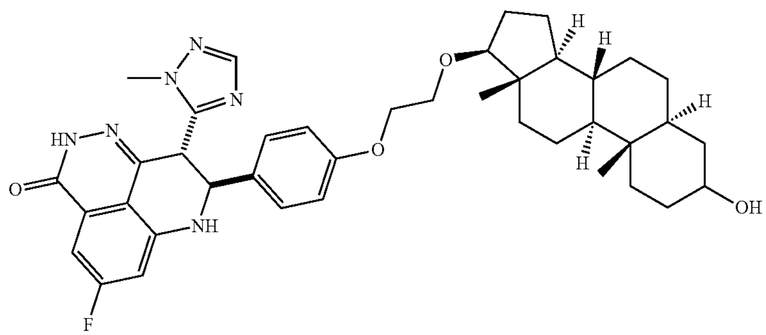 |
| 1.246 | 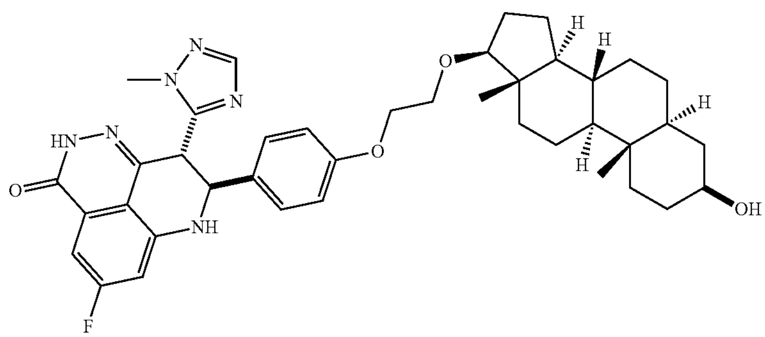 |
| 1.247 | 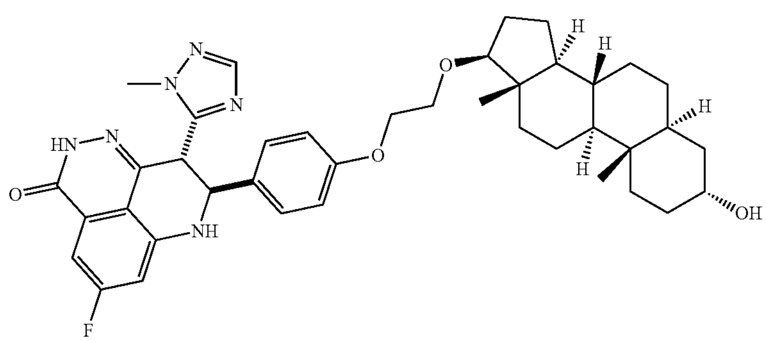 |
| 1.248 | 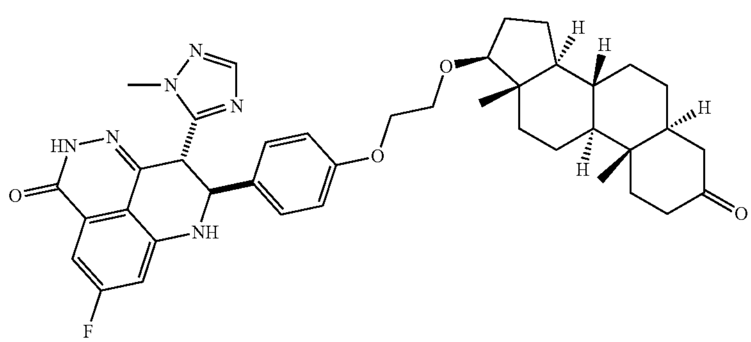 |

TABLE 1-continued

| No. | Structure |
|---|---|
| 1.249 | 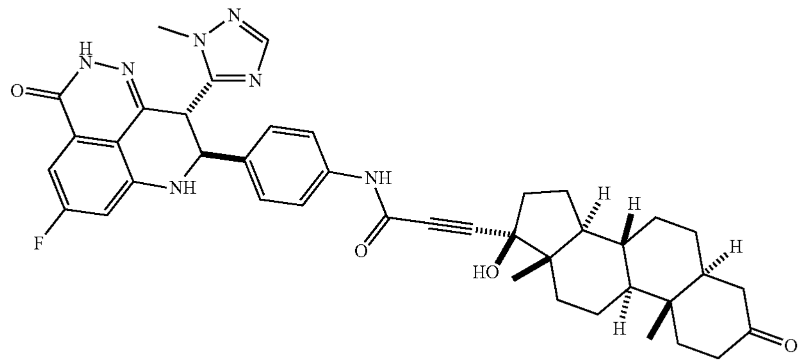 |
| 1.250 | 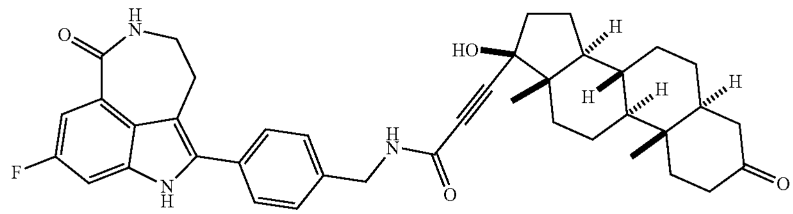 |
| 1.251 | 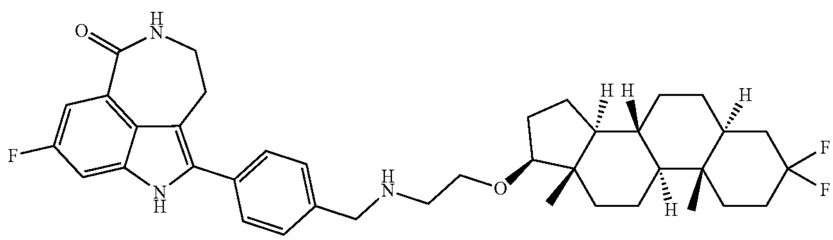 [SMILES: C[C@]12CCC(F)(F)C[C@@H]1CC[C@@H]1[C@@H]2CC[C@]2(C)[C@@H](OCCNCc3ccc(-c4[nH]c5cc(F)cc6c5c4CCNC6=O)cc3)CC[C@@H]12] |
| 1.252 | 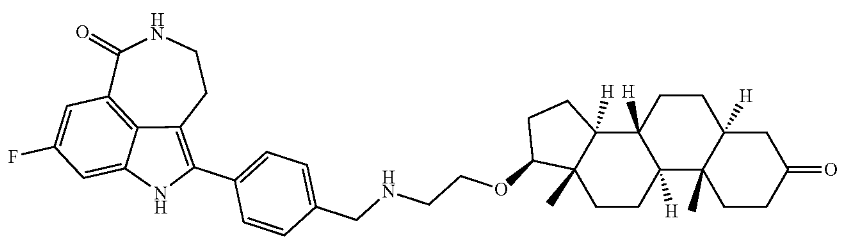 [SMILES: C[C@]12CCC(=O)C[C@@H]1CC[C@@H]1[C@@H]2CC[C@]2(C)[C@@H](OCCNCc3ccc(-c4[nH]c5cc(F)cc6c5c4CCNC6=O)cc3)CC[C@@H]12] |
| 1.253 | 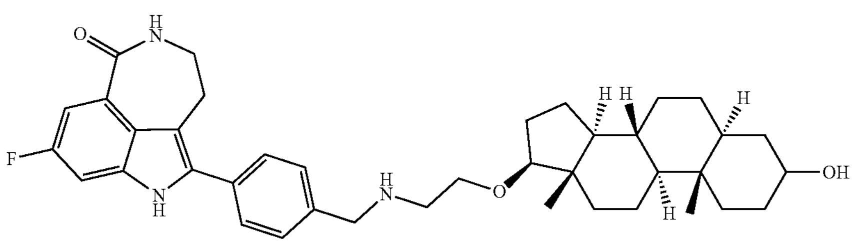 [SMILES: C[C@]12CCC(O)C[C@@H]1CC[C@@H]1[C@@H]2CC[C@]2(C)[C@@H](OCCNCc3ccc(-c4[nH]c5cc(F)cc6c5c4CCNC6=O)cc3)CC[C@@H]12] |
| 1.254 | 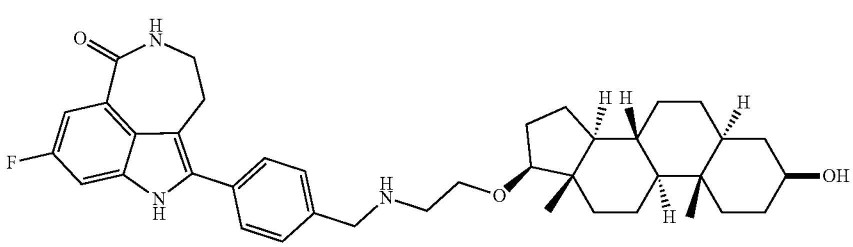 [SMILES: C[C@]12CC[C@H](O)C[C@@H]1CC[C@@H]1[C@@H]2CC[C@]2(C)[C@@H](OCCNCc3ccc(-c4[nH]c5cc(F)cc6c5c4CCNC6=O)cc3)CC[C@@H]12] |

TABLE 1-continued
| No. | Structure |
|---|---|
| 1.255 | 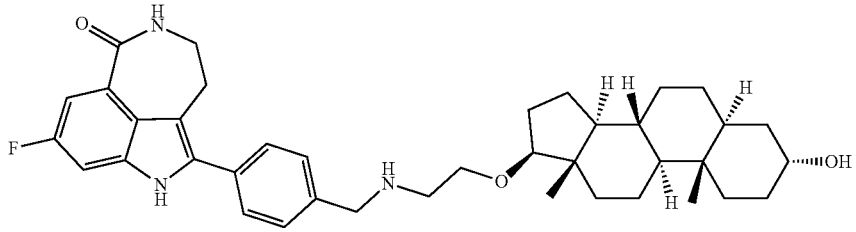 |
| 1.256 | 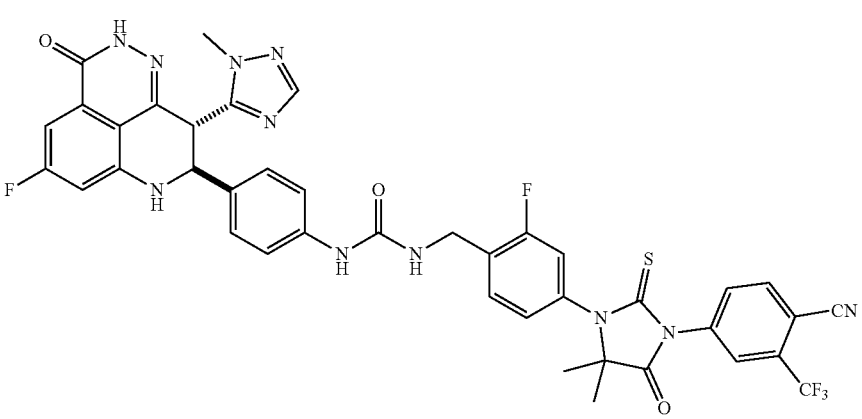 [SMILES: Cn1ncnc1[C@H]1c2n[nH]c(=O)c3cc(F)cc(c23)N[C@@H]1c1ccc(NC(=O)NCc2ccc(N3C(=S)N(c4ccc(C#N)c(C(F)(F)F)c4)C(=O)C3(C)C)cc2F)cc1] |
| 1.257 | 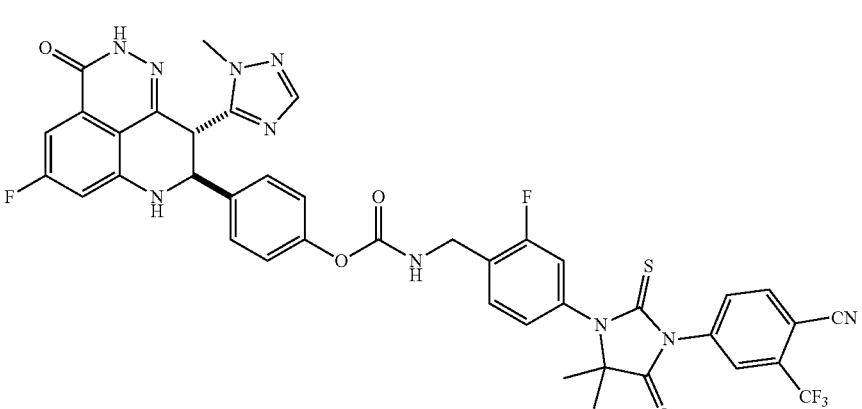 |
| 1.258 | 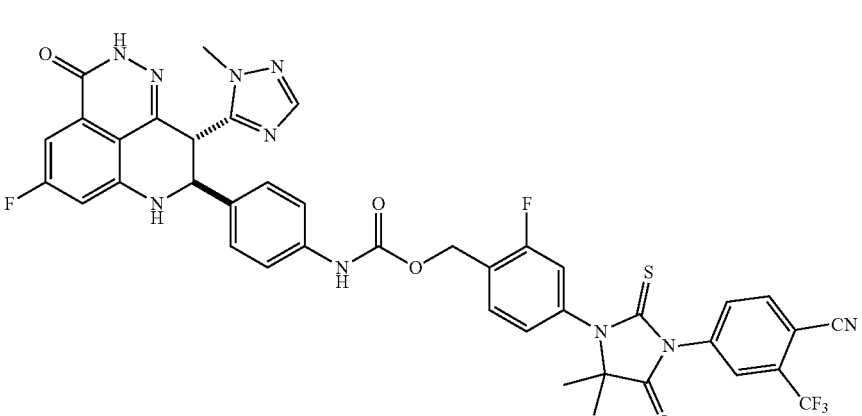 |

TABLE 1-continued

| No. | Structure |
|---|---|
| 1.259 | 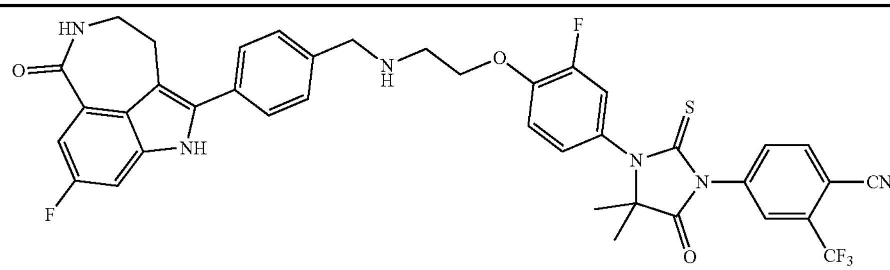 |
| 2.1 | 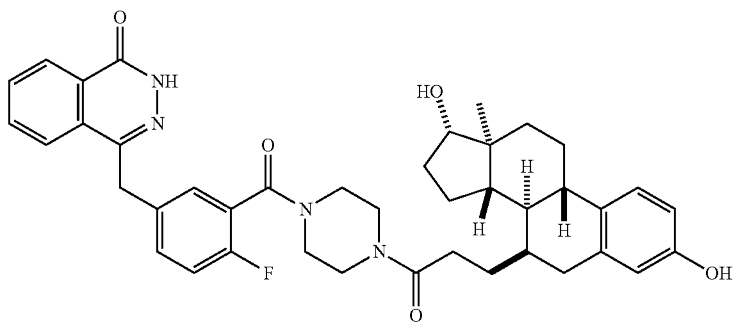 |
| 2.2 | 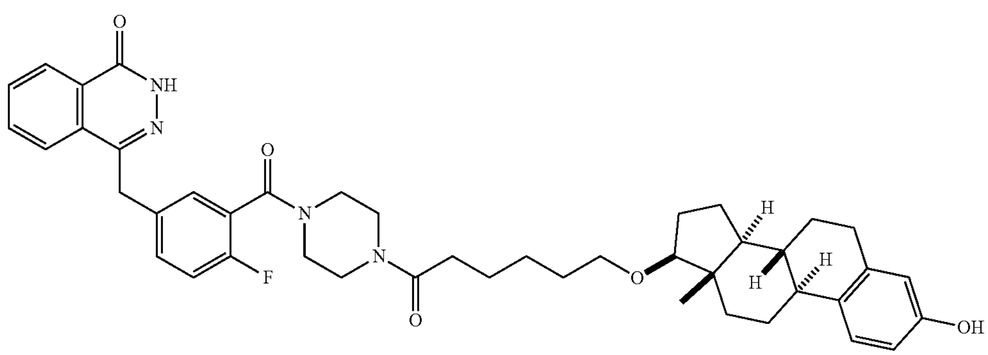 |
| 2.3 | 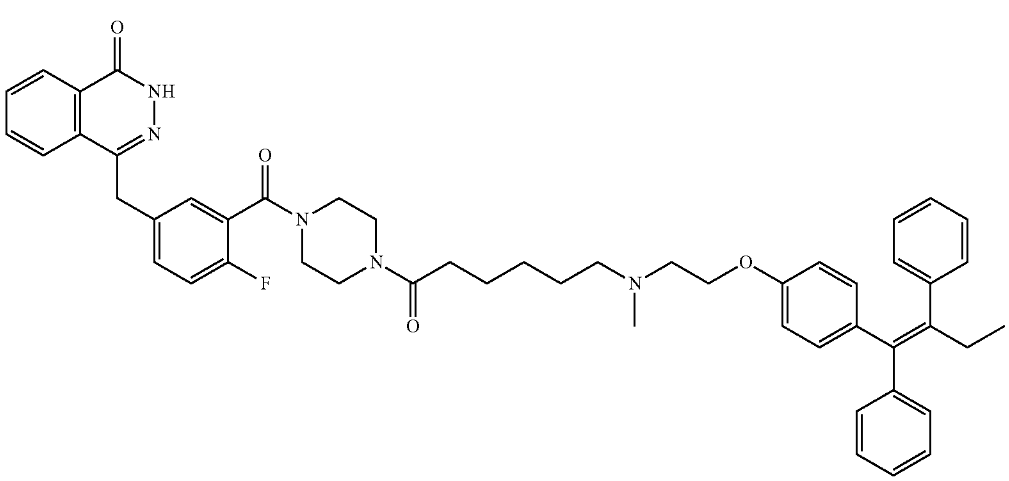 [SMILES: CC/C(=C(\c1ccccc1)c1ccc(OCCN(C)CCCCCC(=O)N2CCN(C(=O)c3cc(Cc4n[nH]c(=O)c5ccccc45)ccc3F)CC2)cc1)c1ccccc1] |

TABLE 1-continued

| No. | Structure |
|---|---|
| 2.4 | 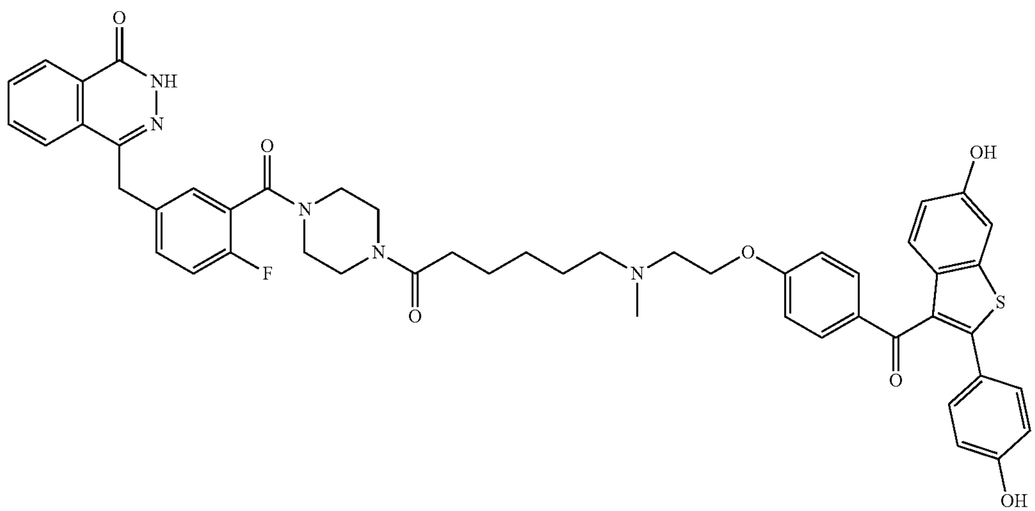 [SMILES: CN(CCCCCC(=O)N1CCN(C(=O)c2cc(Cc3n[nH]c(=O)c4ccccc34)ccc2F)CC1)CCOc1ccc(C(=O)c2c(-c3ccc(O)cc3)sc3cc(O)ccc23)cc1] |
| 2.5 | 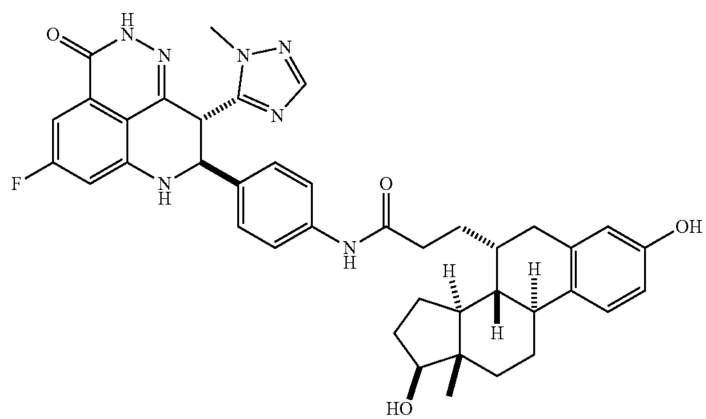 |
| 2.6 | 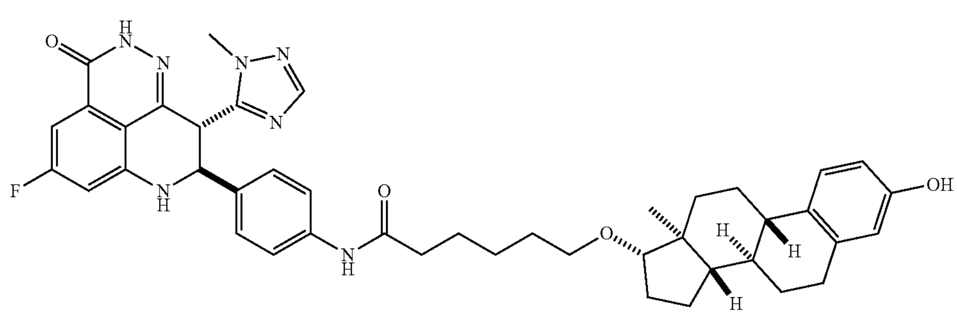 |
| 2.7 | 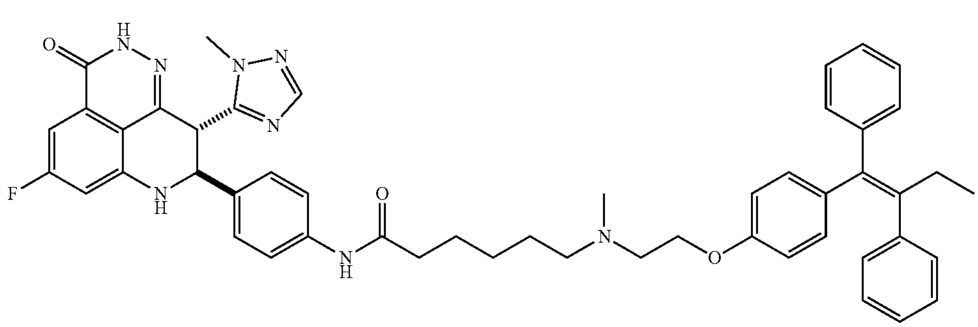 [SMILES: CC/C(=C(\c1ccccc1)c1ccc(OCCN(C)CCCCCC(=O)Nc2ccc([C@H]3Nc4cc(F)cc5c(=O)[nH]nc(c45)[C@@H]3c3ncnn3C)cc2)cc1)c1ccccc1] |

TABLE 1-continued
| No. | Structure |
|---|---|
| 2.8 | 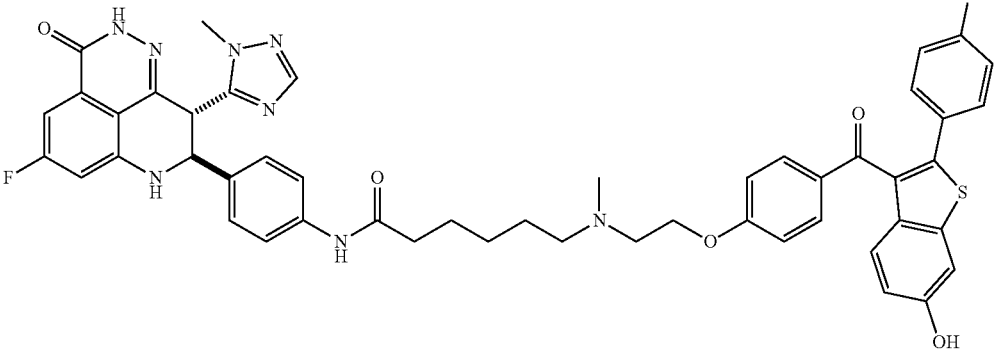 |
| 2.9 | 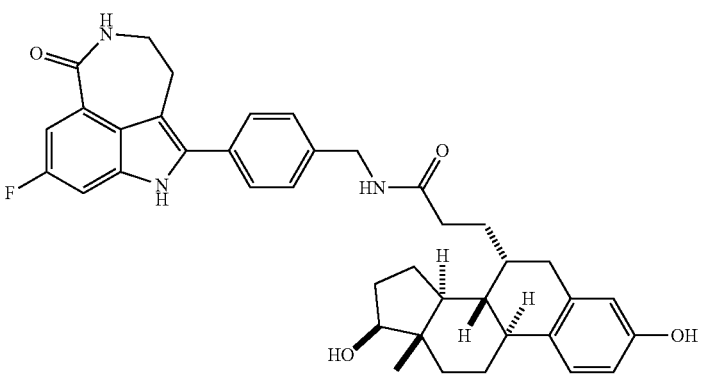 |
| 2.10 | 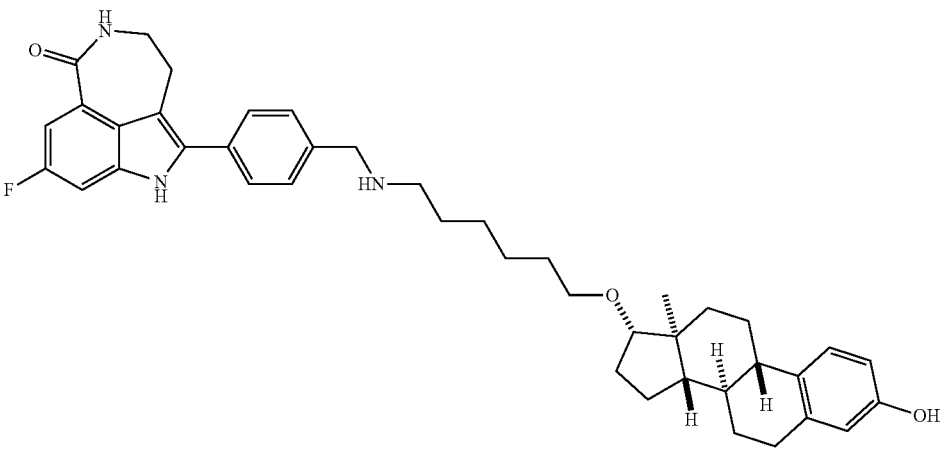 |

TABLE 1-continued

| No. | Structure |
|---|---|
| 2.11 | 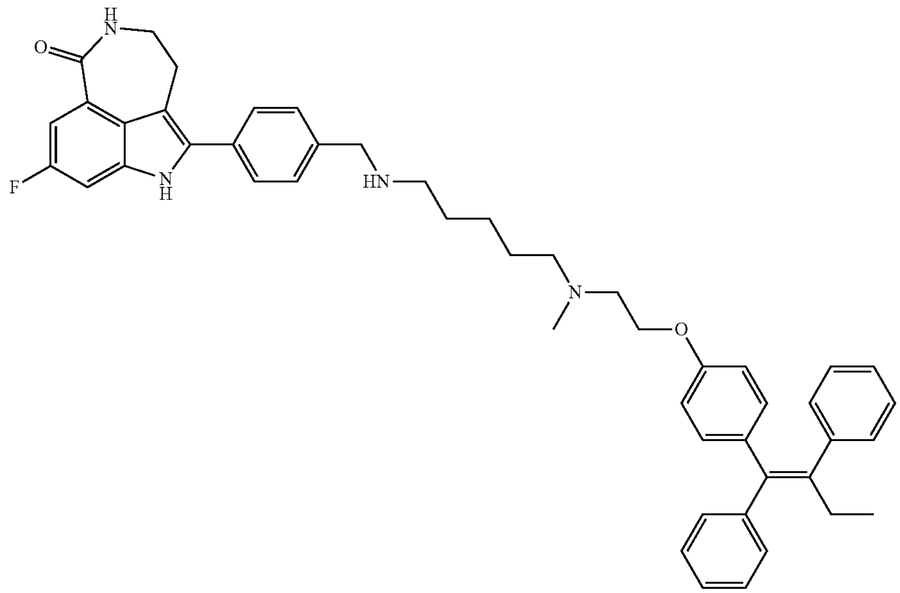 [SMILES: CC/C(=C(\c1ccccc1)c1ccc(OCCN(C)CCCCCNCc2ccc(-c3[nH]c4cc(F)cc5c4c3CCNC5=O)cc2)cc1)c1ccccc1] |
| 2.12 | 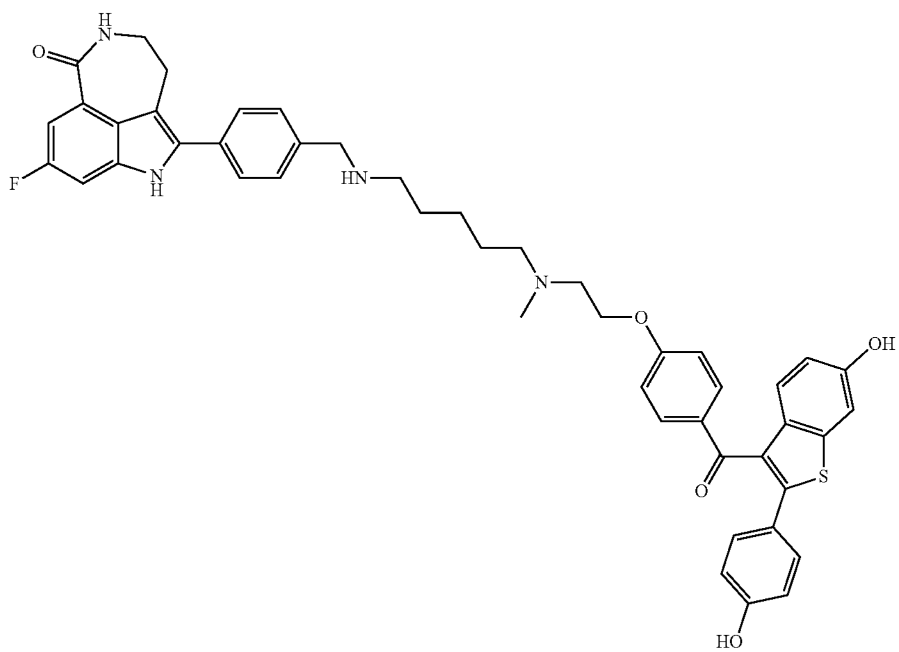 [SMILES: CN(CCCCCNCc1ccc(-c2[nH]c3cc(F)cc4c3c2CCNC4=O)cc1)CCOc1ccc(C(=O)c2c(-c3ccc(O)cc3)sc3cc(O)ccc23)cc1] |
| 2.13 | 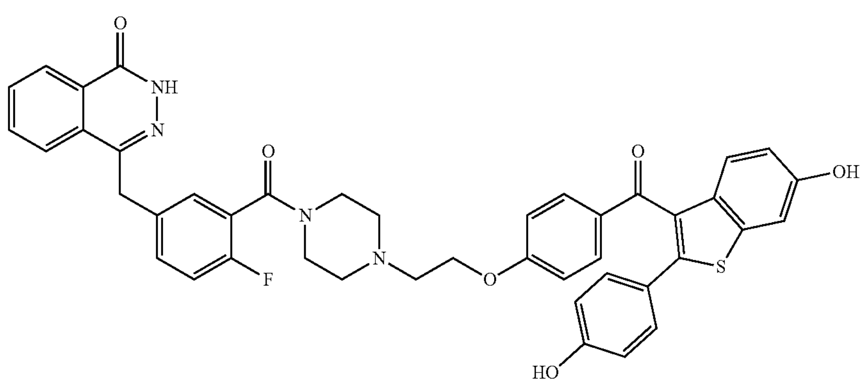 [SMILES: O=C(c1ccc(OCCN2CCN(C(=O)c3cc(Cc4n[nH]c(=O)c5ccccc45)ccc3F)CC2)cc1)c1c(-c2ccc(O)cc2)sc2cc(O)ccc12] |

TABLE 1-continued
| No. | Structure |
|---|---|
| 2.14 | 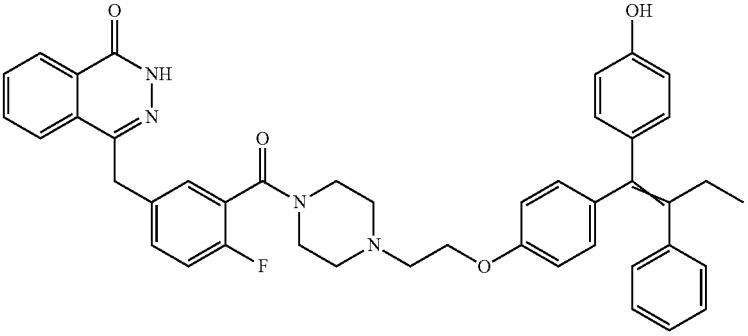 [SMILES: CCC(=C(c1ccc(O)cc1)c1ccc(OCCN2CCN(C(=O)c3cc(Cc4n[nH]c(=O)c5ccccc45)ccc3F)CC2)cc1)c1ccccc1] |
| 2.15 | 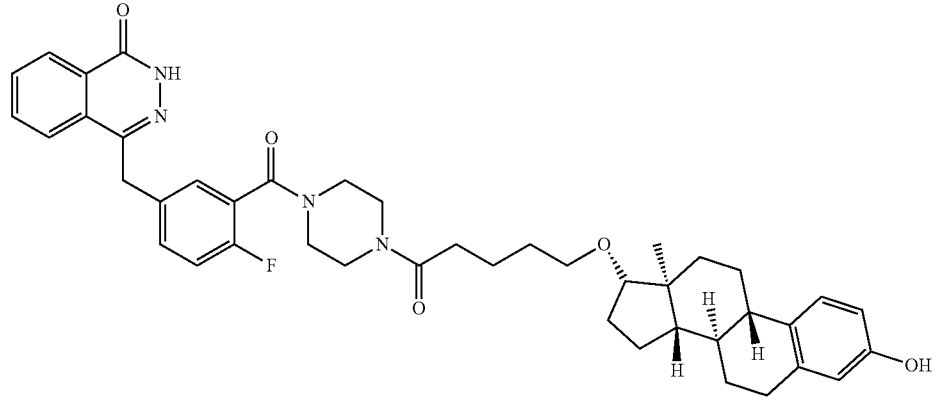 |
| 2.16 | 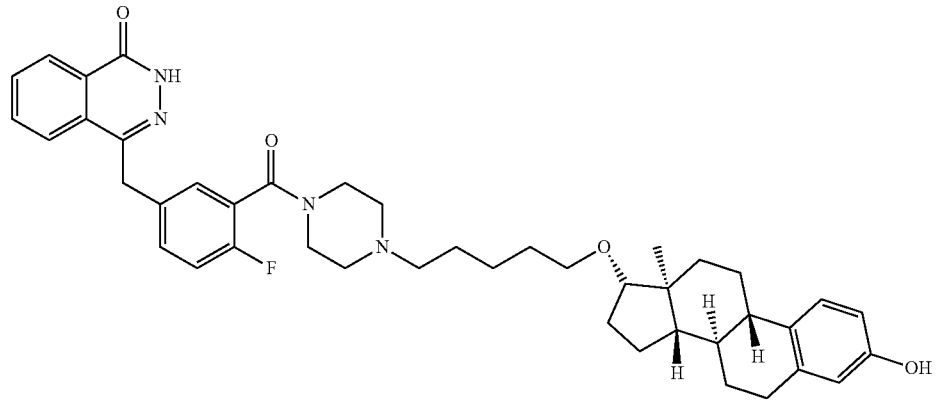 |
| 2.17 | 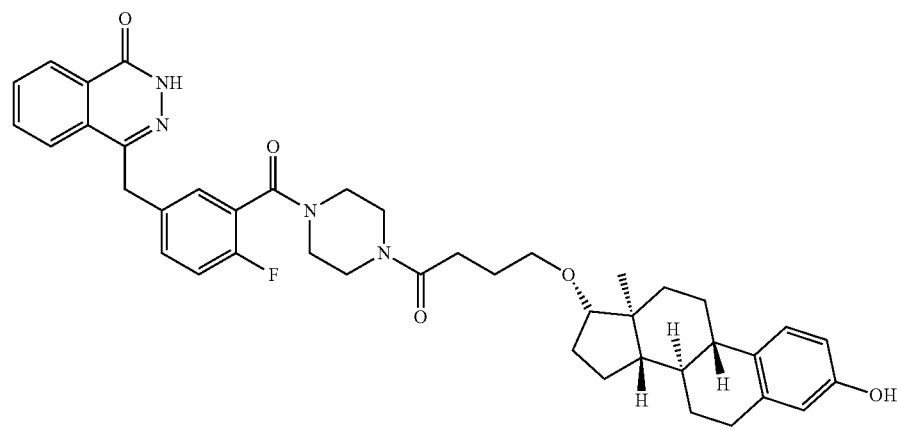 |

TABLE 1-continued

| No. | Structure |
|---|---|
| 2.18 | 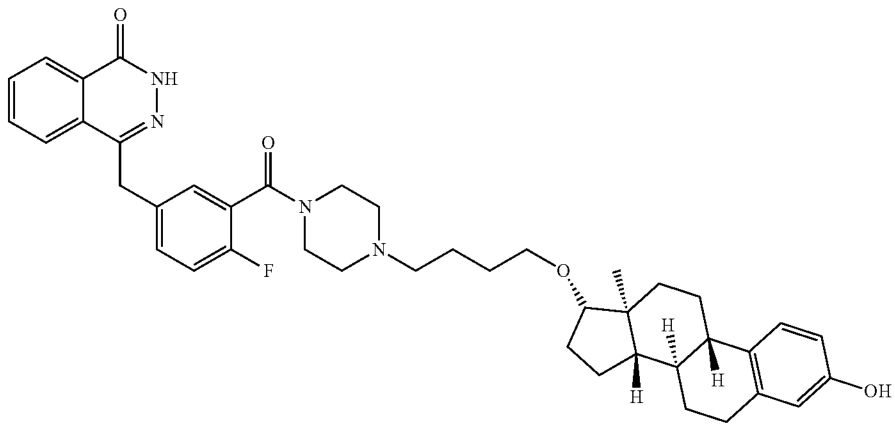 |
| 2.19 | 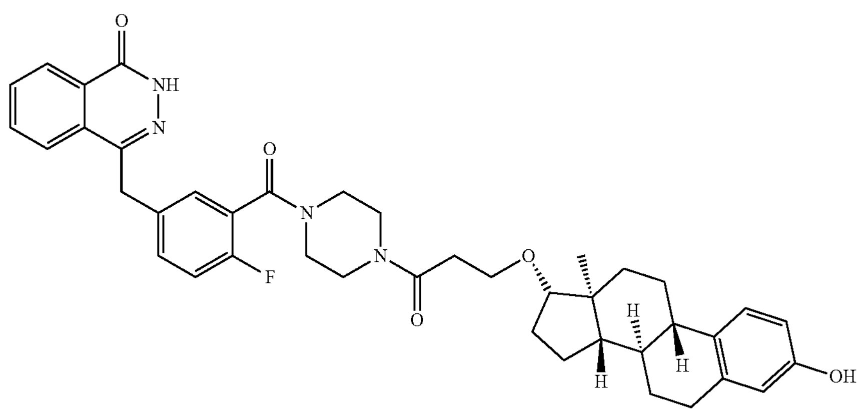 |
| 2.20 | 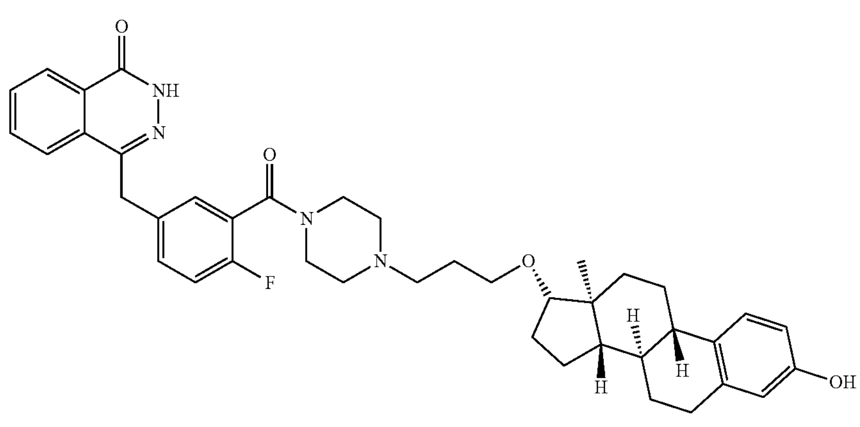 |

TABLE 1-continued

| No. | Structure |
|---|---|
| 2.21 | 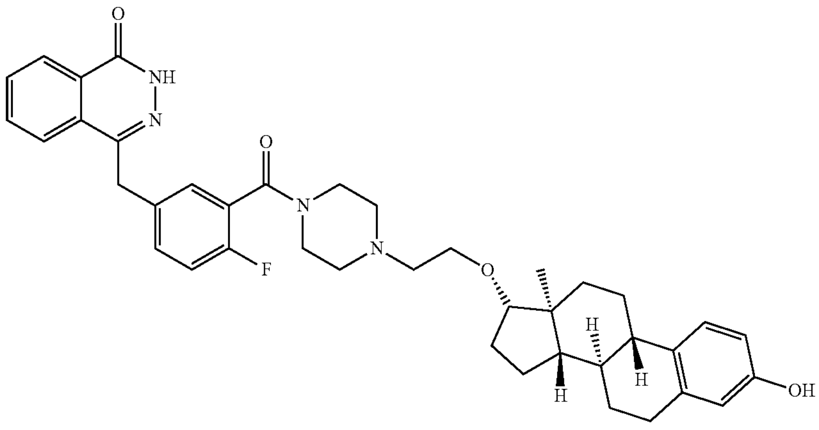 |
| 2.22 | 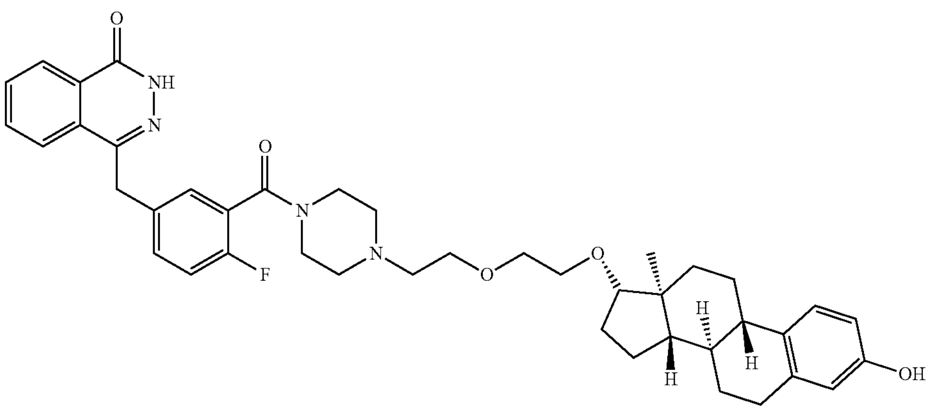 |
| 2.23 | 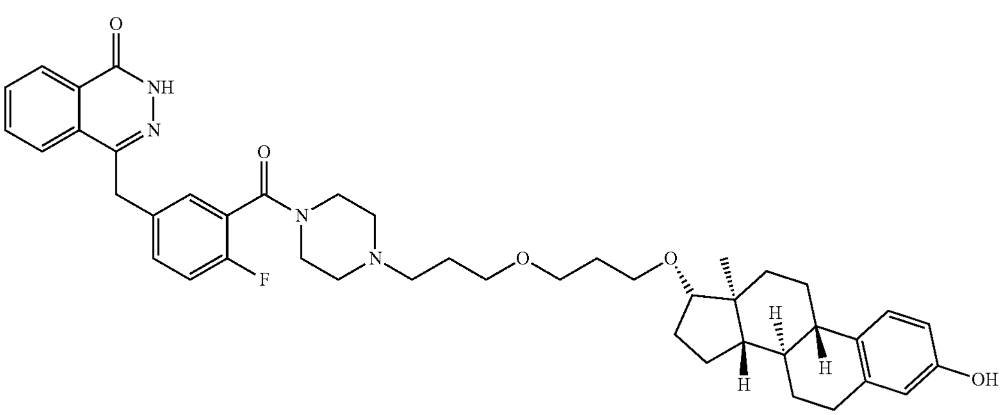 |

TABLE 1-continued

| No. | Structure |
|---|---|
| 2.24 | 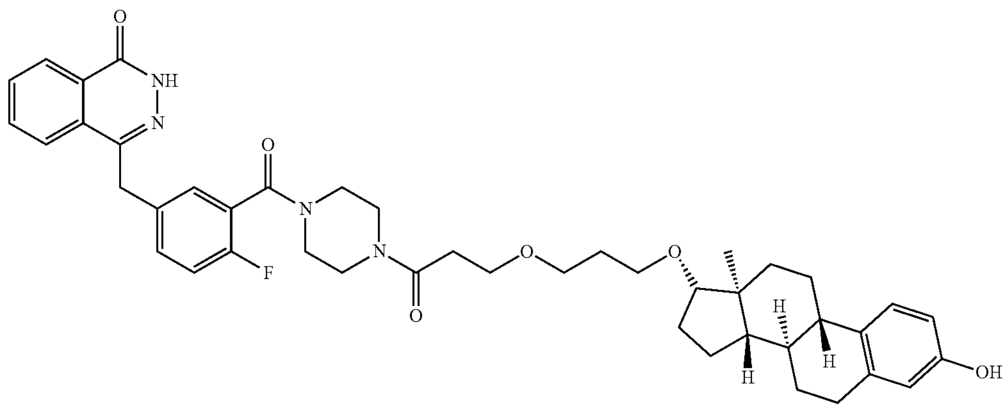 |
| 2.25 | 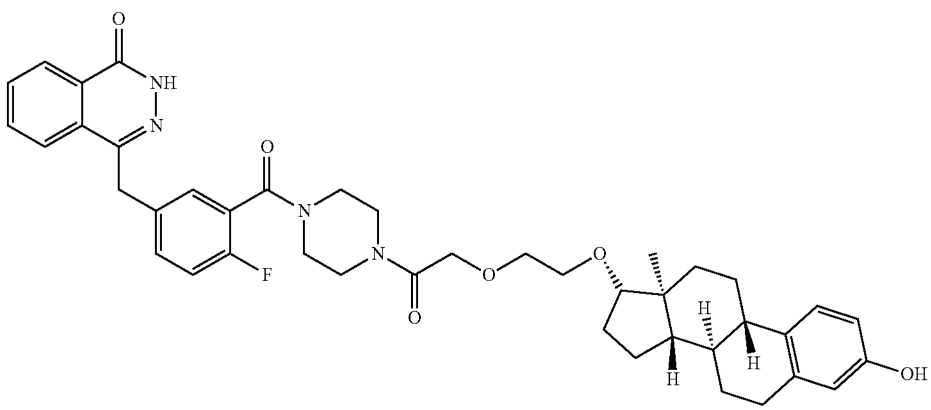 |
| 2.26 | 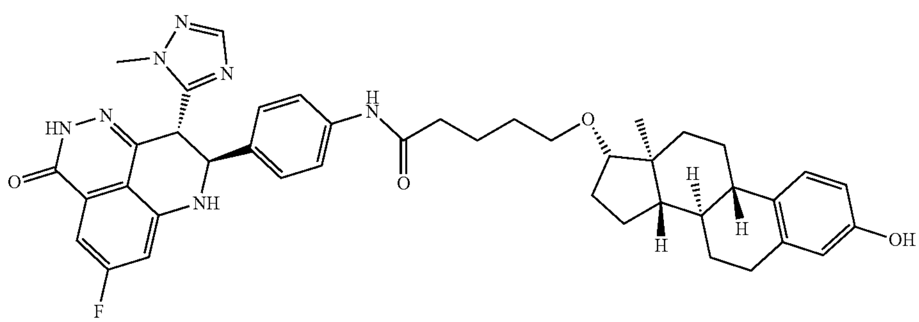 |
| 2.27 | 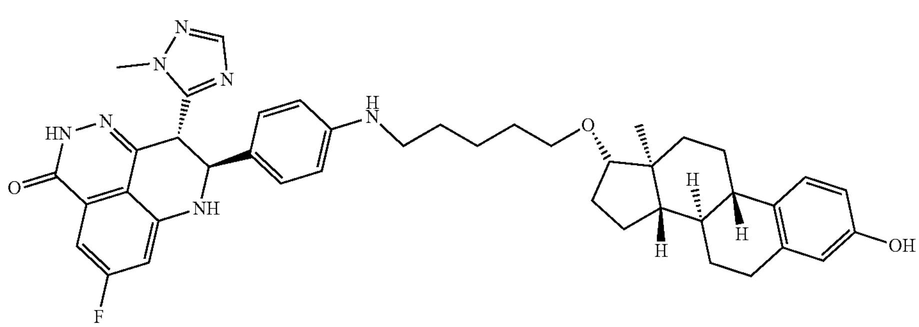 |

TABLE 1-continued

| No. | Structure |
|---|---|
| 2.28 | 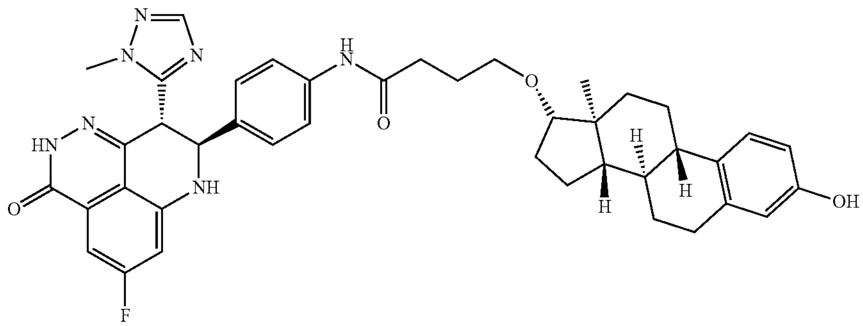 |
| 2.29 | 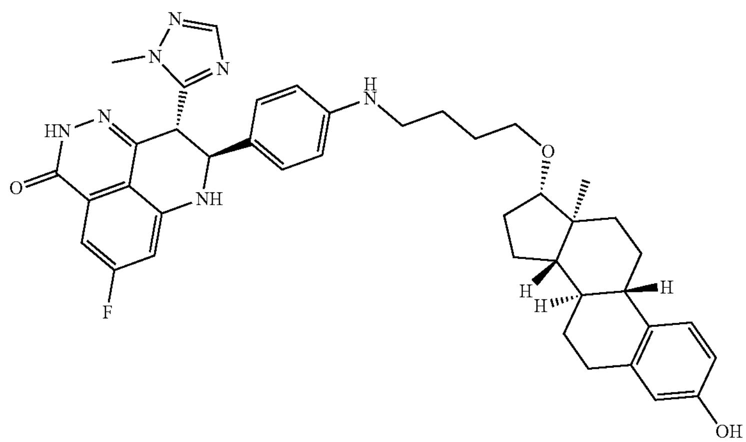 [SMILES: Cn1ncnc1[C@H]1c2n[nH]c(=O)c3cc(F)cc(c23)N[C@@H]1c1ccc(NCCCCO[C@H]2CC[C@H]3[C@@H]4CCc5cc(O)ccc5[C@H]4CC[C@]23C)cc1] |
| 2.30 | 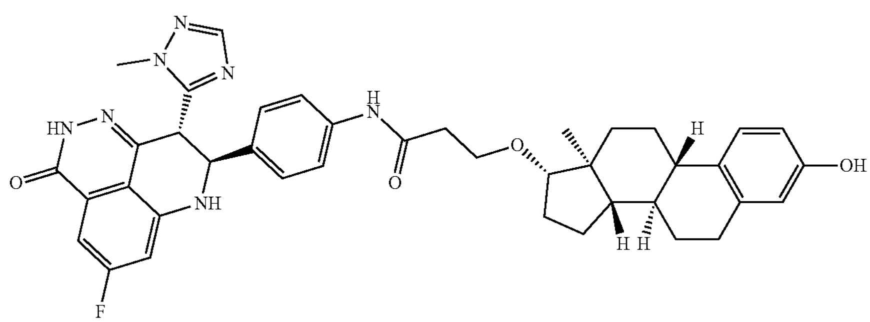 [SMILES: Cn1ncnc1[C@H]1c2n[nH]c(=O)c3cc(F)cc(c23)N[C@@H]1c1ccc(NC(=O)CCO[C@H]2CC[C@H]3[C@@H]4CCc5cc(O)ccc5[C@H]4CC[C@]23C)cc1] |
| 2.31 | 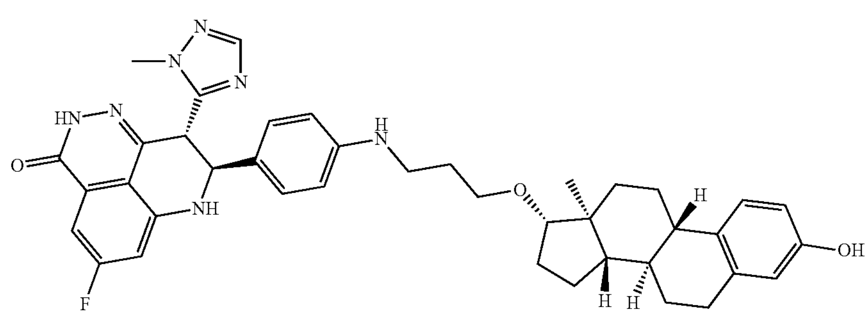 [SMILES: Cn1ncnc1[C@H]1c2n[nH]c(=O)c3cc(F)cc(c23)N[C@@H]1c1ccc(NCCCO[C@H]2CC[C@H]3[C@@H]4CCc5cc(O)ccc5[C@H]4CC[C@]23C)cc1] |

TABLE 1-continued

| No. | Structure |
|---|---|
| 2.32 | 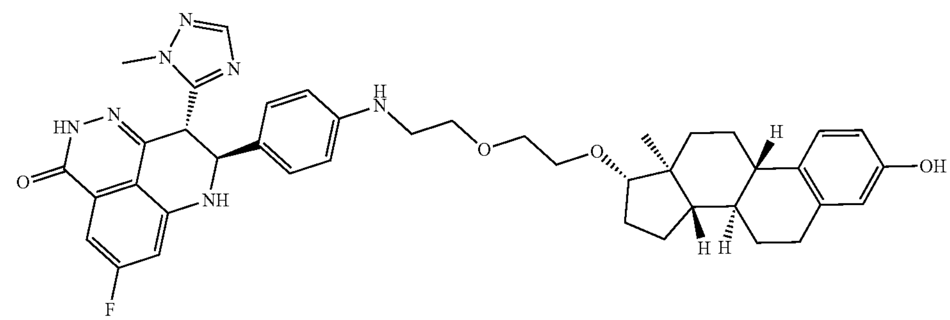 [SMILES: Cn1ncnc1[C@H]1c2n[nH]c(=O)c3cc(F)cc(c23)N[C@@H]1c1ccc(NCCOCCO[C@H]2CC[C@H]3[C@@H]4CCc5cc(O)ccc5[C@H]4CC[C@]23C)cc1] |
| 2.33 | 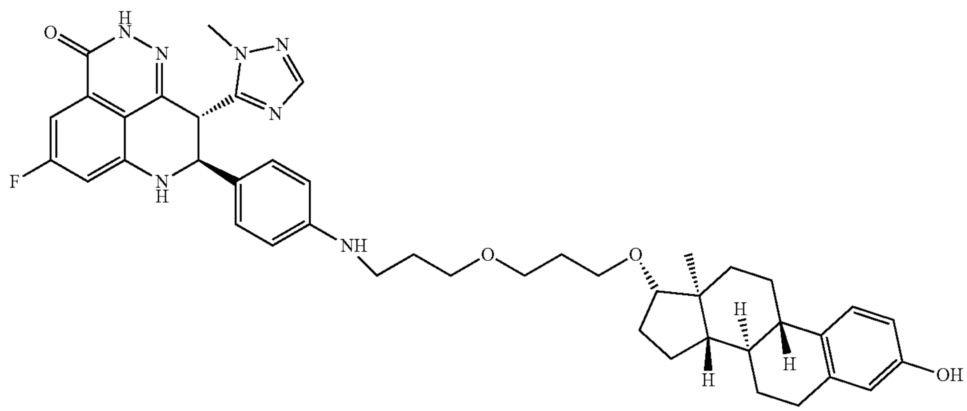 |
| 2.34 | 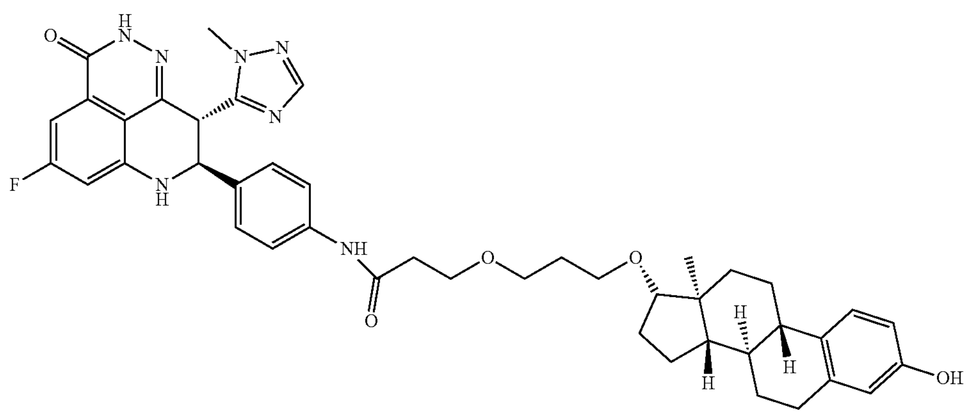 |
| 2.35 | 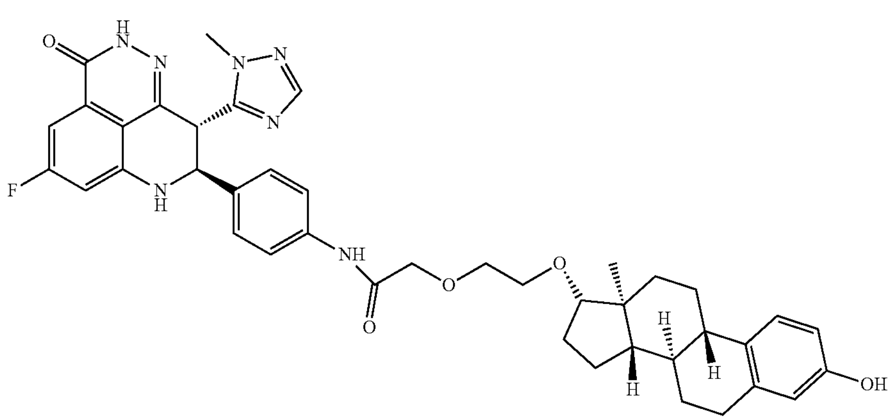 |

TABLE 1-continued
| No. | Structure |
|---|---|
| 2.36 | 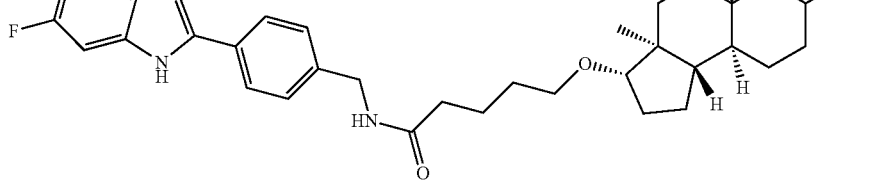 |
| 2.37 | 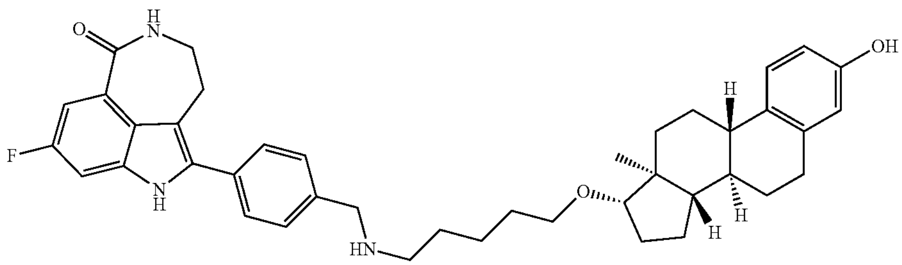 [SMILES: C[C@]12CC[C@@H]3c4ccc(O)cc4CC[C@H]3[C@@H]1CC[C@@H]2OCCCCCNCc1ccc(-c2[nH]c3cc(F)cc4c3c2CCNC4=O)cc1] |
| 2.38 | 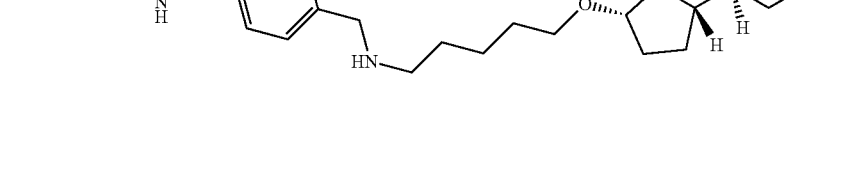 |
| 2.39 | 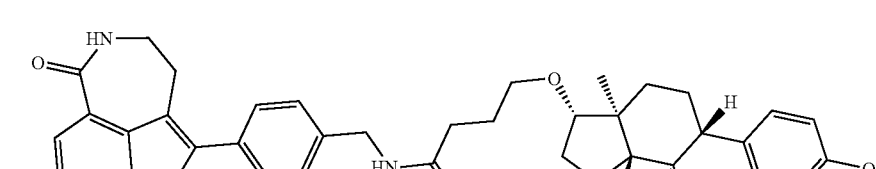 |
| 2.40 | 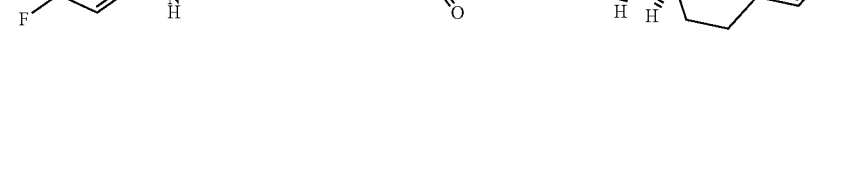 |

TABLE 1-continued

| No. | Structure |
|---|---|
| 2.41 | 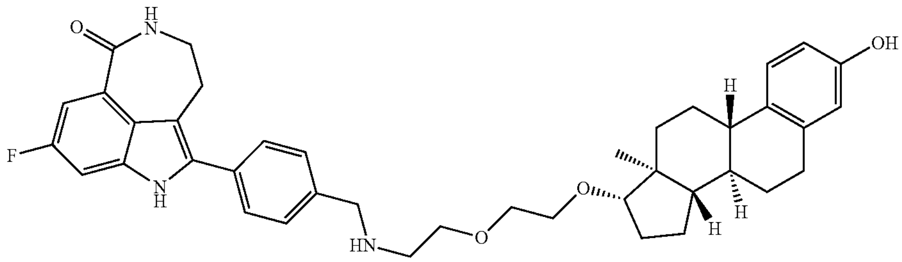 [SMILES: C[C@]12CC[C@@H]3c4ccc(O)cc4CC[C@H]3[C@@H]1CC[C@@H]2OCCOCCNCc1ccc(-c2[nH]c3cc(F)cc4c3c2CCNC4=O)cc1] |
| 2.42 | 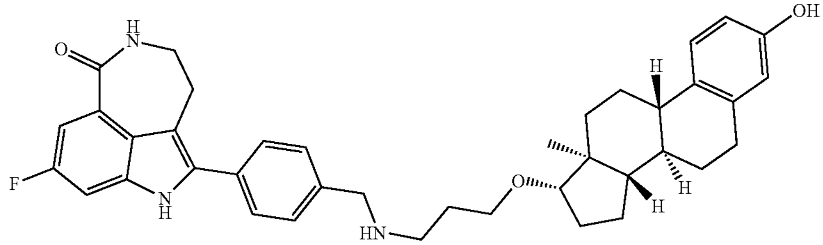 [SMILES: C[C@]12CC[C@@H]3c4ccc(O)cc4CC[C@H]3[C@@H]1CC[C@@H]2OCCCNCc1ccc(-c2[nH]c3cc(F)cc4c3c2CCNC4=O)cc1] |
| 2.43 | 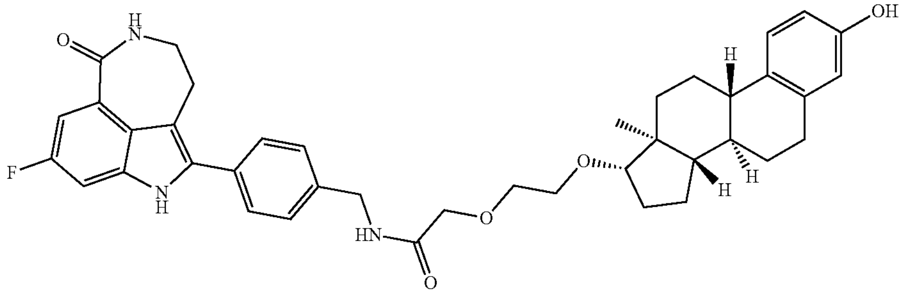 [SMILES: C[C@]12CC[C@@H]3c4ccc(O)cc4CC[C@H]3[C@@H]1CC[C@@H]2OCCOCC(=O)NCc1ccc(-c2[nH]c3cc(F)cc4c3c2CCNC4=O)cc1] |
| 2.44 | 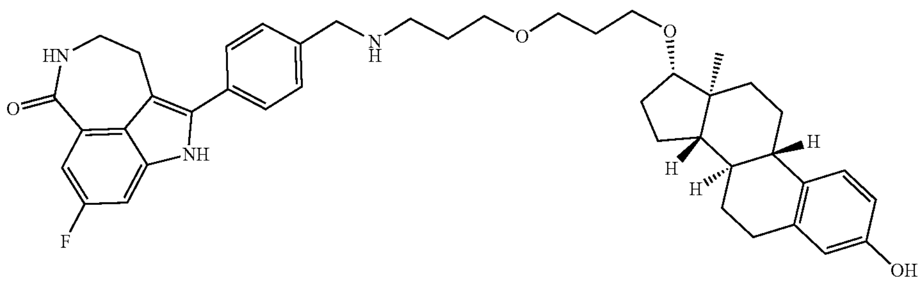 [SMILES: C[C@]12CC[C@@H]3c4ccc(O)cc4CC[C@H]3[C@@H]1CC[C@@H]2OCCCOCCCNCc1ccc(-c2[nH]c3cc(F)cc4c3c2CCNC4=O)cc1] |
| 2.45 | 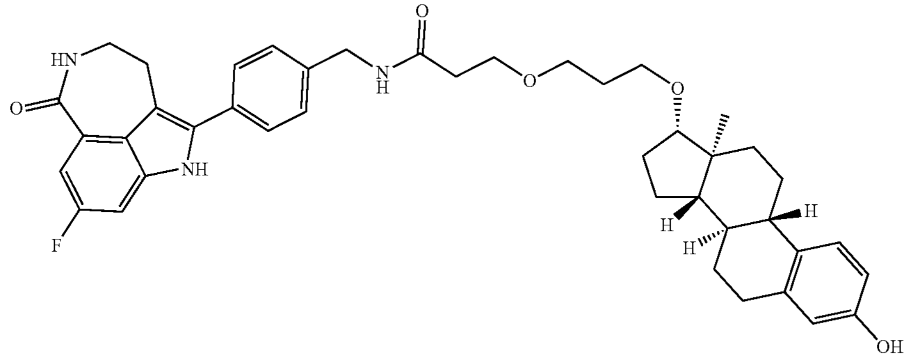 [SMILES: C[C@]12CC[C@@H]3c4ccc(O)cc4CC[C@H]3[C@@H]1CC[C@@H]2OCCCOCCC(=O)NCc1ccc(-c2[nH]c3cc(F)cc4c3c2CCNC4=O)cc1] |

TABLE 1-continued

| No. | Structure |
|---|---|
| 2.46 | 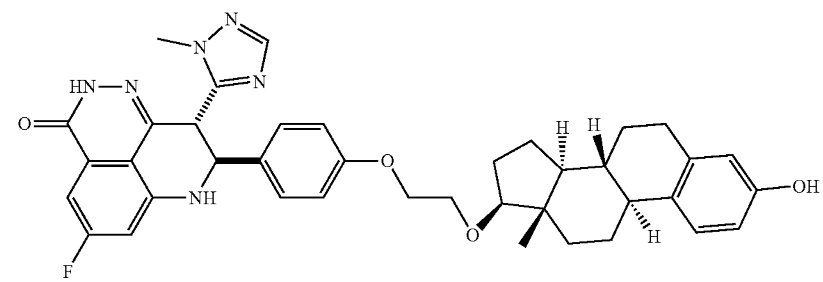 |
| 2.47 | 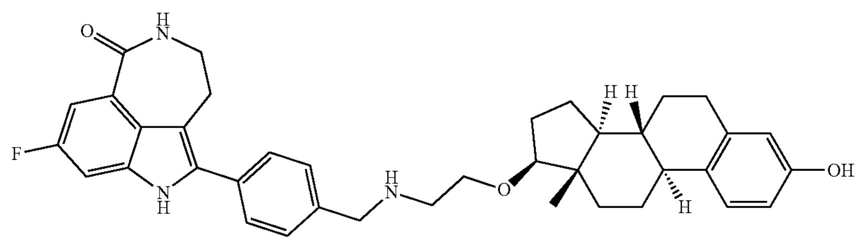 [SMILES: C[C@]12CC[C@@H]3c4ccc(O)cc4CC[C@H]3[C@@H]1CC[C@@H]2OCCNCc1ccc(-c2[nH]c3cc(F)cc4c3c2CCNC4=O)cc1] |
| 3.1 | 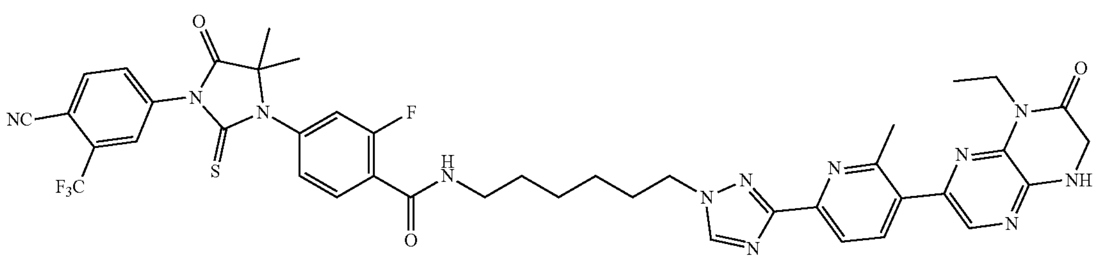 [SMILES: CCN1C(=O)CNc2ncc(-c3ccc(-c4ncn(CCCCCCNC(=O)c5ccc(N6C(=S)N(c7ccc(C#N)c(C(F)(F)F)c7)C(=O)C6(C)C)cc5F)n4)nc3C)nc21] |
| 3.2 | 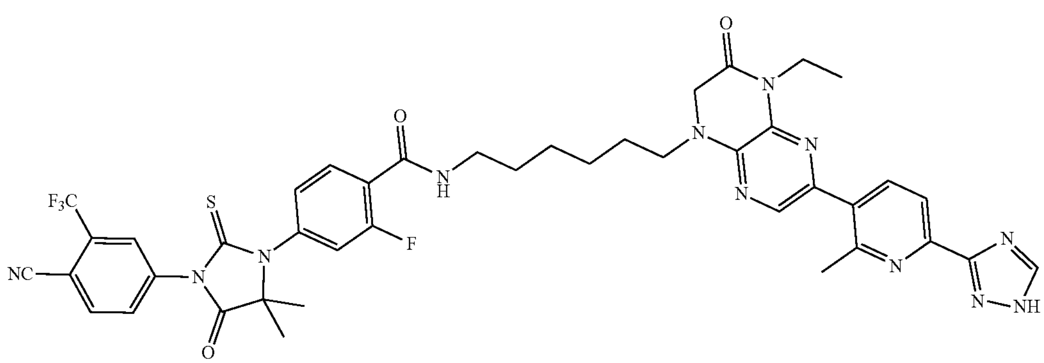 [SMILES: CCN1C(=O)CN(CCCCCCNC(=O)c2ccc(N3C(=S)N(c4ccc(C#N)c(C(F)(F)F)c4)C(=O)C3(C)C)cc2F)c2ncc(-c3ccc(-c4nc[nH]n4)nc3C)nc21] |
| 3.3 | 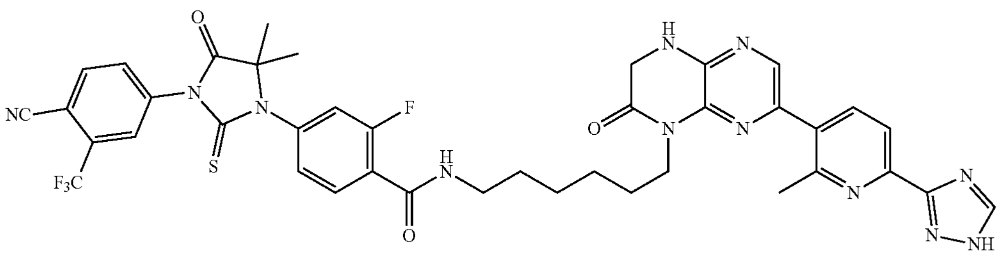 [SMILES: Cc1nc(-c2nc[nH]n2)ccc1-c1cnc2c(n1)N(CCCCCCNC(=O)c1ccc(N3C(=S)N(c4ccc(C#N)c(C(F)(F)F)c4)C(=O)C3(C)C)cc1F)C(=O)CN2] |

TABLE 1-continued

| No. | Structure |
|---|---|
| 3.4 | 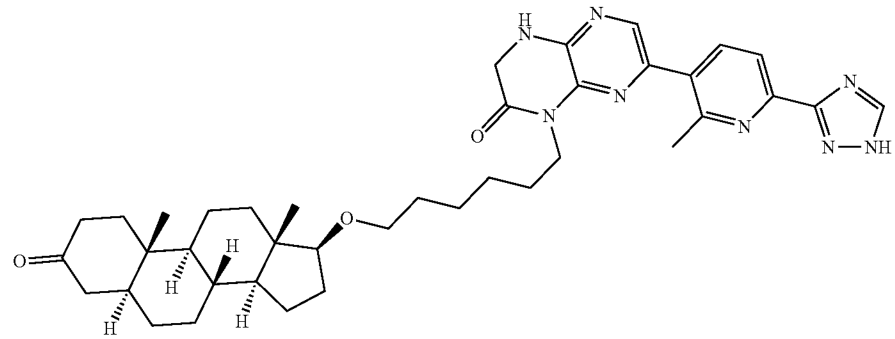 |
| 3.5 | 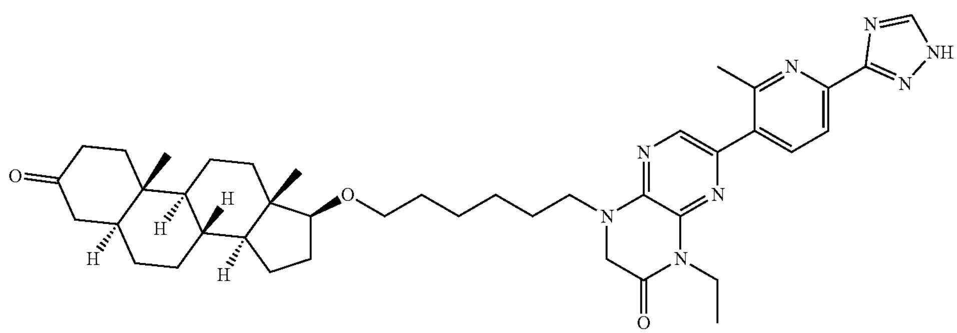 |
| 3.6 | 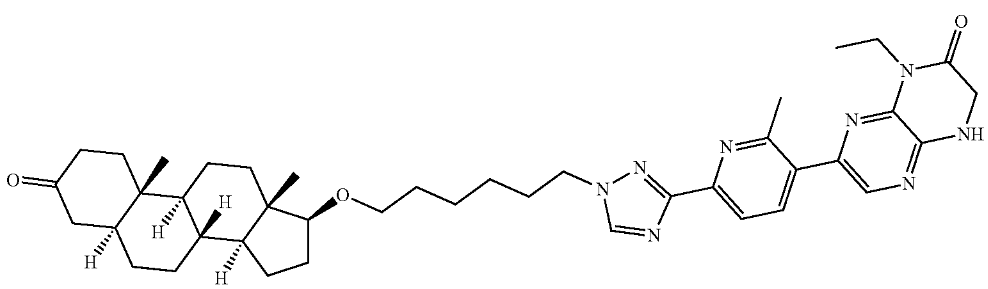 |
| 3.7 | 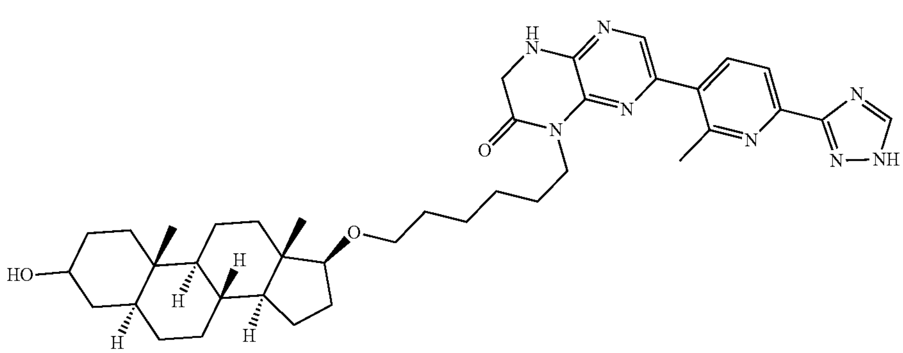 |

TABLE 1-continued

| No. | Structure |
|---|---|
| 3.8 | 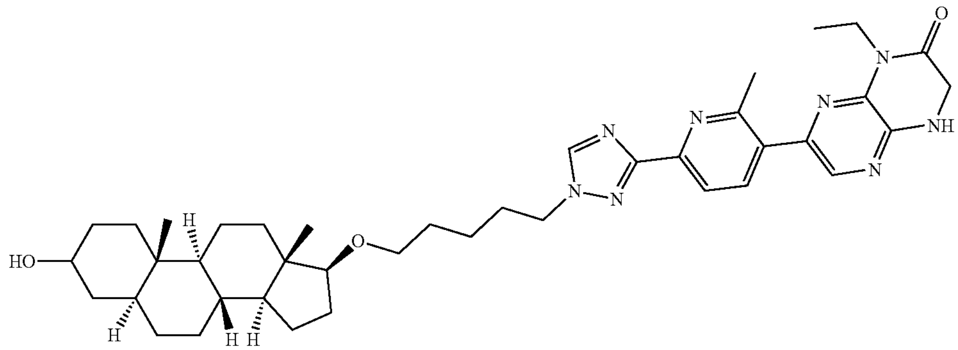 [SMILES: CCN1C(=O)CNc2ncc(-c3ccc(-c4ncn(CCCCCO[C@H]5CC[C@H]6[C@@H]7CC[C@H]8CC(O)CC[C@]8(C)[C@H]7CC[C@]56C)n4)nc3C)nc21] |
| 3.9 | 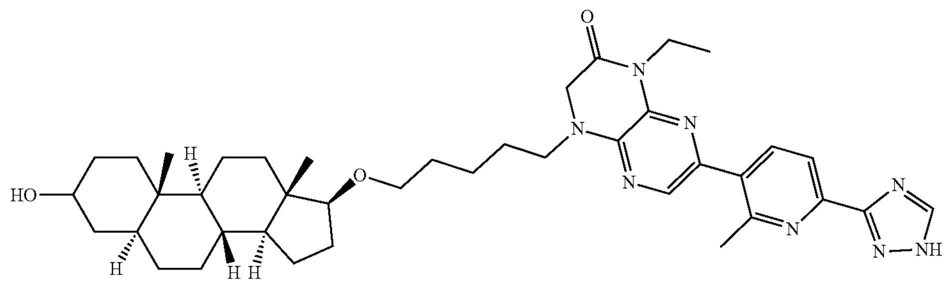 [SMILES: CCN1C(=O)CN(CCCCCO[C@H]2CC[C@H]3[C@@H]4CC[C@H]5CC(O)CC[C@]5(C)[C@H]4CC[C@]23C)c2ncc(-c3ccc(-c4nc[nH]n4)nc3C)nc21] |
| 3.10 | 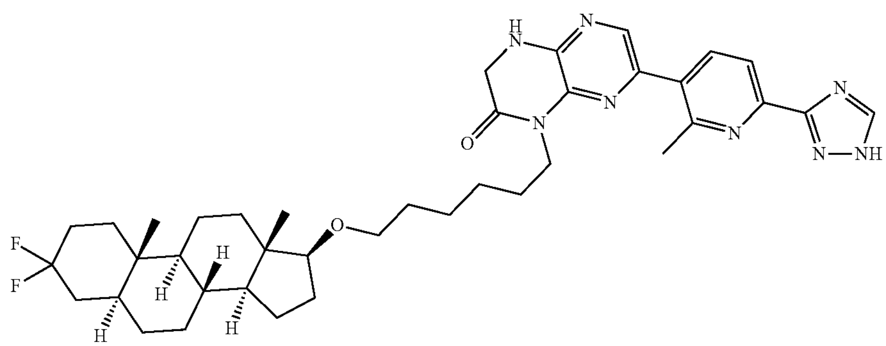 |
| 3.11 | 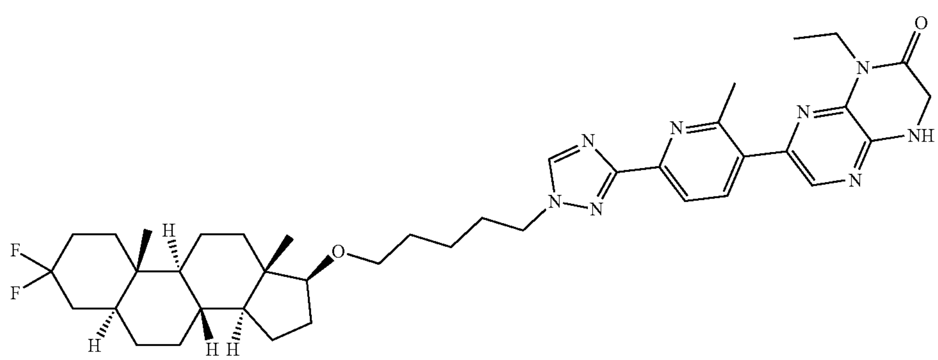 [SMILES: CCN1C(=O)CNc2ncc(-c3ccc(-c4ncn(CCCCCO[C@H]5CC[C@H]6[C@@H]7CC[C@H]8CC(F)(F)CC[C@]8(C)[C@H]7CC[C@]56C)n4)nc3C)nc21] |
| 3.12 | 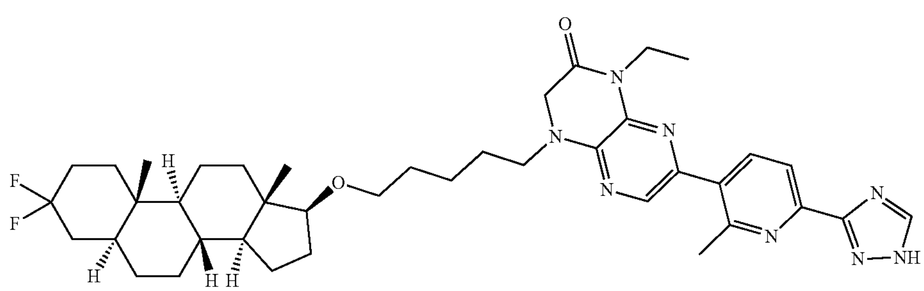 [SMILES: CCN1C(=O)CN(CCCCCO[C@H]2CC[C@H]3[C@@H]4CC[C@H]5CC(F)(F)CC[C@]5(C)[C@H]4CC[C@]23C)c2ncc(-c3ccc(-c4nc[nH]n4)nc3C)nc21] |

TABLE 1-continued
| No. | Structure |
|---|---|
| 3.13 | 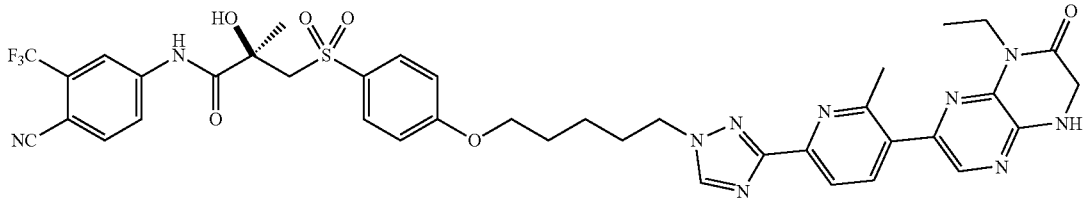 [SMILES: CCN1C(=O)CNc2ncc(-c3ccc(-c4ncn(CCCCCOc5ccc(S(=O)(=O)C[C@](C)(O)C(=O)Nc6ccc(C#N)c(C(F)(F)F)c6)cc5)n4)nc3C)nc21] |
| 3.14 | 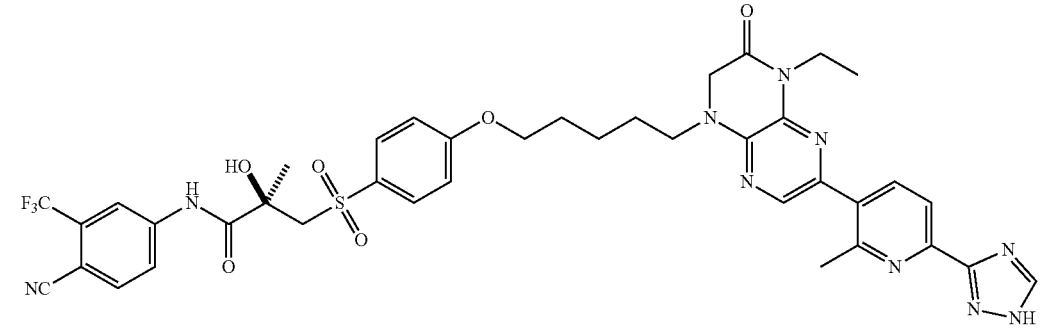 [SMILES: CCN1C(=O)CN(CCCCCOc2ccc(S(=O)(=O)C[C@](C)(O)C(=O)Nc3ccc(C#N)c(C(F)(F)F)c3)cc2)c2ncc(-c3ccc(-c4nc[nH]n4)nc3C)nc21] |
| 3.15 | 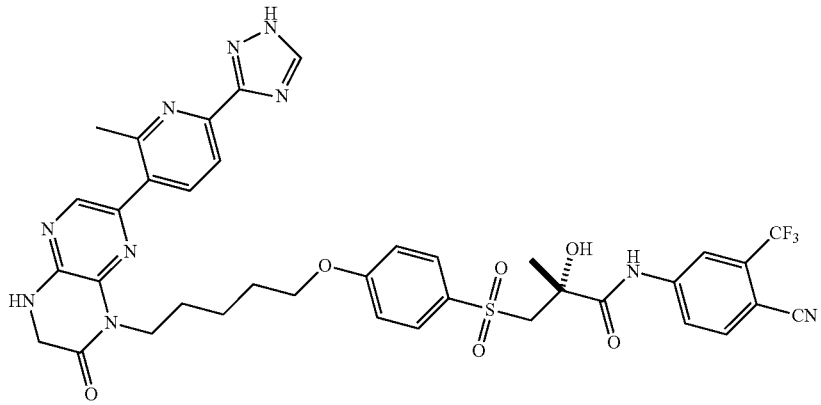 [SMILES: Cc1nc(-c2nc[nH]n2)ccc1-c1cnc2c(n1)N(CCCCCOc1ccc(S(=O)(=O)C[C@](C)(O)C(=O)Nc3ccc(C#N)c(C(F)(F)F)c3)cc1)C(=O)CN2] |
| 3.16 | 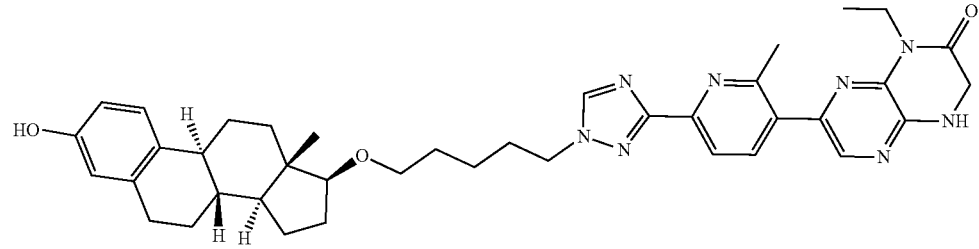 [SMILES: CCN1C(=O)CNc2ncc(-c3ccc(-c4ncn(CCCCCO[C@H]5CC[C@H]6[C@@H]7CCc8cc(O)ccc8[C@H]7CC[C@]56C)n4)nc3C)nc21] |
| 3.17 | 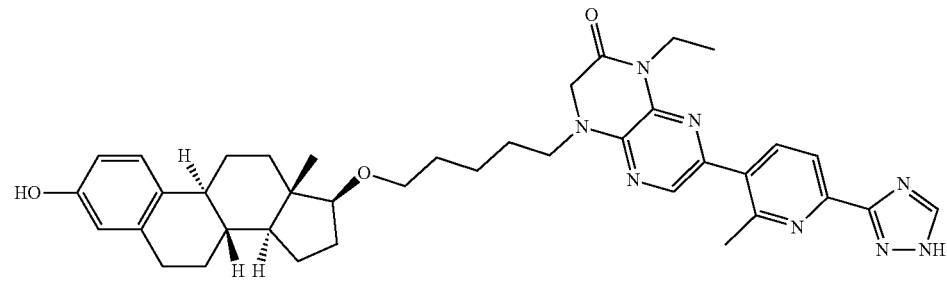 [SMILES: CCN1C(=O)CN(CCCCCO[C@H]2CC[C@H]3[C@@H]4CCc5cc(O)ccc5[C@H]4CC[C@]23C)c2ncc(-c3ccc(-c4nc[nH]n4)nc3C)nc21] |

TABLE 1-continued

| No. | Structure |
|---|---|
| 3.18 | 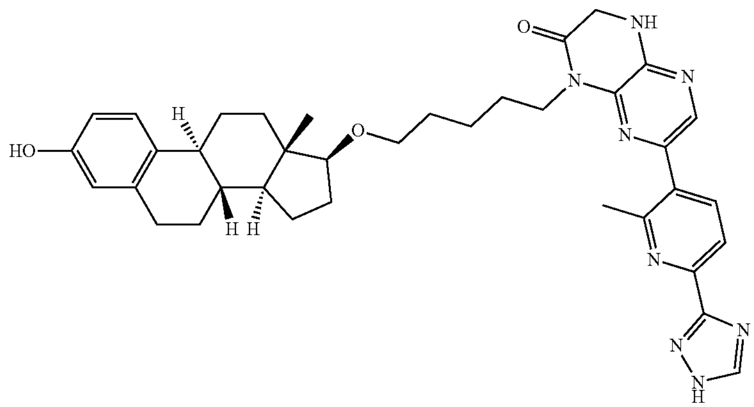 [SMILES: Cc1nc(-c2nc[nH]n2)ccc1-c1cnc2c(n1)N(CCCCCO[C@H]1CC[C@H]3[C@@H]4CCc5cc(O)ccc5[C@H]4CC[C@]13C)C(=O)CN2] |
| 3.19 | 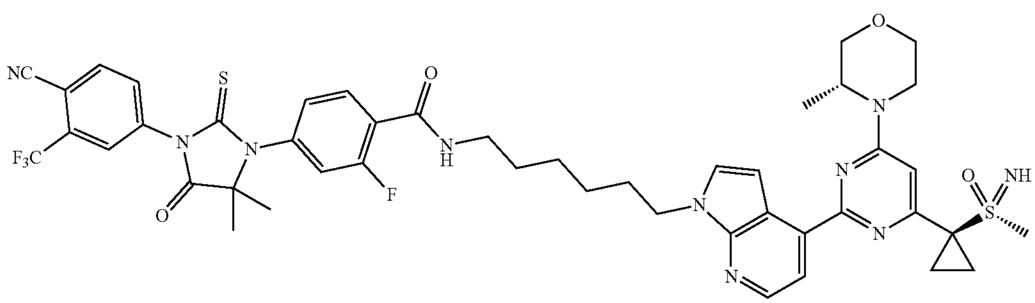 |
| 3.20 | 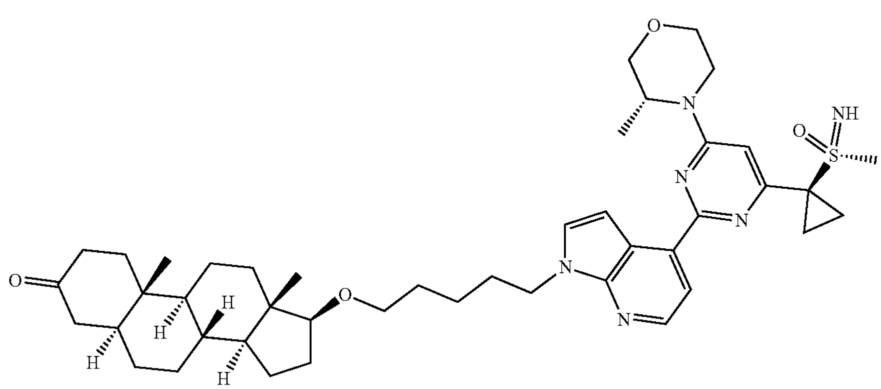 |
| 3.21 | 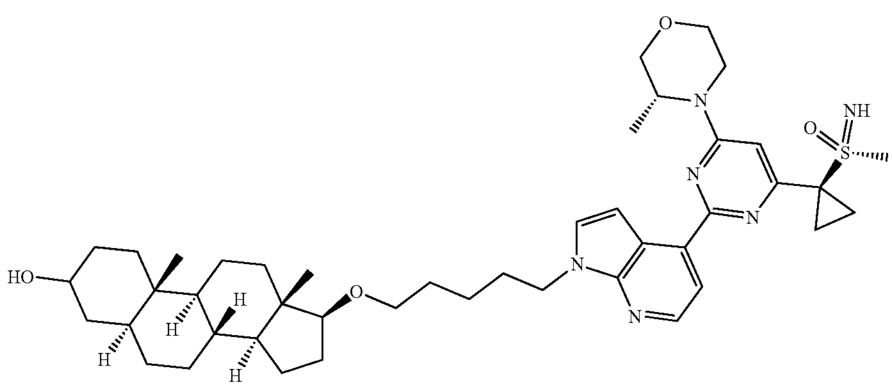 |

TABLE 1-continued

| No. | Structure |
|---|---|
| 3.22 | 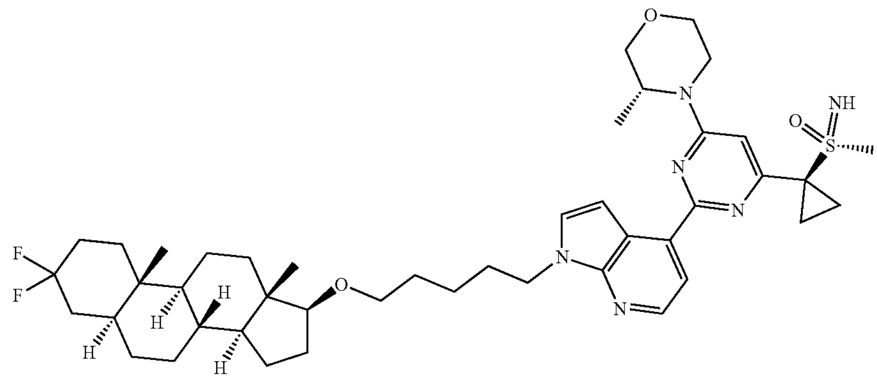 |
| 3.27 | 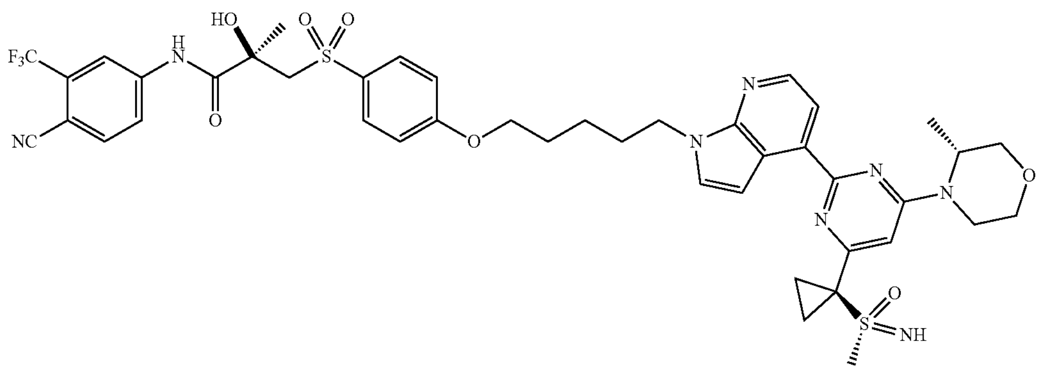 |
| 3.29 | 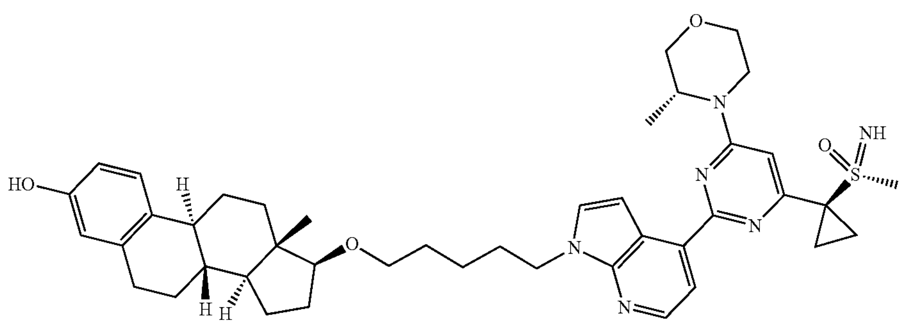 |
| 3.31 | 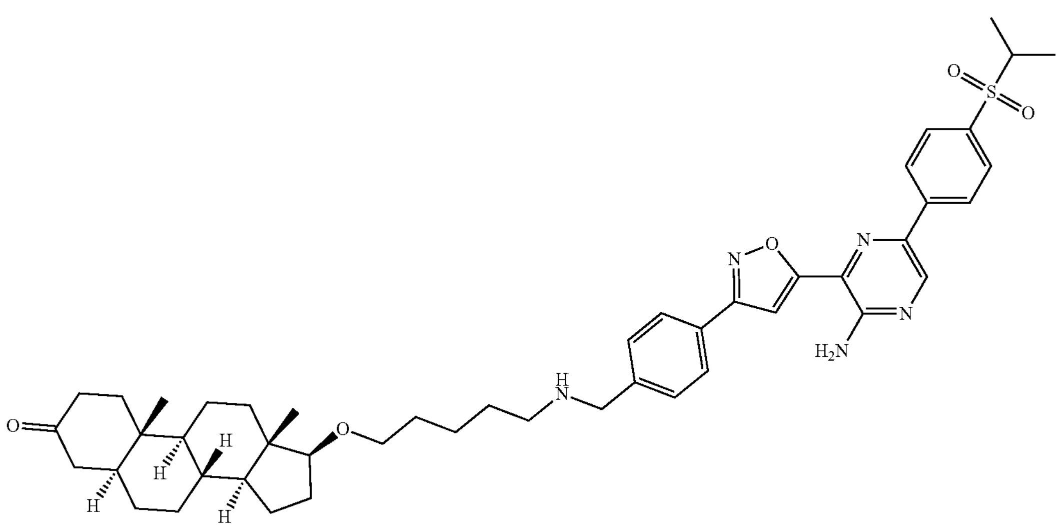 |

TABLE 1-continued
| No. | Structure |
|---|---|
| 3.32 | 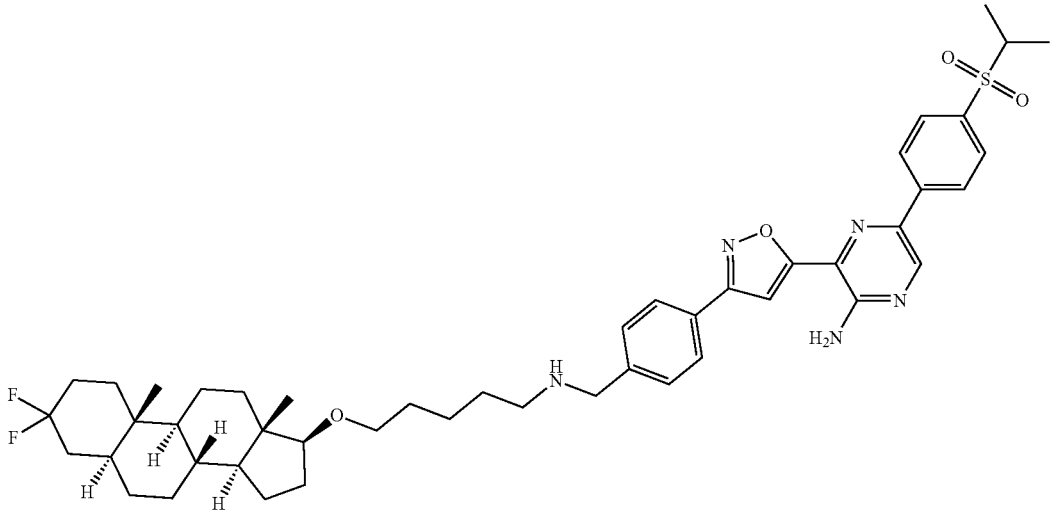 |
| 3.33 | 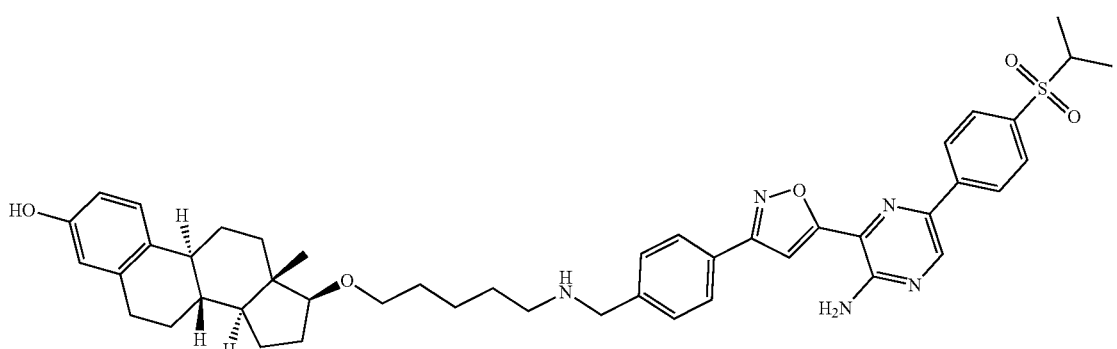 |
| 3.34 | 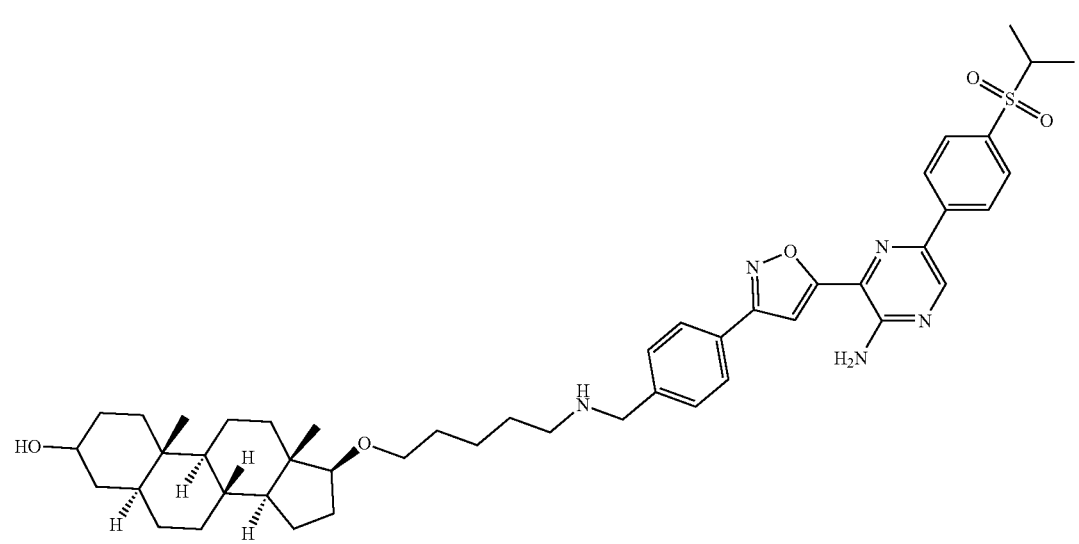 |

TABLE 1-continued
| No. | Structure |
|---|---|
| 3.35 | 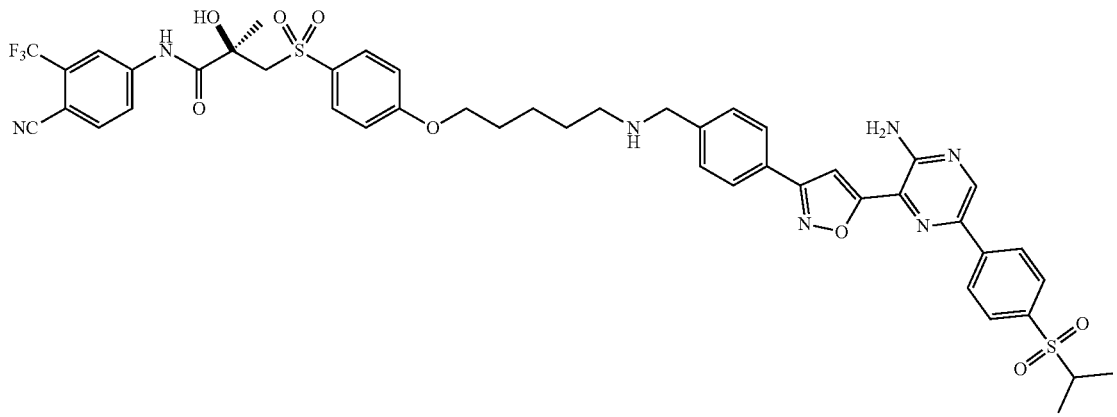 [SMILES: CC(C)S(=O)(=O)c1ccc(-c2cnc(N)c(-c3cc(-c4ccc(CNCCCCCOc5ccc(S(=O)(=O)C[C@](C)(O)C(=O)Nc6ccc(C#N)c(C(F)(F)F)c6)cc5)cc4)no3)n2)cc1] |
| 3.36 | 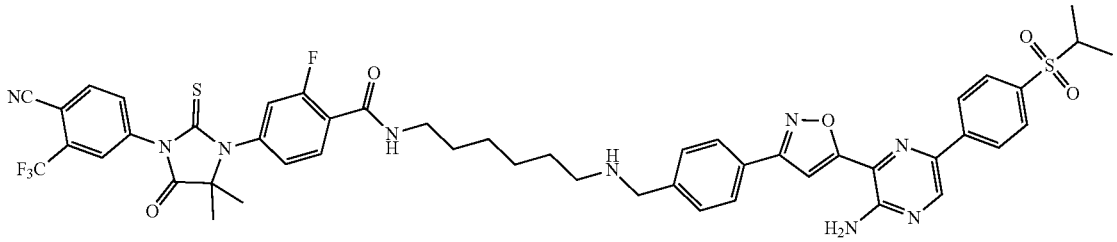 [SMILES: CC(C)S(=O)(=O)c1ccc(-c2cnc(N)c(-c3cc(-c4ccc(CNCCCCCCNC(=O)c5ccc(N6C(=S)N(c7ccc(C#N)c(C(F)(F)F)c7)C(=O)C6(C)C)cc5F)cc4)no3)n2)cc1] |
| 3.37 | 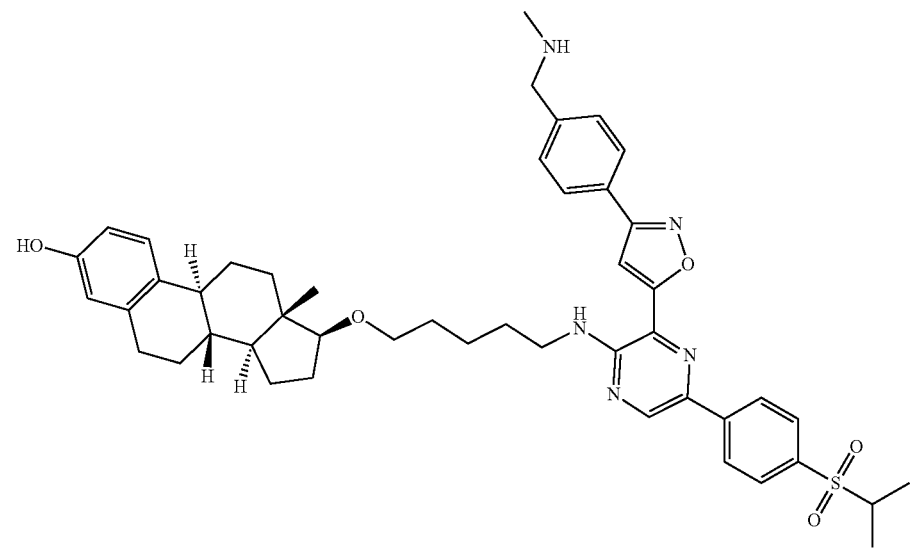 [SMILES: CNCc1ccc(-c2cc(-c3nc(-c4ccc(S(=O)(=O)C(C)C)cc4)cnc3NCCCCCO[C@H]3CC[C@H]4[C@@H]5CCc6cc(O)ccc6[C@H]5CC[C@]34C)on2)cc1] |

TABLE 1-continued
| No. | Structure |
|---|---|
| 3.38 | 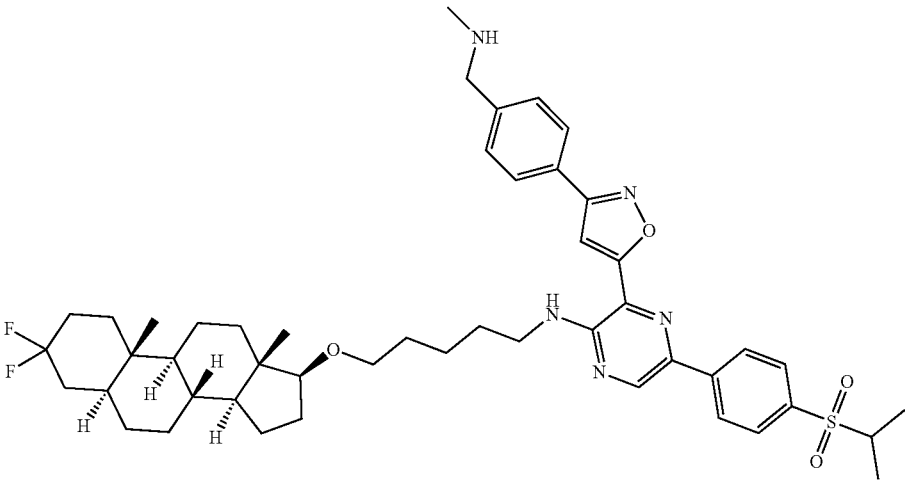 |
| 3.39 | 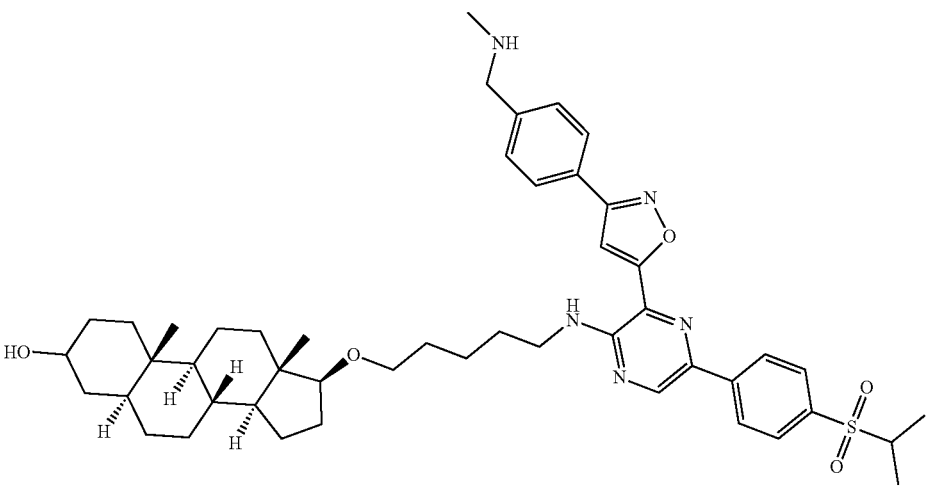 |
| 3.40 | 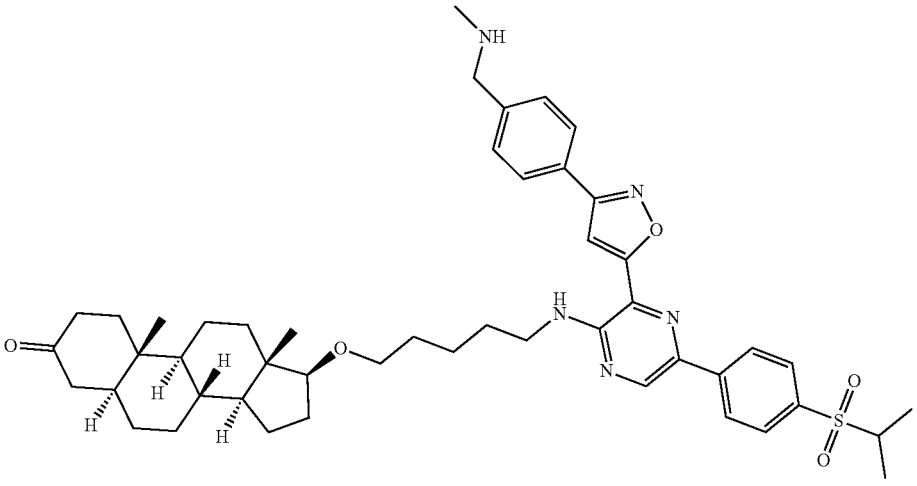 |

TABLE 1-continued
| No. | Structure |
|---|---|
| 3.41 | 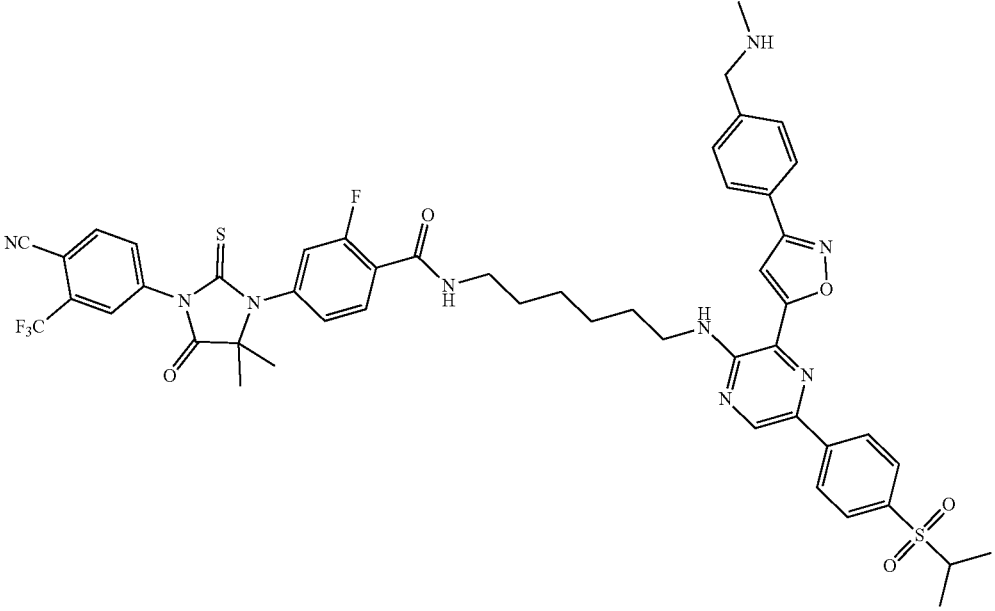 [SMILES: CNCc1ccc(-c2cc(-c3nc(-c4ccc(S(=O)(=O)C(C)C)cc4)cnc3NCCCCCCNC(=O)c3ccc(N4C(=S)N(c5ccc(C#N)c(C(F)(F)F)c5)C(=O)C4(C)C)cc3F)on2)cc1] |
| 3.42 | 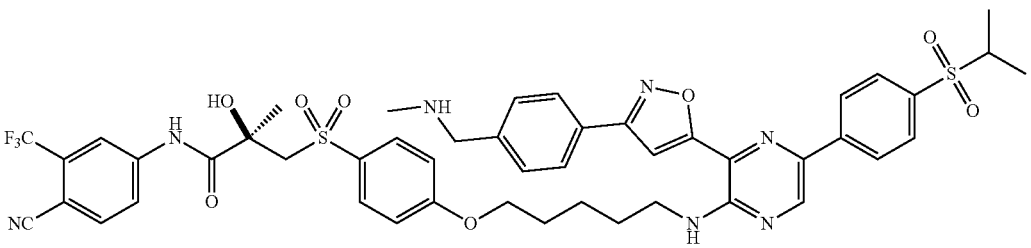 [SMILES: CNCc1ccc(-c2cc(-c3nc(-c4ccc(S(=O)(=O)C(C)C)cc4)cnc3NCCCCCOc3ccc(S(=O)(=O)C[C@](C)(O)C(=O)Nc4ccc(C#N)c(C(F)(F)F)c4)cc3)on2)cc1] |
| 3.43 | 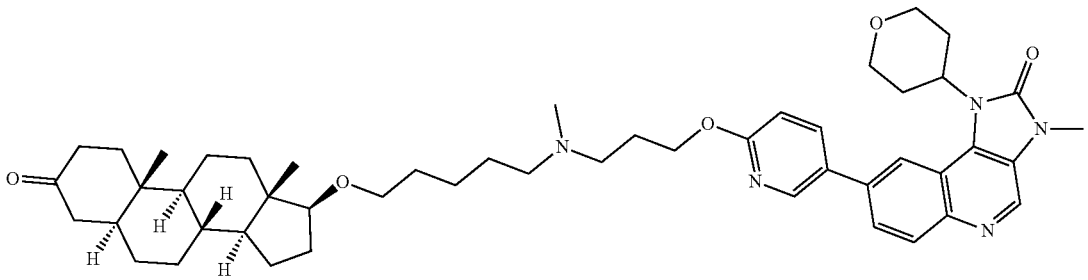 |
| 3.44 | 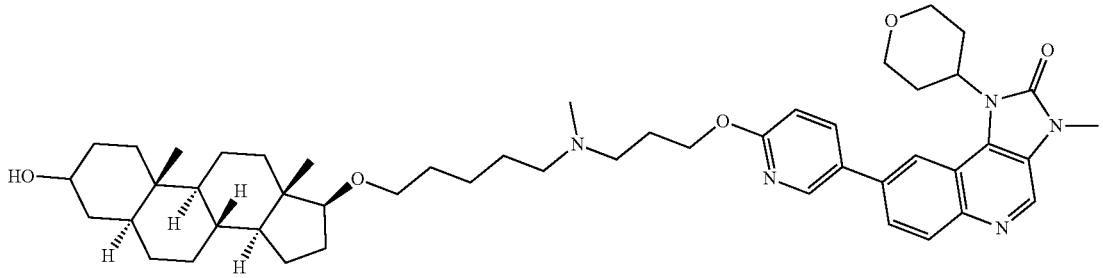 |

TABLE 1-continued

| No. | Structure |
|---|---|
| 3.45 | 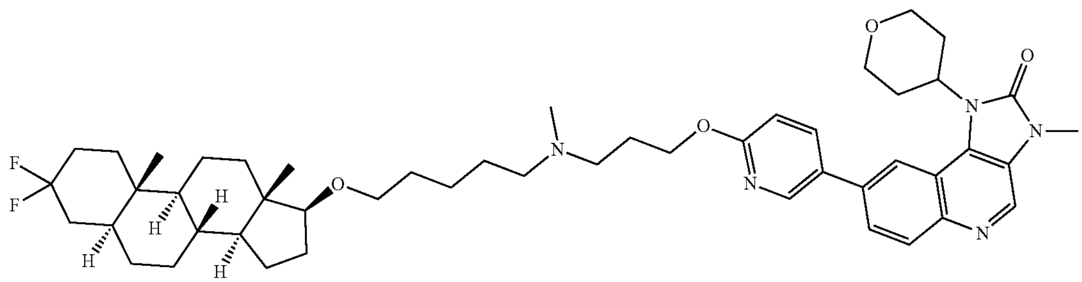 |
| 3.46 | 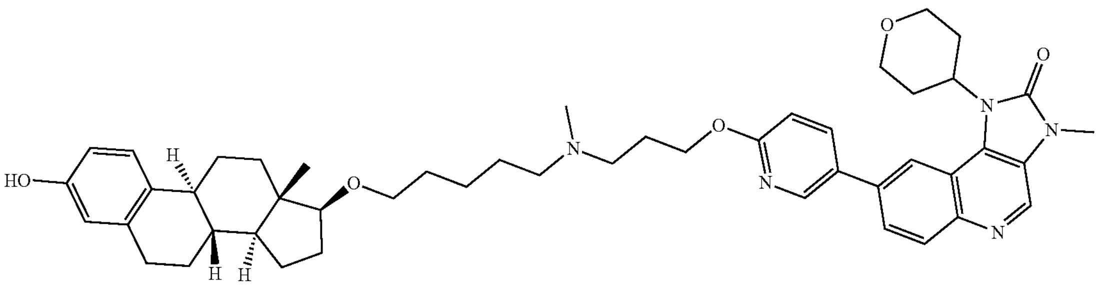 [SMILES: CN(CCCCCO[C@H]1CC[C@H]2[C@@H]3CCc4cc(O)ccc4[C@H]3CC[C@]12C)CCCOc1ccc(-c2ccc3ncc4c(c3c2)n(C2CCOCC2)c(=O)n4C)cn1] |
| 3.47 | 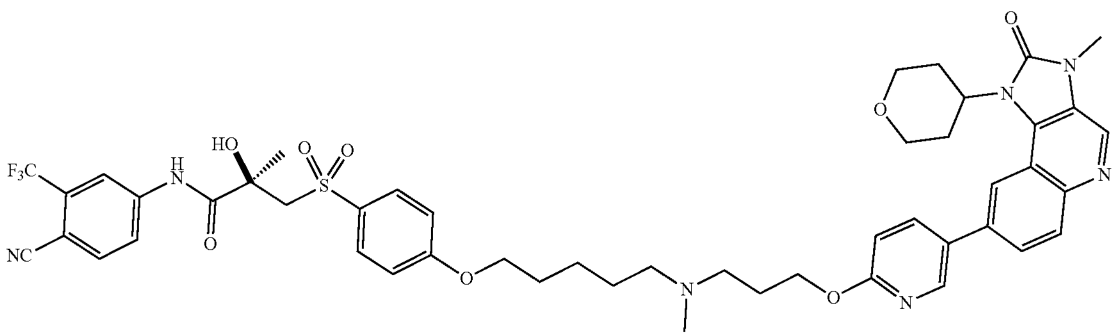 [SMILES: CN(CCCCCOc1ccc(S(=O)(=O)C[C@](C)(O)C(=O)Nc2ccc(C#N)c(C(F)(F)F)c2)cc1)CCCOc1ccc(-c2ccc3ncc4c(c3c2)n(C2CCOCC2)c(=O)n4C)cn1] |
| 3.48 | 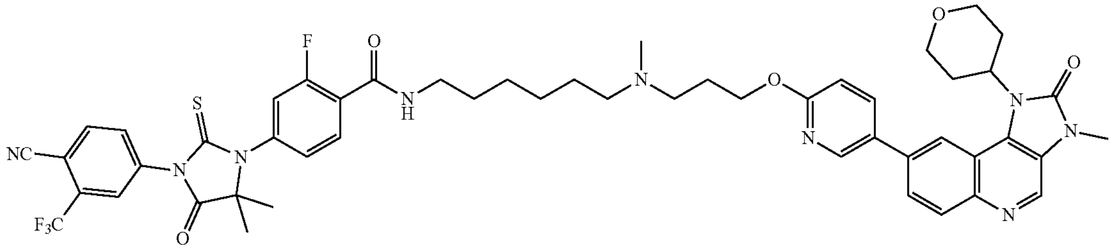 [SMILES: CN(CCCCCCNC(=O)c1ccc(N2C(=S)N(c3ccc(C#N)c(C(F)(F)F)c3)C(=O)C2(C)C)cc1F)CCCOc1ccc(-c2ccc3ncc4c(c3c2)n(C2CCOCC2)c(=O)n4C)cn1] |
| 3.49 | 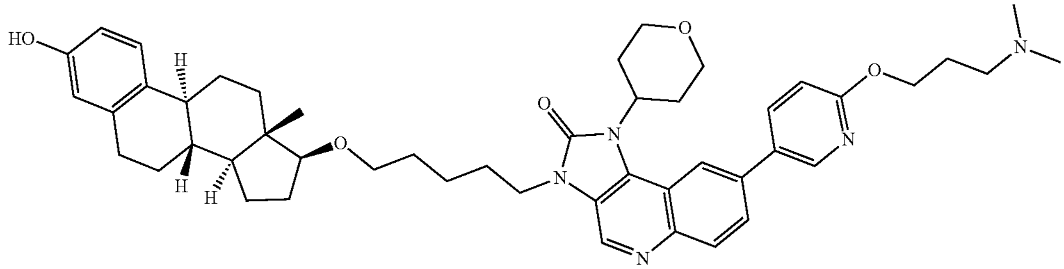 [SMILES: CN(C)CCCOc1ccc(-c2ccc3ncc4c(c3c2)n(C2CCOCC2)c(=O)n4CCCCCO[C@H]2CC[C@H]3[C@@H]4CCc5cc(O)ccc5[C@H]4CC[C@]23C)cn1] |

TABLE 1-continued

| No. | Structure |
|---|---|
| 3.50 | 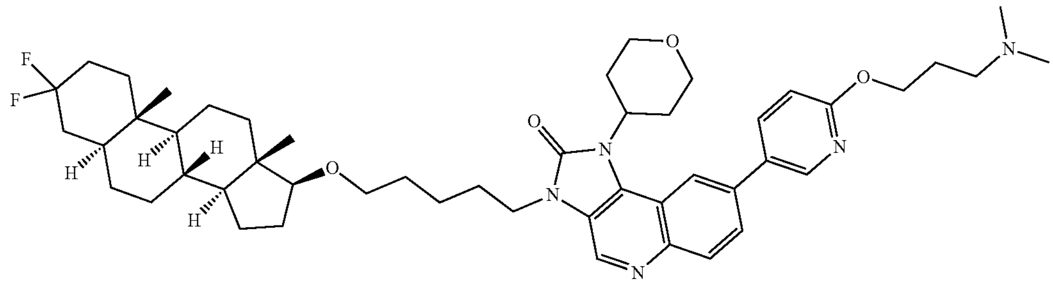 |
| 3.51 | 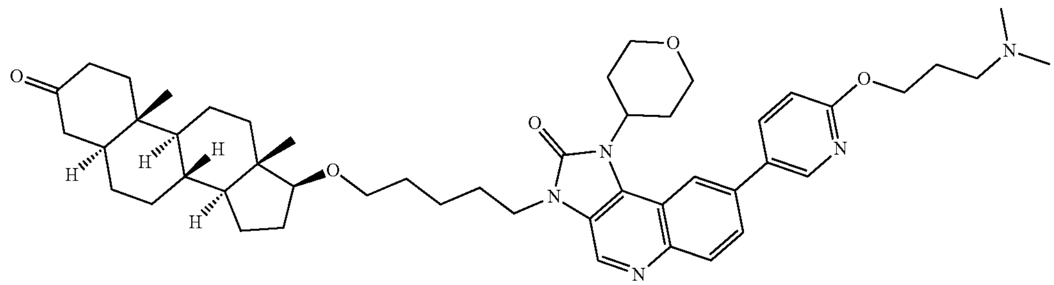 |
| 3.52 | 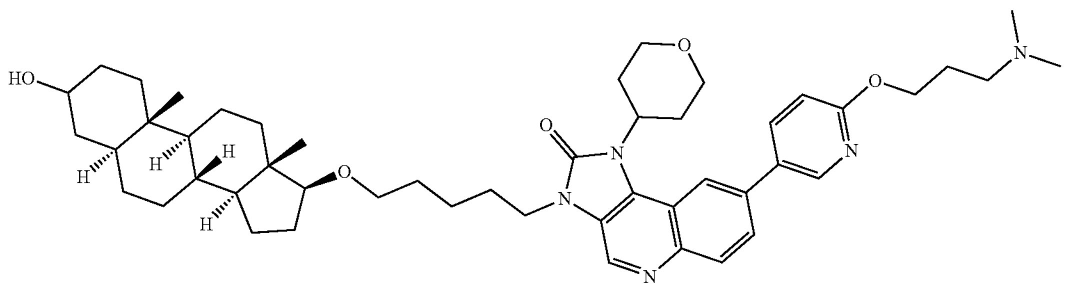 |
| 3.53 | 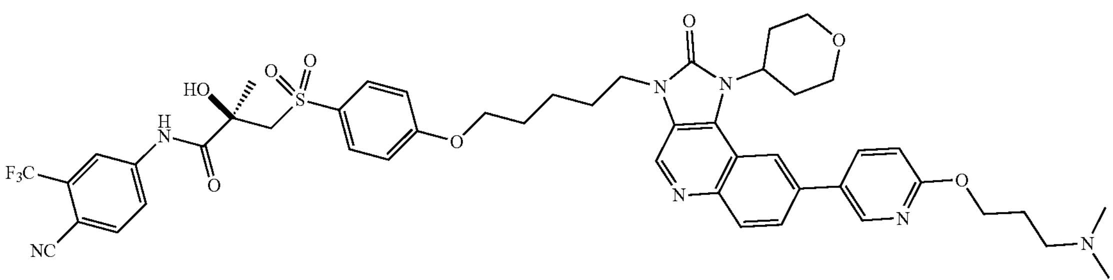 [SMILES: CN(C)CCCOc1ccc(-c2ccc3ncc4c(c3c2)n(C2CCOCC2)c(=O)n4CCCCCOc2ccc(S(=O)(=O)C[C@](C)(O)C(=O)Nc3ccc(C#N)c(C(F)(F)F)c3)cc2)cn1] |
| 3.54 | 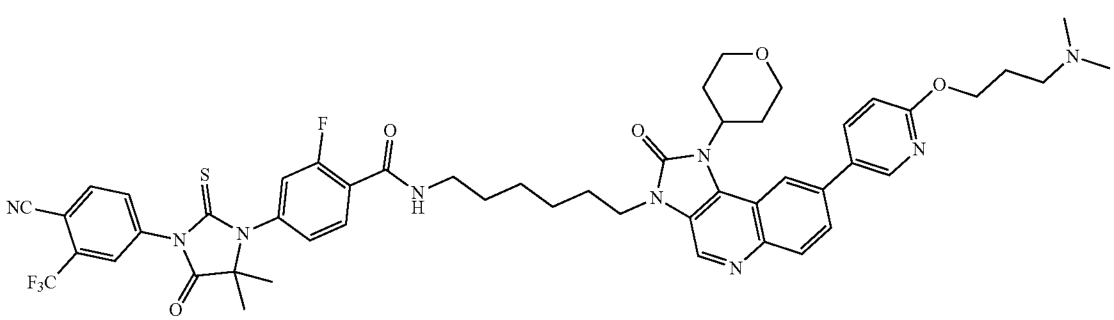 [SMILES: CN(C)CCCOc1ccc(-c2ccc3ncc4c(c3c2)n(C2CCOCC2)c(=O)n4CCCCCCNC(=O)c2ccc(N3C(=S)N(c4ccc(C#N)c(C(F)(F)F)c4)C(=O)C3(C)C)cc2F)cn1] |

TABLE 1-continued
| No. | Structure |
|---|---|
| 3.61 | 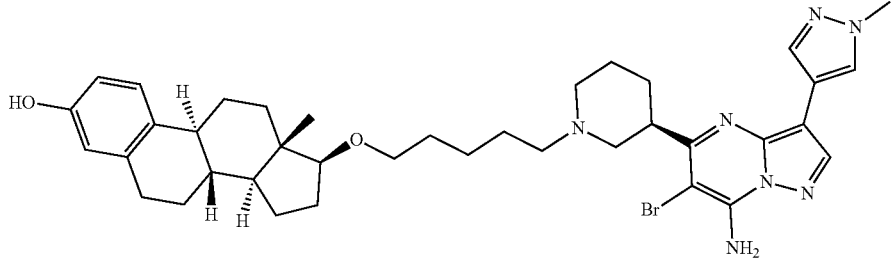 [SMILES: Cn1cc(-c2cnn3c(N)c(Br)c([C@@H]4CCCN(CCCCCO[C@H]5CC[C@H]6[C@@H]7CCc8cc(O)ccc8[C@H]7CC[C@]56C)C4)nc23)cn1] |
| 3.62 | 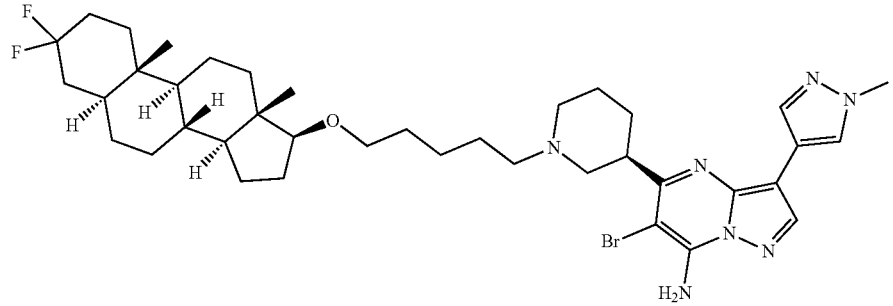 |
| 3.63 | 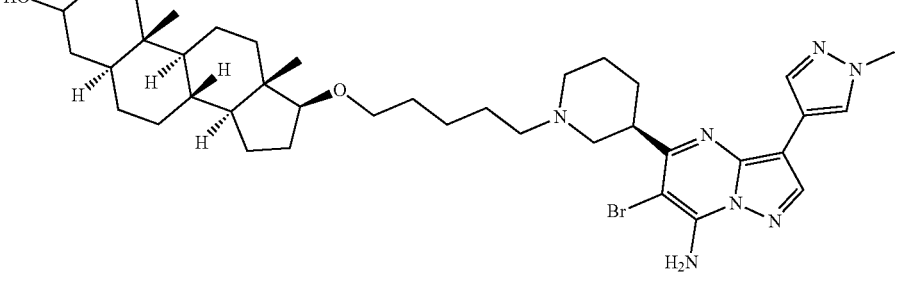 |
| 3.64 | 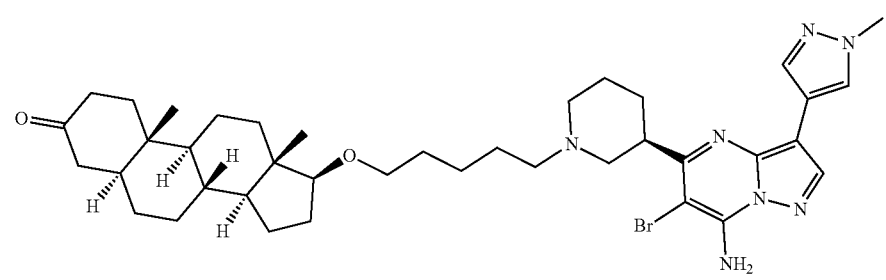 |
| 3.65 | 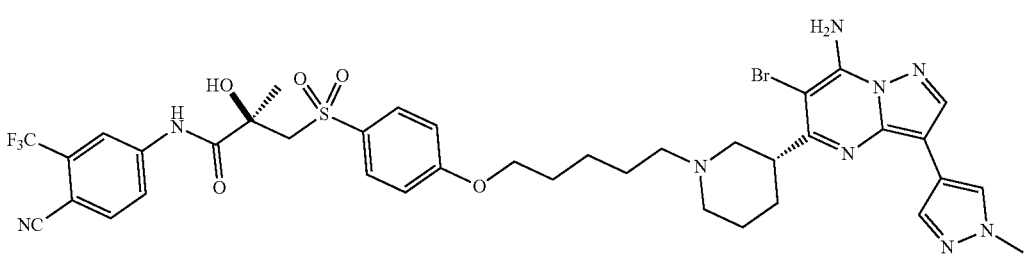 [SMILES: Cn1cc(-c2cnn3c(N)c(Br)c([C@@H]4CCCN(CCCCCOc5ccc(S(=O)(=O)C[C@](C)(O)C(=O)Nc6ccc(C#N)c(C(F)(F)F)c6)cc5)C4)nc23)cn1] |

TABLE 1-continued
| No. | Structure |
|---|---|
| 3.66 | 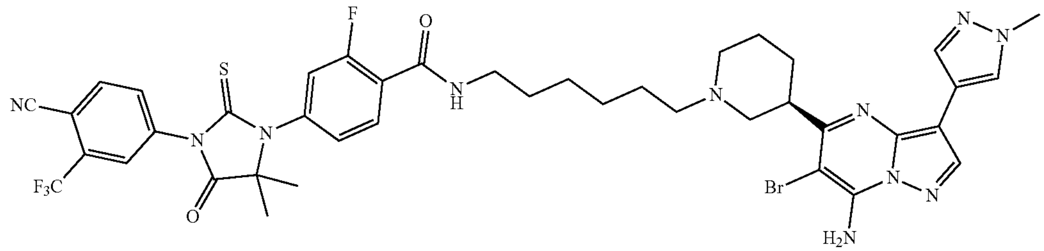 [SMILES: Cn1cc(-c2cnn3c(N)c(Br)c([C@@H]4CCCN(CCCCCCNC(=O)c5ccc(N6C(=S)N(c7ccc(C#N)c(C(F)(F)F)c7)C(=O)C6(C)C)cc5F)C4)nc23)cn1] |
| 3.67 | 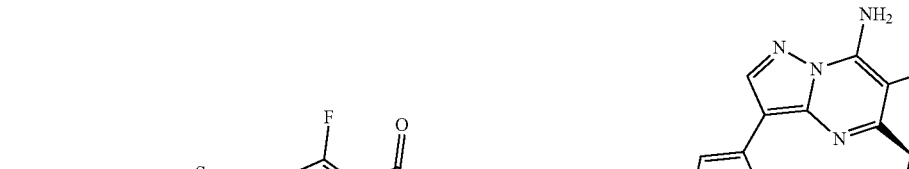 |
| 3.68 | 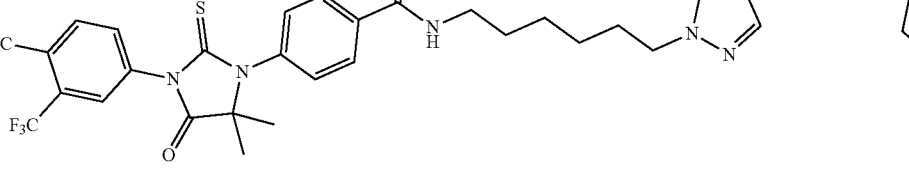 |
| 3.69 | 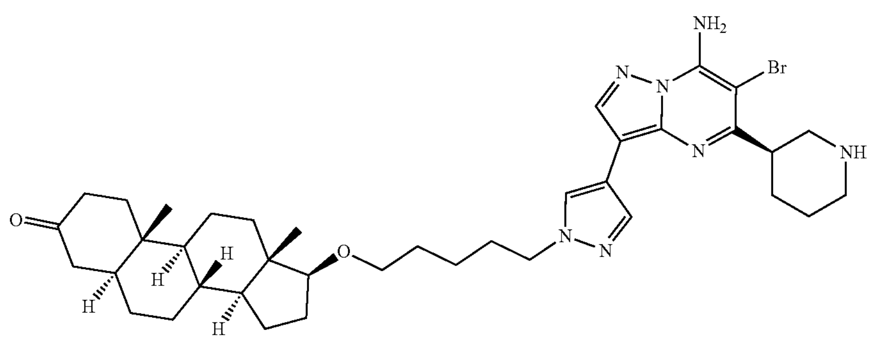 |
| 3.70 | 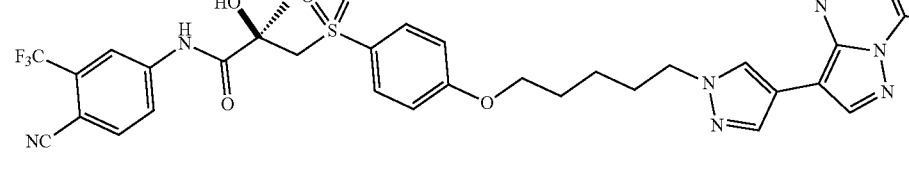 |

TABLE 1-continued

| No. | Structure |
|---|---|
| 3.71 | 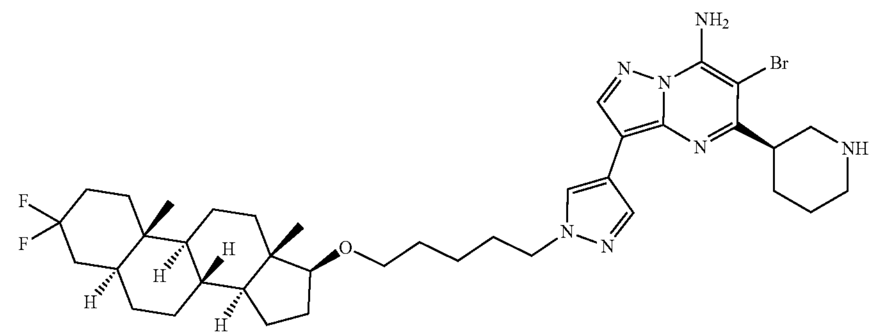 |
| 3.72 | 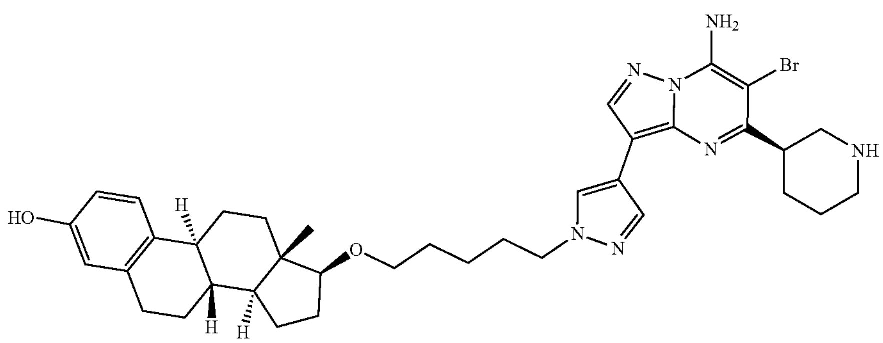 [SMILES: C[C@]12CC[C@@H]3c4ccc(O)cc4CC[C@H]3[C@@H]1CC[C@@H]2OCCCCCn1cc(-c2cnn3c(N)c(Br)c([C@@H]4CCCNC4)nc23)cn1] |
| 3.73 | 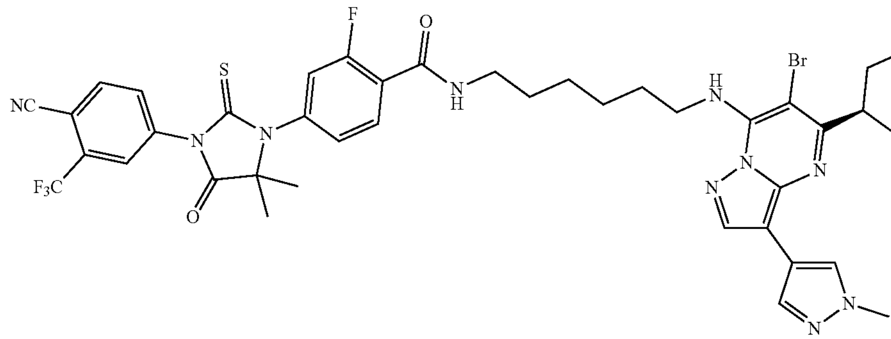 |
| 3.74 | 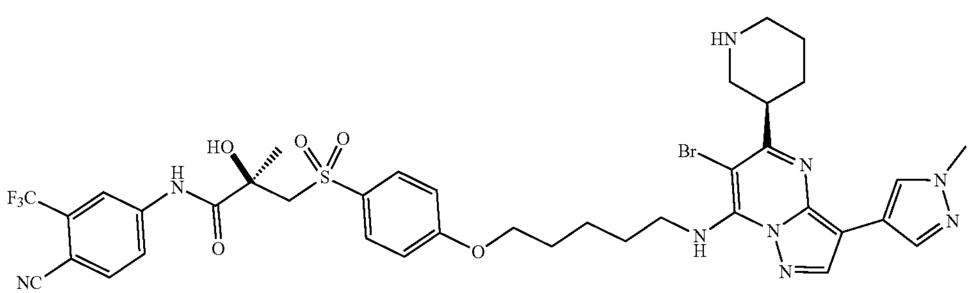 [SMILES: Cn1cc(-c2cnn3c(NCCCCCOc4ccc(S(=O)(=O)C[C@](C)(O)C(=O)Nc5ccc(C#N)c(C(F)(F)F)c5)cc4)c(Br)c([C@@H]4CCCNC4)nc23)cn1] |

TABLE 1-continued

| No. | Structure |
|---|---|
| 3.75 | 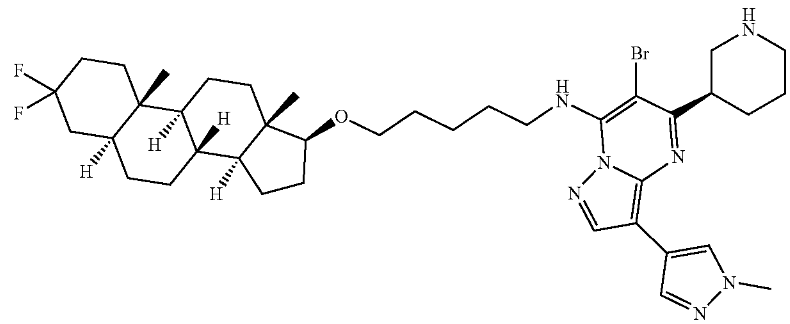 |
| 3.76 | 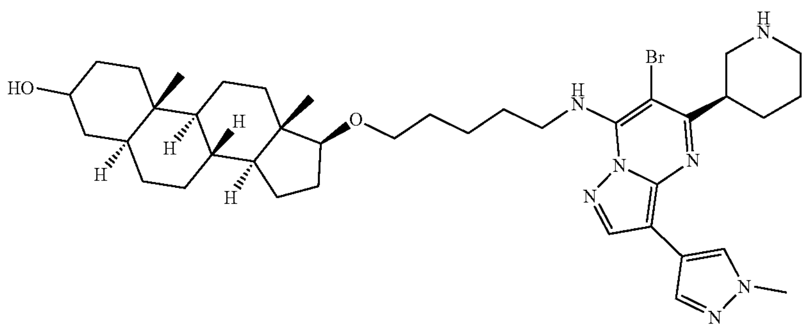 |
| 3.77 | 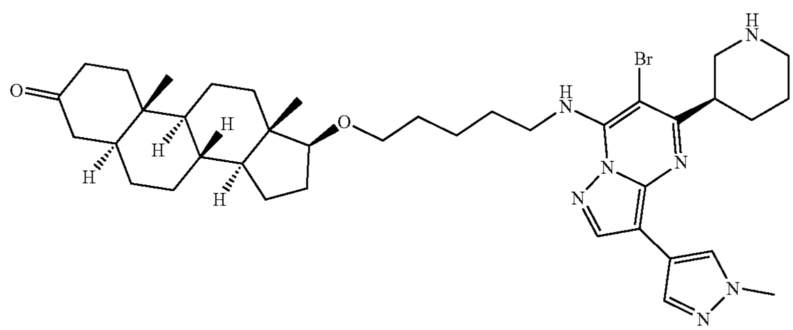 |
| 3.78 | 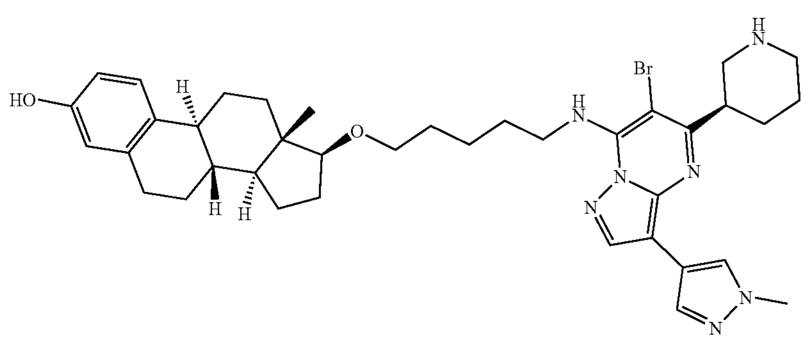 [SMILES: Cn1cc(-c2cnn3c(NCCCCCO[C@H]4CC[C@H]5[C@@H]6CCc7cc(O)ccc7[C@H]6CC[C@]45C)c(Br)c([C@@H]4CCCNC4)nc23)cn1] |
| 3.85 | 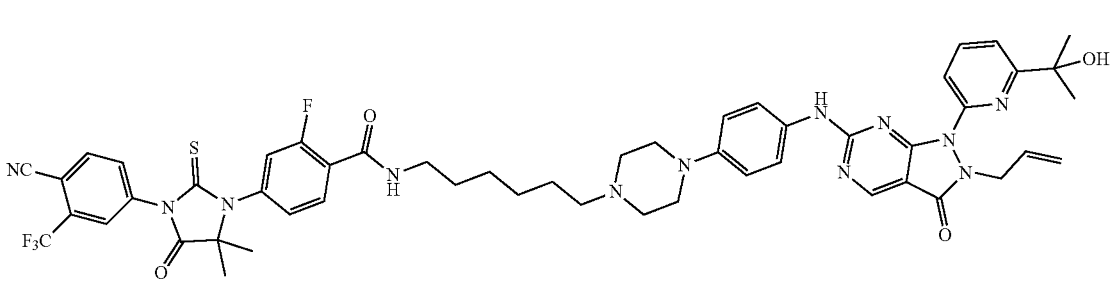 [SMILES: C=CCn1c(=O)c2cnc(Nc3ccc(N4CCN(CCCCCCNC(=O)c5ccc(N6C(=S)N(c7ccc(C#N)c(C(F)(F)F)c7)C(=O)C6(C)C)cc5F)CC4)cc3)nc2n1-c1cccc(C(C)(C)O)n1] |

TABLE 1-continued

| No. | Structure |
|---|---|
| 3.86 | 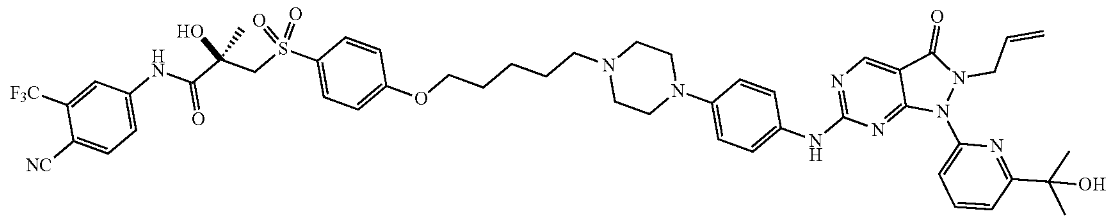 [SMILES: C=CCn1c(=O)c2cnc(Nc3ccc(N4CCN(CCCCCOc5ccc(S(=O)(=O)C[C@](C)(O)C(=O)Nc6ccc(C#N)c(C(F)(F)F)c6)cc5)CC4)cc3)nc2n1-c1cccc(C(C)(C)O)n1] |
| 3.87 | 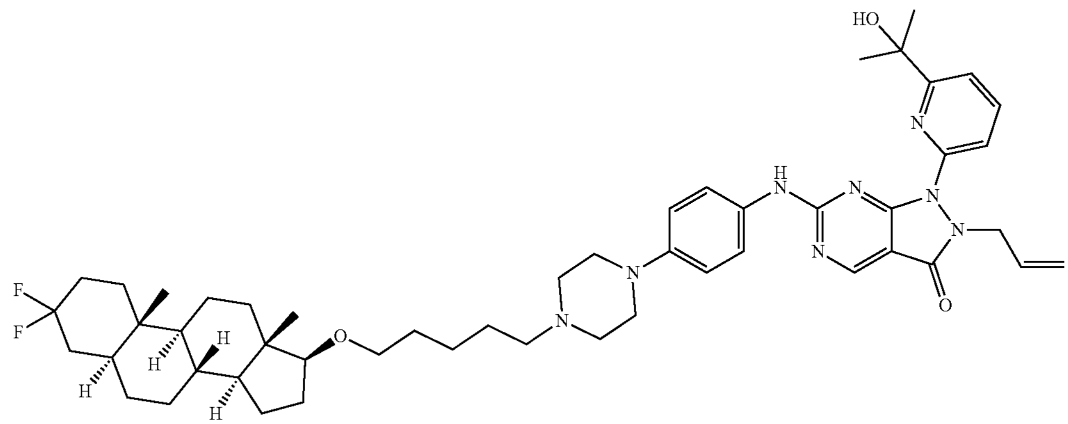 |
| 3.88 | 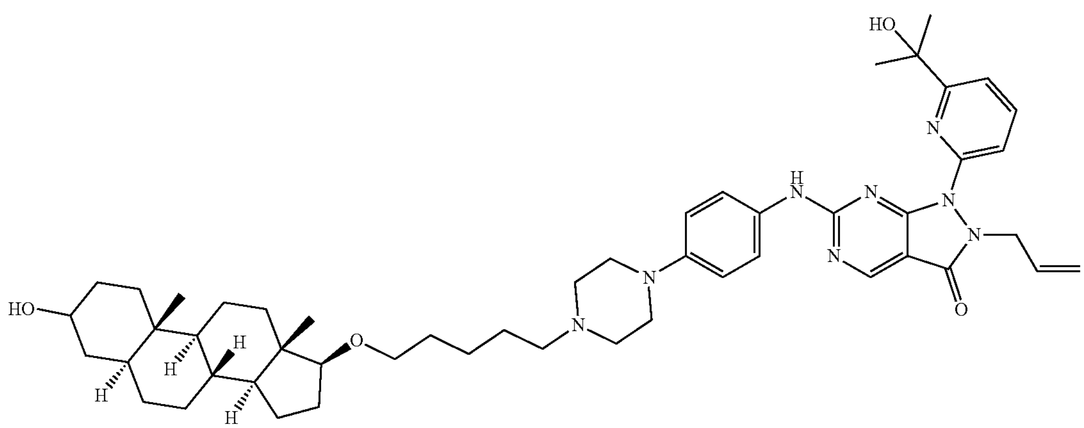 |
| 3.89 | 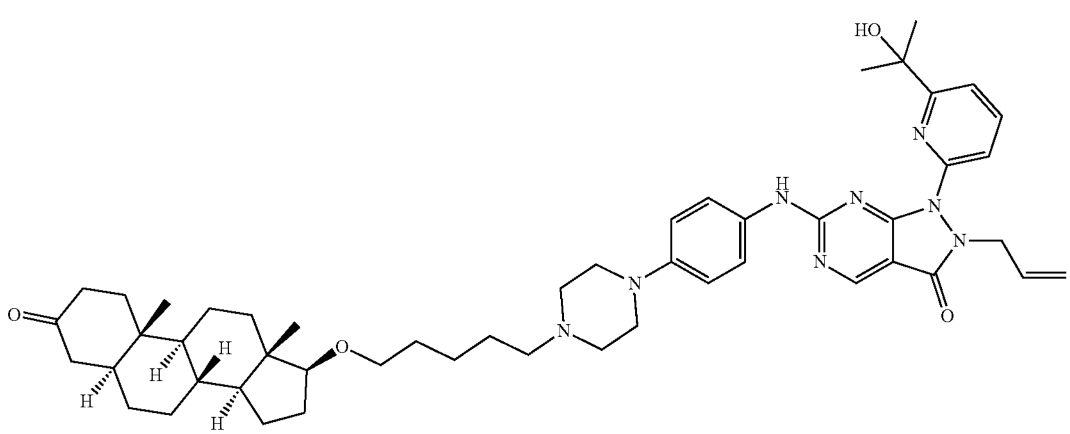 |

TABLE 1-continued
| No. | Structure |
|---|---|
| 3.90 | 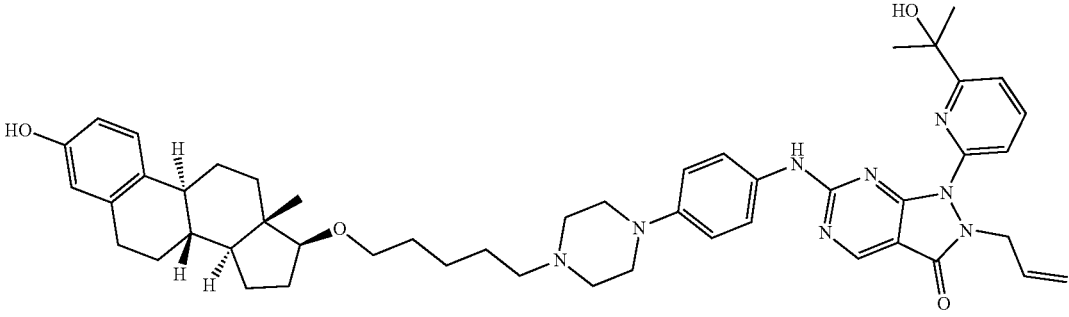 [SMILES: C=CCn1c(=O)c2cnc(Nc3ccc(N4CCN(CCCCCO[C@H]5CC[C@H]6[C@@H]7CCc8cc(O)ccc8[C@H]7CC[C@]56C)CC4)cc3)nc2n1-c1cccc(C(C)(C)O)n1] |
| 3.91 | 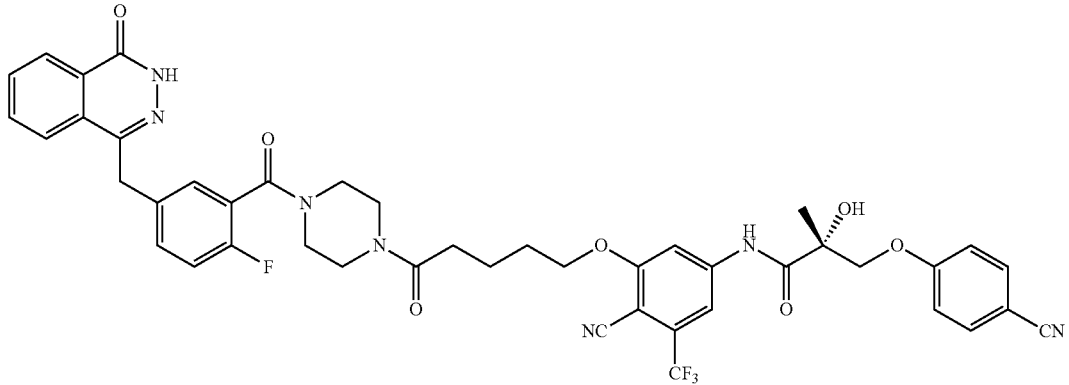 [SMILES: C[C@@](O)(COc1ccc(C#N)cc1)C(=O)Nc1cc(OCCCCC(=O)N2CCN(C(=O)c3cc(Cc4n[nH]c(=O)c5ccccc45)ccc3F)CC2)c(C#N)c(C(F)(F)F)c1] |
| 3.92 | 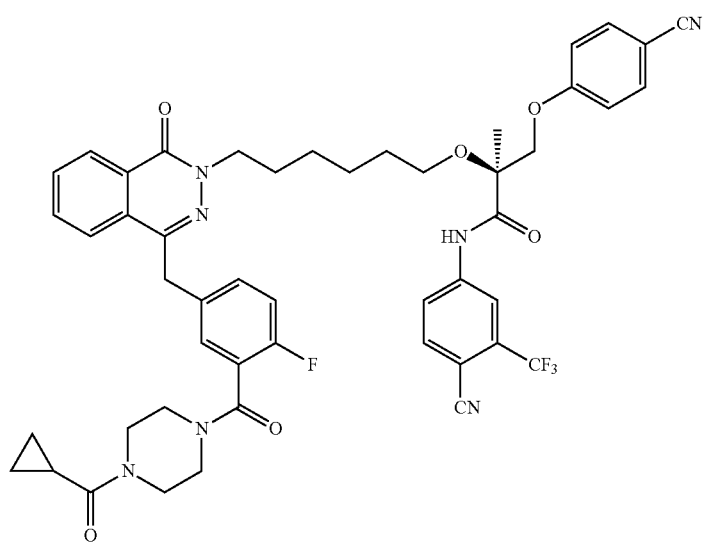 [SMILES: C[C@@](COc1ccc(C#N)cc1)(OCCCCCCn1nc(Cc2ccc(F)c(C(=O)N3CCN(C(=O)C4CC4)CC3)c2)c2ccccc2c1=O)C(=O)Nc1ccc(C#N)c(C(F)(F)F)c1] |

TABLE 1-continued

| No. | Structure |
|---|---|
| 3.93 | 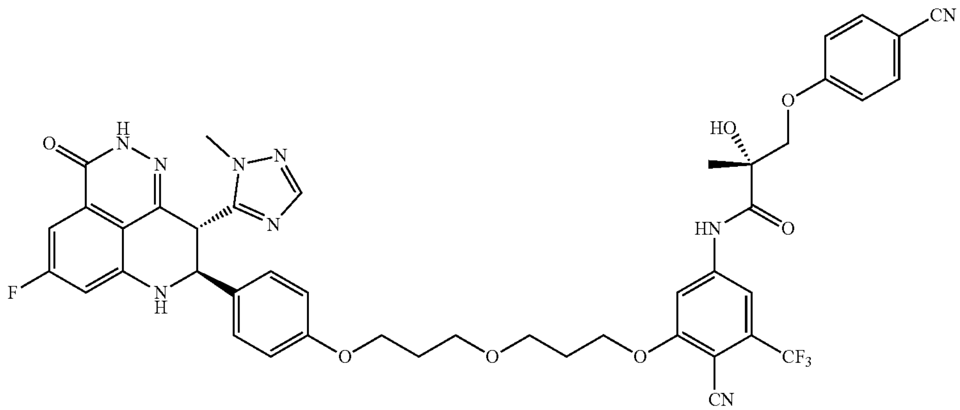 |
| 3.94 | 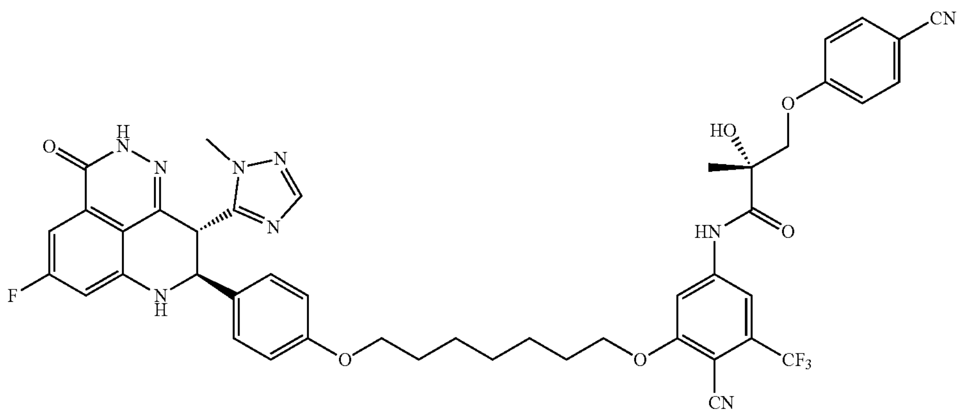 [SMILES: Cn1ncnc1[C@H]1c2n[nH]c(=O)c3cc(F)cc(c23)N[C@@H]1c1ccc(OCCCCCCCOc2cc(NC(=O)[C@](C)(O)COc3ccc(C#N)cc3)cc(C(F)(F)F)c2C#N)cc1] |
| 3.95 | 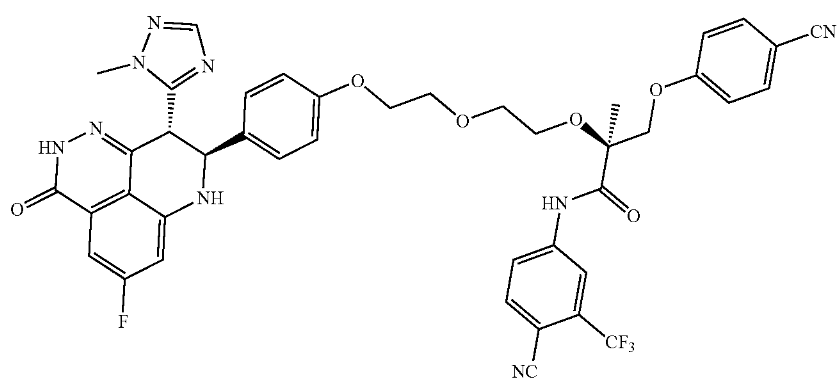 [SMILES: Cn1ncnc1[C@H]1c2n[nH]c(=O)c3cc(F)cc(c23)N[C@@H]1c1ccc(OCCOCCO[C@@](C)(COc2ccc(C#N)cc2)C(=O)Nc2ccc(C#N)c(C(F)(F)F)c2)cc1] |
| 3.96 | 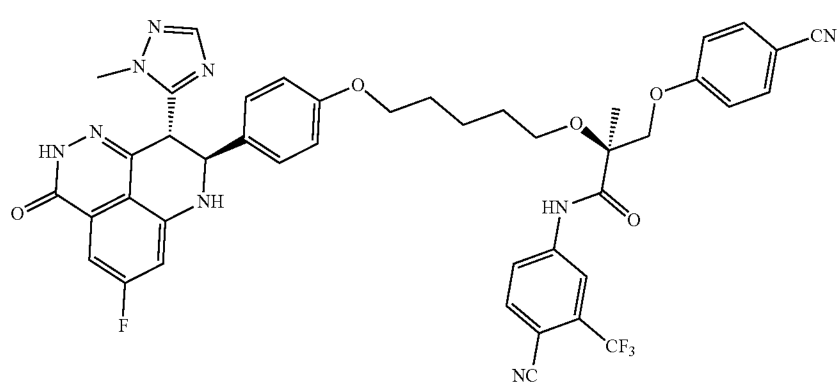 [SMILES: Cn1ncnc1[C@H]1c2n[nH]c(=O)c3cc(F)cc(c23)N[C@@H]1c1ccc(OCCCCCO[C@@](C)(COc2ccc(C#N)cc2)C(=O)Nc2ccc(C#N)c(C(F)(F)F)c2)cc1] |

TABLE 1-continued

| No. | Structure |
|---|---|
| 3.97 | 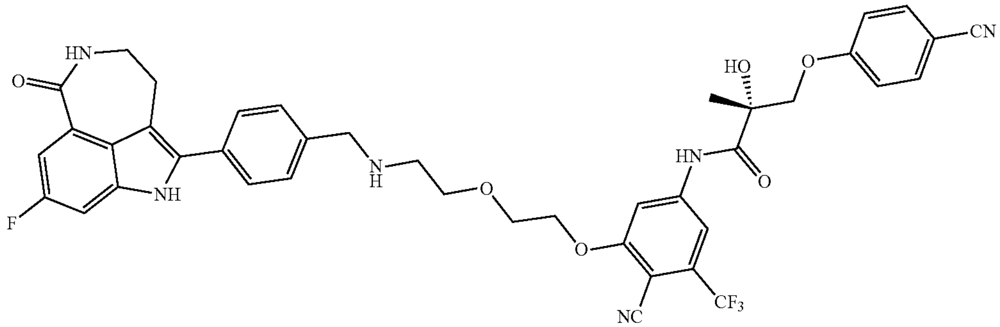 [SMILES: C[C@@](O)(COc1ccc(C#N)cc1)C(=O)Nc1cc(OCCOCCNCc2ccc(-c3[nH]c4cc(F)cc5c4c3CCNC5=O)cc2)c(C#N)c(C(F)(F)F)c1] |
| 3.98 | 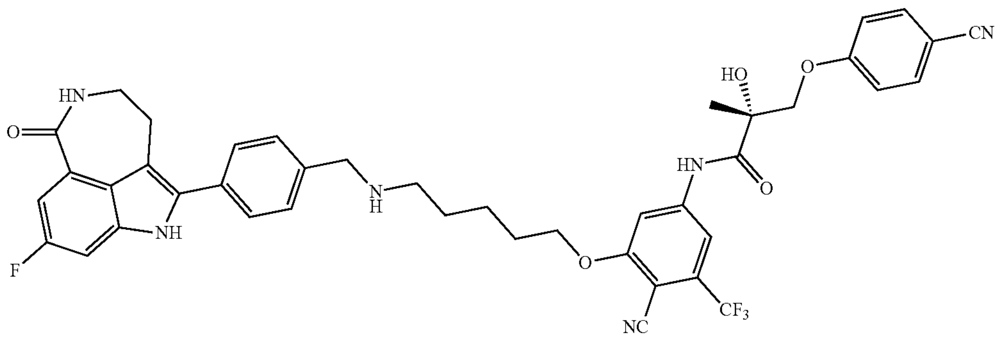 [SMILES: C[C@@](O)(COc1ccc(C#N)cc1)C(=O)Nc1cc(OCCCCCNCc2ccc(-c3[nH]c4cc(F)cc5c4c3CCNC5=O)cc2)c(C#N)c(C(F)(F)F)c1] |
| 3.99 | 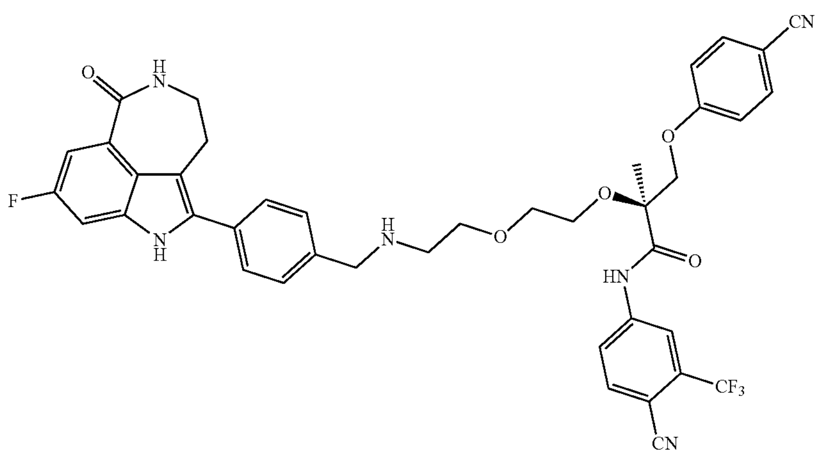 |
| 3.100 | 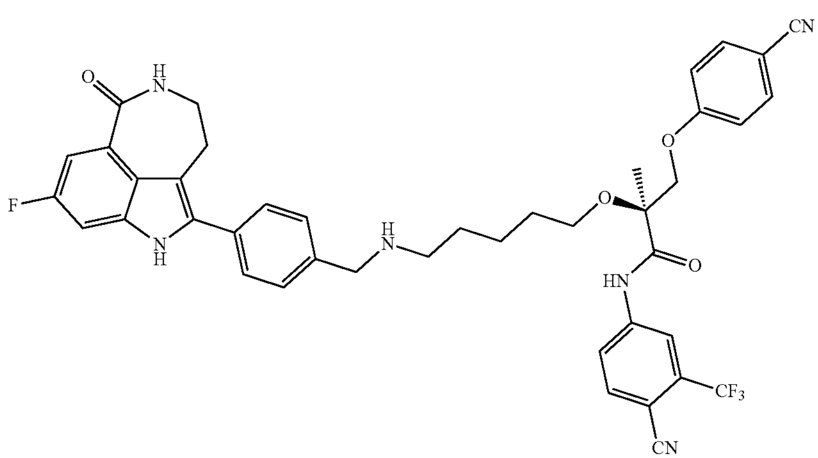 [SMILES: C[C@@](COc1ccc(C#N)cc1)(OCCCCCNCc1ccc(-c2[nH]c3cc(F)cc4c3c2CCNC4=O)cc1)C(=O)Nc1ccc(C#N)c(C(F)(F)F)c1] |

TABLE 1-continued
| No. | Structure |
|---|---|
| 3.101 | 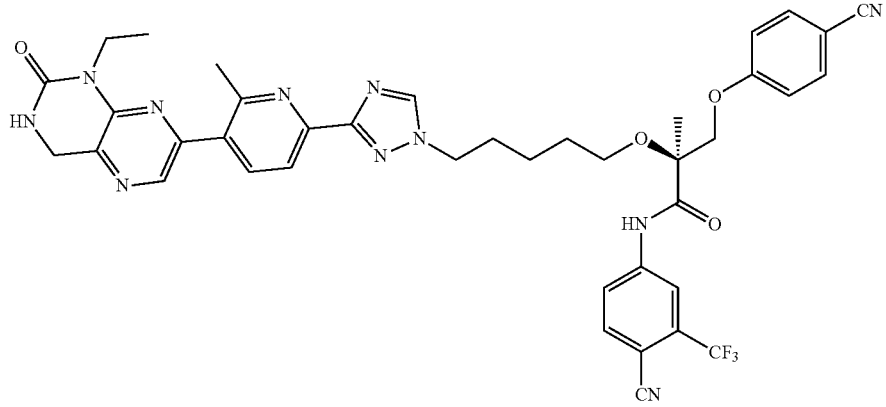 [SMILES: CCN1C(=O)NCc2ncc(-c3ccc(-c4ncn(CCCCCO[C@@](C)(COc5ccc(C#N)cc5)C(=O)Nc5ccc(C#N)c(C(F)(F)F)c5)n4)nc3C)nc21] |
| 3.102 | 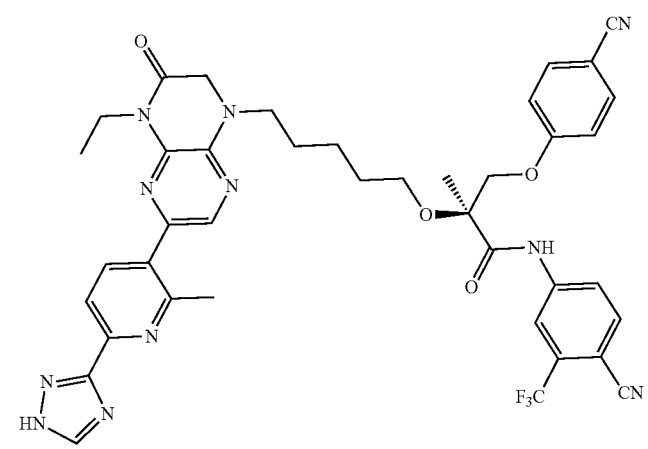 [SMILES: CCN1C(=O)CN(CCCCCO[C@@](C)(COc2ccc(C#N)cc2)C(=O)Nc2ccc(C#N)c(C(F)(F)F)c2)c2ncc(-c3ccc(-c4nc[nH]n4)nc3C)nc21] |
| 3.103 | 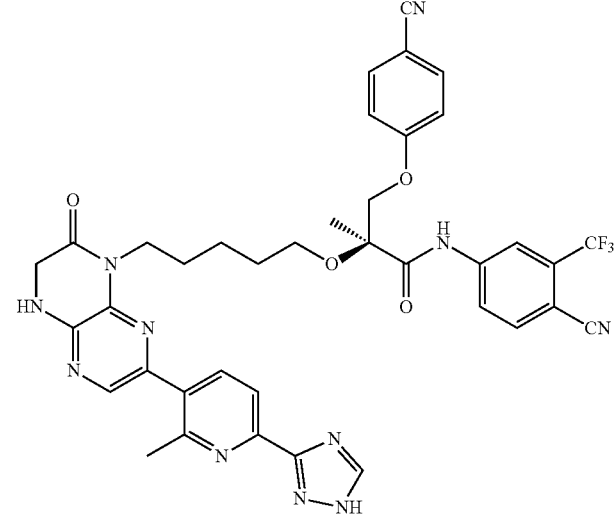 [SMILES: Cc1nc(-c2nc[nH]n2)ccc1-c1cnc2c(n1)N(CCCCCO[C@@](C)(COc1ccc(C#N)cc1)C(=O)Nc1ccc(C#N)c(C(F)(F)F)c1)C(=O)CN2] |

TABLE 1-continued

| No. | Structure |
|---|---|
| 3.104 | 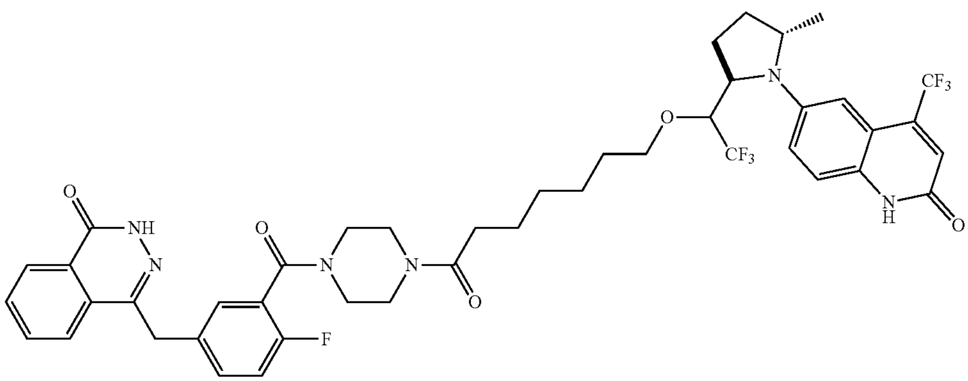 |
| 3.105 | 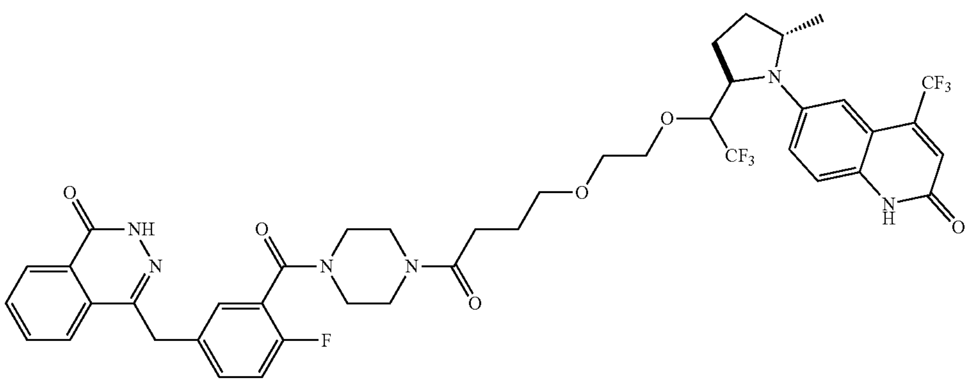 |
| 3.106 | 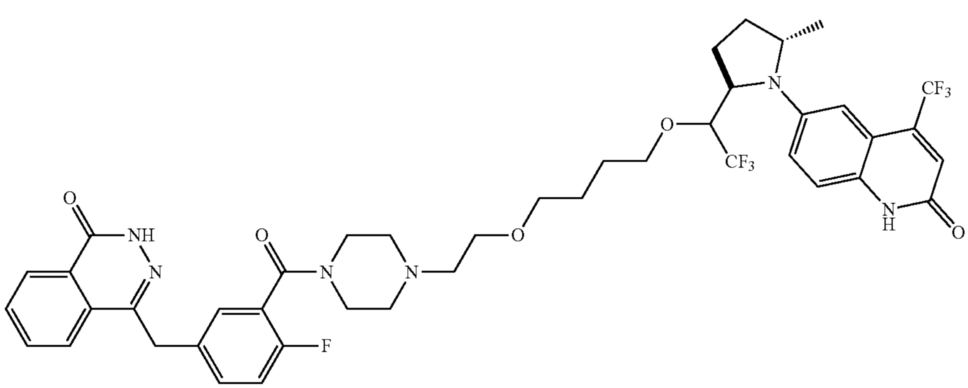 |
| 3.107 | 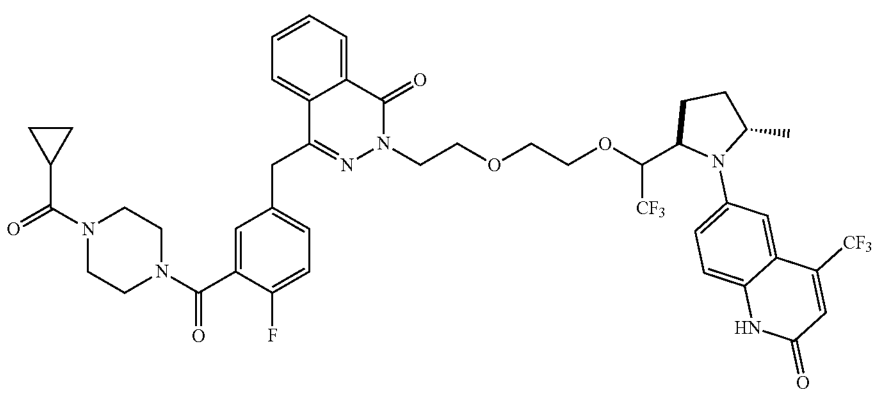 |

TABLE 1-continued

| No. | Structure |
|---|---|
| 3.108 | 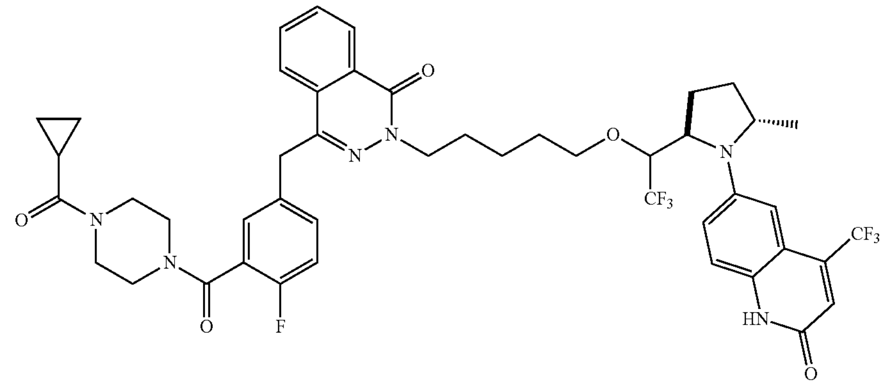 |
| 3.109 | 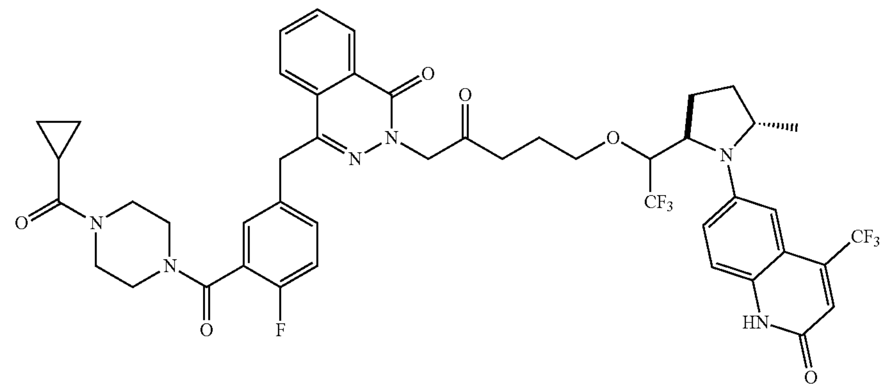 |
| 3.110 | 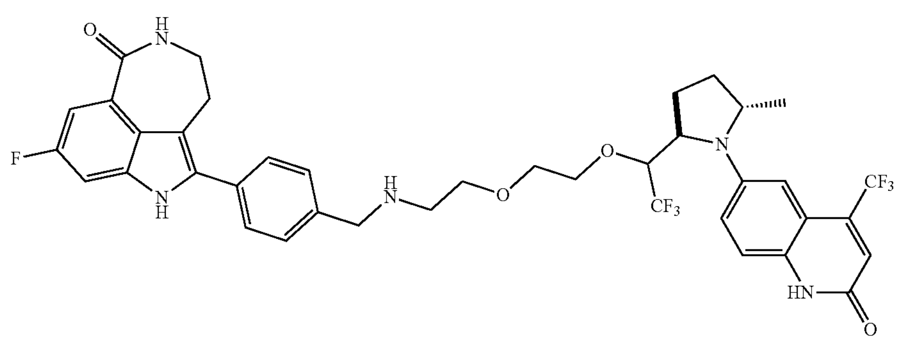 |
| 3.111 | 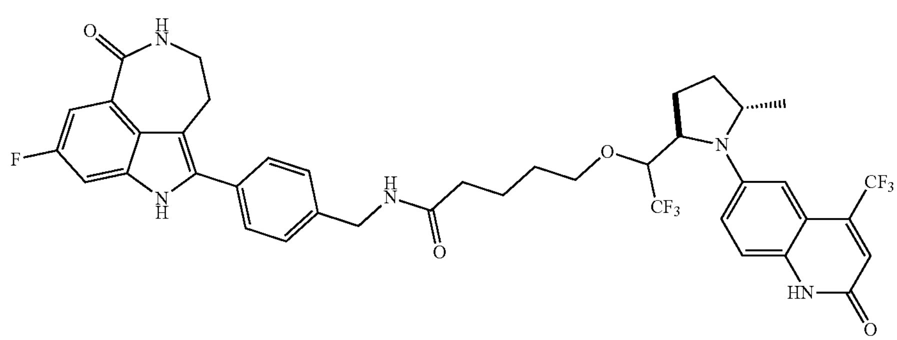 |

TABLE 1-continued
| No. | Structure |
|---|---|
| 3.112 | 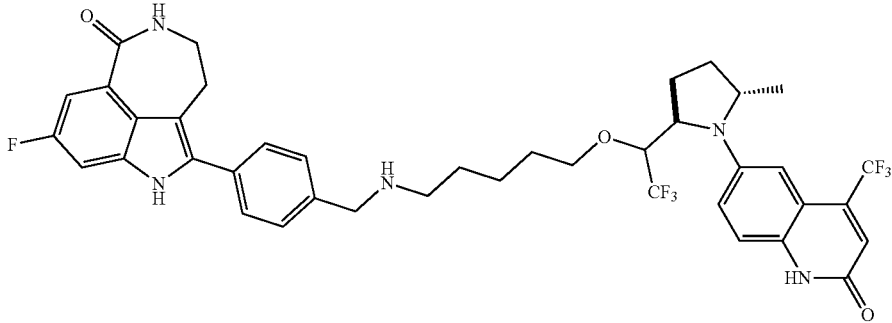 |
| 3.113 | 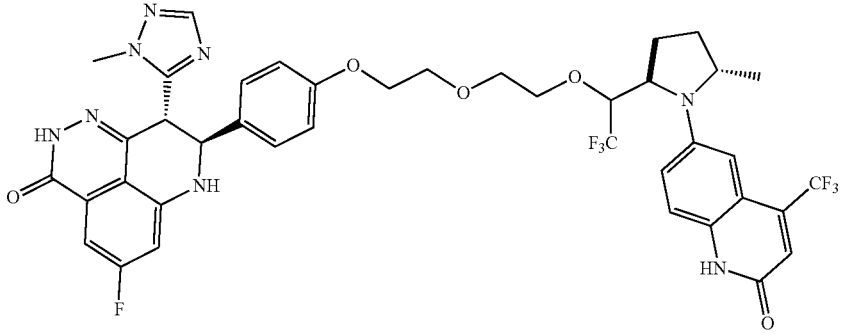 |
| 3.114 | 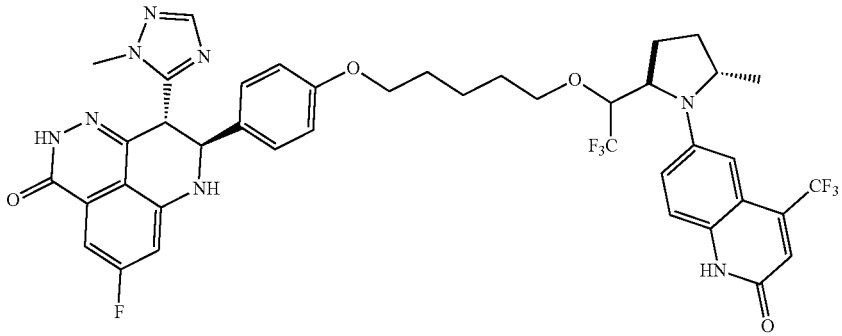 |
| 3.115 | 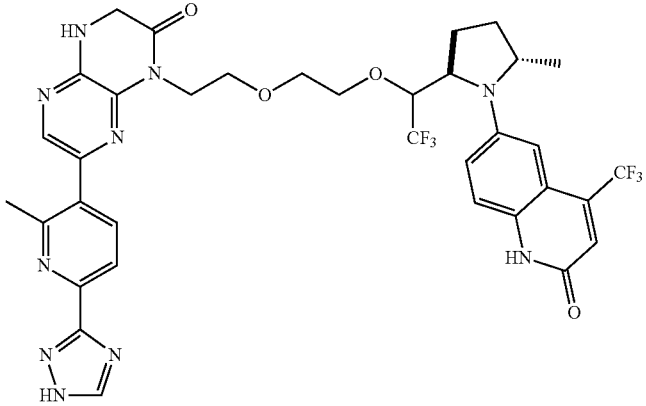 |

TABLE 1-continued

| No. | Structure |
|---|---|
| 3.116 | 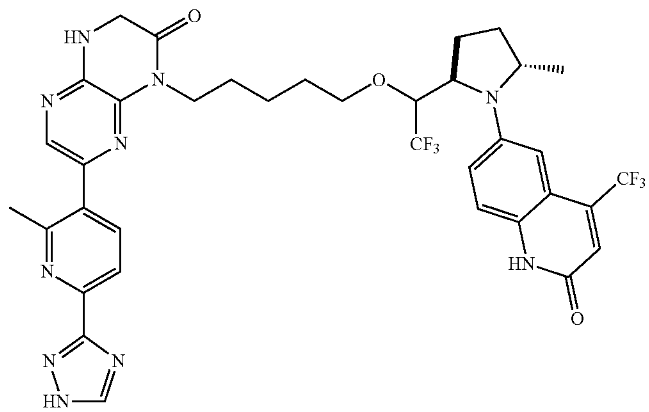 |
| 3.117 | 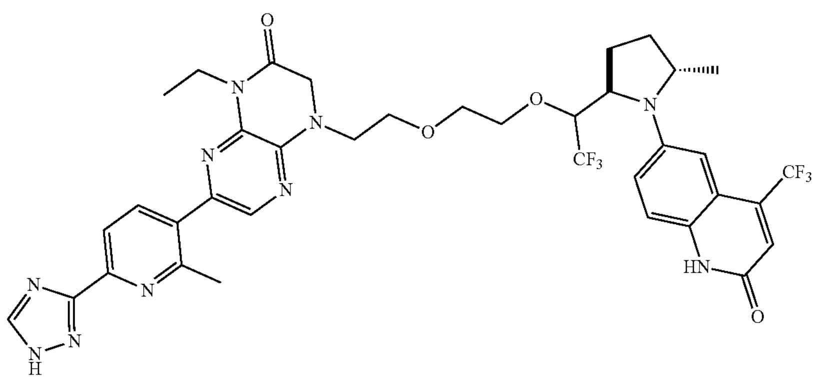 |
| 3.118 | 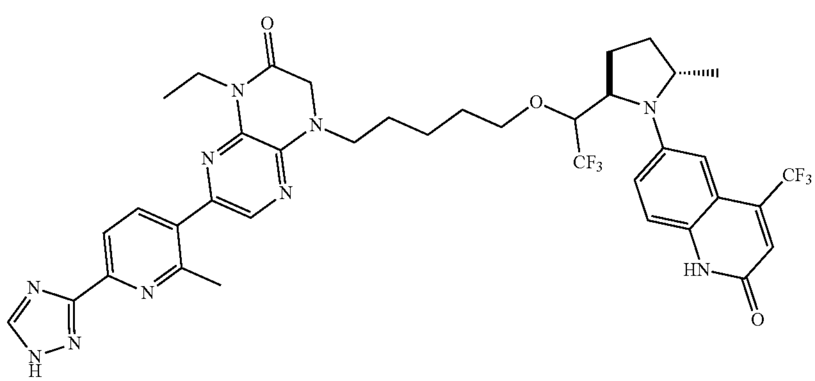 |
| 3.119 | 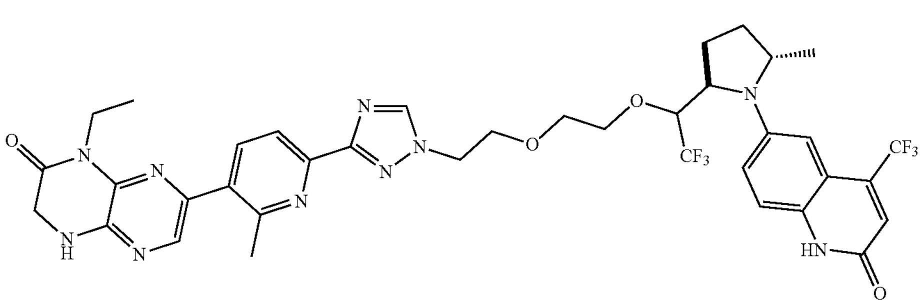 |

TABLE 1-continued

| No. | Structure |
|---|---|
| 3.120 | 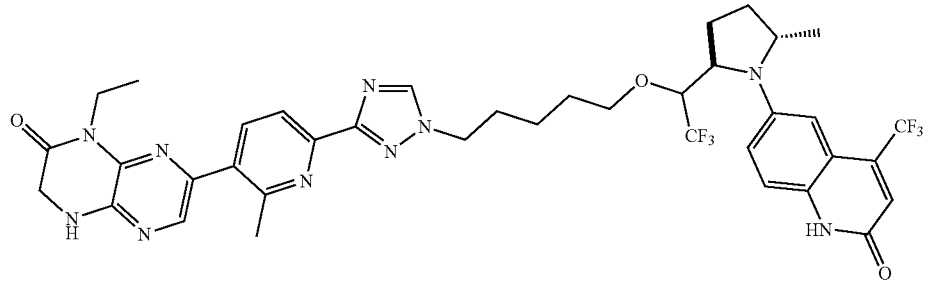 |
| 3.121 | 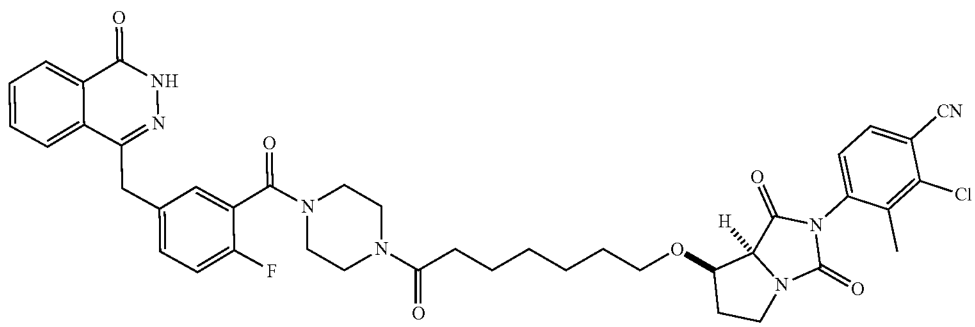 |
| 3.122 | 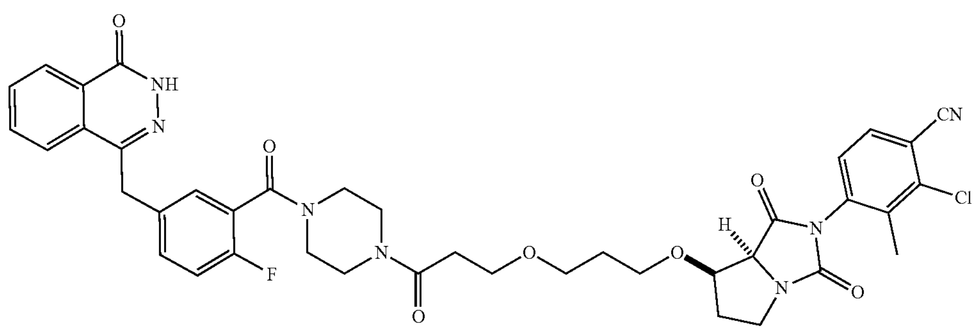 |
| 3.123 | 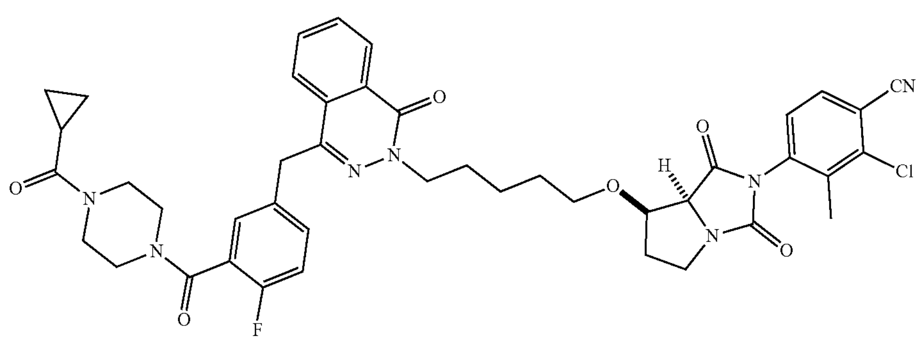 |
| 3.124 | 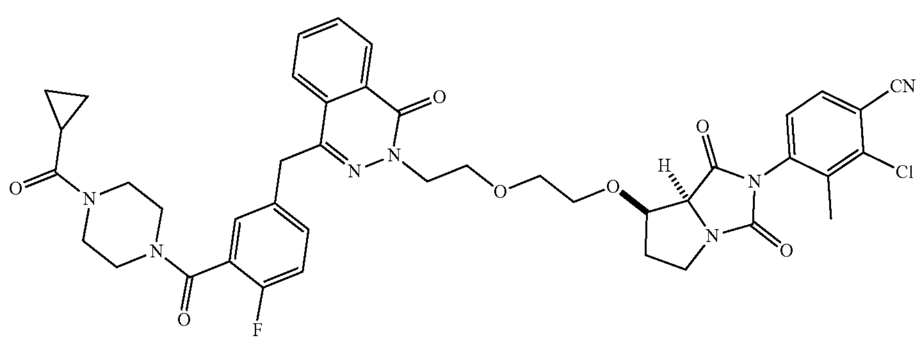 |

TABLE 1-continued

| No. | Structure |
|---|---|
| 3.125 | 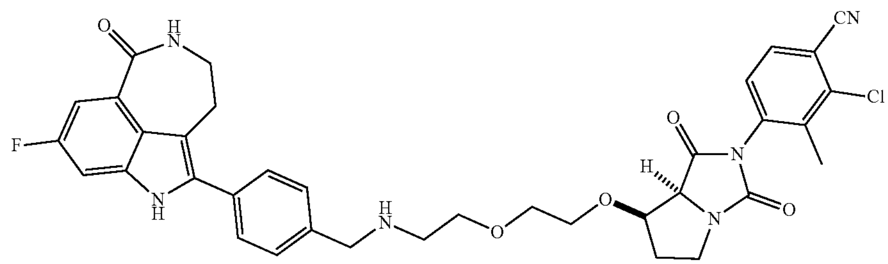 |
| 3.126 | 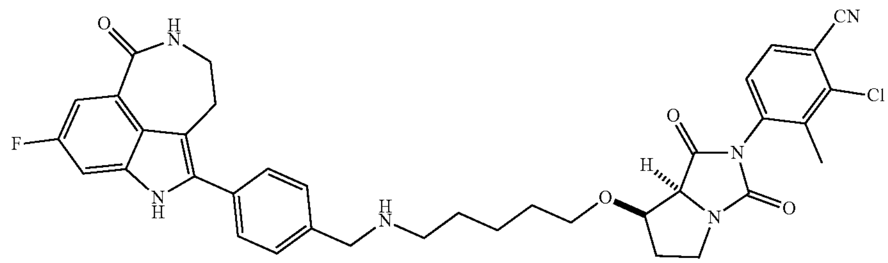 |
| 3.127 | 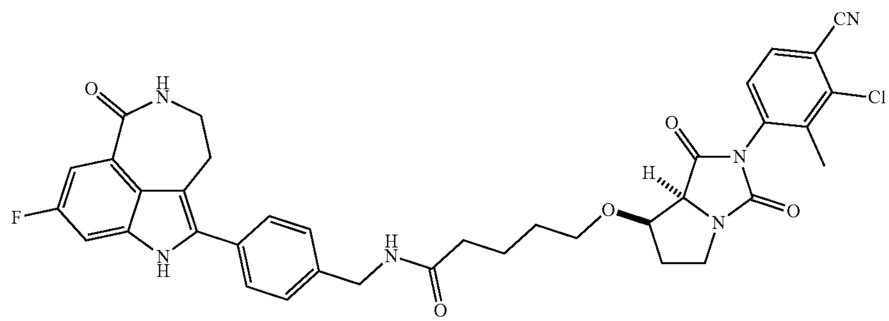 |
| 3.128 | 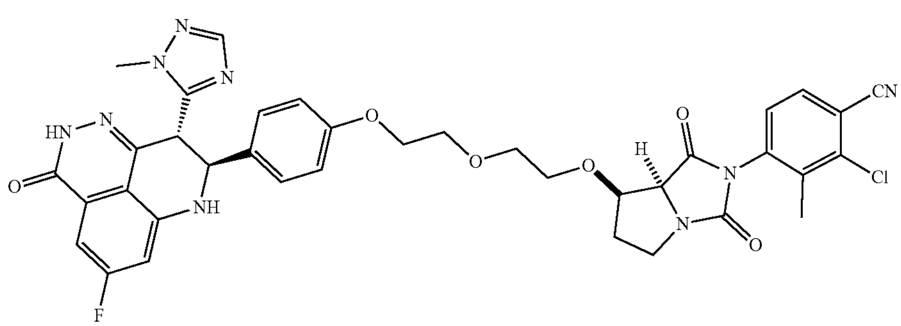 |
| 3.129 | 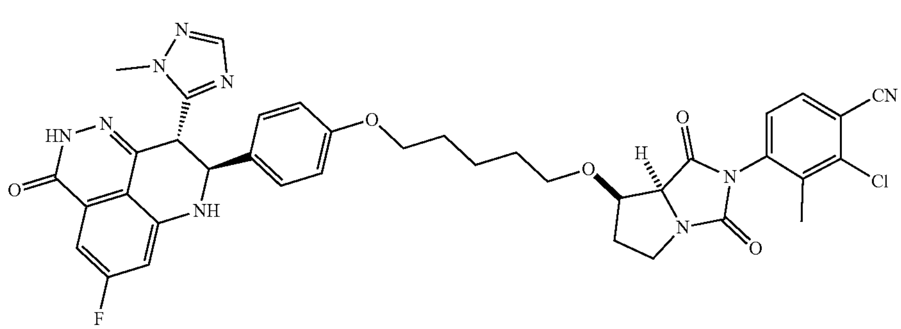 |

TABLE 1-continued

| No. | Structure |
| --- | --- |
| 3.130 | 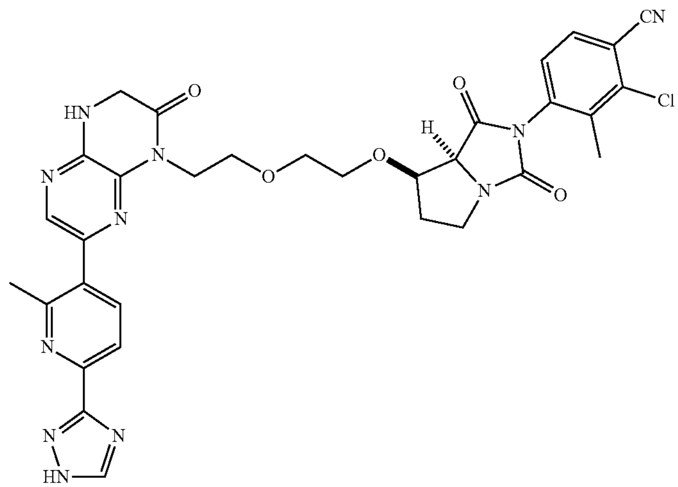 |
| 3.131 | 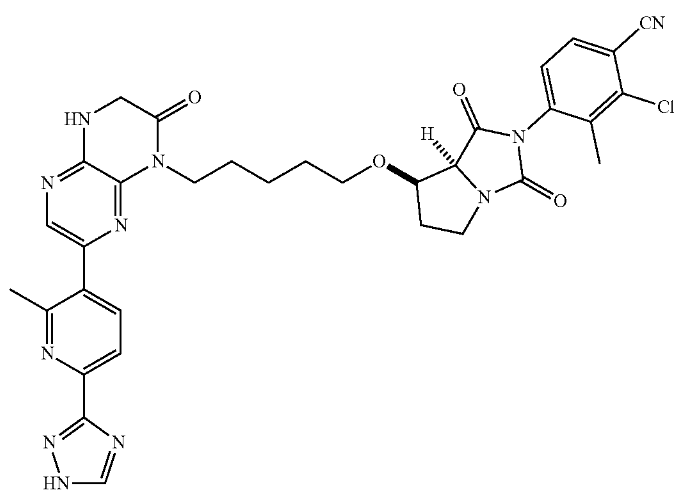 |
| 3.132 | 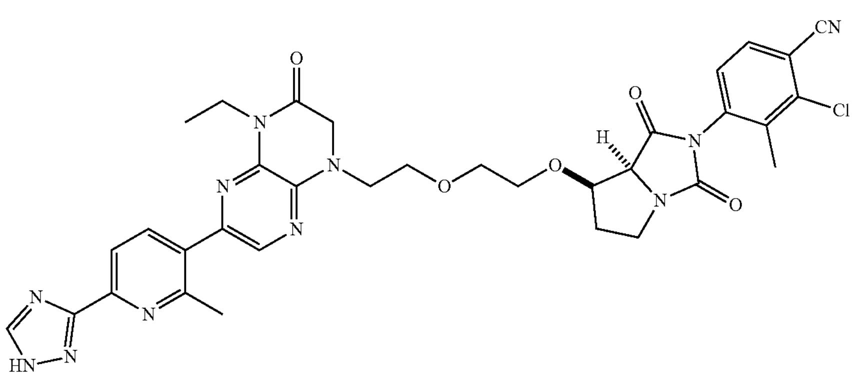 |

TABLE 1-continued

| No. | Structure |
|---|---|
| 3.133 | 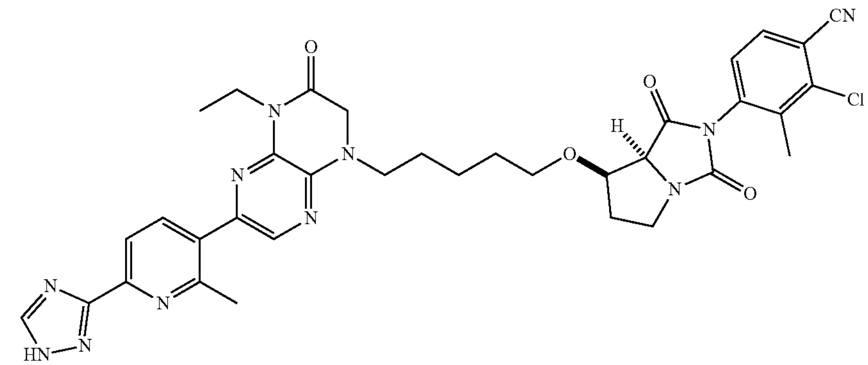 |
| 3.134 | 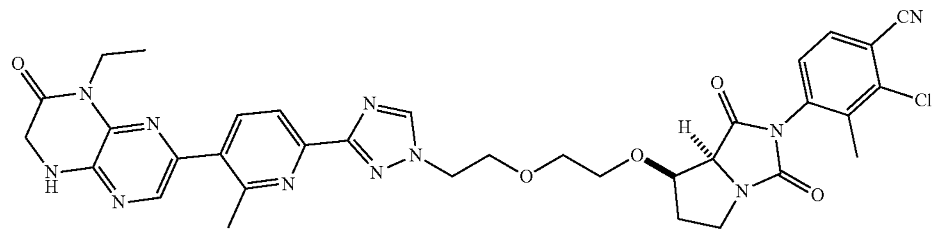 |
| 3.135 | 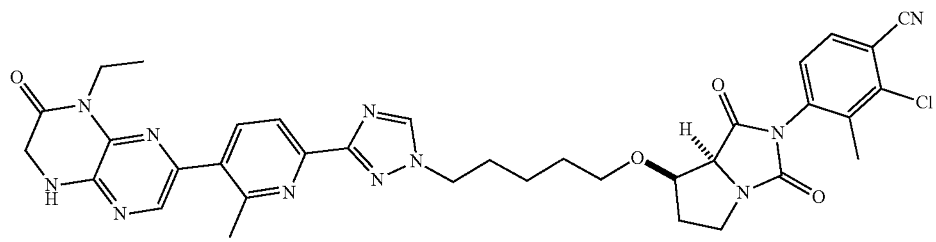 |
| 3.136 | 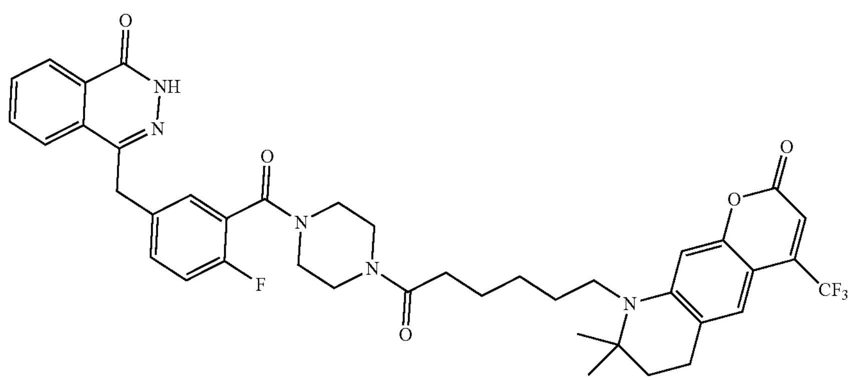 [SMILES: CC1(C)CCc2cc3c(C(F)(F)F)cc(=O)oc3cc2N1CCCCCC(=O)N1CCN(C(=O)c2cc(Cc3n[nH]c(=O)c4ccccc34)ccc2F)CC1] |
| 3.137 | 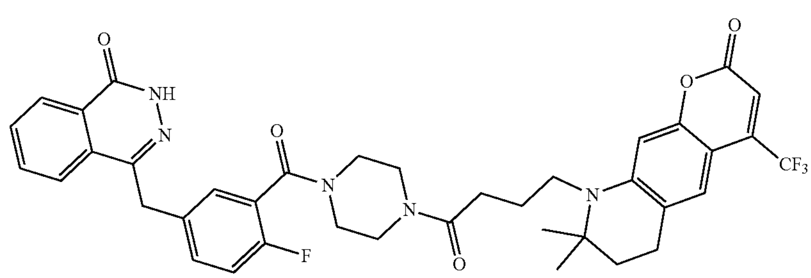 [SMILES: CC1(C)CCc2cc3c(C(F)(F)F)cc(=O)oc3cc2N1CCCC(=O)N1CCN(C(=O)c2cc(Cc3n[nH]c(=O)c4ccccc34)ccc2F)CC1] |

TABLE 1-continued

| No. | Structure |
|---|---|
| 3.138 | 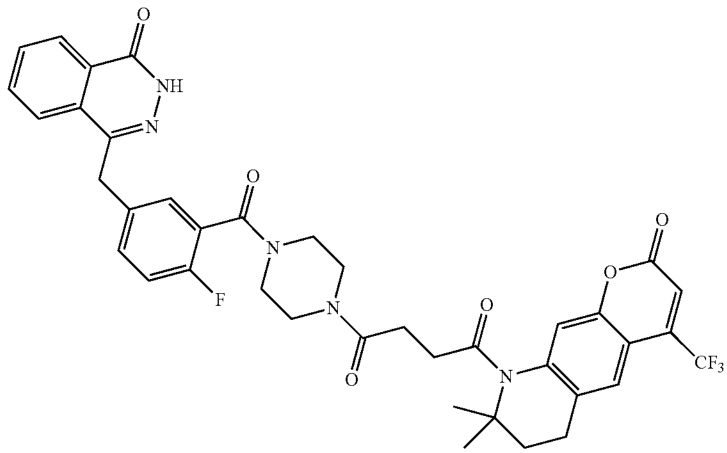 [SMILES: CC1(C)CCc2cc3c(C(F)(F)F)cc(=O)oc3cc2N1C(=O)CCC(=O)N1CCN(C(=O)c2cc(Cc3n[nH]c(=O)c4ccccc34)ccc2F)CC1] |
| 3.139 | 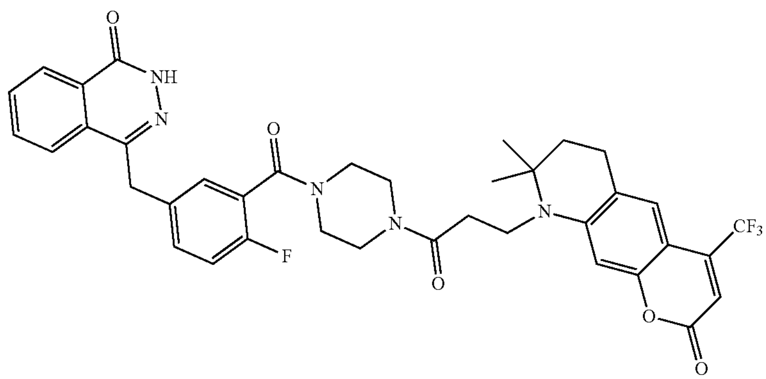 [SMILES: CC1(C)CCc2cc3c(C(F)(F)F)cc(=O)oc3cc2N1CCC(=O)N1CCN(C(=O)c2cc(Cc3n[nH]c(=O)c4ccccc34)ccc2F)CC1] |
| 3.140 | 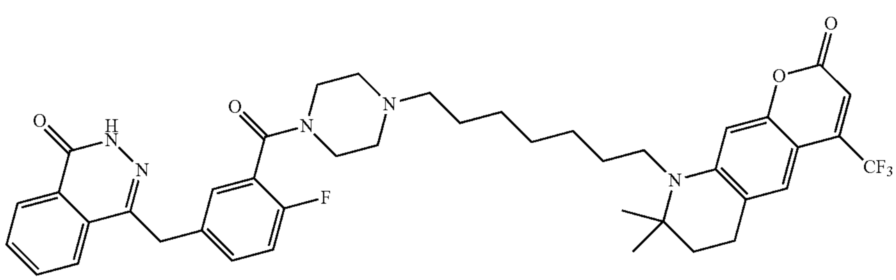 [SMILES: CC1(C)CCc2cc3c(C(F)(F)F)cc(=O)oc3cc2N1CCCCCCCN1CCN(C(=O)c2cc(Cc3n[nH]c(=O)c4ccccc34)ccc2F)CC1] |
| 3.141 | 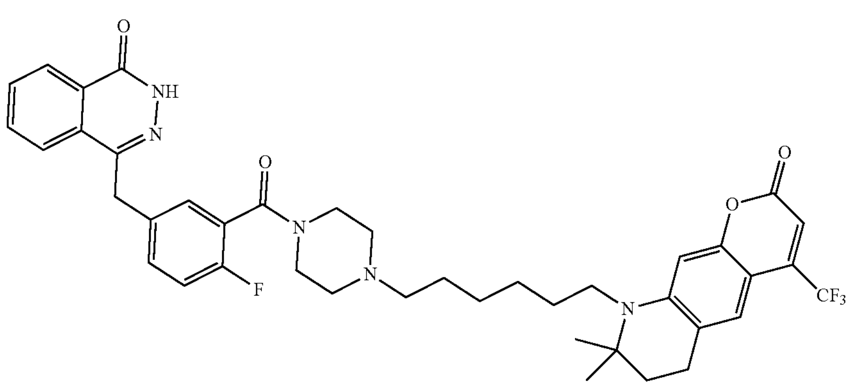 [SMILES: CC1(C)CCc2cc3c(C(F)(F)F)cc(=O)oc3cc2N1CCCCCCN1CCN(C(=O)c2cc(Cc3n[nH]c(=O)c4ccccc34)ccc2F)CC1] |

TABLE 1-continued

| No. | Structure |
|---|---|
| 3.142 | 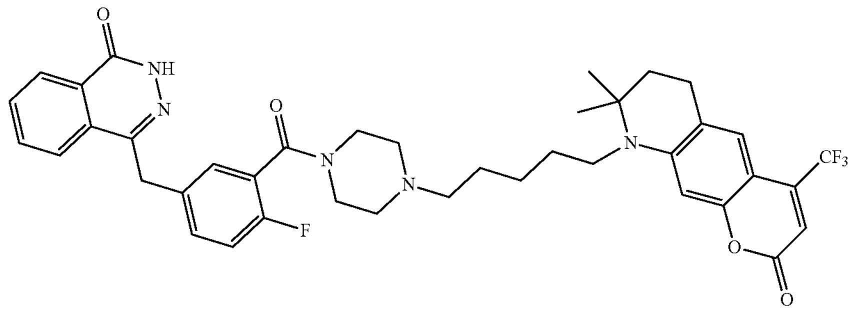 [SMILES: CC1(C)CCc2cc3c(C(F)(F)F)cc(=O)oc3cc2N1CCCCCN1CCN(C(=O)c2cc(Cc3n[nH]c(=O)c4ccccc34)ccc2F)CC1] |
| 3.143 | 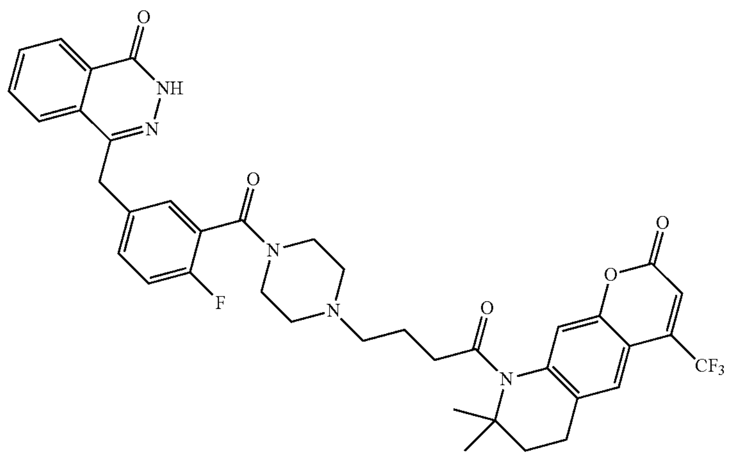 [SMILES: CC1(C)CCc2cc3c(C(F)(F)F)cc(=O)oc3cc2N1C(=O)CCCN1CCN(C(=O)c2cc(Cc3n[nH]c(=O)c4ccccc34)ccc2F)CC1] |
| 3.144 | 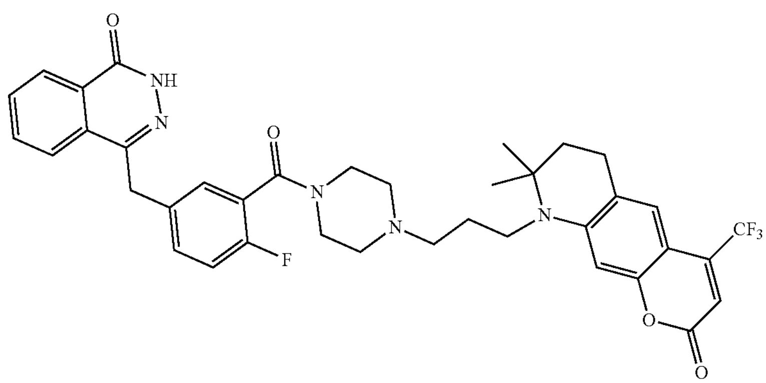 [SMILES: CC1(C)CCc2cc3c(C(F)(F)F)cc(=O)oc3cc2N1CCCN1CCN(C(=O)c2cc(Cc3n[nH]c(=O)c4ccccc34)ccc2F)CC1] |
| 3.145 | 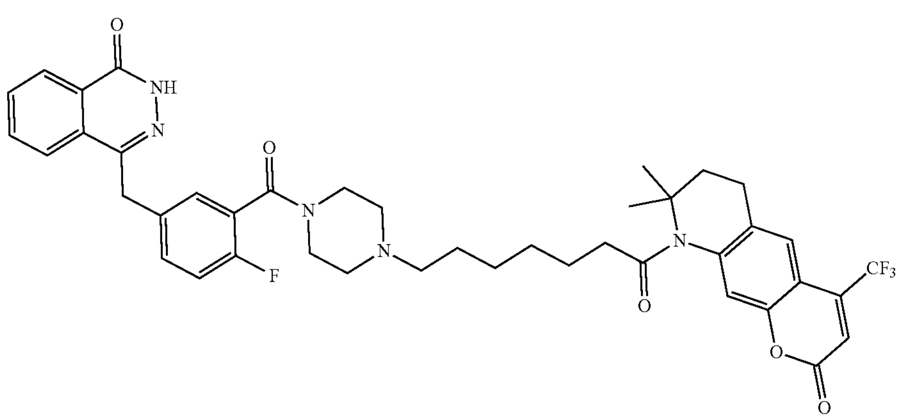 [SMILES: CC1(C)CCc2cc3c(C(F)(F)F)cc(=O)oc3cc2N1C(=O)CCCCCCN1CCN(C(=O)c2cc(Cc3n[nH]c(=O)c4ccccc34)ccc2F)CC1] |

TABLE 1-continued

| No. | Structure |
|---|---|
| 3.146 | 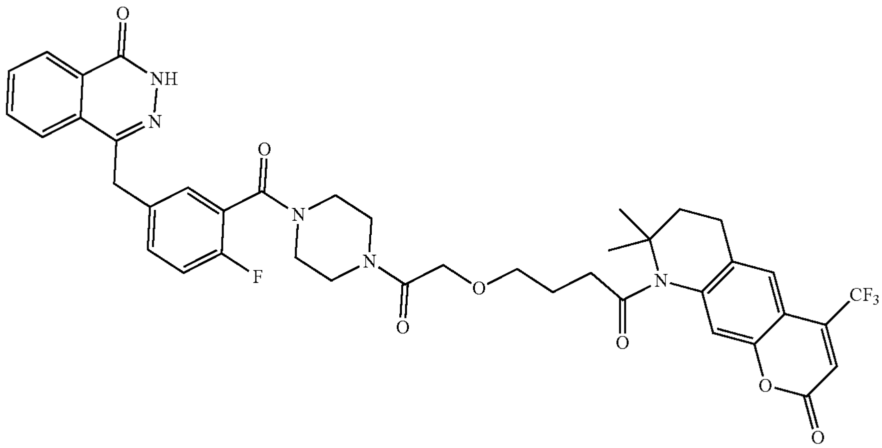 [SMILES: CC1(C)CCc2cc3c(C(F)(F)F)cc(=O)oc3cc2N1C(=O)CCCOCC(=O)N1CCN(C(=O)c2cc(Cc3n[nH]c(=O)c4ccccc34)ccc2F)CC1] |
| 3.147 | 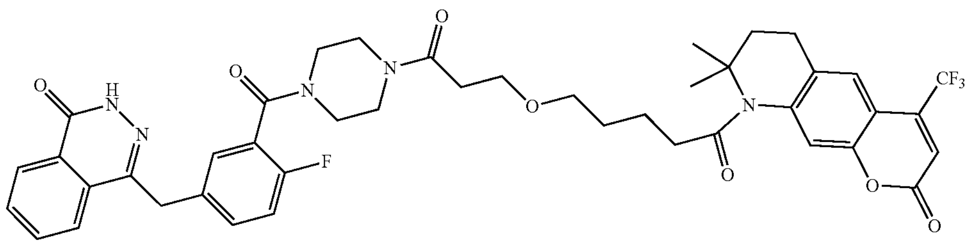 [SMILES: CC1(C)CCc2cc3c(C(F)(F)F)cc(=O)oc3cc2N1C(=O)CCCCOCCC(=O)N1CCN(C(=O)c2cc(Cc3n[nH]c(=O)c4ccccc34)ccc2F)CC1] |
| 3.148 | 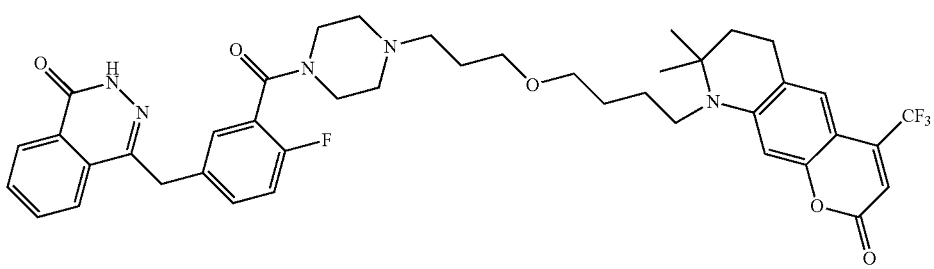 [SMILES: CC1(C)CCc2cc3c(C(F)(F)F)cc(=O)oc3cc2N1CCCCOCCCN1CCN(C(=O)c2cc(Cc3n[nH]c(=O)c4ccccc34)ccc2F)CC1] |
| 3.149 | 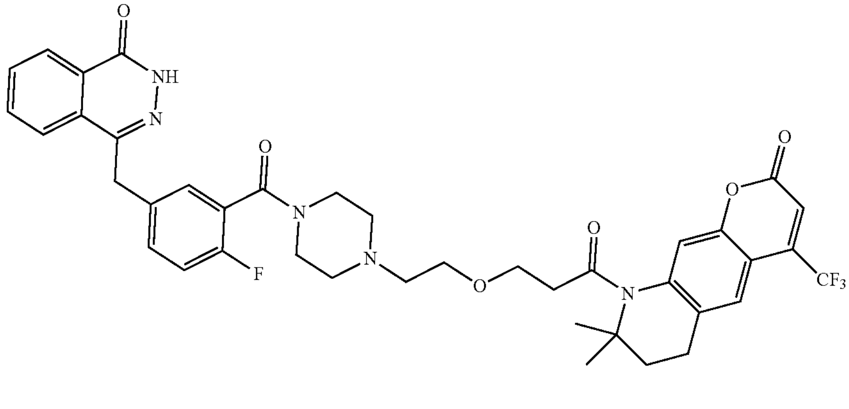 [SMILES: CC1(C)CCc2cc3c(C(F)(F)F)cc(=O)oc3cc2N1C(=O)CCOCCN1CCN(C(=O)c2cc(Cc3n[nH]c(=O)c4ccccc34)ccc2F)CC1] |

TABLE 1-continued

| No. | Structure |
|---|---|
| 3.150 | 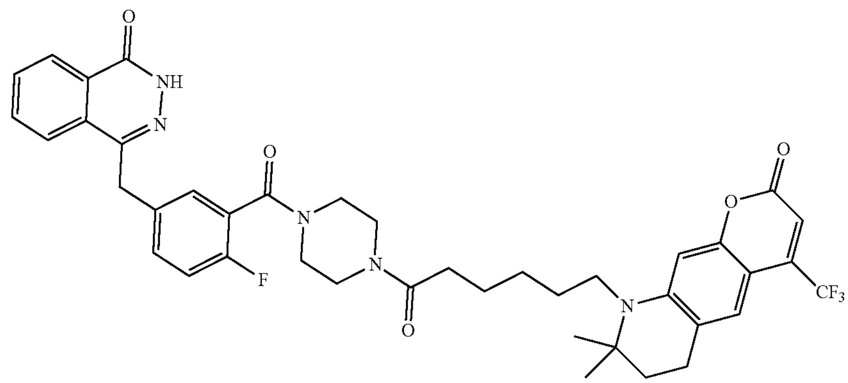 [SMILES: CC1(C)CCc2cc3c(C(F)(F)F)cc(=O)oc3cc2N1CCCCCC(=O)N1CCN(C(=O)c2cc(Cc3n[nH]c(=O)c4ccccc34)ccc2F)CC1] |
| 3.151 | 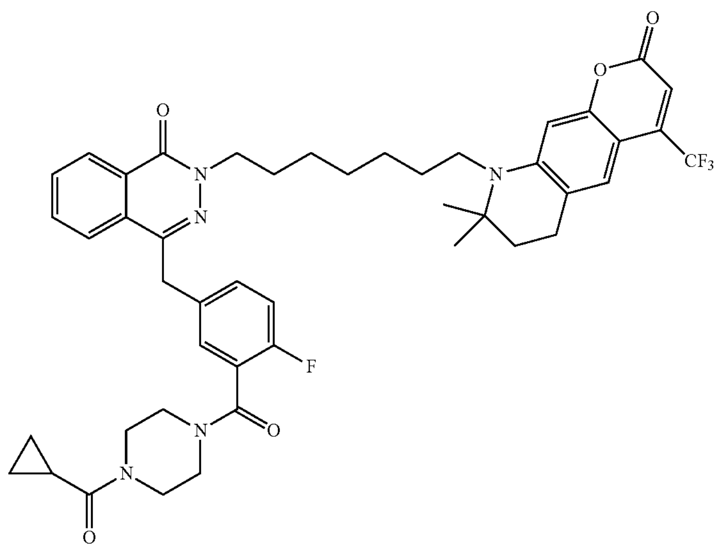 [SMILES: CC1(C)CCc2cc3c(C(F)(F)F)cc(=O)oc3cc2N1CCCCCCCn1nc(Cc2ccc(F)c(C(=O)N3CCN(C(=O)C4CC4)CC3)c2)c2ccccc2c1=O] |
| 3.152 | 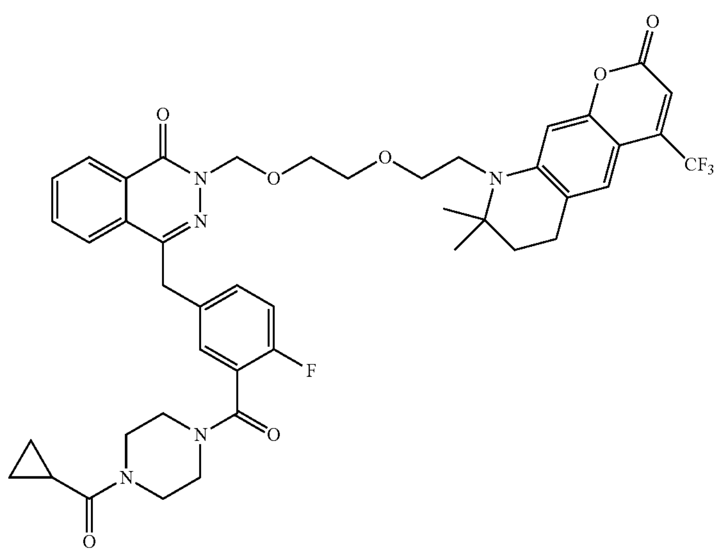 |

TABLE 1-continued

| No. | Structure |
|---|---|
| 3.153 | 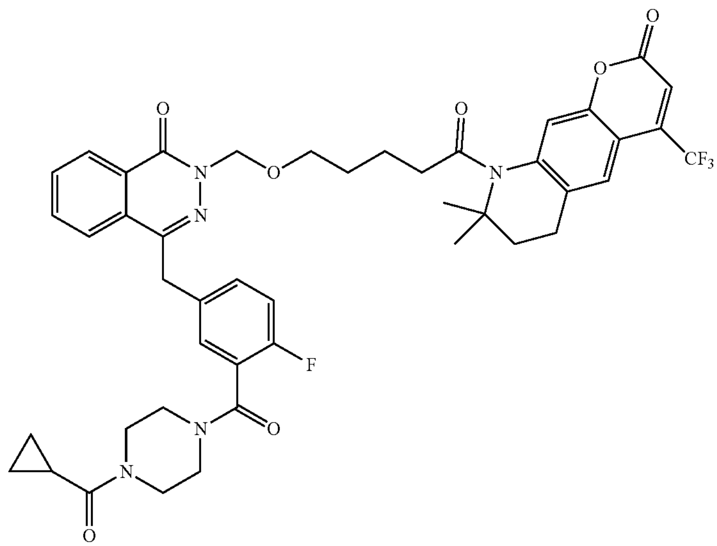 [SMILES: CC1(C)CCc2cc3c(C(F)(F)F)cc(=O)oc3cc2N1C(=O)CCCCOCn1nc(Cc2ccc(F)c(C(=O)N3CCN(C(=O)C4CC4)CC3)c2)c2ccccc2c1=O] |
| 3.154 | 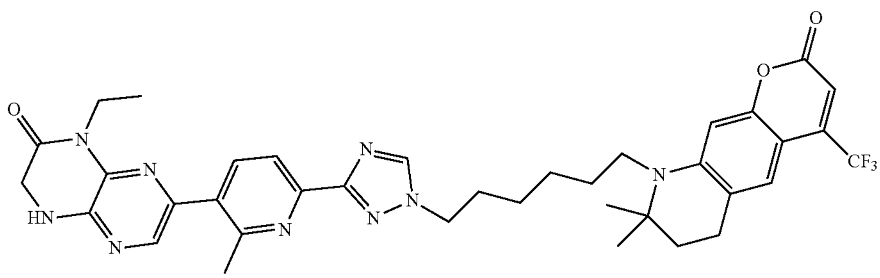 [SMILES: CCN1C(=O)CNc2ncc(-c3ccc(-c4ncn(CCCCCCN5c6cc7oc(=O)cc(C(F)(F)F)c7cc6CCC5(C)C)n4)nc3C)nc21] |
| 3.155 | 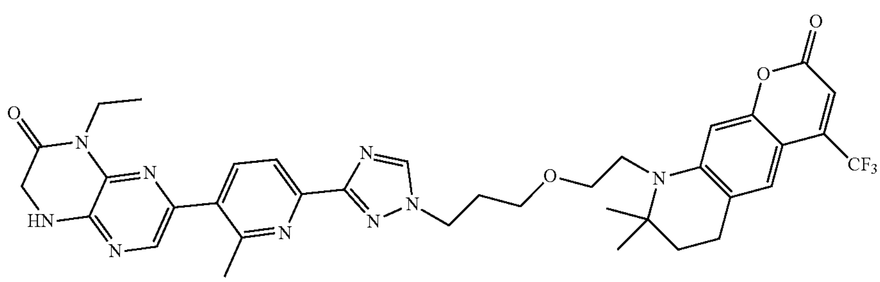 [SMILES: CCN1C(=O)CNc2ncc(-c3ccc(-c4ncn(CCCOCCN5c6cc7oc(=O)cc(C(F)(F)F)c7cc6CCC5(C)C)n4)nc3C)nc21] |
| 3.156 | 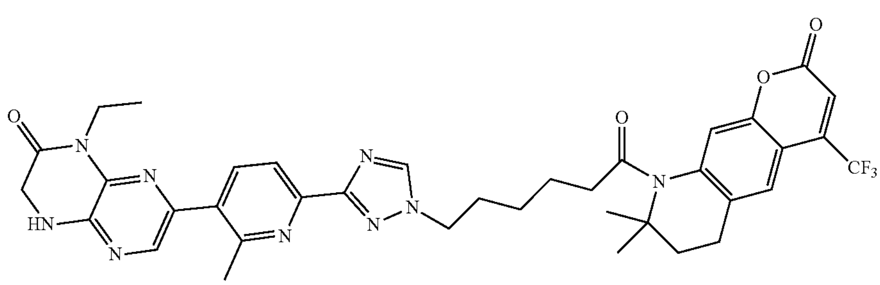 [SMILES: CCN1C(=O)CNc2ncc(-c3ccc(-c4ncn(CCCCCC(=O)N5c6cc7oc(=O)cc(C(F)(F)F)c7cc6CCC5(C)C)n4)nc3C)nc21] |

TABLE 1-continued

| No. | Structure |
|---|---|
| 3.157 | 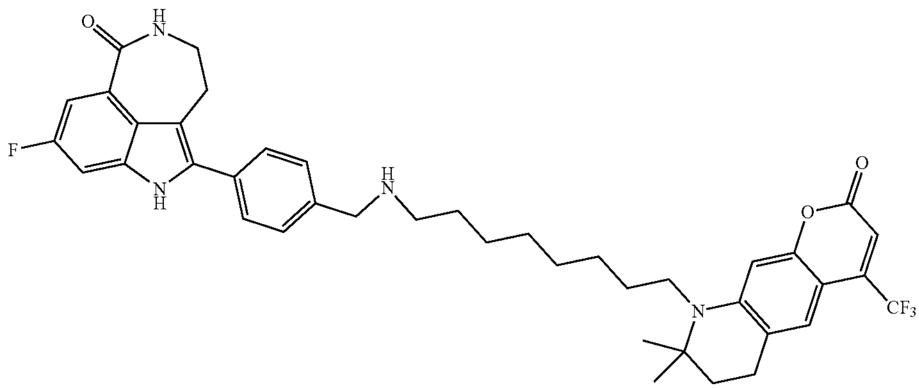 [SMILES: CC1(C)CCc2cc3c(C(F)(F)F)cc(=O)oc3cc2N1CCCCCCCCNCc1ccc(-c2[nH]c3cc(F)cc4c3c2CCNC4=O)cc1] |
| 3.158 | 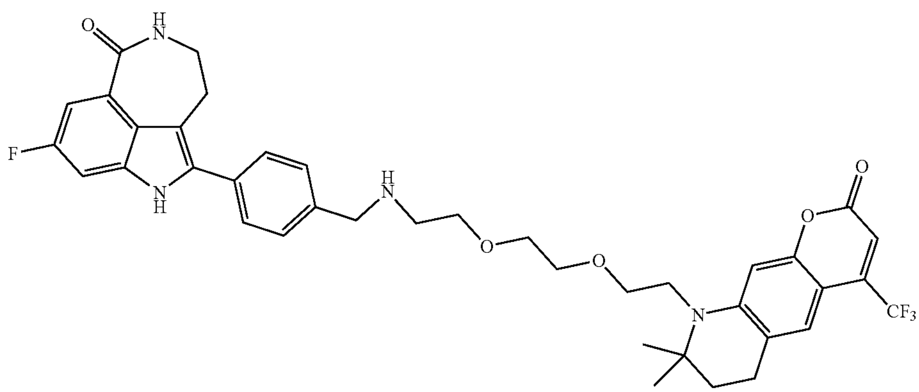 [SMILES: CC1(C)CCc2cc3c(C(F)(F)F)cc(=O)oc3cc2N1CCOCCOCCNCc1ccc(-c2[nH]c3cc(F)cc4c3c2CCNC4=O)cc1] |
| 3.159 | 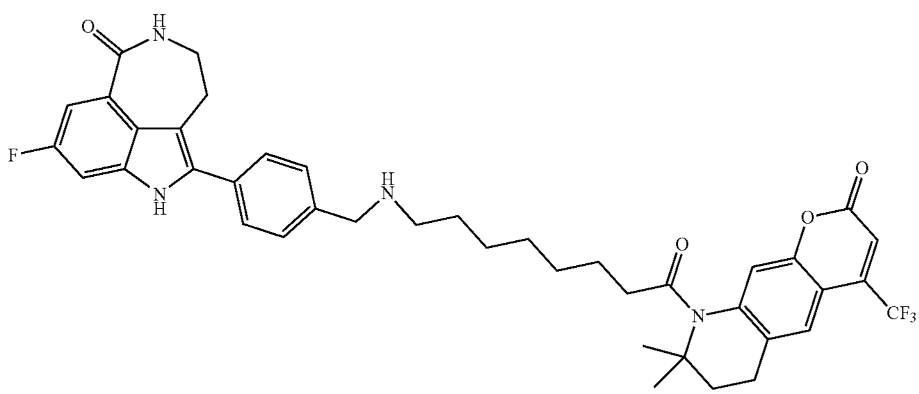 [SMILES: CC1(C)CCc2cc3c(C(F)(F)F)cc(=O)oc3cc2N1C(=O)CCCCCCCNCc1ccc(-c2[nH]c3cc(F)cc4c3c2CCNC4=O)cc1] |
| 3.160 | 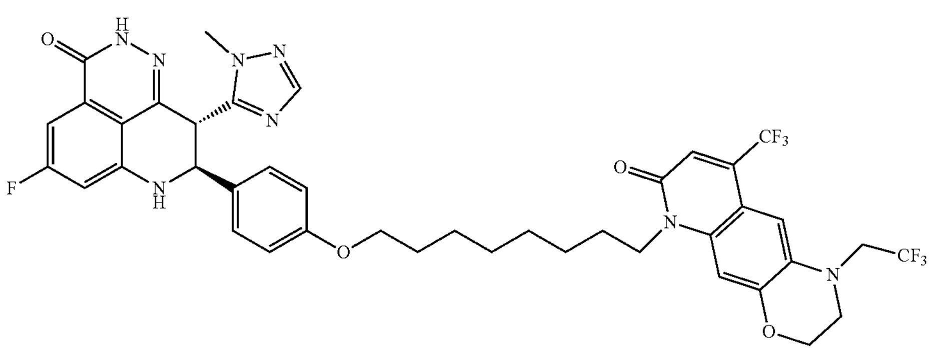 [SMILES: Cn1ncnc1[C@H]1c2n[nH]c(=O)c3cc(F)cc(c23)N[C@@H]1c1ccc(OCCCCCCCCn2c(=O)cc(C(F)(F)F)c3cc4c(cc32)OCCN4CC(F)(F)F)cc1] |

TABLE 1-continued

| No. | Structure |
|---|---|
| 3.161 | 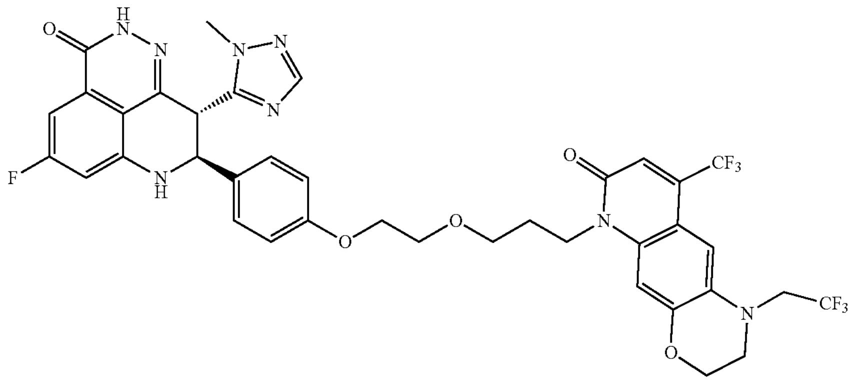 [SMILES: Cn1ncnc1[C@H]1c2n[nH]c(=O)c3cc(F)cc(c23)N[C@@H]1c1ccc(OCCOCCCn2c(=O)cc(C(F)(F)F)c3cc4c(cc32)OCCN4CC(F)(F)F)cc1] |
| 3.162 | 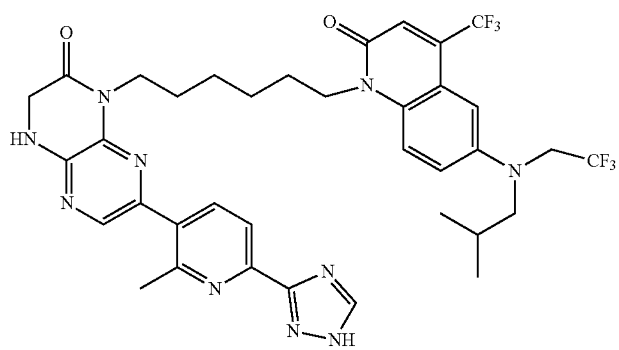 [SMILES: Cc1nc(-c2nc[nH]n2)ccc1-c1cnc2c(n1)N(CCCCCCn1c(=O)cc(C(F)(F)F)c3cc(N(CC(C)C)CC(F)(F)F)ccc31)C(=O)CN2] |
| 3.163 | 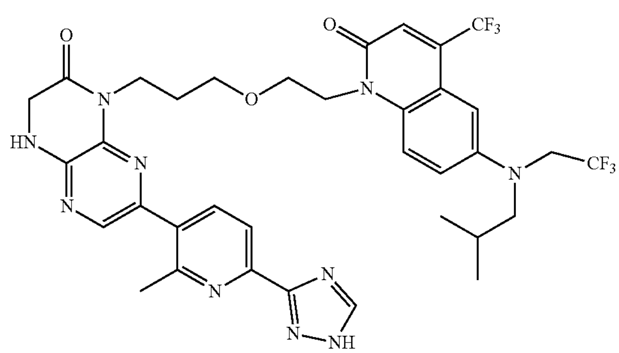 |
| 3.164 | 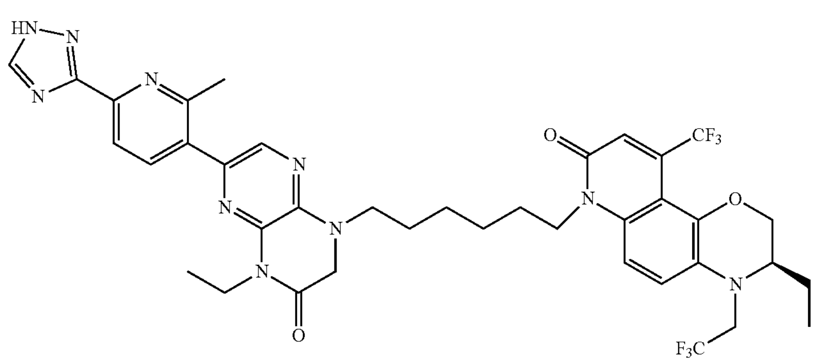 |

TABLE 1-continued

| No. | Structure |
| --- | --- |
| 3.165 | 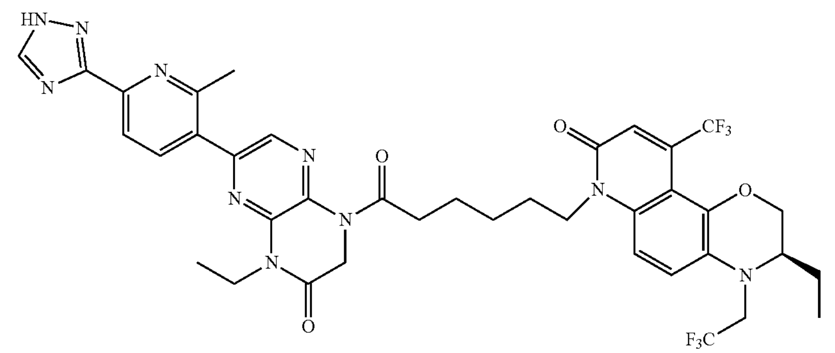 [SMILES: CC[C@@H]1COc2c(ccc3c2c(C(F)(F)F)cc(=O)n3CCCCCC(=O)N2CC(=O)N(CC)c3nc(-c4ccc(-c5nc[nH]n5)nc4C)cnc32)N1CC(F)(F)F] |
| 3.166 | 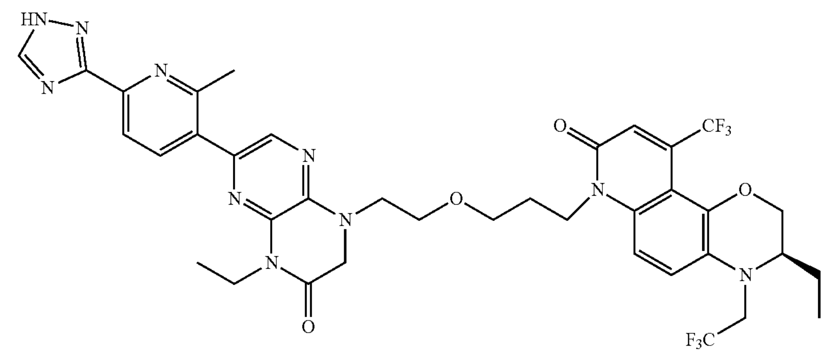 [SMILES: CC[C@@H]1COc2c(ccc3c2c(C(F)(F)F)cc(=O)n3CCCOCCN2CC(=O)N(CC)c3nc(-c4ccc(-c5nc[nH]n5)nc4C)cnc32)N1CC(F)(F)F] |
| 3.167 | 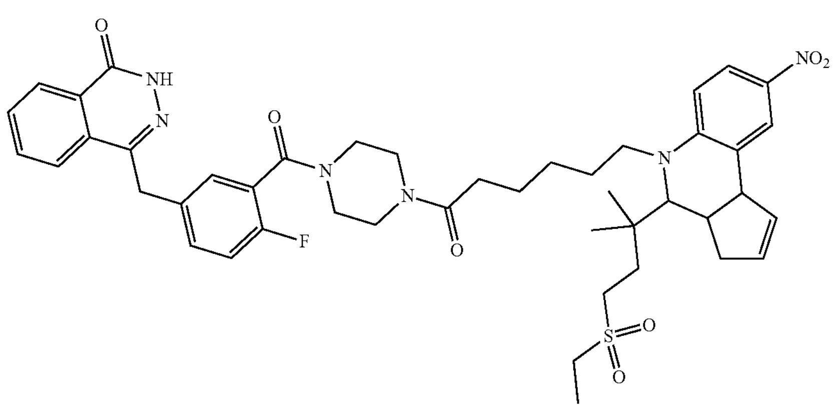 [SMILES: CCS(=O)(=O)CCC(C)(C)C1C2CC=CC2c2cc([N+](=O)[O-])ccc2N1CCCCCC(=O)N1CCN(C(=O)c2cc(Cc3n[nH]c(=O)c4ccccc34)ccc2F)CC1] |
| 3.168 | 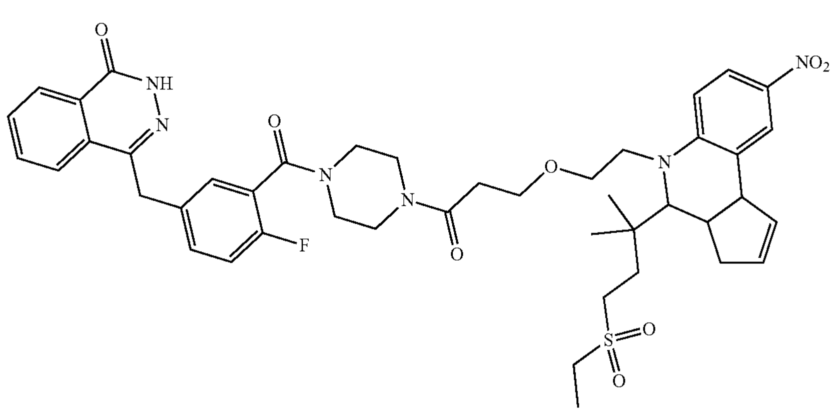 [SMILES: CCS(=O)(=O)CCC(C)(C)C1C2CC=CC2c2cc([N+](=O)[O-])ccc2N1CCOCCC(=O)N1CCN(C(=O)c2cc(Cc3n[nH]c(=O)c4ccccc34)ccc2F)CC1] |

TABLE 1-continued
| No. | Structure |
|---|---|
| 3.169 | 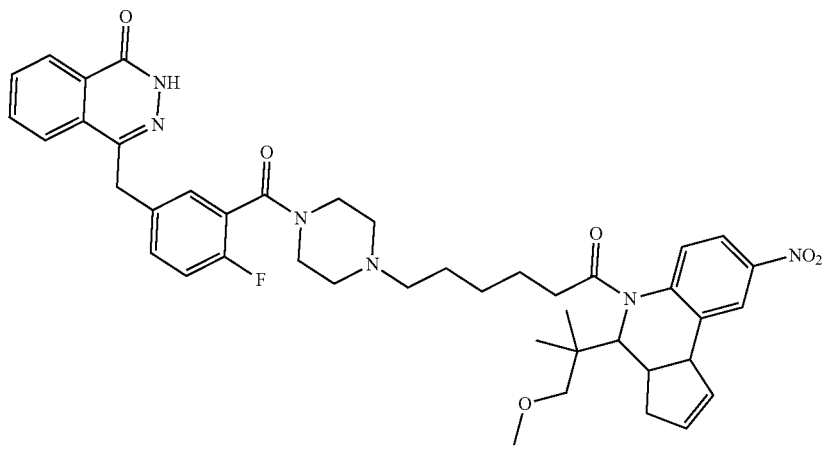 [SMILES: COCC(C)(C)C1C2CC=CC2c2cc([N+](=O)[O-])ccc2N1C(=O)CCCCCN1CCN(C(=O)c2cc(Cc3n[nH]c(=O)c4ccccc34)ccc2F)CC1] |
| 3.170 | 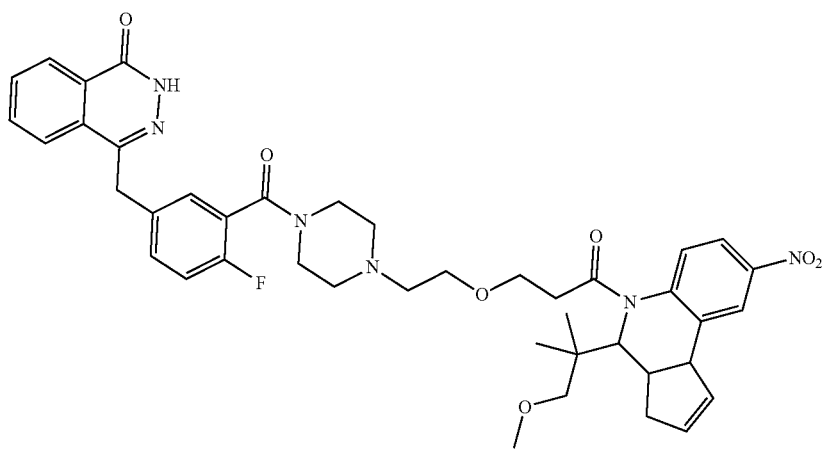 |
| 3.171 | 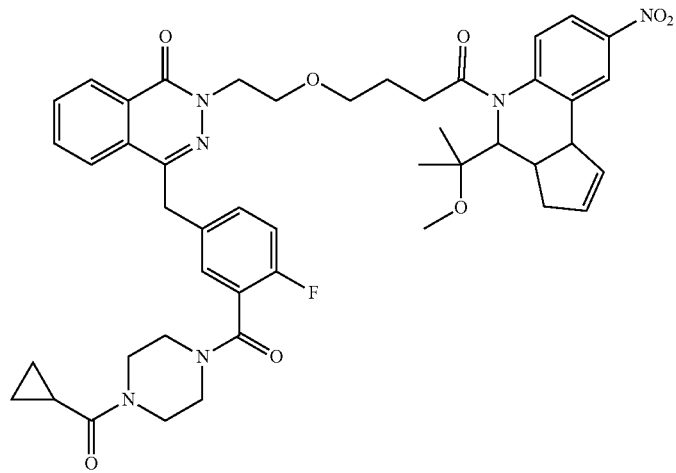 [SMILES: COC(C)(C)C1C2CC=CC2c2cc([N+](=O)[O-])ccc2N1C(=O)CCCOCCn1nc(Cc2ccc(F)c(C(=O)N3CCN(C(=O)C4CC4)CC3)c2)c2ccccc2c1=O] |

TABLE 1-continued

| No. | Structure |
|---|---|
| 3.172 | 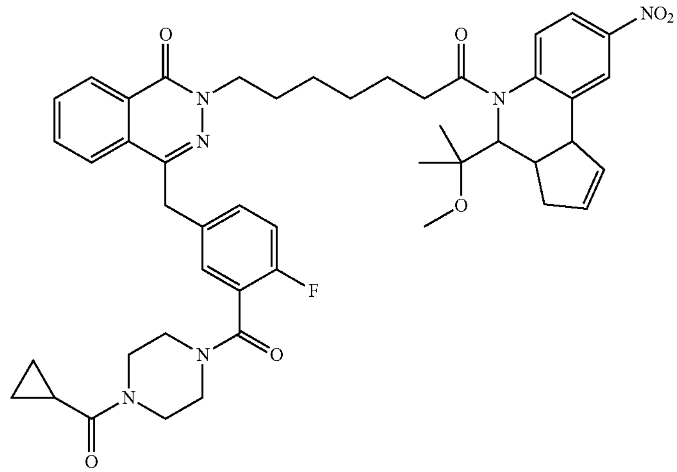 [SMILES: COC(C)(C)C1C2CC=CC2c2cc([N+](=O)[O-])ccc2N1C(=O)CCCCCCn1nc(Cc2ccc(F)c(C(=O)N3CCN(C(=O)C4CC4)CC3)c2)c2ccccc2c1=O] |
| 3.173 | 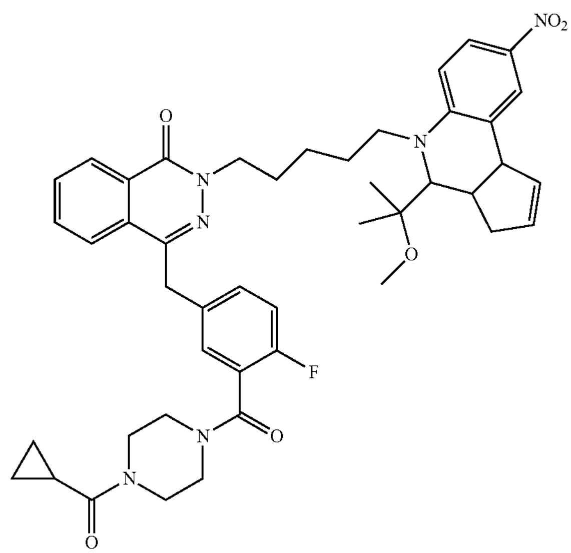 [SMILES: COC(C)(C)C1C2CC=CC2c2cc([N+](=O)[O-])ccc2N1CCCCCn1nc(Cc2ccc(F)c(C(=O)N3CCN(C(=O)C4CC4)CC3)c2)c2ccccc2c1=O] |
| 3.174 | 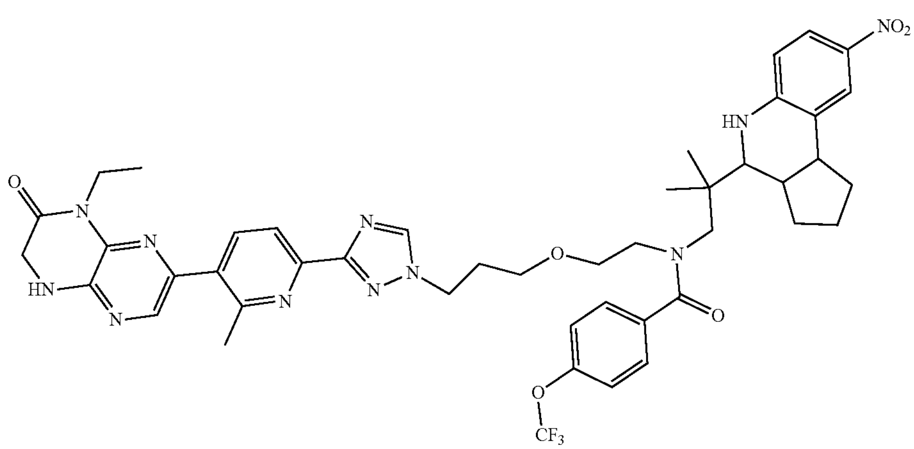 [SMILES: CCN1C(=O)CNc2ncc(-c3ccc(-c4ncn(CCCOCCN(CC(C)(C)C5Nc6ccc([N+](=O)[O-])cc6C6CCCC65)C(=O)c5ccc(OC(F)(F)F)cc5)n4)nc3C)nc21] |

TABLE 1-continued
| No. | Structure |
|---|---|
| 3.175 | 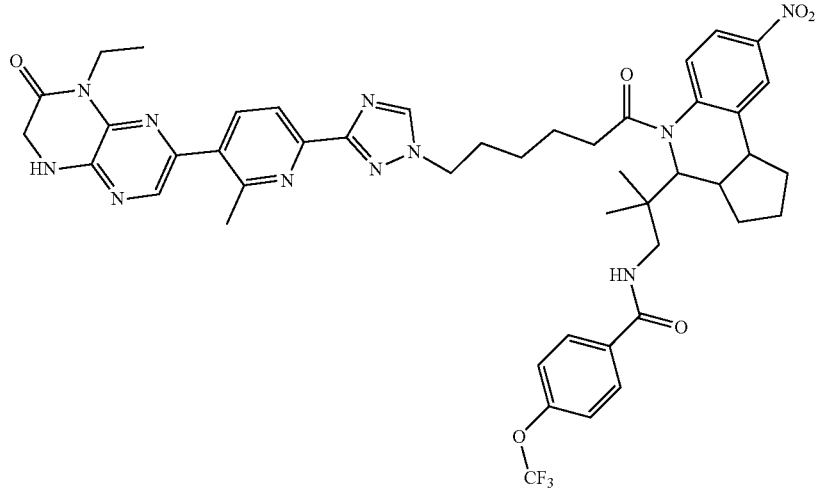 [SMILES: CCN1C(=O)CNc2ncc(-c3ccc(-c4ncn(CCCCCC(=O)N5c6ccc([N+](=O)[O-])cc6C6CCCC6C5C(C)(C)CNC(=O)c5ccc(OC(F)(F)F)cc5)n4)nc3C)nc21] |
| 3.176 | 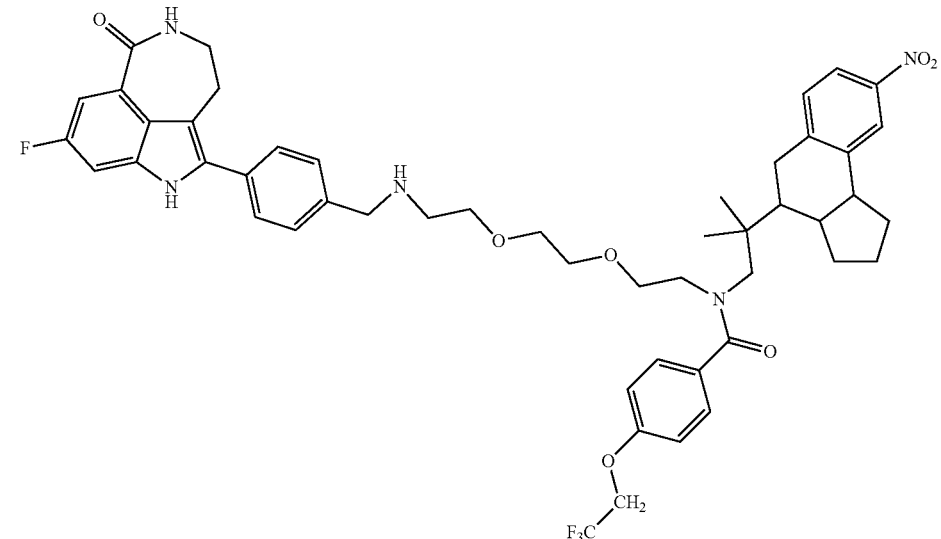 [SMILES: CC(C)(CN(CCOCCOCCNCc1ccc(-c2[nH]c3cc(F)cc4c3c2CCNC4=O)cc1)C(=O)c1ccc(OCC(F)(F)F)cc1)C1Cc2ccc([N+](=O)[O-])cc2C2CCCC21] |
| 3.177 | 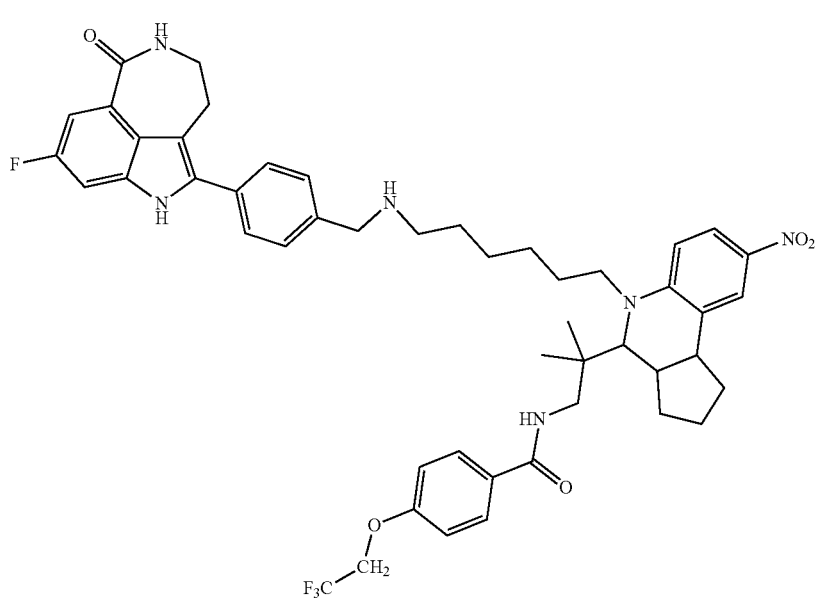 [SMILES: CC(C)(CNC(=O)c1ccc(OCC(F)(F)F)cc1)C1C2CCCC2c2cc([N+](=O)[O-])ccc2N1CCCCCCNCc1ccc(-c2[nH]c3cc(F)cc4c3c2CCNC4=O)cc1] |

TABLE 1-continued

| No. | Structure |
|---|---|
| 3.178 | 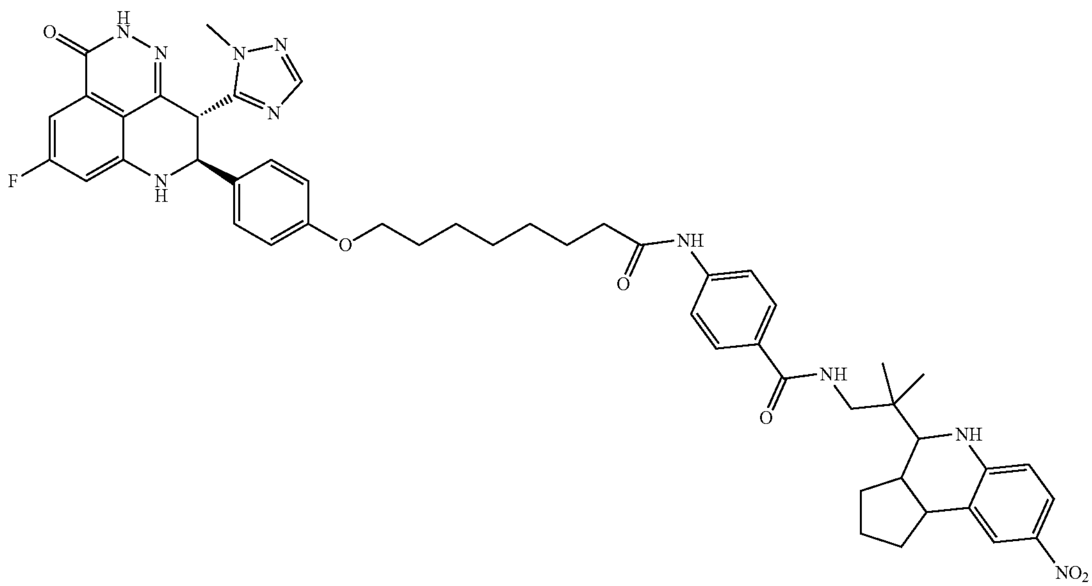 [SMILES: Cn1ncnc1[C@H]1c2n[nH]c(=O)c3cc(F)cc(c23)N[C@@H]1c1ccc(OCCCCCCCC(=O)Nc2ccc(C(=O)NCC(C)(C)C3Nc4ccc([N+](=O)[O-])cc4C4CCCC43)cc2)cc1] |
| 3.179 | 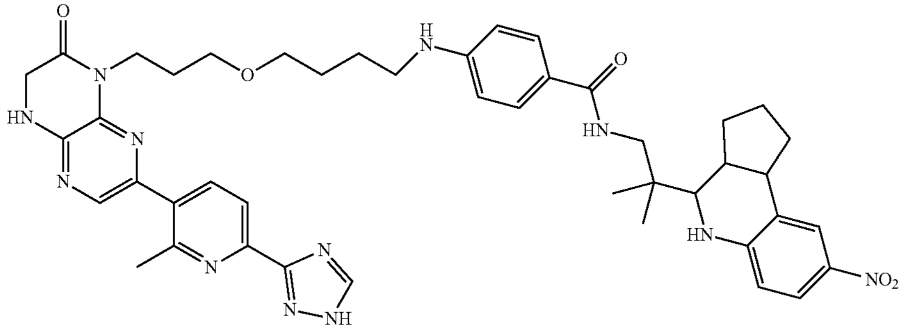 [SMILES: Cc1nc(-c2nc[nH]n2)ccc1-c1cnc2c(n1)N(CCCOCCCCNc1ccc(C(=O)NCC(C)(C)C3Nc4ccc([N+](=O)[O-])cc4C4CCCC43)cc1)C(=O)CN2] |
| 3.180 | 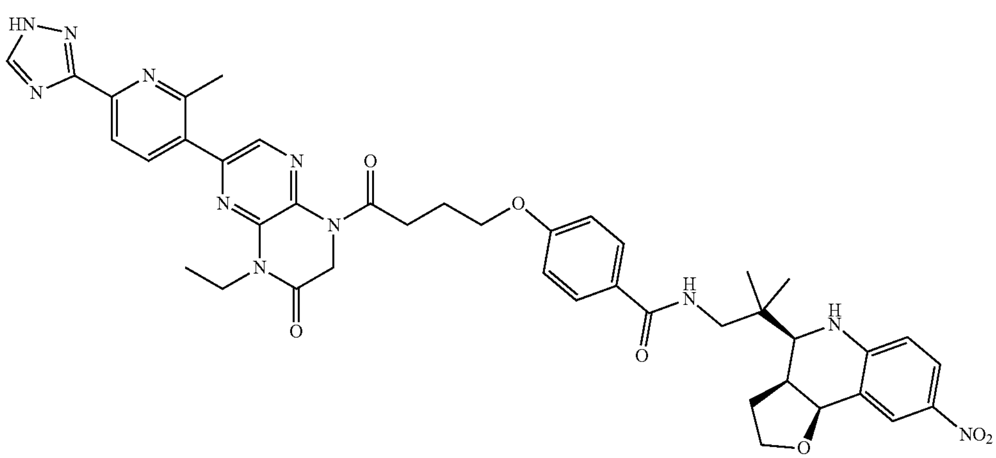 [SMILES: CCN1C(=O)CN(C(=O)CCCOc2ccc(C(=O)NCC(C)(C)[C@H]3Nc4ccc([N+](=O)[O-])cc4[C@H]4OCC[C@H]43)cc2)c2ncc(-c3ccc(-c4nc[nH]n4)nc3C)nc21] |

TABLE 1-continued

| No. | Structure |
|---|---|
| 3.181 | 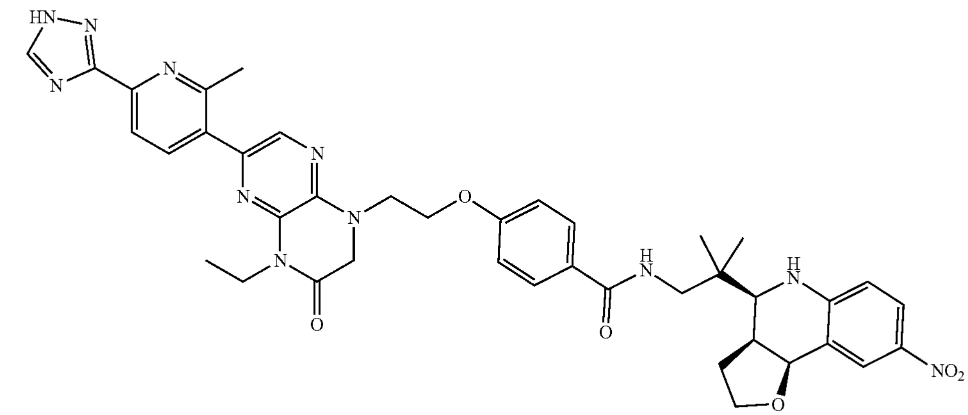 [SMILES: CCN1C(=O)CN(CCOc2ccc(C(=O)NCC(C)(C)[C@H]3Nc4ccc([N+](=O)[O-])cc4[C@H]4OCC[C@H]43)cc2)c2ncc(-c3ccc(-c4nc[nH]n4)nc3C)nc21] |
| 3.182 | 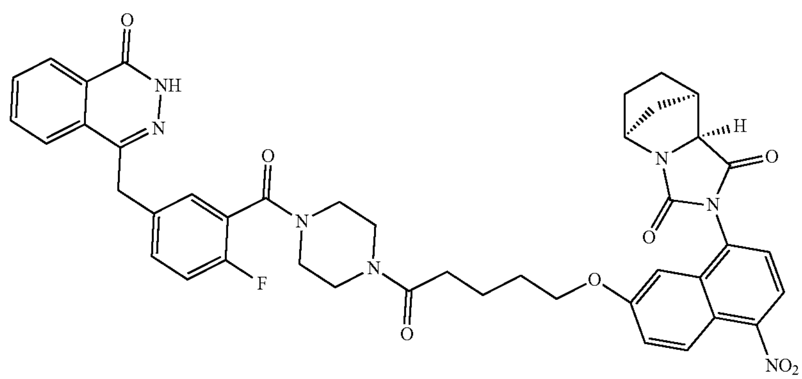 [SMILES: O=C(CCCCOc1ccc2c([N+](=O)[O-])ccc(N3C(=O)[C@@H]4[C@@H]5CC[C@@H](C5)N4C3=O)c2c1)N1CCN(C(=O)c2cc(Cc3n[nH]c(=O)c4ccccc34)ccc2F)CC1] |
| 3.183 | 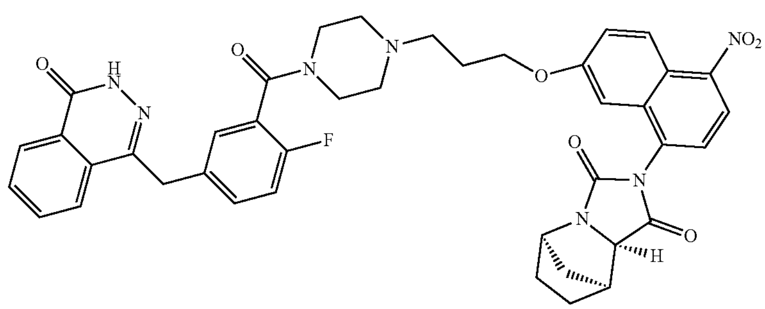 [SMILES: O=C(c1cc(Cc2n[nH]c(=O)c3ccccc23)ccc1F)N1CCN(CCCOc2ccc3c([N+](=O)[O-])ccc(N4C(=O)[C@H]5[C@H]6CC[C@H](C6)N5C4=O)c3c2)CC1] |
| 3.184 | 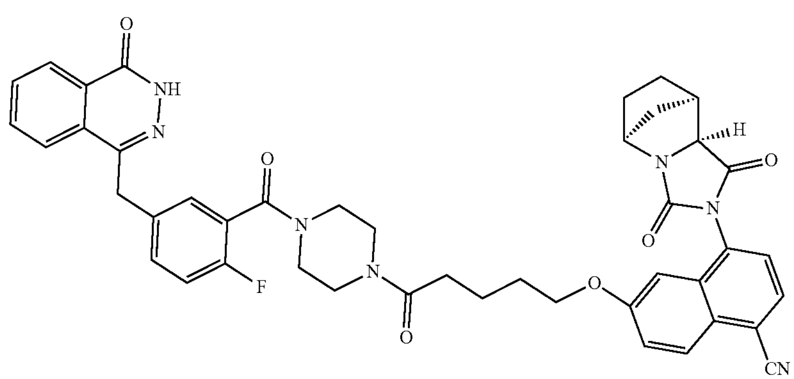 [SMILES: N#Cc1ccc(N2C(=O)[C@@H]3[C@@H]4CC[C@@H](C4)N3C2=O)c2cc(OCCCCC(=O)N3CCN(C(=O)c4cc(Cc5n[nH]c(=O)c6ccccc56)ccc4F)CC3)ccc12] |

TABLE 1-continued
| No. | Structure |
|---|---|
| 3.185 | 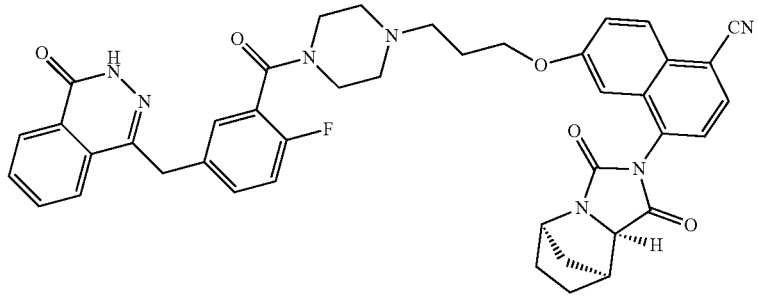 [SMILES: N#Cc1ccc(N2C(=O)[C@H]3[C@H]4CC[C@H](C4)N3C2=O)c2cc(OCCCN3CCN(C(=O)c4cc(Cc5n[nH]c(=O)c6ccccc56)ccc4F)CC3)ccc12] |
| 3.186 | 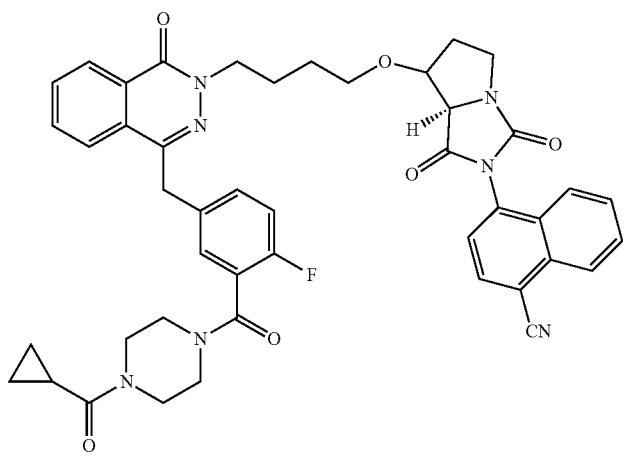 [SMILES: N#Cc1ccc(N2C(=O)[C@H]3C(OCCCCn4nc(Cc5ccc(F)c(C(=O)N6CCN(C(=O)C7CC7)CC6)c5)c5ccccc5c4=O)CCN3C2=O)c2ccccc12] |
| 3.187 | 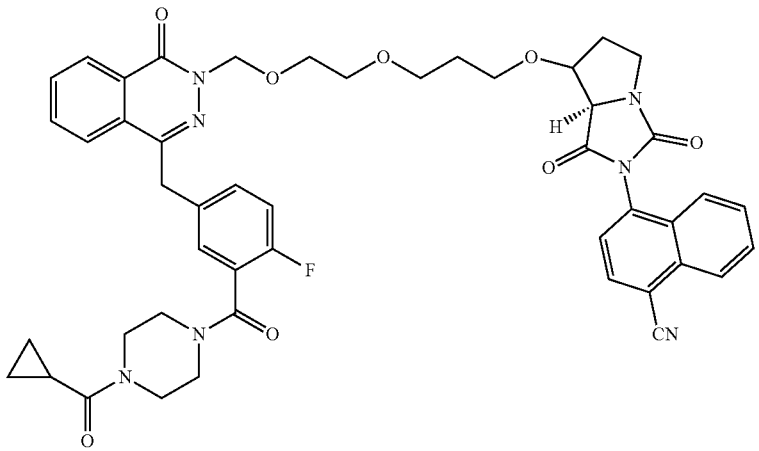 [SMILES: N#Cc1ccc(N2C(=O)[C@H]3C(OCCCOCCOCn4nc(Cc5ccc(F)c(C(=O)N6CCN(C(=O)C7CC7)CC6)c5)c5ccccc5c4=O)CCN3C2=O)c2ccccc12] |
| 3.188 | 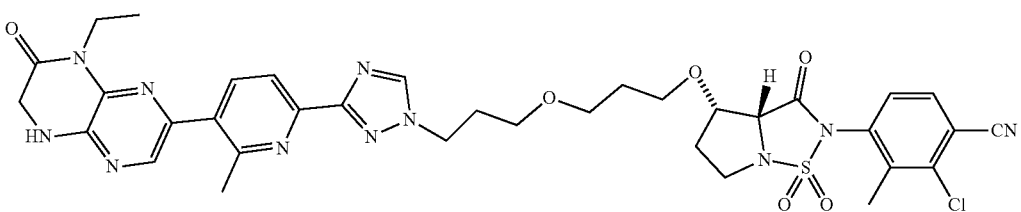 |

TABLE 1-continued

| No. | Structure |
|---|---|
| 3.189 | 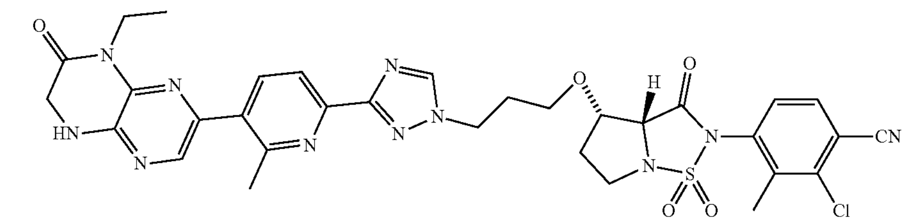 |
| 3.190 | 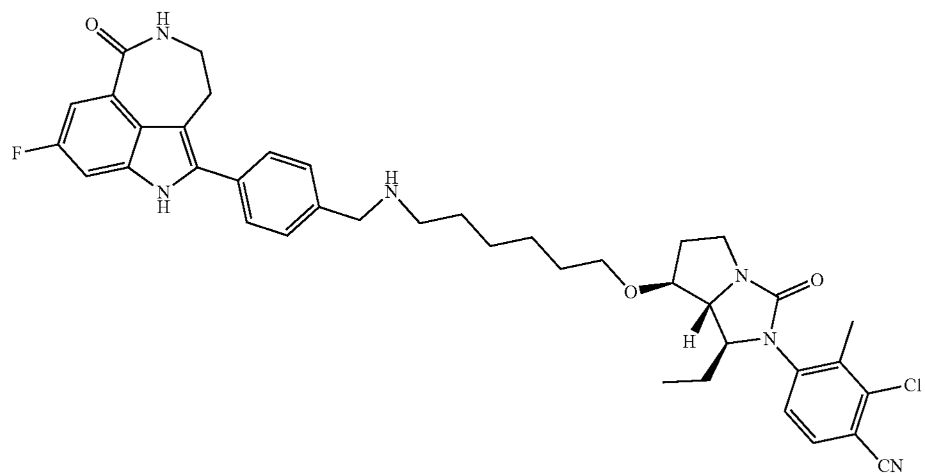 [SMILES: CC[C@H]1[C@@H]2[C@@H](OCCCCCCNCc3ccc(-c4[nH]c5cc(F)cc6c5c4CCNC6=O)cc3)CCN2C(=O)N1c1ccc(C#N)c(Cl)c1C] |
| 3.191 | 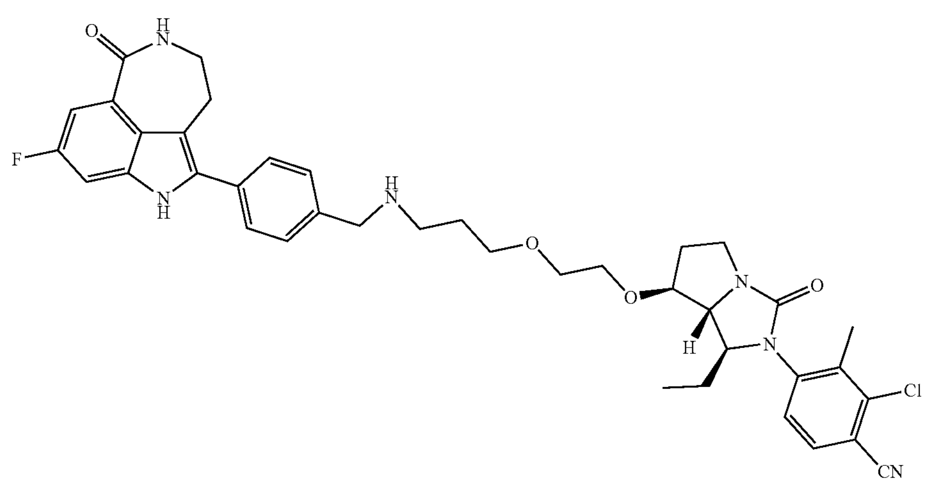 |

TABLE 1-continued

| No. | Structure |
| --- | --- |
| 3.192 | 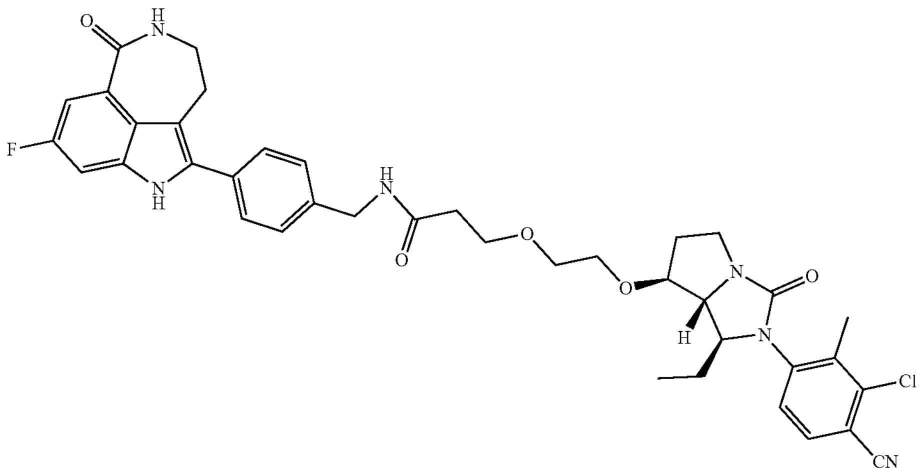 [SMILES: CC[C@H]1[C@@H]2[C@@H](OCCOCCC(=O)NCc3ccc(-c4[nH]c5cc(F)cc6c5c4CCNC6=O)cc3)CCN2C(=O)N1c1ccc(C#N)c(Cl)c1C] |
| 3.193 | 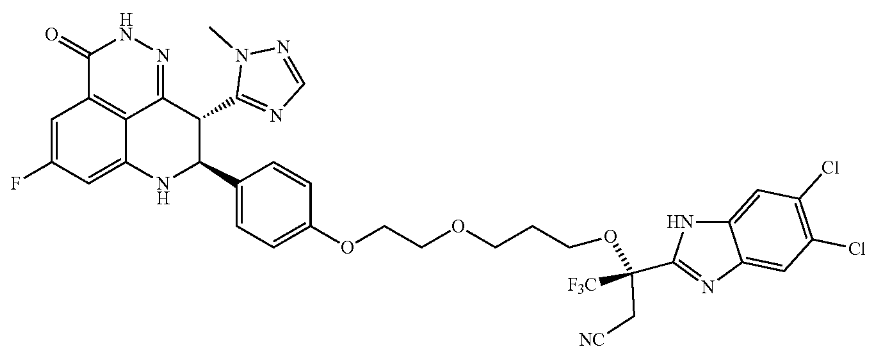 |
| 3.194 | 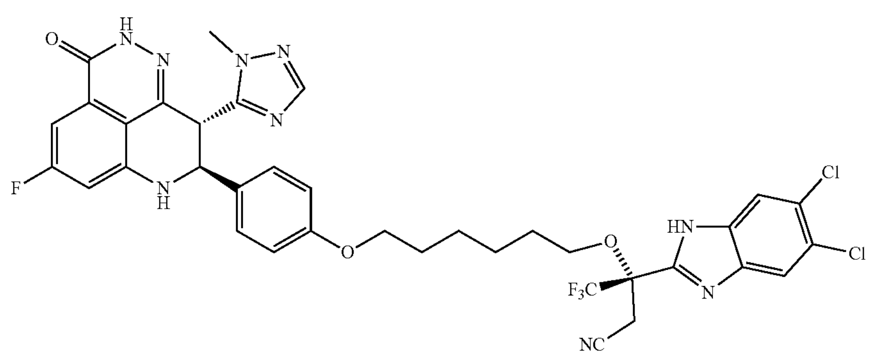 |
| 3.195 | 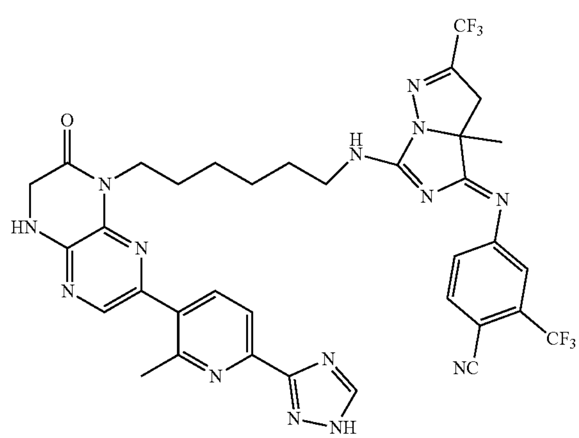 [SMILES: Cc1nc(-c2nc[nH]n2)ccc1-c1cnc2c(n1)N(CCCCCCNC1=N/C(=N\c3ccc(C#N)c(C(F)(F)F)c3)C3(C)CC(C(F)(F)F)=NN13)C(=O)CN2] |

TABLE 1-continued

| No. | Structure |
|---|---|
| 3.196 | 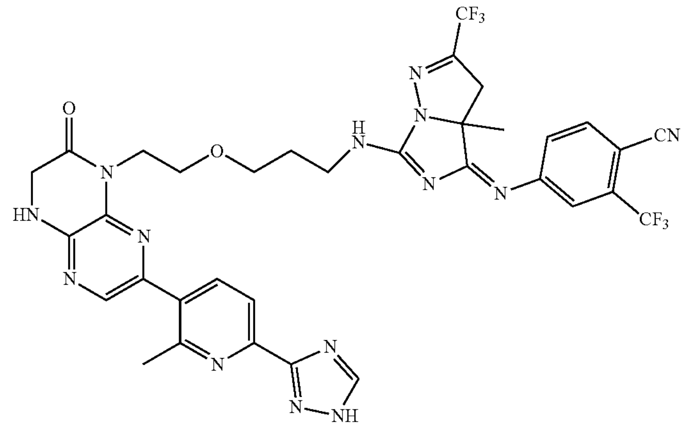 [SMILES: Cc1nc(-c2nc[nH]n2)ccc1-c1cnc2c(n1)N(CCOCCCNC1=N/C(=N/c3ccc(C#N)c(C(F)(F)F)c3)C3(C)CC(C(F)(F)F)=NN13)C(=O)CN2] |
| 3.197 | 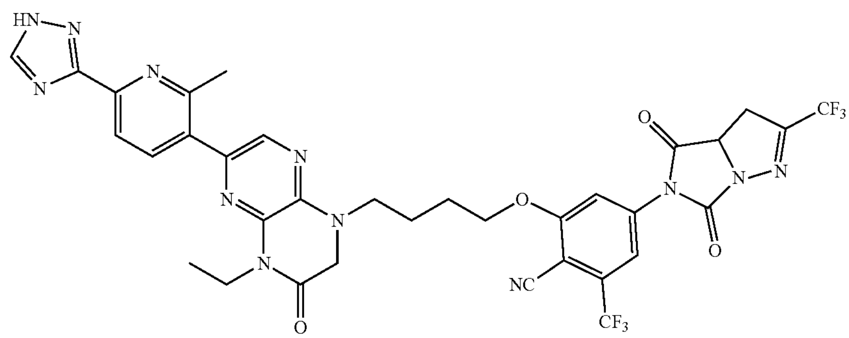 [SMILES: CCN1C(=O)CN(CCCCOc2cc(N3C(=O)C4CC(C(F)(F)F)=NN4C3=O)cc(C(F)(F)F)c2C#N)c2ncc(-c3ccc(-c4nc[nH]n4)nc3C)nc21] |
| 3.198 | 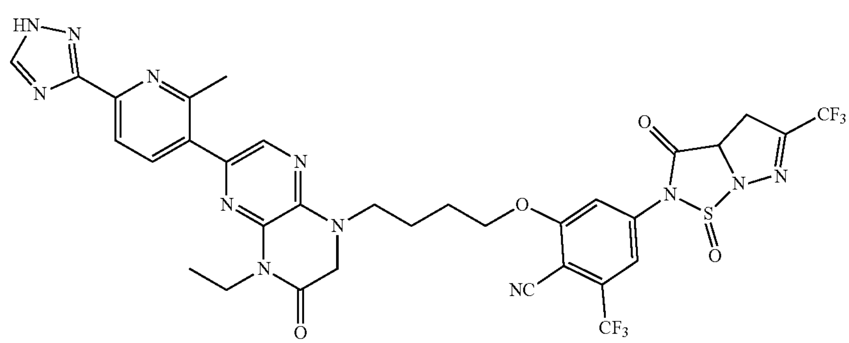 [SMILES: CCN1C(=O)CN(CCCCOc2cc(N3C(=O)C4CC(C(F)(F)F)=NN4S3=O)cc(C(F)(F)F)c2C#N)c2ncc(-c3ccc(-c4nc[nH]n4)nc3C)nc21] |
| 3.199 | 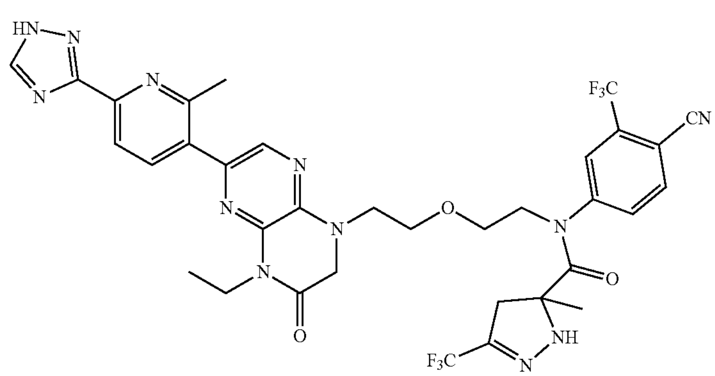 [SMILES: CCN1C(=O)CN(CCOCCN(C(=O)C2(C)CC(C(F)(F)F)=NN2)c2ccc(C#N)c(C(F)(F)F)c2)c2ncc(-c3ccc(-c4nc[nH]n4)nc3C)nc21] |

TABLE 1-continued
| No. | Structure |
|---|---|
| 3.200 | 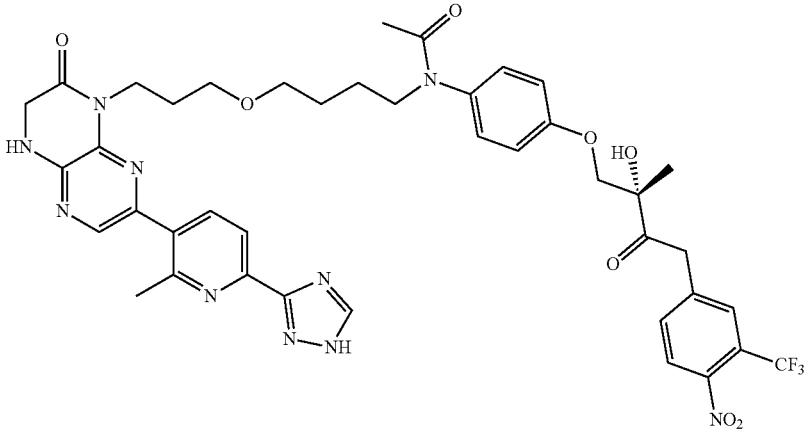 [SMILES: CC(=O)N(CCCCOCCCN1C(=O)CNc2ncc(-c3ccc(-c4nc[nH]n4)nc3C)nc21)c1ccc(OC[C@](C)(O)C(=O)Cc2ccc([N+](=O)[O-])c(C(F)(F)F)c2)cc1] |
| 3.201 | 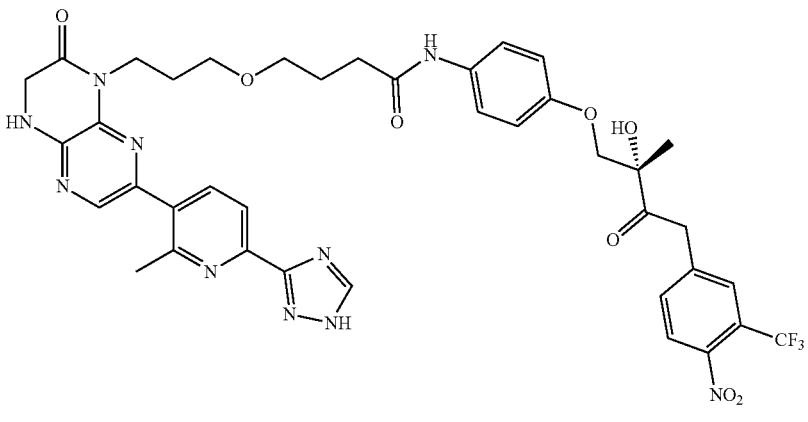 [SMILES: Cc1nc(-c2nc[nH]n2)ccc1-c1cnc2c(n1)N(CCCOCCCC(=O)Nc1ccc(OC[C@](C)(O)C(=O)Cc3ccc([N+](=O)[O-])c(C(F)(F)F)c3)cc1)C(=O)CN2] |
| 3.202 | 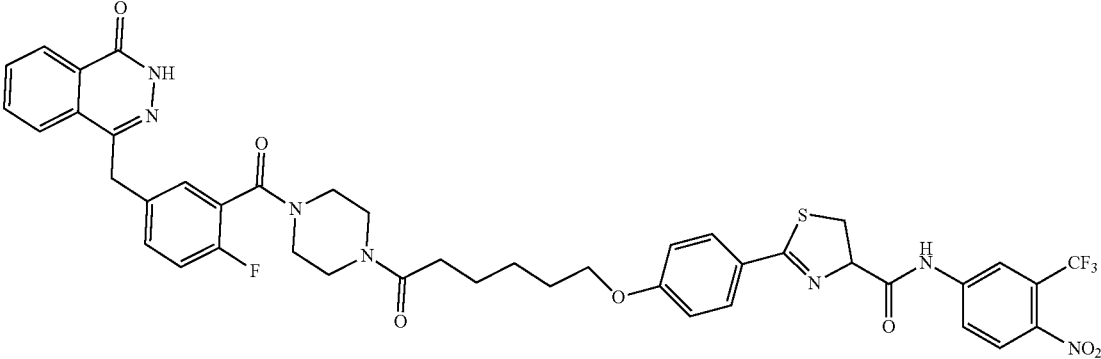 |
| 3.203 | 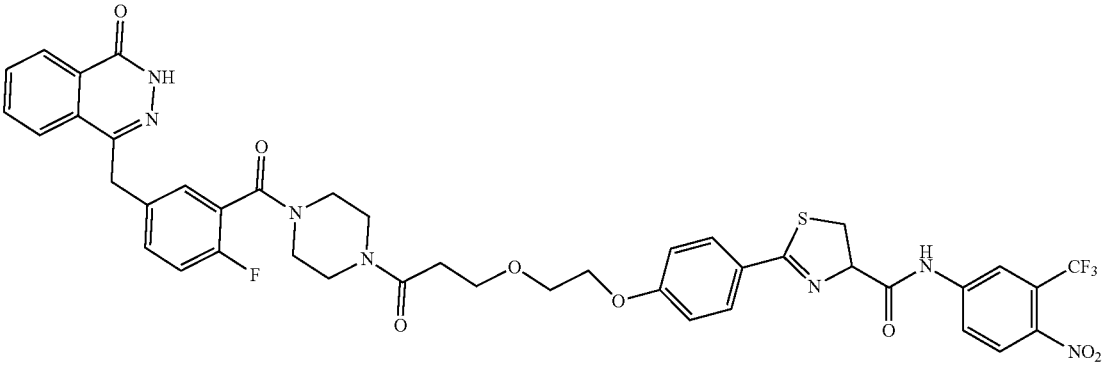 [SMILES: O=C(Nc1ccc([N+](=O)[O-])c(C(F)(F)F)c1)C1CSC(c2ccc(OCCOCCC(=O)N3CCN(C(=O)c4cc(Cc5n[nH]c(=O)c6ccccc56)ccc4F)CC3)cc2)=N1] |

TABLE 1-continued
| No. | Structure |
|---|---|
| 3.204 | 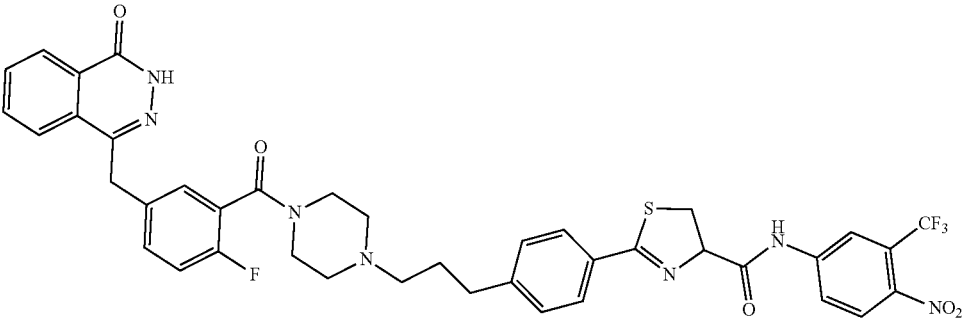 [SMILES: O=C(Nc1ccc([N+](=O)[O-])c(C(F)(F)F)c1)C1CSC(c2ccc(CCCN3CCN(C(=O)c4cc(Cc5n[nH]c(=O)c6ccccc56)ccc4F)CC3)cc2)=N1] |
| 3.205 | 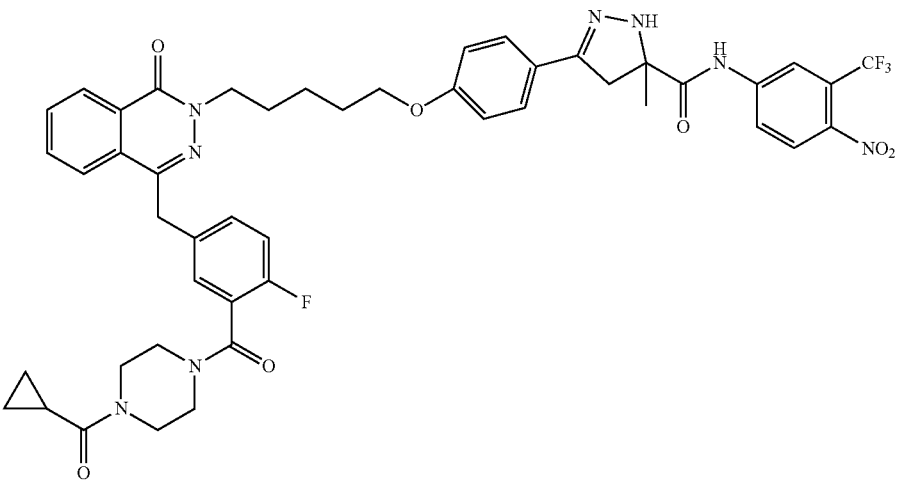 [SMILES: CC1(C(=O)Nc2ccc([N+](=O)[O-])c(C(F)(F)F)c2)CC(c2ccc(OCCOCCn3nc(Cc4ccc(F)c(C(=O)N5CCN(C(=O)C6CC6)CC5)c4)c4ccccc4c3=O)cc2)=NN1] |
| 3.206 | 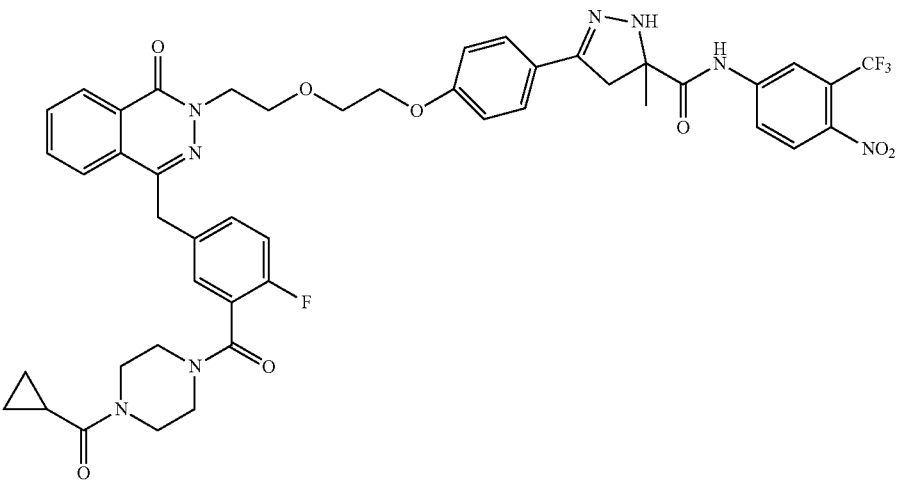 |

TABLE 1-continued

| No. | Structure |
|---|---|
| 3.207 | 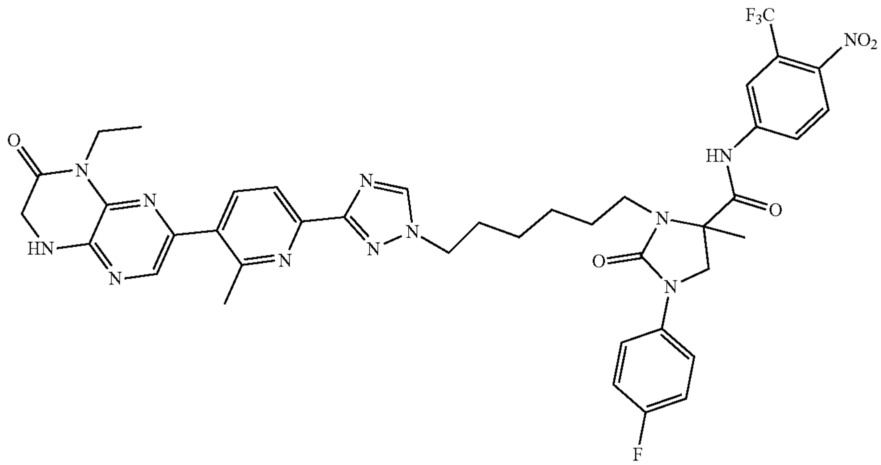 [SMILES: CCN1C(=O)CNc2ncc(-c3ccc(-c4ncn(CCCCCCN5C(=O)N(c6ccc(F)cc6)CC5(C)C(=O)Nc5ccc([N+](=O)[O-])c(C(F)(F)F)c5)n4)nc3C)nc21] |
| 3.208 | 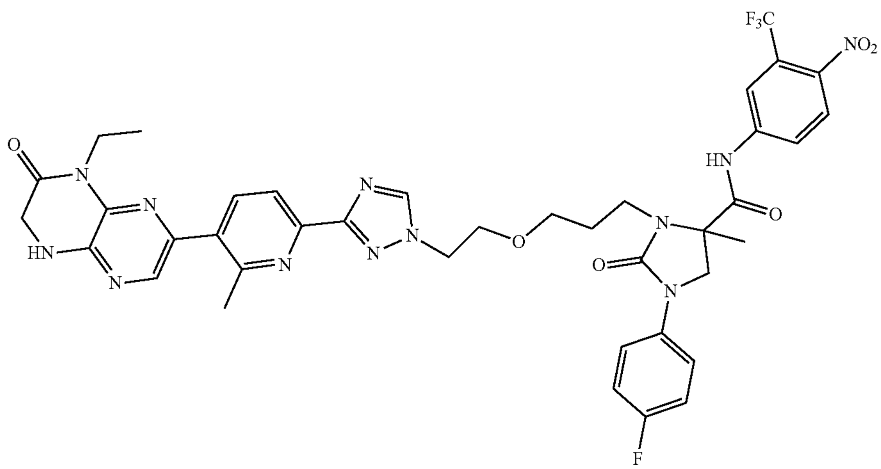 [SMILES: CCN1C(=O)CNc2ncc(-c3ccc(-c4ncn(CCOCCCN5C(=O)N(c6ccc(F)cc6)CC5(C)C(=O)Nc5ccc([N+](=O)[O-])c(C(F)(F)F)c5)n4)nc3C)nc21] |
| 3.209 | 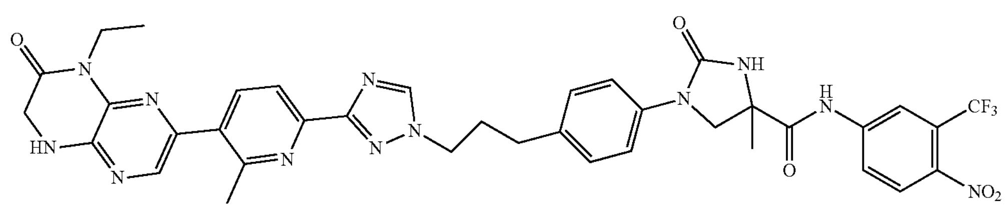 [SMILES: CCN1C(=O)CNc2ncc(-c3ccc(-c4ncn(CCCc5ccc(N6CC(C)(C(=O)Nc7ccc([N+](=O)[O-])c(C(F)(F)F)c7)NC6=O)cc5)n4)nc3C)nc21] |
| 3.210 | 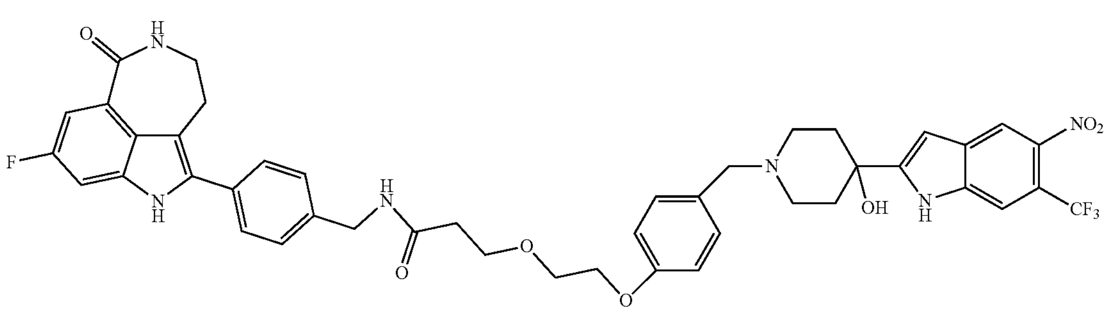 [SMILES: O=C(CCOCCOc1ccc(CN2CCC(O)(c3cc4cc([N+](=O)[O-])c(C(F)(F)F)cc4[nH]3)CC2)cc1)NCc1ccc(-c2[nH]c3cc(F)cc4c3c2CCNC4=O)cc1] |

TABLE 1-continued
| No. | Structure |
|---|---|
| 3.211 | 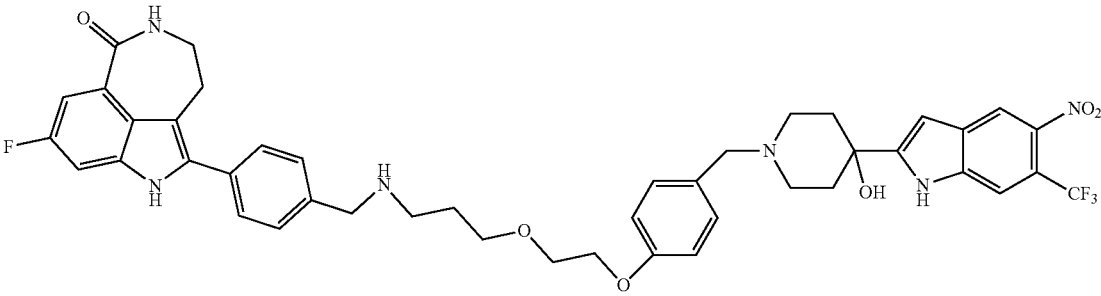 [SMILES: O=C1NCCc2c(-c3ccc(CNCCCOCCOc4ccc(CN5CCC(O)(c6cc7cc([N+](=O)[O-])c(C(F)(F)F)cc7[nH]6)CC5)cc4)cc3)[nH]c3cc(F)cc1c23] |
| 3.212 | 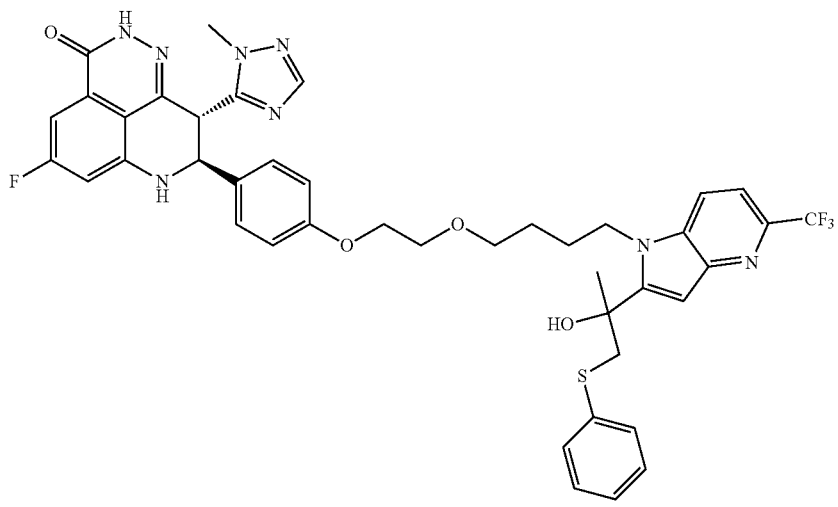 [SMILES: Cn1ncnc1[C@H]1c2n[nH]c(=O)c3cc(F)cc(c23)N[C@@H]1c1ccc(OCCOCCCCn2c(C(C)(O)CSc3ccccc3)cc3nc(C(F)(F)F)ccc32)cc1] |
| 3.213 | 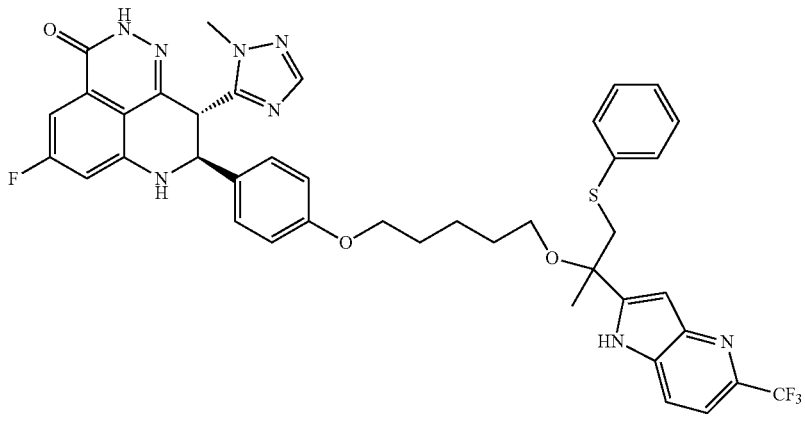 [SMILES: Cn1ncnc1[C@H]1c2n[nH]c(=O)c3cc(F)cc(c23)N[C@@H]1c1ccc(OCCCCCOC(C)(CSc2ccccc2)c2cc3nc(C(F)(F)F)ccc3[nH]2)cc1] |

TABLE 1-continued

| No. | Structure |
|---|---|
| 3.214 | 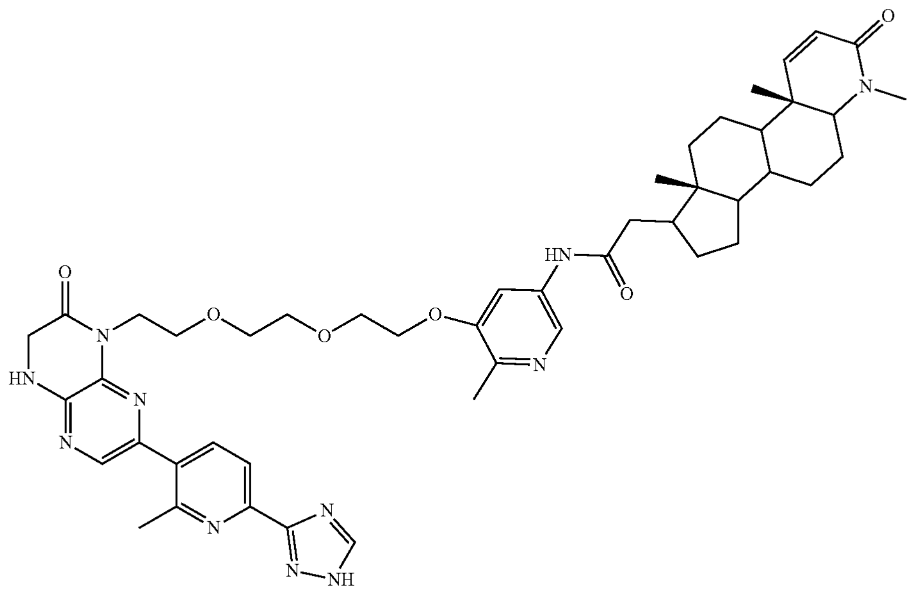 [SMILES: Cc1ncc(NC(=O)CC2CCC3C4CCC5N(C)C(=O)C=C[C@@]5(C)C4CC[C@@]23C)cc1OCCOCCOCCN1C(=O)CNc2ncc(-c3ccc(-c4nc[nH]n4)nc3C)nc21] |
| 3.215 | 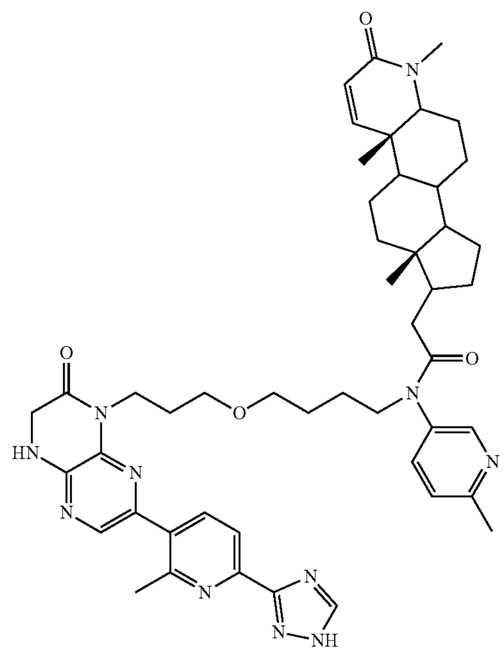 [SMILES: Cc1ccc(N(CCCCOCCCN2C(=O)CNc3ncc(-c4ccc(-c5nc[nH]n5)nc4C)nc32)C(=O)CC2CCC3C4CCC5N(C)C(=O)C=C[C@@]5(C)C4CC[C@@]23C)cn1] |
| 3.216 | 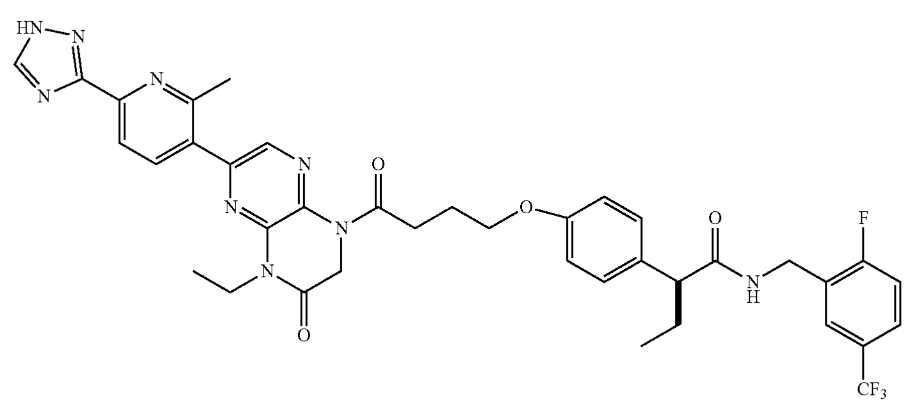 [SMILES: CC[C@H](C(=O)NCc1cc(C(F)(F)F)ccc1F)c1ccc(OCCCC(=O)N2CC(=O)N(CC)c3nc(-c4ccc(-c5nc[nH]n5)nc4C)cnc32)cc1] |

TABLE 1-continued
| No. | Structure |
|---|---|
| 3.217 | 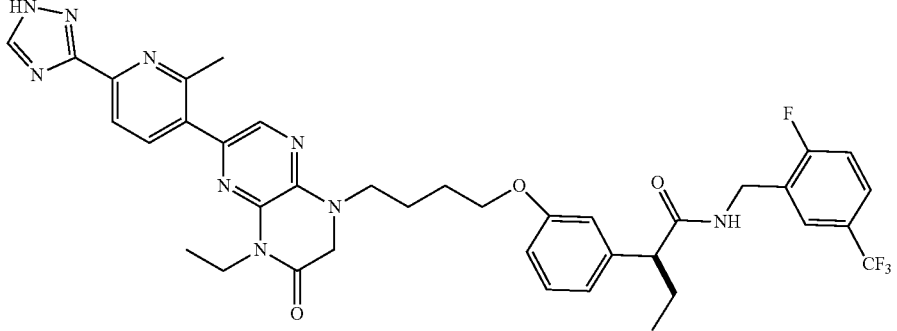 [SMILES: CC[C@H](C(=O)NCc1cc(C(F)(F)F)ccc1F)c1cccc(OCCCCN2CC(=O)N(CC)c3nc(-c4ccc(-c5nc[nH]n5)nc4C)cnc32)c1] |
| 3.218 | 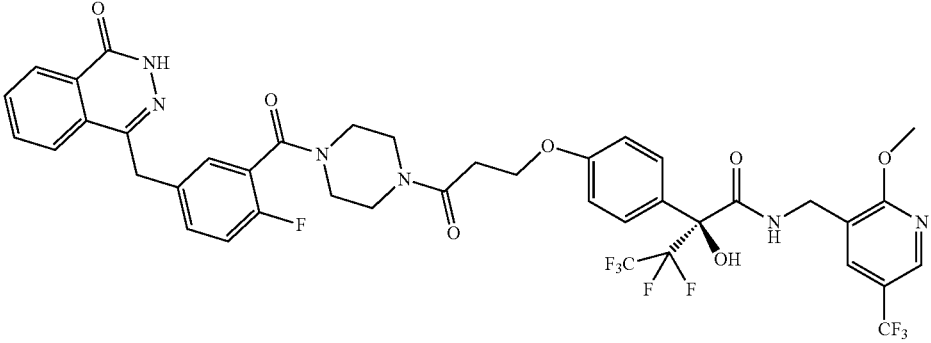 [SMILES: COc1ncc(C(F)(F)F)cc1CNC(=O)[C@@](O)(c1ccc(OCCC(=O)N2CCN(C(=O)c3cc(Cc4n[nH]c(=O)c5ccccc45)ccc3F)CC2)cc1)C(F)(F)C(F)(F)F] |
| 3.219 | 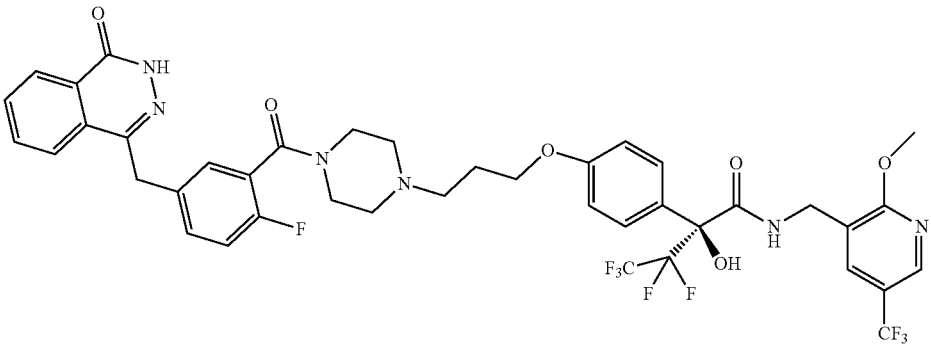 [SMILES: COc1ncc(C(F)(F)F)cc1CNC(=O)[C@@](O)(c1ccc(OCCCN2CCN(C(=O)c3cc(Cc4n[nH]c(=O)c5ccccc45)ccc3F)CC2)cc1)C(F)(F)C(F)(F)F] |
| 3.220 | 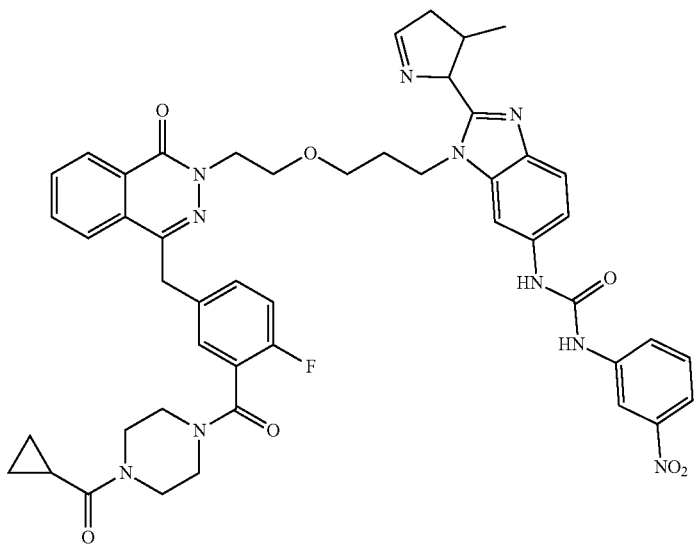 [SMILES: CC1CC=NC1c1nc2ccc(NC(=O)Nc3cccc([N+](=O)[O-])c3)cc2n1CCCOCCn1nc(Cc2ccc(F)c(C(=O)N3CCN(C(=O)C4CC4)CC3)c2)c2ccccc2c1=O] |

TABLE 1-continued
| No. | Structure |
|---|---|
| 3.221 | 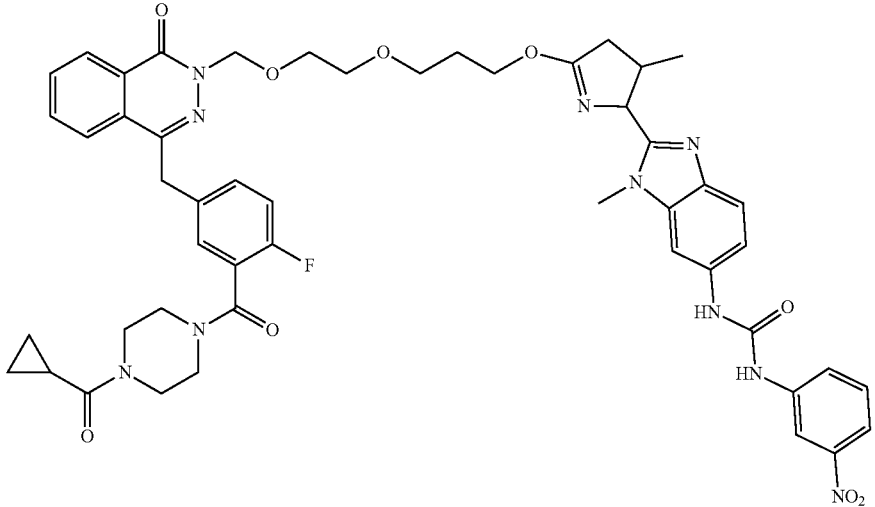 [SMILES: CC1CC(OCCCOCCOCn2nc(Cc3ccc(F)c(C(=O)N4CCN(C(=O)C5CC5)CC4)c3)c3ccccc3c2=O)=NC1c1nc2ccc(NC(=O)Nc3cccc([N+](=O)[O-])c3)cc2n1C] |
| 3.222 | 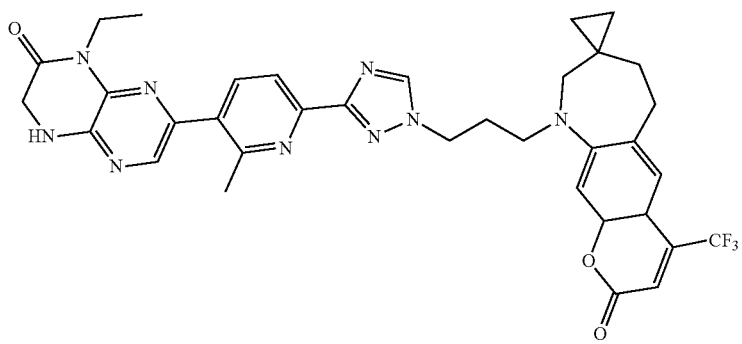 [SMILES: CCN1C(=O)CNc2ncc(-c3ccc(-c4ncn(CCCN5CC6(CCC7=CC8C(C(F)(F)F)=CC(=O)OC8C=C75)CC6)n4)nc3C)nc21] |
| 3.223 | 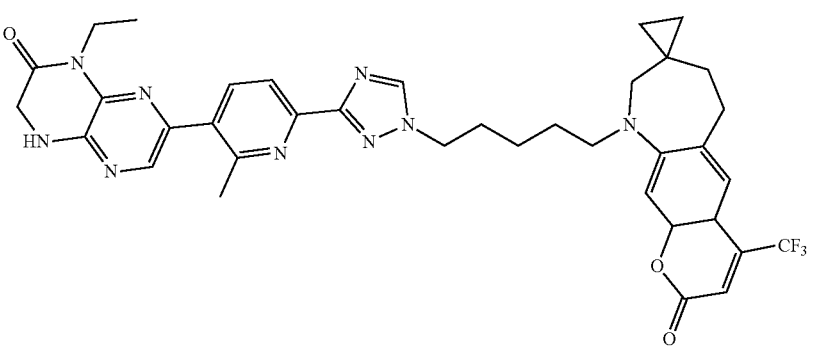 [SMILES: CCN1C(=O)CNc2ncc(-c3ccc(-c4ncn(CCCCCN5CC6(CCC7=CC8C(C(F)(F)F)=CC(=O)OC8C=C75)CC6)n4)nc3C)nc21] |
| 3.224 | 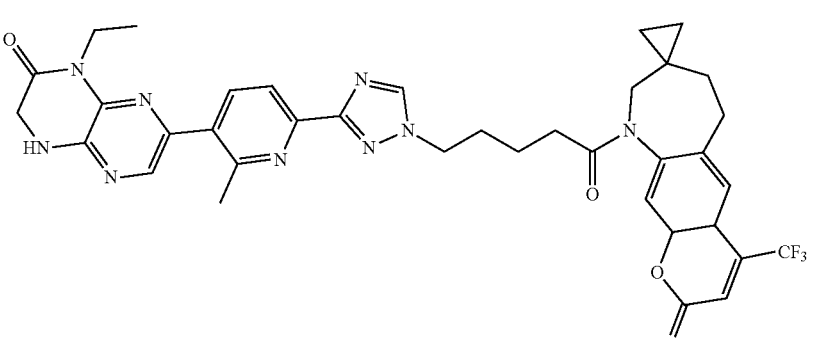 |

TABLE 1-continued

| No. | Structure |
|---|---|
| 3.225 | 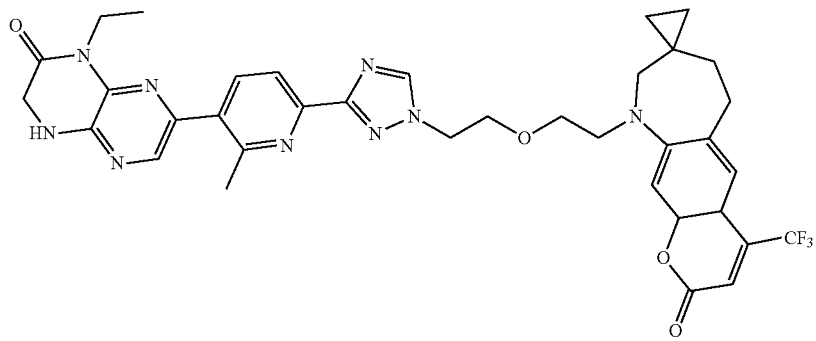 [SMILES: CCN1C(=O)CNc2ncc(-c3ccc(-c4ncn(CCOCCN5CC6(CCC7=CC8C(C(F)(F)F)=CC(=O)OC8C=C75)CC6)n4)nc3C)nc21] |
| 3.226 | 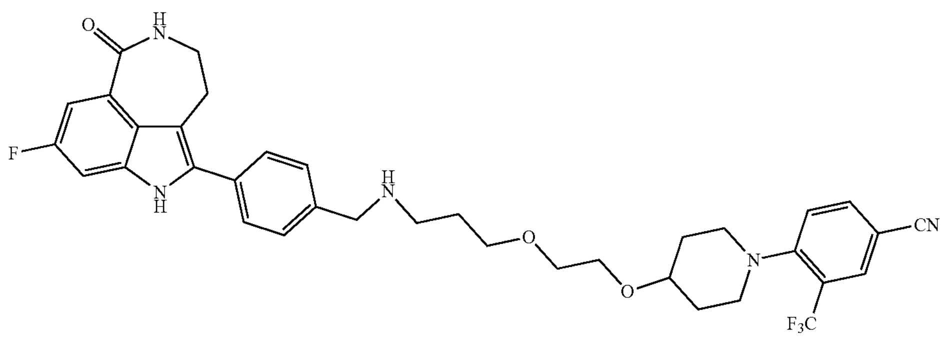 [SMILES: N#Cc1ccc(N2CCC(OCCOCCCNCc3ccc(-c4[nH]c5cc(F)cc6c5c4CCNC6=O)cc3)CC2)c(C(F)(F)F)c1] |
| 3.227 | 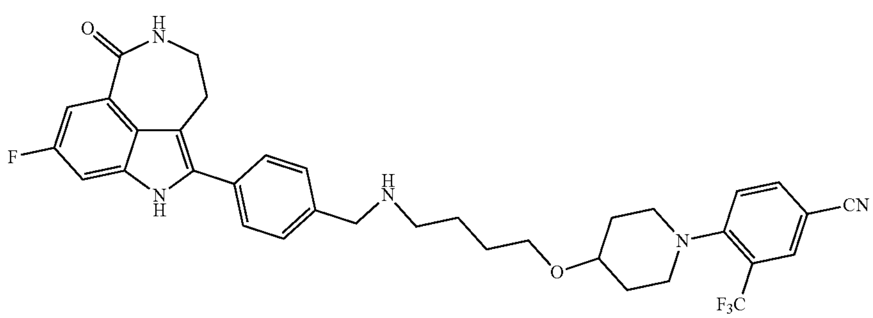 [SMILES: N#Cc1ccc(N2CCC(OCCCCNCc3ccc(-c4[nH]c5cc(F)cc6c5c4CCNC6=O)cc3)CC2)c(C(F)(F)F)c1] |
| 3.228 | 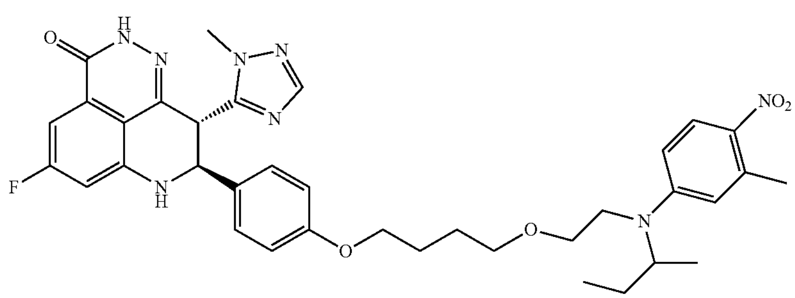 [SMILES: CCC(C)N(CCOCCCCOc1ccc([C@H]2Nc3cc(F)cc4c(=O)[nH]nc(c34)[C@@H]2c2ncnn2C)cc1)c1ccc([N+](=O)[O-])c(C)c1] |

TABLE 1-continued

| No. | Structure |
|---|---|
| 3.229 | 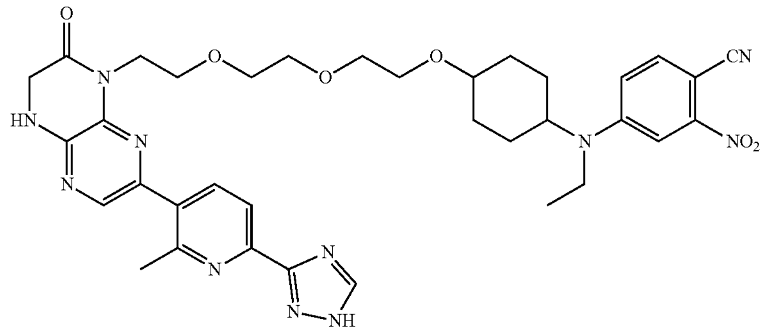 |
| 3.230 | 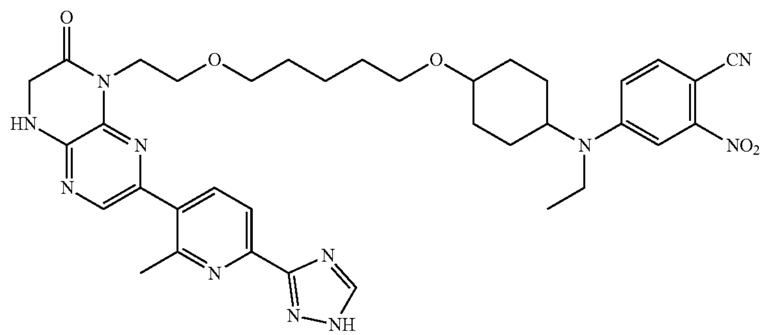 [SMILES: CCN(c1ccc(C#N)c([N+](=O)[O-])c1)C1CCC(OCCCCCOCCN2C(=O)CNc3ncc(-c4ccc(-c5nc[nH]n5)nc4C)nc32)CC1] |
| 3.231 | 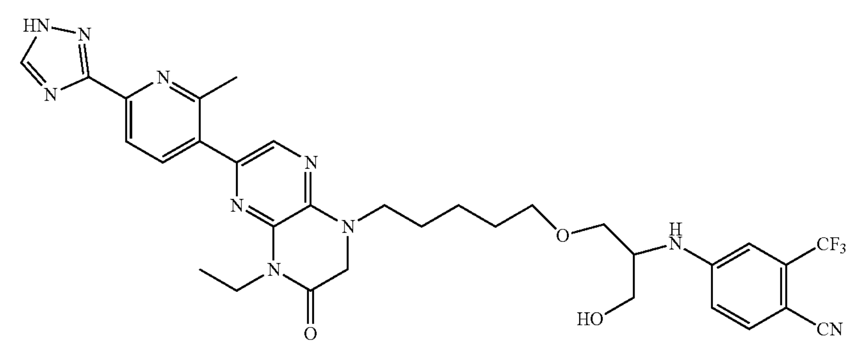 [SMILES: CCN1C(=O)CN(CCCCCOCC(CO)Nc2ccc(C#N)c(C(F)(F)F)c2)c2ncc(-c3ccc(-c4nc[nH]n4)nc3C)nc21] |
| 3.232 | 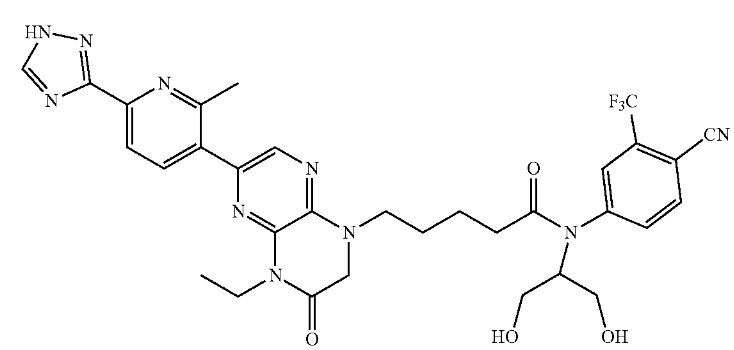 [SMILES: CCN1C(=O)CN(CCCCC(=O)N(c2ccc(C#N)c(C(F)(F)F)c2)C(CO)CO)c2ncc(-c3ccc(-c4nc[nH]n4)nc3C)nc21] |

TABLE 1-continued
| No. | Structure |
|---|---|
| 3.233 | 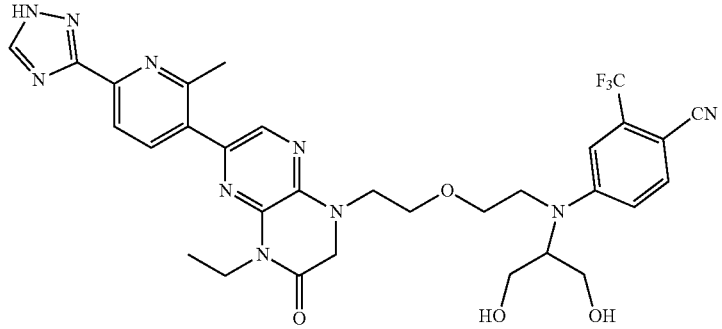 [SMILES: CCN1C(=O)CN(CCOCCN(c2ccc(C#N)c(C(F)(F)F)c2)C(CO)CO)c2ncc(-c3ccc(-c4nc[nH]n4)nc3C)nc21] |
| 3.234 | 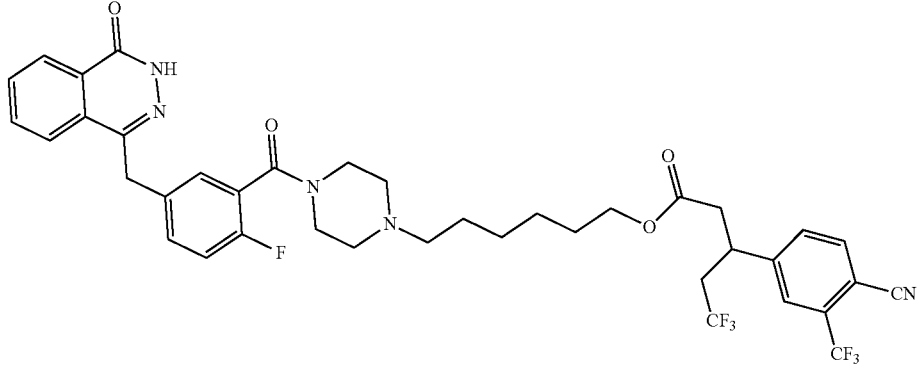 [SMILES: N#Cc1ccc(C(CC(=O)OCCCOCCN2CCN(C(=O)c3cc(Cc4n[nH]c(=O)c5ccccc45)ccc3F)CC2)CC(F)(F)F)cc1C(F)(F)F] |
| 3.235 | 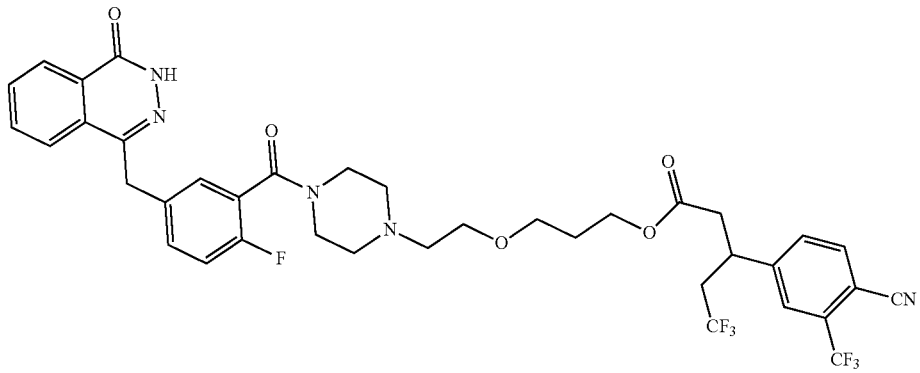 |
| 3.236 | 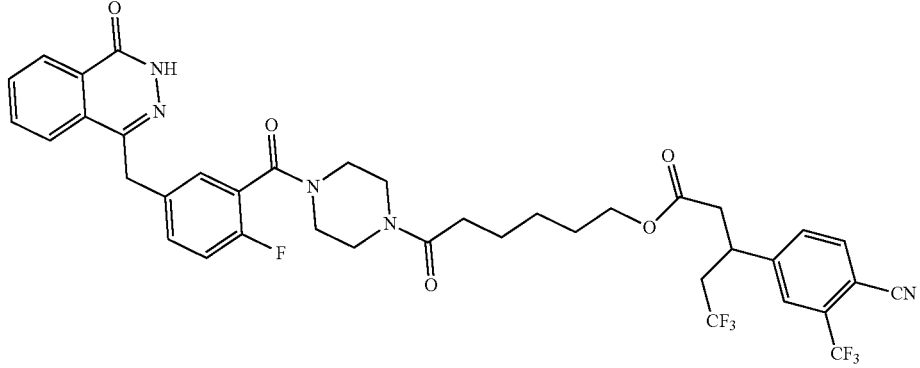 [SMILES: N#Cc1ccc(C(CC(=O)OCCCCCC(=O)N2CCN(C(=O)c3cc(Cc4n[nH]c(=O)c5ccccc45)ccc3F)CC2)CC(F)(F)F)cc1C(F)(F)F] |

TABLE 1-continued

| No. | Structure |
|---|---|
| 3.237 | 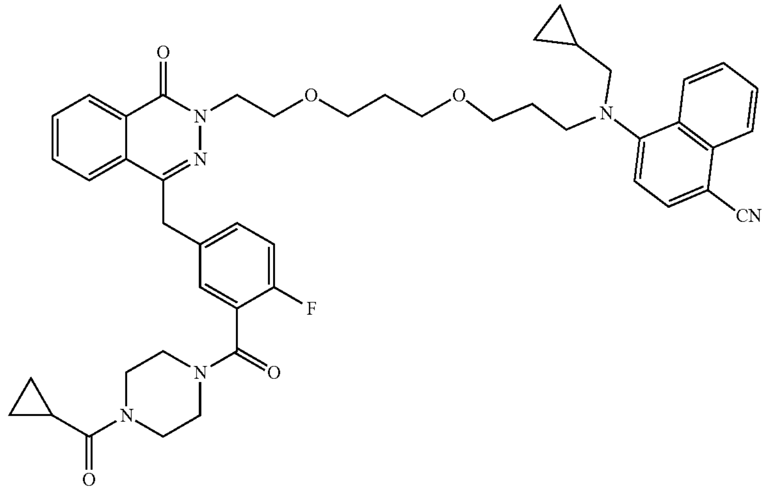 [SMILES: N#Cc1ccc(N(CCCOCCCOCCn2nc(Cc3ccc(F)c(C(=O)N4CCN(C(=O)C5CC5)CC4)c3)c3ccccc3c2=O)CC2CC2)c2ccccc12] |
| 3.238 | 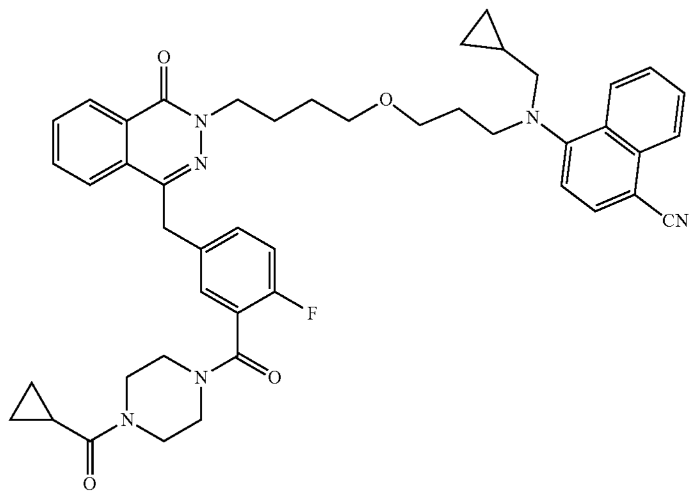 [SMILES: N#Cc1ccc(N(CCCOCCCCn2nc(Cc3ccc(F)c(C(=O)N4CCN(C(=O)C5CC5)CC4)c3)c3ccccc3c2=O)CC2CC2)c2ccccc12] |
| 3.239 | 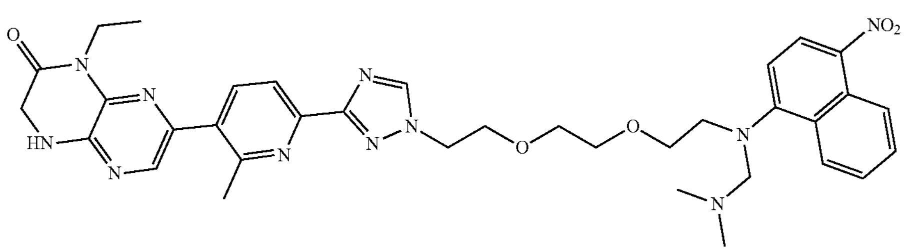 |
| 3.240 | 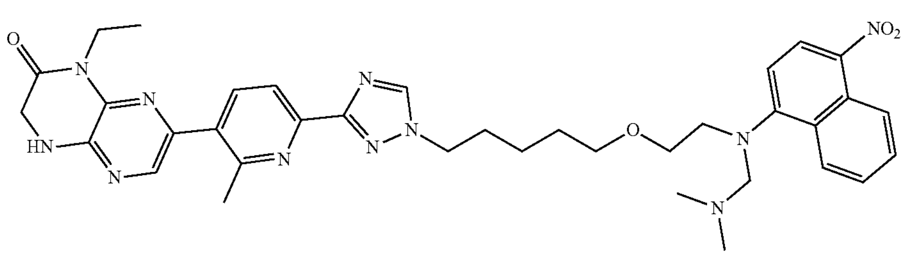 [SMILES: CCN1C(=O)CNc2ncc(-c3ccc(-c4ncn(CCOCCOCCN(CN(C)C)c5ccc([N+](=O)[O-])c6ccccc56)n4)nc3C)nc21] |

TABLE 1-continued
| No. | Structure |
|---|---|
| 3.241 | 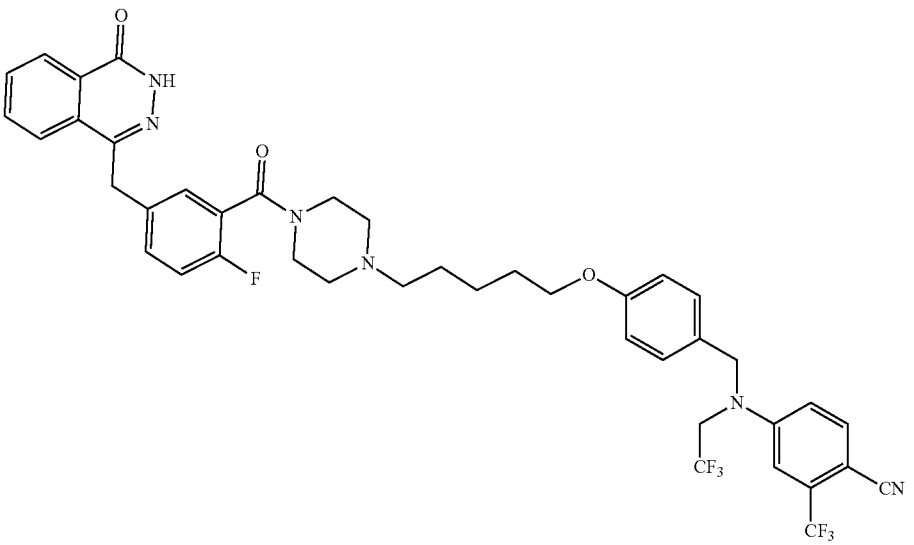 [SMILES: N#Cc1ccc(N(Cc2ccc(OCCCCCN3CCN(C(=O)c4cc(Cc5n[nH]c(=O)c6ccccc56)ccc4F)CC3)cc2)CC(F)(F)F)cc1C(F)(F)F] |
| 3.242 | 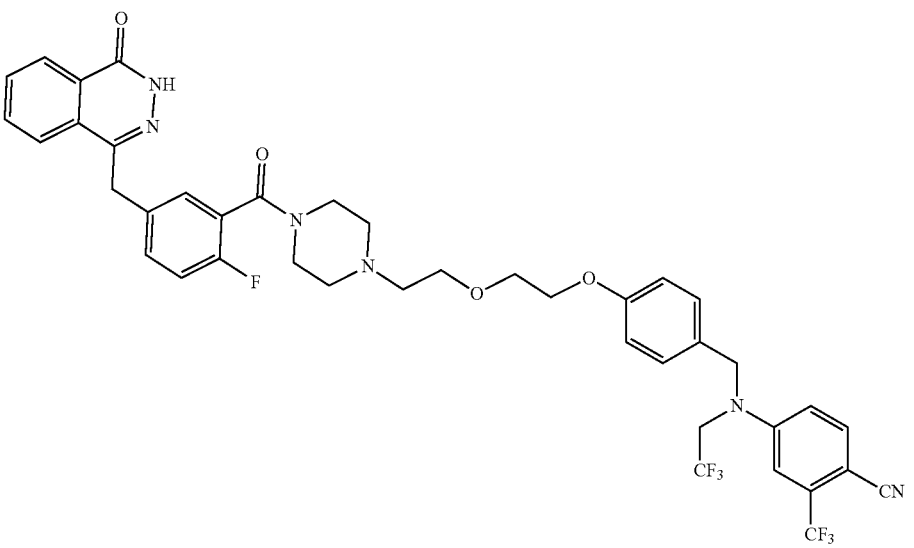 [SMILES: N#Cc1ccc(N(Cc2ccc(OCCOCCN3CCN(C(=O)c4cc(Cc5n[nH]c(=O)c6ccccc56)ccc4F)CC3)cc2)CC(F)(F)F)cc1C(F)(F)F] |
| 3.243 | 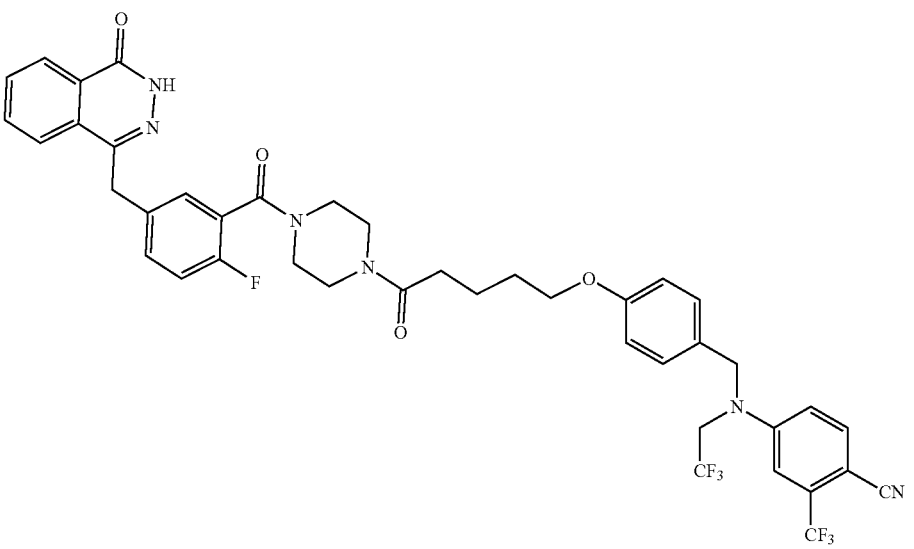 [SMILES: N#Cc1ccc(N(Cc2ccc(OCCCCC(=O)N3CCN(C(=O)c4cc(Cc5n[nH]c(=O)c6ccccc56)ccc4F)CC3)cc2)CC(F)(F)F)cc1C(F)(F)F] |

TABLE 1-continued
| No. | Structure |
|---|---|
| 3.244 | 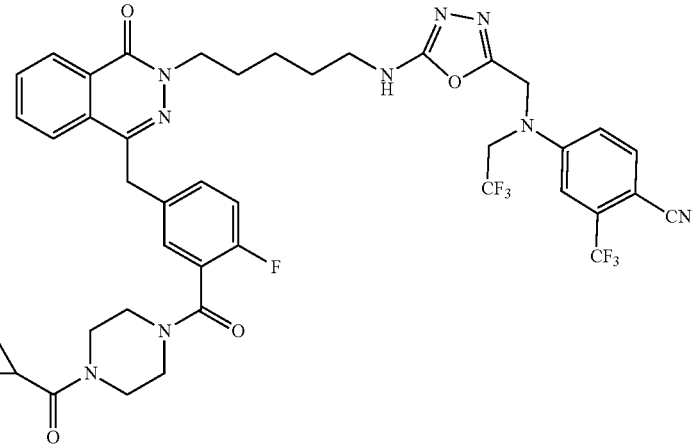 |
| 3.245 | 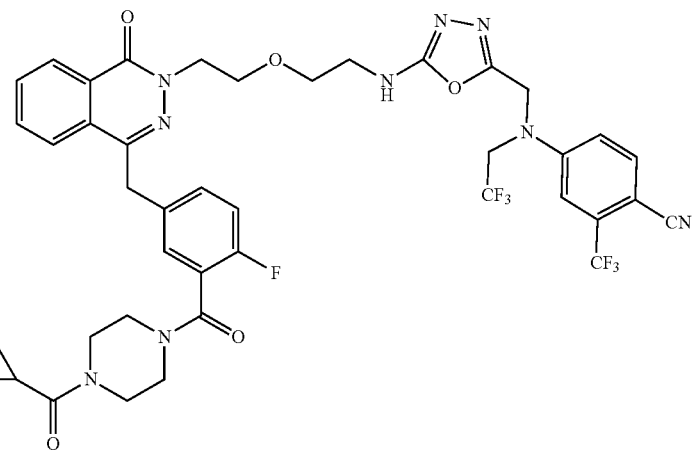 |
| 3.246 | 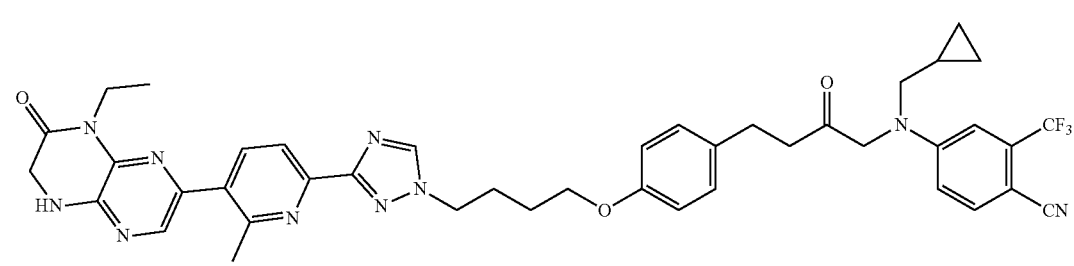 [SMILES: CCN1C(=O)CNc2ncc(-c3ccc(-c4ncn(CCCCOc5ccc(CCC(=O)CN(CC6CC6)c6ccc(C#N)c(C(F)(F)F)c6)cc5)n4)nc3C)nc21] |
| 3.247 | 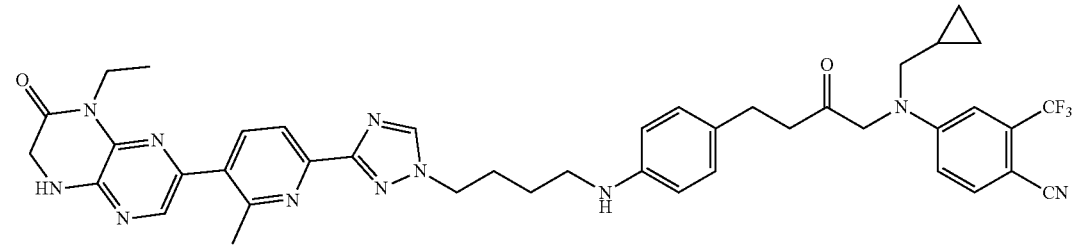 [SMILES: CCN1C(=O)CNc2ncc(-c3ccc(-c4ncn(CCCCNc5ccc(CCC(=O)CN(CC6CC6)c6ccc(C#N)c(C(F)(F)F)c6)cc5)n4)nc3C)nc21] |

TABLE 1-continued

| No. | Structure |
|---|---|
| 3.248 | 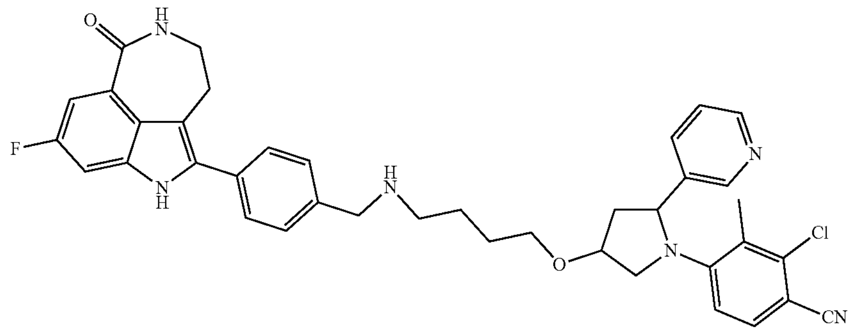 [SMILES: Cc1c(N2CC(OCCCCNCc3ccc(-c4[nH]c5cc(F)cc6c5c4CCNC6=O)cc3)CC2c2cccnc2)ccc(C#N)c1Cl] |
| 3.249 | 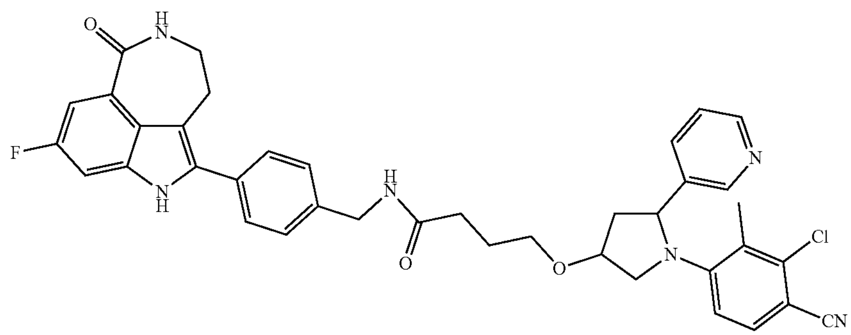 [SMILES: Cc1c(N2CC(OCCCC(=O)NCc3ccc(-c4[nH]c5cc(F)cc6c5c4CCNC6=O)cc3)CC2c2cccnc2)ccc(C#N)c1Cl] |
| 3.250 | 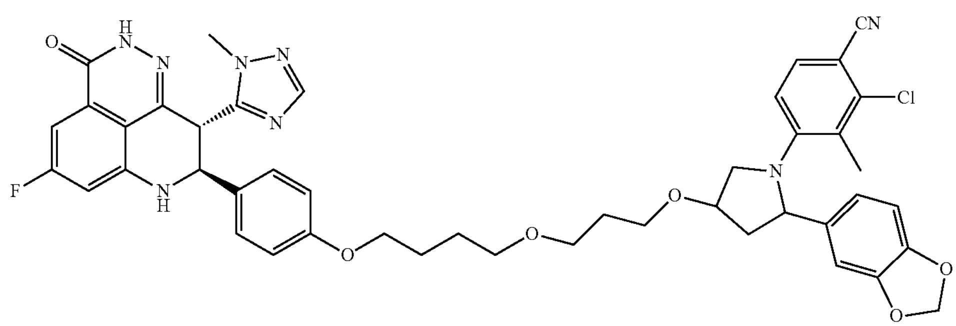 [SMILES: Cc1c(N2CC(OCCCOCCCCOc3ccc([C@H]4Nc5cc(F)cc6c(=O)[nH]nc(c56)[C@@H]4c4ncnn4C)cc3)CC2c2ccc3c(c2)OCO3)ccc(C#N)c1Cl] |
| 3.251 | 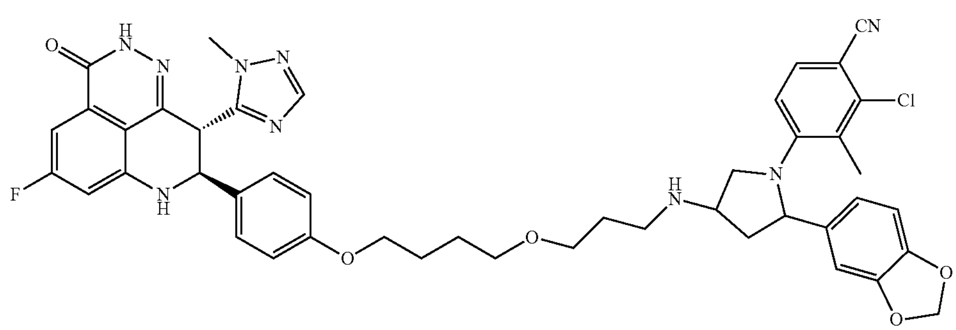 [SMILES: Cc1c(N2CC(NCCCOCCCCOc3ccc([C@H]4Nc5cc(F)cc6c(=O)[nH]nc(c56)[C@@H]4c4ncnn4C)cc3)CC2c2ccc3c(c2)OCO3)ccc(C#N)c1Cl] |

TABLE 1-continued

| No. | Structure |
|---|---|
| 3.252 | 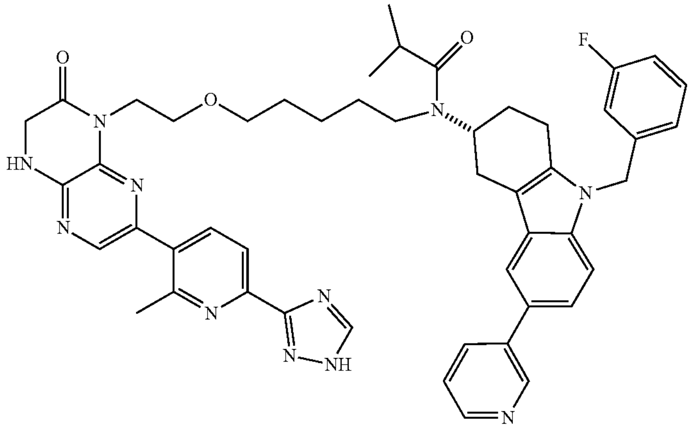 |
| 3.253 | 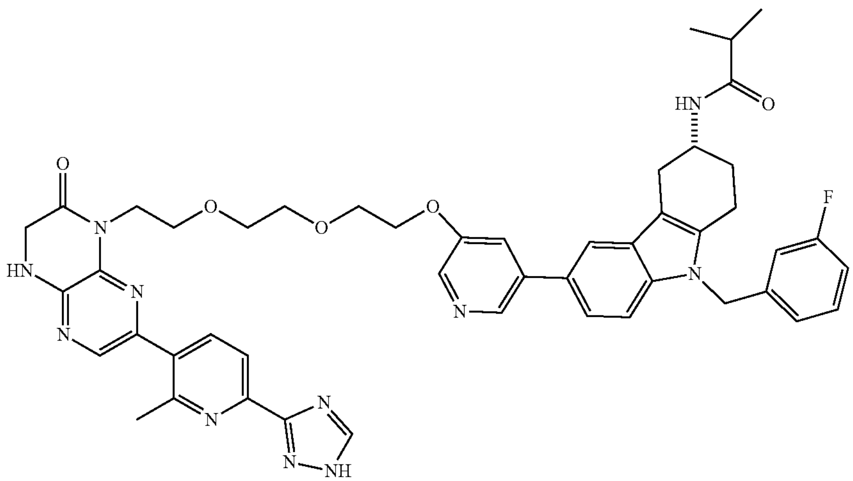 [SMILES: Cc1nc(-c2nc[nH]n2)ccc1-c1cnc2c(n1)N(CCOCCOCCOc1cncc(-c3ccc4c(c3)c3c(n4Cc4cccc(F)c4)CC[C@@H](NC(=O)C(C)C)C3)c1)C(=O)CN2] |
| 3.254 | 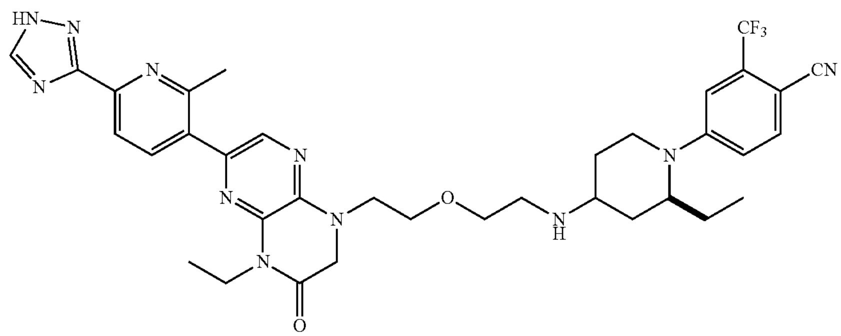 [SMILES: CC[C@H]1CC(NCCOCCN2CC(=O)N(CC)c3nc(-c4ccc(-c5nc[nH]n5)nc4C)cnc32)CCN1c1ccc(C#N)c(C(F)(F)F)c1] |
| 3.255 | 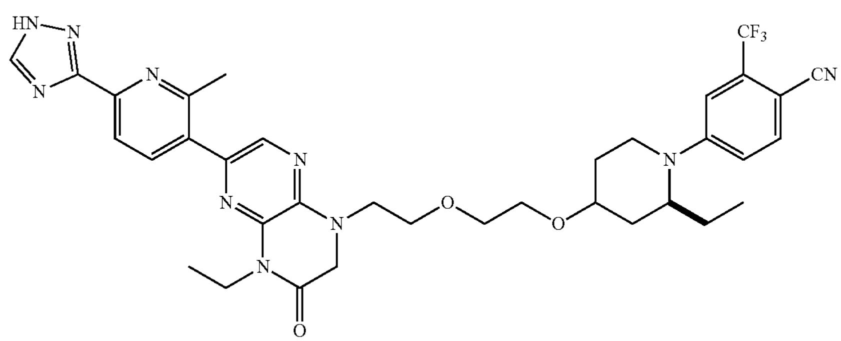 [SMILES: CC[C@H]1CC(OCCOCCN2CC(=O)N(CC)c3nc(-c4ccc(-c5nc[nH]n5)nc4C)cnc32)CCN1c1ccc(C#N)c(C(F)(F)F)c1] |

TABLE 1-continued

| No. | Structure |
|---|---|
| 3.256 | 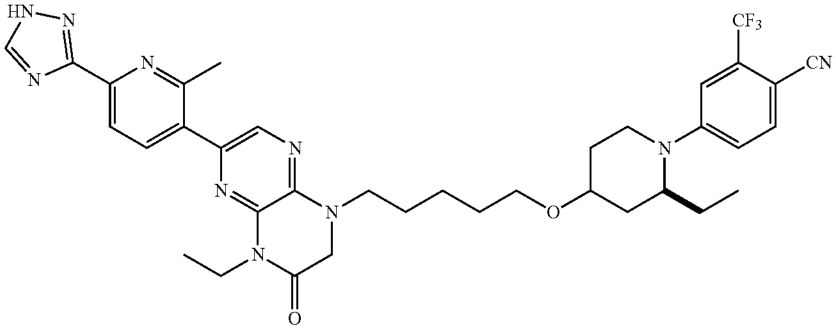 [SMILES: CC[C@H]1CC(OCCCCCN2CC(=O)N(CC)c3nc(-c4ccc(-c5nc[nH]n5)nc4C)cnc32)CCN1c1ccc(C#N)c(C(F)(F)F)c1] |
| 3.257 | 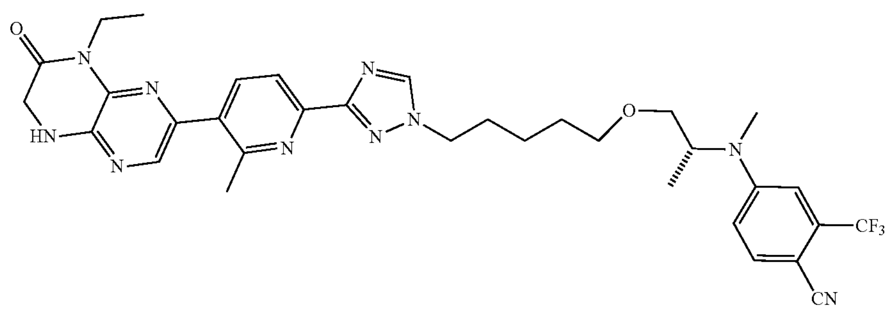 [SMILES: CCN1C(=O)CNc2ncc(-c3ccc(-c4ncn(CCCCCOC[C@@H](C)N(C)c5ccc(C#N)c(C(F)(F)F)c5)n4)nc3C)nc21] |
| 3.258 | 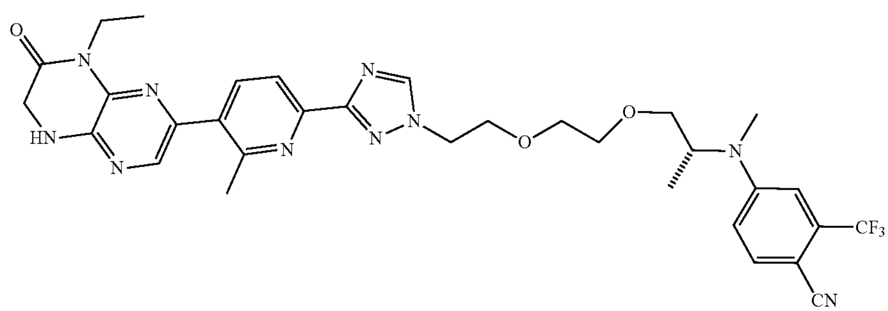 [SMILES: CCN1C(=O)CNc2ncc(-c3ccc(-c4ncn(CCOCCOC[C@@H](C)N(C)c5ccc(C#N)c(C(F)(F)F)c5)n4)nc3C)nc21] |
| 3.259 | 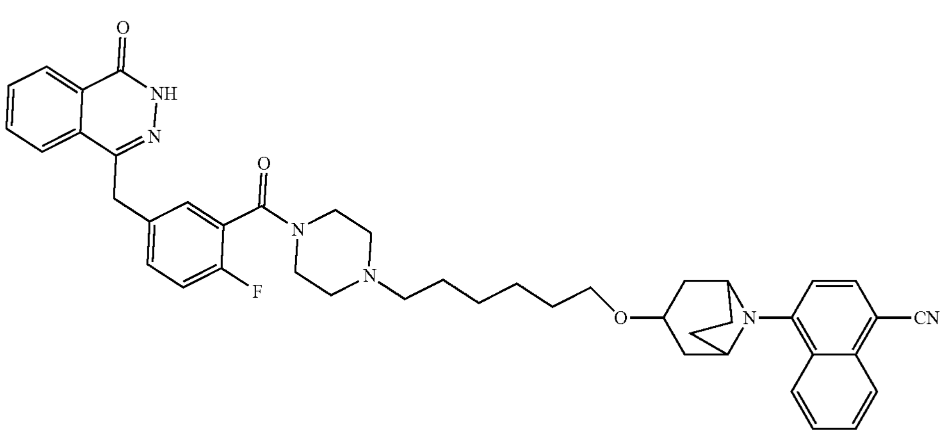 [SMILES: N#Cc1ccc(N2C3CCC2CC(OCCCOCCN2CCN(C(=O)c4cc(Cc5n[nH]c(=O)c6ccccc56)ccc4F)CC2)C3)c2ccccc12] |

TABLE 1-continued
| No. | Structure |
|---|---|
| 3.260 | 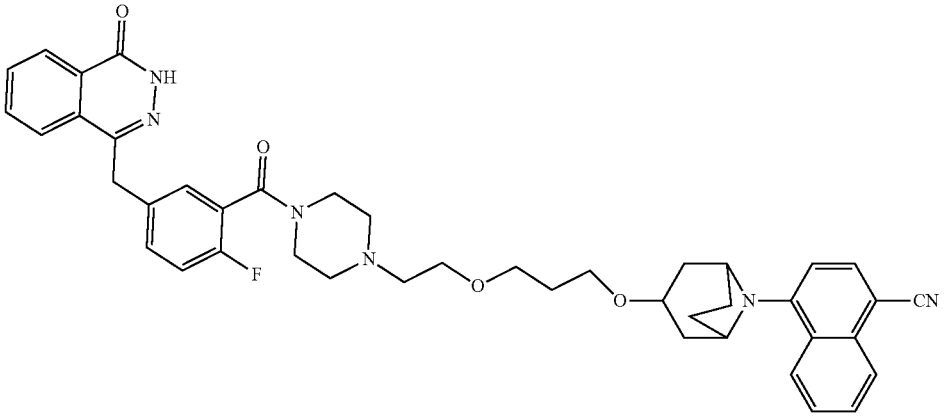 |
| 3.261 | 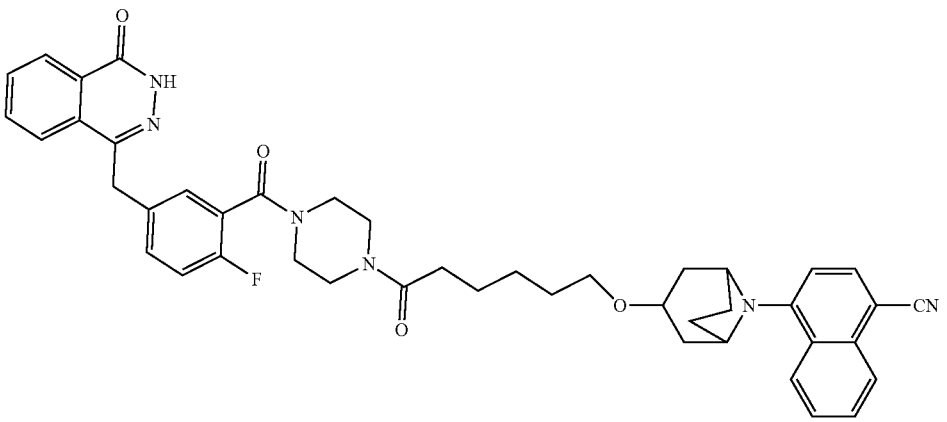 [SMILES: N#Cc1ccc(N2C3CCC2CC(OCCCCCC(=O)N2CCN(C(=O)c4cc(Cc5n[nH]c(=O)c6ccccc56)ccc4F)CC2)C3)c2ccccc12] |
| 3.262 | 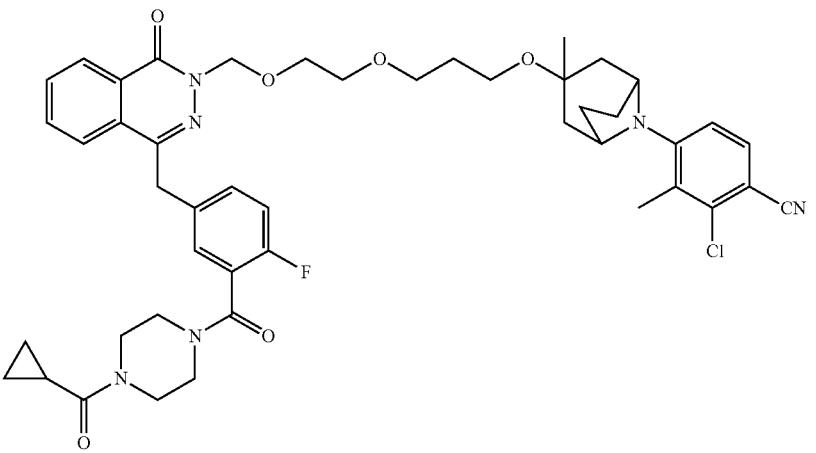 [SMILES: Cc1c(N2C3CCC2CC(C)(OCCCOCCOCn2nc(Cc4ccc(F)c(C(=O)N5CCN(C(=O)C6CC6)CC5)c4)c4ccccc4c2=O)C3)ccc(C#N)c1Cl] |

TABLE 1-continued

| No. | Structure |
|---|---|
| 3.263 | 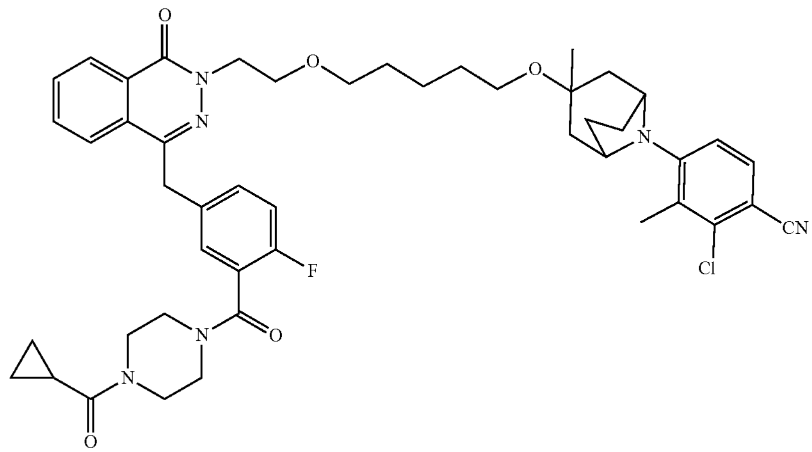 [SMILES: Cc1c(N2C3CCC2CC(C)(OCCCCCOCCn2nc(Cc4ccc(F)c(C(=O)N5CCN(C(=O)C6CC6)CC5)c4)c4ccccc4c2=O)C3)ccc(C#N)c1Cl] |
| 3.264 | 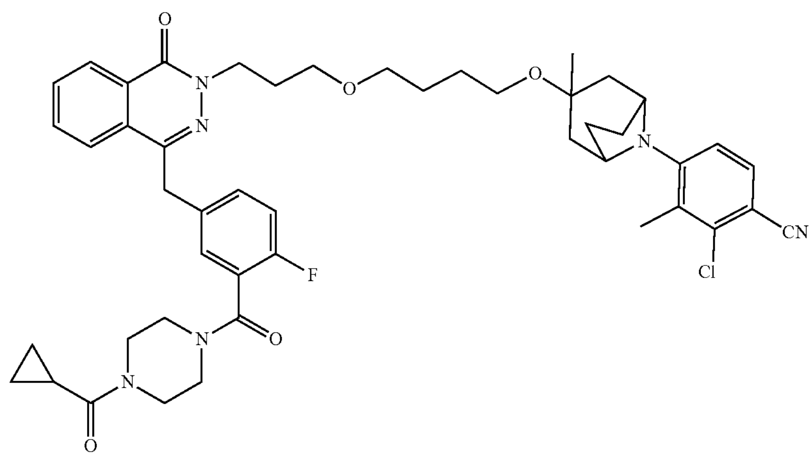 |

Methods of Treatment

Provided herein are compounds which can be used to treat, prevent, and/or delay the onset and/or development of cancer. Accordingly, in certain embodiments, provided is a method for the treatment of cancer, comprising administering to a subject in need of treatment a therapeutically-effective amount of a compound or composition described herein. Certain embodiments provide a method of potentiation of cytotoxic cancer therapy in a subject in recognized need of such treatment comprising administering to the subject a therapeutically acceptable amount of a compound or composition described herein.

It is contemplated that a patient having any cancer may benefit from being treated with the compounds and compositions described herein. Accordingly, in certain embodiments, the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma. In certain embodiments, the cancer is bladder cancer, a blood cancer, such as leukemia (e.g., chronic leukemia, chronic lymphocytic leukemia (CLL, etc.) or lymphoma (e.g., Hodgkin lymphoma, non-Hodgkin lymphoma, low grade lymphoma, high grade lymphoma), lung cancer (e.g., small cell lung cancer), breast cancer, fallopian tube cancer, glioblastoma multiforme, head and neck cancer, esophageal cancer, ovarian cancer, pancreatic cancer, peritoneal cancer, prostate cancer, testicular cancer, skin cancer (e.g., melanoma) or uterine cancer. In certain embodiments, the cancer is bladder cancer, breast cancer, fallopian tube cancer, ovarian cancer, prostate cancer, peritoneal cancer, testicular cancer, endometrial cancer, or uterine cancer.

In certain embodiments, the compounds and compositions as described herein are tailored to target cancers which overexpress a specific receptor, such as, but not limited to, androgen receptors, estrogen receptors, progesterone receptors, and/or glucocorticoid receptors by including an epitope which targets that specific nuclear receptor. The epitope can be derived from a steroid hormone or any non-steroidal drug which targets that particular receptor.

In certain embodiments, provided is a method of treating or preventing an androgen receptor overexpressing cancer, comprising administering an effective amount of a compound, or a pharmaceutically acceptable salt of solvate thereof, comprising at least one nuclear payload and at least one androgen receptor-targeting epitope to an individual in need thereof. Specific cancers which are contemplated to be treated by such methods include, but are not limited to, prostate, breast, triple negative breast cancer, bladder, or liver cancer. Also provided is a method of treating or preventing metastatic castration-resistant prostate cancer (mCRPC), comprising administering an effective amount of a compound or composition as described herein, or a pharmaceutically acceptable salt or solvate thereof, to an individual in need thereof.

In certain embodiments, provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. In certain embodiments, the cancer is prostate, breast, triple negative breast cancer, bladder, or liver cancer. In certain embodiments, the androgen receptor-targeting epitope comprises an androgen receptor agonist, a selective androgen-receptor modulator (SARM), an androgen receptor antagonist, a selective estrogen receptor modulator (SERM), an estrogen receptor antagonist, a progestin, or an estrogen. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, darolutamide, or an analog thereof. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, or an analog thereof. In certain embodiments, the nuclear payload comprises a PARP inhibitor.

In certain embodiments, provided is a method of treating or preventing an estrogen and/or progesterone receptor overexpressing cancer, comprising administering an effective amount of a compound, or a pharmaceutically acceptable salt or solvate thereof, comprising at least one nuclear payload and at least one estrogen and/or progesterone receptor-targeting epitope to an individual in need thereof. Specific cancers which are contemplated to be treated by such methods include, but are not limited to, breast, uterine, or ovarian cancer.

In certain embodiments, provided is a method of treating or preventing a glucocorticoid receptor overexpressing cancer, comprising administering an effective amount of a compound, or a pharmaceutically acceptable salt or solvate thereof, comprising at least one nuclear payload and at least one glucocorticoid receptor-targeting epitope to an individual in need thereof. Specific cancers which are contemplated to be treated by such methods include, but are not limited to, breast, uterine, or ovarian cancer. Specific cancers which are contemplated to be treated by such methods include, but are not limited to, prostate, possibly breast, uterine, ovarian.

Breast cancer includes ductal carcinoma in situ (DCIS) and invasive breast cancer. Breast cancers can occur in milk ducts, milk-producing lobules and connective tissues. Breast cancer includes estrogen receptor (ER) negative and hormone receptor (HR) negative, and also can be categorized as Group 3 (HER-2 positive) or Group 4 (basal-like).

Prostate cancer is a cancer which develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease. Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread. Combination with primarily surgery and radiation therapy, or other treatments such as hormonal therapy, chemotherapy, proton therapy, cryosurgery, high intensity focused ultrasound (HIFU) are also contemplated.

Certain embodiments provide a method of inhibiting PARP in a subject in recognized need of such treatment comprising administering to the subject a therapeutically acceptable amount of a compound or composition described herein. In one embodiment, provided herein is a method of treating a disease ameliorated by the inhibition of PARP comprising administering to a subject in need of treatment a therapeutically-effective amount of a compound or composition described herein.

Certain embodiments provide a method of treating leukemia, colon cancer, glioblastomas, lymphomas, melanomas, carcinomas of breast, or cervical carcinomas in a subject in recognized need of such treatment comprising administering to the subject a therapeutically acceptable amount of a compound or composition described herein.

In some embodiments, provided herein is a method of treatment of a cancer deficient in Homologous Recombination (HR) dependent DNA double strand break (DSB) repair pathway, which includes administering to a subject in need of treatment a therapeutically-effective amount of a compound of composition described herein. In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2. In some embodiments, the method of treatment of a cancer includes treatment of breast, ovary, pancreas and/or prostate cancer. In some embodiments, the method of treatment of a cancer further includes administration of ionizing radiation or a chemotherapeutic agent.

The primary function of the DNA mismatch repair (MMR) system is to eliminate single-base mismatches and insertion-deletion loops that may arise during DNA replication. Insertion-deletion loops result from gains or losses of short repeat units within microsatellite sequences, also known as microsatellite instability (MSI). At least six different MMR proteins are required. For mismatch recognition, the MSH2 protein forms a heterodimer with either MSH6 or MSH3 depending on the type of lesion to be repaired (MSH6 is required for the correction of single-base mispairs, whereas both MSH3 and MSH6 may contribute to the correction of insertion-deletion loops). A heterodimer of MLH1 and PMS2 coordinates the interplay between the mismatch recognition complex and other proteins necessary for MMR. These additional proteins may include at least exonuclease 1 (EXO 1), possibly helicase(s), proliferating cell nuclear antigen (PCNA), single-stranded DNA-binding protein (RPA), and DNA polymerases δ and ε. In addition to PMS2, MLH1 may heterodimerize with two additional proteins, MLH3 and PMS1. Recent observations indicate that PMS2 is required for the correction of single-base mismatches, and PMS2 and MLH3 both contribute to the correction of insertion-deletion loops. Additional homologs of the human MMR proteins are known that are required for functions other than MMR. These proteins include MSH4 and MSH5 that are necessary for meiotic (and possibly mitotic) recombination but are not presumed to participate in MMR.

Germline mutations of human MMR genes cause susceptibility to hereditary nonpolyposis colon cancer (HNPCC), one of the most common cancer syndromes in humans. An excess of colon cancer and a defined spectrum of extracolonic cancers, diagnosed at an early age and transmitted as an autosomal dominant trait, constitute the clinical definition of the syndrome. MSI, the hallmark of HNPCC, occurs in approximately 15% to 25% of sporadic tumors of the colorectum and other organs as well. According to international criteria, a high degree of MSI (MSI-H) is defined as instability at two or more of five loci or >30% to 40% of all microsatellite loci studied, whereas instability at fewer loci is referred to as MSI-low (MSI-L). MSI occurs in a substantial proportion (2% to 50% of tumors) among non-HNPCC cancers (e.g., cancers of the breast, prostate, and lung). On the basis of the proportion of unstable markers, categories MSS, MSI-L, and MSI-H can be distinguished in these cancers in analogy to HNPCC cancers. In one embodiment is a method for treating a cancer deficient in mismatch DNA repair pathway. In another embodiment is a method for treating a cancer demonstrating microsatellite instability due to reduced or impaired DNA repair pathways. In another embodiment is a method for treating a cancer demonstrating genomic instability due to reduced or impaired DNA repair pathways.

In certain embodiments, a compound or composition described herein, may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound or composition.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE1 IA (NM_005590) and NBS 11M_00248_5). Other proteins involved in the HR dependent DNA DSB repair pathway include regulatory factors such as EMSY (Wood, et al., Science, 291, 1284-1289 (2001); Khanna et al., Nat. Genet. 27(3): 247-254 (2001); and Hughes-Davies, et al., Cell, 115, pp 523-535).

In some embodiments, a cancer which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

BRCA1 and BRCA2 are tumor suppressors whose wild-type alleles are frequently lost in tumors of heterozygous carriers. BRCA1 and/or BRCA2 mutations are associated with breast cancer. Amplification of the EMSY gene, which encodes a BRCA2 binding factor, is associated with breast and ovarian cancer (Jasin M., Oncogene, 21(58), 8981-93 (2002); Tutt, et al, *Trends Mol. Med.,* 8(12), 571-6, (2002); and Radice, P. J., *Exp Clin Cancer Res.,* 21(3 Suppl), 9-12 (2002)).

Carriers of mutations in BRCA1 and/or BRCA2 are also at elevated risk of cancer of the ovary, prostate and pancreas.

In some embodiments, the individual is heterozygous for one or more variations, such as mutations and polymorphisms, in BRCA1 and/or BRCA2 or a regulator thereof. The detection of variation in BRCA1 and BRCA2 is described, for example in EP 699 754, EP 705 903, Neuhausen, S. L. and Ostrander, E. A., Genet. Test, 1, 75-83 (1992); Janatova M., et al, *Neoplasma,* 50(4), 246-50 (2003). Determination of amplification of the BRCA2 binding factor EMSY is described in Hughes-Davies, et al., *Cell,* 115, 523-535.

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

In certain embodiments, it is contemplated that the compounds described herein are useful for patients who have relapsed or become refractory. The term "relapsed" refers to disease (or cancer) that reappears or grows again after a period of remission. The term "refractory" is used to describe when the cancer does not respond to treatment or when the response to treatment does not last very long. For example, the compounds herein may be useful for treating cancer in patients who have previously been treated with the cancer therapies described herein, e.g. enzalutamide.

Compositions

Compositions, including pharmaceutical compositions, of any of the compounds detailed herein are embraced by this disclosure. Thus, provided herein are pharmaceutical compositions comprising a compound of the disclosure, or a pharmaceutically acceptable salt thereof, and a pharmaceutically acceptable carrier or excipient. The pharmaceutical compositions provided herein may take a form suitable for oral, buccal, parenteral (e.g., intravenous, intramuscular, infusion or subcutaneous injection), nasal, topical or rectal administration, or a form suitable for administration by inhalation.

A compound as described herein may, in one aspect, be in a purified form. Compositions comprising a compound as described herein, or a salt thereof, are provided, such as compositions of substantially pure compounds. In some embodiments, a composition comprising a compound as described herein, or a salt thereof, is in substantially pure form. Unless otherwise stated, "substantially pure" refers to a composition which contains no more than 35% impurity, wherein the impurity denotes a compound other than the desired compound, or a salt thereof, which comprises the majority of the composition. In one variation, a composition of substantially pure compound, or a salt thereof, is provided wherein the composition contains no more than 25% impurity. In another variation, a composition of substantially pure compound, or a salt thereof, is provided wherein the composition contains or no more than 20% impurity. In still another variation, a composition of substantially pure compound, or a salt thereof, is provided wherein the composition contains or no more than 10% impurity. In a further variation, a composition of substantially pure compound, or a salt thereof, is provided wherein the composition contains or no more than 5% impurity. In another variation, a composition of substantially pure compound, or a salt thereof, is provided wherein the composition contains or no more than 3% impurity. In still another variation, a composition of substantially pure compound, or a salt thereof, is provided wherein the composition contains or no more than 1% impurity. In a further variation, a composition of substantially pure compound, or a salt thereof, is provided wherein the composition contains or no more than 0.5% impurity.

In certain embodiments, pharmaceutical compositions are formulated in any manner, including using one or more physiologically acceptable carriers comprising excipients and/or auxiliaries which facilitate processing of the active compounds into pharmaceutical compositions. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical compositions which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (c) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Dosing and Treatment Regimens

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administered is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules.

In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In certain embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the LM) (the dose lethal to 50% of the population) and the ED$_{50}$ (the dose therapeutically effective in 50% of the population). The dose ratio between the toxic and therapeutic effects is the therapeutic index and it can be expressed as the ratio between LD$_{50}$ and ED$_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the ED$_{50}$ with minimal toxicity. In certain embodiments, the dosage varies within this range depending upon the dosage form employed and the route of administration utilized.

In certain embodiments, the disclosed compounds exhibit an increased affinity for a nuclear target, increased potency or increased therapeutic index as compared to an unmodified nuclear payload from which the compound was derived. In certain embodiments, this higher affinity, potency or therapeutic index may provide benefits, such as allowing for the administration of lower doses and thus reduced potential for toxicity, improvement in therapeutic index and decreased overall cost of therapy. In certain embodiments, the daily dosages appropriate for administration of the compounds described herein is less than 100% of the recommended daily dose of the unmodified nuclear payload, or less than about 90%, or less than about 80% or less than about 70%, or less than about 60%, or less than about 50%, or less than about 40%, or from about 20% to about 90%, or from about 30% to about 90%, or from about 40% to about 90%, or from about 50% to about 90%, or from about 60% to about 90%, or from about 70% to about 90%, or from about 20% to about 80%, or from about 30% to about 80%, or from about 40% to about 80%, or from about 50% to about 80%, or from about 60% to about 80%, or from about 70% to about 80%, or from about 20% to about 70%, or from about 30% to about 70%, or from about 40% to about 70%, or from about 50% to about 70%, or from about 60% to about 70%, of the recommended daily dose of the unmodified nuclear payload.

In certain embodiments, the compounds described herein are used in the preparation or manufacture of medicaments for the treatment of diseases or conditions that are mediated by the enzyme poly(ADP-ribose)polymerase (PARP) or in which inhibition of the enzyme poly(ADP-ribose)polymerase (PARP) ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

Combination Therapy

Compounds described herein (e.g., a compound of Table 1, a compound of Formula I or II, or any other formula disclosed herein) can also be used in combination with other active ingredients. Such combinations are selected based on the condition to be treated, cross-reactivities of ingredients and pharmaco-properties of the combination. In one embodiment, the disclosure provides a use of a compound as described herein used in combination with another agent or therapy method, such as another cancer treatment. For example, when treating cancer, the compositions can be combined with other anti cancer compounds (such as paclitaxel or rapamycin).

It is also possible to combine a compound of the disclosure with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Administration of the compounds and compositions of the present disclosure to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described active agent(s). These therapies include but are not limited to chemotherapy, radiotherapy, immunotherapy, gene therapy and surgery.

In some embodiments, provided herein is a method for the treatment of cancer, comprising administering to a subject in need of treatment a therapeutically-effective amount of a compound or composition described herein in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound or composition described herein in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

In certain embodiments, provided herein is a method for the treatment of cancer, which includes administering to a subject in need of treatment a therapeutically-effective amount of a compound or composition described herein in combination with ionizing radiation. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 5 times per week. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 6 times per week. It is contemplated that by administering radiation in combination with a compound or composition described herein, prostate specific chemical prostatectomy can be achieved while avoiding detrimental side effects, such as the impotence and incontinence of surgical prostatectomy due to disruption of vessels and nerves.

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, tamoxifen, 5-fluorouracil, methoxtrexate, temozolomide, cyclophosphamide, SCH 66336, R115777, L778,123, BMS 214662, IRESSA® (gefitinib), TARCEVAR® (erlotinib hydrochloride), antibodies to EGFR, GLEEVEC® (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, teniposide, 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux® (cetuximab), Liposomal, Thiotepa, Altretamine, Melphalan, Trastuzumab, Lerozole, Fulvestrant, Exemestane, Ifosfomide, Rituximab, C225, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, paclitaxel, gemcitabine, navelbine, farnesylprotein transferase inhibitors, transplatinum, 5-fluorouracil, vincristine, vinblastine and methotrexate, or any analog or derivative variant of the foregoing.

Other factors that cause DNA damage, such as radiotherapy, have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (e.g., 3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Administration of the compound or composition as described herein may precede or follow the other anti-cancer agent or treatment by intervals ranging from minutes to weeks. In embodiments where the other anti-cancer agent and expression construct are applied separately, one would generally ensure that a significant period of time did not elapse between the time of each delivery, such that the agent and expression construct would still be able to exert an advantageously combined effect on a cell. For example, in such instances, it is contemplated that one may contact a cell, tissue or organism with two, three, four or more modalities substantially simultaneously (i.e., within less than about a minute) with the active agent(s). In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the active agent(s). In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the active agent(s). In some situations, it may be desirable to extend the time period for treatment significantly, however, where several weeks (e.g., about 1, about 2, about 3, about 4, about 6, or about 8 weeks or more) lapse between the respective administrations.

Kits

Kits for use to achieve anti-cancer effects comprising a compound or composition described herein are provided. In certain embodiments, the kit comprises a unit dose of a compound or composition described herein and instructions for administering the same. In certain aspects, the kit further comprises a second drug suitable for anti-cancer therapy, or instructions for co-administering an additional anti cancer therapy (such as radiation or gene therapy). In another aspect, kits for use to achieve anti-cancer effects comprise a low dose (e.g., less than about 500 mg/day, or less than about 400 mg/day, or less than about 300 mg/day, or less than about 200 mg/day) of a compound or composition described herein and a second drug suitable for anti-cancer therapy. In yet another variation, kits for use to achieve anti-cancer effects comprise a high dose (e.g., greater than about 500 mg/day) of a compound or composition as described herein and a second drug suitable for anti-cancer therapy.

Methods of Manufacturing a Medicament

In a further aspect of the disclosure, use of the compounds and compositions described herein in the manufacture of a medicament is provided. In particular, the manufacture of a medicament for use in the treatment of cancer, or diseases or conditions which can be mediated, at least in part, by blocking DNA repair and/or transcription activation, such as by inhibition of PARP, are provided. Further, pharmaceutical compositions of a compound described herein are also intended for use in the manufacture of a medicament for use in treatment of diseases or conditions which can be mediated, at least in part, by inhibition of PARP.

EXAMPLES

The disclosure is further illustrated by the following examples. The examples below are non-limiting are merely representative of various aspects of the disclosure. Solid and dotted wedges within the structures herein disclosed illustrate relative stereochemistry, with absolute stereochemistry depicted only when specifically stated or delineated.

Compounds as disclosed herein, or any formula or sub-formula described herein, can be synthesized using standard synthetic techniques known to those of skill in the art. Compounds of the present disclosure can be synthesized using the general synthetic procedures set forth in General Methods 1-5 Synthetic Examples.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Information $^1$H NMR spectra and $^{13}$C NMR spectra were recorded on Varian 400 MHz or Broker Avance III 500 MHz spectrometers. Spectra are referenced to residual chloroform (δ 7.26, $^1$H), DMSO (δ 2.54, $^1$H) or methanol (δ 3.34, $^1$H) unless otherwise noted. Chemical shifts are reported in ppm (δ); multiplicities are indicated by s (singlet), d (doublet), t (triplet), q (quartet), quint (quintet), sext (sextet), m (multiplet) and br (broad). Coupling constants, J, are reported in Hertz. Silica gel chromatography was performed using a Teledyne Isco CombiFlash® Rf+ instrument using Hi-Purit Silica Flash Cartridges (National Chromatography Inco) or RediSep Rf Gold C18 Cartridges (Teledyne Isco). Analytical HPLC was performed on a Waters ACQUITY UPLC with a photodiode array detector using and a Waters ACQUITY BEH Shield RPC18 (2.1×50 mm, 1.7 µm) column. Analytical LCMS was performed on a Waters ACQUITY UPLC with a Waters 3100 mass detector. Chiral HPLC was performed on a Waters Alliance e2695 with a photodiode array detector using Daicel Chiralpak® AD-H, Chiralpak® IA, Chiralpak® IB, Chiralpak® IC, Chiralcel® OD-H or Chiralcel® OJ-H columns. Optical rotations were obtained on a Jasco P-2000 digital polarimeter and are reported as $[\alpha]_D^T$ temperature (T), concentration (c=g/100 mL) and solvent. Commercially available reagents and solvents were used as received unless otherwise indicated.

General Methods

General Method 1

Olaparib-containing analogs can be prepared following the method described by Menear et al. (Menear, K. A. et al. J. Med. Chem. 2008, 51, 6581-6591).

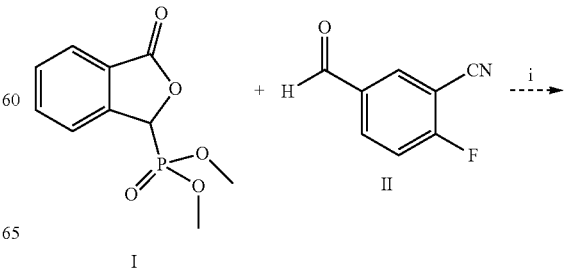

Scheme 1.

-continued

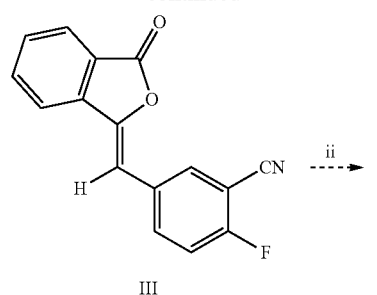

III

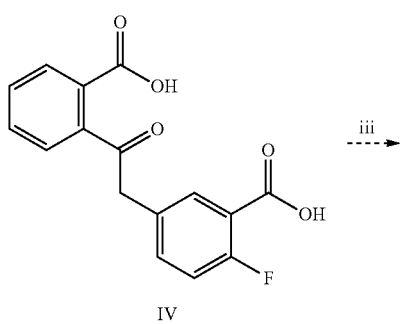

IV

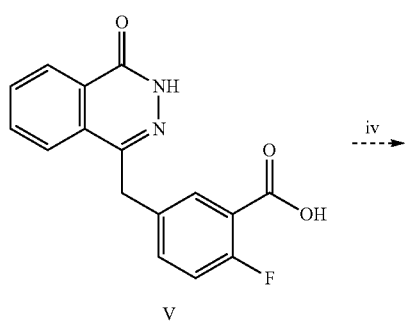

V

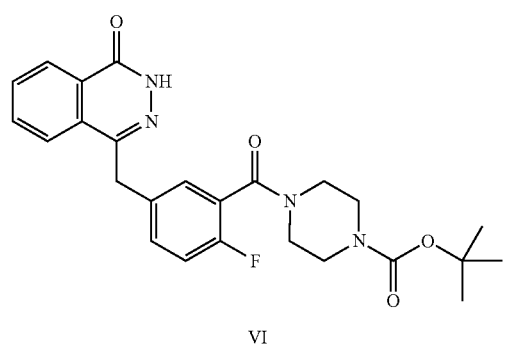

VI olaparib-containing analogues

Proposed route to olaparib-containing analogs: (i) Et₃N, THF, RT; (ii) a. aq. NaOH, THF, 100° C.; b. 2M HCl; (iii) H₂NNH₂, H₂O; (iv) Boc-piperazine, HATU, DIPEA, DMA; (v) HCl, dioxane; (vi) using intermediates A or intermediates C, HATU, HOBt, DMF or using intermediates B or intermediates D, Et₃N, DMF.

General Method 2

Rucaparib-containing analogs can be prepared following the method described by Gillmore et. al. (Gillmore, A. T. el al. *Org. Process Res. Dev.* 2012, 16, 1897-1904).

Scheme 2.

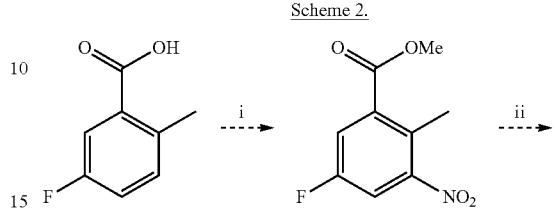

VII → VIII

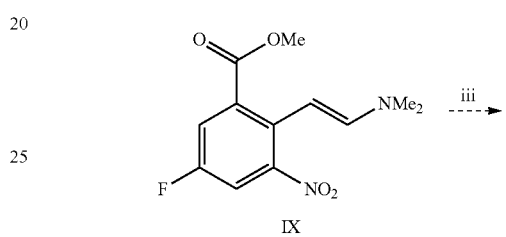

IX

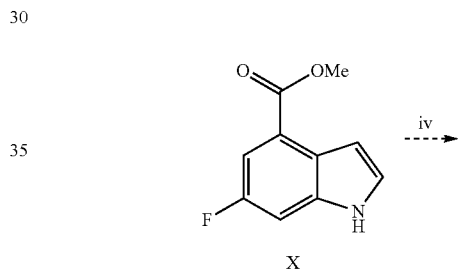

X

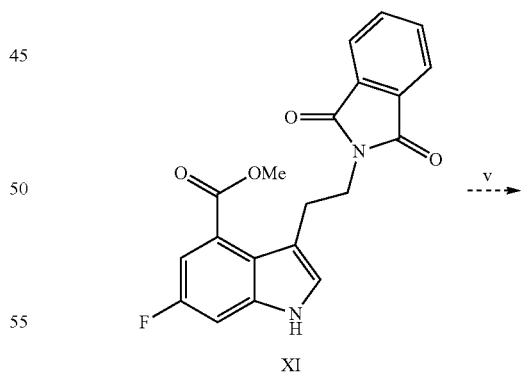

XI

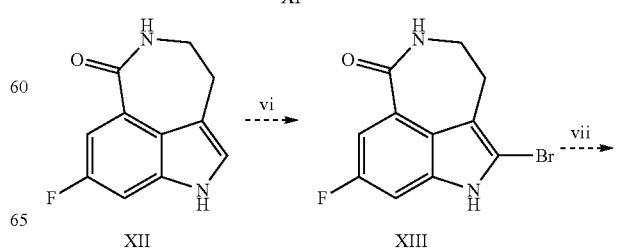

XII → XIII

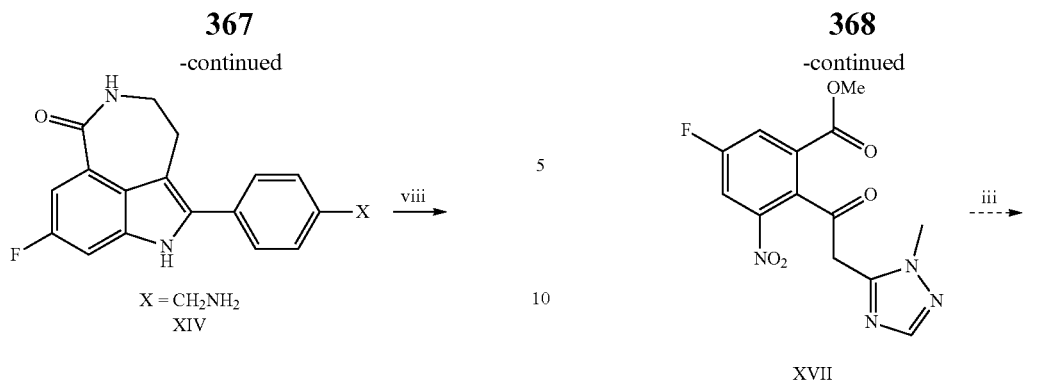

Proposed route to rucaparib-containing analogues: (i) a. HNO₃, H₂SO₄; b. MeOH, H₂SO₄; (ii) DMF, DMA, Et₃N, 120° C.; (iii) H₂, Pd/C, AcONa, MeOH; (iv) phthalimidoacetaldehyde, TFA, TES, CH₂Cl₂; (v) aq. MeNH₂; (vi) pyr•HBr₃, THF, CH₂Cl₂; (vii) Ar—B(OR)₂, Pd(dppf)Cl₂•CH₂Cl₂, aq. Na₂CO₃, DMA; (viii) using intermediates A or intermediates C, HATU, HOBt, DMF or using intermediates B or intermediates D, Et₃N, DMF.

General Method 3

Talazoparib-containing analogues can be prepared following the method described by Wang et al. (Wang, B. et al. *J. Med. Chem.* 2016, 59, 335-357).

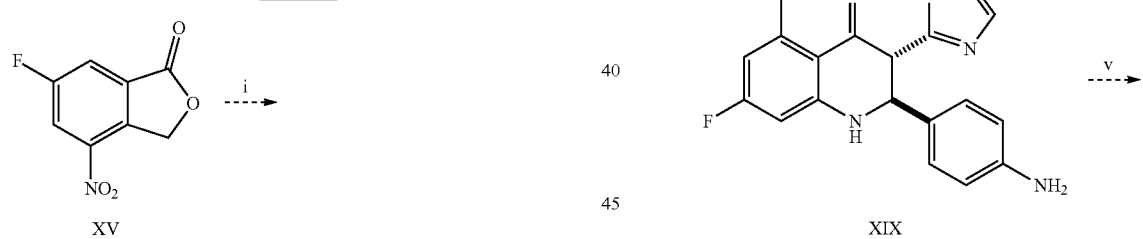

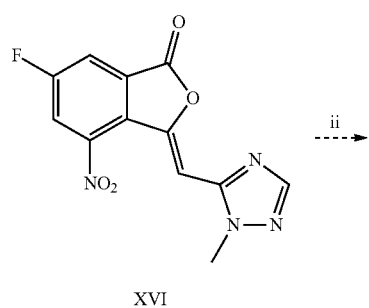

Proposed route to talazoparib-containing analogs: (i) 1-methyl-1H-1,2,4-triazole-5-carbaldehyde, Et₃N, Ac₂O, 2-Me-THF, RT to 80° C., 2 h; (ii) MeOH, RT, overnight; (iii) aminobenzaldehyde, TiCl₃, THF, MeOH, 0° C. to RT; (iv) a. H₂NNH₂, MeOH, RT, overnight; b. chiral separation; (v) using intermediates A or intermediates C, HATU, HOBt, DMF or using intermediates B or intermediates D, Et₃N, DMF.

General Method 4

DHT-containing intermediates can be prepared by treating commercially available DHT (XX) with the desired tethering group to afford intermediates such as XXI. When R=CO₂Me, the ester group can be mildly saponified to provide the carboxylate intermediates A. When R=OAc, mild saponification releases the primary alcohol which can then be treated with methanesulfonyl chloride to afford intermediates B.

Scheme 4.

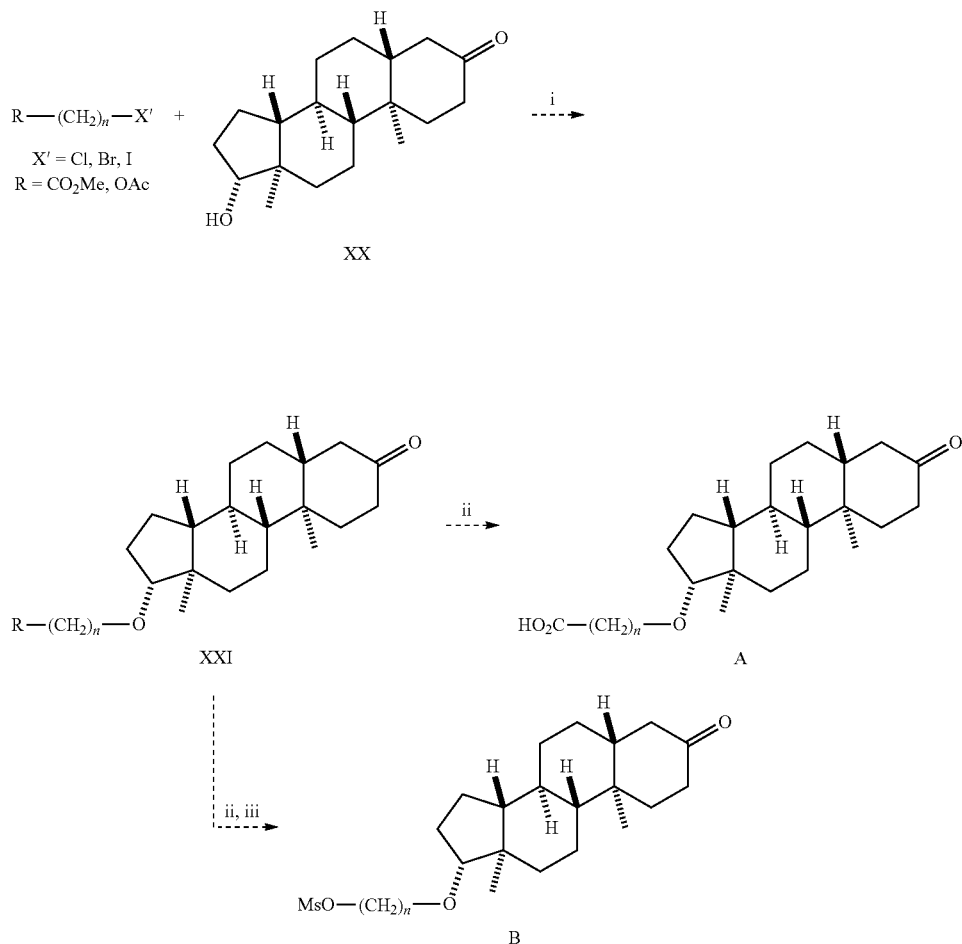

Proposed route to DHT-containing intermediates: (i) Et₃N, DMF; (ii) aq. LiOH, MeOH; (iii) MsCl, Et₃N, DMF.

General Method 5

Enzalutamide-containing intermediates can be prepared starting with carboxylic acid XXII (Jadhavar, et al. *Bioorg. Med. Chem. Lett.* 2016, 26, 5222-5228) and coupling with the desired tethering group to afford intermediates such as XXIII. When R=CO₂Me, the ester group can be mildly saponified to provide the carboxylate intermediates C. When R=OAc, mild saponification releases the primary alcohol which can then be treated with methanesulfonyl chloride to afford intermediates D.

Scheme 5.

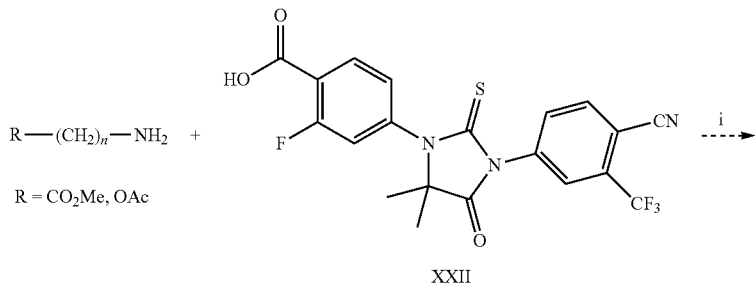

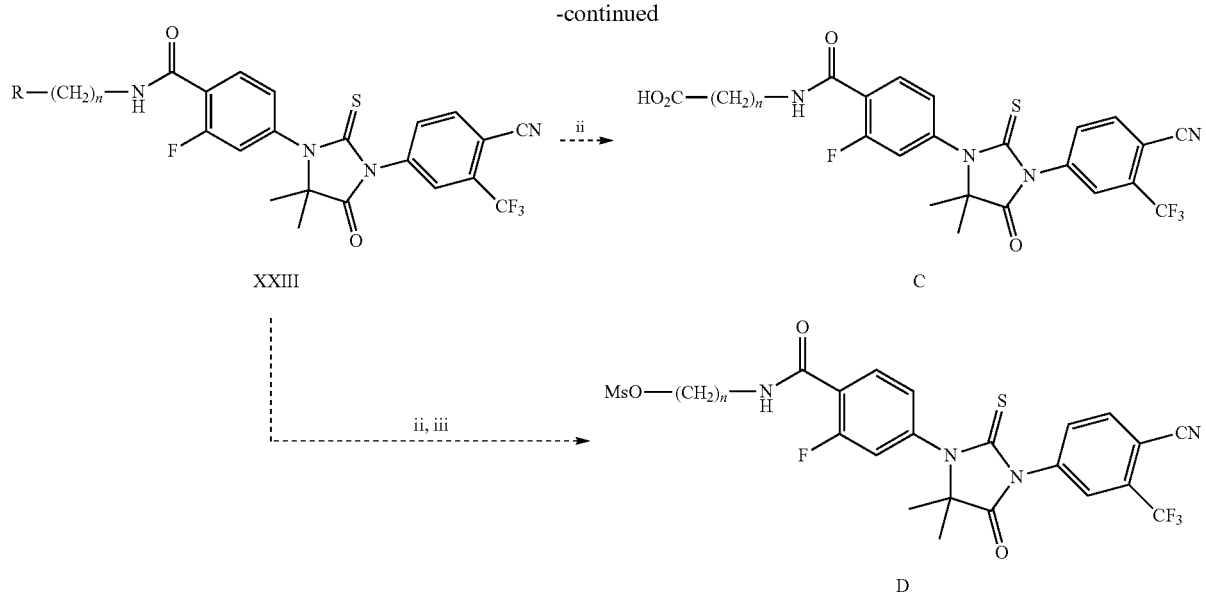
Proposed route to enzalutamide-containing intermediates: (i) HATU, HOBt, DMF; (ii) aq. LiOH, MeOH; (iii) MsCl, Et₃N, DMF.
General Method 6
CC-115 containing analogs can be prepared following the method described by Mortensen et al. (Mortensen, D. S. et al. *J. Med. Chem.* 2015, 58, 5599-5608).
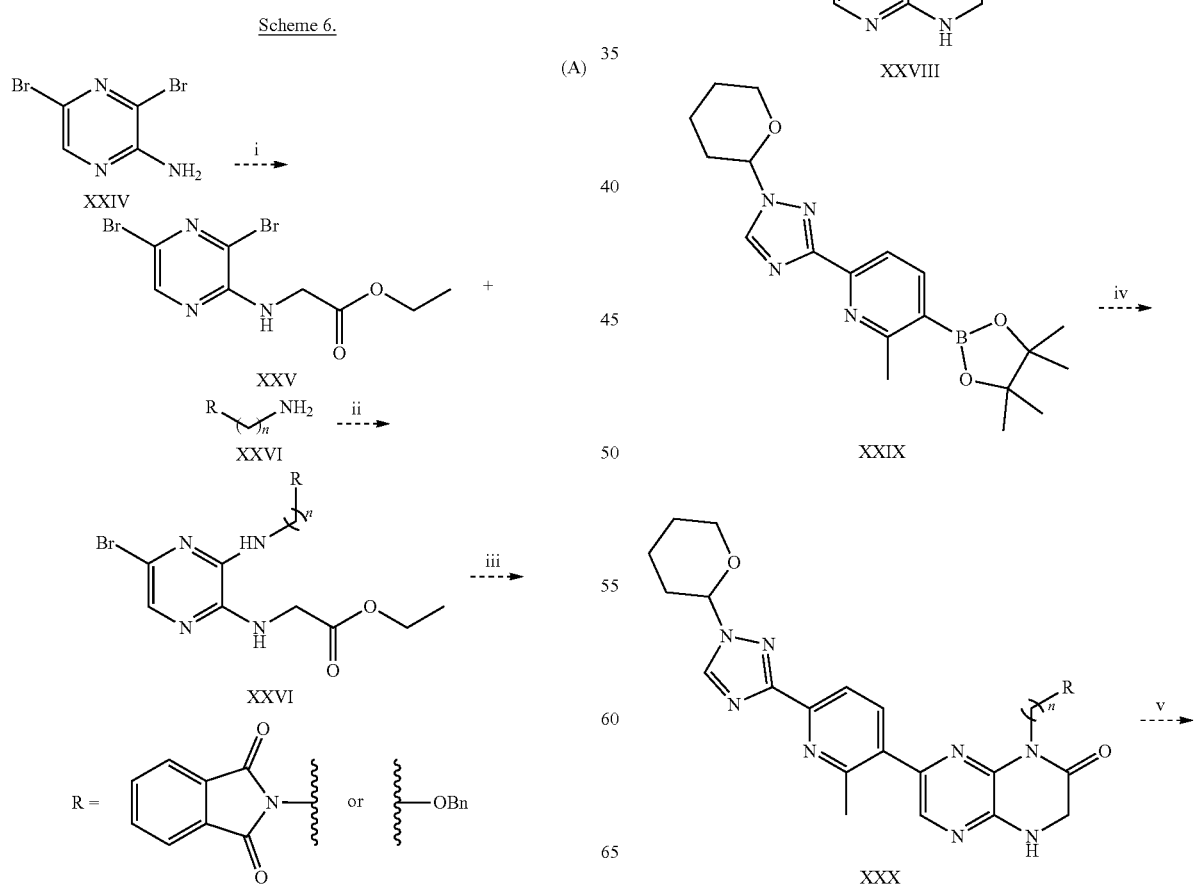

-continued
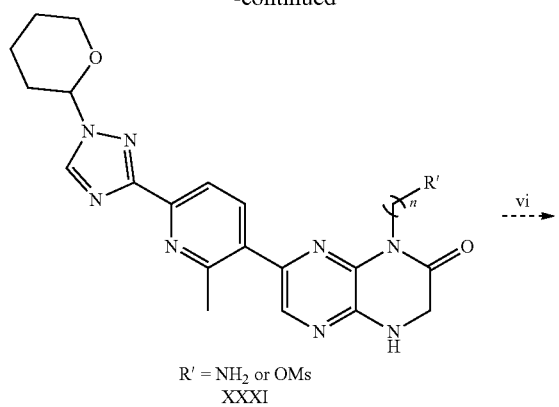
R' = NH₂ or OMs
XXXI
CC-115 containing analogues
(B)
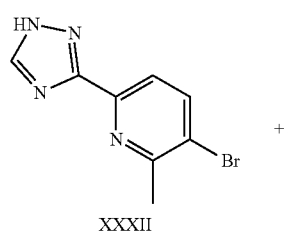
XXXII
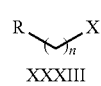
XXXIII
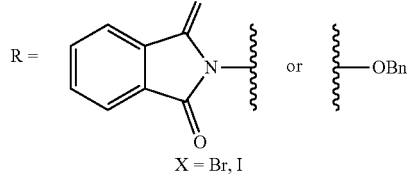
X = Br, I
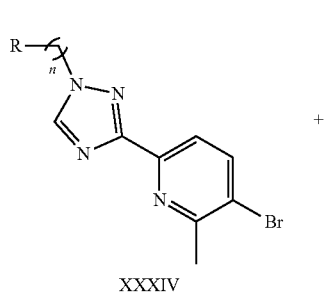
XXXIV
-continued
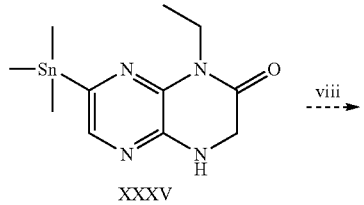
XXXV
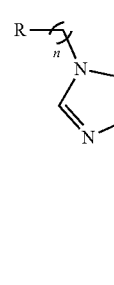
XXXVI
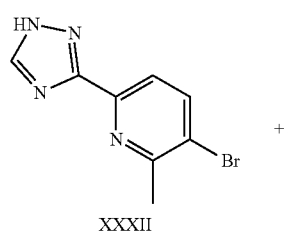
R' = NH₂ or OMs
XXXVII
CC-115 containing analogues
X = Br, I
R' = NH₂ or OMs
(C)
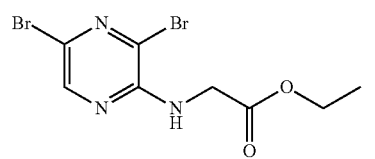
XXV

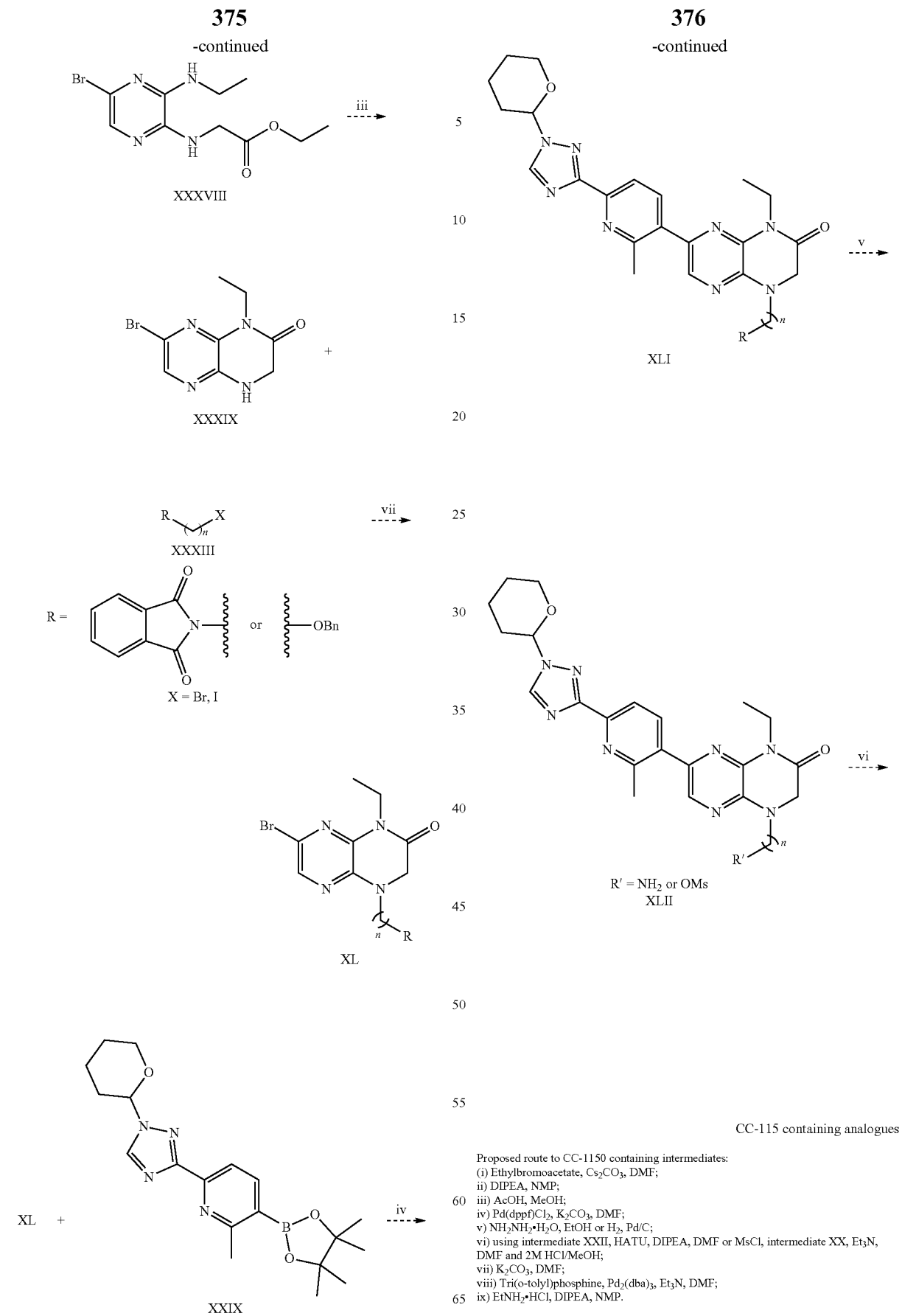
CC-115 containing analogues
Proposed route to CC-1150 containing intermediates:
(i) Ethylbromoacetate, Cs₂CO₃, DMF;
ii) DIPEA, NMP;
iii) AcOH, MeOH;
iv) Pd(dppf)Cl₂, K₂CO₃, DMF;
v) NH₂NH₂·H₂O, EtOH or H₂, Pd/C;
vi) using intermediate XXII, HATU, DIPEA, DMF or MsCl, intermediate XX, Et₃N, DMF and 2M HCl/MeOH;
vii) K₂CO₃, DMF;
viii) Tri(o-tolyl)phosphine, Pd₂(dba)₃, Et₃N, DMF;
ix) EtNH₂·HCl, DIPEA, NMP.

Synthetic Examples
Example S-1. Preparation of 4-(3-(4-cyano-3-(trifluoromethyl)phenyl)-5,5-dimethyl-4-oxo-2-thioxoimidazolidin-1-yl)-2-fluoro-N-(6-(4-(2-fluoro-5-((4-oxo-3,4-dihydrophthalazin-1-yl)methyl)benzoyl)piperazin-1-yl)-6-oxohexyl)benzamide (Compound 1.1)
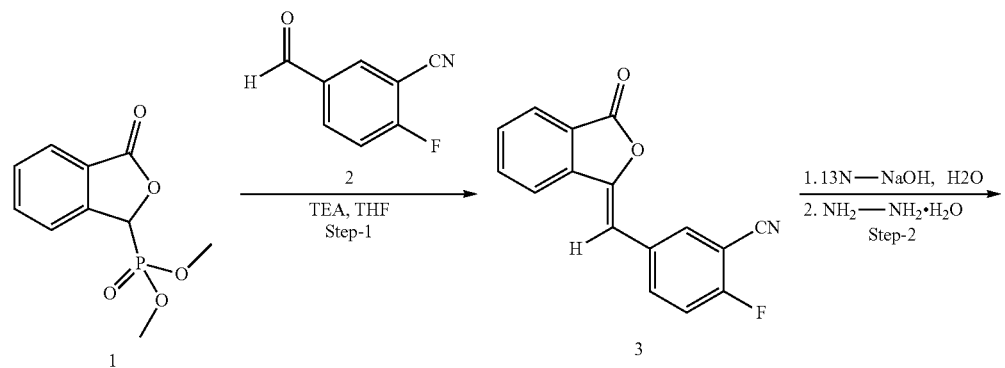
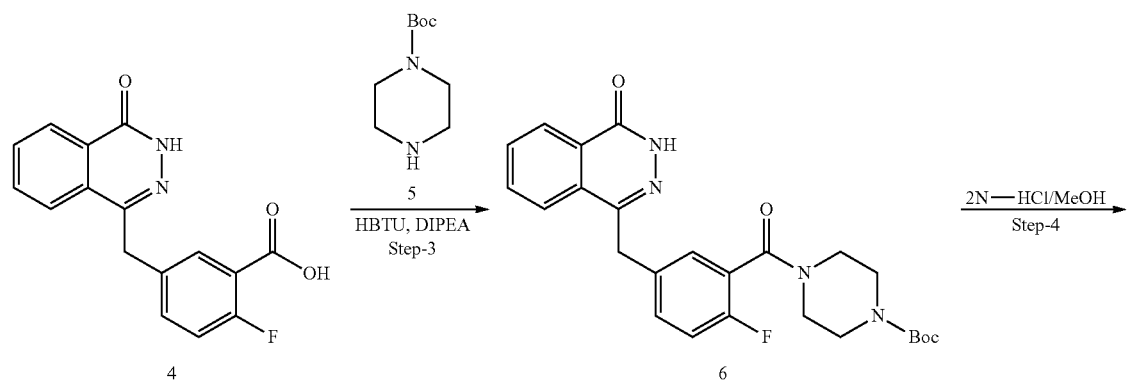
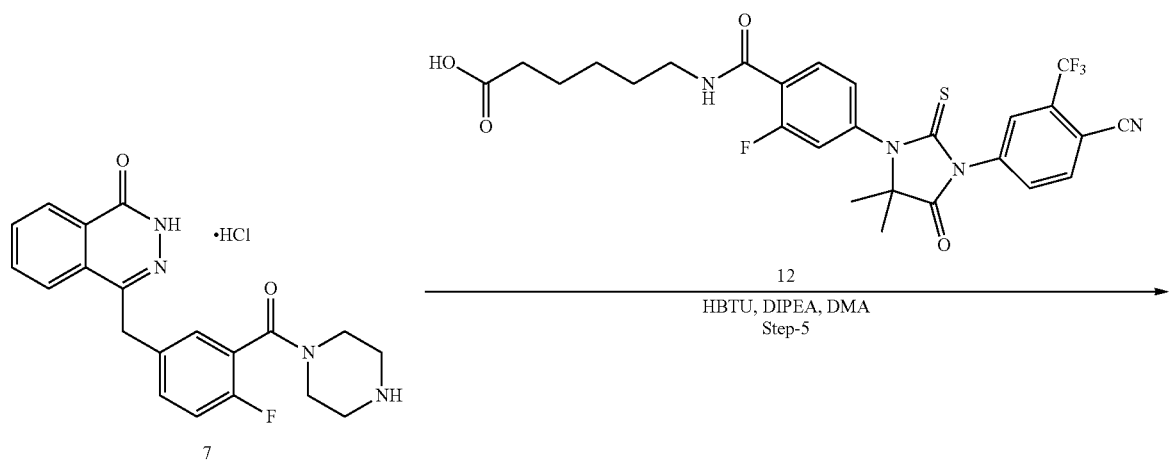

-continued
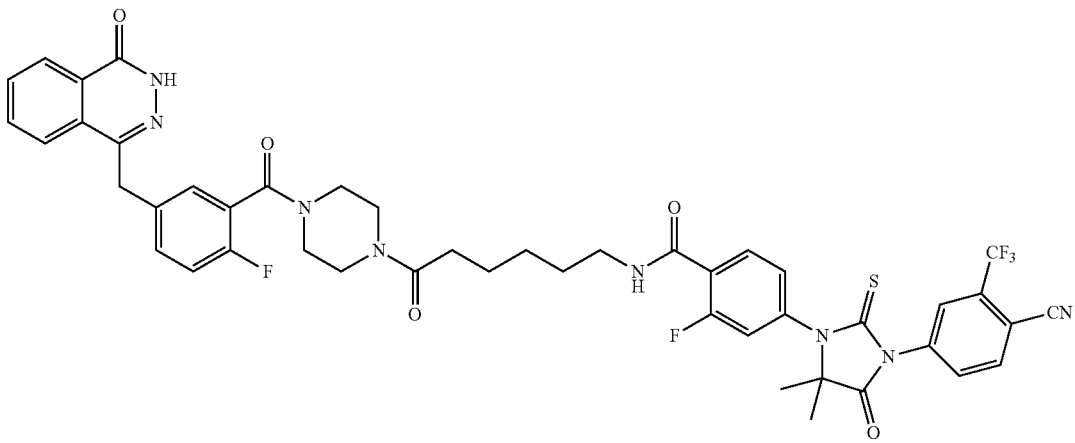
Compound 1.1
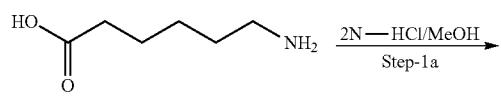
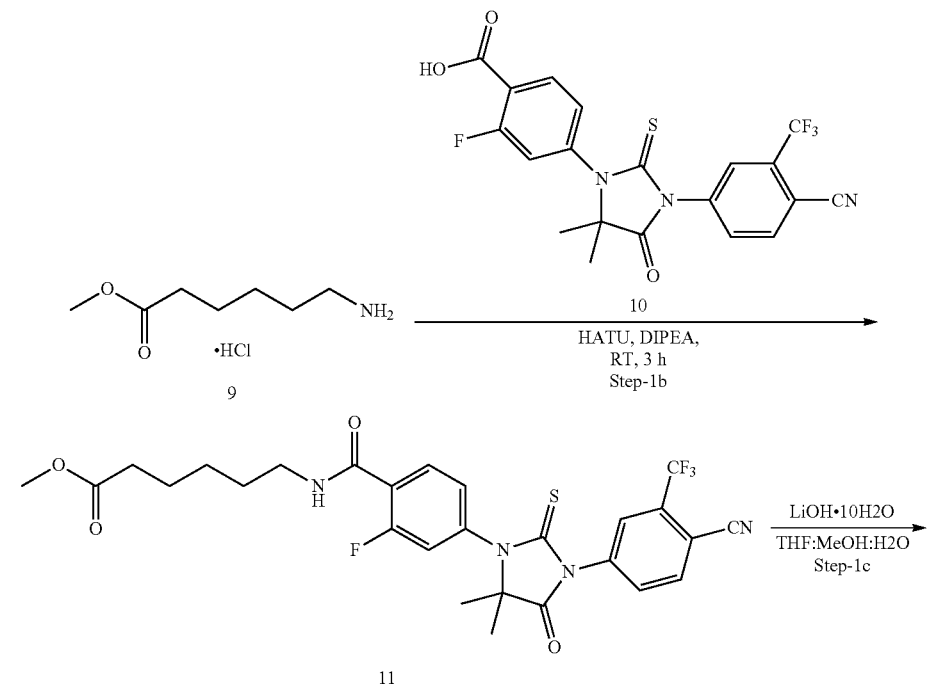

Step-1: Preparation of (Z)-2-fluoro-5-((3-oxoisobenzofuran-1(3H)-ylidene)methyl)benzonitrile To a stirred solution of dimethyl 3-oxo-1,3-dihydroisobenzofuran-1-yl phosphonate (10 g, 41.3 mmol) and 2-fluoro-5-formylbenzonitrile (6.15 g, 41.3 mmol) in THF (50 mL) was added triethylamine (5.76 mL, 41.3 mmol) at 0° C. slowly. The resultant mixture was stirred at RT for 16 h. The reaction was monitored by TLC. Upon completion, water (200 mL) was added and the resulting precipitate was filtered via a Buchner funnel. The product obtained was washed with water (50 mL), hexanes (50 mL), diethyl ether (30 mL), dried under vacuum afford to afford (Z)-2-fluoro-5-((3-oxoisobenzofuran-1(3H)-ylidene)methyl)benzonitrile (50:50 mixture of E and Z isomers) which was used in next step without further purification. LC-MS: 266 [M+H]$^+$. $^1$H NMR (400 MHz, CDCl$_3$) δ 8.13 (1H, m), 8.05 (1H, m), 7.98 (1H, m), 7.79 (2H, m), 7.61 (1H, m), 7.30 (1H, m), 6.35 (1H, s).

Step-2: Preparation of 2-fluoro-5-((4-oxo-3,4-dihydrophthalazin-1 yl)methyl)benzoic acid To a stirred suspension of (Z)-2-fluoro-5-((3-oxoisobenzofuran-1(3H)-ylidene)methyl)benzonitrile (3.7 g, 13.9 mmol) in water (20 mL) was added 13N aqueous NaOH (5 mL) and the mixture was heated under nitrogen at 90° C. for 16 h. The reaction mixture was then cooled to 70° C. and hydrazine hydrate (10 mL) was added and stirred for 16 hours at 70° C. The reaction was monitored by TLC. Upon completion, the reaction was cooled to RT and acidified using 2N aqueous HCl (pH 1-2) at 0-5° C. to obtain a precipitate. The slurry was filtered via a Buchner funnel, washed with water (50 mL), hexanes (50 mL), diethyl ether (30 mL) and dried under vacuum afford to afford 2-fluoro-5-((4-oxo-3,4-dihydrophthalazin-1-yl)methyl)benzoic acid. LC-MS 299 [M+H]$^+$. $^1$H NMR (400 MHz, DMSO-d$_6$) δ 13.22 (1H, br. s), 12.61 (1H, s), 8.27 (1H, m), 7.99-7.81 (4H, m), 7.59 (1H, m), 7.25 (1H, m), 4.36 (2H, s).

Step-3: Preparation of tert-butyl 4-(2-fluoro-5-((4-oxo-3,4-dihydrophthalazin-1-yl)methyl)benzoyl)piperazine-1-carboxylate To a stirred suspension of 2-fluoro-5-((4-oxo-3,4-dihydrophthalazin-1-yl)methyl)benzoic acid (0.1 g, 0.335 mmol) in DMA (4 mL) was added HBTU (0.15 g, 0.402 mmol, 1.2 eq) at 0° C. and the mixture was stirred for 10 min. DIPEA (0.17 mL, 1 mmol, 3 eq) and tert-butyl piperazine-1-carboxylate (0.075 g, 0.402 mmol, 1.2 eq) were then successively added to the reaction mixture at 0° C. and the resultant reaction mixture was stirred at RT for 75 min. The reaction was monitored by TLC. After completion, water (10 mL) was added and the resulting precipitate was filtered via a Buchner funnel. The product obtained was washed with water (10 mL×2) and n-pentane (10 mL×2), dried under reduced pressure to afford tert-butyl 4-(2-fluoro-5-((4-oxo-3,4-dihydrophthalazin-1-yl)methyl)benzoyl)piperazine-1-carboxylate which was taken to next step without further purification. LC-MS 467 [M+H]$^+$.

Step-4: Preparation of 4-(4-fluoro-3-(piperazine-1-carbonyl)benzyl)phthalazin-1(2H)-one To a stirred solution of tert-butyl 4-(2-fluoro-5-((4-oxo-3,4-dihydrophthalazin-1-yl)methyl)benzoyl)piperazine-1-carboxylate (0.150 g, 0.321 mmol) was added 2N aqueous HCl in MeOH (5 mL) at RT and the mixture was stirred at RT for 16 h. The reaction was monitored by LC-MS. Upon completion, the reaction mixture was concentrated under reduced pressure to afford 4-(4-fluoro-3-(piperazine-1-carbonyl)benzyl)phthalazin-1(2H)-one as an HCl salt. LC-MS 367 [M+H]+.

Step-1a: Preparation of methyl 6-aminohexanoate

To 6-aminohexanoic acid (10.0 g, 76.23 mmol) was added 2N aqueous HCl in MeOH (30 mL) at RT and the mixture was stirred for 16 h. The reaction was monitored by $^1$H NMR. Upon completion, the reaction mixture was concentrated under reduced pressure to afford methyl 6-aminohexanoate which was triturated with diethyl ether and pentane (1:3) to obtain the title compound as a hydrochloride salt. $^1$H NMR (400 MHz, MeOD-d$_4$) δ 3.66 (s, 3H), 2.92 (t, J=7.67 Hz, 2H), 2.37 (t, J=7.45 Hz, 2H), 1.62-1.71 (m, 6H), 1.37-1.45 (m, 2H).

Step-1b: Preparation of methyl 6-(4-(3-(4-cyano-3-(trifluoromethyl)phenyl)-5,5-dimethyl-4-oxo-2-thioxoimidazolidin-1 yl)-2-fluorobenzamido)hexanoate To a stirred solution of 4-(3-(4-cyano-3-(trifluoromethyl)phenyl)-5,5-dimethyl-4-oxo-2-thioxoimidazolidin-1-yl)-2-fluorobenzoic acid (3 g, 6.64 mmol) in DMF (25 mL) was added HATU (5.05 g, 13.29 mmol, 2 eq) at 0° C. and the mixture was stirred for 30 min. DIPEA (5.78 mL, 33.2 mmol, 5 eq) and 6-aminohexanoate (1.81 g, 9.96 mmol, 1.5 eq) were then successively added to the reaction mixture and the mixture was stirred at RT for 4 h. The reaction was monitored by TLC and LC-MS. After completion, the reaction was diluted with EtOAc (250 mL). The organic layer was washed with saturated aqueous NaHCO$_3$ (100 mL), saturated aqueous NH$_4$Cl (100 mL), water (100 mL), brine (50 mL), dried over anhydrous Na$_2$SO$_4$, filtered and concentrated under reduced. The crude material was purified by CombiFlash to afford methyl 6-(4-(3-(4-cyano-3-(trifluoromethyl)phenyl)-5,5-dimethyl-4-oxo-2-thioxoimidazolidin-1-yl)-2-fluorobenzamido)hexanoate. LC-MS 579 [M+H]$^+$.

Step-1c: Preparation of 6-(4-(3-(4-cyano-3-(trifluoromethyl)phenyl)-5,5-dimethyl-4-oxo-2-thioxoimidazolidin-1 yl)-2-fluorobenzamido)hexanoic acid To a stirred solution of methyl 6-(4-(3-(4-cyano-3-(trifluoromethyl)phenyl)-5,5-dimethyl-4-oxo-2-thioxoimidazolidin-1-yl)-2-fluorobenzamido)hexanoate (3.5 g, 6.05 mmol) in THF (30 mL) and MeOH (15 mL) was added LiOH·10H$_2$O (2.53 g, 60.5 mmol, 10 eq). The solids were dissolved in water (5 mL) at RT and the mixture was stirred at RT for 16 h. The reaction was monitored by TLC. After completion, the reaction mixture was concentrated under reduced pressure. The residue obtained was diluted with water (30 mL) and acidified using 2N aqueous HCl (pH ~2). The aqueous layer was then extracted with EtOAc (300 mL×3). The combined organic layers were washed with brine (200 mL), dried over Na$_2$SO$_4$, filtered and concentrated under reduced pressure to afford 6-(4-(3-(4-cyano-3-(trifluoromethyl)phenyl)-5,5-dimethyl-4-oxo-2-thioxoimidazolidin-1-yl)-2-fluorobenzamido)hexanoic acid which was taken to next step without further purification. LC-MS 565 [M+H]$^+$. $^1$H NMR (400 MHz, DMSO-d$_6$) δ 8.51 (br. s., 1H), 8.41 (d, J=7.83 Hz, 1H), 8.30 (s, 1H), 8.08 (d, J=8.31 Hz, 1H), 7.75 (t, J=7.83 Hz, 1H), 7.42 (d, J=10.27 Hz, 1H), 7.33 (d, J=7.83 Hz, 1H), 3.25 (d, J=6.36 Hz, 2H), 2.72-66 (m, 4H), 2.51-2.4 (m, 2H), 2.21 (t, J=7.58 Hz, 2H), 1.54 (s, 6H), 1.34 (d, J=6.85 Hz, 2H).

Step-5: Preparation of 4-(3-(4-cyano-3-(trifluoromethyl)phenyl)-5,5-dimethyl-4-oxo-2-thioxoimidazolidin-1-yl)-2-fluoro-N-(6-(4-(2-fluoro-5-((4-oxo-3,4-dihydrophthalazin-1-yl)methyl)benzoyl)piperazin-1-yl)-6-oxohexyl)benzamide (Compound 1.1)

To a stirred solution of 6-(4-(3-(4-cyano-3-(trifluoromethyl)phenyl)-5,5-dimethyl-4-oxo-2-thioxoimidazolidin-1-yl)-2-fluorobenzamido)hexanoic acid (0.150 g, 0.265 mmol) in DMA (4 mL) was added HBTU (0.12 g, 0.319 mmol, 1.2 eq) at 0° C. and the mixture was stirred for 10 min. DIPEA (0.16 mL, 0.93 mmol, 3.5 eq) and 4-(4-fluoro-3-(piperazine-1-carbonyl)benzyl)phthalazin-1(2H)-one hydrochloride salt (0.128 g, 0.319 mmol, 1.2 eq) were then successively added to the reaction mixture and the mixture was stirred at RT for 1.5 h. The reaction was monitored by TLC and LC-MS. After completion, water (10 mL) was added and the resulting precipitate was filtered via a Buchner funnel. The product obtained was washed with water (10 mL×2) and n-pentane (10 mL×2), dried under reduced pressure to obtain a crude product which was purified by reversed-phase HPLC to afford Compound 1.1. LC-MS 913 [M+H]$^+$. $^1$H NMR (400 MHz, CD$_3$OD-d$_4$) δ 8.36 (d, J=7.8 Hz, 1H), 8.16 (d, J=7.8 Hz, 2H), 7.99 (dd, J=7.9, 2.1 Hz, 1H), 7.94 (dd, J=8.3, 3.4 Hz, 1H), 7.91-7.78 (m, 3H), 7.47 (p, J=4.5, 4.0 Hz, 1H), 7.36 (td, J=9.2, 8.8, 5.1 Hz, 3H), 7.15 (td, J=9.0, 2.4 Hz, 1H), 4.37 (s, 2H), 3.83-3.69 (m, 2H), 3.69-3.62 (m, 2H), 3.50 (dt, J=9.2, 4.9 Hz, 2H), 3.42 (q, J=6.4, 6.0 Hz, 2H), 3.35 (m, 2H), 3.28 (m, 2H), 2.48 (t, J=7.3 Hz, 1H), 2.41 (t, J=7.5 Hz, 1H), 1.67 (q, J=7.5 Hz, 4H), 1.59 (s, 6H), 1.53-1.40 (m, 2H).

Example S-2. Preparation of 4-(3-(4-(6-(((5S,8R,9S,10S,13S,14S,17S)-10,13-dimethyl-3-oxohexadecahydro-1H-cyclopenta[a]phenanthren-17-yl)oxy)hexanoyl)piperazine-1-carbonyl)-4-fluorobenzyl)phthalazin-1(2H)-one (Compound 1.2)

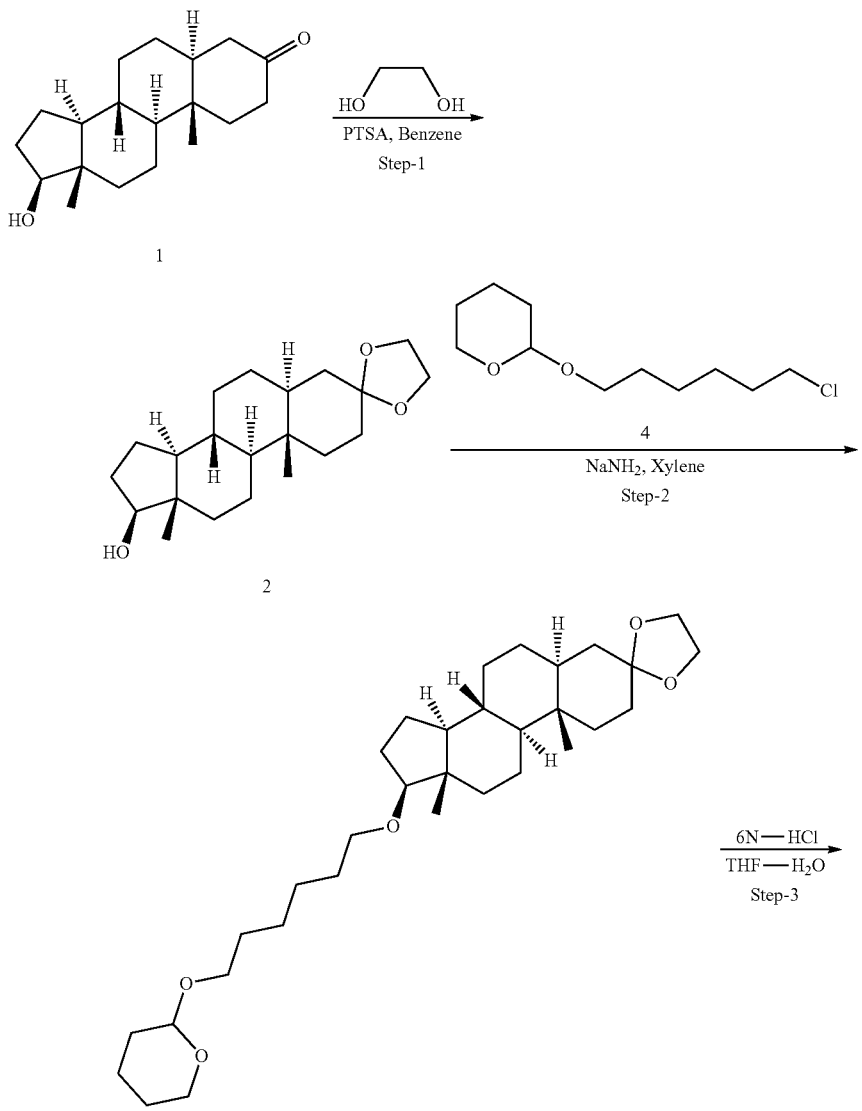

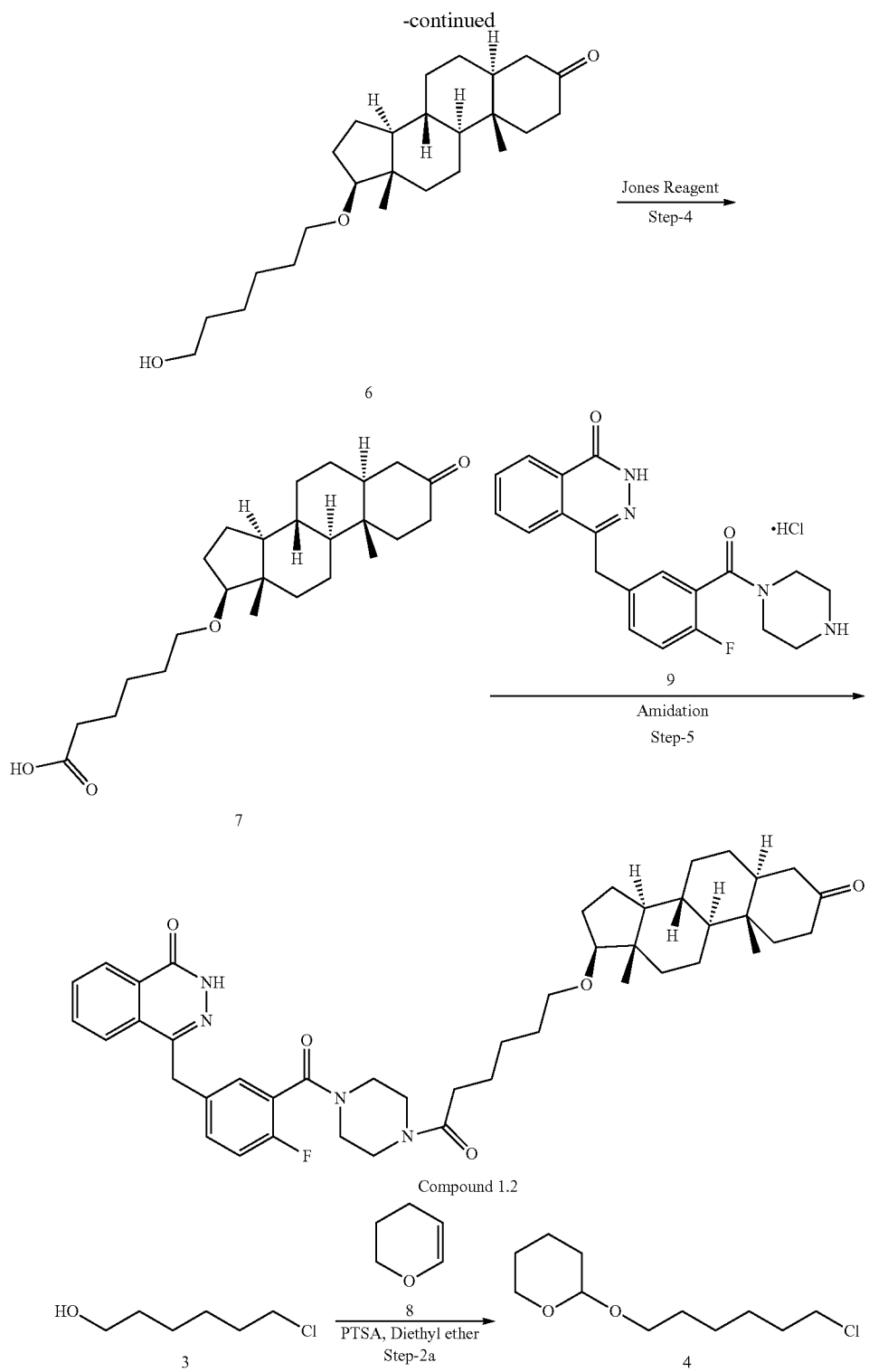

Step-1: Preparation of (5S,8R,9S,10S,13S,14S,17S)-10,13-dimethylhexadecahydrospiro[cyclopenta[a]phenanthrene-3,2'-[1,3]dioxolan]-17-ol To a stirred solution of (5 S,8R,9S,10S,13S,14S,17S)-17-hydroxy-10,13-dimethyltetradecahydro-1H-cyclopenta[a]phenanthren-3(2H)-one (3 g, 10.3 mmol) in benzene (100 mL) was added PTSA (0.982 g, 5.1 mmol, 0.5 eq) followed by addition of ethylene glycol (2.88 g, 51.61 mmol, 5 eq) at RT. The resultant mixture was heated to 120° C. using a Dean-Stark apparatus for 16 h. The reaction was monitored by TLC. Upon completion, the reaction mixture was diluted with water (200 mL) and extracted with EtOAc (350 mL). The organic layer was washed with saturated NaHCO₃ solution (100 mL), water (200 mL), brine (100 mL) dried over Na$_2$SO$_4$, filtered and concentrated under reduced pressure to afford (5 S,8R,9S,10S,13S,14S,17S)-10,13-dimethylhexadecahydrospiro[cyclopenta[a]phenanthrene-3,2'-[1,3]dioxolan]-17-ol. LC-MS 335 [M+H]+. $^1$H NMR (400 MHz, DMSO-d$_6$) δ 4.40 (d, J=5.26 Hz, 1H), 3.81 (s, 3H), 3.37-3.45 (m, 2H), 1.82 (br. s., 2H), 1.70 (d, J=12.72 Hz, 2H), 1.59 (d, J=13.15 Hz, 2H), 1.52 (d, J=10.52 Hz, 3H), 1.35 (br. s., 1H), 1.23-1.33 (m, 3H), 1.03-1.21 (m, 5H), 0.87 (dt, J=7.89, 19.95 Hz, 4H), 0.76 (s, 3H), 0.61 (s, 3H).

Step-2a: Preparation of 2-(6-chlorohexyloxy)tetrahydro-2-1-1 pyran

To a stirred solution of 6-chlorohexan-1-ol (10 g, 73.158 mmol) in diethyl ether (100 mL) was added pTSA (0.05 g, 0.365 mmol, 0.005 eq) followed by addition of 3,4-dihydro-2H-pyran (8.4 g, 102.48 mmol, 1.4 eq). The resulting reaction mixture was stirred at RT for 16 h. The reaction was monitored by TLC. Upon completion, the reaction mixture was diluted with diethyl ether (350 mL). The organic layer was washed with 20% KOH solution (100 mL), water (300 mL), brine (200 mL) dried over Na$_2$SO$_4$, filtered and concentrated under reduced pressure to afford 2-(6-chlorohexyloxy)tetrahydro-2H-pyran. $^1$H NMR (400 MHz, DMSO-d$_6$) δ 4.50 (br. s., 1H), 4.25 (t, J=6.80 Hz, 2H), 4.20 (s, 1H), 4.00-4.08 (m, 2H), 3.66-3.74 (m, 2H), 3.59 (dd, J=6.36, 16.01 Hz, 2H), 2.66 (s, 2H), 1.81-1.90 (m, 2H), 1.67 (br. s., 1H), 1.38-1.45 (m, 2H), 1.20-1.27 (m, 2H), 1.17 (t, J=7.02 Hz, 2H).

Step-2: Preparation of (5S,8R,9S,10S,13S,14S,17S)-10,13-dimethyl-17-(6-(tetrahydro-2H-pyran-2-yloxy) hexyloxy) hexadecahydrospiro[cyclopenta[a]phenanthrene-3,2'-[1,3]dioxolane]

To a stirred solution of (5S,8R,9S,10S,13S,14S,17S)-10,13-dimethylhexadecahydrospiro[cyclopenta[a]phenanthrene-3,2'-[1,3]dioxolan]-17-ol (2 g, 5.97 mmol) in xylene (50 mL) was added NaNH$_2$ (50% suspension in toluene, 1.4 mL) and the mixture was heated at 150° C. for 1 h. The reaction mixture was gradually cooled to RT, 2-(6-chlorohexyloxy) tetrahydro-2H-pyran (2.8 mL) was added to it and the resultant mixture was again heated to 150° C. for 16 h. The reaction was monitored by TLC.

Upon completion, the mixture was cooled to RT, quenched slowly with ice cold water (250 mL) and extracted with EtOAc (300 mL). The organic layer was washed with water (100 mL×2), brine (100 mL) dried over Na$_2$SO$_4$, filtered and concentrated under reduced pressure to obtain a crude product which was purified by CombiFlash chromatography (Teledyne Isco Rf+); compound eluting 30% EtOAc/hexane to afford (5S,8R,9S,10S,13S,14S,17S)-10,13-dimethyl-17-(6-(tetrahydro-2H-pyran-2-yloxy)hexyloxy)hexadecahydrospiro[cyclopenta[a]phenanthrene-3,2'-[1,3]dioxolane]. $^1$H NMR (400 MHz, CDCl3) δ 4.57 (d, J=3.95 Hz, 1H), 3.91-3.95 (m, 4H), 3.82-3.91 (m, 2H), 3.73 (td, J=6.80, 9.65 Hz, 2H), 3.42-3.53 (m, 3H), 3.33-3.42 (m, 3H), 3.26 (t, J=8.55 Hz, 2H), 1.91-2.01 (m, 2H), 1.75-1.90 (m, 3H), 1.46-1.74 (m, 13H), 1.31-1.42 (m, 6H), 1.07-1.28 (m, 4H), 0.83-0.97 (m, 4H), 0.81 (s, 4H), 0.70-0.76 (m, 4H), 0.07 (s, 3H), 0.00 (s, 3H).

Step-3: Preparation of (5S,8R,9S,10S,13S,14S,17S)-17-(6-hydroxyhexyloxy)-10,13-dimethyltetradecahydro-1H-cyclopenta[a]phenanthren-3(2H)-one To a stirred solution of (5S,8R,9S,10S,13S,14S,17S)-10,13-dimethyl-17-(6-(tetrahydro-2H-pyran-2-yloxy)hexyloxy)hexadecahydrospiro[cyclopenta[a]phenanthrene-3,2'-[1,3]dioxolane] (1 g, 1.92 mmol) in THF (25 mL) water (5 mL) was added 6N HCl (15 mL) at RT and the resultant reaction mixture was stirred at RT for 16 h. The reaction was monitored by TLC. Upon completion, the reaction mixture was diluted with water (150 mL) and basified using with saturated NaHCO$_3$ solution (pH ~8). The aqueous layer was then extracted with EtOAc (200 mL×3). The organic layer was washed with saturated NaHCO$_3$ solution (100 mL), water (100 mL), brine (100 mL) dried over Na$_2$SO$_4$, filtered and concentrated under reduced pressure to afford (5S,8R,9S,10S,13S,14S,17S)-17-(6-hydroxyhexyloxy)-10,13-dimethyltetradecahydro-1H-cyclopenta[a]phenanthren-3(2H)-one which was used in the next step without further purification. $^1$H NMR (400 MHz, CDCl3) δ 4.90 (br. s., 1H), 4.12 (d, J=7.45 Hz, 1H), 4.00 (br. s., 1H), 3.64 (t, J=6.58 Hz, 3H), 3.49-3.58 (m, 1H), 3.37-3.47 (m, 3H), 3.27 (t, J=8.55 Hz, 1H), 2.22-2.43 (m, 3H), 2.10 (br. s., 1H), 1.93-2.07 (m, 2H), 1.90 (d, J=11.84 Hz, 2H), 1.82 (d, J=7.89 Hz, 2H), 1.70 (d, J=10.09 Hz, 2H), 1.48 (d, J=4.38 Hz, 2H), 1.30-1.42 (m, 8H), 1.22-1.29 (m, 2H), 1.01 (s, 3H), 0.77 (s, 3H).

Step-4: Preparation of 6-((5S,8R,9S,10S,13S,14S,17S)-10,13-dimethyl-3-oxohexadecahydro-1H-cyclopenta[a]phenanthren-17-yloxy)hexanoic acid To a stirred solution of (5S,8R,9S,10S,13S,14S,17S)-17-(6-hydroxyhexyloxy)-10,13-dimethyltetradecahydro-1H-cyclopenta[a]phenanthren-3(2H)-one (0.1 g, 0.256 mmol) in acetone (5 mL) was added Jones reagent (0.5 mL) at 0° C. dropwise over a period of 20 min. The resultant mixture was stirred at 0° C. for 5 min. The reaction was monitored by TLC. After completion, water (10 mL) was added and the resulting precipitate was filtered over Buchner funnel. The product obtained was washed with water (5 mL×2) and n-pentane (5 mL×2), dried under vacuum to afford 6 ((5S,8R,9S,10S,13S,14S,17S)-10,13-dimethyl-3-oxohexadecahydro-1H-cyclopenta[a]phenanthren-17-yloxy)hexanoic acid which was taken to next step without further purification. $^1$H NMR (400 MHz, DMSO-d$_6$) δ 3.19-3.28 (m, 3H), 2.24-2.35 (m, 2H), 2.18 (t, J=7.24 Hz, 2H), 2.08 (d, J=13.59 Hz, 2H), 1.84-1.95 (m, 3H), 1.79 (d, J=10.52 Hz, 2H), 1.61 (d, J=13.59 Hz, 2H), 1.40-1.54 (m, 8H), 1.22-1.38 (m, 8H), 1.19 (br. s., 1H), 1.09-1.18 (m, 2H), 0.97 (s, 3H), 0.69 (s, 3H).

Step-5: Preparation of 4-(3-(4-(6-((5S,8R,9S,10S,13S,14S,17S)-10,13-dimethyl-3-oxohexadecahydro-1H-cyclopenta[a]phenanthren-17-yloxy)hexanoyl) piperazine-1-carbonyl)-4-fluorobenzyl)phthalazin-1 (2H)-one (Compound 2)

To a stirred solution of 6-((5S,8R,9S,10S,13S,14S,17S)-10,13-dimethyl-3-oxohexadecahydro-1H-cyclopenta[a]phenanthren-17-yloxy)hexanoic acid (0.1 g, 0.247 mmol) in DMA (5 mL) was added HBTU (0.112 g, 0.296 mmol, 1.2 eq) at 0° C. and the resulting reaction mixture was stirred for 10 min. DIPEA (0.94 mL, 0.544 mmol, 2.2 eq) and 4-(4-fluoro-3-(piperazine-1-carbonyl)benzyl)phthalazin-1(2H)-one (0.108 g, 0.296 mmol, 1.2 eq) were then successively added to the mixture and the mixture was stirred at RT for 1 h. The reaction was monitored by TLC & LC-MS. After completion, water (10 mL) was added and the resulting precipitate was filtered via a Buchner funnel. The product obtained was washed with water (5 mL×2) and n-pentane (5 mL×2), dried under vacuum to obtain a crude product which was purified by reverse phase HPLC to afford Compound 1.2. LC-MS 753 [M+H]+. ¹H NMR (400 MHz, DMSO-$d_6$) δ 8.37 (d, J=7.6 Hz, 1H), 7.99-7.91 (m, 1H), 7.91-7.79 (m, 2H), 7.48 (t, J=6.4 Hz, 1H), 7.36 (d, J=6.1 Hz, 1H), 7.21-7.11 (m, 1H), 4.38 (s, 2H), 3.82-3.61 (m, 4H), 3.47 (ddt, J=22.1, 14.2, 6.3 Hz, 4H), 3.37-3.33 (m, 2H), 2.53-2.30 (m, 4H), 2.26-2.16 (m, 1H), 2.08-1.95 (m, 3H), 1.88 (t, J=11.6 Hz, 1H), 1.75-1.50 (m, 10H), 1.50-1.13 (m, 12H), 1.05 (s, 3H), 1.01-0.86 (m, 2H), 0.76 (d, J=9.0 Hz, 4H).
Example S-3. Preparation of 4-(3-(4-cyano-3-(trifluoromethyl)phenyl)-5,5-dimethyl-4-oxo-2-thioxoimidazolidin-1-yl)-2-fluoro-N-(6-((4-((8S,9R)-5-fluoro-9-(1-methyl-1H-1,2,4-triazol-5-yl)-3-oxo-2,7,8,9-tetrahydro-3H-pyrido[4,3,2-de]phthalazin-8-yl)phenyl)amino)-6-oxohexyl)benzamide (Compound 1.3)
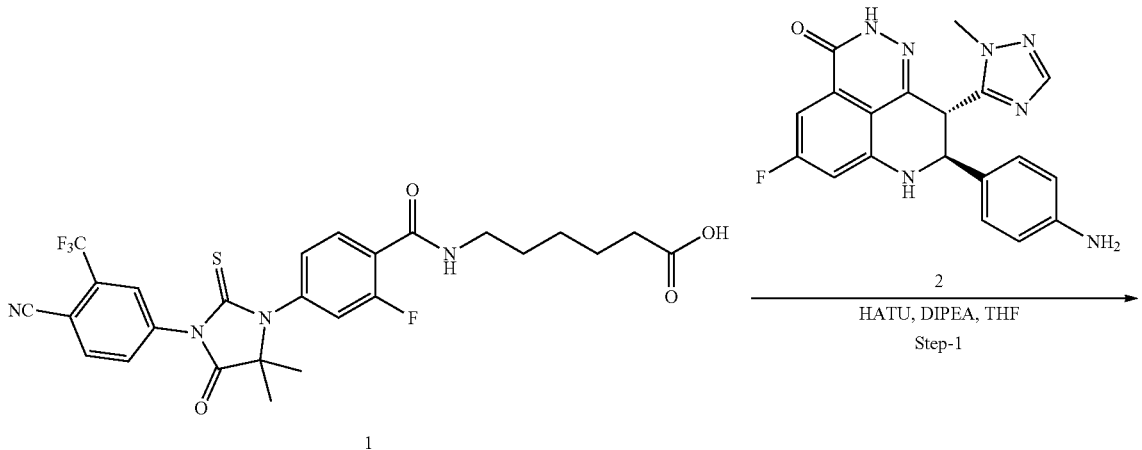
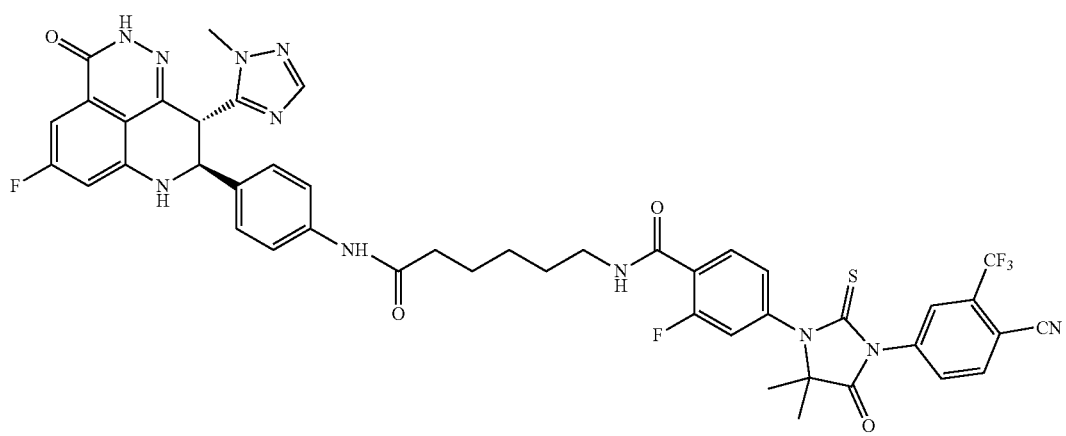
Compound 1.3
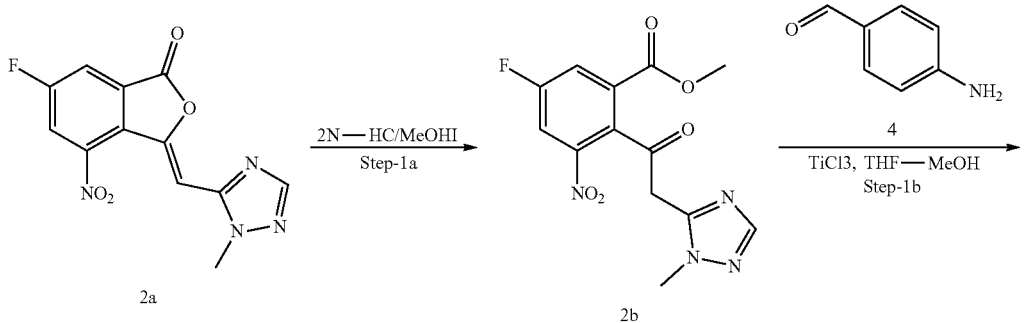

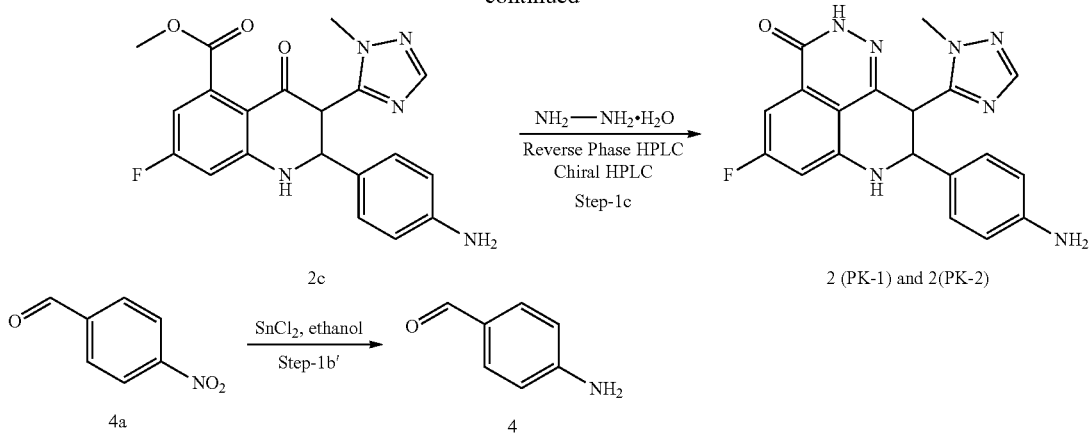

Step-1a: Preparation of methyl 5-fluoro-2-(2-(1-methyl-1H-1,2,4-triazol-5 yl)acetyl)-3-nitrobenzoate (Z)-6-fluoro-3-((1-methyl-1H-1,2,4-triazol-5-yl)methylene)-4-nitroisobenzofuran-1(3H)-one (10 g, 34.48 mmol) was added to a reaction vessel containing 2N aqueous HCl in MeOH (50 mL) at RT and the mixture was stirred at RT for 16 h. The reaction was monitored by TLC. Upon completion, the reaction mixture was concentrated under reduced pressure to obtain a sticky solid which was further lyophilized to afford methyl 5-fluoro-2-(2-(1-methyl-1H-1,2,4-triazol-5-yl) acetyl)-3-nitrobenzoate as a hydrochloride salt. LC-MS 323 [M+H]$^+$.

Step-1b': Preparation of 4-aminobenzaldehyde

To a stirred solution of 4-nitrobenzaldehyde (5 g, 33.1 mmol) in ethanol (50 mL) was added SnCl$_2$ (37.35 g, 165.5 mmol, 5 eq) at 0° C. and the mixture was heated at 80° C. for 1 h. The reaction was monitored by TLC. Upon completion, the reaction mixture was concentrated under reduced pressure to afford a crude residue which was suspended in water (100 mL) and basified using NaHCO$_3$ solution (pH~8). The aqueous layer was then extracted with EtOAc (500 mL×3). The combined organic layers were washed with saturated NaHCO$_3$ solution (300 mL), water (200 mL), brine (150 mL) dried over Na$_2$SO$_4$, filtered and concentrated under reduced pressure to afford 4-aminobenzaldehyde which was used in the next step without further purification. LC-MS 122 [M+H]$^+$.

Step-1b: Preparation of methyl 2-(4-aminophenyl)-7-fluoro-3-(1-methyl-1H-1,2,4-triazol-5-yl)-4-oxo-1,2,3,4-tetrahydroquinoline-5-carboxylate To a stirred solution of methyl 5-fluoro-2-(2-(1-methyl-1H-1,2,4-triazol-5-yl) acetyl)-3-nitrobenzoate hydrochloride salt (5.6 g, 15.6 mmol) in THF (60 mL) MeOH (10 mL) was added 4-aminobenzaldehyde (3.8 g, 31.2 mmol, 2 eq). Titanium (III) chloride (20% w/v solution in 2N-HCl (50 mL) was then added to the mixture at RT dropwise over a period of 20 min and the mixture was stirred at 50° C. for 3 h. The reaction was monitored by TLC. Upon completion, the solvent is removed under reduced pressure to obtain crude residue which was dissolved in water (300 mL) and basified using saturated NaHCO$_3$ solution (pH~8). The aqueous layer was then extracted with EtOAc (400 mL×3). The combined organic layers were washed saturated NaHCO$_3$ solution (300 mL), water (300 mL), brine (100 mL) dried over Na$_2$SO$_4$, filtered and concentrated under reduced pressure to afford a crude product which was purified by CombiFlash chromatography (Teledyne Isco Rf+); compound eluting 40% EtOAc/hexane to afford methyl 2-(4-aminophenyl)-7-fluoro-3-(1-methyl-1H-1,2,4-triazol-5-yl)-4-oxo-1,2,3,4-tetrahydroquinoline-5-carboxylate. LC-MS 396 [M+H]$^+$.

Step-1c: Preparation of 8-(4-aminophenyl)-5-fluoro-9-(1-methyl-1H-1,2,4-triazol-5-yl)-8,9-dihydro-2H-pyrido[4,3,2-de]phthalazin-3(7H)-one To a stirred suspension of methyl 2-(4-aminophenyl)-7-fluoro-3-(1-methyl-1H-1,2,4-triazol-5-yl)-4-oxo-1,2,3,4-tetrahydroquinoline-5-carboxylate (1.5 g, 37.9 mmol) in methanol (20 mL) was added hydrazine hydrate (3 mL) at 0° C. and the resultant mixture was stirred at RT for 4 h. The reaction was monitored by TLC. After completion, the reaction mixture was concentrated under reduced pressure and water (20 mL) was added. The resulting precipitate was filtered over Buchner funnel. The product obtained was washed with water (10 mL×2) and n-pentane (10 mL×2), dried under reduced pressure to afford a crude product which was purified by reverse phase chromatography to afford of 8-(4-aminophenyl)-5-fluoro-9-(1-methyl-1H-1,2,4-triazol-5-yl)-8,9-dihydro-2H-pyrido[4,3,2-de]phthalazin-3(7H)-one as a racemic mixture. The compound obtained was further separated by chiral chromatography to afford 4-(3-(4-cyano-3-(trifluoromethyl)phenyl)-5,5-dimethyl-4-oxo-2-thioxoimidazolidin-1-yl)-2-fluoro-N-(6-(4-((8 S, 9R)-5-fluoro-9-(1-methyl-1H-1,2,4-triazol-5-yl)-3-oxo-3,7,8,9-tetrahydro-2H-pyrido[4,3,2-de]phthalazin-8-yl) phenylamino)-6-oxohexyl)benzamide (PK-1) (0.300 g) and 4-(3-(4-cyano-3-(trifluoromethyl)phenyl)-5,5-dimethyl-4-oxo-2-thioxoimidazolidin-1-yl)-2-fluoro-N-(6-(4-((8 S, 9R)-5-fluoro-9-(1-methyl-1H-1,2,4-triazol-5-yl)-3-oxo-3,7,8,9-tetrahydro-2H-pyrido[4,3,2-de]phthalazin-8-yl)phenylamino)-6-oxohexyl)benzamide (PK-2).

(PK-1 was used for Compound 1.3 and PK-2 was used for ent-Compound 1.3)

PK-1: LC-MS 378 [M+H]$^+$. $^1$H NMR (400 MHz, DMSO-d$_6$) δ 12.30 (s, 1H), 7.78 (s, 1H), 7.56 (s, 1H), 7.02 (t, J=6.7 Hz, 3H), 6.90 (d, J=11.2 Hz, 1H), 6.45 (d, J=7.9 Hz, 2H), 5.10 (s, 2H), 4.85 (d, J=11.4 Hz, 1H), 4.72 (d, J=11.4 Hz, 1H), 3.62 (s, 3H).

PK-2: LC-MS 378 [M+H]⁺. ¹H NMR (400 MHz, DMSO-d₆) δ 12.29 (s, 1H), 7.78 (s, 1H), 7.56 (s, 1H), 7.02 (t, J=6.7 Hz, 3H), 6.89 (d, J=11.2 Hz, 1H), 6.44 (d, J=7.9 Hz, 2H), 5.10 (s, 2H), 4.85 (d, J=11.4 Hz, 1H), 4.71 (d, J=11.4 Hz, 1H), 3.61 (s, 3H).

Step-1: Preparation of 4-(3-(4-cyano-3-(trifluoromethyl)phenyl)-S,S-dimethyl-4-oxo-2-thioxoimidazolidin-1 yl)-2-fluoro-N-(6-(4-(5-fluoro-9-(1-methyl-1H-1,2,4-triazol-5 yl)-3-oxo-3,7,8,9-tetrahydro-2H pyrido[4,3,2-de]phthalazin-8 yl)phenylamino)-6-oxohexyl)benzamide (Compound 1.3)

To a stirred solution of 6-(4-(3-(4-cyano-3-(trifluoromethyl)phenyl)-5,5-dimethyl-4-oxo-2-thioxoimidazolidin-1-yl)-2-fluorobenzamido)hexanoic acid (0.125 g, 0.221 mmol) in DMF (7 mL) was added HATU (0.168 g, 0.442 mmol, 2 eq) at 0° C. and the resulting mixture was stirred for 30 min. DIPEA (0.19 mL, 1.11 mmol, 5 eq) and 8-(4-aminophenyl)-5-fluoro-9-(1-methyl-1H-1,2,4-triazol-5-yl)-8,9-dihydro-2H-pyrido[4,3,2-dc]phthalazin-3(7H)-one (PK-1) (0.10 g, 0.265 mmol, 1.2 eq) were then successively added to the reaction mixture and the resultant mixture was stirred at RT for 4 h. The reaction was monitored by TLC. Upon completion, the reaction mixture was diluted with water (50 mL) and extracted using EtOAc (100 mL×2). The combined organic layer were washed with saturated NaHCO₃ solution (100 mL), saturated NH₄Cl solution (100 mL), water (100 mL), brine (50 mL) dried over Na₂SO₄, filtered and concentrated under reduced pressure to afford a crude product which was purified by reverse phase HPLC to afford Compound 1.3. LC-MS 924 [M+H]⁺. ¹H NMR (400 MHz, CD₃OD-d₄) δ 8.15 (d, J=9.1 Hz, 2H), 7.97 (d, J=8.5 Hz, 1H), 7.87 (d, J=3.0 Hz, 1H), 7.82 (t, J=8.8 Hz, 1H), 7.56-7.48 (m, 2H), 7.34 (d, J=8.4 Hz, 4H), 7.19 (dd, J=7.1, 4.7 Hz, 1H), 6.90 (d, J=10.4 Hz, 1H), 3.58 (d, J=3.0 Hz, 3H), 3.46-3.36 (m, 2H), 2.38 (d, J=7.6 Hz, 2H), 1.93 (s, 2H), 1.80-1.64 (m, 6H), 1.59 (d, J=2.8 Hz, 6H), 1.48 (ddt, J=14.6, 10.8, 4.6 Hz, 2H).

Example S-4. Preparation of 4-(3-(4-cyano-3-(trifluoromethyl)phenyl)-5,5-dimethyl-4-oxo-2-thioxoimidazolidin-1-yl)-2-fluoro-N-(6-((4-((8R,9S)-5-fluoro-9-(1-methyl-1H-1,2,4-triazol-5-yl)-3-oxo-2,7,8,9-tetrahydro-3H-pyrido[4,3,2-de]phthalazin-8-yl)phenyl)amino)-6-oxohexyl)benzamide (Compound ent-1.3)

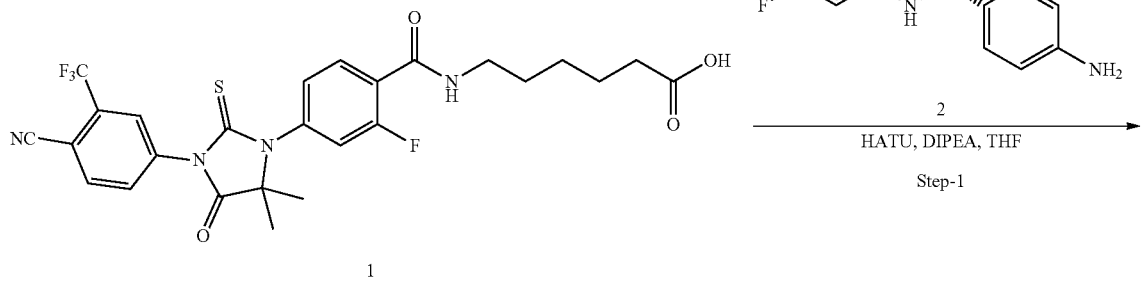

1

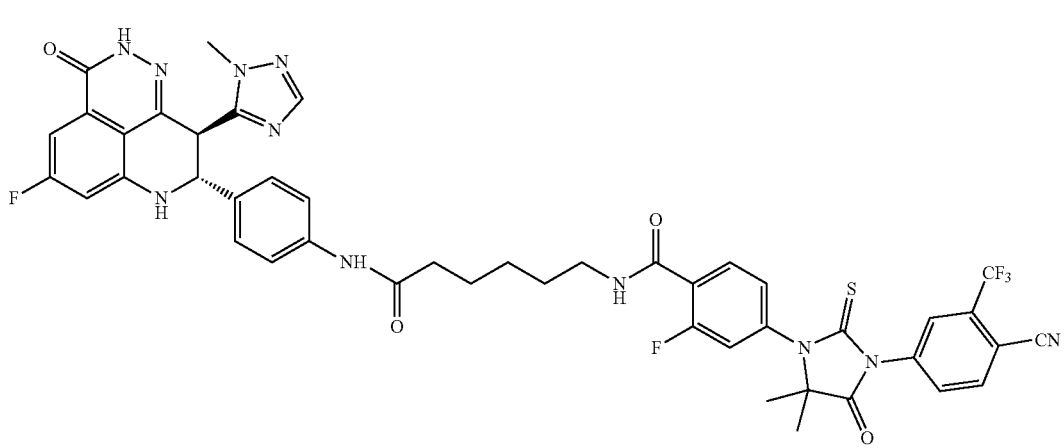

Compound ent-1.3

Step-1: Preparation of 4-(3-(4-cyano-3-(trifluoromethyl)phenyl)-5,5-dimethyl-4-oxo-2-thioxoimidazolidin-1 yl)-2-fluoro-N-(6-(4-(5-fluoro-9-(1-methyl-1H-1,2,4-triazol-5 yl)-3-oxo-3,7,8,9-tetrahydro-2H-pyrido[4,3,2-de]phthalazin-8-yl)phenylamino)-6-oxohexyl)benzamide To a stirred solution of 6-(4-(3-(4-cyano-3-(trifluoromethyl)phenyl)-5,5-dimethyl-4-oxo-2-thioxoimidazolidin-1-yl)-2-fluorobenzamido)hexanoic acid (0.210 g, 0.371 mmol) in DMF (8 mL) was added HATU (0.282 g, 0.743 mmol, 2 eq) at 0° C. and the resulting mixture was stirred for 30 min. DIPEA (0.32 mL, 1.86 mmol, 5 eq) and 8-(4-aminophenyl)-5-fluoro-9-(1-methyl-1H-1,2,4-triazol-5-yl)-8,9-dihydro-2H-pyrido[4,3,2-de]phthalazin-3(7H)-one (PK-2) (0.17 g, 0.446 mmol, 1.2 eq) were then successively added to the reaction mixture and the resultant mixture was stirred at RT for 4 h. The reaction was monitored by TLC. Upon completion, the reaction mixture was diluted with water (50 mL) and extracted using EtOAc (100 mL×2). The combined organic layer were washed with saturated NaHCO₃ solution (100 mL), saturated NH₄Cl solution (100 mL), water (100 mL), brine (50 mL) dried over Na₂SO₄, filtered and concentrated under reduced pressure to afford a crude product which was purified by reverse phase HPLC to afford Compound ent-1.3. LC-MS 924 [M+H]⁺. ¹H NMR (400 MHz, CD₃OD-d₄) δ 8.15 (d, J=9.1 Hz, 2H), 7.98 (dd, J=8.1, 2.1 Hz, 1H), 7.90-7.79 (m, 2H), 7.52 (d, J=8.9 Hz, 2H), 7.34 (d, J=8.4 Hz, 4H), 7.21 (dd, J=9.0, 2.5 Hz, 1H), 6.90 (dd, J=10.8, 2.5 Hz, 1H), 3.59 (d, J=3.2 Hz, 3H), 3.46-3.36 (m, 2H), 2.40 (t, J=7.4 Hz, 2H), 1.93 (s, 2H), 1.72 (dp, J=26.6, 7.3 Hz, 4H), 1.60 (s, 6H), 1.48 (ddt, J=14.6, 10.8, 4.6 Hz, 2H).

Example S-5. Preparation of 6-(((5S,8R,9S,10S,13S,14S,17S)-10,13-dimethyl-3-oxohexadecahydro-1H-cyclopenta[a]phenanthren-17-yl)oxy)-N-(4-(5-fluoro-9-(1-methyl-1H-1,2,4-triazol-5-yl)-3-oxo-2,7,8,9-tetrahydro-3H-pyrido[4,3,2-de]phthalazin-8-yl)phenyl)hexanamide (Compound 1.4)

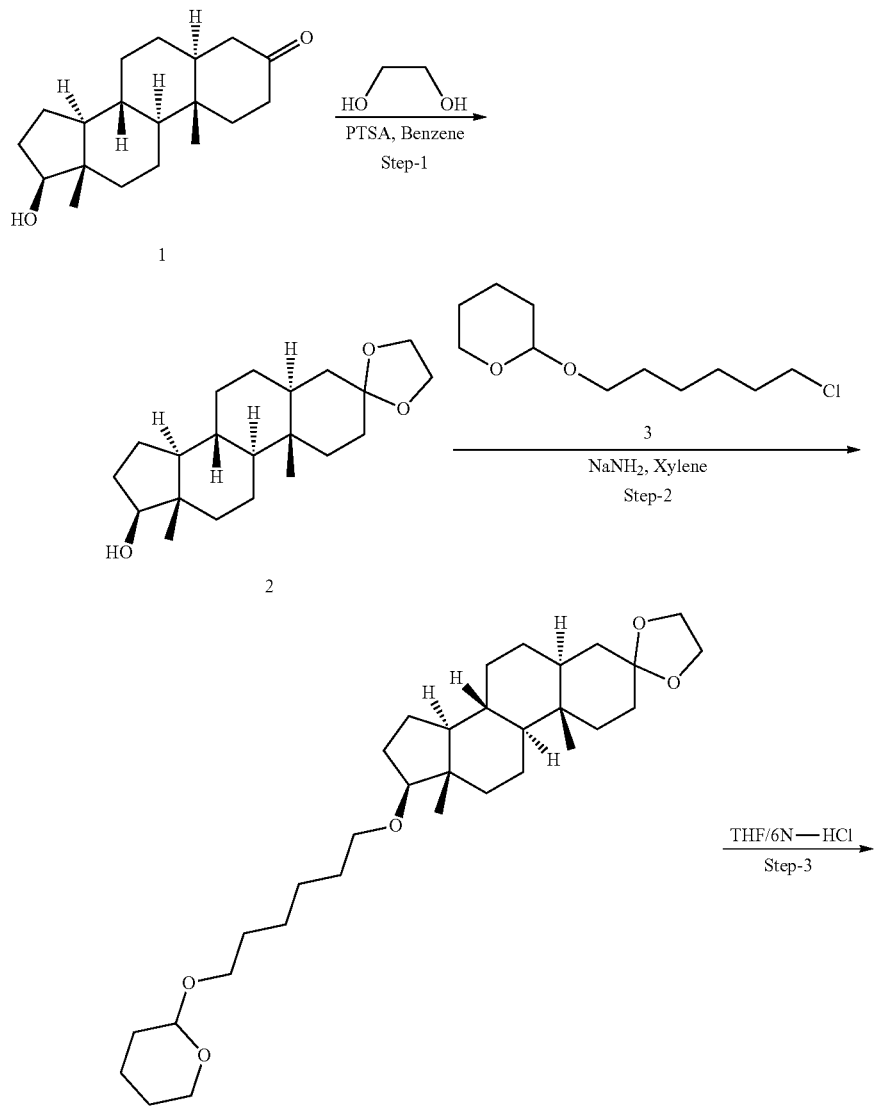

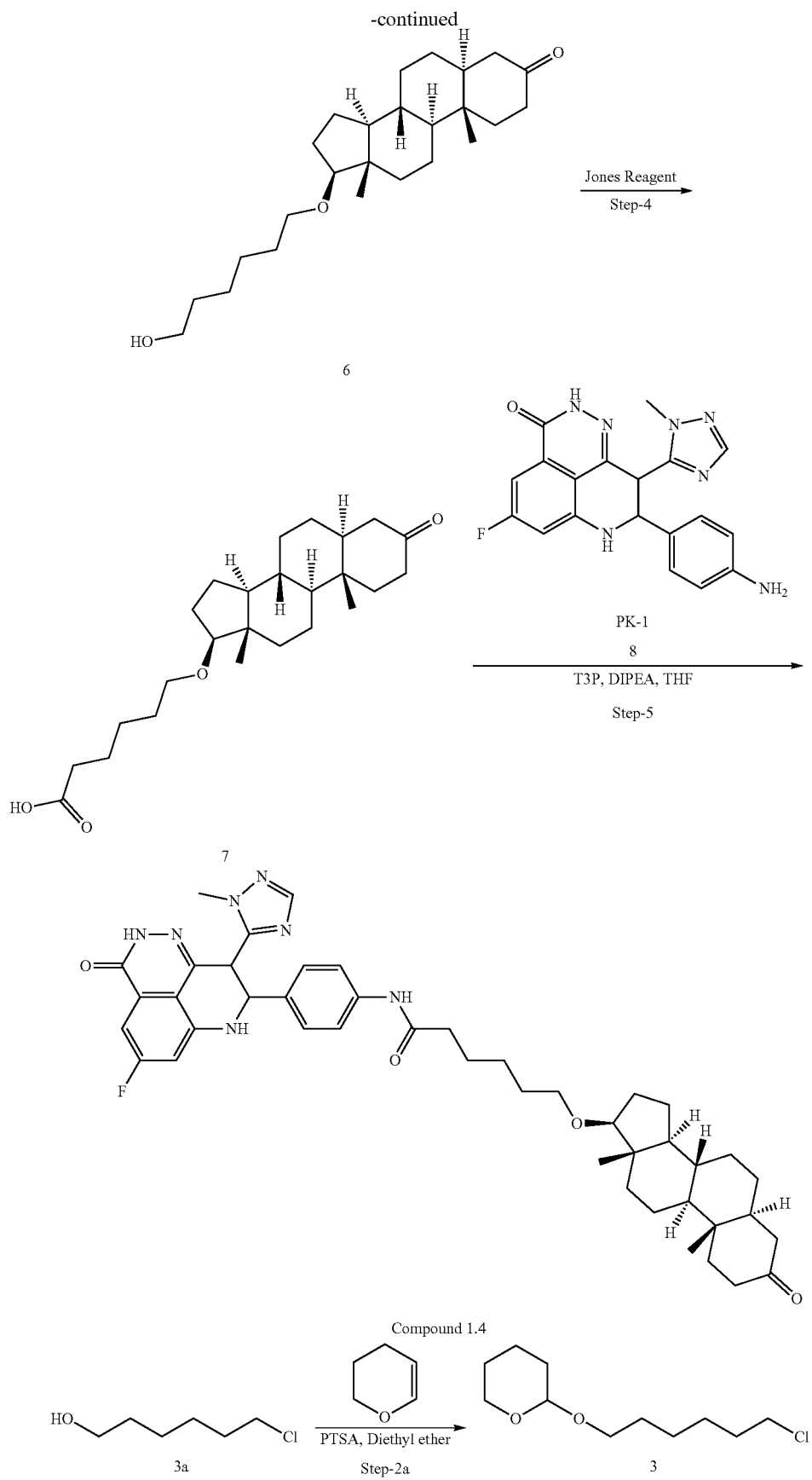

Step-1: Preparation of (5S,8R,9S,10S,13S,14S,17S)-10,13-dimethylhexadecahydrospiro[cyclopenta[a]phenanthrene-3,2'-[1,3]dioxolan]-17-ol To a stirred solution of (5S,8R,9S,10S,13S,14S,17S)-17-hydroxy-10,13-dimethyltetradecahydro-1H-cyclopenta[a]phenanthren-3(2H)-one (3 g, 10.3 mmol) in benzene (100 mL) was added PTSA (0.982 g, 5.1 mmol, 0.5 eq) followed by addition of ethylene glycol (2.88 g, 51.61 mmol, 5 eq) at RT. The resultant mixture was heated at 120° C. using Dean-Stark apparatus for 16 h. Reaction was monitored by TLC. Upon completion, the reaction mixture was diluted with water (200 mL) and extracted with EtOAc (350 mL). The organic layer was washed with saturated NaHCO$_3$ solution (100 mL), water (200 mL), brine (100 mL) dried over Na$_2$SO$_4$, filtered and concentrated under reduced pressure to afford (5S,8R,9S,10S,13S,14S,17S)-10,13-dimethylhexadecahydro spiro[cyclopenta[a]phenanthrene-3,2'-[1,3]dioxolan]-17-ol. LC-MS 335 [M+H]$^+$. $^1$H NMR (400 MHz, DMSO-d$_6$) δ 4.40 (d, J=5.26 Hz, 1H), 3.81 (s, 3H), 3.37-3.45 (m, 2H), 1.82 (br. s., 2H), 1.70 (d, J=12.72 Hz, 2H), 1.59 (d, J=13.15 Hz, 2H), 1.52 (d, J=10.52 Hz, 3H), 1.35 (br. s., 1H), 1.23-1.33 (m, 3H), 1.03-1.21 (m, 5H), 0.87 (dt, J=7.89, 19.95 Hz, 4H), 0.76 (s, 3H), 0.61 (s, 3H).

Step-2a: Preparation of 2-(6-chlorohexyloxy)tetrahydro-2H-pyran

To a stirred solution of 6-chlorohexan-1-ol (10 g, 73.158 mmol) in diethyl ether (100 mL) was added pTSA (0.05 g, 0.365 mmol, 0.005 eq) followed by addition of 3,4-dihydro-2H-pyran (8.4 g, 102.48 mmol, 1.4 eq). The resulting reaction mixture was stirred at RT for 16 h. The reaction was monitored by TLC. Upon completion, the reaction mixture was diluted with diethyl ether (350 mL). The organic layer was washed with 20% KOH solution (100 mL), water (300 mL), brine (200 mL) dried over Na$_2$SO$_4$, filtered and concentrated under reduced pressure to afford 2-(6-chlorohexyloxy)tetrahydro-2H-pyran. $^1$H NMR (400 MHz, DMSO-d$_6$) δ 4.50 (br. s., 1H), 4.25 (t, J=6.80 Hz, 2H), 4.20 (s, 1H), 4.00-4.08 (m, 2H), 3.66-3.74 (m, 2H), 3.59 (dd, J=6.36, 16.01 Hz, 2H), 2.66 (s, 2H), 1.81-1.90 (m, 2H), 1.67 (br. s., 1H), 1.38-1.45 (m, 2H), 1.20-1.27 (m, 2H), 1.17 (t, J=7.02 Hz, 2H).

Step-2: Preparation of (5S,8R,9S,10S,13S,14S,17S)-10,13-dimethyl-17-(6-(tetrahydro-2H-pyran-2-yloxy) hexyloxy) hexadecahydrospiro[cyclopenta[a]phenanthrene-3,2'-[1,3]dioxolane]

To a stirred solution of (5S,8R,9S,10S,13S,14S,17S)-10,13-dimethylhexadecahydrospiro[cyclopenta[a]phenanthrene-3,2'-[1,3]dioxolan]-17-ol (2 g, 5.97 mmol) in xylene (50 mL) was added NaNH$_2$ (50% suspension in toluene, 1.4 mL) and the mixture was heated at 150° C. for 1 h. The reaction mixture was gradually cooled to RT, 2-(6-chlorohexyloxy) tetrahydro-2H-pyran (2.8 mL) was added to it and the resultant mixture was again heated to 150° C. for 16 h. The reaction was monitored by TLC. Upon completion, the mixture was cooled to RT, quenched slowly with ice cold water (250 mL) and extracted with EtOAc (300 mL). The organic layer was washed with water (100 mL×2), brine (100 mL) dried over Na$_2$SO$_4$, filtered and concentrated under reduced pressure to obtain a crude product which was purified by CombiFlash chromatography (Teledyne Isco Rf+); compound eluting 30% EtOAc/hexane to afford (5S,8R,9S,10S,13S,14S,17S)-10,13-dimethyl-17-(6-(tetrahydro-2H-pyran-2-yloxy)hexyloxy)hexadecahydrospiro[cyclopenta[a]phenanthrene-3,2'-[1,3]dioxolane]. $^1$H NMR (400 MHz, CDCl3) δ 4.57 (d, J=3.95 Hz, 1H), 3.91-3.95 (m, 4H), 3.82-3.91 (m, 2H), 3.73 (td, J=6.80, 9.65 Hz, 2H), 3.42-3.53 (m, 3H), 3.33-3.42 (m, 3H), 3.26 (t, J=8.55 Hz, 2H), 1.91-2.01 (m, 2H), 1.75-1.90 (m, 3H), 1.46-1.74 (m, 13H), 1.31-1.42 (m, 6H), 1.07-1.28 (m, 4H), 0.83-0.97 (m, 4H), 0.81 (s, 4H), 0.70-0.76 (m, 4H), 0.07 (s, 3H), 0.00 (s, 3H).

Step-3: Preparation of (5S,8R,9S,10S,13S,14S,17S)-17-(6-hydroxyhexyloxy)-10,13-dimethyltetradecahydro-1H-cyclopenta[a]phenanthren-3(2H)-one To a stirred solution of (5S,8R,9S,10S,13S,14S,17S)-10,13-dimethyl-17-(6-(tetrahydro-2H-pyran-2-yloxy)hexyloxy)hexadecahydrospiro[cyclopenta[a]phenanthrene-3,2'-[1,3]dioxolane] (1 g, 1.92 mmol) in THF (25 mL) water (5 mL) was added 6N HCl (15 mL) at RT and the resultant reaction mixture was stirred at RT for 16 h. The reaction was monitored by TLC. Upon completion, the reaction mixture was diluted with water (150 mL) and basified using with saturated NaHCO$_3$ solution (pH ~8). The aqueous layer was then extracted with EtOAc (200 mL×3). The organic layer was washed with saturated NaHCO$_3$ solution (100 mL), water (100 mL), brine (100 mL) dried over Na$_2$SO$_4$, filtered and concentrated under reduced pressure to afford (5S,8R,9S,10S,13S,14S,17S)-17-(6-hydroxyhexyloxy)-10,13-dimethyltetradecahydro-1H-cyclopenta[a]phenanthren-3(2H)-one which was used in the next step without further purification. $^1$H NMR (400 MHz, CDCl3) δ 4.90 (br. s., 1H), 4.12 (d, J=7.45 Hz, 1H), 4.00 (br. s., 1H), 3.64 (t, J=6.58 Hz, 3H), 3.49-3.58 (m, 1H), 3.37-3.47 (m, 3H), 3.27 (t, J=8.55 Hz, 1H), 2.22-2.43 (m, 3H), 2.10 (br. s., 1H), 1.93-2.07 (m, 2H), 1.90 (d, J=11.84 Hz, 2H), 1.82 (d, J=7.89 Hz, 2H), 1.70 (d, J=10.09 Hz, 2H), 1.48 (d, J=4.38 Hz, 2H), 1.30-1.42 (m, 8H), 1.22-1.29 (m, 2H), 1.01 (s, 3H), 0.77 (s, 3H).

Step-4: Preparation of 6-((5S,8R,9S,10S,13S,14S,17S)-10,13-dimethyl-3-oxohexadecahydro-1H-cyclopenta[a]phenanthren-17-yloxy)hexanoic acid To a stirred solution of (5S,8R,9S,10S,13S,14S,17S)-17-(6-hydroxyhexyloxy)-10,13-dimethyltetradecahydro-1H-cyclopenta[a]phenanthren-3(2H)-one (0.1 g, 0.256 mmol) in acetone (5 mL) was added Jones reagent (0.5 mL) at 0° C. dropwise over a period of 20 min. The resultant mixture was stirred at 0° C. for 5 min. The reaction was monitored by TLC. After completion, water (10 mL) was added and the resulting precipitate was filtered over Buchner funnel. The product obtained was washed with water (5 mL×2) and n-pentane (5 mL×2), dried under vacuum to afford 6-((5S,8R,9S,10S,13S,14S,17S)-10,13-dimethyl-3-oxohexadecahydro-1H-cyclopenta[a]phenanthren-17-yloxy)hexanoic acid which was taken to next step without further purification. $^1$H NMR (400 MHz, DMSO-d$_6$) δ 3.19-3.28 (m, 3H), 2.24-2.35 (m, 2H), 2.18 (t, J=7.24 Hz, 2H), 2.08 (d, J=13.59 Hz, 2H), 1.84-1.95 (m, 3H), 1.79 (d, J=10.52 Hz, 2H), 1.61 (d, J=13.59 Hz, 2H), 1.40-1.54 (m, 8H), 1.22-1.38 (m, 8H), 1.19 (br. s., 1H), 1.09-1.18 (m, 2H), 0.97 (s, 3H), 0.69 (s, 3H).

Step-5: Preparation of 6-((5S,8R,9S,10S,13S,14S,17S)-10,13-dimethyl-3-oxohexadecahydro-1H-cyclopenta[a]phenanthren-17-yloxy)-N-(4-(5-fluoro-9-(1-methyl-1H-1,2,4-triazol-5 yl)-3-oxo-3,7,8,9-tetrahydro-2H pyrido[4,3,2-de]phthalazin-8 yl)phenyl)hexanamide To a stirred solution of 6-((5S,8R,9S,10S,13S,14S,17S)-10,13-dimethyl-3-oxohexadecahydro-1H-cyclopenta[a]

phenanthren-17-yloxy)hexanoic acid (0.080 g, 0.197 mmol) in THF (5 mL) was added T$_3$P solution (50% in EtOAc, 0.25 mL, 0.435 mmol, 2.2 eq) at 0° C. and the resulting mixture was stirred for 30 min. DIPEA (0.24 mL, 1.38 mmol, 7 eq) 8-(4-aminophenyl)-5-fluoro-9-(1-methyl-1H-1,2,4-triazol-5-yl)-8,9-dihydro-2H-pyrido[4,3,2-de]phthalazin-3(7H)-one (PK-1) (0.074 g, 0.197 mmol, 1 eq) were then successively added to the reaction mixture and the resultant mixture was stirred at RT for 16 h. The reaction was monitored by TLC. Upon completion, the reaction mixture was diluted with water (50 mL) and extracted using EtOAc (100 mL×3). The combined organic layer were washed with saturated NaHCO$_3$ solution (80 mL), saturated NH$_4$Cl solution (60 mL), water (80 mL), brine (60 mL) dried over Na$_2$SO$_4$, filtered and concentrated under reduced pressure to afford a crude product which was purified by reverse phase HPLC to afford Compound 1.4. LC-MS 764 [M+H]$^+$. $^1$H NMR (400 MHz, MeOD-d$_4$) δ 7.88 (s, 1H), 7.56-7.49 (m, 2H), 7.35 (d, J=8.5 Hz, 2H), 7.21 (dd, J=9.0, 2.4 Hz, 1H), 6.92 (dd, J=2.41, 10.74 Hz, 1H), 3.60 (s, 3H), 3.42-3.50 (m, 3H), 2.31-2.40 (m, 2H), 1.91-2.12 (m, 5H), 1.88 (br. s., 2H), 1.64-1.78 (m, 4H), 1.57 (dd, J=6.36, 13.81 Hz, 4H), 1.46 (dd, J=7.45, 15.79 Hz, 4H), 1.13-1.40 (m, 10H), 0.82-0.97 (m, 4H), 0.71-0.82 (m, 3H).

Example S-6. Preparation of 4-(3-(4-cyano-3-(trifluoromethyl)phenyl)-5,5-dimethyl-4-oxo-2-thioxo-imidazolidin-1-yl)-2-fluoro-N-(6-((4-(8-fluoro-1-oxo-2,3,4,6-tetrahydro-1H-azepino[5,4,3-cd]indol-5-yl)benzyl)amino)hexyl)benzamide (Compound 1.5)

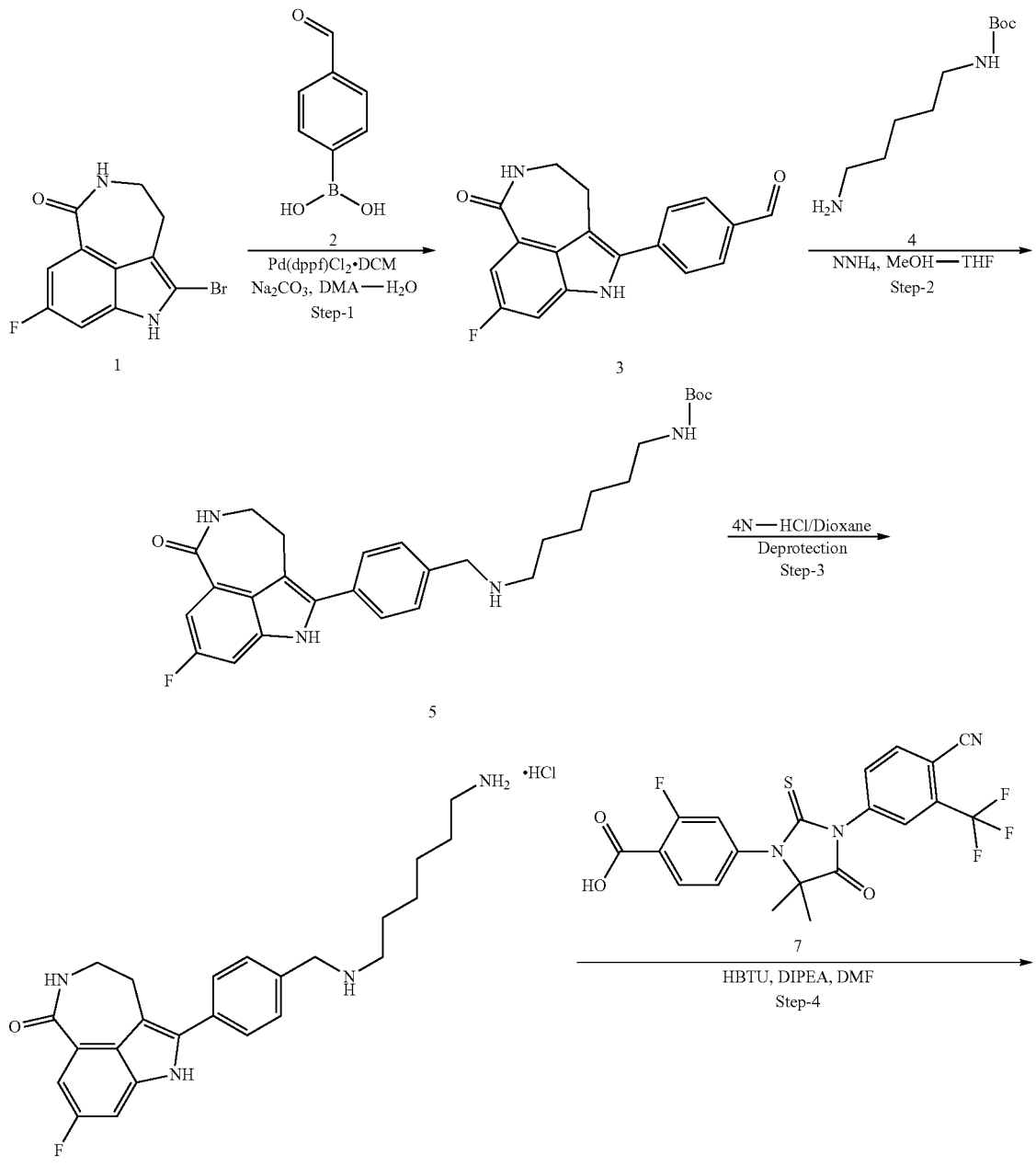

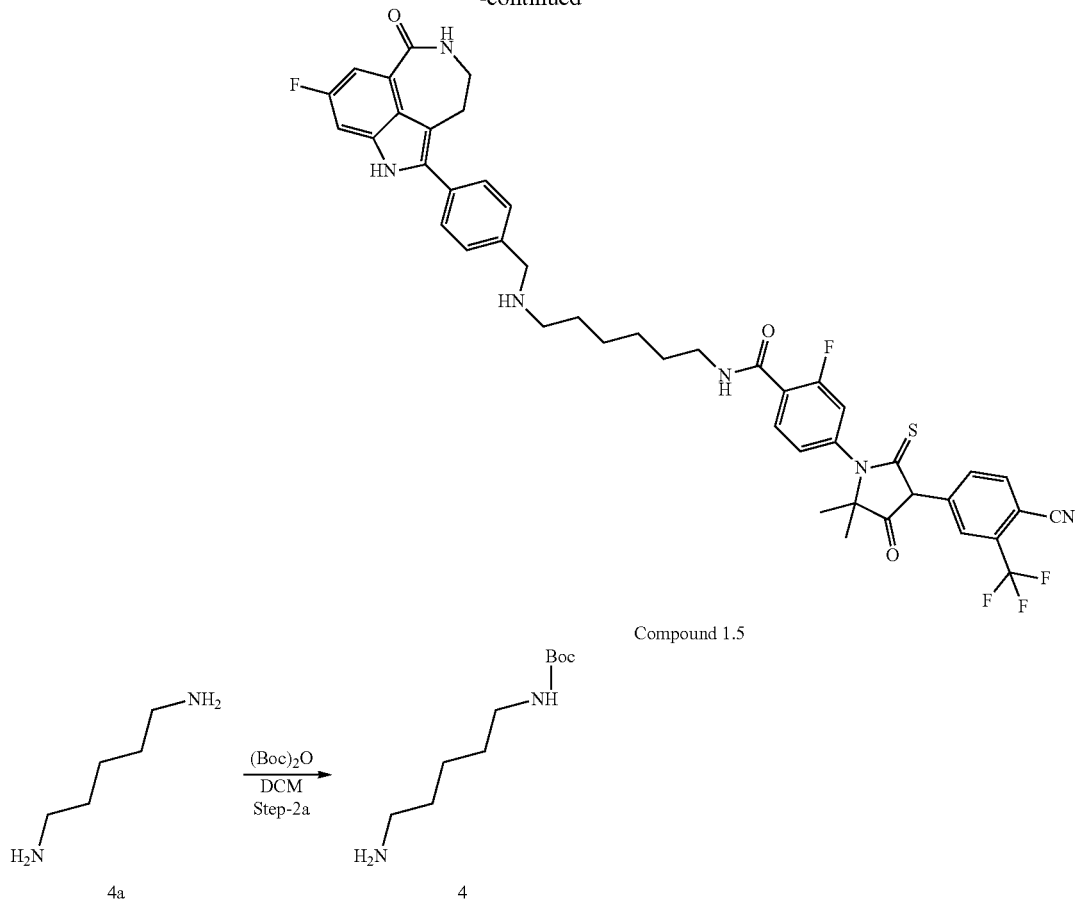

Compound 1.5

Step-1: Preparation of 4-(8-fluoro-6-oxo-3,4,5,6-tetrahydro-1H-azepino[5,4,3-cd]indol-2-yl)benzaldehyde To a stirred solution of 2-bromo-8-fluoro-4,5-dihydro-1H-azepino[5,4,3-cd]indol-6(3H)-one (2 g, 7.06 mmol, 1 eq) in DMA (37.5 mL) were added the solution of Na$_2$CO$_3$ (1.48 g, 14.1 mmol, 2 eq) in H$_2$O (18.5 mL) and 4-formylphenylboronic acid (1.27 g, 8.4 mmol, 1.2 eq) at RT. The resulting mixture was degassed under nitrogen for 30 min at RT, followed by addition of Pd(dppf)Cl$_2$.DCM (0.142 g, 0.18 mmol, 0.025 eq). The mixture was further degassed using nitrogen for 15 min. The reaction mixture was then heated at 9.5° C. for 4 h. The reaction was monitored by TLC. Upon completion, the mixture was cooled to RT, water (30 mL) was added and the resulting precipitate was filtered over Buchner funnel. The crude obtained was washed with water (20 mL×2) and n-pentane (10 mL×2), dried under reduced pressure to afford 4-(8-fluoro-6-oxo-3,4,5,6-tetrahydro-1H-azepino[5,4,3-cd]indol-2-yl)benzaldehyde.
LC-MS 309 [M+H]$^+$. $^1$H NMR (400 MHz, DMSO-d$_6$) δ 11.90 (s, 1H), 10.06 (s, 1H), 8.31 (br. s., 1H), 8.02-8.08 (m, J=7.89 Hz, 2H), 7.81-7.89 (m, J=7.89 Hz, 2H), 7.46 (d, J=10.96 Hz, 1H), 7.37 (d, J=9.21 Hz, 1H), 3.41 (br. s., 2H), 3.11 (br. s., 2H).

Step-2a: Preparation of tert-butyl 6-aminohexylcarbamate

To a stirred solution of hexane-1,6-diamine (10 g, 86.05 mmol) in DCM (400 mL) was added di-tert-butyl dicarbonate (4.69 g, 21.5 mmol, 0.25 eq) dissolved in DCM (100 mL) dropwise over a period of 1 h and the resultant mixture was stirred at RT for 16 h. The reaction was then filtered over Buchner funnel to remove the unreacted hexane-1,6-diamine. The crude residue obtained was dissolved in water (200 mL) and then extracted with DCM (200 mL×3). The combined organic layers were washed with saturated NaHCO$_3$ solution (300 mL), water (200 mL), brine (150 mL) dried over Na$_2$SO$_4$, filtered and concentrated under reduced pressure to afford tert-butyl 6-aminohexylcarbamate which was used in the next step without further purification. $^1$H NMR (400 MHz, CDCl$_3$) δ 4.70 (br, 1H), 3.02 (m, 2H), 2.62 (m, 2H), 1.37 (s, 15H), 1.26 (m, 4H).

Step-2: Preparation of tert-butyl 6-(4-(8-fluoro-6-oxo-3,4,5,6-tetrahydro-1H-azepino[5,4,3-cd]indol-2-yl)benzyl-amino)hexylcarbamate To a stirred solution of 4-(8-fluoro-6-oxo-3,4,_5,6-tetrahydro-1H-azepino[_5,4,3-cd]indol-2-yl)benzaldehyde (0.6 g, 1.94 mmol) in MeOH (36 mL) and THF (18 mL) was added tert-butyl 6-aminohexylcarbamate (1.26 g, 5.8 mmol, 3 eq) and the reaction mixture was stirred at RT for 2 h. NaBH$_4$ (0.22 g, 5.8 mmol, 3 eq) was then slowly added to the mixture at 0° C. and the resulting mixture was stirred at RT for 2 h. Reaction was monitored by TLC. Upon completion, the reaction mixture was diluted with water (100 mL) and extracted with EtOAc (150 mL×2). The combined organic layers were washed with water (75 mL) and brine (75 mL) dried over Na$_2$SO$_4$, filtered and concentrated under reduced pressure to afford crude which was triturated using DCM/hexane (1:4) to afford tert-butyl 6-(4-(8-fluoro-6-oxo-3,4,5,6-tetrahydro-1H-azepino[5,4,3-cd]indol-2-yl)benzylamino)hexylcarbamate. LC-MS 509 [M+H]$^+$. $^1$H NMR (400 MHz, MeOD-d$_4$) 7.60 (d, J=7.89 Hz, 2H), 7.46-7.56 (m, 3H), 7.30 (br. s., 1H), 3.83 (s, 2H), 3.54 (br. s., 2H), 3.14 (m, 3H), 3.02 (s, 1H), 2.62 (t, J=7.24 Hz, 2H), 1.57 (br. s., 4H), 1.46 (m, 4H), 1.42 (s, 5H), 1.36 (br. s., 4H).

Step-3: Preparation of 2-(4-((6-aminohexylamino)methyl)phenyl)-8-fluoro-4,5-dihydro-1H-azepino[5,4,3-cd]indol-6(3H)-one To a stirred solution of tert-butyl 6-(4-(8-fluoro-6-oxo-3,4,5,6-tetrahydro-1H-azepino[5,4,3-cd]indol-2-yl)benzylamino)hexylcarbamate (0.3 g, 0.58 mmol, 1 eq) in MeOH (1 mL) was added 4N-HCl in 1,4 dioxane (10 mL) at 0° C. The mixture was stirred at RT for 1 h. Reaction was monitored by TLC. Upon completion, the solvent is removed under reduced pressure to afford residue which was triturated using diethyl ether to afford 2-(4-((6-aminohexylamino)methyl)phenyl)-8-fluoro-4,5-dihydro-1H-azepino[5,4,3-cd]indol-6(3H)-one as a hydrochloride salt. LC-MS 445 [M+H]$^+$.

Step-4: Preparation of 4-(3-(4-cyano-3-(trifluoromethyl)phenyl)-5,5-dimethyl-4-oxo-2-thioxoimidazolidin-1 yl)-2-fluoro-N-(6-(4-(8-fluoro-6-oxo-3,4,5,6-tetrahydro-1H-azepino[5,4,3-cd]indol-2-yl)benzylamino)hexyl)benzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (0.15 g, 0.32 mmol) in DMA (6 mL) was added HBTU (0.15 g, 0.39 mmol, 1.2 eq) at 0° C. and the resulting mixture was stirred at same temperature for 30 min. DIPEA (0.128 g, 0.99 mmol, 3 eq) and 2-(4-((6-aminohexylamino)methyl)phenyl)-8-fluoro-4,5-dihydro-1H-azepino[5,4,3-cd]indol-6(3H)-one (0.221 g, 0.43 mmol, 1.5 eq) were then successively added to the reaction mixture and the resulting mixture was stirred at RT for 2 h. The reaction was monitored by TLC. Upon completion, the mixture was cooled to RT, water (30 mL) was added and the resulting precipitate was filtered over Büchner funnel. The crude obtained was purified by reverse phase HPLC to afford Compound 1.5. LC-MS 842 [M+H]$^+$. $^1$H NMR (400 MHz, DMSO-d$_6$) δ 11.67 (s, 1H), 8.50 (br. s., 1H), 8.40 (d, J=8.33 Hz, 1H), 8.29 (s, 1H), 8.24 (br. s., 1H), 8.09 (s, 1H), 7.74 (s, 1H), 7.54-7.61 (m, J=7.89 Hz, 2H), 7.44-7.51 (m, J=7.89 Hz, 2H), 7.40 (s, 1H), 7.43 (s, 1H), 7.27-7.36 (m, 2H), 3.5-3.3 (m, 4H), 3.26 (d, J=5.70 Hz, 2H), 3.04 (br. s., 2H), 1.89 (s, 2H), 1.48-1.58 (m, 6H), 1.47 (br. s., 2H), 1.33 (br. s., 4H).

Example S-7. Preparation of 4-[[4-fluoro-3-(piperazine-1-carbonyl)phenyl]methyl]-2H-phthalazin-1-one

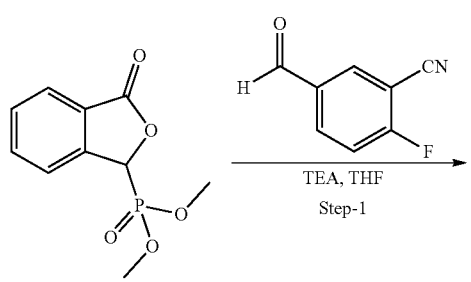

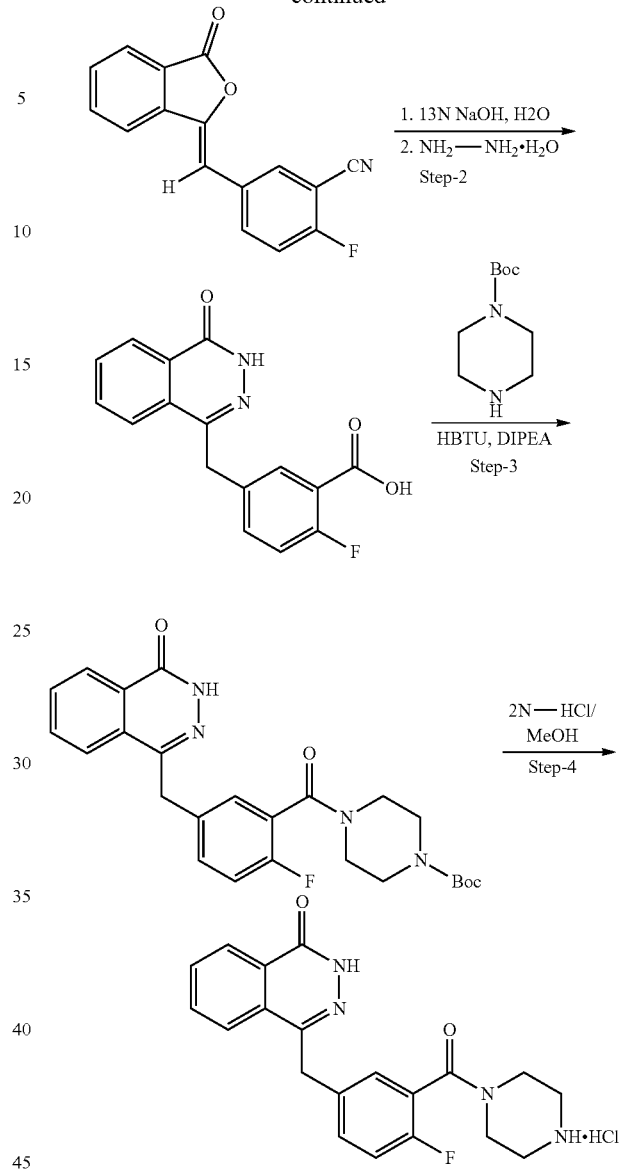

Step-1: Preparation of (Z)-2-fluoro-5-((3-oxoisobenzofuran-1(3H) ylidene)methyl)benzonitrile To a stirred solution of dimethyl 3-oxo-1,3-dihydroisobenzofuran-1-yl phosphonate (10 g, 41.28 mmol) and 2-fluoro-5-formylbenzonitrile (6.15 g, 41.28 mmol, 1 eq) in THF (50 mL) was added triethylamine (5.76 mL, 41.28 mmol, 1 eq) at 0° C. slowly. The resultant mixture was stirred at RT for 16 h. Reaction was monitored by TLC. Upon completion, water (200 mL) was added and the resulting precipitate was filtered over Buchner funnel. The product obtained was washed with water (50 mL), hexanes (50 mL), diethyl ether (30 mL), dried under vacuum afford to afford the title compound, as a mixture of E- and Z-isomers, which was used in next step without further purification. LC-MS 266 [M+H]+$^1$H NMR (400 MHz, CDCl$_3$) δ 8.13 (1H, m), 8.05 (1H, m), 7.98 (1H, m), 7.79 (2H, m), 7.61 (1H, m), 7.30 (1H, m), 6.35 (1H, s).

Step-2: Preparation of (Z)-2-fluoro-5-((4-oxo-3,4-dihydrophthalazin-1-yl)methyl)benzoic acid To a stirred suspension of (Z)-2-fluoro-5-((3-oxoisobenzofuran-1(3H)-ylidene)methyl)benzonitrile (3.7 g, 13.94 mmol) in water (20 mL) was added 13N NaOH solution (5 mL) and the mixture was heated under nitrogen at 90° C. for 16 h. The reaction mixture was cooled to 70° C. and hydrazine hydrate (10 mL) was added and stirred for 16 hours at 70° C. Reaction was monitored by TLC. Upon completion, the reaction was cooled to RT and acidified using 2N HCl (pH 1-2) at 0-5° C. to obtain a precipitate. The precipitated solid was filtered over Buchner funnel, washed with water (50 mL), n-hexanes (50 mL), diethyl ether (30 mL), dried under vacuum afford to afford the title compound. LC-MS 299 [M+H]$^+$. $^1$H NMR (400 MHz, DMSO-d$_6$) δ 13.22 (1H, br s), 12.61 (1H, s), 8.27 (1H, m), 7.99-7.81 (4H, m), 7.59 (1H, m), 7.25 (1H, m), 4.36 (2H, s).

Step-3: Preparation of tert-butyl 4-(2-fluoro-5-((4-oxo-3,4-dihydrophthalazin-1 yl)methyl)benzoyl)piperazine-1-carboxylate To a stirred suspension of 2-fluoro-5-((4-oxo-3,4-dihydrophthalazin-1-yl)methyl)benzoic acid (0.100 g, 0.335 mmol) in DMA (4 mL) was added HBTU (0.15 g, 0.402 mmol, 1.2 eq) at 0° C. and the mixture was stirred for 10 min. DIPEA (0.17 mL, 1.00 mmol, 3 eq) and tert-butyl piperazine-1-carboxylate (0.075 g, 0.402 mmol, 1.2 eq) were then successively added to the reaction mixture at 0° C. and the resultant reaction mixture was stirred at RT for 75 min. Reaction was monitored by TLC. After completion, water (10 mL) was added and the resulting precipitate was filtered over Buchner funnel. The product obtained was washed with water (10 mL×2) and n-pentane (10 mL×2), dried under reduced pressure to afford the title compound which was taken to next step without further purification. LC-MS 467 [M+H]$^+$.

Step-4: Preparation of 4-[[4-fluoro-3-(piperazine-1-carbonyl)phenyl]methyl]-2H phthalazin-1-one To tert-butyl 4-(2-fluoro-5-((4-oxo-3,4-dihydrophthalazin-1-yl)methyl)benzoyl)piperazine-1-carboxylate (10.0 g, 76.23 mmol) was added 2N HCl in MeOH (30 mL) at RT and the mixture was stirred at RT for 16 h. The reaction was monitored by $^1$H NMR. Upon completion, the reaction mixture was concentrated under reduced pressure to afford compound, the compound was triturated with diethylether and pentane afford the title compound as an hydrochloride salt. LC-MS 403 [M+H]$^+$. $^1$H NMR (400 MHz, MeOD-d$_4$) δ 3.66 (s, 3H), 2.92 (t, J=7.67 Hz, 2H), 2.37 (t, J=7.45 Hz, 2H), 1.62-1.71 (m, 6H), 1.37-1.45 (m, 2H).

Example S-8. Preparation of (R)-methyl 6-(4-(3-(4-cyano-3-(trifluoromethyl)phenylamino)-2-hydroxy-2-methyl-3-oxopropylsulfonyl)phenylamino)hexanoate

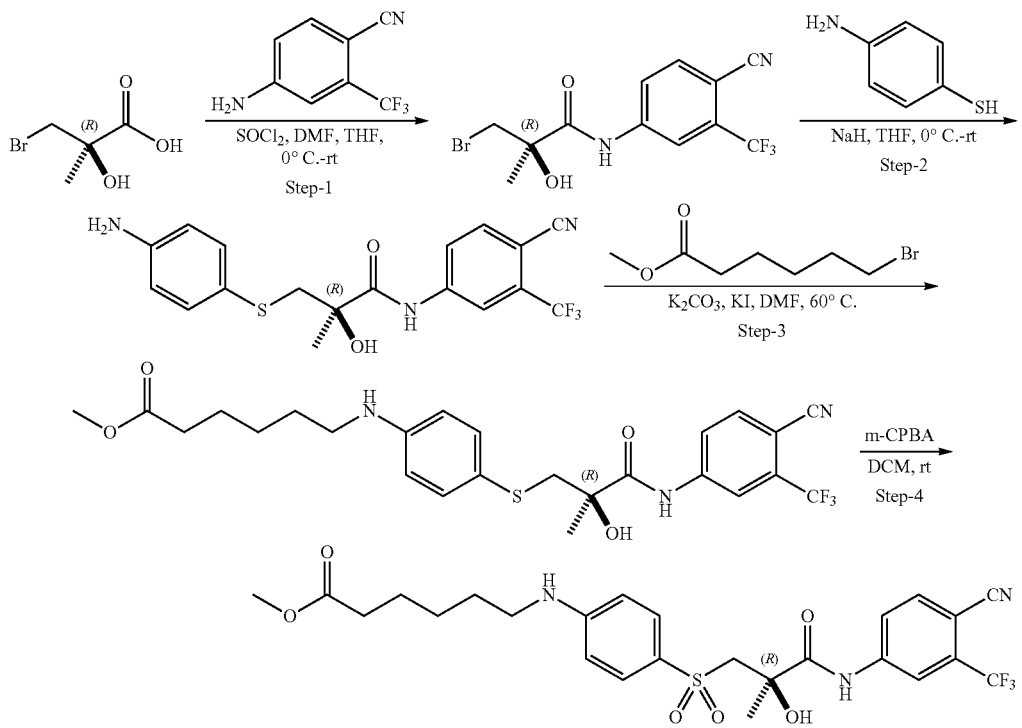

Step 1: Preparation of (R)-3-bromo-N-(4-cyano-3-(trifluoromethyl)phenyl)-2-hydroxy-2-methylpropanamide To a solution of (R)-3-bromo-2-hydroxy-2-methylpropanoic acid (13 g, 71.04 mmol) in THF (250 mL) cooled to 0° C. was added SOCl$_2$ (14.1 g, 118.53 mmol) dropwise and catalytic amount of DMF. The solution was stirred at this temperature for 1.5 h. Then a solution of 4-amino-2-(trifluoromethyl)-benzonitrile (7.4 g, 39.78 mmol) and TEA (15.8 g, 156.29 mmol) in THF (50 mL) was added dropwise at this temperature. The mixture was allowed to warm to room temperature overnight. TLC showed the reaction was completed. The mixture was quenched with NaHCO₃ and extracted with EtOAc. The organic layer was dried with Na₂SO₄ and concentrated under reduced pressure. The crude product was purified by silica gel column to afford the title compound.

Step 2: Preparation of (R)-3-(4-aminophenylthio)-N-(4-cyano-3-(trifluoromethyl)phenyl)-2-hydroxy-2-methylpropanamide To a solution of NaH (251 mg, 6.26 mmol) in THF (30 ml) was added 4-aminobenzenethiol (712 mg, 5.68 mmol) in THF (20 mL) dropwise at 0° C. under N₂. The mixture was allowed to warm to room temperature and stirred for 1 h. Then a solution of (R)-3-bromo-N-(4-cyano-3-(trifluoromethyl)phenyl)-2-hydroxy-2-methylpropanamide (2 g, 5.68 mmol) in THF (20 mL) was added dropwise to the mixture at 0° C. The mixture was stirred at room temperature overnight. TLC showed the reaction was completed. Water was added carefully and the mixture was extracted with EtOAc, dried with Na₂SO₄ and concentrated under reduce pressure. The compound was purified by silica gel column to afford the title compound.

Step 3: Preparation of (R)-methyl 6-(4-(3-(4-cyano-3-(trifluoromethyl)phenylamino)-2-hydroxy-2-methyl-3-oxopropylthio)phenylamino)hexanoate To a solution of (R)-3-(4-aminophenylthio)-N-(4-cyano-3-(trifluoromethyl)phenyl)-2-hydroxy-2-methylpropanamide (2 g, 5 mmol) in DMF (100 mL) was added K2CO₃ (2.1 g, 15 mmol), KI (100 mg, 0.5 mmol), and methyl 6-bromohexanoate (10 g, 50 mmol). The mixture was stirred at 60° C. overnight. TLC showed the reaction was completed. The mixture was washed with water, and extracted with EtOAc, dried over Na₂SO₄. The organic layer was concentrated under reduce pressure and purified by flash chromatography to afford the title compound.

Step 4: Preparation of (R)-methyl 6-(4-(3-(4-cyano-3-(trifluoromethyl)phenylamino)-2-hydroxy-2-methyl-3-oxopropylsulfonyl)phenylamino)hexanoate To a solution of (R)-methyl 6-(4-(3-(4-cyano-3-(trifluoromethyl)phenylamino)-2-hydroxy-2-methyl-3-oxopropylthio)phenylamino)hexanoate (2 g, 2.8 mmol) in DCM (60 mL) was added m-CPBA (1.83 g, 8.4 mmol), the mixture was stirred at room temperature for 2 h. The mixture was quenched with aq. NaHCO₃ and washed with water and extracted with DCM. The organic layer was dried over Na₂SO₄ and purified by flash chromatography to afford the title compound. $^1$H NMR (400 MHz, DMSO-$d_6$) δ 10.27 (s, 1H), 8.41 (s, 1H), 8.16 (d, J=8.6 Hz, 1H), 8.04 (d, J=8.6 Hz, 1H), 7.45 (d, J=8.9 Hz, 2H), 6.63-6.37 (m, 3H), 6.30 (s, 1H), 3.79 (d, J=14.5 Hz, 1H), 3.58 (s, 3H), 3.47 (d, J=14.5 Hz, 1H), 2.89 (dq, J=11.8, 7.0, 6.3 Hz, 2H), 2.31 (t, J=7.4 Hz, 2H), 1.55 (p, J=7.5 Hz, 2H), 1.47 (q, J=7.2 Hz, 2H), 1.38 (s, 3H), 1.36-1.26 (m, 2H).

Example S-9. Preparation of (S)-methyl 6-(4-(3-(4-cyano-3-(trifluoromethyl)phenylamino)-2-hydroxy-2-methyl-3-oxopropoxy)phenylamino)hexanoate

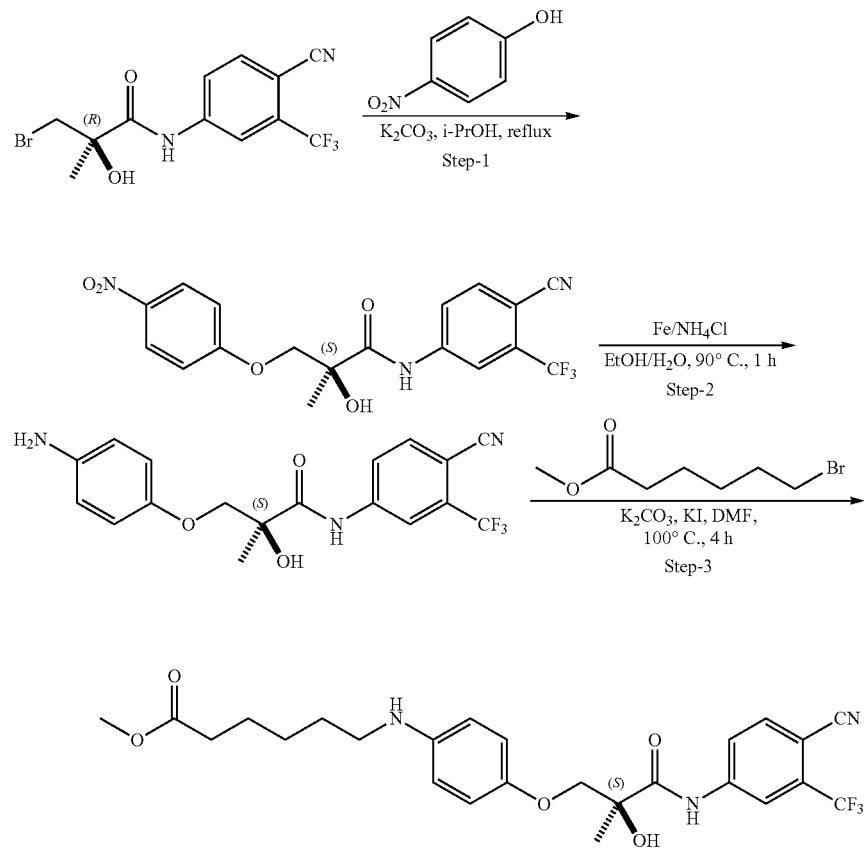

Step 1: Preparation of (S)-N-(4-cyano-3-(trifluoromethyl)phenyl)-2-hydroxy-2-methyl-3-(4-nitrophenoxy) propanamide To a stirring suspension of 4-nitrophenol (1.2 g, 8.55 mmol) and $K_2CO_3$ (3.9 g, 28.50 mmol) in isopropyl alcohol (40 mL) was added (R)-3-bromo-N-(4-cyano-3-(trifluoromethyl)phenyl)-2-hydroxy-2-methylpropanamide (2 g, 5.70 mol). The reaction was refluxed for 2 h. TLC indicated the reaction was complete. The reaction mixture was concentrated in vacuo, diluted with water and extracted with EtOAc. The combined organic phases were washed with sat. $NaHCO_3$ and brine, dried over anhydrous $Na_2SO_4$ and concentrated in vacuo to give the residue as an oil. The residue were purified by column chromatography on silica gel to afford the title compound.

Step 2: Preparation of (S)-3-(4-aminophenoxy)-N-(4-cyano-3-(trifluoromethyl)phenyl)-2-hydroxy-2-methylpropanamide To a stirring suspension of (S)-N-(4-cyano-3-(trifluoromethyl)phenyl)-2-hydroxy-2-methyl-3-(4-nitrophenoxy) propanamide 3 (2.0 g, 4.64 mmol) in EtOH (20 mL) and $H_2O$ (20 mL) was added $NH_4Cl$ (2.5 g, 46.42 mmol) and iron powder (2.1 g, 3.71 mmol). The reaction was degassed with $N_2$ and stirred at 90° C. for 1 h. TLC indicated the reaction was complete. The mixture was diluted with EtOAc, filtered off with a pad of Celite, washed with brine, dried over anhydrous $Na_2SO_4$ and concentrated in vacuo to afford the title compound.

Step 3: Preparation of (S)-methyl 6-(4-(3-(4-cyano-3-(trifluoromethyl)phenylamino)-2-hydroxy-2-methyl-3-oxopropoxy)phenylamino)hexanoate To a solution of (S)-3-(4-aminophenoxy)-N-(4-cyano-3-(trifluoromethyl)phenyl)-2-hydroxy-2-methylpropanamide (1.7 g, 4.48 mmol) and methyl 6-bromohexanoate (0.7 g, 3.45 mmol) in DMF (30 mL) was added $K_2CO_3$ (1.0 g, 7.56 mmol) and KI (0.6 g, 3.80 mmol). The reaction was stirred at 100° C. for 4 h. TLC indicated ~30% of (S)-3-(4-aminophenoxy)-N-(4-cyano-3-(trifluoromethyl)phenyl)-2-hydroxy-2-methylpropanamide was still remained. The mixture was diluted with water, extracted with EtOAc. The combined organic phases were washed with brine, dried over anhydrous $Na_2SO_4$ and concentrated in vacuo to give the residue. The residue was purified by column chromatography on silica gel to afford the title compound. LCMS 508.6 $[M+1]^+$. $^1H$ NMR (400 MHz, DMSO-$d_6$) δ 10.54 (s, 1H), 8.57 (d, J=2 Hz, 1H), 8.32 (dd, J=2 Hz, 8.4 Hz 1H), 8.11 (d, J=8.8 Hz, 1H), 6.70-6.68 (m, 1H), 6.48-6.46 (m, 1H), 6.17 (s, 1H), 5.18 (s, 1H), 4.10 (d, J=9.6 Hz, 1H), 3.87 (d, J=9.6 Hz, 1H), 3.58 (s, 1H), 2.32 (t, J=7.2 Hz), 1.57-1.49 (m, 4H), 1.41 (s, 3H), 1.36-1.33 (m, 2H).

Example S-10. Preparation of (R)-3-(4-(6-bromohexyloxy)phenylsulfonyl)-N-(4-cyano-3-(trifluoromethyl)phenyl)-2-hydroxy-2-methylpropanamide

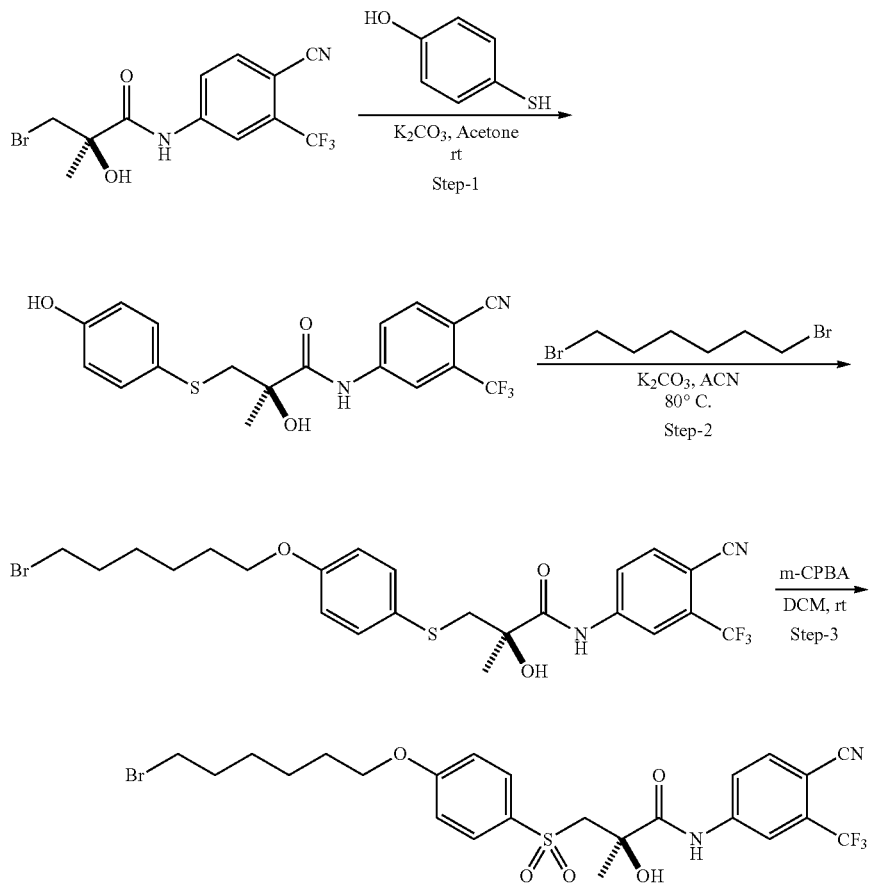

Step 1: Preparation of (R)-N-(4-cyano-3-(trifluoromethyl)phenyl)-2-hydroxy-3-(4-hydroxyphenylthio)-2-methylpropanamide A solution of (R)-3-bromo-N-(4-cyano-3-(trifluoromethyl)phenyl)-2-hydroxy-2-methylpropanamide (1.5 g, 4.27 mmol), 4-mercaptophenol (0.539 g, 4.27 mmol) and K2CO₃ (0.649 g, 4.69 mmol) in acetone (15 mL). The reaction mixture was stirred at rt for 3 h. TLC showed the reaction mixture was complete. The solution was concentrated in vacuo. The crude product was purified by column chromatography to afford the title compound.

Step 2: Preparation of (R)-3-(4-(6-bromohexyloxy)phenylthio)-N-(4-cyano-3-(trifluoromethyl)phenyl)-2-hydroxy-2-methylpropanamide A mixture of (R)-N-(4-cyano-3-(trifluoromethyl)phenyl)-2-hydroxy-3-(4-hydroxyphenylthio)-2-methylpropanamide (1.34 g, 3.38 mmol), 1,6-dibromohexane (8.25 g, 33.81 mmol) and K2CO₃ (2.34 g, 16.9 mmol) in ACN (20 mL). The reaction mixture was stirred at rt for 3 h. TLC showed the mixture was complete. The solution was concentrated in vacuo, and purified by column chromatography to afford the title compound.

Step 3: Preparation of (R)-3-(4-(6-bromohexyloxy)phenylsulfonyl)-N-(4-cyano-3-(trifluoromethyl)phenyl)-2-hydroxy-2-methylpropanamide A mixture of (R)-3-(4-(6-bromohexyloxy)phenylthio)-N-(4-cyano-3-(trifluoromethyl)phenyl)-2-hydroxy-2-methyl-propanamide (1.5 g, 2.68 mmol) in DCM (15 mL) was cooled to 0° C., and m-CPBA (1.39 g, 8.04 mmol) was added. The reaction mixture was stirred at rt for 2 h. TLC showed the mixture was complete. The solution was poured into 1N NaOH and extracted with DCM (50 mL×3). The organic layer was washed with brine, dried over Na₂SO₄, concentrated and purified by column chromatography to afford the title compound. ¹H NMR (400 MHz, CDCl₃) δ 8.94 (s, 1H), 7.88 (d, J=2.8 Hz 1H), 7.74-7.68 (m, 2H), 7.34-7.30 (m, 2H), 6.66-6.62 (m, 2H), 3.81-3.71 (m, 4H), 3.43 (t, J=6.8 Hz 2H), 2.99 (d, J=14.4 Hz 1H), 1.93-1.86 (m, 2H), 1.78-1.71 (m, 2H), 1.57-1.43 (m, 7H).

Example S-11. Preparation of 4-(1-(4-(2-bromoethoxy)phenyl)-2-phenylbut-1-enyl)phenyl pivalate

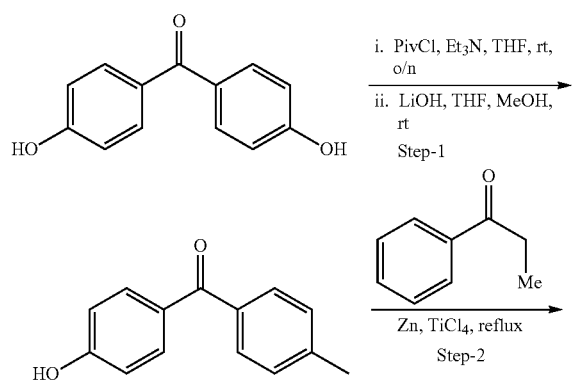

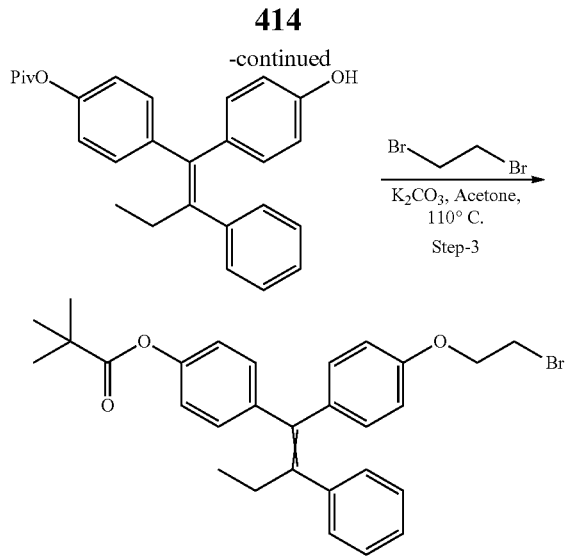

Step 1: Preparation of 4-(4-hydroxybenzoyl)phenyl

Part 1: To a solution of bis(4-hydroxyphenyl)methanone 1 (2 g, 9.34 mmol) in 100 mL of THF was added Et₃N (3.8 g, 37.36 mmol). Then PivCl (2.82 g, 23.35 mmol) was added dropwise to the mixture at 0° C. The mixture was allowed to wane to rt and stirred overnight. The reaction mixture was quenched with water and extracted with EtOAc. The organic layers were washed with 1N HCl and brine, dried over Na₂SO₄, concentrated under reduced pressure to get a crude product.

Part 2: To a solution of the crude product (3.5 g) in THF (45 mL) and MeOH (3 mL) was added LiOH (290 mg, 12.14 mmol), the mixture was stirred at rt overnight. The reaction mixture was concentrated under reduced pressure and purified by silica gel chromatography to afford the title compound.

Step 2: Preparation of (E)-4-(1-(4-hydroxyphenyl)-2 phenylbut-1-enyl)phenyl pivalate To a suspension of Zn (1.7 g, 26.8 mmol) in anhydrous THF (150 mL) under N₂ was added TiCl₄ (2.5 g, 13.4 mmol) at 0° C. The mixture was refluxed for 2 h and cooled at 40° C. A mixture of 4-(4-hydroxybenzoyl)phenyl pivalate (1 g, 3.35 mmol) and propiophenone (1.5 g, 10.72 mmol) in anhydrous THF (50 mL) was added at once and the mixture was refluxed for 1 h. The reaction mixture was quenched with 10% K2CO₃, extracted with EtOAc, washed with brine, dried over Na₂SO₄, purified by silica gel chromatography to get a crude product, then added MeOH (10 mL) and stirred for 20 min to obtain the title compound.

Step 3: Preparation of 4-(1-(4-(2-bromoethoxy)phenyl)-2-phenylbut-1-enyl)phenyl pivalate To a solution of (E)-4-(1-(4-hydroxyphenyl)-2-phenylbut-1-enyl)phenyl pivalate 4 (0.4 g, 1 mmol) in acetone (6 mL) was added K2CO₃ (0.56 g, 4 mmol), 1,2-dibromoethane 5 (1.9 g, 10 mmol). The mixture was stirred at 110° C. overnight. TLC showed the reaction was completed. The mixture was washed with water, and extracted with EtOAc, dried over Na₂SO₄. The organic layer was concentrated under reduced pressure and purified by silica gel column to afford the title compound. ¹H NMR (400 MHz, CDCl₃, E/Z=1:1) δ 7.23 (d, J=8.7 Hz, 2H), 7.20-7.14 (m, 6H), 7.14-7.07 (m, 6H), 7.05 (d, J=8.6 Hz, 2H), 6.87 (dd, J=15.3, 8.8 Hz, 4H), 6.77 (d, J=8.9 Hz, 2H), 6.70 (d, J=8.8 Hz, 2H), 6.55 (d, J=8.9 Hz, 2H), 4.31 (t, J=6.3 Hz, 2H), 4.15 (t, J=6.3 Hz, 2H), 3.66 (t, J=6.3 Hz, 2H), 3.55 (t, J=6.3 Hz, 2H), 2.57-2.39 (m, 4H), 1.37 (s, 9H), 1.28 (s, 9H), 0.97-0.89 (m, 6H).

Example S-12. Preparation of (R)-3-(4-(2-bromo-ethylamino)phenylsulfonyl)-N-(4-cyano-3-(trifluoromethyl)-phenyl)-2-hydroxy-2-methylpropanamide

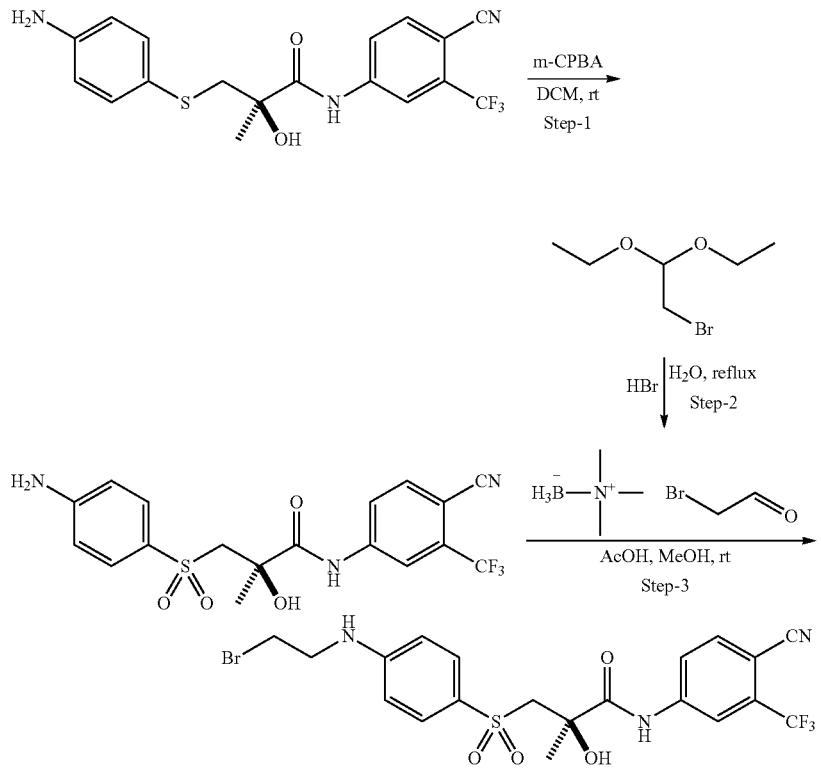

Step 1: Preparation of (R)-3-(4-aminophenylsulfonyl)-N-(4-cyano-3-(trifluoromethyl)phenyl)-2-hydroxy-2-methylpropanamide To a solution of (R)-3-(4-aminophenylthio)-N-(4-cyano-3-(trifluoromethyl)phenyl)-2-hydroxy-2-methylpropanamide 1 (3.0 g, 7.59 mmol) in DCM (20 mL) remained at 0° C. was added 85% mCPBA (4.6 g, 22.76 mmol). The reaction was stirred at rt for 4 h. TLC indicated the reaction was complete. The mixture was washed with sat. NaHCO$_3$. The organic phase was washed with brine, dried over anhydrous Na$_2$SO$_4$, concentrated under reduced pressure and purified by column chromatography to afford the title compound.

Step 2: Synthesis of 2-bromoacetaldehyde

A mixture of 2-bromo-1,1-diethoxyethane (20 g, 0.101 mol) in HBr (47%, 32 mL) was stirred at 100° C. for 2 h. The mixture was extracted with Et$_2$O. The combined organic layers were washed with brine, dried over anhydrous Na$_2$SO$_4$ and concentrated under reduced pressure to give the title compound, which was used in the next step directly.

Step 3: Synthesis of (R)-3-(4-(2-bromoethylamino)phenylsulfonyl)-JV-(4-cyano-3-(trifluoromethyl)-phenyl)-2-hydroxy-2-methylpropanamide To a solution of (R)-3-(4-aminophenylsulfonyl)-N-(4-cyano-3-(trifluoromethyl)phenyl)-2-hydroxy-2-methylpropanamide (2 g, 4.68 mmol) and 2-bromo-1,1-diethoxyethane (5.2 g, 42.11 mmol) in MeOH (40 mL) was added AcOH (0.18 g, 3.04 mmol) followed by BH$_3$NMe$_3$ (4.8 g, 65.51 mmol). The reaction was monitored by TLC and additional portions of 2-bromo-1,1-diethoxyethane was added until the conversion was complete. The mixture was diluted with EtOAc, washed with sat. NaHCO$_3$ and brine, dried over anhydrous Na$_2$SO$_4$ and concentrated under reduced pressure. The crude material was purified by column chromatography to afford the title compound. LCMS 536.1 [M+1]$^+$. $^1$H NMR (600 MHz, DMSO-d$_6$) δ 10.33 (s, 1H), 8.44 (d, J=3 Hz, 1H), 8.20 (dd, J=3 Hz, 12.6 Hz, 1H), 8.08 (d, J=12.6 Hz, 1H), 7.51 (d, J=13.8 Hz, 2H), 6.60 (d, J=13.8 Hz, 2H), 6.33 (s, 1H), 2.98 (s, 3H), 3.82 (d, J=21.6 Hz, 1H), 3.53 (m, 6H), 1.39 (s, 3H).

Example S-13. Preparation of (R)-N-(4-cyano-3-(trifluoromethyl)phenyl)-3-(4-(6-(4-(2-fluoro-5-((4-oxo-3,4-dihydrophthalazin-1-yl)methyl)benzoyl)piperazin-1-yl)-6-oxohexylamino)phenylsulfonyl)-2-hydroxy-2-methylpropanamide (Compound 1.68)

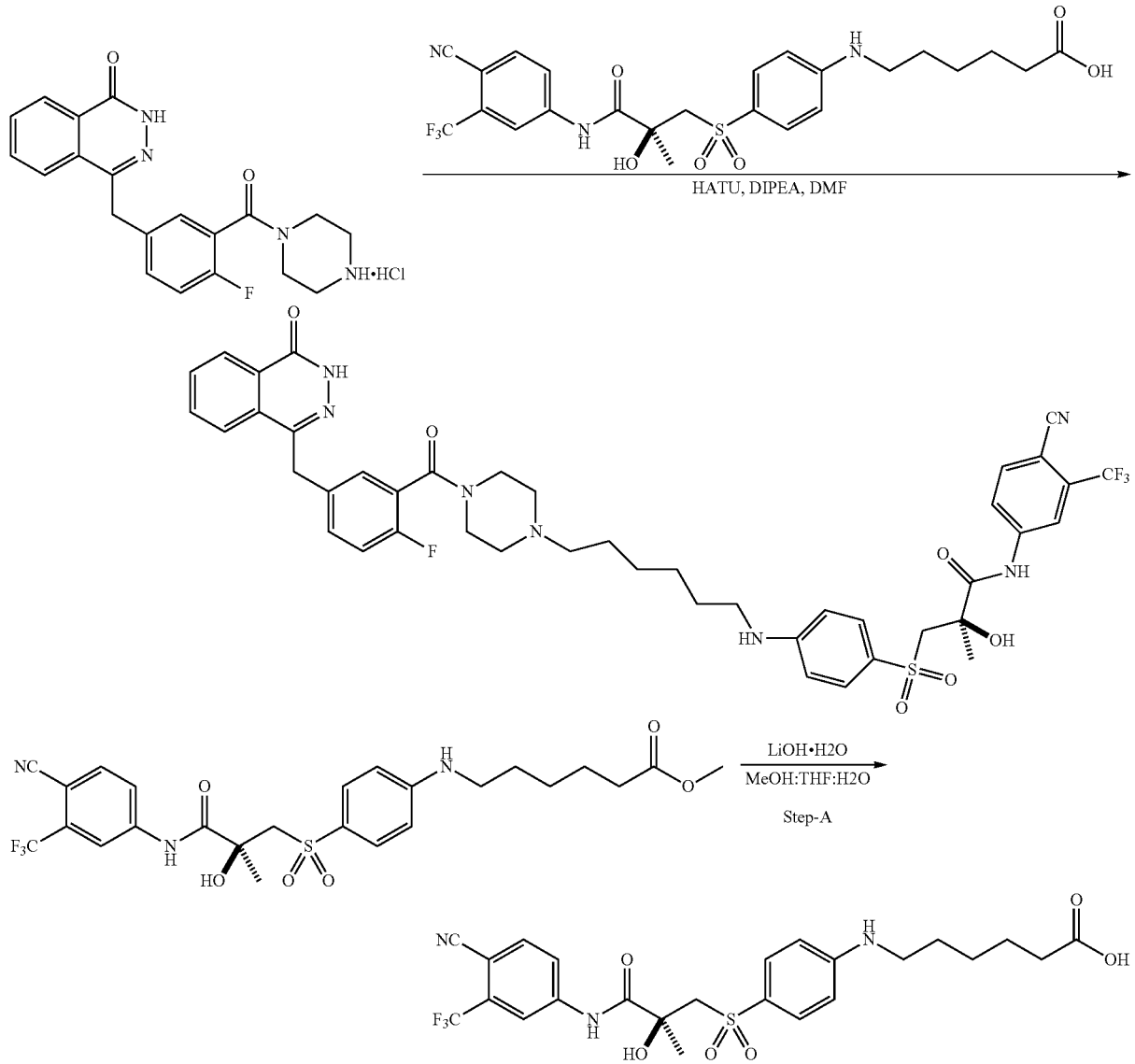

Step-A: Preparation of (S)-6-(4-(3-(4-cyano-3-(trifluoromethyl)phenylamino)-2-hydroxy-2-methyl-3-oxopropylsulfonyl)phenylamino)hexanoic acid To (S)-methyl 6-(4-(3-(4-cyano-3-(trifluoromethyl)phenylamino)-2-hydroxy-2-methyl-3-oxopropyl sulfonyl)phenylamino)hexanoate (0.20 g, 0.360 mmol) in THF:MeOH:H₂O (6 mL:3 mL:1 mL) was added lithium hydroxide monohydrate (0.151 mg, 3.6 mmol, 10 eq) and the mixture was heated at 50° C. for 2 h. After completion, the mixture was concentrated under reduced pressure. The residue obtained was acidified with 1N HCl (pH ~2) to obtain a precipitate which was filtered over Buchner funnel to afford the title compound. LC-MS 542 [M+H]⁺.

Preparation of (R)-N-(4-cyano-3-(trifluoromethyl)phenyl)-3-(4-(6-(4-(2-fluoro-5-((4-oxo-3,4-dihydrophthalazin-1 yl)methyl)benzoyl)piperazin-1 yl)-6-oxohexylamino)phenylsulfonyl)-2-hydroxy-2-methylpropanamide (Compound 1.68)

To a stirred solution of (S)-6-(4-(3-(4-cyano-3-(trifluoromethyl)phenylamino)-2-hydroxy-2-methyl-3-oxopropylsulfonyl)phenylamino)hexanoic acid (0.20 g, 0.369 mmol) in DMF (5 mL) was added HATU (0.21 g, 0.554 mmol, 1.5 eq) at 0° C. and the mixture was stirred at 0° C. for 30 min. DIPEA (0.34 mL, 1.84 mmol, 5 eq) and 4-(4-fluoro-3-(piperazine-1-carbonyl)benzyl)phthalazin-1(2H)-one hydrochloride salt (0.297 g, 0.739 mmol, 2.0 eq) were then successively added to the mixture and the resultant mixture was stirred at RT for 16 h. The reaction was monitored by TLC and LC-MS. After completion, the reaction was diluted with EtOAc (250 mL). The organic layer was washed with water (100 mL), brine (50 mL) dried over Na$_2$SO$_4$, filtered and concentrated under reduced pressure to obtain a crude residue which was purified by reversed phase HPLC to afford Compound 1.68. LC-MS 890 [M+H]$^+$. $^1$H NMR (400 MHz, CD$_3$OD-d$_4$) δ 8.36 (d, J=7.8 Hz, 1H), 8.21 (s, 1H), 7.98-7.77 (m, 5H), 7.56-7.43 (m, 3H), 7.38 (d, J=6.4 Hz, 1H), 7.15 (t, J=9.0 Hz, 1H), 6.42 (dd, J=9.0, 5.2 Hz, 2H), 4.38 (s, 2H), 4.00 (d, J=14.5 Hz, 1H), 3.80-3.60 (m, 4H), 3.55-3.38 (m, 3H), 3.28 (s, 1H), 2.89 (tt, J=12.3, 6.0 Hz, 2H), 2.43 (dt, J=28.6, 7.4 Hz, 2H), 1.60 (ddt, J=36.4, 15.2, 7.6 Hz, 4H), 1.44 (d, J=14.4 Hz, 5H).

Example S-14. Preparation of (S)-N-(4-cyano-3-(trifluoromethyl)phenyl)-3-(4-(6-(4-(2-fluoro-5-((4-oxo-3,4-dihydrophthalazin-1-yl)methyl)benzoyl)piperazin-1-yl)-6-oxohexylamino)phenoxy)-2-hydroxy-2-methylpropanamide (Compound 1.83)

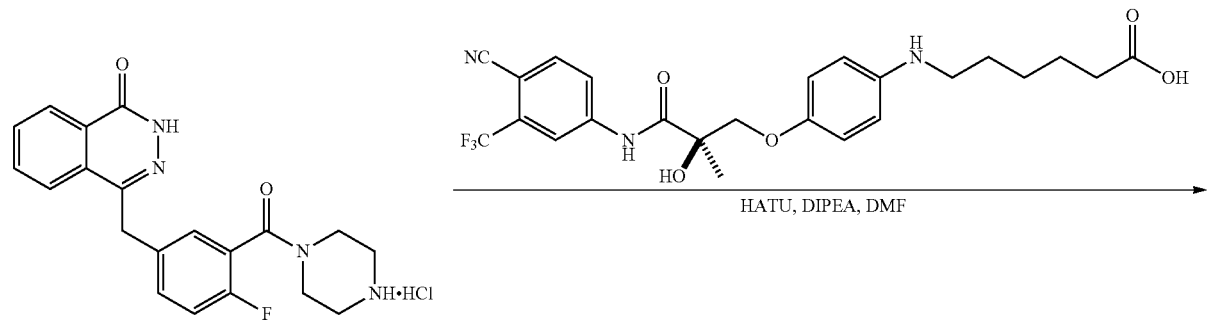

HATU, DIPEA, DMF

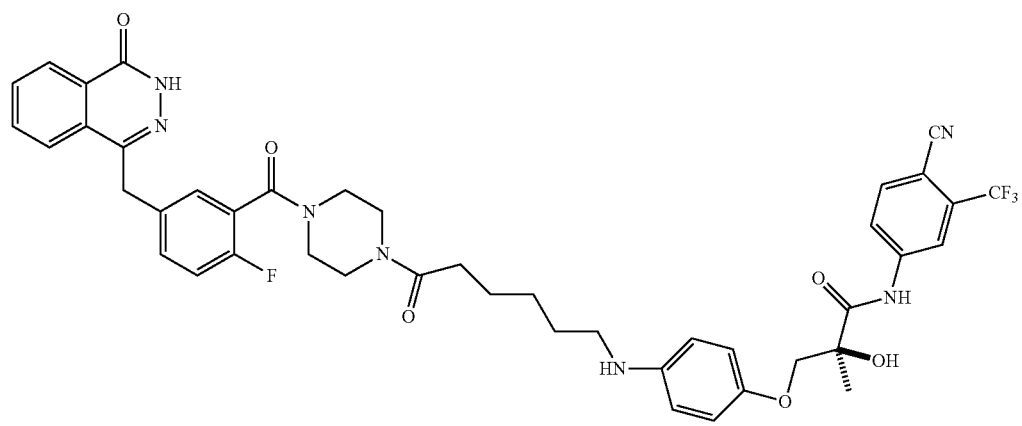

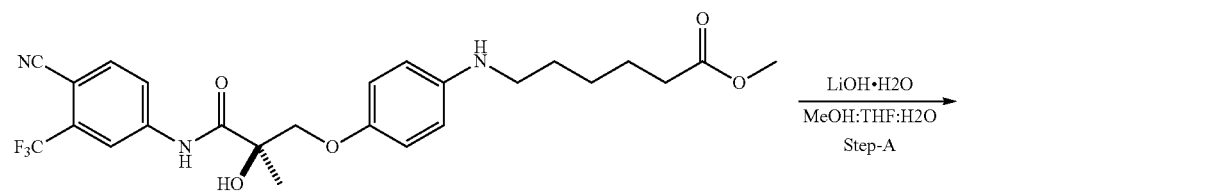

LiOH·H2O / MeOH:THF:H2O
Step-A

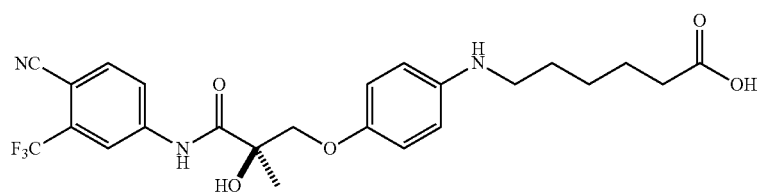

Step-A: Preparation of (R)-6-(4-(3-(4-cyano-3-(trifluoromethyl)phenylamino)-2-hydroxy-2-methyl-3-oxopropoxy)phenylamino)hexanoic acid To (R)-methyl 6-(4-(3-(4-cyano-3-(trifluoromethyl)phenylamino)-2-hydroxy-2-methyl-3-oxopropoxy)phenylamino)hexanoate (0.20 g, 0.360 mmol) in THF:MeOH:H$_2$O (6 mL:3 mL:1 mL) was added lithium hydroxide monohydrate (0.151 mg, 3.6 mmol, 10 eq)) and the mixture was heated at 50° C. for 2 h. After completion, the mixture was concentrated under reduced pressure. The residue obtained was acidified with 1N-HCl (pH~2) to obtain a precipitate which was filtered over Buchner funnel to afford the title compound. LC-MS 494 [M+H]$^+$.

Preparation of (S)-N-(4-cyano-3-(trifluoromethyl)phenyl)-3-(4-(6-(4-(2-fluoro-5-((4-oxo-3,4-dihydrophthalazin-1 yl)methyl)benzoyl)piperazin-1-yl)-6-oxohexylamino) phenoxy)-2-hydroxy-2-methylpropanamide (Compound 1.83)

To a stirred solution of (R)-6-(4-(3-(4-cyano-3-(trifluoromethyl)phenylamino)-2-hydroxy-2-methyl-3-oxopropoxy)phenylamino)hexanoic acid (0.20 g, 0.405 mmol) in DMF (5 mL) was added HATU (0.23 g, 0.608 mmol, 1.5 eq) at 0° C. and the mixture was stirred at 0° C. for 30 min. DIPEA (0.37 mL, 2.02 mmol, 5 eq) and 4-(4-fluoro-3-(piperazine-1-carbonyl)benzyl)phthalazin-1(2H)-one hydrochloride (0.24 g, 0.608 mmol, 1.5 eq) were then successively added to the reaction mixture and the mixture was stirred at RT for 16 h. The reaction was monitored by TLC and LC-MS. After completion, the mixture was diluted with EtOAc (250 mL). The organic layer was washed with water (100 mL), brine (50 mL) dried over Na$_2$SO$_4$, filtered and concentrated under reduced pressure to obtain a crude residue which was purified by reversed phase HPLC to afford Compound 1.83. LC-MS 842.8 [M+H]$^+$. $^1$H NMR (400 MHz, DMSO-d$_6$) δ 8.55 (d, J=2.9 Hz, 1H), 8.28 (d, J=10.5 Hz, 2H), 8.08 (d, J=8.6 Hz, 1H), 7.96 (d, J=8.1 Hz, 1H), 7.89 (t, J=7.4 Hz, 1H), 7.83 (t, J=7.5 Hz, 1H), 7.44 (t, J=6.6 Hz, 1H), 7.36 (s, 1H), 7.23 (t, J=9.0 Hz, 1H), 7.06 (d, J=8.5 Hz, 1H), 6.89 (s, 1H), 6.67 (d, J=7.8 Hz, 2H), 6.45 (d, J=8.1 Hz, 2H), 5.06 (t, J=5.5 Hz, 1H), 4.33 (s, 2H), 4.06 (d, J=9.5 Hz, 1H), 3.86 (t, J=9.9 Hz, 1H), 3.62 (s, 2H), 3.51 (t, J=4.9 Hz, 2H), 3.15 (d, J=14.4 Hz, 2H), 2.91 (d, J=17.5 Hz, 2H), 2.28 (d, J=7.9 Hz, 1H), 1.69 (s, 2H), 1.51 (q, J=6.5, 5.7 Hz, 4H), 1.38 (d, J=12.8 Hz, 6H).

Example S-15. Preparation of (R)-N-(4-cyano-3-(trifluoromethyl)phenyl)-3-(4-(6-(4-(2-fluoro-5-((4-oxo-3,4-dihydrophthalazin-1-yl)methyl)benzoyl)piperazin-1-yl)hexyloxy)phenylsulfonyl)-2-hydroxy-2-methylpropanamide (Compound 1.96)

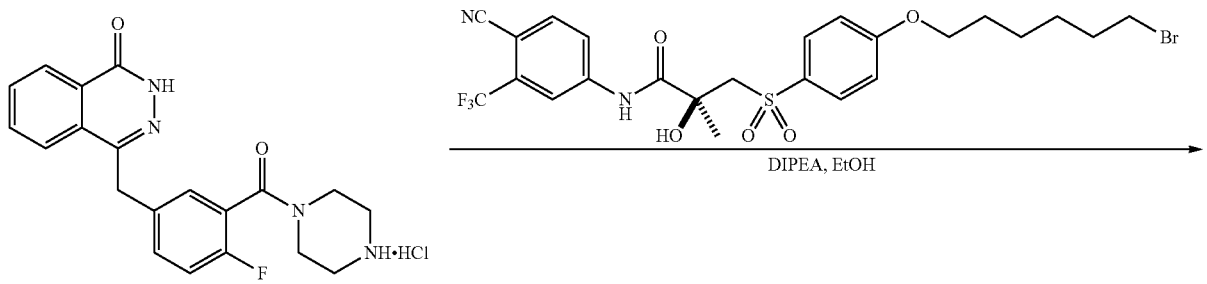

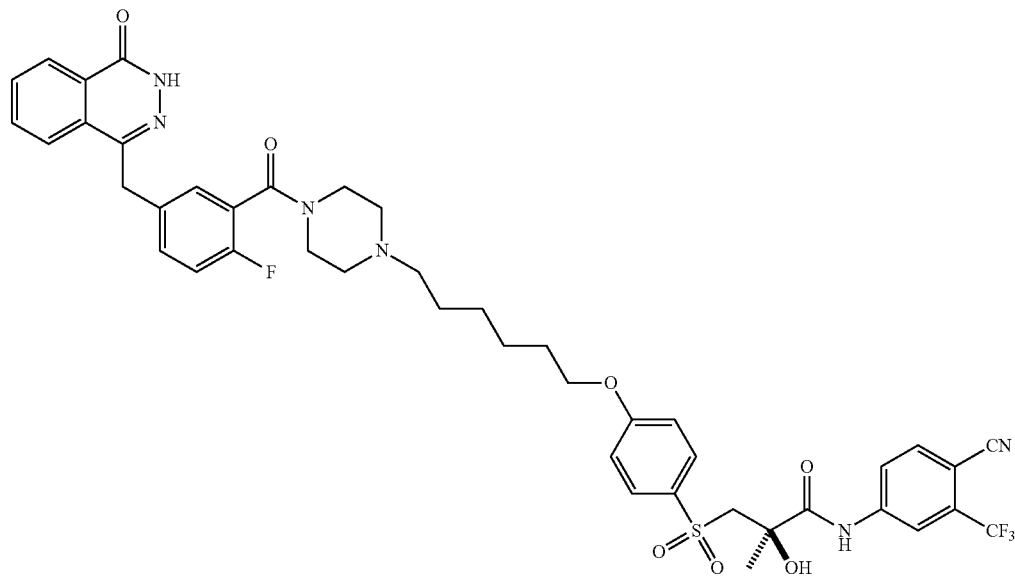

To a stirred solution of 4-(4-fluoro-3-(piperazine-1-carbonyl)benzyl)phthalazin-1(2H)-one hydrochloride (0.15 g, 0.254 mmol) in EtOH (4 mL) was added DIPEA (0.234 mL, 1.27 mmol, 5 eq) followed by the addition of (S)-3-(4-(6-bromohexyloxy)phenylsulfonyl)-N-(4-cyano-3-(trifluoromethyl)phenyl)-2-hydroxy-2-methylpropanamide (0.153 g, 0.381 mmol, 2.0 eq) and the mixture was stirred at 80° C. for 16 h. The reaction was monitored by TLC and LC-MS. After completion, the reaction was concentrated under reduced pressure to obtain a crude residue which was purified by reversed phase HPLC to afford Compound 1.96. LC-MS 877 [M+H]$^+$. $^1$H NMR (400 MHz, DMSO-d$_6$) δ 12.53 (d, J=39.4 Hz, 1H), 10.47 (s, 1H), 8.39 (d, J=2.1 Hz, 1H), 8.26 (d, J=7.8 Hz, 1H), 8.18-8.10 (m, 1H), 8.05 (d, J=8.6 Hz, 1H), 7.96 (d, J=8.0 Hz, 1H), 7.88 (t, J=7.5 Hz, 1H), 7.82 (t, J=7.4 Hz, 1H), 7.73 (d, J=8.4 Hz, 2H), 7.42 (ddd, J=8.2, 5.1, 2.4 Hz, 1H), 7.30 (dd, J=6.4, 2.4 Hz, 1H), 7.21 (t, J=9.0 Hz, 1H), 6.94 (d, J=8.5 Hz, 2H), 4.32 (s, 2H), 3.85 (dt, J=15.8, 11.9 Hz, 3H), 3.65-3.56 (m, 3H), 3.13 (t, J=5.0 Hz, 2H), 2.37 (t, J=5.0 Hz, 2H), 2.27 (t, J=7.3 Hz, 2H), 2.24-2.17 (m, 2H), 1.78 (s, 2H), 1.66 (p, J=7.2 Hz, 2H), 1.50-1.27 (m, 7H).

Example S-16. Preparation of (S)-N-(4-cyano-3-(trifluoromethyl)phenyl)-3-(4-(2-(4-((4-(2-fluoro-5-((4-oxo-3,4-dihydrophthalazin-1-yl)methyl)benzoyl)piperazin-1-yl)methyl)-1H-1,2,3-triazol-1-yl)ethylamino)phenylsulfonyl)-2-hydroxy-2-methylpropanamide (Compound 1.97)

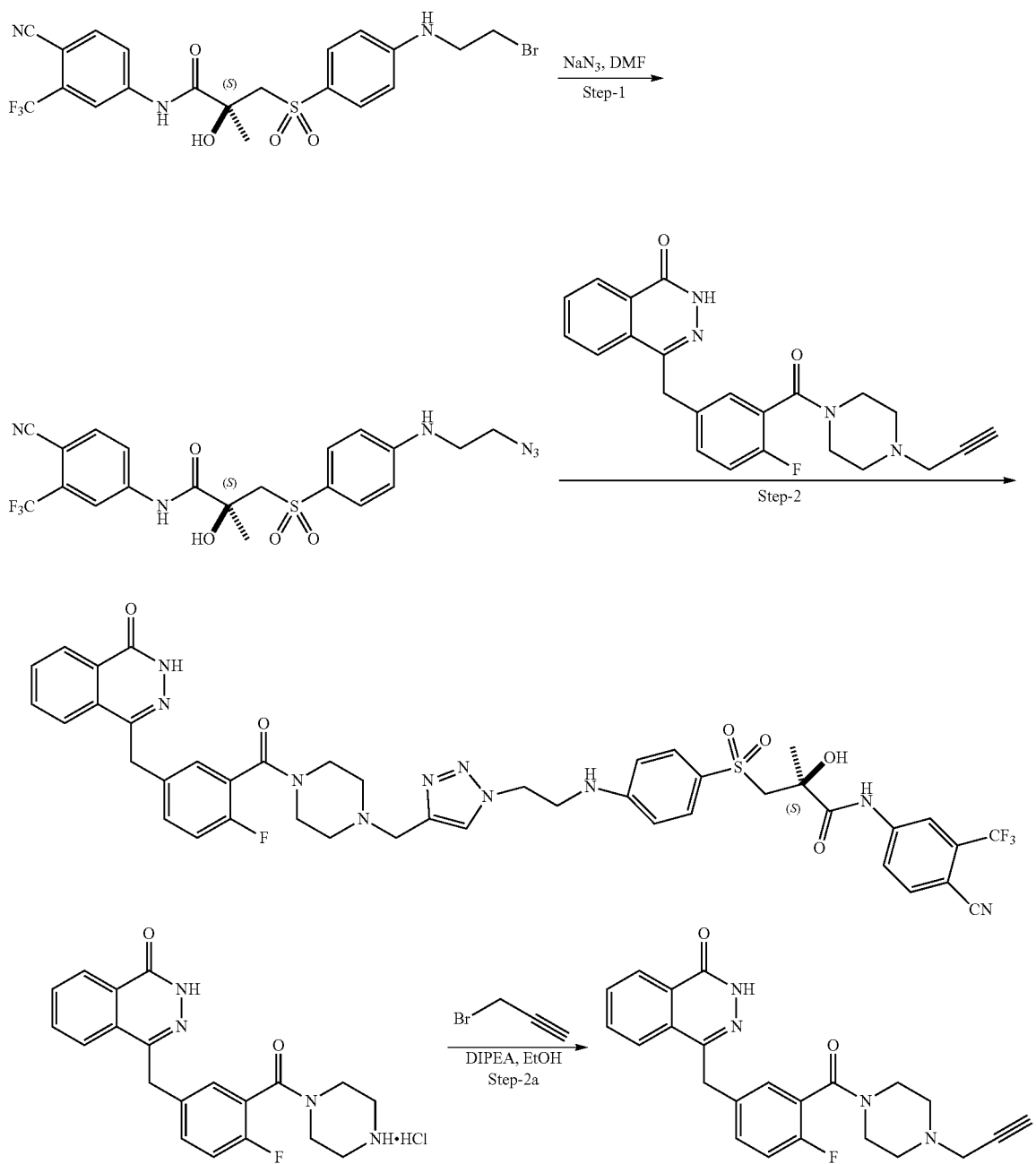

Step-1: Preparation of (S)-3-(4-(2-azidoethylamino)phenylsulfonyl)-N-(4-cyano-3-(trifluoromethyl)phenyl)-2-hydroxy-2-methylpropanamide To a stirred solution of (S)-3-(4-(2-bromoethylamino)phenylsulfonyl)-N-(4-cyano-3-(trifluoromethyl)phenyl)-2-hydroxy-2-methylpropanamide (0.30 g, 0.56 mmol) in DMF (5 mL) was added sodium azide (0.073, 0.112 mmol, 2 eq)) at RT and the mixture was heated at 80° C. for 2 h. The reaction was monitored by TLC. Upon completion, the mixture was diluted with EtOAc (250 mL). The organic layer was washed with water (100 mL×2), brine (100 mL), dried with anhydrous $Na_2SO_4$, filtered and concentrated under reduced pressure to obtain a crude which was purified by CombiFlash chromatography to afford the title compound. LC-MS 497 [M+H]$^+$.

Step-2a: Preparation of 4-(4-fluoro-3-(4-(prop-2 ynyl)piperazine-1-carbonyl)benzyl)phthalazin-1 (2H)-one To a stirred solution of 4-(4-fluoro-3-(piperazine-1-carbonyl)benzyl)phthalazin-1(2H)-one hydrochloride (0.40 g, 0.99 mmol) in EtOH (5 mL) was added DIPEA (0.91 mL, 4.97 mmol, 5 eq) followed by the addition of bromoethyne (0.176 g, 1.49 mmol, 2.0 eq) and the mixture was heated at 80° C. for 16 h. The reaction was monitored by TLC and LC-MS. After completion, the mixture was concentrated under reduced pressure to obtain a crude which was purified by CombiFlash chromatography to afford the title compound. LC-MS 405 [M+H]$^+$.

Step-2: Preparation of (S)-N-(4-cyano-3-(trifluoromethyl)phenyl)-3-(4-(2-(4-((4-(2-fluoro-5-((4-oxo-3,4-dihydrophthalazin-1 yl)methyl)benzoyl)piperazin-1 yl)methyl)-1H-1,2,3-triazol-1-yl)ethylamino) phenylsulfonyl)-2-hydroxy-2-methylpropanamide (Compound 1.97)

To a stirred solution of (S)-3-(4-(2-azidoethylamino)phenylsulfonyl)-N-(4-cyano-3-(trifluoromethyl)phenyl)-2-hydroxy-2-methylpropanamide (0.150 g, 0.301 mmol) and 4-(4-fluoro-3-(4-(prop-2-ynyl) piperazine-1-carbonyl)benzyl)phthalazin-1(2H)-one (0.182 g, 0.452 mmol, 15 eq) in MeCN:$H_2O$ (2:1) (6 mL) were successively added cupper suphate pentahydrate (0.024 g, 0.15 mmol, 0.5 eq) and hydrazine hydrate (0.011 mg, 1.00 mmol, 1 eq) and the resultant mixture was heated at 60° C. for 2 h. The reaction was monitored by TLC and LC-MS. After completion, the mixture was diluted with water (50 mL) and extracted with ethylacetate (50 mL×2). The combined organic layers were washed with 10% $NH_4OH$ solution, dried with anhydrous $Na_2SO_4$, filtered and concentrated under reduced pressure to obtain a crude which was purified by CombiFlash chromatography to afford Compound 1.97. LC-MS 901 [M+H]$^+$. $^1$H NMR (400 MHz, DMSO-$d_6$) δ 12.59 (s, 1H), 10.35 (s, 1H), 8.43 (d, J=2.1 Hz, 1H), 8.29-8.15 (m, 2H), 8.06 (d, J=8.6 Hz, 1H), 8.00 (s, 1H), 7.96 (d, J=8.0 Hz, 1H), 7.88 (t, J=7.5 Hz, 1H), 7.82 (t, J=7.5 Hz, 1H), 7.48 (d, J=8.5 Hz, 2H), 7.42 (s, 1H), 7.32 (d, J=6.1 Hz, 1H), 7.22 (t, J=8.9 Hz, 1H), 6.72 (t, J=6.0 Hz, 1H), 6.56 (d, J=8.5 Hz, 2H), 6.32 (s, 1H), 4.47 (s, 2H), 4.32 (s, 2H), 3.78 (d, J=14.5 Hz, 1H), 3.52 (dt, J=19.4, 11.7 Hz, 6H), 3.14 (s, 2H), 2.40 (s, 2H), 2.28 (s, 1H), 1.38 (s, 3H), 1.23 (s, 1H).

Example S-17. Preparation of (R)-N-(4-cyano-3-(trifluoromethyl)phenyl)-3-(4-(2-(4-(2-fluoro-5-((4-oxo-3,4-dihydrophthalazin-1-yl)methyl)benzoyl) piperazin-1-yl)-2-oxoethylamino)phenylsulfonyl)-2-hydroxy-2-methylpropanamide (Compound 1.98)

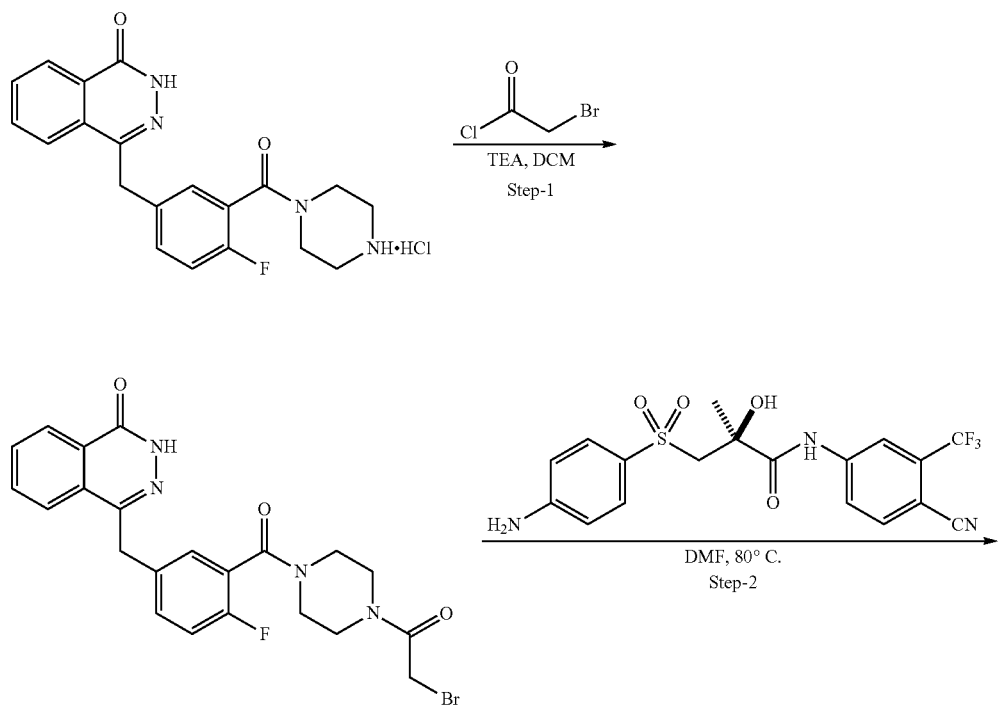

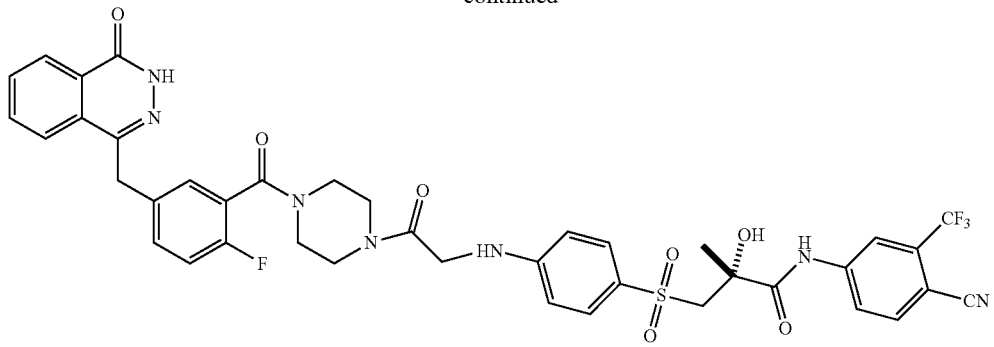

Step-1: Preparation of 4-(3-(4-(2-bromoacetyl)piperazine-1-carbonyl)-4-fluorobenzyl)phthalazin-1(2H)-one To 4-(4-fluoro-3-(piperazine-1-carbonyl)benzyl)phthalazin-1(2H)-one hydrochloride (1.0 g, 2.48 mmol) in DCM (5 mL) was added Et$_3$N (3.58 mL, 24.8 mmol) at RT and the mixture was slowly added to a previously stirred solution of 2-bromoacetyl chloride (3.85 g, 24.8 mmol) in DCM (20 mL) at 0° C. The resultant mixture was stirred at RT for 10 min and monitored by TLC and LC-MS. After completion, the reaction was quenched with saturated NaHCO$_3$ solution (30 mL) and extracted with DCM (200 mL×2). The combined organic layers were washed with H$_2$O (100 mL), brine (50 mL), dried over anhydrous sodium sulphate and concentrated under reduced pressure to obtain a crude residue which was purified by CombiFlash chromatography to afford the title compound. LC-MS 487 [M+H]$^+$

Step-2: Preparation of (R)-N-(4-cyano-3-(trifluoromethyl)phenyl)-3-(4-(2-(4-(2-fluoro-5-((4-oxo-3,4-dihydrophthalazin-1 yl)methyl)benzoyl)piperazin-1 yl)-2-oxoethylamino)phenylsulfonyl)-2-hydroxy-2-methylpropanamide To a stirred solution of (R)-3-(4-aminophenylsulfonyl)-N-(4-cyano-3-(trifluoromethyl)phenyl)-2-hydroxy-2-methylpropanamide (0.105 g, 0.246 mmol, 1 eq) in DMF (5 ml) was added 4-(3-(4-(2-bromoacetyl)piperazine-1-carbonyl)-4-fluorobenzyl)phthalazin-1(2H)-one (0.12 g, 0.246 mmol, 1 eq) and the reaction mixture was stirred at 80° C. for 16 h. The reaction was monitored by TLC and LC-MS. Upon completion, the mixture was diluted with EtOAc (100 mL). The organic layer was washed with ice-cold H$_2$O (50 mL×2), brine (30 mL), dried with anhydrous sodium sulphate and concentrated under reduced pressure to obtain a crude residue which was purified by reversed phase HPLC to afford the title compound. LC-MS: 487 [M+H]$^+$. $^1$HNMR (400 MHz, DMSO-d$_6$) δ 12.60 (s, 1H), 10.33 (s, 1H), 8.43 (d, J=2.1 Hz, 1H), 8.31-8.23 (m, 1H), 8.21-8.15 (m, 1H), 8.06 (d, J=8.5 Hz, 1H), 7.97 (t, J=5.2 Hz, 1H), 7.90 (d, J=6.6 Hz, 1H), 7.85 (d, J=7.9 Hz, 1H), 7.48 (t, J=9.7 Hz, 1H), 7.42-7.33 (m, 3H), 7.25 (q, J=7.6 Hz, 2H), 6.64 (dd, J=11.7, 8.2 Hz, 2H), 6.32 (s, 1H), 4.34 (s, 2H), 3.90 (d, J=19.0 Hz, 2H), 3.79 (d, J=14.5 Hz, 1H), 3.70 (s, 1H), 3.63 (s, 1H), 3.57 (s, 2H), 3.52 (s, 1H), 3.42 (s, 2H), 3.26 (s, 2H), 3.20 (s, 1H), 1.39 (s, 3H).

Example S-18. Preparation of (R)-N-(4-cyano-3-(trifluoromethyl)phenyl)-3-(4-(2-(4-(2-fluoro-5-((4-oxo-3,4-dihydrophthalazin-1-yl)methyl)benzoyl)piperazin-1-yl)ethylamino)phenylsulfonyl)-2-hydroxy-2-methylpropanamide (Compound 1.99)

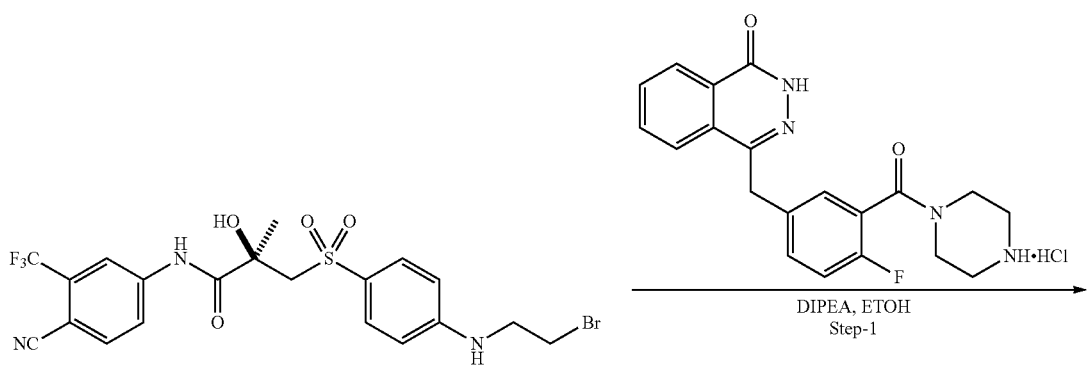

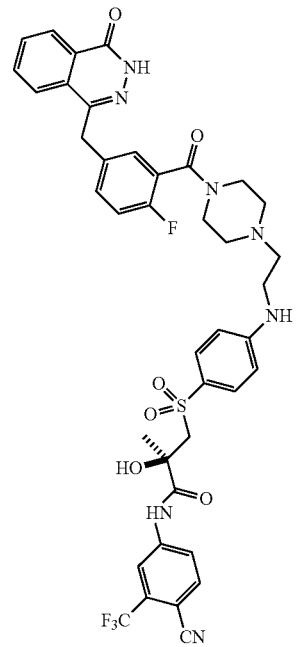

Step-1: Preparation of (R)-N-(4-cyano-3-(trifluoromethyl)phenyl)-3-(4-(2-(4-(2-fluoro-5-((4-oxo-3,4-dihydrophthalazin-1 yl)methyl)benzoyl)piperazin-1 yl)ethylamino)phenyl sulfonyl)-2-hydroxy-2-methylpropanamide To a stirred solution of 4-(4-fluoro-3-(piperazine-1-carbonyl)benzyl)phthalazin-1(2H)-one hydrochloride (0.075 g, 0.187 mmol, 1.0 eq) in EtOH (10 mL) was added DIPEA (0.201 mL, 1.12 mmol, 6 eq) followed by the addition of (R)-3-(4-(2-bromoethylamino)phenylsulfonyl)-N-(4-cyano-3-(trifluoromethyl)phenyl)-2-hydroxy-2-methylpropanamide (0.10 g, 0.187 mmol) and the mixture was stirred at 80° C. for 16 h. The reaction was monitored by TLC and LC-MS. After completion, the reaction was concentrated under reduced pressure to obtain a crude residue which was purified by reversed phase HPLC to afford the title compound. LC-MS=820 [M+H]$^+$. $^1$HNMR (400 MHz, DMSO-d$_6$) δ 12.61 (br. s., 1H), 8.41 (br. s., 1H), 8.26 (d, J=7.5 Hz, 1H), 8.14 (d, J=7.0 Hz, 1H), 8.03 (d, J=7.9 Hz, 1H), 7.96 (d, J=7.5 Hz, 1H), 7.91-7.80 (m, 2H), 7.50-7.38 (m, 3H), 7.32 (d, J=4.4 Hz, 1H), 7.22 (t, J=9.0 Hz, 1H), 6.58-6.48 (m, 2H), 6.40 (br. s., 1H), 3.76 (d, J=14.0 Hz, 1H), 3.62 (br. s., 2H), 3.50 (d, J=14.5 Hz, 1H), 3.16 (br. s., 2H), 3.07 (d, J=5.3 Hz, 2H), 2.49-2.4 (m, 4H), 2.31 (br. s., 2H), 1.68 (s, 2H), 1.37 (s, 3H).

Example S-19. Preparation of 4-(3-(4-(2-(2-((5S,8R,9S,10S,13S,14S,17S)-10,13-dimethyl-3-oxohexadeca hydro-1H-cyclopenta[a]phenanthren-17-yloxy)ethoxy)acetyl)piperazine-1-carbonyl)-4-fluorobenzyl)phthalazin-1(2H)-one (Compound 1.104)

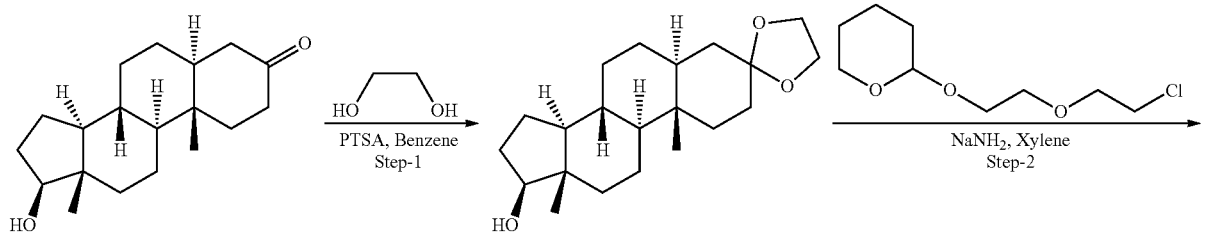

431
432
-continued
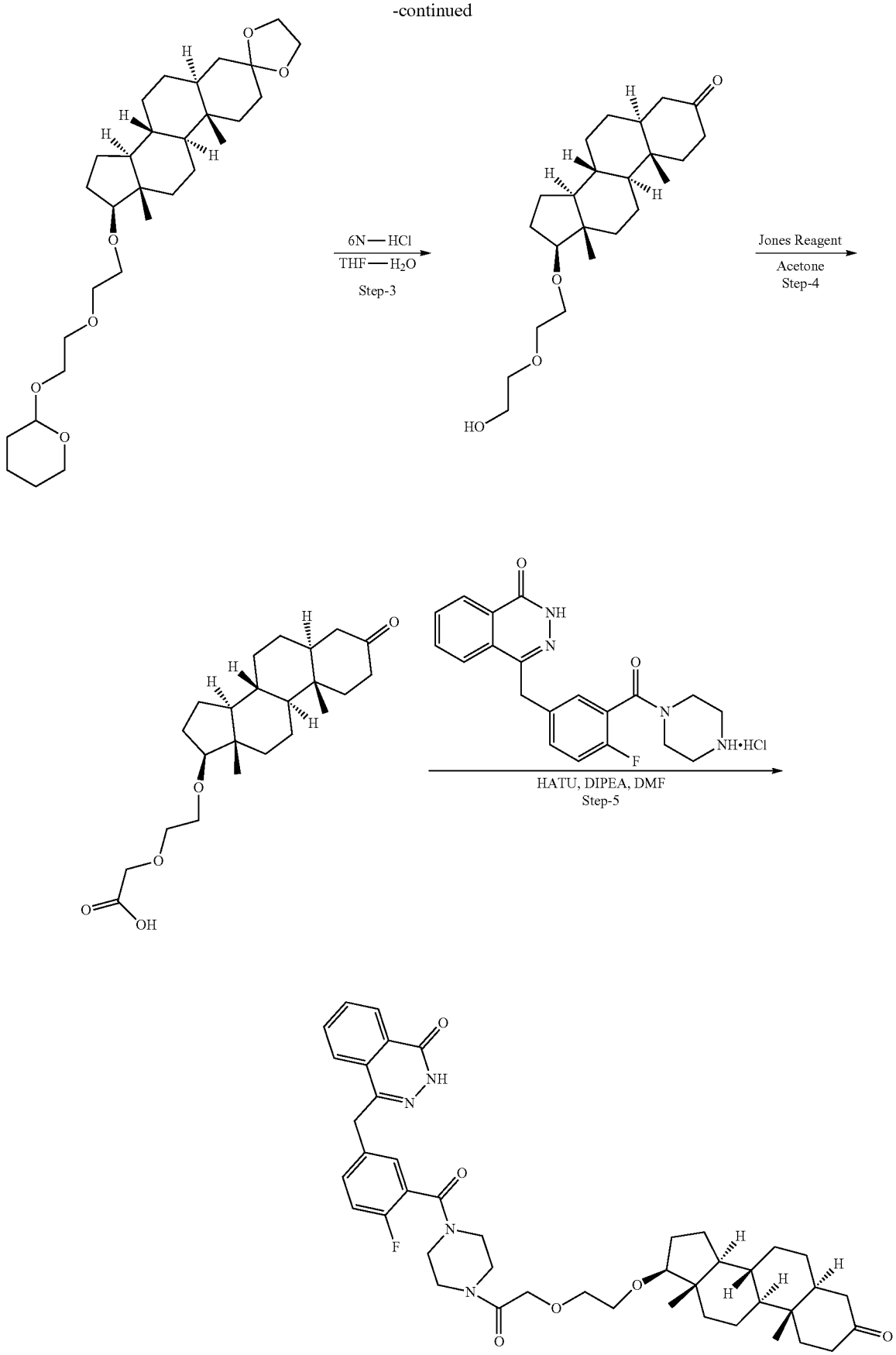

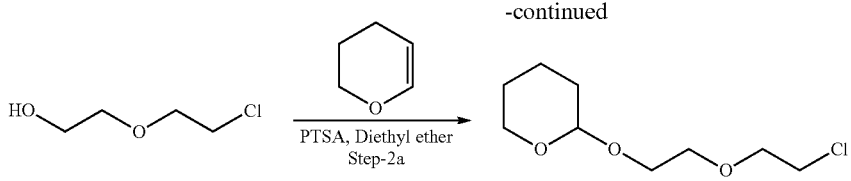

Step-1: Preparation of (5S,8R,9S,10S,13S,14S,17S)-10,13-dimethylhexadecahydrospiro[cyclopenta[a]phenanthrene-3,2'-[1,3]dioxolan]-17-ol To a stirred solution of (5S,8R,9S,10S,13S,14S,17S)-17-hydroxy-10,13-dimethyltetradecahydro-1H-cyclopenta[a]phenanthren-3(2H)-one (15 g, 51.65 mmol) in benzene (500 mL) was added PTSA (4.85 g, 25.8 mmol, 0.5 eq) followed by addition of ethylene glycol (14.5 mL, 258 mmol, 5 eq) at RT. The resultant mixture was refluxed using Dean-Stark apparatus for 16 h. The reaction was monitored by TLC. Upon completion, the reaction mixture was diluted with water (500 mL) and extracted with EtOAc (500 mL×2). The combined organic layers were washed with saturated NaHCO$_3$ solution (250 mL), water (400 mL), brine (200 mL) dried over Na$_2$SO$_4$, filtered and concentrated under reduced pressure to afford the title compound. $^1$HNMR (400 MHz, DMSO-d$_6$) δ 4.40 (d, J=5.26 Hz, 1H), 3.81 (s, 3H), 3.45-3.37 (m, 2H), 1.82 (br. s., 2H), 1.70 (d, J=12.72 Hz, 2H), 1.59 (d, J=13.15 Hz, 2H), 1.52 (d, J=10.52 Hz, 3H), 1.35 (br. s., 1H), 1.33-1.23 (m, 3H), 1.21-1.03 (m, 5H), 0.87 (dt, J=7.89, 19.95 Hz, 4H), 0.76 (s, 3H), 0.61 (s, 3H)

Step-2a: Preparation of 2-(2-(2-chloroethoxy)ethoxy)tetrahydro-2H-pyran

To a stirred solution of 2-(2-chloroethoxy)ethanol (10 g, 80.6 mmol) in diethyl ether (150 mL) was added PTSA (1.54 g, 0.806 mmol, 0.1 eq) followed by addition of 3,4-dihydro-2H-pyran (8.12 g, 96.7 mmol, 1.2 eq). The resulting reaction mixture was stirred at RT for 16 h. The reaction was monitored by TLC. Upon completion, the reaction mixture was diluted with diethyl ether (700 mL). The organic layer was washed with 20% KOH solution (300 mL), water (600 mL), brine (300 mL) dried over Na$_2$SO$_4$, filtered and concentrated under reduced pressure to afford the title compound which was taken to next step without further purification. $^1$HNMR (400 MHz, DMSO-d$_6$) δ 4.62-4.56 (m, 1H), 3.75-3.66 (m, 6H), 3.63-3.56 (m, 2H), 3.53-3.46 (m, 1H), 3.46-3.39 (m, 1H), 1.75-1.67 (m, 1H), 1.65-1.57 (m, 1H), 1.52-1.39 (m, 4H).

Step-2: Preparation of (5S,8R,9S,10S,13S,14S,17S)-10,13-dimethyl-17-(2-(2-(tetrahydro-2H pyran-2-yloxy)ethoxy)ethoxy)hexadecahydrospiro[cyclopenta[a]phenanthrene-3,2'-[1,3]dioxolane]

To a stirred solution of (5S,8R,9S,10S,13S,14S,17S)-10,13-dimethylhexadecahydrospiro[cyclopenta[a]phenanthrene-3,2'-[1,3]dioxolan]-17-ol (1.2 g, 3.59 mmol) in xylene (12 mL) was added NaNH$_2$ (50% suspension in toluene, 3.5 mL) and the mixture was heated at 150° C. for 1 h. The reaction mixture was gradually cooled to 25° C., 2-(6-chlorohexyloxy)tetrahydro-2H-pyran (7.47 g, 35.9 mmol) was added to it and the resultant mixture was further heated at 150° C. for 16 h. The reaction was monitored by TLC. Upon completion, the mixture was cooled to RT, quenched slowly with ice cold water (500 mL) and extracted with EtOAc (300 mL×2). The combined organic layer were washed with water (250 mL×2), brine (200 mL) dried over Na$_2$SO$_4$, filtered and concentrated under reduced pressure to obtain a crude product which was purified by CombiFlash chromatography to afford the title compound. $^1$HNMR (400 MHz, CDCl3) δ 4.64 (t, J=3.5 Hz, 1H), 3.93 (s, 4H), 3.90-3.81 (m, 4H), 3.74 (dd, J=5.5, 3.7 Hz, 1H), 3.70-3.64 (m, 4H), 3.64-3.54 (m, 4H), 3.54-3.44 (m, 2H), 3.32 (t, J=8.3 Hz, 2H), 2.02-1.93 (m, 2H), 1.90-1.80 (m, 2H), 1.66-1.60 (m, 6H), 1.44-1.33 (m, 4H), 1.28-1.16 (m, 6H), 0.98-0.84 (m, 4H), 0.84-0.77 (m, 2H), 0.76-0.69 (m, 2H).

Step-3: Preparation of (5S,8R,9S,10S,13S,14S,17S)-17-(2-(2-hydroxyethoxy)ethoxy)-10,13-dimethyltetradecahydro-1H-cyclopenta[a]phenanthren-3(2H)-one To a stirred solution of (5S,8R,9S,10S,13S,14S,17S)-10,13-dimethyl-17-(2-(2-(tetrahydro-2H-pyran-2-yloxy)ethoxy)ethoxy)hexadecahydrospiro[cyclopenta[a]phenanthrene-3,2'-[1,3]dioxolane] (0.5 g, 0.988 mmol) in THF (30 mL)-H$_2$O (10 mL) was added 6N TLC (20 mL) at RT and the resultant reaction mixture was stirred at RT for 16 h. The reaction was monitored by TLC. Upon completion, the reaction mixture was diluted water (30 mL) and basified using with saturated NaHCO$_3$ solution (pH ~8). The aqueous layer was then extracted with EtOAc (40 mL×3). The organic layer was washed with saturated NaHCO$_3$ solution (30 mL), water (30 mL), brine (20 mL) dried over Na$_2$SO$_4$, filtered and concentrated under reduced pressure to afford the title compound which was used in the next step without further purification. $^1$HNMR (400 MHz, CDCl3) δ 3.75-3.69 (m, 2H), 3.69-3.60 (m, 4H), 3.36 (t, 0.1=8.3 Hz, 1H), 2.66 (t, J=6.4 Hz, 1H), 2.37 (dd, J=13.8, 6.4 Hz, 1H), 2.33-2.25 (m, 2H), 2.12-2.08 (m, 1H), 2.07-1.96 (m, 2H), 1.96-1.87 (m, 2H), 1.70 (dd, J=13.4, 3.3 Hz, 2H), 1.47-1.40 (m, 2H), 1.27-1.28 (m, 4H), 1.27-1.15 (m, 4H), 1.04-0.99 (m, 4H), 0.97 (d, J=7.9 Hz, 2H), 0.88-0.81 (m, 2H), 0.79 (s, 2H).

Step-4: Preparation of 2-(2-((5S,8R,9S,10S,13S,14S,17S)-10,13-dimethyl-3-oxohexadeca hydro-1H-cyclopenta[a]phenanthren-17-yloxy)ethoxy) acetic acid To a stirred solution of (5S,8R,9S,10S,13S,14S,17S)-17-(2-(2-hydroxyethoxy)ethoxy)-10,13-dimethyltetradecahydro-1H-cyclopenta[a]phenanthren-3(2H)-one (0.40 g, 0.947 mmol) in acetone (2.5 mL) was added Jones reagent (2.4 mL) at 0° C. dropwise over a period of 30 min. The resultant mixture was stirred at 0° C. for 10 min. The reaction was monitored by TLC. After completion, water (100 mL) was added and the resulting precipitate was filtered over Buchner funnel. The product obtained was washed with water (50 mL×2) and n-pentane (50 mL×2), dried under vacuum to afford the title compound which was taken to next step without further purification. ¹HNMR (400 MHz, DMSO-d₆) δ 12.51 (br. s., 1H), 4.02 (s, 2H), 3.58-3.46 (m, 3H), 2.39 (dd, J=6.8, 14.7 Hz, 2H), 2.34-2.23 (m, 2H), 2.08 (d, J=13.6 Hz, 2H), 1.97-1.85 (m, 3H), 1.80 (d, J=12.7 Hz, 1H), 1.61 (d, J=13.2 Hz, 1H), 1.51 (br. s., 3H), 1.42-1.33 (m, 2H), 1.32-1.06 (m, 8H), 1.00-0.92 (m, 2H), 0.70 (s, 2H)

Step-5: Preparation of 9S,10S,13S,14S,17S)-10,13-dimethyl-3-oxohexadeca hydro-1H-cyclopenta[a]phenanthren-17-yloxy)ethoxy) acetyl)piperazine-1-carbonyl)-4-fluorobenzyl)phthalazin-1(2H)-one To a stirred solution of 2-(2-(((5S,8R,9S,10S,13S,14S,17S)-10,13-dimethyl-3-oxohexadecahydro-1H-cyclopenta[a]phenanthren-17-yloxy)ethoxy)acetic acid (0.05 g, 0.127 mmol) in DMF (5 mL) was added HATU (0.058 g, 0.153 mmol, 1.2 eq) at 0° C. and the resulting reaction mixture was stirred for 10 min. DIPEA (0.114 mL, 0.637 mmol, 5 eq) and 4-(4-fluoro-3-(piperazine-1-carbonyl)benzyl)phthalazin-1(2H)-one hydrochloride (0.035 g, 0.089 mmol, 0.7 eq) were then successively added to the mixture and the mixture was stirred at RT for 2 h. The reaction was monitored by TLC & LC-MS. After completion, water (10 mL) was added and the resulting precipitate was filtered over Buchner funnel. The product obtained was washed with water (25 mL×2) and n-pentane (25 mL×2), dried under vacuum to obtain a crude residue which was purified by reversed phase HPLC to afford the title compound. LC-MS 741 [M+H]⁺. ¹HNMR (400 MHz, MeOD-d₄) δ 8.37 (d, J=7.8 Hz, 1H), 7.96 (t, J=7.5 Hz, 1H), 7.86 (dt, J=18.5, 7.4 Hz, 2H), 7.48 (t, J=7.0 Hz, 1H), 7.45-7.33 (m, 1H), 7.16 (td, J=9.0, 3.5 Hz, 1H), 4.39 (s, 2H), 4.28 (s, 1H), 4.21 (s, 1H), 3.85-3.72 (m, 2H), 3.71-3.48 (m, 9H), 3.39-3.32 (m, 2H), 3.17 (s, 2H), 3.12 (s, 2H), 2.53-2.30 (m, 1H), 2.09-1.95 (m, 1H), 1.88 (ddd, J=13.8, 10.0, 6.3 Hz, 2H), 1.79-1.20 (m, 11H), 1.04 (dd, J=14.2, 8.7 Hz, 2H), 0.90 (td, J=11.9, 11.3, 6.7 Hz, 1H), 0.79 (dd, J=13.2, 6.4 Hz, 4H), 0.60 (d, J=11.1 Hz, 2H).

Example S-20. Preparation of 4-(4-fluoro-3-(4-(2-(4-((5S,8R,9S,10S,13S,14S,17S)-17-hydroxy-10,13-dimethyl-3-oxohexadecahydro-1H-cyclopenta[a]phenanthren-17-yl)-1H-1,2,3-triazol-1-yl)acetyl)piperazine-1-carbonyl)benzyl)phthalazin-1(2H)-one (Compound 1.107)

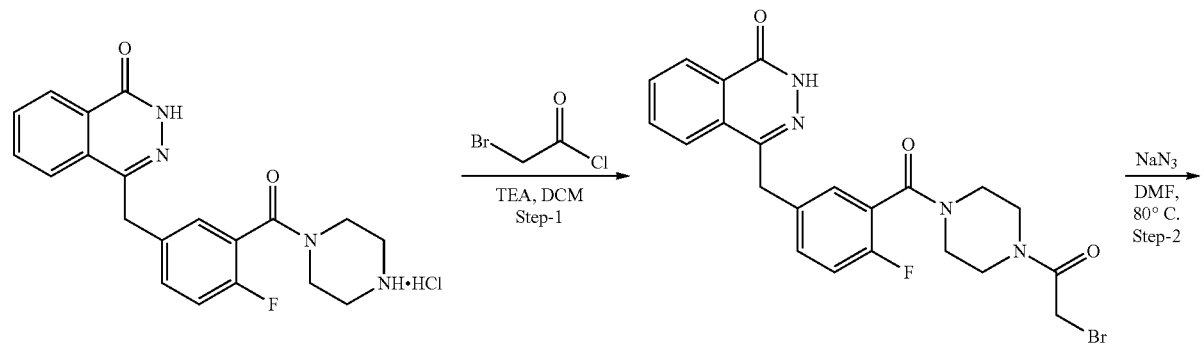

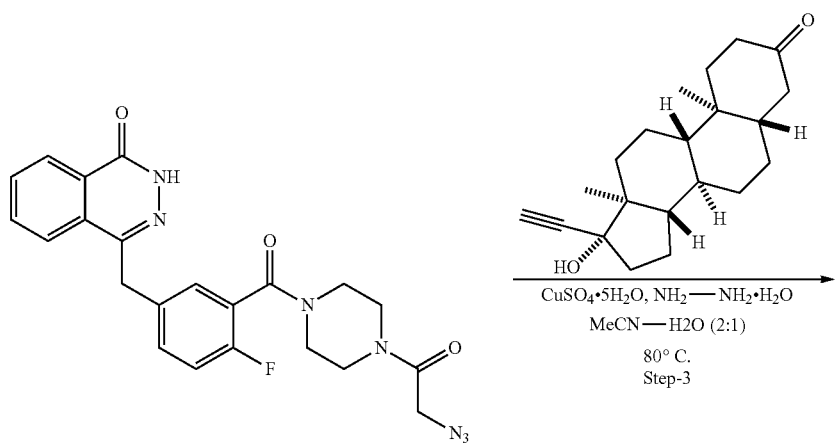

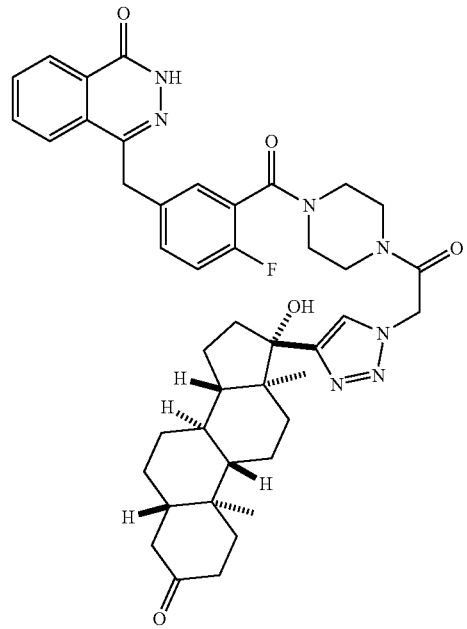

Step-1: Preparation of 4-(3-(4-(2-bromoacetyl)piperazine-1-carbonyl)-4-fluorobenzyl)phthalazin-1(2H)-one To 4-(4-fluoro-3-(piperazine-1-carbonyl)benzyl)phthalazin-1(2H)-one hydrochloride (1.0 g, 2.48 mmol) in DCM (5 mL) was added Et$_3$N (3.58 mL, 24.8 mmol) at RT and the mixture was slowly added to a previously stirred solution of 2-bromoacetyl chloride (3.85 g, 24.8 mmol) in DCM (20 mL) at 0° C. The resultant mixture was stirred at RT for 10 min and monitored by TLC and LC-MS. After completion, the reaction was quenched with saturated NaHCO$_3$ solution (30 mL) and extracted with DCM (200 mL×2). The combined organic layers were washed with H$_2$O (100 mL), brine (50 mL), dried over anhydrous sodium sulphate and concentrated under reduced pressure to obtain a crude residue which was purified by CombiFlash chromatography to afford the title compound. LC-MS 487 [M+H]$^+$

Step-2: Preparation of 4-(3-(4-(2-azidoacetyl)piperazine-1-carbonyl)-4-fluorobenzyl) phthalazin-1(2H)-one To a stirred solution of 4-(3-(4-(2-bromoacetyl)piperazine-1-carbonyl)-4-fluorobenzyl) phthalazin-1(2H)-one (0.20 g, 0.411 mmol, 1 eq) in DMF (10 ml) was added sodium azide (0.053, 0.83 m mol, 2 eq) at RT and the mixture was heated at 80° C. for 2 h. The reaction was monitored by TLC. After completion, the mixture was diluted with EtOAc (100 mL). The organic layer was washed with ice-cold water (80 mL×2), brine (50 mL), dried over anhydrous sodium sulphate and concentrated under reduced pressure to obtain a crude residue which was purified by CombiFlash chromatography to afford the title compound. LC-MS 450 [M+H]$^+$

Step-3: Preparation of 4-(4-fluoro-3-(4-(2-(4-((5S,8R,9S,10S,13S,14S,17S)-17-hydroxy-10,13-dimethyl-3-oxohexadecahydro-1H-cyclopenta[a]phenanthren-17-yl)-1H-1,2,3-triazol-1 yl)acetyl)piperazine-1-carbonyl)benzyl)phthalazin-1(2H)-one To a stirred solution of 4-(3-(4-(2-azidoacetyl)piperazine-1-carbonyl)-4-fluorobenzyl) phthalazin-1(2H)-one (0.120 g, 0.27 mmol, 1 eq) and (5S,8R,9S,10S,13S,14S,17R)-17-ethynyl-17-hydroxy-10,13-dimethyltetradecahydro-1H-cyclopenta[a]phenanthren-3(2H)-one (0.093 g, 0.32 mmol, 1.2 eq) in MeCN:H$_2$O (2:1) (6 mL) was added CuSO$_4$·5H$_2$O (0.021 g, 0.13 mmol, 0.5 eq) and hydrazine hydrate (0.0085 g, 0.26 mmol, 1 eq) and the resultant reaction mixture was heated at 80° C. for 16 h. The reaction was monitored by TLC and LC-MS. After completion, the mixture was diluted with water (30 mL) and extracted with EtOAc (40×2 mL). The combined organic layers were washed with brine (30 mL), dried with anhydrous sodium sulphate and concentrated under reduced pressure to obtain a crude which was purified by reversed phase HPLC to afford the title compound. LC-MS 764 [M+H]$^+$. $^1$HNMR (400 MHz, DMSO-d$_6$) δ 12.60 (s, 1H), 8.30-8.23 (m, 1H), 8.01-7.79 (m, 3H), 7.68 (s, 1H), 1.30-1.12 (m, 4H), 0.96 (s, 3H), 0.91 (s, 3H), 0.84 (d, J=10.5 Hz, 1H), 0.48-0.38 (m, 2H). 7.48-7.33 (m, 2H), 7.25 (td, J=9.2, 5.9 Hz, 1H), 5.46 (s, 1H), 5.40 (s, 1H), 5.05 (s, 1H), 4.34 (s, 2H), 3.71 (s, 1H), 3.68-3.53 (m, 3H), 3.46 (s, 1H), 3.40 (s, 2H), 3.28 (d, J=7.5 Hz, 1H), 3.20 (s, 1H), 2.42-2.21 (m, 2H), 2.10-1.99 (m, 1H), 1.95-1.78 (m, 3H), 1.71 (dd, J=22.7, 10.8 Hz, 2H), 1.47-1.31 (m, 5H).

Example S-21. Preparation of 4-(3-(4-(2-((5S,8R, 9S,10S,13S,14S,17S)-10,13-dimethyl-3-oxohexadecahydro-1H-cyclopenta[a]phenanthren-17-yloxy) acetyl)piperazine-1-carbonyl)-4-fluorobenzyl) phthalazin-1(2H)-one (Compound 1.110)
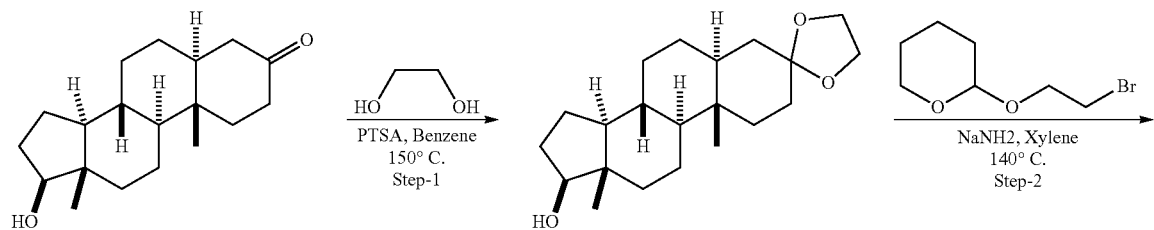
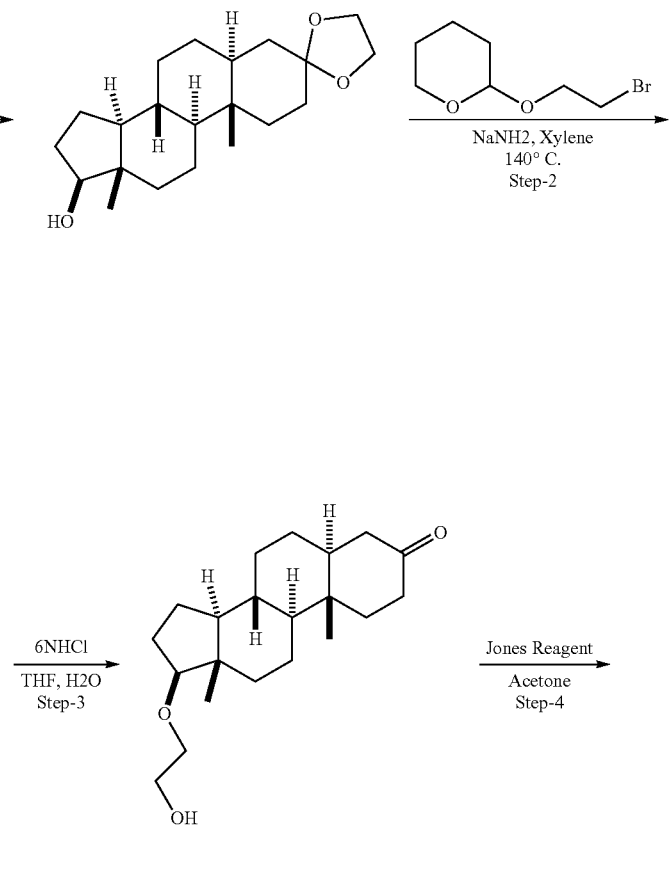
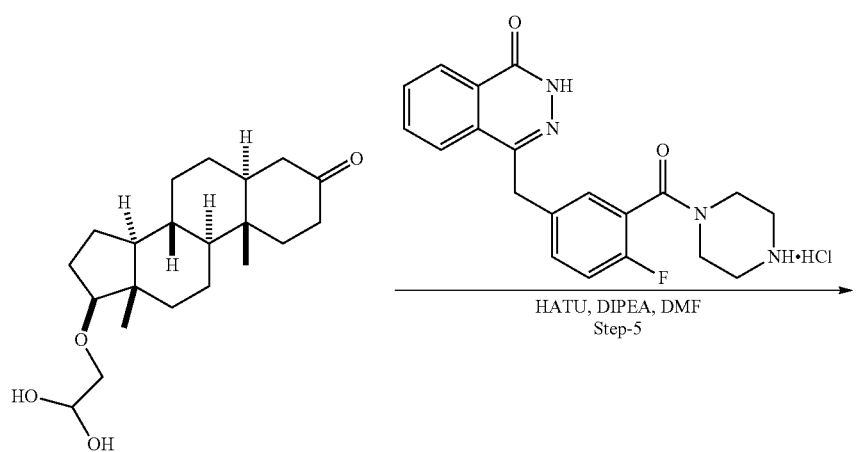

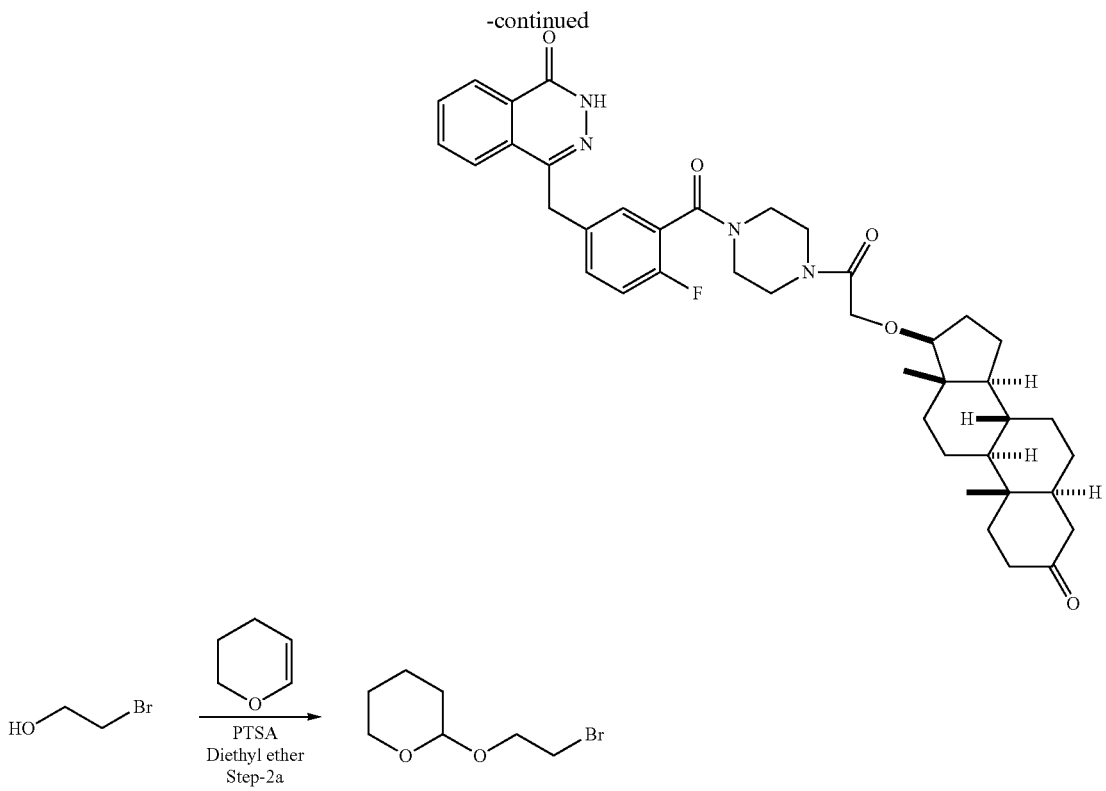

Step-1: Preparation of (5S,8R,9S,10S,13S,14S,17S)-10,13-dimethylhexadecahydrospiro[cyclopenta[a]phenanthrene-3,2'-[1,3]dioxolan]-17-ol To a stirred solution of (5S,8R,9S,10S,13S,14S,17S)-17-hydroxy-10,13-dimethyltetradecahydro-1H-cyclopenta[a]phenanthren-3(2H)-one (10 g, 34.48 mmol) in benzene (330 mL) was added PTSA (1.54 g, 17.27 mmol, 0.1 eq) followed by addition of ethylene glycol (9.63 g, 172.7 mmol, 5.0 eq) at RT. The resultant mixture was heated at 150° C. 16 h. Reaction was monitored by TLC. Upon completion, the reaction mixture was diluted with water (200 mL) and extracted with EtOAc (350 mL). The organic layer was washed with saturated NaHCO$_3$ solution (100 mL), water (200 mL), brine (100 mL) dried over Na$_2$SO$_4$, filtered and concentrated under reduced pressure to afford (5S,8R,9S,10S,13S,14S,17S)-10,13-dimethylhexadecahydrospiro[cyclopenta[a]phenanthrene-3,2'-[1,3]dioxolan]-17-ol. $^1$H NMR (400 MHz, DMSO-d$_6$) δ 4.40 (d, J=5.26 Hz, 1H), 3.81 (s, 3H), 3.37-3.45 (m, 2H), 1.82 (brs, 2H), 1.70 (d, J=12.72 Hz, 2H), 1.59 (d, J=13.15 Hz, 2H), 1.52 (d, J=10.52 Hz, 3H), 1.35 (br. s., 1H), 1.23-1.33 (m, 3H), 1.03-1.21 (m, 5H), 0.87 (dt, J=7.89, 19.95 Hz, 4H), 0.76 (s, 3H), 0.61 (s, 3H)/

Step-2a: Preparation of 2-(2-bromoethoxy)tetrahydro-2H-pyran

To a stirred solution of 2-bromoethanol (10 g, 80.6 mmol) in diethyl ether (150 mL) was added PTSA (1.54 g, 8.0 mmol, 0.1 eq) followed by addition of 3,4-dihydro-2H-pyran (8.83 g, 96.5 mmol, 1.2 eq) and the resultant mixture was stirred at RT for 16 h. Reaction was monitored by TLC. Upon completion, the reaction mixture was diluted with water (200 mL) and extracted with EtOAc (350 mL). The organic layer was washed with saturated NaHCO$_3$ solution (100 mL), water (200 mL), brine (100 mL) dried over Na$_2$SO$_4$, filtered and concentrated under reduced pressure to afford the title compound as a yellowish liquid which was taken to next-step without further purification. $^1$H NMR (400 MHz, DMSO-d$_6$) δ 4.66 (t, J=3.3 Hz, 1H), 3.93-3.85 (m, 1H), 3.82-3.66 (m, 2H), 3.66-3.57 (m, 2H), 3.49-3.39 (m, 1H), 1.72 (d, J=9.2 Hz, 1H), 1.62 (d, J=2.2 Hz, 1H), 1.53-1.40 (m, 4H).

Step-2: Preparation of (5S,8R,9S,10S,13S,14S,17S)-10,13-dimethyl-17-(2-(tetrahydro-2H pyran-2-yloxy)ethoxy)hexadecahydrospiro[cyclopenta[a]phenanthrene-3,2'-[1,3]dioxolane]

To a stirred solution of (5S,8R,9S,10S,13S,14S,17S)-10,13-dimethylhexadecahydrospiro[cyclopenta[a]phenanthrene-3,2'-[1,3]dioxolan]-17-ol (1 g, 2.99 mmol) in xylene (10 mL) was added NaNH$_2$ (50% suspension in toluene, 3 mL) and the mixture was heated at 150° C. for 1 h. The reaction mixture was gradually cooled to RT, 2-(6-chlorohexyloxy) tetrahydro-2H-pyran (6 g, 29.9 mmol)) was added to it and the resultant mixture was again heated to 150° C. for 16 h. The reaction was monitored by TLC. Upon completion, the mixture was cooled to RT, quenched slowly with ice cold water (250 mL) and extracted with EtOAc (300 mL). The organic layer was washed with water (100 mL×2), brine (100 mL) dried over Na$_2$SO$_4$, filtered and concentrated under reduced pressure to obtain a crude product which was purified by CombiFlash chromatography to afford the title compound. LC-MS 463 [M+H]$^+$ Step-3: Preparation of (5S,8R,9S,10S,13S,14S,17S)-17-(2-hydroxyethoxy)-10,13-dimethyltetradecahydro-1H-cyclopenta[a]phenanthren-3(2H)-one To a stirred solution of (5S,8R,9S,10S,13S,14S,17S)-10,13-dimethyl-17-(2-((tetrahydro-2H-pyran-2-yloxy)ethoxy)

hexadecahydrospiro[cyclopenta[a]phenanthrene-3,2'-[1,3]dioxolane] (0.635 g, 1.37 mmol) in THF (25 mL) water (5 mL) was added 6N HCl (15 mL) at RT and the resultant reaction mixture was stirred at RT for 16 h. The reaction was monitored by TLC. Upon completion, the reaction mixture was diluted with water (150 mL) and basified using with saturated NaHCO$_3$ solution (pH ~8). The aqueous layer was then extracted with EtOAc (200 mL×3). The organic layer was washed with saturated NaHCO$_3$ solution (100 mL), water (100 mL), brine (100 mL) dried over Na$_2$SO$_4$, filtered and concentrated under reduced pressure to afford the title compound which was used in the next step without further purification. LC-MS 335 [M+H]$^+$ Step-4: Preparation of 2-((5S,8R,9S,10S,13S,14S,17S)-10,13-dimethyl-3-oxohexadecahydro-1H-cyclopenta[a]phenanthren-17-yloxy) acetic acid To a stirred solution of (5S,8R,9S,10S,13S,14S,17S)-17-(2-hydroxyethoxy)-10,13-dimethyltetradecahydro-1H-cyclopenta[a]phenanthren-3(2H)-one (0.31 g, 0.928 mmol) in acetone (25 mL) was added Jones reagent (2.5 mL) at 0° C. dropwise over a period of 20 min. The resultant mixture was stirred at 0° C. for 5 min. The reaction was monitored by TLC. After completion, water (10 mL) was added and the resulting precipitate was filtered over Buchner funnel. The product obtained was washed with water (5 mL×2) and n-pentane (5 mL×2), dried under vacuum to afford the title compound which was taken to next step without further purification. LC-MS 349 [M+H]$^+$ Step-5: Preparation of 4-(3-(4-(2-((5S,8R,9S,10S,13S,14S,17S)-10,13-dimethyl-3-oxohexadecahydro-1H-cyclopenta[a]phenanthren-17-yloxy)acetyl)piperazine-1-carbonyl)-4-fluorobenzyl)phthalazin-1(2H)-one To a stirred solution of 2-((5S,8R,9S,10S,13S,14S,17S)-10,13-dimethyl-3-oxohexadecahydro-1H-cyclopenta[a]phenanthren-17-yloxy)acetic acid (0.025 g, 0.071 mmol) in DMF (3 mL) was added HATU (0.032 g, 0.086 mmol, 1.2 eq) at 0° C. and the resulting reaction mixture was stirred for 10 min. DIPEA (0.062 mL, 0.358 mmol, 5 eq) and 4-(4-fluoro-3-(piperazine-1-carbonyl)benzyl)phthalazin-1(2H)-one hydrochloride (0.020 g, 0.0.5 mmol, 07 eq) were then successively added to the mixture and the mixture was stirred at RT for 1 h. The reaction was monitored by TLC & LC-MS. After completion, water (10 mL) was added and the resulting precipitate was filtered over Buchner funnel. The product obtained was washed with water (5 mL×2) and n-pentane (5 mL×2), dried under vacuum to obtain a crude product which was purified by reverse phase HPLC to afford the title compound. LC-MS 697 [M+H]$^+$, $^1$H NMR (400 MHz, MeOD-d$_4$) δ 8.41-8.34 (m, 1H), 8.00-7.92 (m, 1H), 7.86 (dtd, J=18.0, 7.3, 1.4 Hz, 2H), 7.49 (t, J=6.3 Hz, 1H), 7.39 (t, J=6.0 Hz, 1H), 7.17 (t, J=9.0 Hz, 1H), 4.61 (s, 2H), 4.39 (s, 2H), 4.21 (s, 1H), 4.15 (s, 1H), 3.76 (d, J=7.6 Hz, 2H), 3.66 (q, J=5.9, 5.3 Hz, 2H), 3.51 (s, 2H), 3.47-3.37 (m, 1H), 3.35 (d, J=4.2 Hz, 1H), 2.46 (d, J=15.1 Hz, 1H), 2.37 (t, J=14.3 Hz, 1H), 2.22 (d, J=15.0 Hz, 1H), 2.11-1.80 (m, 6H), 1.73 (d, J=13.8 Hz, 1H), 1.63 (d, J=10.8 Hz, 2H), 1.52 (m, 3H), 1.39-1.27 (m, 6H), 1.25 (s, 1H), 1.06 (d, J=6.6 Hz, 3H), 0.99-0.88 (m, 1H), 0.83 (s, 1H).

Example S-22. Preparation of 4-(4-fluoro-3-(4-(6-((5S,8R,9S,10S,13S,14S,17S)-3-hydroxy-10,13-dimethylhexadecahydro-1H-cyclopenta[a]phenanthren-17-yloxy)hexanoyl)piperazine-1-carbonyl)benzyl)phthalazin-1(2H)-one (Compound 1.111)

Step-1: Preparation of 4-(3-(4-(6-((5S,8R,9S,10S,13S,14S,17S)-10,13-dimethyl-3-oxohexadecahydro-1H-cyclopenta[a]phenanthren-17-yloxy)hexanoyl)piperazine-1-carbonyl)-4-fluorobenzyl)phthalazin-1(2H)-one

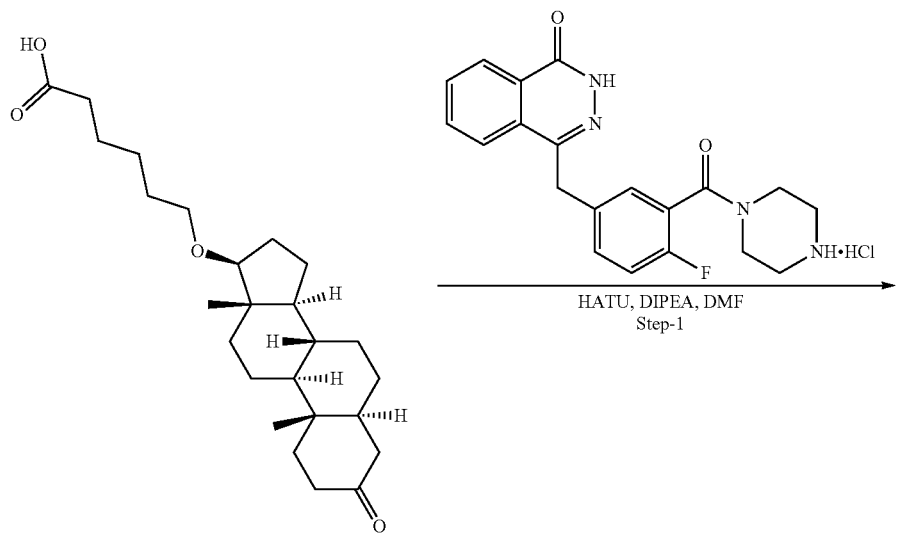

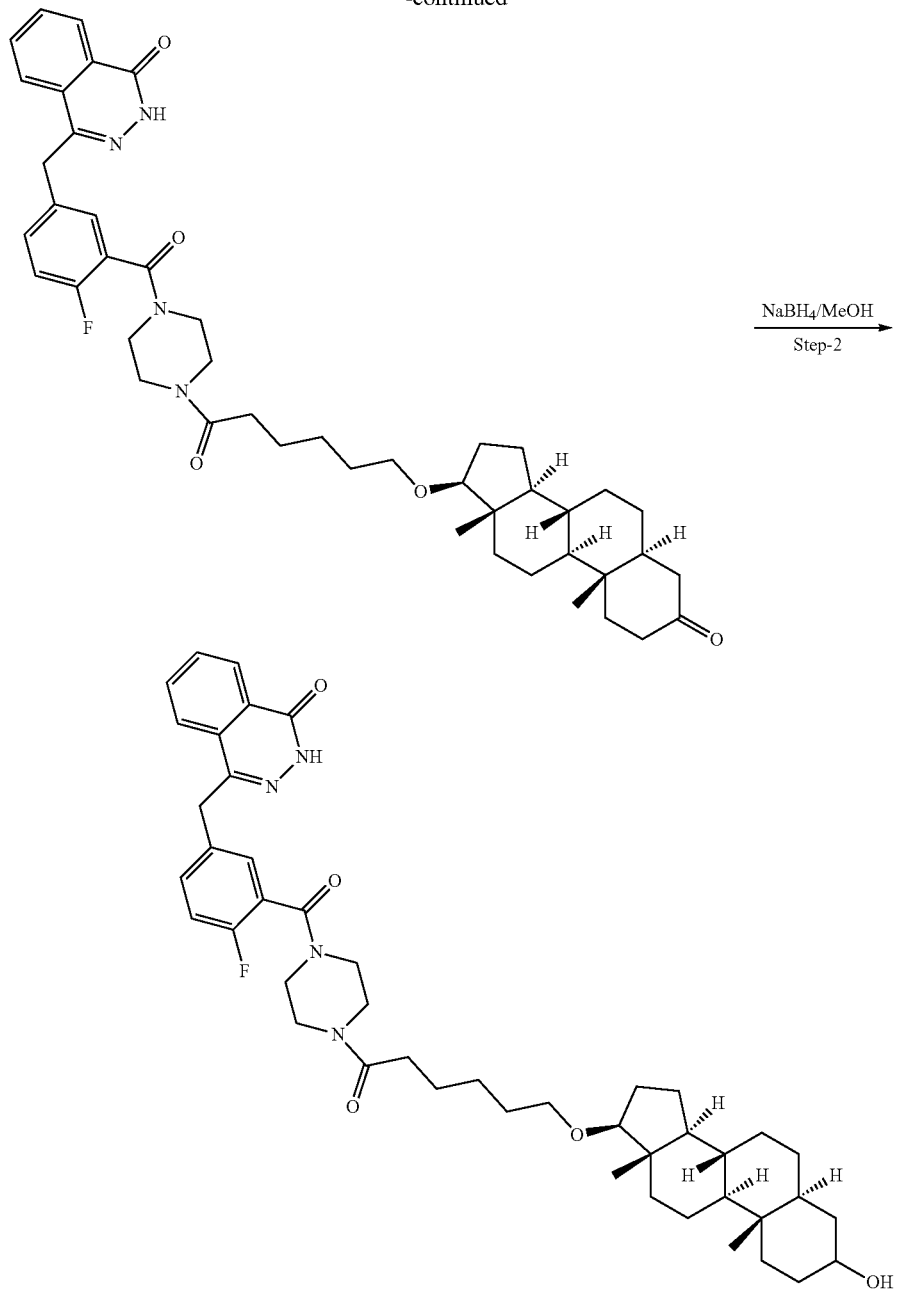

To a stirred solution of 6-((5S,8R,9S,10S,13S,14S,17S)-10,13-dimethyl-3-oxohexadecahydro-1H-cyclopenta[a]phenanthren-17-yloxy)hexanoic acid (0.10 g, 0.247 mmol) in DMF (15 mL) was added HATU (0.141 g, 0.371 mmol, 1.5 eq) at 0° C. and the resulting reaction mixture was stirred for 10 min. DIPEA (0.17 mL, 0.99 mmol, 4 eq) and 4-(4-fluoro-3-(piperazine-1-carbonyl)benzyl)phthalazin-1(2H)-one hydrochloride (0.119 g, 0.297 mmol, 0.1.2 eq) were then successively added to the mixture and the mixture was stirred at RT for 4 h. The reaction was monitored by TLC & LC-MS. After completion, water (10 mL) was added and the resulting precipitate was filtered over Buchner funnel. The product obtained was washed with water (25 mL×2) and n-pentane (25 mL×2), dried under vacuum to afford the title compound. LC-MS 753 [M+H]$^+$ Step-6: Preparation of 4-(4-fluoro-3-(4-(6-((5S,8R,9S,10S,13S,14S,17S)-3-hydroxy-10,13-dimethylhexadecahydro-1H-cyclopenta[a]phenanthren-17-yloxy)hexanoyl)piperazine-1-carbonyl)benzyl)phthalazin-1(2H)-one To a stirred solution of 4-(3-(4-(6-((5S,8R,9S,10S,13S,14S,17S)-10,13-dimethyl-3-oxohexadecahydro-1H-cyclopenta[a]phenanthren-17-yloxy)hexanoyl)piperazine-1-carbonyl)-4-fluorobenzyl)phthalazin-1(2H)-one (0.070 g, 0.093 mmol) in methanol (10 mL) was added NaBH$_4$ (0.0068 g, 0.186 mmol, 2.0 eq) at 0° C. slowly and the mixture was stirred at RT 30 min. The reaction was monitored by TLC. After completion, water (10 mL) was added and the resulting precipitate was filtered over Buchner funnel to obtain a crude residue which was purified by reversed phase HPLC to afford the title compound. LC-MS 755 [M+H]⁺, ¹H NMR (400 MHz, MeOD-d₄) δ 8.37 (d, J=7.7 Hz, 1H), 7.95 (s, 1H), 7.86 (dt, J=15.5, 7.3 Hz, 2H), 7.49 (d, J=7.1 Hz, 1H), 7.37 (d, J=6.1 Hz, 1H), 7.16 (t, J=9.0 Hz, 1H), 4.39 (s, 2H), 3.82-3.61 (m, 4H), 3.49 (ddd, J=22.0, 12.8, 5.5 Hz, 6H), 3.28 (d, J=7.6 Hz, 1H), 2.45 (t, J=7.6 Hz, 1H), 2.38 (t, J=7.6 Hz, 1H), 2.00-1.91 (m, 1H), 1.85 (t, J=11.3 Hz, 1H), 1.78-1.47 (m, 10H), 1.48-1.19 (m, 10H), 1.14 (d, J=14.1 Hz, 2H), 0.98 (q, J=10.6, 9.9 Hz, 2H), 0.88 (s, 2H), 0.83 (s, 3H), 0.73 (d, J=8.8 Hz, 3H).

Example S-23. Preparation of 4-(3-(4-(6-((5S,8R,9S,10S,13S,14S,17S)-3,3-difluoro-10,13-dimethyl-hexadecahydro-1H-cyclopenta[a]phenanthren-17-yloxy)hexanoyl)piperazine-1-carbonyl)-4-fluorobenzyl)phthalazin-1(2H)-one (Compound 1.114)

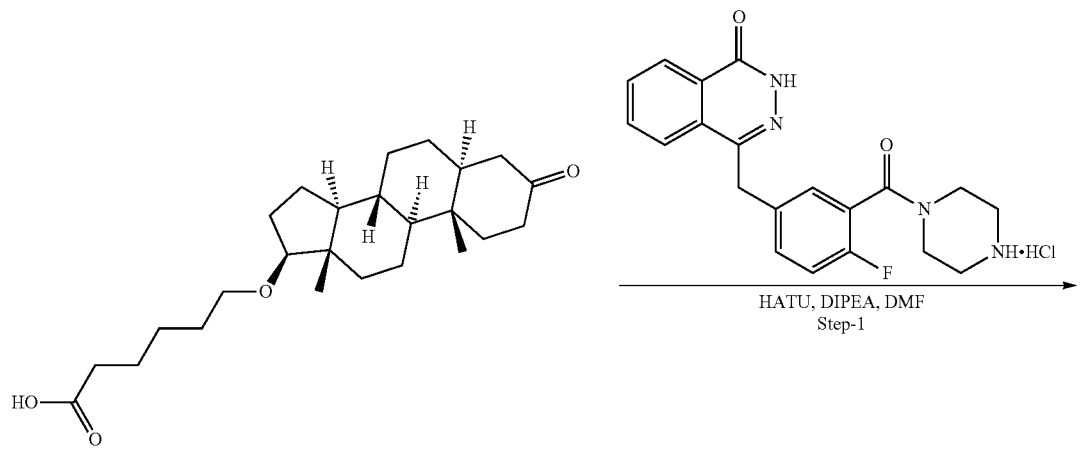

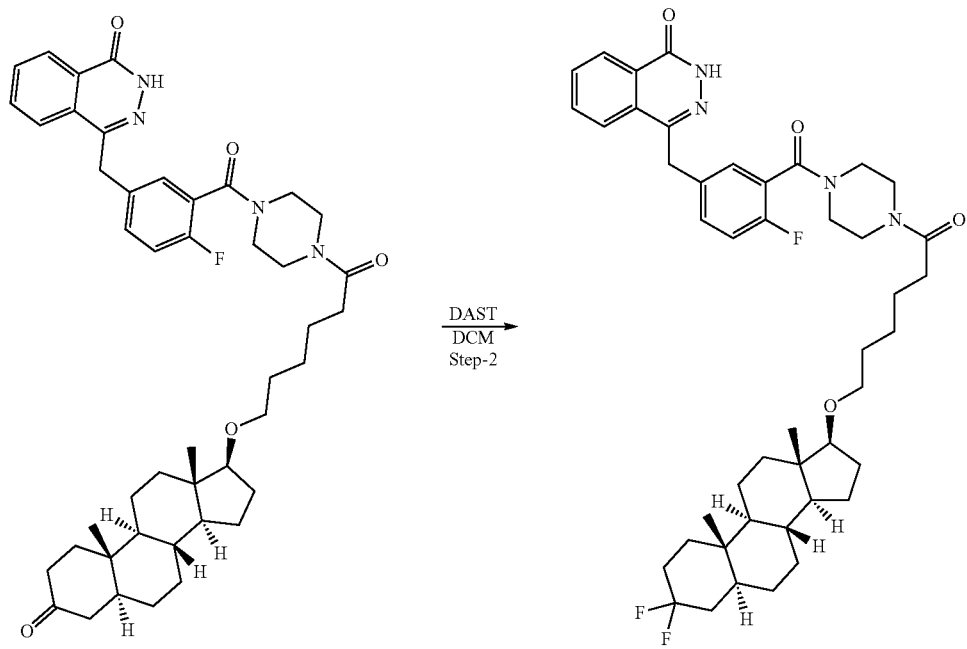

Step-1: Preparation of 4-(3-(4-(6-((5S,8R,9S,10S,13S,14S,17S)-10,13-dimethyl-3-oxohexa decahydro-1H-cyclopenta[a]phenanthren-17-yloxy)hexanoyl)piperazine-1-carbonyl)-4-fluoro benzyl)phthalazin-1(2H)-one To a stirred solution of 6-((5S,8R,9S,10S,13S,14S,17S)-10,13-dimethyl-3-oxohexadecahydro-1H-cyclopenta[a]phenanthren-17-yloxy)hexanoic acid (0.50 g, 1.23 mmol) in DMF (20 mL) was added HATU (0.70 g, 1.84 mmol, 1.5 eq) at 0° C. and the mixture was stirred for 10 min. DIPEA (1.1 mL, 6.18 mmol, 5 eq) and 4-(4-fluoro-3-(piperazine-1-carbonyl)benzyl)phthalazin-1(2H)-one hydrochloride (0.497 g, 1.23 mmol, 1.0 eq) were then successively added to the reaction mixture at 0° C. and the resultant reaction mixture was stirred at RT for 75 min. Reaction was monitored by TLC. After completion, water (10 mL) was added and the resulting precipitate was filtered over Buchner funnel. The product obtained was washed with water (10 mL×2) and n-pentane (10 mL×2), dried under reduced pressure to obtain a crude which was purified by Combi-Flash chromatography to the title compound. LC-MS 753 [M+H]$^+$ Step-2: Preparation of 4-(3-(4-(6-((5S,8R,9S,10S,13S,14S,17S)-3,3-difluoro-10,13-dimethylhexadecahydro-1H-cyclopenta[a]phenanthren-17-yloxy)hexanoyl)piperazine-1-carbonyl)-4-fluorobenzyl)phthalazin-1(2H)-one To a stirred solution of 4-(3-(4-(6-((5S,8R,9S,10S,13S,14S,17S)-10,13-dimethyl-3-oxohexa decahydro-1H-cyclopenta[a]phenanthren-17-yloxy)hexanoyl)piperazine-1-carbonyl)-4-fluoro benzyl)phthalazin-1(2H)-one (0.25 g, 0.332 mmol) in 1,2-dichlorethane (10 mL) was added DAST (0.535 g, 3.32 mmol, 10 eq) dropwise and the mixture was heated 50° C. for 1 h. The reaction was monitored by TLC. After completion, the mixture was quenched slowly with saturated NaHCO$_3$ solution (50 mL) and extracted with DCM (100 mL×2). The combined organic layers were washed with H$_2$O (100 mL), brine (50 mL), dried with anhydrous sodium sulphate and concentrated under reduced pressure to obtain a crude which was purified by reversed phase HPLC to afford the title compound. LC-MS 775 [M+H]$^+$, $^1$H NMR (400 MHz, DMSO-d$_6$) δ 12.59 (s, 1H), 8.26 (d, J=7.8 Hz, 1H), 7.96 (d, J=8.0 Hz, 1H), 7.89 (t, J=7.5 Hz, 1H), 7.83 (t, J=7.5 Hz, 1H), 7.44 (t, J=6.7 Hz, 1H), 7.36 (t, J=6.0 Hz, 1H), 7.23 (t, J=9.0 Hz, 1H), 4.33 (s, 2H), 3.62 (s, 1H), 3.59-3.47 (m, 3H), 3.36 (d, J=9.2 Hz, 3H), 3.24 (q, J=7.5 Hz, 1H), 3.20-3.10 (m, 2H), 2.33-2.22 (m, 2H), 1.87 (dd, J=16.6, 6.2 Hz, 2H), 1.81-1.56 (m, 6H), 1.48 (q, J=9.3, 8.2 Hz, 6H), 1.39-1.01 (m, 12H), 0.98-0.81 (m, 2H), 0.79 (s, 2H), 0.66 (d, J=6.7 Hz, 4H).

Example S-24. Preparation of (R)-N-(4-cyano-3-(trifluoromethyl)phenyl)-3-(4-(6-(4-(2-fluoro-5-((4-oxo-3,4-dihydrophthalazin-1-yl)methyl)benzoyl)piperazin-1-yl)-6-oxohexylamino)phenylsulfonyl)-2-hydroxy-2-methylpropanamide (Compound 1.115)

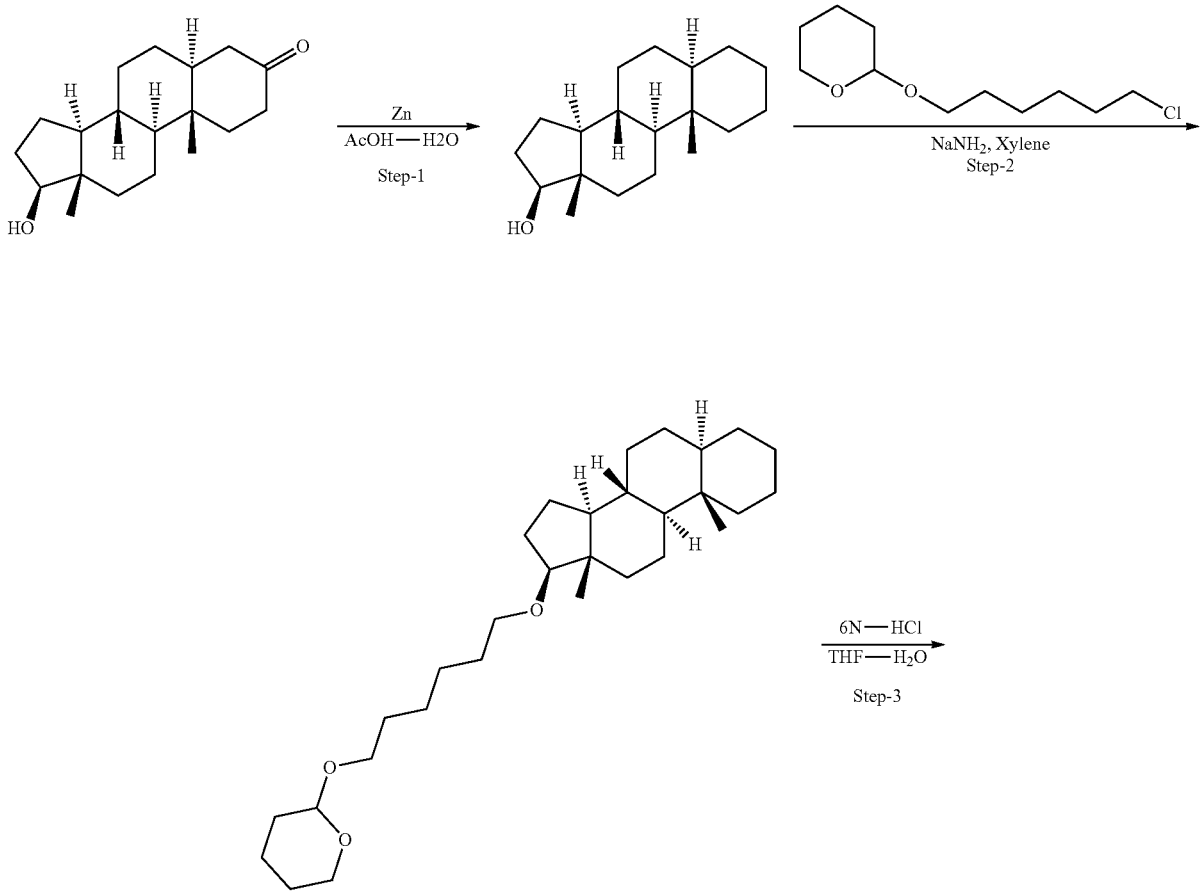

451
452
-continued
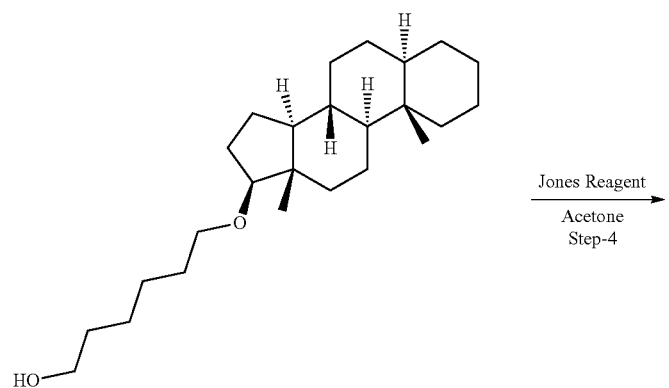
Jones Reagent
Acetone
Step-4
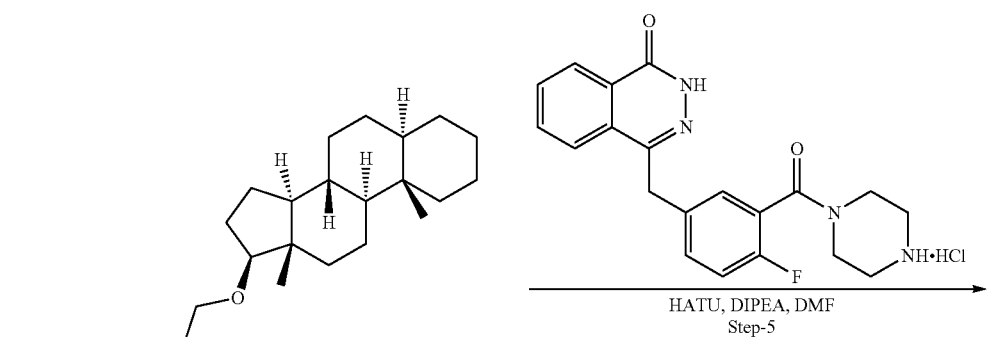
HATU, DIPEA, DMF
Step-5
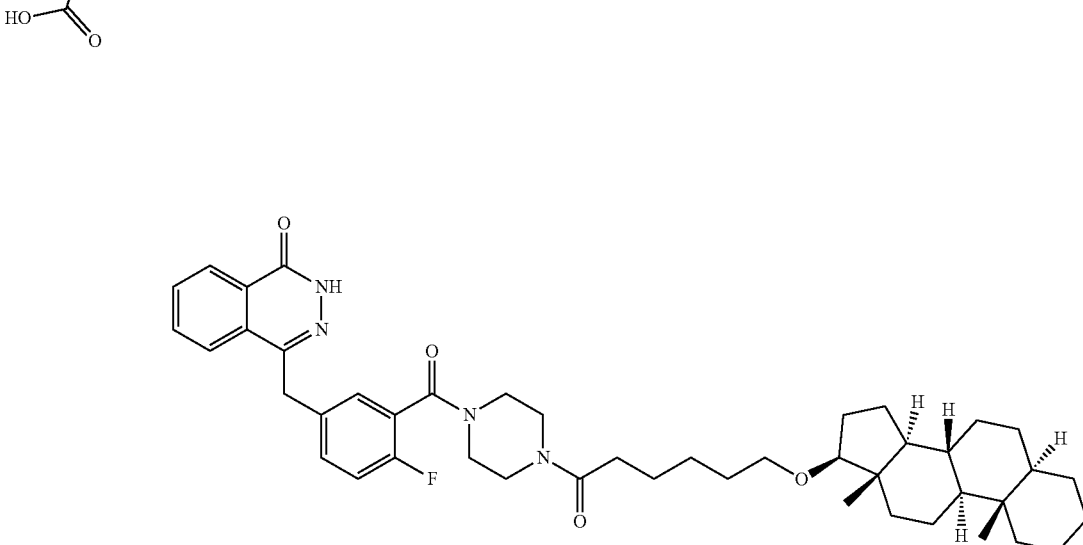
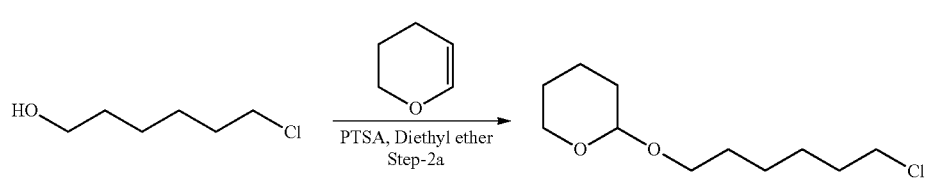
PTSA, Diethyl ether
Step-2a

Step-1: Preparation of (5R,8R,9S,10S,13S,14S,17S)-10,13-dimethylhexadecahydro-1H-cyclopenta[a]phenanthren-17-ol To a stirred solution of (5S,8R,9S,10S,13S,14S,17S)-17-hydroxy-10,13-dimethyltetradecahydro-1H-cyclopenta[a]phenanthren-3(2H)-one (1.0 g, 3.4 mmol) in acetic acid (20 mL)-H$_2$O (10 mL) was added zinc metal (10.0 g) at room temperature and the mixture was stirred at RT for 16 h. The reaction was monitored by TLC. Upon completion, the mixture was diluted with water (20 mL) and filtered through the celite bed, the crude residue obtained from the celite bed was dissolved in methanol (100 mL) and concentrated under reduced pressure to afford the title compound. $^1$HNMR (400 MHz, DMSO-d$_6$) δ 4.40 (d, J=4.8 Hz, 1H), 3.45-3.38 (m, 1H), 1.81 (d, J=7.5 Hz, 1H), 1.71 (d, J=11.4 Hz, 1H), 1.66-1.55 (m, 4H), 1.53-1.41 (m, 4H), 1.37-1.27 (m, 4H), 1.25-1.13 (m, 6H), 1.01 (br. s., 1H), 0.93 (dd, J=3.7, 12.9 Hz, 1H), 0.89-0.79 (m, 4H), 0.76 (s, 2H), 0.61 (s, 2H).

Step-2a: Preparation of 2-(6-chlorohexyloxy)tetrahydro-2H pyran

To a stirred solution of 6-chlorohexan-1-ol (10 g, 73.5 mmol) in diethyl ether (100 mL) was added PTSA (1.4 g, 7.35 mmol, 0.1 eq) followed by addition of 3,4-dihydro-2H-pyran (7.41 g, 88.0 mmol, 1.2 eq) at RT and the mixture was stirred at RT for 16 h. The reaction was monitored by TLC. Upon completion, the mixture was diluted with water (200 mL) and extracted with EtOAc (350 mL). The organic layer was washed with saturated NaHCO$_3$ solution (100 mL), water (200 mL), brine (100 mL) dried over Na$_2$SO$_4$, filtered and concentrated under reduced pressure to afford the title compound which was taken to next step without further purification. $^1$HNMR (400 MHz, DMSO-d$_6$) δ 4.50 (br. s., 1H), 4.25 (t, J=6.80 Hz, 2H), 4.20 (s, 1H), 4.08-4.00 (m, 2H), 3.74-3.66 (m, 2H), 3.59 (dd, J=6.36, 16.01 Hz, 2H), 2.66 (s, 2H), 1.90-1.81 (m, 2H), 1.67 (br. s., 1H), 1.45-1.38 (m, 2H), 1.27-1.20 (m, 2H), 1.17 (t, J=7.02 Hz, 2H).

Step-2: Preparation of 2-(6-((5R,8R,9S,10S,13S,14S,17S)-10,13-dimethylhexadecahydro-1H-cyclopenta[a]phenanthren-17-yloxy)hexyloxy)tetrahydro-2H-pyran To a stirred solution of (5R,8R,9S,10S,13S,14S,17S)-10,13-dimethylhexadecahydro-1H-cyclopenta[a]phenanthren-17-ol (1.0 g, 2.40 mmol) in xylene (10 mL) was added NaNH$_2$ (50% suspension in toluene, 3 mL) and the mixture was heated at 150° C. for 1 h. The reaction mixture was gradually cooled to RT, 2-(6-chlorohexyloxy)tetrahydro-2H-pyran (4.2 g, 24.0 mmol)) was added to it and the resultant mixture was again heated to 150° C. for 16 h. The reaction was monitored by TLC. Upon completion, the mixture was cooled to RT, quenched slowly with ice cold water (250 mL) and extracted with EtOAc (300 mL). The organic layer was washed with water (100 mL×2), brine (100 mL) dried over Na$_2$SO$_4$, filtered and concentrated under reduced pressure to obtain a crude residue which was purified by CombiFlash chromatography to afford the title compound. $^1$HNMR (400 MHz, CDCl3) δ 5.82 (ddt, J=17.0, 10.3, 6.7 Hz, 1H), 5.05-4.91 (m, 2H), 4.57 (d, J=4.4 Hz, 2H), 3.87 (ddd, J=11.2, 7.7, 3.1 Hz, 2H), 3.79-3.66 (m, 2H), 3.55-3.45 (m, 2H), 3.24-3.32 (m, 2H), 3.26 (t, J=8.3 Hz, 1H), 2.12-2.01 (m, 2H), 2.00-1.90 (m, 2H), 1.90-1.75 (m, 2H), 1.68-1.56 (m, 8H), 1.54-1.41 (m, 8H), 1.41-1.31 (m, 4H), 1.26-1.17 (m, 4H), 0.94-0.8 (m, 2H), 0.78 (s, 2H), 0.73 (s, 2H).

Step-3: Preparation of 6-((5R,8R,9S,10S,13S,14S,17S)-10,13-dimethylhexadecahydro-H1-cyclopenta[a]phenanthren-17-yloxy)hexan-1-ol To a stirred solution of 2-(6-((5R,8R,9S,10S,13S,14S,17S)-10,13-dimethylhexadecahydro-1H-cyclopenta[a]phenanthren-17-yloxy)hexyloxy)tetrahydro-2H-pyran (1.0 g, 2.17 mmol, 1 eq) in THF (28 mL)-H$_2$O (7 nit) was added 6N-HCl (20 mL) at RT and the mixture was stirred at RT for 16 h. The reaction was monitored by TLC. Upon completion, the reaction mixture was diluted with water (150 mL) and basified using with saturated NaHCO$_3$ solution (pH ~8). The aqueous layer was then extracted with EtOAc (200 mL×3). The organic layer was washed with saturated NaHCO$_3$ solution (100 mL), water (100 mL), brine (100 mL) dried over Na$_2$SO$_4$, filtered and concentrated under reduced pressure to afford the title compound which was used in the next step without further purification. $^1$HNMR (400 MHz, DMSO-d$_6$) δ 5.76 (s, 1H), 4.32 (t, J=5.3 Hz, 1H), 3.42-3.33 (m, 4H), 3.24 (t, J=8.3 Hz, 1H), 2.01 (d, J=7.0 Hz, 1H), 1.95-1.86 (m, 1H), 1.77 (d, J=11.8 Hz, 1H), 1.66-1.54 (m, 4H), 1.48-1.32 (m, 8H), 1.32-1.23 (m, 6H), 1.22-1.09 (m, 6H), 1.01 (br. s., 1H), 0.90-0.79 (m, 4H), 0.75 (s, 2H), 0.69-0.61 (m, 2H).

Step-4: Preparation of 6-((5R,8R,9S,10S,13S,14S,17S)-10,13-dimethylhexadecahydro-1H-cyclopenta[a]phenanthren-17-yloxy)hexanoic acid To a stirred solution of 6-((5R,8R,9S,10S,13S,14S,17S)-10,13-dimethylhexadecahydro-1H-cyclopenta[a]phenanthren-17-yloxy)hexan-1-ol (0.40 g, 1.09 mmol, 1 eq) in acetone (25 mL) was added Jones reagent (1.2 mL) at 0° C. dropwise over a period of 20 min. The resultant mixture was stirred at 0° C. for 5 min. The reaction was monitored by TLC. After completion. H$_2$O (20 mL) was added and the resulting precipitate was filtered over Buchner funnel. The product obtained was washed with water (5 mL×2) and n-pentane (5 mL×2), dried under vacuum to afford the title compound which was taken to next step without further purification. $^1$HNMR (400 MHz, DMSO-d$_6$) δ 11.96 (br. s., 1H), 3.28-3.18 (m, 2H), 2.18 (t, J=7.5 Hz, 2H), 1.89 (d, J=5.7 Hz, 2H), 1.77 (d, J=11.4 Hz, 2H), 1.53-1.40 (m, 8H), 1.39-1.26 (m, 6H), 1.23 (br. s., 2H), 1.23-1.06 (m, 10H), 0.96-0.80 (m, 4H), 0.75 (s, 2H), 0.71-0.56 (m, 2H).

Step-5: Preparation of (R)-N-(4-cyano-3-(trifluoromethyl)phenyl)-3-(4-(6-(4-(2-fluoro-5-((4-oxo-3,4-dihydrophthalazin-1 yl)methyl)benzoyl)piperazin-1 yl)-6-oxohexylamino)phenylsulfonyl)-2-hydroxy-2-methylpropanamide To a stirred solution of 6-((5R,8R,9S,10S,13S,14S,17S)-10,13-dimethylhexadecahydro-1H-cyclopenta[a]phenanthren-17-yloxy)hexanoic acid (0.190 g, 0.487 mmol, 1 eq) in DMF (12 mL) was added HATU (0.277 g, 0.73 mmol, 1.2 eq) at 0° C. and the resulting reaction mixture was stirred for 10 min. DIPEA (0.36 mL, 1.94 mmol, 4.0 eq) and 4-(4-fluoro-3-(piperazine-1-carbonyl)benzyl)phthalazin-1 (2H)-one hydrochloride (0.156 g, 0.389 mmol, 0.8 eq) were then successively added to the mixture and the mixture was stirred at RT for 2 h. The reaction was monitored by TLC & LC-MS. After completion, water (10 mL) was added and the resulting precipitate was filtered over Büchner funnel. The product obtained was washed with water (5 mL×2) and n-pentane (5 mL×2), dried under vacuum to obtain a crude residue which was purified by reversed phase HPLC to afford the title compound. LC-MS 739[M+H]$^+$. $^1$HNMR 400 MHz, DMSO-d$_6$) δ 12.59 (s, 1H), 8.26 (d, J=7.9 Hz, 1H), 8.01-7.93 (m, 1H), 7.89 (t, J=7.2 Hz, 1H), 7.86-7.77 (m, 1H), 7.44 (br. s., 1H), 7.36 (br. s., 1H), 7.23 (t, J=9.0 Hz, 1H), 4.33 (s, 2H), 3.62 (br. s., 1H), 3.56 (br. s., 1H), 3.51 (br. s., 2H), 3.27-3.02 (m, 3H), 2.33 (br. s., 1H), 2.26 (br. s., 1H), 1.90 (br. s., 2H), 1.76 (br. s., 1H), 1.59-1.47 (m, 8H), 1.35-1.28 (m, 6H), 1.20-1.16 (m, 10H), 1.13 (br. s., 2H), 0.83 (br. s., 4H), 0.74 (br. s., 3H), 0.65 (d, J=6.6 Hz, 4H).

Example S-25. Preparation of 4-(4-fluoro-3-(4-(3-((5S,8R,9S,10S,13S,14S,17S)-17-hydroxy-10,13-dimethyl-3-oxohexadecahydro-1H-cyclopenta[a]phenanthren-17-yl)propioloyl)piperazine-1-carbonyl)benzyl)phthalazin-1(2H)-one (Compound 1.116)

Step-1: Preparation of 4-(4-fluoro-3-(4-(3-((5S,8R,9S,10S,13S,14S,17S)-17-hydroxy-10,13-dimethyl-3-oxohexadecahydro-1H-cyclopenta[a]phenanthren-17-yl)propioloyl)piperazine-1-carbonyl)benzyl)phthalazin-1(2H)-one To a stirred suspension of 3-((5S,8R,9S,10S,13S,14S,17S)-17-hydroxy-10,13-dimethyl-3-oxohexadecahydro-1H-cyclopenta[a]phenanthren-17-yl)propiolic acid (0.50 g, 1.39 mmol) in DMF (20 mL) was added HATU (0.795 g, 2.095 mmol, 1.5 eq) at 0° C. and the mixture was stirred for 10 min. DIPEA (1.45 mL, 8.35 mmol, 6 eq) and 4-(4-fluoro-3-(piperazine-1-carbonyl)benzyl)phthalazin-1(2H)-one hydrochloride (0.503 g, 1.25 mmol, 0.9 eq) were then successively added to the reaction mixture at 0° C. and the resultant reaction mixture was stirred at RT for 75 min. The reaction was monitored by TLC. After completion, water (10 mL) was added and the resulting precipitate was filtered over Buchner funnel. The product obtained was washed with water (10 mL×2) and n-pentane (10 mL×2), dried under

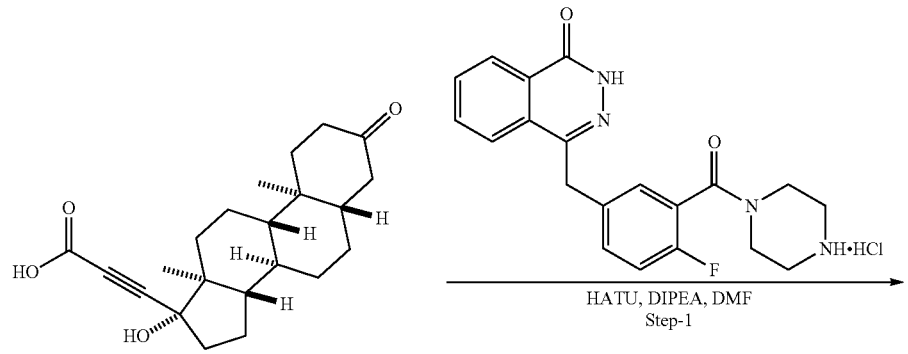

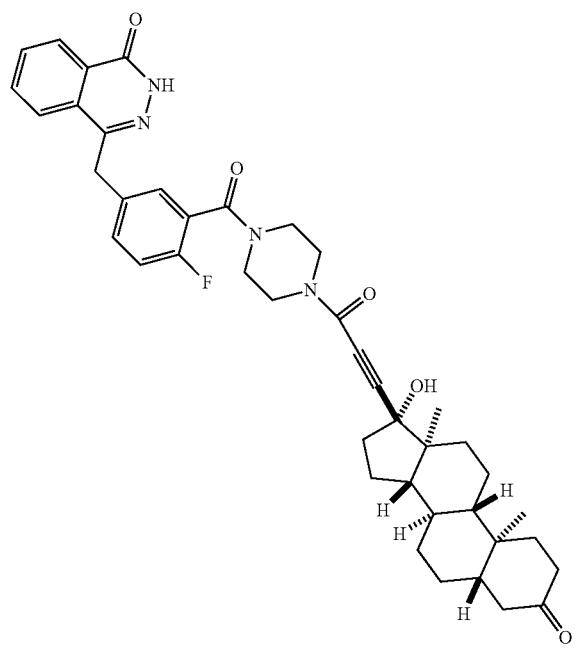

reduced pressure to obtain a crude which was purified by CombiFlash chromatography to afford the title compound. LC-MS 707 [M+H]+. 1HNMR (400 MHz, DMSO-d6) δ 12.58 (d, J=2.6 Hz, 1H), 8.24 (d, J=7.9 Hz, 1H), 8.00-7.92 (m, 1H), 7.87 (t, J=7.2 Hz, 1H), 7.83-7.73 (m, 1H), 7.41 (d, J=6.1 Hz, 1H), 7.33 (d, J=7.0 Hz, 1H), 7.24-7.14 (m, 1H), 5.70-5.63 (m, 1H), 4.30 (d, J=7.9 Hz, 2H), 3.74 (br. s., 1H), 3.63 (br. s., 3H), 3.39 (br. s., 1H), 3.24-3.10 (m, 2H), 2.39-2.20 (m, 2H), 2.15-1.98 (m, 2H), 1.94-1.75 (m, 2H), 1.61 (br. s., 2H), 1.56 (br. s., 4H), 1.48-1.33 (m, 4H), 1.33-1.11 (m, 8H), 0.97-0.91 (m, 3H), 0.76-0.73 (m, 3H).

Example S-26. Preparation of 4-(4-fluoro-3-(4-(3-((5S,8R,9S,10S,13S,14S,17R)-17-hydroxy-10,13-dimethyl-3-oxohexadecahydro-1H-cyclopenta[a]phenanthren-17-yl)propanoyl)piperazine-1-carbonyl)benzyl)phthalazin-1(2H)-one (Compound 1.117)

Step-1: Preparation of 4-(4-fluoro-3-(4-(3-((5S,8R,9S,10S,13S,14S,17S)-17-hydroxy-10,13-dimethyl-3-oxohexadecahydro-1H-cyclopenta[a]phenanthren-17-yl)propioloyl)piperazine-1-carbonyl)benzyl)phthalazin-1(2H)-one To a stirred suspension of 3-((5S,8R,9S,10S,13S,14S,17S)-17-hydroxy-10,13-dimethyl-3-oxohexadecahydro-1H-cyclopenta[a]phenanthren-17-yl)propiolic acid (0.50 g, 1.39 mmol) in DMF (20 mL) was added HATU (795 g, 2.095 mmol, 1.5 eq) at 0° C. and the mixture was stirred for 10 min. DIPEA (1.45 mL, 8.35 mmol, 6 eq) and 4-(4-fluoro-3-(piperazine-1-carbonyl)benzyl)phthalazin-1(2H)-one hydrochloride (0.503 g, 1.25 mmol, 0.9 eq) were then successively added to the reaction mixture at 0° C. and the resultant reaction mixture was stirred at RT for 75 min. The reaction was monitored by TLC. After completion, water (10 mL) was added and the resulting precipitate was filtered

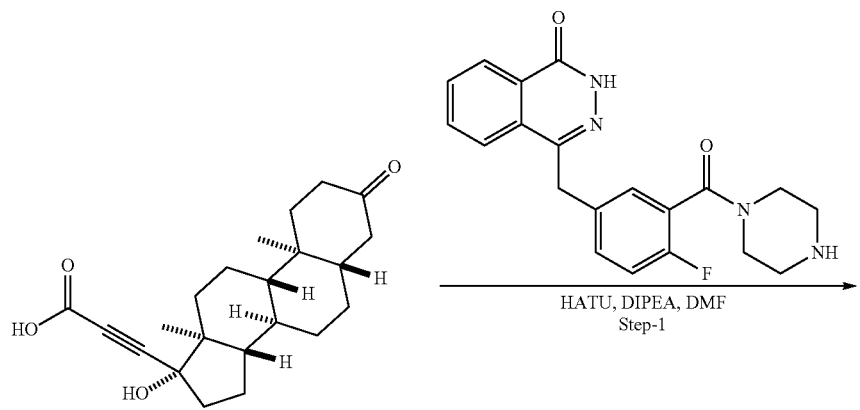

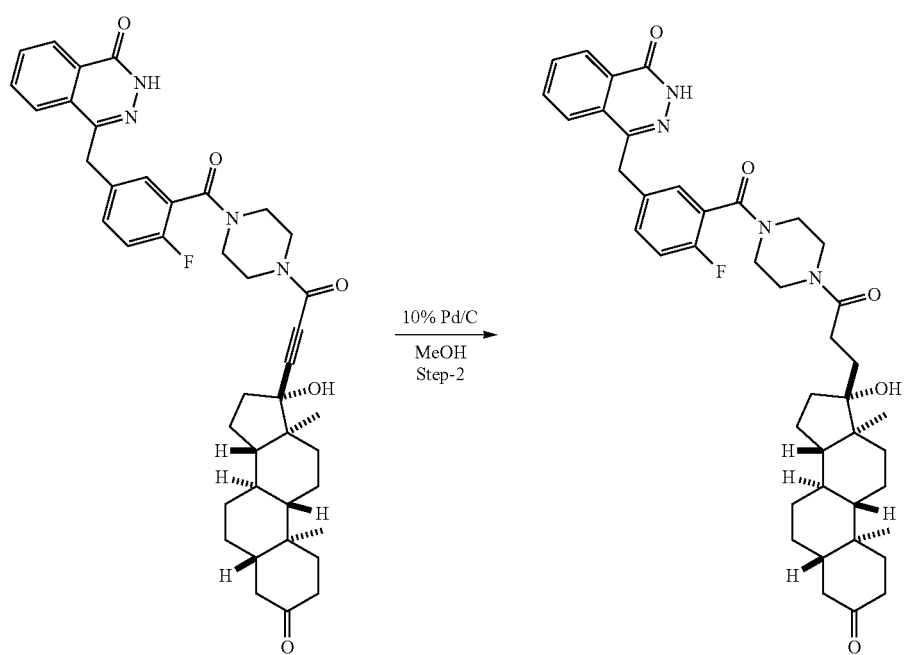

over Buchner funnel. The product obtained was washed with water (10 mL×2) and n-pentane (10 mL×2), dried under reduced pressure to obtain a crude which was purified by CombiFlash chromatography to afford the title compound. LC-MS 707 [M+H]⁺. ¹HNMR (400 MHz, DMSO-d₆) δ 12.58 (d, J=2.6 Hz, 1H), 8.24 (d, J=7.9 Hz, 1H), 8.00-7.92 (m, 1H), 7.87 (t, J=7.2 Hz, 1H), 7.83-7.73 (m, 1H), 7.41 (d, J=6.1 Hz, 1H), 7.33 (d, J=7.0 Hz, 1H), 7.24-7.14 (m, 1H), 5.70-5.63 (m, 1H), 4.30 (d, J=7.9 Hz, 2H), 3.74 (br. s., 1H), 3.63 (br. s., 3H), 3.39 (br. s., 1H), 3.24-3.10 (m, 2H), 2.39-2.20 (m, 2H), 2.15-1.98 (m, 2H), 1.94-1.75 (m, 2H), 1.61 (br. s., 2H), 1.56 (br. s., 4H), 1.48-1.33 (m, 4H), 1.33-1.11 (m, 8H), 0.97-0.91 (m, 3H), 0.76-0.73 (m, 3H).

Step-2: Preparation of 4-(4-fluoro-3-(4-(3-((5S,8R, 9S,10S,13S,14S,17R)-17-hydroxy-10,13-dimethyl-3-oxohexadecahydro-1H-cyclopenta[a]phenanthren-17-yl)propanoyl)piperazine-1-carbonyl)benzyl) phthalazin-1(2H)-one To a stirred suspension of 4-(4-fluoro-3-(4-(3-((5S,8R,9S, 10S,13S,14S,17S)-17-hydroxy-10,13-dimethyl-3-oxohexadecahydro-1H-cyclopenta[a]phenanthren-17-yl)propioloyl) piperazine-1-carbonyl)benzyl)phthalazin-1(2H)-one (0.100 g, 0.141 mmol) in methanol (10 mL) was added 10% Pd/C (10 mg) and the mixture was hydrogenated using hydrogen bladder for 16 h. The reaction was monitored by TLC and LC-MS. After completion, the mixture was filtered through celite bed and the filtrate was concentrated under reduced pressure to obtain a crude which was purified by reversed phase HPLC to afford the title compound. LC-MS 711 [M+H]⁺. ¹H NMR (400 MHz, DMSO-d₆) 12.59 (s, 1H), 8.26 (d, J=7.8 Hz, 1H), 7.96 (d, J=8.0 Hz, 1H), 7.89 (t, J=7.6 Hz, 1H), 7.83 (t, J=7.5 Hz, 1H), 7.44 (dd, J=8.7, 5.0 Hz, 1H), 7.35 (d, J=6.9 Hz, 1H), 7.24 (t, J=9.0 Hz, 1H), 4.33 (s, 2H), 3.98 (dd, J=15.2, 8.0 Hz, 1H), 3.68-3.49 (m, 2H), 3.40-3.34 (m, 2H), 3.23-3.11 (m, 2H), 3.05 (s, 1H), 3.00 (s, 1H), 2.44-2.34 (m, 1H), 2.28 (d, J=14.2 Hz, 1H), 2.13-2.04 (m, 1H), 1.97-1.76 (m, 1H), 1.72-1.51 (m, 6H), 1.45 (d, J=16.1 Hz, 6H), 1.36-1.13 (m, 8H), 0.98 (s, 2H), 0.91-0.58 (m, 4H).

Example S-27. Preparation of 4-(4-fluoro-3-(4-(3-((5S,8R,9S,10S,13S,14S,17S)-17-hydroxy-10,13-dimethyl-3-oxohexadecahydro-1H-cyclopenta[a] phenanthren-17-yl)prop-2-ynyl)piperazine-1-carbonyl)benzyl)phthalazin-1(2H)-one (Compound 1.118)

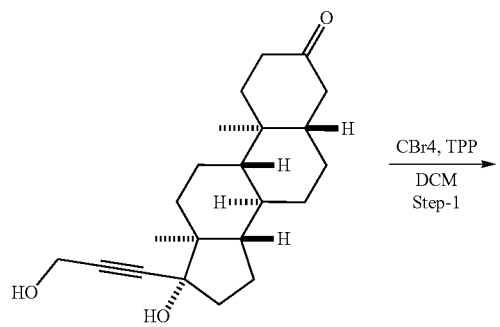

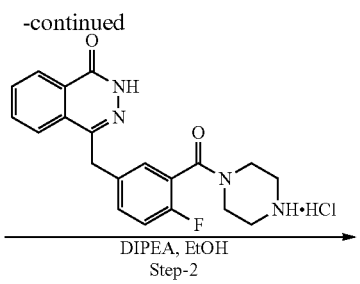

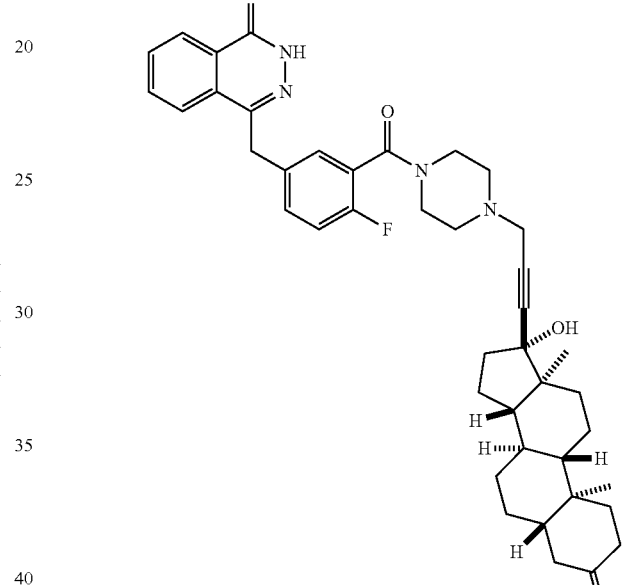

Step-1: Preparation of (5S,8R,9S,10S,13S,14S,17S)-17-(3-bromoprop-1 ynyl)-17-hydroxy-10,13-dimethyltetradecahydro-1H-cyclopenta[a]phenanthren-3 (2H)-one To a stirred suspension of (5S,8R,9S,10S,13S,14S,17S)-17-hydroxy-17-(3-hydroxyprop-1-ynyl)-10,13-dimethyltetradecahydro-1H-cyclopenta[a]phenanthren-3(2H)-one (1.0 g, 2.90 mmol, 1 eq) in DCM (20 mL) were successively added triphenylphosphine (2.28 g, 8.72 mmol, 3.0 eq) and carbon tetrabromide (1.98 gm, 5.98 mmol, 2 eq) at RT and the mixture was stirred at RT for 3 h. The reaction was monitored by TLC. After completion, water (50 mL) was added and the aqueous layer was extracted with DCM (100 mL×2). The combined organic layers were washed with water (50 mL), brine (50 mL), dried over anhydrous sodium sulphate and concentrated under reduced pressure to afford crude residue which was purified by CombiFlash chromatography to afford the title compound. ¹H NMR (400 MHz, DMSO-d₆) δ 5.36 (d, J=5.3 Hz, 1H), 4.49 (s, 2H), 4.30 (s, 2H), 2.29 (s, 2H), 1.90 (br. s., 6H), 1.55 (br. s., 4H), 1.30 (br. s., 4H), 1.29-1.20 (m, 4H), 0.98 (s, 2H), 0.74 (s, 4H).

Step-2: Preparation of 4-(4-fluoro-3-(4-(3-((5S,8R,9S,10S,13S,14S,17S)-17-hydroxy-10,13-dimethyl-3-oxohexadecahydro-1H-cyclopenta[a]phenanthren-17-yl)prop-2 ynyl) piperazine-1-carbonyl)benzyl) phthalazin-1(2H)-one To a stirred solution of 4-(4-fluoro-3-(piperazine-1-carbonyl)benzyl)phthalazin-1(2H)-one hydrochloride (0.20 g, 0.497 mmol) in EtOH (10 mL) was added DIPEA (0.44 mL, 2.48 mmol, 5 eq) followed by the addition of (5S,8R,9S,10S,13S,14S,17S)-17-(3-bromoprop-1-ynyl)-17-hydroxy-10,13-dimethyltetradecahydro-1H-cyclopenta[a]phenanthren-3(2H)-one (0.201 g, 0.497 mmol, 1.0 eq) and the mixture was heated at 80° C. for 1 h. The reaction was monitored by TLC and LC-MS. After completion, the mixture was concentrated under reduced pressure to obtain a crude residue which was purified by CombiFlash chromatography to afford the title compound. LC-MS 693 [M+H]$^+$. $^1$HNMR (400 MHz, DMSO-d$_4$) δ 12.58 (s, 1H), 8.26 (d, 0.1=7.0 Hz, 1H), 7.98-7.91 (m, 1H), 7.90-7.76 (m, 2H), 7.43 (br. s., 1H), 7.25 (d, J=4.8 Hz, 1H), 7.22-7.13 (m, 1H), 5.17 (s, 1H), 4.32 (s, 2H), 3.63 (br. s., 2H), 3.35 (s, 2H), 3.17 (d, J=5.3 Hz, 2H), 2.38 (br. s., 2H), 2.35-2.30 (m, 1H), 2.00 (d, J=14.5 Hz, 2H), 1.89-1.75 (m, 4H), 1.60-1.52 (m, 6H), 1.47-1.40 (m, 6H), 1.22 (d, J=6.6 Hz, 6H), 1.06-0.95 (m, 2H), 0.94 (s, 2H), 0.72 (s, 2H).

Example S-28. Preparation of (R)-N-(4-cyano-3-(trifluoromethyl)phenyl)-3-(4-(6-(4-(2-fluoro-5-((4-oxo-3,4-dihydrophthalazin-1-yl)methyl)benzoyl)piperazin-1-yl)-6-oxohexylamino)phenylsulfonyl)-2-hydroxy-2-methylpropanamide (Compound 1.119)

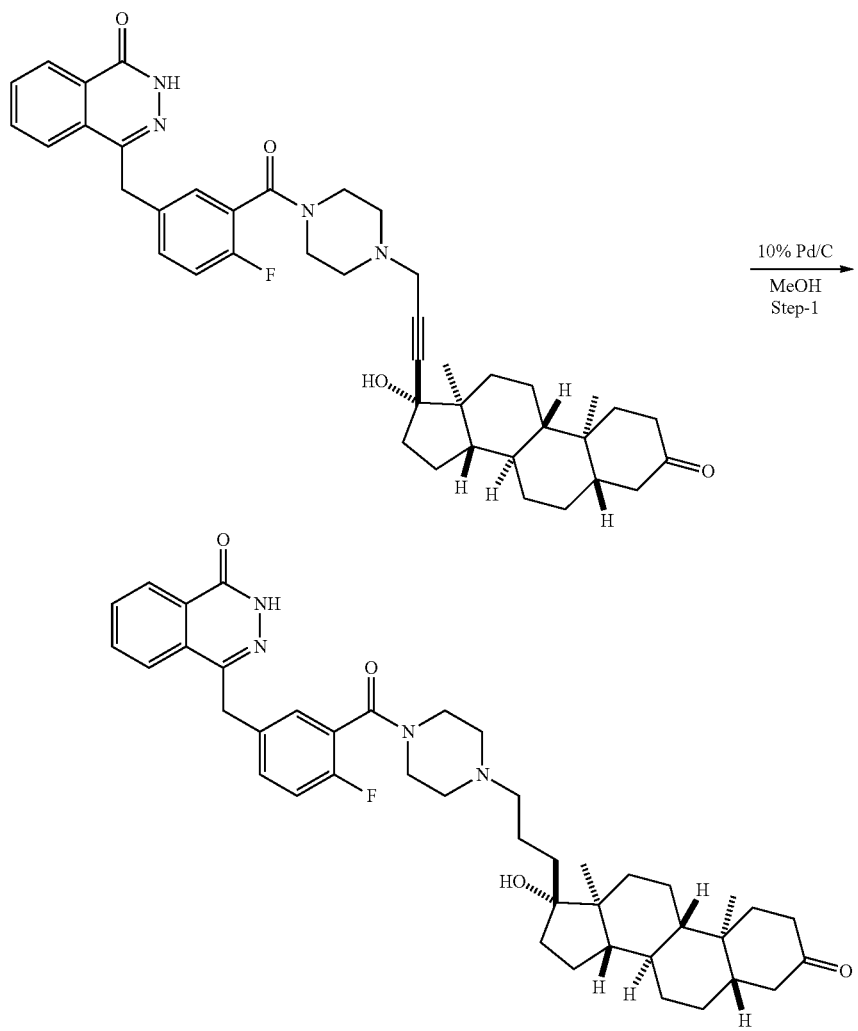

Step-1: Preparation of 4-(4-fluoro-3-(4-(3-((5S,8R,9S,10S,13S,14S,17R)-17-hydroxy-10,13-dimethyl-3-oxohexadecahydro-1H-cyclopenta[a]phenanthren-17-yl)propyl)piperazine-1-carbonyl)benzyl) phthalazin-1(2H)-one To a stirred suspension of 4-(4-fluoro-3-(4-(3-((5S,8R,9S,10S,13S,14S,17S)-17-hydroxy-10,13-dimethyl-3-oxohexadecahydro-1H-cyclopenta[a]phenanthren-17-yl)prop-2-ynyl)piperazine-1-carbonyl)benzyl)phthalazin-1(2H)-one (0.120 g, 0.173 mmol, 1 eq) in methanol (10 mL) was added 10% Pd/C (12 mg) and the mixture was hydrogenated under hydrogen atmosphere for 16 h. The reaction was monitored by TLC and LC-MS. After completion, the mixture was filtered through celite bed and the filtrate obtained was concentrated under reduced pressure to obtain a crude residue which was purified by CombiFlash chromatography to afford the title compound. LC-MS 697 [M+H]⁺. ¹HNMR (400 MHz, DMSO-d$_6$) δ 12.59 (s, 1H), 8.26 (d, J=7.5 Hz, 1H), 7.96 (d, J=7.9 Hz, 1H), 7.92-7.76 (m, 2H), 7.45-7.36 (m, 1H), 7.30 (d, J=6.1 Hz, 1H), 7.22 (t, J=9.0 Hz, 1H), 4.32 (s, 2H), 3.99 (br. s., 1H), 3.59 (br. s., 1H), 3.13 (br. s., 2H), 2.44-2.36 (m, 2H), 2.33 (br. s., 2H), 2.25 (dd, J=11.6, 19.1 Hz, 4H), 2.09 (d, J=10.1 Hz, 1H), 1.89 (t, J=13.6 Hz, 1H), 1.72 (br. s., 2H), 1.60 (br. s., 2H), 1.55 (br. s., 2H), 1.50 (br. s., 2H), 1.46-1.42 (br. s., 4H), 1.37-1.33 (d, J=12.3 Hz, 4H), 1.31-1.04 (m, 8H), 0.98 (s, 2H), 0.80-0.74 (m, 2H).

Example S-29. Preparation of 4-(4-fluoro-3-(4-(6-((8R,9S,13S,14S,17S)-3-hydroxy-13-methyl-7,8,9,11,12,13,14,15,16,17-decahydro-6H-cyclopenta[a]phenanthren-17-yloxy)hexanoyl)piperazine-1-carbonyl)benzyl)phthalazin-1(2H)-one (Compound 2.2)

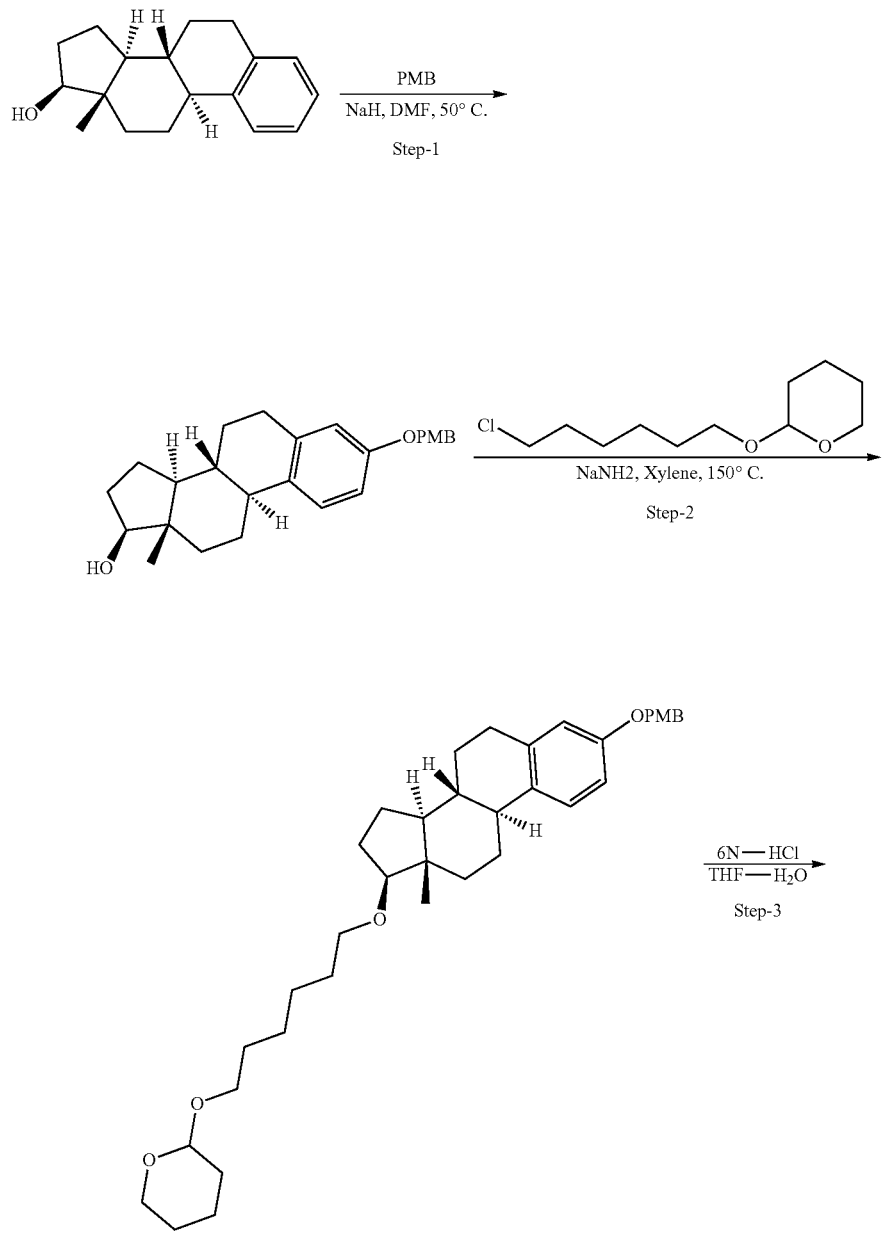

-continued
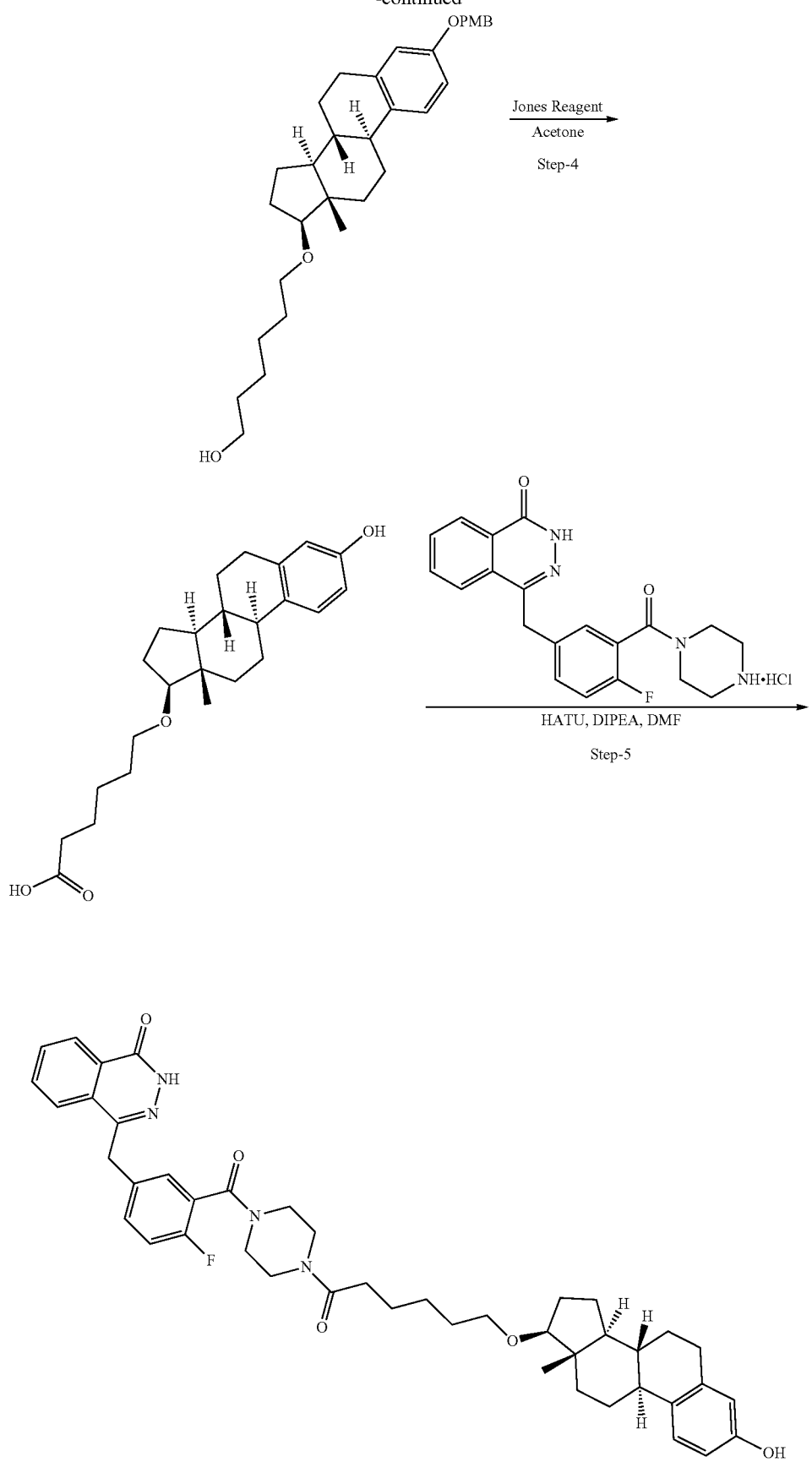

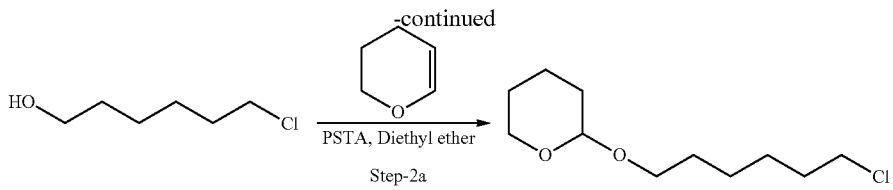

Step-1: Preparation of (8R,9S,13S,14S,17S)-3-(4-methoxybenzyloxy)-13-methyl-7,8,9,11,12,13,14,15,16,17-decahydro-6H-cyclopenta[a]phenanthren-17-ol To a stirred solution of (8R,9S,13S,14S,17S)-13-methyl-7,8,9,11,12,13,14,15,16,17-decahydro-6H-cyclopenta[a]phenanthrene-3,17-diol (1.0 g, 3.6 mmol) in DMF (20 mL) was added sodium hydride (60% suspension in mineral oil; 0.22 g, 5.5 mmol) at RT and the mixture was heated at 50° C. for 2 h. The reaction was monitored by TLC. Upon completion, the mixture was quenched with ice-cold water (20 mL) and extracted with ethyl acetate (100 mL×2). The combined organic layers were washed with chilled water (50 mL×3), brine (50 mL) dried with anhydrous sodium sulphate, concentrated under reduced pressure to obtain a crude which was purified by CombiFlash chromatography to afford the title compound. $^1$HNMR (400 MHz, CDCl$_3$) δ 7.39-7.32 (m, J=8.8 Hz, 2H), 7.26 (s, 1H), 7.20 (d, J=8.8 Hz, 1H), 6.95-6.85 (m, J=8.8 Hz, 2H), 6.77 (dd, J=2.6, 8.3 Hz, 1H), 6.74-6.67 (m, 1H), 5.30 (s, 1H), 4.95 (s, 2H), 3.82 (s, 3H), 3.73 (t, J=8.6 Hz, 2H), 3.54 (t, J=6.8 Hz, 1H), 2.84 (d, J=4.8 Hz, 2H), 2.31 (dd, J=3.1, 13.6 Hz, 1H), 2.20-2.10 (m, 2H), 1.99-1.84 (m, 2H), 1.74-1.67 (m, 1H), 1.62 (d, J=14.0 Hz, 2H), 1.51-1.39 (m, 3H), 1.24-1.14 (m, 1H), 0.89-0.78 (m, 2H).

Step-2a: Preparation of 2-(6-chlorohexyloxy)tetrahydro-2H pyran

To a stirred solution of 6-chlorohexan-1-ol (10 g, 73.5 mmol) in diethyl ether (100 mL) was added PTSA (1.4 g, 7.3.5 mmol, 0.1 eq) followed by addition of 3,4-dihydro-2H-pyran (7.41 g, 88.0 mmol, 1.2 eq) at RT and the mixture was stirred at RT for 16 h. The reaction was monitored by TLC. Upon completion, the mixture was diluted with water (200 mL) and extracted with EtOAc (350 mL). The organic layer was washed with saturated NaHCO$_3$ solution (100 mL), water (200 mL), brine (100 mL) dried over Na$_2$SO$_4$, filtered and concentrated under reduced pressure to afford the title compound (12.0 g, 74%) as a yellow liquid which was taken to next step without further purification. $^1$HNMR (400 MHz, DMSO-d$_6$) δ 4.50 (br. s., 1H), 4.25 (t, J=6.80 Hz, 2H), 4.20 (s, 1H), 4.08-4.00 (m, 2H), 3.74-3.66 (m, 2H), 3.59 (dd, J=6.36, 16.01 Hz, 2H), 2.66 (s, 2H), 1.90-1.81 (m, 2H), 1.67 (br. s., 1H), 1.45-1.38 (m, 2H), 1.27-1.20 (m, 2H), 1.17 (t, J=7.02 Hz, 2H).

Step-2: Preparation of 2-(6-((8R,9S,13S,14S,17S)-3-(4-methoxybenzyloxy)-13-methyl-7,8,9,11,12,13,14,15,16,17-decahydro-6H-cyclopenta[a]phenanthren-17-yloxy)hexyloxy)tetrahydro-2H-pyran To a stirred solution of (8R,9S,13S,14S,17S)-3-(4-methoxybenzyloxy)-13-methyl-7,8,9,11,12,13,14,15,16,17-decahydro-6H-cyclopenta[a]phenanthren-17-ol (0.50 g, 1.27 mmol) in xylene (5 mL) was added NaNH$_2$ (50% suspension in toluene, 1.5 mL) and the mixture was heated at 150° C. for 1 h. The reaction mixture was gradually cooled to RT, 2-(6-chlorohexyloxy)tetrahydro-2H-pyran (2.8 g, 12.5 mmol, 10 eq) was added to it and the resultant mixture was again heated to 150° C. for 16 h. The reaction was monitored by TLC. Upon completion, the mixture was cooled to RT, quenched slowly with ice cold water (250 mL) and extracted with EtOAc (300 mL). The organic layer was washed with water (100 mL×2), brine (100 mL) dried over Na$_2$SO$_4$, filtered and concentrated under reduced pressure to obtain a crude residue which was purified by CombiFlash chromatography to afford the title compound. $^1$HNMR (400 MHz, DMSO-d$_6$) δ 7.37-7.31 (m, J=8.3 Hz, 2H), 7.14 (d, J=8.3 Hz, 1H), 6.94-6.90 (m, J=8.3 Hz, 2H), 6.72 (d, J=7.9 Hz, 1H), 6.67 (br. s., 1H), 4.53 (br. s., 2H), 3.76-3.73 (m, 3H), 3.64-3.56 (m, 2H), 3.45-3.36 (m, 4H), 2.75 (br. s., 2H), 2.26 (br. s., 2H), 2.10 (d, J=12.7 Hz, 2H), 1.99 (s, 2H), 1.90 (d, J=8.3 Hz, 2H), 1.80 (br. s., 2H), 1.69 (br. s., 1H), 1.60 (br. s., 2H), 1.55-1.39 (m, 8H), 1.35-1.27 (m, 6H), 1.25 (br. s., 2H), 0.90-0.81 (m, 2H).

Step-3: Preparation of 6-((8R,9S,13S,14S,17S)-3-(4-methoxybenzyloxy)-13-methyl-7,8,9,11,12,13,14,15,16,17-decahydro-6H-cyclopenta[a]phenanthren-17-yloxy)hexan-1-ol To a stirred solution of 2-(6-((8R,9S,13S,14S,17S)-3-(4-methoxybenzyloxy)-13-methyl-7,8,9,11,12,13,14,15,16,17-decahydro-6H-cyclopenta[a]phenanthren-17-yloxy)hexyloxy)tetrahydro-2H-pyran (0.42 g, 0.72 mmol) in THF (12 mL) water (3 mL) was added 6-N HCl (9 mL) at RT and the resultant mixture was stirred at RT for 16 h. The reaction was monitored by TLC. Upon completion, the reaction mixture was diluted with water (40 mL) and basified using with saturated NaHCO$_3$ solution (pH~8). The aqueous layer was then extracted with EtOAc (50 mL×3). The organic layer was washed with saturated NaHCO$_3$ solution (40 mL), water (40 mL), brine (50 mL) dried over Na$_2$SO$_4$, filtered and concentrated under reduced pressure to afford the title compound. LC-MS 493[M+H]$^+$ Step-4: Preparation of 6-((8R,9S,13S,14S,17S)-3-hydroxy-13-methyl-7,8,9,11,12,13,14,15,16,17-decahydro-6H-cyclopenta[a]phenanthren-17-yloxy) hexanoic acid To a stirred solution of 6-((8R,9S,13S,14S,17S)-3-(4-methoxybenzyloxy)-13-methyl-7,8,9,11,12,13,14,15,16,17-decahydro-6H-cyclopenta[a]phenanthren-17-yloxy)hexan-1-ol (0.18 g, 0.365 mmol) in acetone (18 mL) was added Jones reagent (1.2 mL) at 0° C. dropwise over a period of 20 min. The resultant mixture was stirred at 0° C. for 5 min. The reaction was monitored by TLC. After completion, water (20 mL) was added and the resulting precipitate was filtered over Büchner funnel. The product obtained was washed with water (5 mL×2) and n-pentane (5 mL×2), dried under vacuum to afford the title compound which was taken to next step without further purification. LC-MS 387[M+H]$^+$ Step-5: Preparation of 4-(4-fluoro-3-(4-(6-((8R,9S, 13S,14S,17S)-3-hydroxy-13-methyl-7,8,9,11,12,13, 14,15,16,17-decahydro-6H-cyclopenta[a] phenanthren-17-yloxy)hexanoyl) piperazine-1-carbonyl)benzyl)phthalazin-1(2H)-one To a stirred solution of 6-((8R,9S,13S,14S,17S)-3-hydroxy-13-methyl-7,8,9,11,12,13,14,15,16,17-decahydro-6H-cyclopenta[a]phenanthren-17-yloxy)hexanoic acid (0.190 g, 0.466 mmol) in DMF (8 mL) was added HATU (0.277 g, 0.699 mmol, 1.5 eq) at 0° C. and the resulting reaction mixture was stirred for 10 min. DIPEA (0.24 mL, 1.86 mmol, 4.0 eq) and 4-(4-fluoro-3-(piperazine-1-carbonyl)benzyl)phthalazin-1(2H)-one hydrochloride (0.149 g, 0.373 mmol, 0.8 eq) were then successively added to the mixture and the mixture was stirred at RT for 2 h. The reaction was monitored by TLC & LC-MS. After completion, water (10 mL) was added and the resulting precipitate was filtered over Buchner funnel. The product obtained was washed with water (5 mL×2) and n-pentane (5 mL×2), dried under vacuum to obtain a crude residue which was purified by reversed phase HPLC to afford the title compound. LC-MS 735[M+H]$^+$. $^1$HNMR (400 MHz, DMSO-d$_6$) δ 12.59 (s, 1H), 8.99 (s, 1H), 8.26 (d, J=7.8 Hz, 1H), 7.96 (d, J=7.9 Hz, 1H), 7.89 (t, J=7.6 Hz, 1H), 7.83 (t, J=7.5 Hz, 1H), 7.48-7.32 (m, 2H), 7.23 (t, J=9.0 Hz, 1H), 7.06-6.98 (m, 1H), 6.49 (dd, J=8.3, 2.6 Hz, 1H), 6.42 (d, J=2.6 Hz, 1H), 4.32 (s, 2H), 3.63 (d, J=6.0 Hz, 1H), 3.54 (d, J=22.1 Hz, 3H), 3.39 (dt, J=17.2, 5.3 Hz, 4H), 3.15 (dd, J=13.2, 8.4 Hz, 2H), 2.70 (d, J=10.9 Hz, 2H), 2.35 (d, J=7.7 Hz, 1H), 2.28 (d, J=7.6 Hz, 1H), 2.24-2.16 (m, 1H), 2.12-2.03 (m, 2H), 2.02-1.81 (m, 3H), 1.75 (t, J=7.5 Hz, 1H), 1.64-1.41 (m, 4H), 1.41-1.10 (m, 8H), 0.70 (d, J=6.7 Hz, 3H).

Example S-30. Preparation of 4-(4-fluoro-3-(4-(6-((2-(4-(6-hydroxy-2-(4-hydroxyphenyl)benzo[b] thiophene-3-carbonyl)phenoxy)ethyl)(methyl)amino) hexanoyl)piperazine-1-carbonyl)benzyl)phthalazin-1 (2H)-one (Compound 2.4)

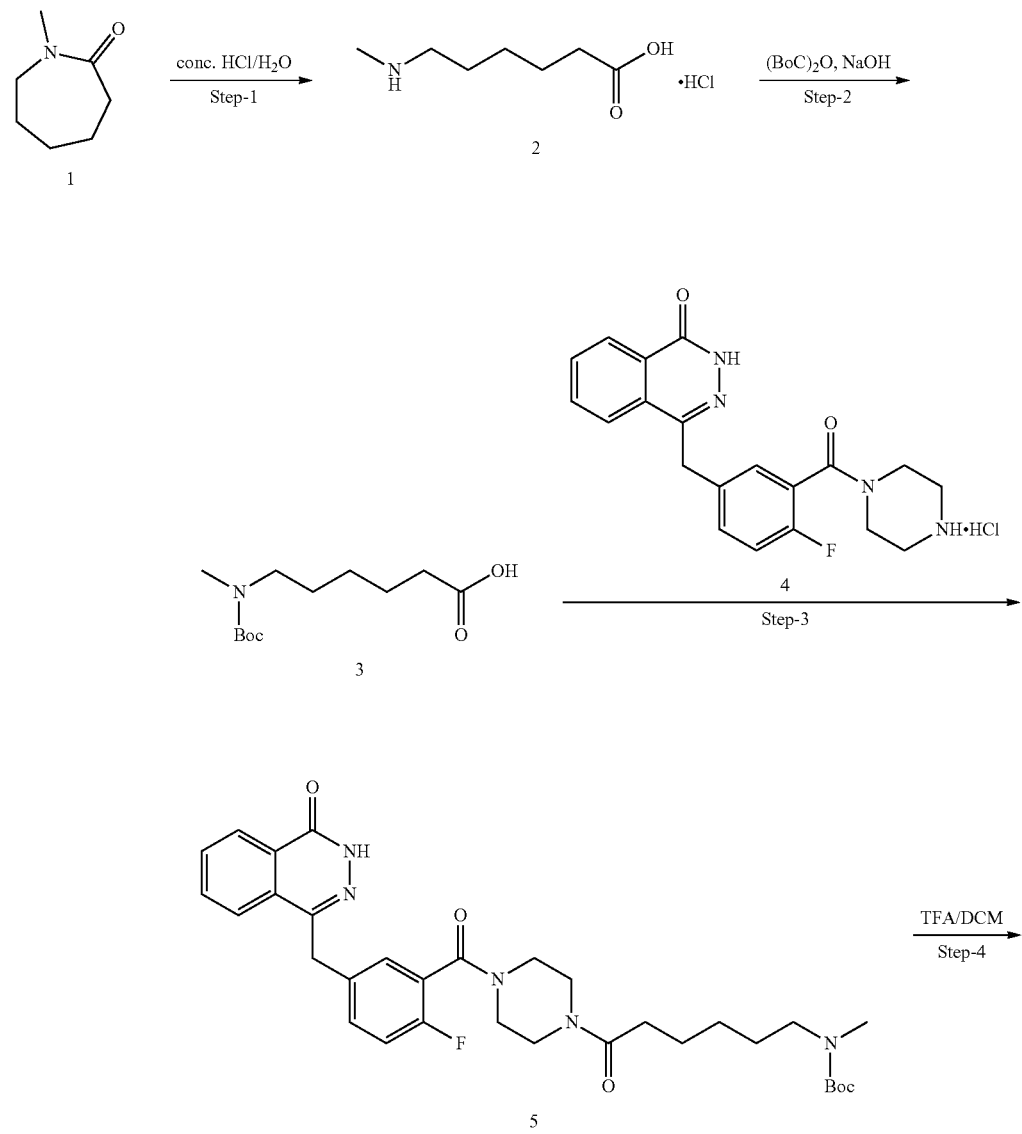

471
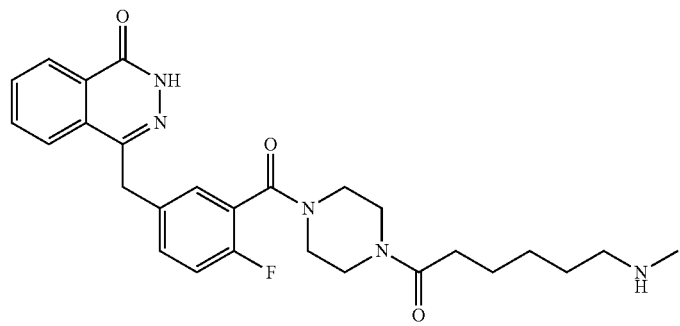
6
472
-continued
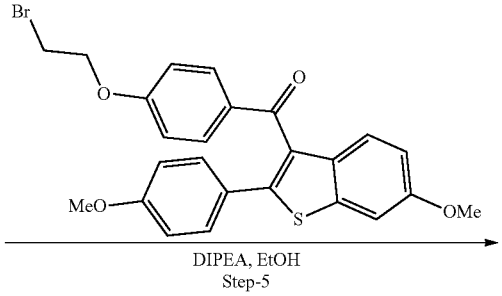
DIPEA, EtOH
Step-5
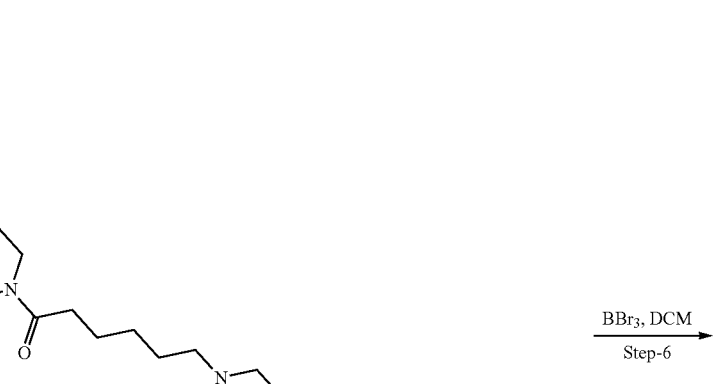
BBr₃, DCM
Step-6
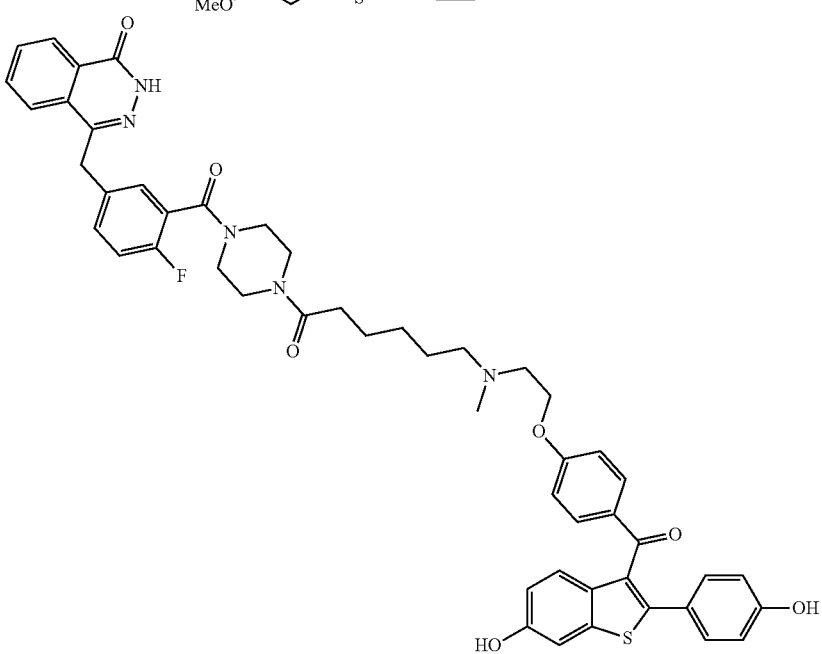

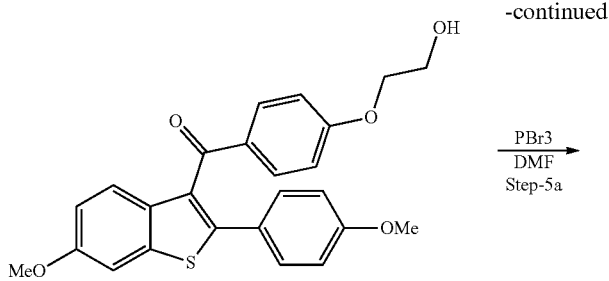 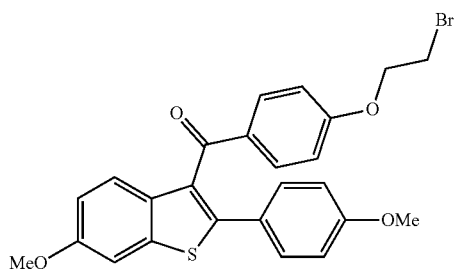

PBr3
DMF
Step-5a

Step-1: Preparation of 6-(methylamino)hexanoic acid hydrochloride

To N-methylcaprolactam (5 g, 39.3 mmol) was added conc. HCl (25 mL)-H$_2$O (36 mL) at RT and the mixture was refluxed at 110° C. for 16 h. The reaction was monitored by TLC. After 16 h, the mixture was concentrated under reduced pressure. To the residue obtained was added 10 mL of H$_2$O and again concentrated. The crude obtained was triturated with acetone/n-pentane (1:5) twice to afford the title compound. $^1$H NMR (400 MHz, DMSO-d$_6$) δ 12.05 (1H, s, br), 8.70 (2H, br), 3.6 (s, 3H), 2.18-2.23 (2H, m), 2.77-2.86 (2H, m), 1.44-1.62 (2H, m), 1.24-1.34 (2H, m).

Step-2: Preparation of 6-(tert-butoxycarbonyl(methyl)amino)hexanoic acid

To a stirred solution 6-(methylamino)hexanoic acid hydrochloride (1.5 g, 10.3 mmol) in 1,4-dioxane was added 1N-NaOH (20.7 mL, 2.5 eq) followed by the addition of di-tert-butyl dicarbonate (2.7 g, 12.4 mmol, 1.2 eq) at 0° C. and the mixture was stirred at RT for 16 h. The reaction was monitored by TLC. Upon completion, the mixture was concentrated under reduced pressure to afford the title compound which was taken forward without further purification. $^1$H NMR (400 MHz, DMDO-d$_6$) δ 11.97 (br s, 1H), 3.57 (s, 3H), 3.12 (t, J=6.6 Hz, 2H), 2.29 (t, J=7.1 Hz, 2H), 2.19 (t, J=7.1 Hz, 2H), 1.52 (d, J=6.4 Hz, 2H), 1.38 (s, 9H), 1.20 (br s, 2H).

Step-3: Preparation of tert-butyl 6-(4-(2-fluoro-5-((4-oxo-3,4-dihydrophthalazin-1 yl)methyl)benzoyl)piperazin-1 yl)-6-oxohexyl(methyl)carbamate To a stirred suspension of 6-(tert-butoxycarbonyl(methyl)amino)hexanoic acid (0.20 g, 0.8 mmol) in DMF (4 mL) was added HATU (0.62 g, 1.6 mmol, 2 eq) at 0° C. and the mixture was stirred at 0° C. for 10 min. DIPEA (0.45 mL, 2.4 mmol, 3 eq) and 4-(4-fluoro-3-(piperazine-1-carbonyl)benzyl)phthalazin-1(2H)-one hydrochloride (0.36 g, 0.89 mmol, 1.1 eq) were then successively added to the reaction mixture at 0° C. and the resultant reaction mixture was stirred at RT for 16 h. The reaction was monitored by TLC. After completion, the mixture was diluted with H$_2$O (50 mL) and extracted with EtOAc (50 mL×2). The combined organic layers were washed with water (50 mL), brine (50 mL), dried over anhydrous Na$_2$SO$_4$, filtered and concentrated under reduced pressure to obtain a crude which was purified by CombiFlash chromatography to afford the title compound. LC-MS 594 [M+H]$^+$.

Step-4: Preparation of 4-(4-fluoro-3-(4-(6-(methylamino)hexanoyl)piperazine-1-carbonyl)benzyl)phthalazin-1(2H)-one To tert-butyl 6-(4-(2-fluoro-5-((4-oxo-3,4-dihydrophthalazin-1-yl)methyl)benzoyl)piperazin-1-yl)-6-oxohexyl (methyl)carbamate (0.23 g, 0.38 mmol) in DCM (5 mL) was added TFA (0.3 mL) at 0° C. slowly and the mixture was heated at 60° C. for 2 h. The reaction was monitored by TLC and LC-MS. Upon completion, the mixture was concentrated under reduced pressure to obtain a crude residue which was triturated with n-pentane (10 mL×2) to afford the title compound as a trifluoroacetate salt. LC-MS 494 [M+H]$^+$.

Step 5a: Preparation of (4-fluorophenyl)(6-methoxy-2-(4-methoxyphenyl)benzo[b]thiophen-3-yl)methanone A mixture of 6-methoxy-2-(4-methoxyphenyl)benzo[b]thiophene (8.5 g, 31.44 mmol) in DCM (100 mL) was cooled to 0° C., and then 4-fluorobenzoyl chloride (5.73 g, 36.16 mmol) and AlCl$_3$ (4.61 g, 34.58 mmol) was added. The reaction mixture was stirred at rt for 4 h. TLC showed the reaction mixture was complete. The solution was poured into water and extracted with DCM/MeOH (100 mL×3). The organic layer was washed with brine, dried over NaSO$_4$, and concentrated in vacuo. The crude product was purified by column chromatography to afford the title compound.

Step 5b: Preparation of (4-(2-hydroxyethoxy)phenyl)(6-methoxy-2-(4-methoxyphenyl)benzo[b]thiophen-3 yl)methanone A mixture of ethylene glycol (25.59 g, 412.8 mmol) in DMF (100 mL) and cooled to 0° C., NaH (3.3 g, 82.56 mmol) was added slowly. The reaction mixture was stirred at rt for 1 h. A solution of (4-fluorophenyl)(6-methoxy-2-(4-methoxyphenyl)benzo[b]thiophen-3-yl)methanone (10.8 g, 27.52 mmol) in DMF (20 mL) was added dropwise at 0°

C. The reaction mixture was stirred at 90° C. for 1 h. TLC showed the mixture was complete. The solution was concentrated in vacuo, and purified by column chromatography to afford the title compound. LC-MS 435.3 [M+1]$^+$. $^1$H NMR (400 MHz, DMSO-d$_6$) δ 7.70-7.65 (m, 3H), 7.34-7.31 (m, 3H), 7.0 (dd, J=6.8, 2.4 Hz, 1H), 6.95-6.88 (m, 4H), 4.88 (t, J=1.6 Hz, 1H), 4.01 (t, J=4.8 Hz, 2H), 3.84 (s, 3H), 3.72 (s, 3H), 3.71-3.67 (m, 2H).

Step-5c: Preparation of (4-(2-bromoethoxy)phenyl) (6-methoxy-2-(4-methoxyphenyl)benzo[b]thiophen-3-yl)methanone To a stirred solution of (4-(2-hydroxyethoxy)phenyl)(6-methoxy-2-(4-methoxyphenyl)benzo[b]thiophen-3-yl) methanone (200 mg, 0.460 mmol) in DMF (5 mL) was added PBr$_3$ (0.87 mL, 0.92 mmol, 2 eq) at 0° C. and the mixture was stirred at 50° C. for 1 h. The reaction was monitored by TLC. Upon completion, the mixture was quenched with saturated NaHCO$_3$ solution and extracted with EtOAc (60 mL×3). The combined organic layers were washed with water (60 mL), brine (60 mL) and dried over Na$_2$SO$_4$, filtered and concentrated under reduced pressure to afford the title compound. LC-MS 497 [M+H]$^+$.

Step-5: Preparation of 4-(4-fluoro-3-(4-(6-((2-(4-(6-methoxy-2-(4-methoxyphenyl)benzo[b]thiophene-3-carbonyl)phenoxy)ethyl)(methyl)amino)hexanoyl) piperazine-1-carbonyl)benzyl) phthalazin-1(2H)-one To a stirred solution of 4-(4-fluoro-3-(4-(6-(methylamino) hexanoyl)piperazine-1-carbonyl)benzyl) phthalazin-1(2H)-one trifluoroacetate (0.080 g, 0.162 mmol) in EtOH (2 mL) was added DIPEA (0.15 mL, 0.81 mmol, 5 eq) followed by the addition of (4-(2-bromoethoxy)phenyl)(6-methoxy-2-(4-methoxy phenyl)benzo[b]thiophen-3-yl)methanone (0.08 g, 0.162 mmol, 1 eq) and the mixture was heated at 80° C. for 16 h. The reaction was monitored by TLC and LC-MS. Upon completion, the mixture was concentrated under reduced pressure to obtain a crude which was purified by CombiFlash chromatography to afford the title compound. LC-MS 910 [M+H]$^+$.

Step-6: Preparation of 4-(4-fluoro-3-(4-(6-((2-(4-(6-hydroxy-2-(4-hydroxyphenyl)benzo[b]thiophene-3-carbonyl)phenoxy)ethyl)(methyl)amino)hexanoyl) piperazine-1-carbonyl)benzyl) phthalazin-1(2H)-one (Compound 2.4)

To a stirred solution of 4-(4-fluoro-3-(4-(6-((2-(4-(6-methoxy-2-(4-methoxyphenyl)benzo[b]thiophene-3-carbonyl)phenoxy)ethyl)(methyl)amino)hexanoyl)piperazine-1-carbonyl)benzyl) phthalazin-1(2H)-one (100 mg, 0.11 mmol) in DCM (2 mL) was added BBr$_3$ (1M in DCM; 1.09 mL, 1.1 mmol, 10 eq) at 0° C. and the mixture was stirred at RT for 16 h. The reaction was monitored by LC-MS and TLC. Upon completion, the mixture was quenched with saturated NaHCO$_3$ solution (60 mL). The aqueous layer was then extracted with EtOAc (60 mL×3). The combined organic layers were washed with water (60 mL), brine (60 mL) and dried over Na$_2$SO$_4$, filtered and concentrated under reduced pressure to obtain a crude which was purified by reversed-phase HPLC to afford Compound 2.4. LC-MS 882 [M+H]$^+$. $^1$H NMR (400 MHz, CD$_3$OD-d$_4$) δ 8.54 (s, 1H), 8.39-8.31 (m, 1H), 7.98-7.91 (m, 1H), 7.83 (p, J=7.3 Hz, 1H), 7.75-7.66 (m, 2H), 7.47 (d, J=8.6 Hz, 2H), 7.42 (d, J=8.7 Hz, 1H), 7.36 (s, 1H), 7.25 (d, J=2.3 Hz, 1H), 7.17 (dd, J=8.6, 6.7 Hz, 2H), 6.91-6.81 (m, 3H), 6.62 (d, J=8.3 Hz, 2H), 4.38 (s, 2H), 4.16 (d, J=4.9 Hz, 2H), 3.78-3.69 (m, 2H), 3.63 (d, J=7.0 Hz, 2H), 3.35 (s, 2H), 2.93 (s, 1H), 2.59 (s, 1H), 2.42 (d, J=6.8 Hz, 3H), 1.58 (d, J=15.1 Hz, 4H).

Example S-31. Preparation of 4-(4-fluoro-3-(4-(2-(4-(6-hydroxy-2-(4-hydroxyphenyl)benzo[b]thiophene-3-carbonyl)phenoxy)ethyl)piperazine-1-carbonyl)benzyl)phthalazin-1(2H)-one (Compound 2.13)

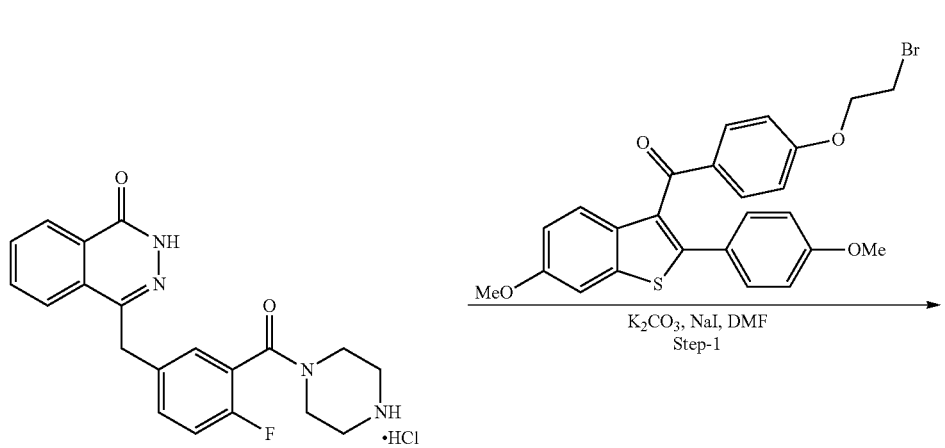

477 478
-continued
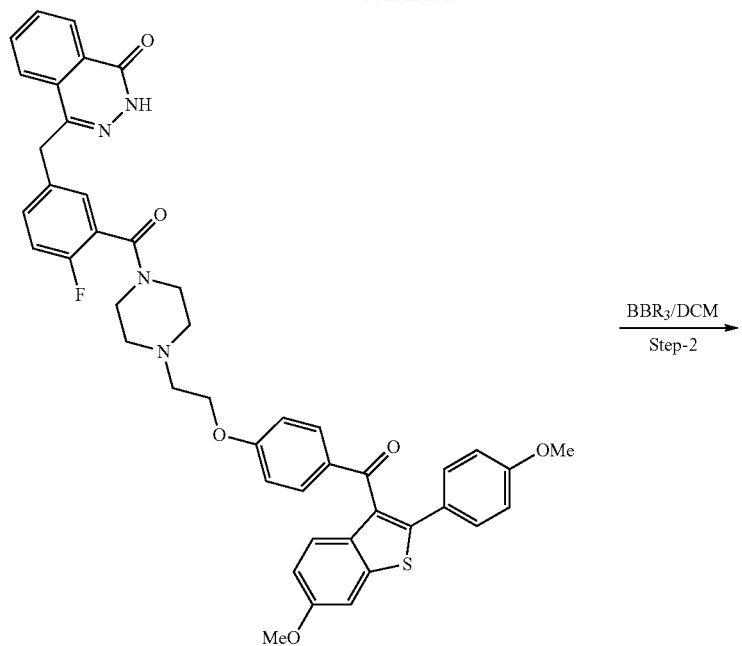
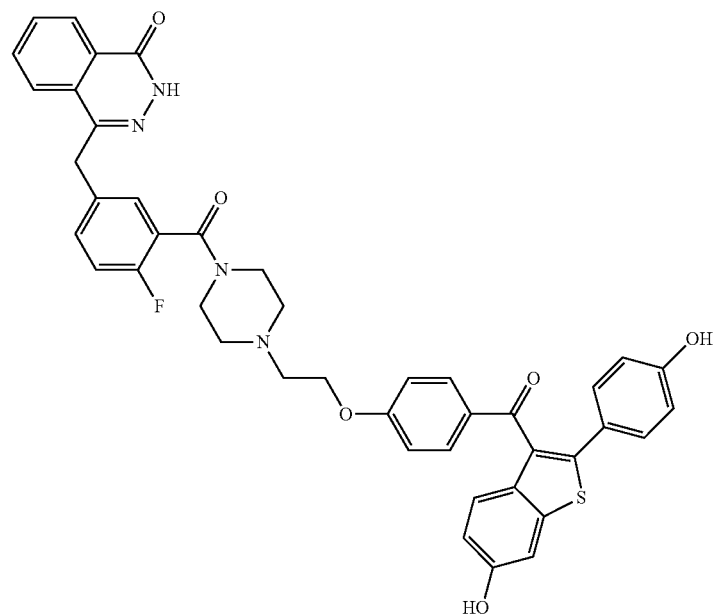
Compound 2.18
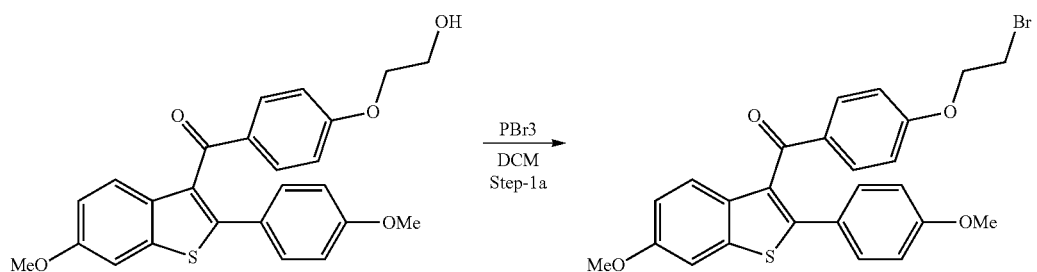 [SMILES: COc1ccc(-c2sc3cc(OC)ccc3c2C(=O)c2ccc(OCCO)cc2)cc1 ; "PBr3" ; COc1ccc(-c2sc3cc(OC)ccc3c2C(=O)c2ccc(OCCBr)cc2)cc1]

Step-1a: Preparation of (4-(2-bromoethoxy)phenyl) (6-methoxy-2-(4-methoxyphenyl)benzo[b]thiophen-3-yl)methanone To a stirred solution of (4-(2-hydroxyethoxy)phenyl)(6-methoxy-2-(4-methoxyphenyl)benzo[b]thiophen-3-yl)methanone (200 mg, 0.460 mmol) in DMF (5 mL) was added $PBr_3$ (0.87 mL, 0.92 mmol, 2 eq) at 0° C. and the mixture was stirred at 50° C. for 1 h. The reaction was monitored by TLC. Upon completion, the mixture was quenched with saturated $NaHCO_3$ solution and extracted with EtOAc (60 mL×3). The combined organic layers were washed with water (60 mL), brine (60 mL) and dried over $Na_2SO_4$, filtered and concentrated under reduced pressure to afford (4-(2-bromoethoxy)phenyl)(6-methoxy-2-(4-methoxyphenyl)benzo[b]thiophen-3-yl)methanone. LC-MS 497 $[M+H]^+$

Step-1: Preparation of 4-(4-fluoro-3-(4-(2-(4-(6-methoxy-2-(4-methoxyphenyl)benzo[b]thiophene-3-carbonyl)phenoxy)ethyl)piperazine-1-carbonyl)benzyl)phthalazin-1(2H)-one To a stirred suspension of 4-(4-fluoro-3-(piperazine-1-carbonyl)benzyl)phthalazin-1(2H)-one hydrochloride (150 mg, 0.372 mmol) in DMF (5 mL) were successively added $K_2CO_3$ (102 mg, 0.744 mmol, 2 eq), NaI (11.16 mg, 0.0743 mmol, 0.2 eq) and (4-(2-bromoethoxy)phenyl)(6-methoxy-2-(4-methoxyphenyl)benzo[b]thiophen-3-yl)methanone (222 mg, 0.444 mmol, 1.2 eq) and the resultant mixture was stirred at 100° C. for 6 h. The reaction was monitored by TLC. After completion, the mixture was diluted with water (20 mL). The resulting precipitate was filtered over Buchner funnel to obtain a crude product which was purified by combi flash chromatography to afford 4-(4-fluoro-3-(4-(2-(4-(6-methoxy-2-(4-methoxyphenyl)benzo[b]thiophene-3-carbonyl)phenoxy)ethyl)piperazine-1-carbonyl)benzyl)phthalazin-1(2H)-one. LC-MS 783$[M+H]^+$

Step-2: Preparation of 4-(4-fluoro-3-(4-(2-(4-(6-hydroxy-2-(4-hydroxyphenyl)benzo[b]thiophene-3-carbonyl)phenoxy)ethyl)piperazine-1-carbonyl)benzyl)phthalazin-1(2H)-one To a stirred solution of 4-(4-fluoro-3-(4-(2-(4-(6-methoxy-2-(4-methoxyphenyl)benzo[b]thiophene-3-carbonyl)phenoxy)ethyl)piperazine-1-carbonyl)benzyl)phthalazin-1(2H)-one (100 mg, 0.127 mmol) in DCM (5 mL) was added $BBr_3$ (1M in DCM; 1.5 mL, 1.53 mmol, 12 eq) at 0° C. and the mixture was stirred at RT for 16 h. The reaction was monitored by LC-MS and TLC. Upon completion, the mixture was quenched with saturated $NaHCO_3$ solution (60 mL). The aqueous layer was then extracted with EtOAc (60 mL×3). The combined organic layers were washed with water (60 mL), brine (60 mL) and dried over $Na_2SO_4$, filtered and concentrated under reduced pressure to obtain a crude which was purified by reversed phase HPLC to afford 4-(4-fluoro-3-(4-(2-(4-(6-hydroxy-2-(4-hydroxyphenyl)benzo[b]thiophene-3-carbonyl)phenoxy)ethyl)piperazine-1-carbonyl)benzyl)phthalazin-1(2H)-one. LC-MS 755 $[M+H]^+$. $^1H$ NMR (400 MHz, DMSO-$d_6$) δ 12.60 (s, 1H), 9.79 (s, 1H), 9.74 (s, 1H), 8.25 (d, J=7.9 Hz, 1H), 7.96 (d, J=8.1 Hz, 1H), 7.88 (t, J=7.7 Hz, 1H), 7.81 (t, J=7.5 Hz, 1H), 7.65 (d, J=8.5 Hz, 2H), 7.41 (t, J=6.9 Hz, 1H), 7.34 (d, J=2.3 Hz, 1H), 7.31 (dd, J=6.7, 2.1 Hz, 1H), 7.27-7.19 (m, 2H), 7.19-7.14 (m, 2H), 6.92 (d, J=8.7 Hz, 2H), 6.85 (dd, J=8.6, 2.3 Hz, 1H), 6.70-6.64 (m, 2H), 4.32 (s, 2H), 4.10 (dt, J=7.6, 5.3 Hz, 2H), 3.59 (s, 2H), 3.17 (d, J=5.2 Hz, 1H), 3.13 (s, 2H), 2.69 (t, J=5.5 Hz, 2H), 2.44 (s, 2H), 2.34 (s, 1H).

Example S-32. Synthesis of 4-(4-fluoro-3-(4-(2-(4-(1-(4-hydroxyphenyl)-2-phenylbut-1-enyl)phenoxy)ethyl)piperazine-1-carbonyl)benzyl)pthalazin-1(2H)-one (Compound 2.14)

Step-1: Preparation of 4-(1-(4-(2-(4-(2-fluoro-5-((4-oxo-3,4-dihydrophthalazin-1 yl)methyl)benzoyl)piperazin-1 yl)ethoxy)phenyl)-2 phenylbut-1-enyl) phenyl pivalate To a stirred solution of 4-(4-fluoro-3-(piperazine-1-carbonyl)benzyl)phthalazin-1(2H)-one hydrochloride (0.10 g, 0.197 mmol) in EtOH (2 mL) was added DIPEA (0.91 mL, 4.97 mmol, 5 eq) followed by the addition of 4-(1-(4-(2-bromoethoxy)phenyl)-2-phenylbut-1-enyl)phenyl pivalate (0.119 g, 0.296 mmol, 1.5 eq) and the mixture was heated at 80° C. for 16 h. The reaction was monitored by TLC and LC-MS. Upon completion, the mixture was concentrated under reduced pressure to obtain a crude which was purified by reversed-phase HPLC to afford the title compound. LC-MS 793 $[M+H]^+$.

Step-2: Preparation of 4-(4-fluoro-3-(4-(2-(4-(1-(4-hydroxyphenyl)-2 phenylbut-1-enyl) phenoxy)ethyl) piperazine-1-carbonyl)benzyl)phthalazin-1(2H)-one To 4-(1-(4-(2-(4-(2-fluoro-5-((4-oxo-3,4-dihydrophthalazin-1-yl)methyl)benzoyl)piperazin-1-yl)ethoxy)phenyl)-2-phenylbut-1-enyl)phenyl pivalate (0.035 g, 0.044 col) was added 1.25 N HCl in EtOH (2 mL) and the mixture was stirred at RT for 24 h. The reaction was monitored by TLC and LC-MS. After completion, the mixture was concentrated under reduced pressure to obtain a crude which was purified by reversed phase HPLC to afford Compound 2.14. LC-MS 709 $[M+H]^+$. $^1H$ NMR (400 MHz, DMSO-$d_6$) δ 12.59 (br s, 1H), 9.41 (s, 1H), 9.16 (s, 1H), 8.21-8.29 (m, 1H), 7.94-8.00 (m, 1H), 7.88 (d, J=6.1 Hz, 1H), 7.81 (d, J=4.8 Hz, 1H), 7.41 (br s, 1H), 7.32 (br s, 1H), 7.12-7.25 (m, 2H), 7.08 (d, J=8.3 Hz, 2H), 6.93 (d, J=8.8 Hz, 3H), 6.66-6.79 (m, 2H), 6.59 (dd, J=8.8, 3.5 Hz, 2H), 6.39 (d, J=8.8 Hz, 1H), 4.32 (d, J=4.4 Hz, 2H), 4.08 (d, J=5.7 Hz, 1H), 3.92 (d, J=5.3 Hz, 1H), 3.60 (d, J=18.0 Hz, 2H), 3.14 (d, J=19.7 Hz, 2H), 2.73 (d, J=5.7 Hz, 1H), 2.63 (br s, 1H), 2.39 (t, J=7.2 Hz, 4H), 0.84 (t, J=7.5 Hz, 3H).

Example S-33. Preparation of 4-(3-(4-cyano-3-(trifluoromethyl)phenyl)-5,5-dimethyl-4-oxo-2-thioxo imidazolidin-1-yl)-N-(6-(3-(5-(8-ethyl-7-oxo-5,6,7,8-tetrahydropyrazino[2,3-b]pyrazin-2-yl)-6-methylpyridin-2-yl)-1H-1,2,4-triazol-1-yl)hexyl)-2-fluorobenzamide (Compound 3.1)
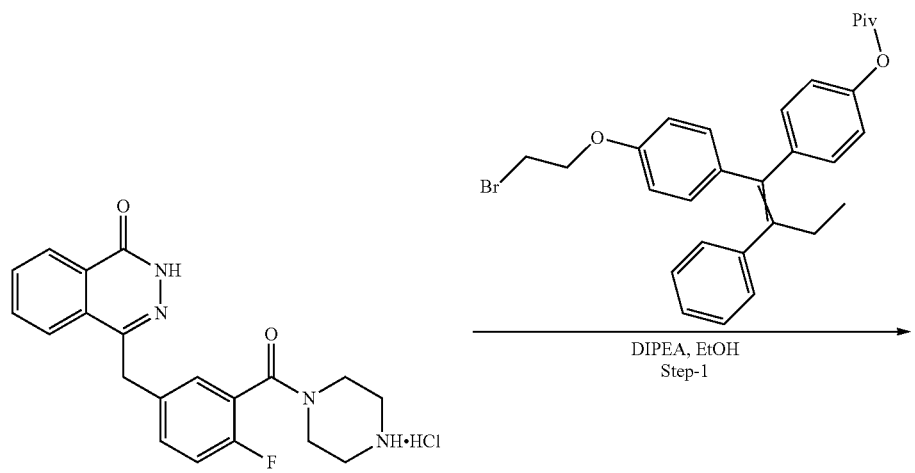
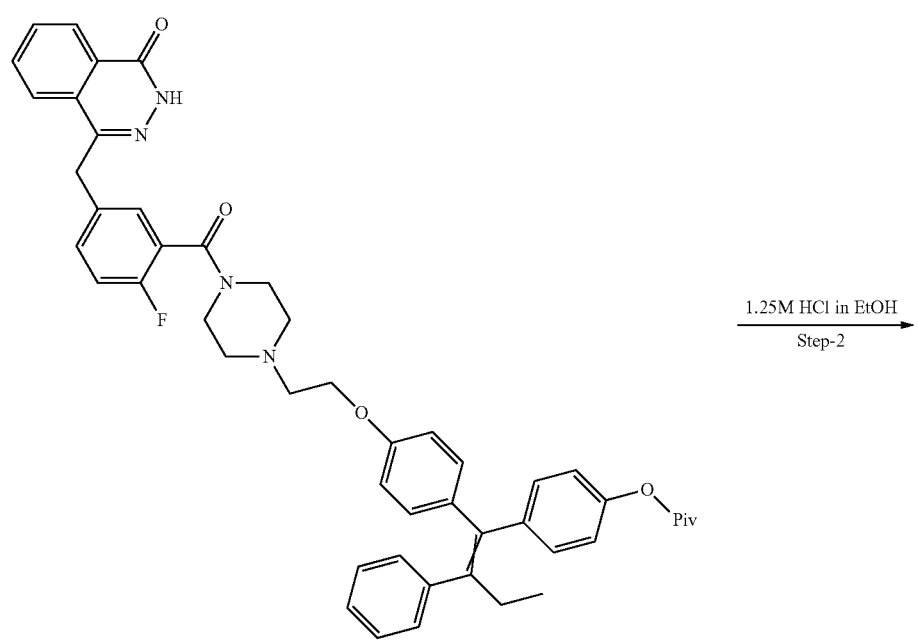

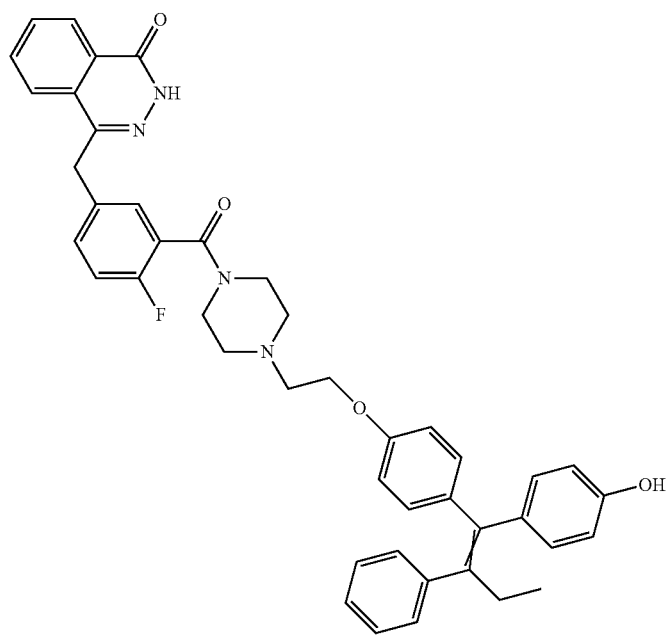
Step-1: Preparation of 3-bromo-2-methyl-6-(1H-1,2,4-triazol-3 yl)pyridine
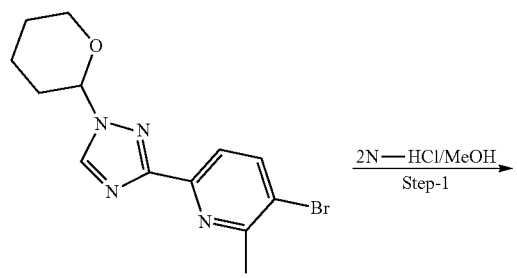
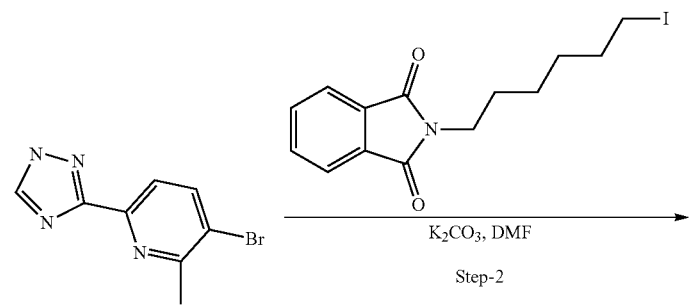

-continued
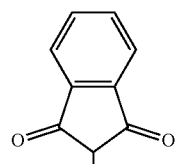
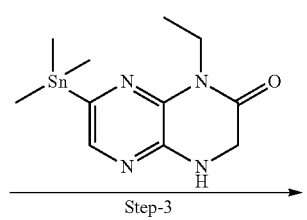
Step-3
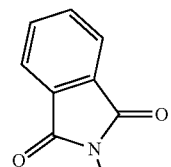
$NH_2-NH_2 \cdot H_2O$
Step-4
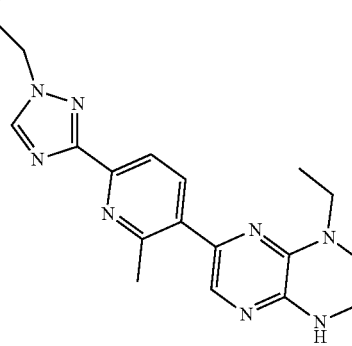
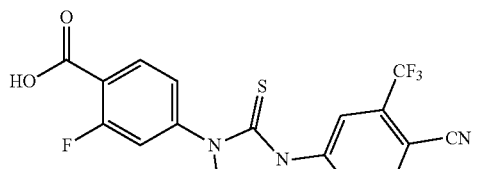
HBTU, DIPEA, DMA
Step-5

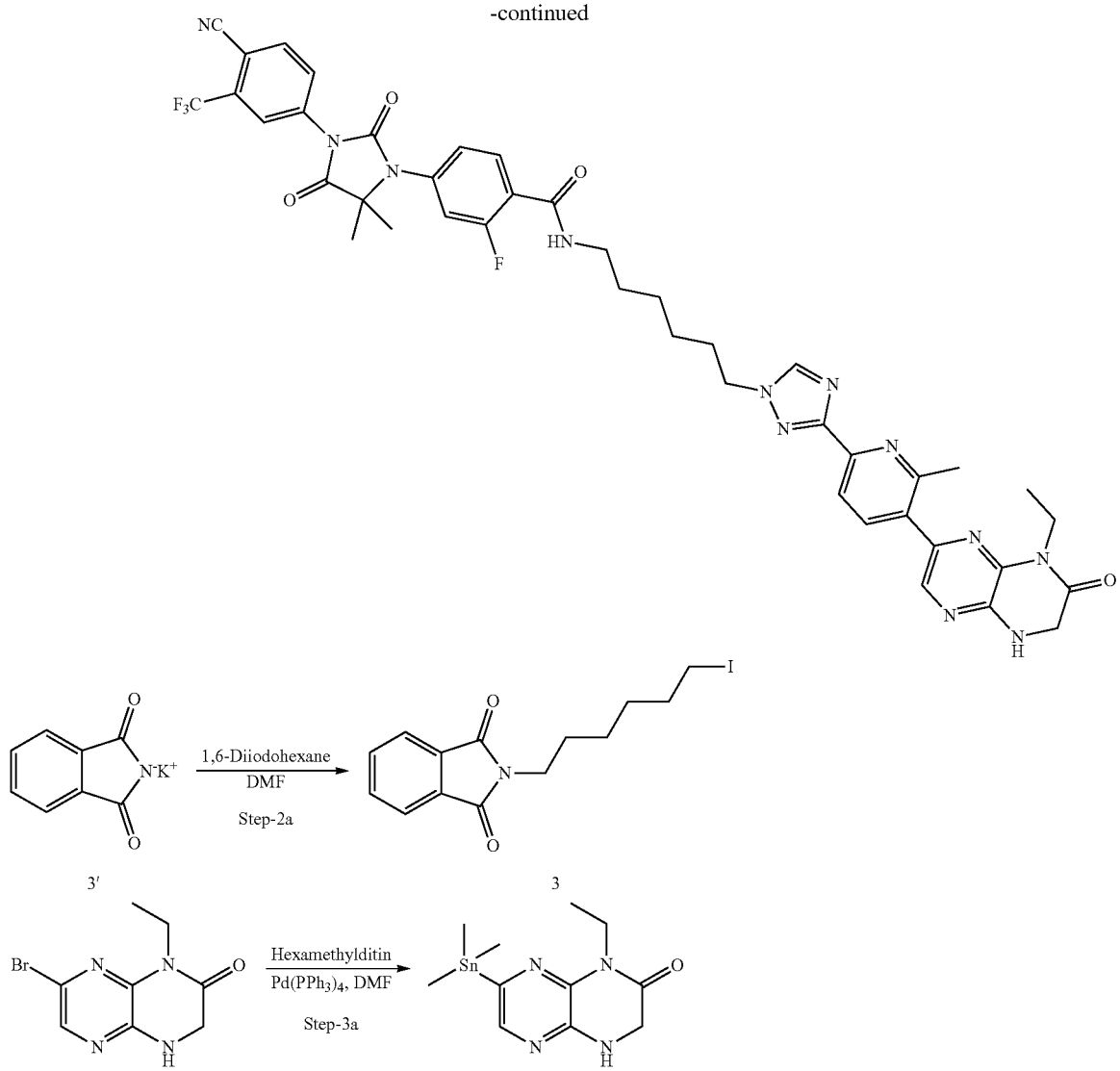

To 3-bromo-2-methyl-6-(1-(tetrahydro-2H-pyran-2-yl)-1H-1,2,4-triazol-3-yl)pyridinic (1.6 g, 4.95 mmol) was added 2M-HCl in MeOH (15 mL) and resulting mixture was stirred at RT for 16 h. The reaction was monitored by TLC & LC-MS. After completion, the mixture was concentrated under reduced pressure to afford the title compound. LC-MS 239 [M+H]$^+$

Step-2a: Preparation of 2-(6-iodohexyl)isoindoline-1,3-dione

To a solution of potassium 1,3-dioxoisoindolin-2-ide (5.0 g, 26.99 mmol) in DMF (50 mL) was added 1,6-Diiodohexane (22.8 g, 67.49 mmol) and the mixture was heated at 70° C. for 2.5 h. The reaction was monitored by TLC. After completion, the mixture was diluted with H$_2$O (100 mL) and extracted with EtOAc (200 mL×2). The combined organic layers were washed with brine (100 mL), dried over anhydrous Na$_2$SO$_4$, filtered and concentrated under reduced pressure to obtain a crude which was purified by CombiFlash chromatography to afford the title compound. LC-MS 358 [M+H]$^+$

Step-2: Preparation of 2-(6-(3-(5-bromo-6-methylpyridin-2 yl)-1H-1,2,4-triazol-1 yl)hexyl)isoindoline-1,3-dione To a solution of 3-bromo-2-methyl-6-(1H-1,2,4-triazol-3-yl)pyridine (1.4 g, 5.08 mmol) in DMF (25 mL) was added K2CO$_3$ (1.75 g, 12.70 mmol) at 0° C. and the mixture was stirred at RT for 15 min. 2-(6-iodohexyl)isoindoline-1,3-dione (1.99 g, 5.58 mmol) and then added to the mixture and the resultant mixture was heated at 70° C. for 1.5 h. The reaction was monitored by TLC. Upon completion, the mixture was diluted with H$_2$O (50 mL) and extracted with EtOAc (100 mL×2). The combined organic layers were washed with brine (100 mL), dried over anhydrous Na$_2$SO$_4$, filtered and concentrated under reduced pressure to obtain a crude which was purified by CombiFlash chromatography to afford the title compound. LC-MS 468[M+H]$^+$

Step 3a: Preparation of 1-ethyl-7-(trimethylstannyl)-3,4-dihydropyrazino[2,3-b]pyrazin-2(1H)-one To a stirred solution of 7-bromo-1-ethyl-3,4-dihydropyrazino[2,3-b]pyrazin-2(1H)-one (0.5 g, 1.94 mmol) in DMF (8 mL) was added hexamethylditin (0.48 mg, 2.33 mmol, 1.2 eq) at RT and the mixture was degassed under nitrogen for 15 min. Pd(PPh$_3$)$_4$ (0.224 mg, 0.194 mmol, 0.1 eq) was then added to the mixture resultant reaction mixture was heated at 100° C. for 90 min. The reaction monitored by TLC. After completion, the mixture was diluted with water (200 mL) and extracted with EtOAC (200 mL×2). The combined organic layers were washed with water (100 mL), brine (150 mL) dried over anhydrous Na$_2$SO$_4$, filtered and concentrated under reduced pressure to afford a crude which was purified by CombiFlash chromatography to afford the title compound. LC-MS 343 [M+H]$^+$ Step-3: Preparation of 2-(6-(3-(5-(8-ethyl-7-oxo-5,6,7,8-tetrahydropyrazino[2,3-b]pyrazin-2 yl)-6-methylpyridin-2-yl)-1H-1,2,4-triazol-1 yl)hexyl)isoindoline-1,3-dione To a stirred solution of 2-(6-(3-(5-bromo-6-methylpyridin-2-yl)-1H-1,2,4-triazol-1-yl)hexyl) isoindoline-1,3-dione (0.5 g, 1.94 mmol) in DMF (8 mL) were added 1-ethyl-7-(trimethylstannyl)-3,4-dihydropyrazino[2,3-b]pyrazin-2(1H)-one (0.507 g, 1.48 mmol, 1.7 eq) and triethylamine (0.48 mL, 3.50 mmol, 4.0 eq) at RT and the mixture was degassed under nitrogen for 15 min. Tri(o-tolyl)phosphine (0.053 g, 0.0175 mmol, 0.2 eq) and Pd$_2$(dba)$_3$ (0.080 mg, 0.087 mmol, 0.1 eq) were then successively added to the mixture and the resultant mixture was heated at 100° C. for 16 h. The reaction was monitored by TLC. After completion, the mixture was diluted with water (50 mL) and extracted with EtOAc (200 mL×2). The combined organic layers was washed with brine (100 mL), dried over anhydrous Na$_2$SO$_4$, filtered and concentrated under reduced pressure to afford a crude which was purified by CombiFlash chromatography to afford the title compound. LC-MS 566 [M+H]$^+$ Step 4: Preparation of 5-(5-amino-2-(p-tolyloxy)phenyl)-1-methyl-3-(methylamino)pyridin-2(1H)-one To a stirred solution of 2-(6-(3-(5-(8-ethyl-7-oxo-5,6,7,8-tetrahydropyrazino[2,3-b]pyrazin-2-yl)-6-methylpyridin-2-yl)-1H-1,2,4-triazol-1-yl)hexyl)isoindoline-1,3-dione (0.20 g, 0.353 mmol) in EtOH (10 mL) was added NH$_2$NH$_2$·H$_2$O (0.52 mL, 1.06 mmol, 3.0 eq) and the mixture was heated at 100° C. for 4 h. The reaction monitored by TLC and LC-MS. After completion, the mixture was diluted with water (200 mL) and extracted with 10% MeOH/DCM (200 mL×3). The combined organic layers were washed with water (100 mL), brine (150 mL) dried over anhydrous Na$_2$SO$_4$, filtered and concentrated under reduced pressure to afford the title compound. LC-MS 436 [M+H]$^+$ Step-5: Preparation of 4-(3-(4-cyano-3-(trifluoromethyl)phenyl)-5,5-dimethyl-4-oxo-2-thioxo imidazolidin-1 yl)-N-(6-(3-(5-(8-ethyl-7-oxo-5,6,7,8-tetrahydropyrazino[2,3-b]pyrazin-2-yl)-6-methylpyridin-2-yl)-1H-1,2,4-triazol-1 yl)hexyl)-2-fluorobenzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (0.13 g, 0.287 mmol) in DMA (5 mL) was added HBTU (0.130 g, 0.345 mmol, 1.2 eq) at 0° C. and the resulting mixture was stirred for 10 min. DIPEA (0.150 mL, 0.575 mmol, 2.0 eq) and 5-(5-amino-2-(p-tolyloxy)phenyl)-1-methyl-3-(methylamino)pyridin-2(1H)-one (0.150 g, 0.345 mmol, 1.2 eq) were then successively added to the mixture and the resultant mixture was stirred at RT for 2 h. The reaction was monitored by TLC & LC-MS. After completion, water (20 mL) was added and the resulting precipitate was filtered over Buchner funnel. The product obtained was washed with water (5 mL×2) and n-pentane (5 mL×2), dried under vacuum to obtain a crude residue which was purified by reversed phase HPLC to afford the title compound. LC-MS 869 [M+H]$^+$, $^1$HNMR (400 MHz, MeOD-d$_4$) δ 8.17 (dd, J=5.2, 3.1 Hz, 2H), 8.06-7.95 (m, 4H), 7.86 (s, 1H), 7.80 (t, J=8.2 Hz, 1H), 7.41-7.29 (m, 2H), 4.27 (s, 2H), 4.18 (q, J=7.0 Hz, 2H), 3.38 (t, J=6.9 Hz, 2H), 2.76 (s, 3H), 2.06-1.91 (m, 3H), 1.61 (d, J=8.6 Hz, 3H), 1.58 (s, 6H), 1.50-1.43 (m, 3H), 1.26 (m, 2H).

Example S-34. Preparation of 4-(3-(4-cyano-3-(trifluoromethyl)phenyl)-5,5-dimethyl-4-oxo-2-thioxo-imidazolidin-1-yl)-N-(6-(4-ethyl-6-(2-methyl-6-(1H-1,2,4-triazol-3-yl)pyridin-3-yl)-3-oxo-3,4-dihydropyrazino[2,3-b]pyrazin-1(2H)-yl)hexyl)-2-fluorobenzamide (Compound 3.2)

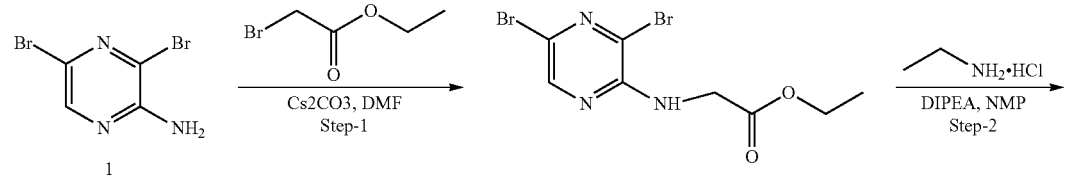

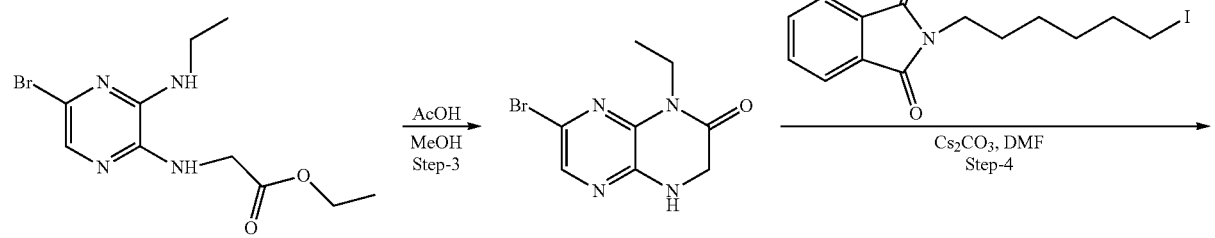

491
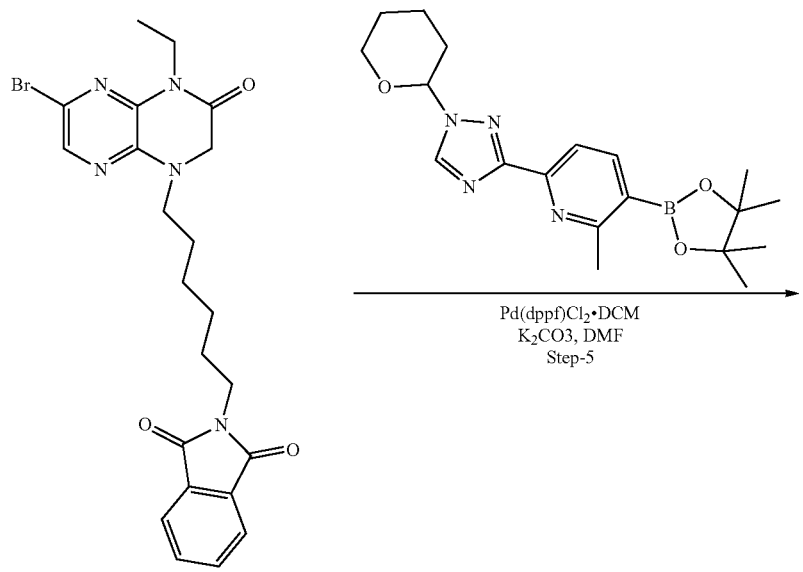
492
-continued
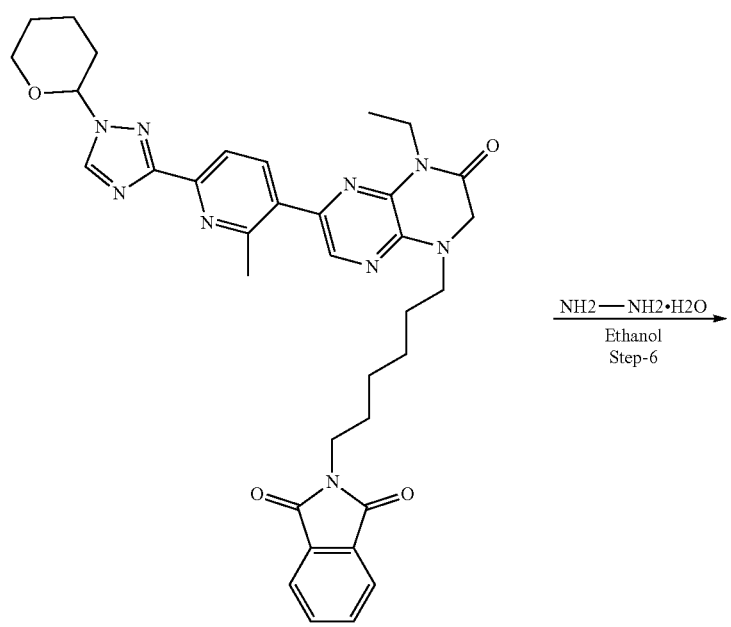

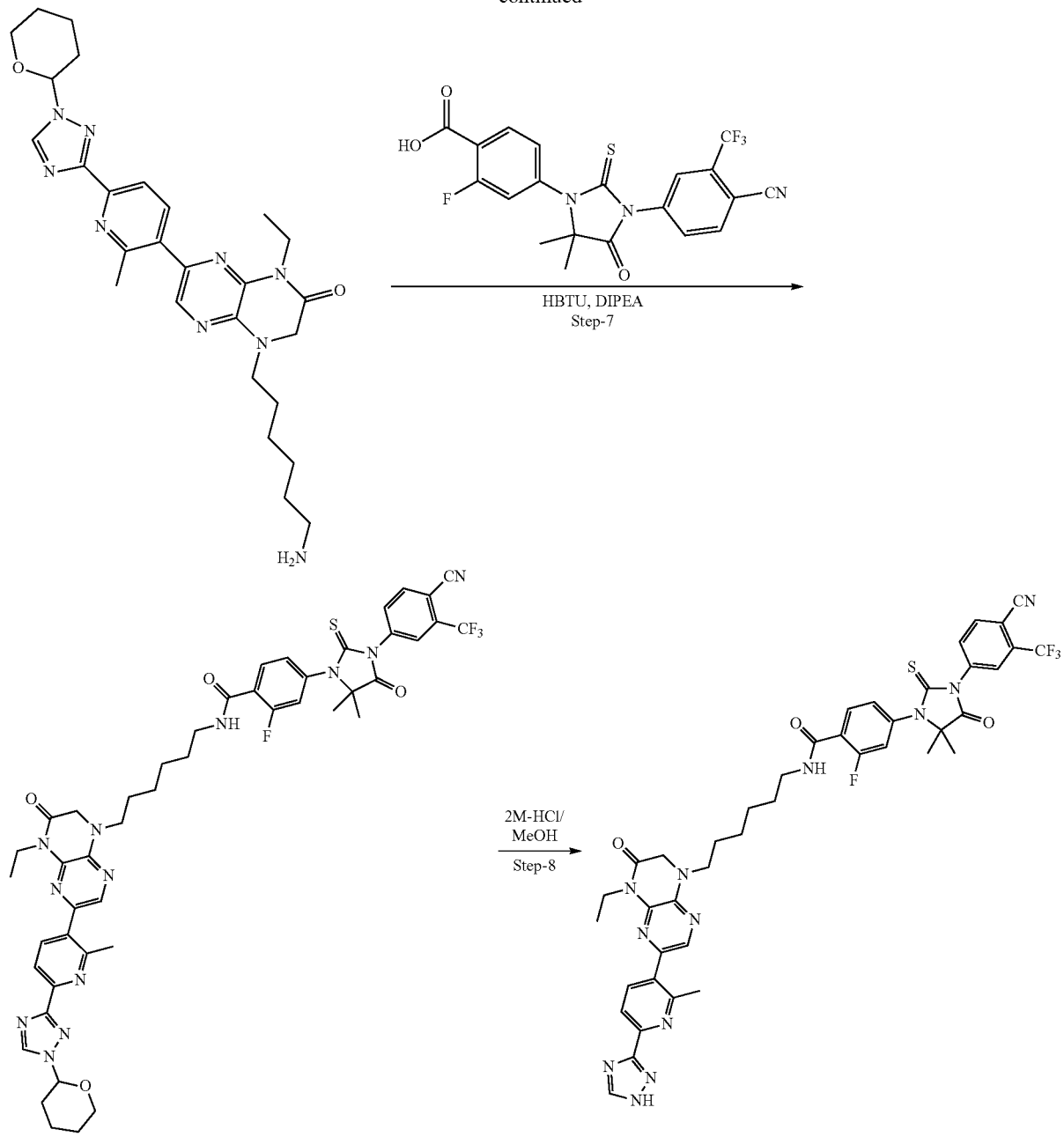

Step-1: Preparation of ethyl 2-(3,5-dibromopyrazin-2 ylamino)acetate

To a stirred solution of 3,5-dibromopyrazin-2-amine (20.0 g, 79.6 mmol) in DMF (100 mL) was added $Cs_2CO_3$ (36.2 g, 102.8 mmol) at 0° C. and the mixture was stirred for 15 min. Ethyl 2-bromoacetate (10.4 g, 94.8 mmol) was then added to the mixture and the mixture was heated at 80° C. for 3 h. The reaction was monitored by TLC. Upon completion, the mixture was diluted with water (200 mL) to obtain a precipitate which was filtered over Buchner funnel and dried under vacuum to afford the title compound. LC-MS 338 [M+H]$^+$ Step-2: Preparation of ethyl 2-(5-bromo-3-(ethylamino)pyrazin-2 ylamino)acetate To a stirred solution of ethyl 2-(3,5-dibromopyrazin-2-ylamino)acetate (1.1 g, 3.22 mmol) in NMP (9 mL) was added DIPEA (2.82 mL, 16.2 mmol, 5 eq) and ethanamine hydrochloride (70% solution in water; 1.04 mL, 12.9 mmol, 2.0 eq) and the mixture was heated at 120° C. in sealed tube for 16 h. The reaction was monitored by TLC and LC-MS. After completion. The mixture was diluted with $NaHCO_3$ solution (100 mL) and extracted with EtOAc (200 mL×2). The combined organic layers were washed with brine (100 mL), dried over anhydrous $Na_2SO_4$, filtered and concentrated under reduced pressure to obtain a get crude which was purified by CombiFlash chromatography to afford the title compound LC-MS 303[M+H]$^+$

Step-3: Preparation of 7-bromo-1-ethyl-3,4-dihydropyrazino[2,3-b]pyrazin-2(1H)-one To a stirred solution of ethyl 2-(5-bromo-3-(ethylamino)pyrazin-2-ylamino)acetate (0.97 g, 3.20 mmol) in methanol (1 mL) was added AcOH (5 mL) at RT and the mixture heated 120° C. in sealed tube for 16 h. The reaction was monitored by TLC and LC-MS. After completion, the mixture was diluted with saturated NaHCO$_3$ solution (100 mL) and extracted with EtOAc (100 mL×3). The combined organic layers were washed with brine (50 mL), dried over anhydrous Na$_2$SO$_4$, filtered and concentrated under reduced pressure to obtain a crude which q was purified by CombiFlash chromatography to afford the title compound. LC-MS 257[M+H]$^+$

Step-4: Preparation of 2-(6-(6-bromo-4-ethyl-3-oxo-3,4-dihydropyrazino[2,3-b]pyrazin-1(2H)-yl)hexyl)isoindoline-1,3-dione To a stirred solution of 7-bromo-1-ethyl-3,4-dihydropyrazino[2,3-b]pyrazin-2(1H)-one (0.8 g, 3.11 mmol) in DMF (25 mL) was added Cs$_2$CO$_3$ (2.02 g, 6.24 mmol, 2 eq) at RT and the mixture was stirred for 15 min. 2-(6-iodohexyl)isoindoline-1,3-dione (2.2 g, 6.24 mmol, 2 eq) was then added to the mixture and the resultant mixture was heated at 80° C. for 2 h. The reaction was monitored by TLC. After completion, ice-cold water (50 mL) was added to the mixture to obtain a precipitate which was filtered over Buchner funnel and dried under vacuum to afford the title compound. LC-MS 486[M+H]$^+$

Step-5: Preparation of 2-(6-(4-ethyl-6-(2-methyl-6-(1-(tetrahydro-2H pyran-2-yl)-1H-1,2,4-triazol-3-yl)pyridin-3-yl)-3-oxo-3,4-dihydropyrazino[2,3-b]pyrazin-1(2H) yl)hexyl)isoindoline-1,3-dione To a stirred solution of 2-(6-(6-bromo-4-ethyl-3-oxo-3,4-dihydropyrazino[2,3-b]pyrazin-1(2H)-yl)hexyl)isoindoline-1,3-dione (1.0 g, 2.06 mmol) in DMF (20 mL) was added 2-methyl-6-(1-(tetrahydro-2H-pyran-2-yl)-1H-1,2,4-triazol-3-yl)-3-(4,4,5,5-tetramethyl-1,3,2-dioxaborolan-2-yl)pyridine (1.52 g, 4.12 mmol, 2.0 eq) and K$_2$CO$_3$ (0.567 mg, 4.11 mmol, 2 eq) dissolved in water (3 mL) and the mixture was degassed under nitrogen for 15 min. Pd(dppf)Cl$_2$ (0.032 mg, 0.043 mmol, 0.1 eq) was then added to the mixture and the resultant mixture was heated at 70° C. for 16 h. The reaction monitored by TLC. After completion, the mixture was diluted with water (200 mL) and extracted with 10% MeOH/DCM (300 mL×3). The combined organic layers were washed with water (100 mL), brine (150 mL) dried over anhydrous Na$_2$SO$_4$, filtered and concentrated under reduced pressure to afford a crude residue which was purified by CombiFlash chromatography to afford the title compound. LC-MS 650 [M+H]$^+$

Step-6: Preparation of 4-(6-aminohexyl)-1-ethyl-7-(2-methyl-6-(1-(tetrahydro-2l1 pyran-2 yl)-1H-1,2,4-triazol-3 yl)pyridin-3 yl)-3,4-dihydropyrazino[2,3-b]pyrazin-2(1H)-one To a stirred solution of 2-(6-(4-ethyl-6-(2-methyl-6-(1-(tetrahydro-2H-pyran-2-yl)-1H-1,2,4 triazol-3-yl)pyridin-3-yl)-3-oxo-3,4-dihydropyrazino[2,3-b]pyrazin-1(2H)-yl) hexyl)isoindoline-1,3-dione (0.30 g, 1.38 mmol) in EtOH (8 mL) was added NH$_2$NH$_2$·H$_2$O (0.067. 1.38 mmol) and the mixture was heated at 100° C. for 16 h. The reaction monitored by TLC and LC-MS. After completion, the mixture was diluted with water (200 mL) and extracted with 10% MeOH/DCM (300 mL×3). The combined organic layers were washed with water (100 mL), brine (1.50 mL) dried over anhydrous Na$_2$SO$_4$, filtered and concentrated under reduced pressure to afford the title compound. LC-MS 520[M+H]$^+$

Step-7: Preparation of 4-(3-(4-cyano-3-(trifluoromethyl)phenyl)-4-hydroxy-5,5-dimethyl-2-thioxoimidazolidin-1 yl)-N-(6-(4-ethyl-6-(2-methyl-6-(1-(tetrahydro-2H-pyran-2 yl)-1H-1,2,4-triazol-3-yl)pyridin-3-yl)-3-oxo-3,4-dihydropyrazino[2,3-b]pyrazin-1(2H)-yl)hexyl)-2-fluorobenzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (0.08 g, 0.177 mmol) in DMA (6 mL) was added HBTU (0.08 g, 0.212 mmol, 1.2 eq) at 0° C. and the resulting mixture was stirred for 10 min. DIPEA (0.067 mL, 0.389 mmol, 2.2 eq) and 2-(6-(4-ethyl-6-(2-methyl-6-(1-(tetrahydro-2H-pyran-2-yl)-1H-1,2,4-triazol-3-yl)pyridin-3-yl)-3-oxo-3,4-dihydropyrazino[2,3-b]pyrazin-1(2H)-yl)hexyl)isoindoline-1,3-dione (0.110 g, 0.212 mmol, 1.2 eq) were then successively added to the mixture and the mixture was stirred at RT for 2 h. The reaction was monitored by TLC & LC-MS. After completion, water (10 mL) was added and the resulting precipitate was filtered over Buchner funnel. The product obtained was washed with water (5 mL×2) and n-pentane (5 mL×2), dried under vacuum to obtain a crude residue which was purified CombiFlash chromatography to afford the title compound. LC-MS 955 [M+H]$^+$

Step-8: Preparation of 4-(3-(4-cyano-3-(trifluoromethyl)phenyl)-5,5-dimethyl-4-oxo-2-thioxoimidazolidin-1 yl)-N-(6-(4-ethyl-6-(2-methyl-6-(1H-1,2,4-triazol-3-yl)pyridin-3-yl)-3-oxo-3,4-dihydropyrazino[2,3-b]pyrazin-1(2H)-yl)hexyl)-2-fluorobenzamide To 4-(3-(4-cyano-3-(trifluoromethyl)phenyl)-5,5-dimethyl-4-oxo-2-thioxoimidazolidin-1-yl)-N-(6-(4-ethyl-6-(2-methyl-6-(1-(tetrahydro-2H-pyran-2-yl)-1H-1,2,4-triazol-3-yl)pyridin-3-yl)-3-oxo-3,4-dihydropyrazino[2,3-b]pyrazin-1(2H)-yl)hexyl)-2-fluorobenzamide (0.18 g, 0.188 mmol) was added 2M-HCl in MeOH (7 mL) and resulting reaction mixture was stirred at RT for 16 h. The reaction was monitored by TLC & LC-MS. After completion, the mixture was quenched by NaHCO$_3$ solution (30 mL) and extracted with 10% MeOH/DCM (200 mL×2). The combined organic layers were washed with water (100 mL), brine (150 mL) dried over anhydrous Na$_2$SO$_4$, filtered and concentrated under reduced pressure to afford a crude residue which was purified by reversed phase HPLC to afford the title compound. LC-MS 871 [M+H]$^+$. $^1$HNMR (400 MHz, MeOD-d$_4$) δ 8.31 (s, 1H), 8.19-8.09 (m, 2H), 8.04-7.95 (m, 3H), 7.93 (s, 1H), 7.83 (t, J=8.1 Hz, 1H), 7.39-7.29 (m, 2H), 4.31 (s, 2H), 4.19 (q, J=7.0 Hz, 2H), 3.63 (t, J=7.5 Hz, 2H), 3.43 (t, J=6.9 Hz, 2H), 2.76 (s, 3H), 1.93 (d, J=7.4 Hz, 1H), 1.79-1.60 (m, 3H), 1.57 (s, 6H), 1.50 (qd, J=13.4, 10.6, 5.3 Hz, 4H), 1.27 (q, J=7.0, 5.6 Hz, 3H).

Example S-35. Preparation of 4-(3-(4-cyano-3-(trifluoromethyl)phenyl)-5,5-dimethyl-4-oxo-2-thioxoimidazolidin-1-yl)-2-fluoro-N-(5-(7-(2-methyl-6-(1H-1,2,4-triazol-3-yl)pyridin-3-yl)-2-oxo-3,4-dihydropyrazino[2,3-b]pyrazin-1(2H)-yl)pentyl)benzamide (Compound 3.3)
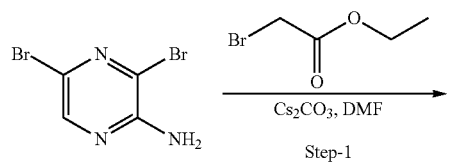
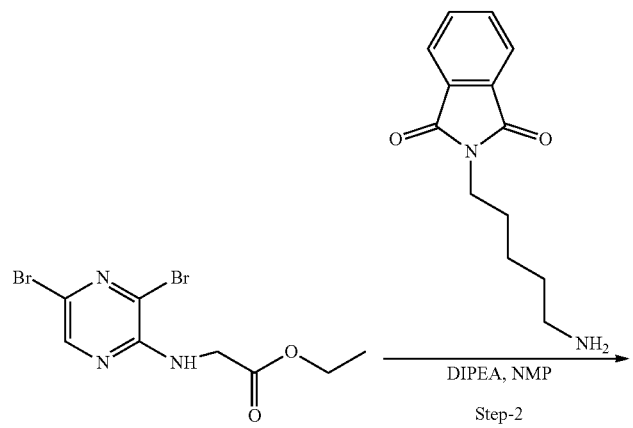
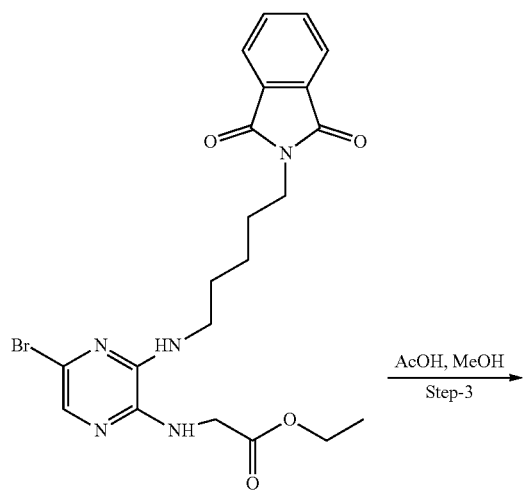

499
500
-continued
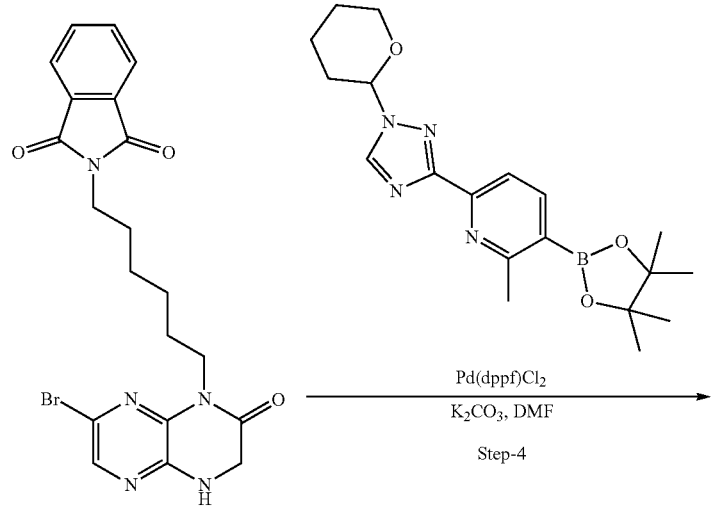
Pd(dppf)Cl₂
K₂CO₃, DMF
Step-4
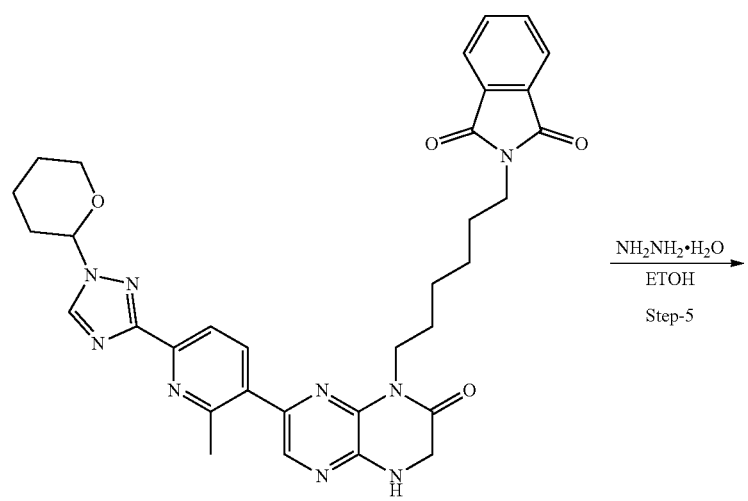
NH₂NH₂•H₂O
ETOH
Step-5
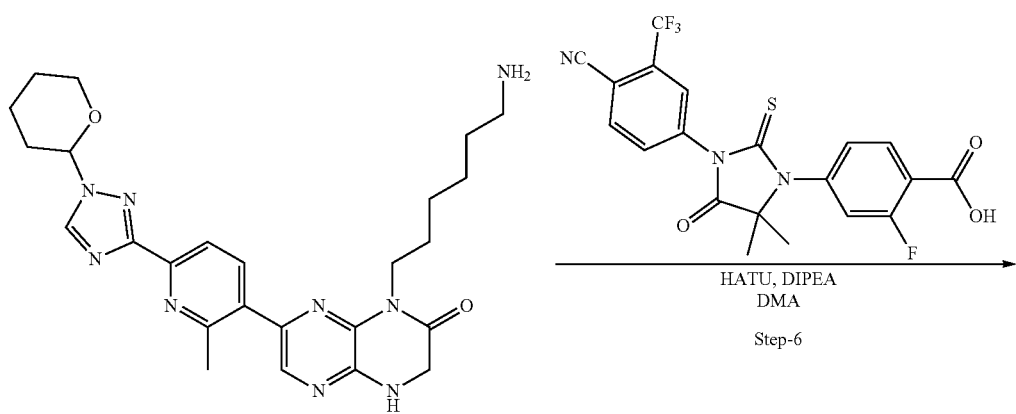
HATU, DIPEA
DMA
Step-6

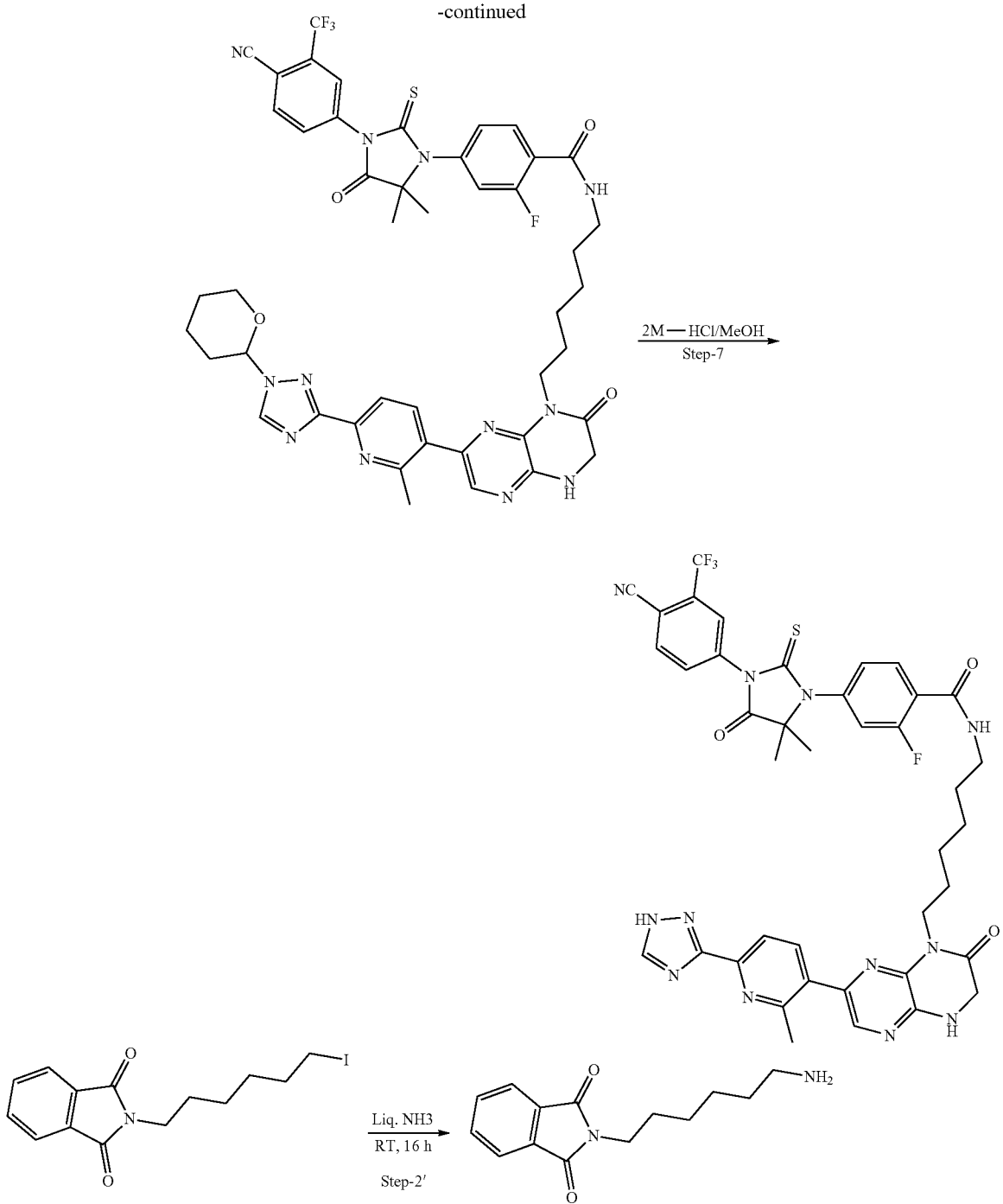

Step-1: Preparation of ethyl 2-(3,5-dibromopyrazin-2 ylamino)acetate

To a stirred solution of 3,5-dibromopyrazin-2-amine (20.0 g, 79.6 mmol) in DMF (100 mL) was added Cs₂CO₃ (36.2 g, 102.8 mmol) at 0° C. and the mixture was stirred for 15 min. Ethyl 2-bromoacetate (10.4 g, 94.8 mmol) was then added to the mixture and the mixture was heated at 80° C. for 3 h. The reaction was monitored by TLC. Upon completion, the mixture was diluted with water (200 mL) to obtain a precipitate which was filtered over Buchner funnel and dried under vacuum to afford the title compound. LC-MS 338 [M+H]⁺

Step-2': Preparation of 2-(6-aminohexyl)isoindoline-1,3-dione

To compound 2-(6-iodohexyl)isoindoline-1,3-dione (6.2 g, 17.35 mmol) was added liquor NH₃ (35 mL) and the mixture was heated at 80° C. for 3 h. The reaction was monitored by TLC and LC-MS. After completion, the mixture was concentrated under reduced pressure and washed with DCM/Hexane (30 mL/100 mL) and dried under vacuum to afford the title compound. LC-MS 247 [M+H]⁺

Step-2: Preparation of ethyl 2-(5-bromo-3-(5-(1,3-dioxoisoindolin-2-yl)pentylamino) pyrazin-2-ylamino)acetate To a stirred solution of 2-(5-aminopentyl)isoindoline-1,3-dione (3.2 g, 9.44 mmol) in NMP (15 mL) was added DIPEA (8.2 mL, 47.20 mmol, 5 eq) and 2-(6-aminohexyl)isoindoline-1,3-dione (4.6 g, 18.88 mmol, 2.0 eq) and the mixture was heated at 120° C. in sealed tube for 16 h. The reaction was monitored by TLC and LC-MS. After completion, the mixture was diluted with saturated NaHCO$_3$ solution (50 mL) and extracted with EtOAc (100 mL×2). The combined organic layers were washed with brine (50 mL), dried over anhydrous Na$_2$SO$_4$, filtered and concentrated under reduced pressure to obtain a crude which was purified by column chromatography to afford the title compound. LC-MS 490 [M+H]$^+$

Step-3: Preparation of 2-(6-(7-bromo-2-oxo-3,4-dihydropyrazino[2,3-b]pyrazin-1(2H) yl) hexyl) isoindoline-1,3-dione To a stirred solution of ethyl 2-(5-bromo-3-(5-(1,3-dioxoisoindolin-2-yl)pentylamino) pyrazin-2-ylamino)acetate (2.0 g, 3.97 mmol) in methanol (5 mL) was added AcOH (15 mL) and the mixture was heated at 120° C. in sealed tube for 16 h. The reaction was monitored by TLC and LC-MS. After completion, the mixture was diluted with saturated NaHCO$_3$ solution (50 mL) and extracted with EtOAc (100 mL×2). The combined organic layers were washed with brine (50 mL), dried over anhydrous Na$_2$SO$_4$, filtered and concentrated under reduced pressure to obtain a crude which was purified by column chromatography to afford the title compound. LC-MS 458 [M+H]$^+$

Step-4: Preparation of 2-(6-(7-(2-methyl-6-(1-(tetrahydro-2H-pyran-2 yl)-1H-1,2,4-triazol-3-yl)pyridin-3-yl)-2-oxo-3,4-dihydropyrazino[2,3-b]pyrazin-1 (2H) yl)hexyl)isoindoline-1,3-dione To a stirred solution of 2-(6-(7-bromo-2-oxo-3,4-dihydropyrazino[2,3-b]pyrazin-1(2H)-yl) hexyl)isoindoline-1,3-dione (0.20 g, 0.43 mmol) in DMF (6 mL) was added 2-methyl-6-(1-(tetrahydro-2H-pyran-2-yl)-1H-1,2,4-triazol-3-yl)-3-(4,4,5,5-tetramethyl-1,3,2-dioxaborolan-2-yl)pyridine (0.32 mg, 0.872 mmol, 2.0 eq) and K$_2$CO$_3$ (0.12 mg, 0.872 mmol, 2 eq) dissolved in water (3 mL) and the mixture was degassed under nitrogen for 15 min. Pd(dppf)Cl$_2$ (0.032 mg, 0.043 mmol, 0.1 eq) was then added to the mixture and the resultant mixture was heated at 70° C. for 16 h. The reaction monitored by TLC. After completion, the mixture was diluted with water (200 mL) and extracted with DCM (200 mL×3). The combined organic layers were washed with water (100 mL), brine (150 mL) dried over anhydrous Na$_2$SO$_4$, filtered and concentrated under reduced pressure to afford a crude which was purified by CombiFlash chromatography to afford the title compound. LC-MS 622 [M+H]$^+$

Step-5: Preparation of 5-(5-amino-2-(p-tolyloxy)phenyl)-1-methyl-3-(methylamino)pyridin-2(1H)-one To a stirred solution of 2-(6-(7-(2-methyl-6-(1-(tetrahydro-2H-pyran-2-yl)-1H-1,2,4-triazol-3-yl)pyridin-3-yl)-2-oxo-3,4-dihydropyrazino[2,3-b]pyrazin-1(2H)-yl)hexyl)isoindoline-1,3-dione (0.21 g, 0.427 mmol) in EtOH (5 mL) was added NH$_2$NH$_2$·H$_2$O (0.80 mL) at RT and the mixture was heated at 100° C. for 16 h. The reaction was monitored by TLC and LC-MS. After completion, the mixture was diluted with water (200 mL) and extracted with 10% MeOH/DCM (200 mL×2). The combined organic layers were washed with water (100 mL), brine (150 mL) dried over anhydrous Na$_2$SO$_4$, filtered and concentrated under reduced pressure to afford the title compound. LC-MS 492 [M+H]$^+$

Step-6: Preparation of 4-(3-(4-cyano-3-(trifluoromethyl)phenyl)-5,5-dimethyl-4-oxo-2-thioxoimidazolidin-1-yl)-2-fluoro-N-(5-(7-(2-methyl-6-(1-(tetrahydro-2H-pyran-2-yl)-1H-1,2,4-triazol-3-yl)pyridin-3-yl)-2-oxo-3,4-dihydropyrazino[2,3-b]pyrazin-1(2H) yl)pentyl)benzamide To a stirred solution of 4-(3-(4-cyano-3-(trifluoromethyl)phenyl)-5,5-dimethyl-4-oxo-2-thioxoimidazolidin-1-yl)-2-fluorobenzoic acid (0.12 g, 0.265 mmol) in DMA (7 mL) was added HBTU (0.129 g, 0.319 mmol, 1.2 eq) at 0° C. and the mixture was stirred AT 0° C. for 10 min. DIPEA (0.94 mL, 0.524 mmol, 2.2 eq) and 5-(5-amino-2-(p-tolyloxy)phenyl)-1-methyl-3-(methylamino)pyridin-2(1H)-one (0.156 g, 0.319 mmol, 1.2 eq) were then successively added to the mixture and the mixture was stirred at RT for 2 h. The reaction was monitored by TLC & LC-MS. After completion, water (10 mL) was added and the resulting precipitate was filtered over Buchner funnel. The product obtained was washed with water (5 mL×2) and n-pentane (5 mL×2), dried under vacuum to obtain a crude product which was purified CombiFlash chromatography to afford the title compound. LC-MS 925 [M+H]$^+$

Step-7: Preparation of 4-(3-(4-cyano-3-(trifluoromethyl)phenyl)-5,5-dimethyl-4-oxo-2-thioxoimidazolidin-1 yl)-2-fluoro-N-(6-(7-(2-methyl-6-(1H-1,2,4-triazol-3-yl)pyridin-3-yl)-2-oxo-3,4-dihydropyrazino[2,3-b]pyrazin-1(2H)-yl)hexyl)benzamide The 4-(3-(4-cyano-3-(trifluoromethyl)phenyl)-5,5-dimethyl-4-oxo-2-thioxoimidazolidin-1-yl)-2-fluoro-N-(5-(7-(2-methyl-6-(1-(tetrahydro-2H-pyran-2-yl)-1H-1,2,4-triazol-3-yl)pyridin-3-yl)-2-oxo-3,4-dihydropyrazino[2,3-b]pyrazin-1(2H)-yl)pentyl)benzamide (0.13 g, 0.140 mmol) was added 2M-HCl in MeOH (10 mL) and resulting reaction mixture was stirred at RT for 16 h. The reaction was monitored by TLC & LC-MS. After completion, the reaction mixture was quenched by NaHCO$_3$ solution (25 mL) and extracted with 10% MeOH×DCM (100 mL×2). The combined organic layers were washed with water (100 mL), brine (150 mL) dried over anhydrous Na$_2$SO$_4$, filtered and concentrated under reduced pressure to afford a crude residue which was purified by reversed phase HPLC to afford the title compound. LC-MS 841 [M+H]$^+$. $^1$H NMR (400 MHz, MeOD-d$_4$) δ 8.20-8.13 (m, 2H), 8.01 (dd, J=10.3, 7.6 Hz, 4H), 7.85 (s, 1H), 7.79 (t, J=8.1 Hz, 1H), 7.38-7.28 (m, 2H), 4.29 (s, 2H), 4.15 (t, J=7.6 Hz, 2H), 3.41-3.34 (m, 2H), 2.76 (s, 3H), 1.76 (q, J=7.3 Hz, 2H), 1.67-1.59 (m, 2H), 1.57 (s, 6H), 1.51-1.43 (m, 2H), 1.30 (d, J=8.8 Hz, 2H).

The compounds of Table 1 are prepared according to the experimental details exemplified in the Synthetic Examples using the appropriate starting materials and reagents.

BIOLOGICAL ASSAYS

The following methods are for evaluating the in vitro biology properties of the test articles.

a. RBC HotSpot Poly(ADP-ribose) Polymerases 1 (PARP1) and Poly(ADP-ribose) Polymerases 2 (PARP2) Assays: The assay principle is radioisotope-based filter binding assay where incorporation of radio-isotope-labeled NAD$^+$ into the substrate captured on filter is detected after washout free NAD$^+$. Data were analyzed using Excel and GraphPad Prism software for IC$_{50}$ curve fits. Each assay was conducted with PJ34 as a positive control.
  i. PARP1 assay: Human recombinant PARP1 at a final concentration of 2.5 nM was combined with histone H4 (20 µM) and test articles at various concentrations in reaction buffer (50 mM Tris-HCL, pH 8.0, 50 mM NaCl, 10 mM MgCl$_2$, 1 mM DTT, 1% DMSO, and 20 µg/mL activated DNA). The solution was inoculated for 20 min at room temperature and the reaction initiated by adding [adenylate-$^{32}$P]-Nicotinamide Adenine Dinucleotide, $^{32}$P-NAD$^+$ at a final concentration of 10 µM. After incubation for 2 hour at room temperature, the reaction mixture was filtered and washed with 0.75% phosphoric acid for radioactivity detection.
  ii. PARP2 assay: Human recombinant PARP2 at a final concentration of 2.5 nM was combined with histone H3 (20 µM) and test articles at various concentrations in reaction buffer (50 mM Tris-HCL, pH 8.0, 50 mM NaCl, 10 mM MgCl$_2$, 1 mM DTT, 1% DMSO, and 20 µg/mL activated DNA). The solution was inoculated for 20 min at room temperature and the reaction was initiated by adding [adenylate-$^{32}$P]-Nicotinamide Adenine Dinucleotide, $^{32}$P-NAD$^+$ at a final concentration of 10 µM. After incubation for 2 hour at room temperature, the reaction mixture was filtered and washed with 0.75% phosphoric acid for radioactivity detection.
b. AR binding assay: AR in LNCaP cytosol was used for determining the binding affinity of test articles and the reference compound—progesterone (Sigma, Cat: E2785, St. Louis, MO). IC$_{50}$s were determined using 8 concentrations/compound. Cytosol was plated at 200 µg/well (100 µL) into a 96-well conical polypropylene plate (Agilent, Cat: 5042-1385, Santa Clara, CA) and mixed with 3 µL of test compound. After adding 100 µL of $^3$H-methyltrienolone (PerkinElmer, Cat: NET590250UC, San Jose, CA), the plate was sealed and shaken at 300 rpm at 4° C. for 24 hours. Post incubation, 100 µL of radioligand adsorption buffer containing 10 mM Tris-HCl, pH 7.4; 1.5 mM EDTA; 1 mM DTT; 0.25% charcoal; 0.0025% dextran was added to individual well. Plate was shaken for 15 min at 4'C followed by centrifugation at 3000 rpm for 30 min at 4° C. 150 µL of supernatant was transferred into scint-tube (PerkinElmer, Cat: 6000192) and mixed with 2 mL of Ultima Gold Cocktail (PerkinElmer, Cat: 6013329). Radioactivity was counted using a TriCarb 2910 TR scintillation counter (PerkinElmer). Inhibition of the radioactivity by test articles were calculated using the equation below:

% Inhibition=(1−(Assay well−Average_$LC$)/(Average_$HC$−Average_$LC$))×100%.

IC$_{50}$ values were calculated and graphed using the model "log(inhibitor) vs. response—Variable slope" included in GraphPad Prism 5 (San Diego, CA). The Ki values were further calculated using the equation below where [L] was the radioligand concentration (1 nM) using in this study. Kd value was 0.332 nM. Results are listed in Table 3.

Ki=IC$_{50}$/(1+[L]/Kd)

c. AR transactivation: Human AR cloned into a CMV vector backbone was used for the transactivation study. HEK-293 cells were plated at 80,000 cells per well of a 24 well plate in DME+5% csFBS. Twenty four hours later, the cells were transfected using Lipofectamine (Invitrogen, Carlsbad, CA) with 0.25 µg GRE-LUC, 0.01 µg CMV-LUC (renilla luciferase) and 25 ng of the AR in OPTIMEM medium. The cells were treated 24 hrs after transfection with various ligands ($10^{-12}$ to $10^{-5}$ M final concentrations) and luciferase assay were performed 48 hours after transfection. Firefly values were normalized to renilla luciferase values and the values were represented as relative light units (RLU). Agonist and antagonist assays for the test article were performed in the absence and in the combination with 0.1 nM R1881, respectively. Data were represented as EC$_{50}$ (for agonists) and IC$_{50}$ (for antagonists) obtained from four parameter logistics curve. Each experiment was performed with R1881 as an agonist Results for AR antagonism are shown in Table 2.

d. Cell culture and proliferation assays: LNCaP, PC-3, 22RV1, MCF-7, HT-29, and HCT-116 cells were procured from American Type Culture Collection (ATCC). Cells were cultured in medium recommended by the ATCC. Cell culture medium was obtained from Fisher scientific (Waltham, MA) and serum was obtained from Hyclone (San Angelo, TX).

Cells were plated at varying density in the respective growth medium in 96 well plates. 24 hr later, cells were treated, in triplicate or quadruplicate, with test articles prepared in a range of concentrations by series dilution of DMSO stock solutions in growth medium and incubated for three to seven days. The number of viable 22RV1 and HT-29 cells was measured using CellTiter Glo assay (CTG, Promega, Madison, WI) after three days of treatment. The other types of cancer cells were re-treated at three or four days and the number of viable cells was measured using CTG assay after a total treatment time of six or seven days. Cell viability data were plotted using GraphPad Prism (GraphPad Software, Inc., San Diego, CA). In addition, a nonlinear regression model with a sigmoidal dose response and variable slope within GraphPad Prism was used to calculate the IC$_{50}$ value of individual test articles. Results of the assays are shown in Table 4.

e. Additional cell proliferation assays: Other cancer cell lines are tested in a cell proliferation assay. For example, SK-OV-3 or OVCAR3 ovarian cancer cells are tested. Cells are cultured in medium recommended by the supplier (e.g., ATCC or JCRB Cell Bank), at 37° C. in a 5% CO$_2$ environment. For the proliferation assay, cells are plated in the growth medium in 96 well plates. Seeding density is adjusted according to the cell type. 24 hr later, cells are treated, in triplicate or quadruplicate, with test articles prepared in a range of concentrations by series dilution of DMSO stock solutions in growth medium, and typically incubated for three to seven days, with test article-containing medium replaced after three or four days. The number of viable cells is measured using CellTiter Glo assay (CTG, Promega, Madison, WI) or similar. Cell viability data are plotted using GraphPad Prism (GraphPad Software, Inc., San Diego, CA). In addition, a nonlinear regression model with a sigmoidal dose response and variable slope within GraphPad Prism is used to calculate the IC$_{50}$ value of individual test articles. Similarly, HEK-293 and HeLa calls can also be tested by methods known in the art.

f. Nuclear translocation: LNCaP cells are plated on coverslips in 24 well plates in growth medium. Twenty-four hours after plating, medium is changed to RPMI+1% csFBS and the cells are maintained in this medium for two days. Medium is replaced again and the cells are treated. Cells are fixed 4 hours after treatment and the AR immunostained using AR N20 antibody (Santa Cruz Biotechnology, Santa Cruz, CA). Nucleus is stained with DAPI. Cells are imaged with a confocal microscope.

g. ER binding assay: ERα binding was assessed by the LanthaScreen® TR-FRET ER Alpha Competitive Binding Assay at Thermo Fisher. In this assay, a terbium-labeled anti-GST antibody was used to indirectly label GST-tagged ER Alpha-ligand binding domain (LBD) by binding to its GST tag. Competitive binding to the ER Alpha-LBD (GST) was detected by a test compound's ability to displace a fluorescent ligand (Fluormone™ ES2 Green tracer) from the ER Alpha-LBD (GST), which results in a loss of FRET signal between the Tb-anti-GST antibody and the tracer. When running the assay, Fluormone™ ES2 Green tracer was added to ligand test compounds or solvent controls followed by addition of a mixture of the ER Alpha-LBD (GST) and terbium anti-GST antibody. After an incubation period at room temperature, the TR-FRET ratio of 520:495 emissions were calculated and was used to determine the $IC_{50}$ from a dose response curve of the compound. Results of the assay are shown in Table 3.

h. ER and PR functional assays: COS cells are transfected with 25 ng rat progesterone receptor (PR) and 250 ng GRE-LUC or 50 ng human estrogen receptor a (ER) and 250 ng ERE-LUC. Cells are also transfected with 10 ng CMV-renilla LUC in OptiMEM medium using lipofectamine transfection reagent. Twenty-our hours after transfection medium is changed to DME+5% csFBS w/o and treated with compounds in the presence of 0.1 nM progesterone for PR and estradiol for ER. Twenty four hours after treatment, cells are harvested and luciferase assay is performed using dual luciferase assay kit. The firefly values are normalized to renilla luciferase values and represented as a ratio.

i. Evaluation of test compound in mouse xenograft model: To examine the in vivo antitumor activity of test compound, tumor growth experiments are performed in a cell line xenograft model. Male NOD SCID Gamma (NSG) mice are housed as five animals per cage and are allowed free access to water and commercial rodent chow. 22RV1 cells (grown in RPM1+10% FBS) mixed with 50% matrigel basement membrane are implanted subcutaneously in castrated mice. Alternatively, an antiandrogen resistant cell line other than 22RV1, such as MR49F or VCaP, is used. Once the tumors reach 200-500 mm$^3$, the animals are randomized and treated intraperitoneally with vehicle (DMSO:PEG-300:corn oil 10:30:60 ratio) or test compound. Tumors are measured thrice weekly and the volume is calculated using the formula length*width*width*0.5. Animals are sacrificed at the end of 28 days of treatment and the tumors are weighed and stored for further processing. The tumor growth inhibition (TGI) is calculated by comparing the control group's tumor measurements with the other study groups. TGI is calculated for each group using the formula listed below:

TGI (%)=[1-(TV$_{Treatment\_DayN}$-TV$_{Treatment\_Day0}$)/(TV$_{Vehicle\_DayN}$-TV$_{Vehicle\_Day0}$)]×100%

TV$_{Treatment\_DayN}$ is the average tumor volume of a treatment group on a given day, TV$_{Treatment\_Day0}$ is the average tumor volume of the treatment group on the first day of treatment, TV$_{Vehicle\_DayN}$ is the average tumor volume of the vehicle control group on a given day, and TV$_{Vehicle\_Day0}$ is the average tumor volume of the vehicle group on the first day of treatment.

j. DNA-PK Inhibition Inhibition of DNA-PK activity by test compounds was assessed in a radioisotope-based filter binding assay (Reaction Biology Corporation HotSpot Kinase Assay). Test compounds were dissolved in 100% DMSO to specific concentrations. Serial dilution of the test compounds was conducted by Integra Viaflo Assist in DMSO. The substrate, DNA-PKtide (Anaspec, Fremont, CA; #60210-5), was prepared in Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO) so that its final concentration in the reaction would be 20 µM. DNA-PK activator containing dsDNA was delivered to the solution (10 µg/mL in final reaction). DNA-PK (Invitrogen, Carlsbad, CA; #PR9107A) was delivered to the substrate solution (5 nM in final reaction) and the solution gently mixed. Compounds in 100% DMSO were delivered into the kinase reaction mixture by Acoustic technology (Echo550; nanoliter range), and the reaction incubated for 20 min at room temperature. $^{33}$P-ATP (Specific activity 10 µCi/µL) was delivered into the reaction mixture to initiate the reaction, which was incubated for 2 hours at room temperature. Radioactivity was detected by a filter-binding method. Kinase activity data were expressed as the percent remaining kinase activity in test samples compared to vehicle (dimethyl sulfoxide) reactions. $IC_{50}$ values and curve fits were obtained using GraphPad Prism. Results of the assay are shown in Table 5.

TABLE 2

In vitro results

| Compound No. | PARP1 $IC_{50}$ (µM) | PARP2 $IC_{50}$ (µM) | AR Ant. $IC_{50}$ (µM) |
|---|---|---|---|
| 1.1 | 0.002 | 0.0002 | 0.033 |
| 1.2 | 0.003 | 0.0002 | 0.481 |
| 1.3 | 0.002 | 0.0005 | |
| ent-1.3 | 0.079 | 0.016 | |
| 1.4 | 0.002 | 0.0004 | |
| 1.5 | 0.023 | 0.002 | 0.75 |
| 1.68 | 0.0003 | 0.0002 | 3.3 |
| 1.83 | 0.0007 | 0.0003 | 0.57 |
| 1.96 | 0.006 | 0.0005 | |
| 1.97 | 0.002 | 0.0004 | |
| 1.98 | 0.0002 | 0.0001 | |
| 1.99 | 0.0008 | 0.0002 | |
| 1.104 | 0.0012 | 0.0003 | |
| 1.107 | 0.0003 | 0.0001 | |
| 1.110 | 0.0007 | 0.0002 | |
| 1.111 | 0.0016 | 0.0002 | |
| 1.114 | 0.0279 | 0.0019 | |
| 1.115 | 0.0257 | 0.0015 | |
| 1.116 | 0.0005 | 0.0002 | |
| 1.117 | 0.0003 | 0.0001 | |
| 1.118 | 0.0136 | 0.0010 | |
| 1.119 | 0.0016 | 0.0003 | |
| 2.4 | 0.004 | 0.0003 | |
| 2.13 | 0.0033 | 0.0005 | |
| 2.14 | 0.274 | 0.0124 | |

TABLE 3

In vitro NHR binding

| Compound No. | AR K$_i$ (nM) | ERαK$_i$ (nM) |
|---|---|---|
| 1.2 | 1.31 | |
| 1.5 | 291 | |
| 1.68 | 907 | |
| 1.83 | 139 | |
| 1.97 | 504 | |
| 1.98 | 181 | |
| 1.99 | 197 | |
| 1.104 | 167 | |
| 1.107 | >7469 | |
| 1.110 | 60 | |
| 1.111 | 36 | |
| 1.114 | 19 | |
| 1.115 | 30 | |
| 1.116 | 4969 | |
| 1.117 | 60 | |
| 1.118 | >7469 | |
| 1.119 | 20 | |
| 2.4 | | 5 |
| 2.13 | | 3.3 |
| 2.14 | | 3.5 |
| 3.1 | 21 | |
| 3.2 | 19 | |
| 3.3 | 14 | |

TABLE 4

In-vitro cell growth inhibition

| Compound No. | 22RV1 IC$_{50}$ (µM) | MCF-7 IC$_{50}$ (µM) | HT-29 IC$_{50}$ (µM) | LNCaP IC$_{50}$ (µM) | PC-3 IC$_{50}$ (µM) | HCT-116 IC$_{50}$ (µM) |
|---|---|---|---|---|---|---|
| 1.1 | | | 0.30 | 0.59 | 0.05 | 0.31 |
| 1.2 | 0.40 | >10 | | 0.79 | 0.24 | 0.11 |
| 1.3 | | | | 0.49 | 8.8 | >30 |
| ent-1.3 | | | | >100 | | |
| 1.4 | | | | 0.09 | 0.02 | 0.11 |
| 1.5 | 4.5 | | 5.0 | | | |
| 1.68 | 4.7 | | >10 | | | |
| 1.83 | >30 | | >10 | | | |
| 1.97 | >30 | | >30 | | | |
| 1.98 | 3.5 | | | | | |
| 1.99 | 3.6 | | | | | |
| 1.104 | 1.1 | | 9.3 | | | |
| 1.107 | 1.3 | | | | | |
| 1.110 | 0.84 | | 9.5 | | | |
| 1.111 | 0.89 | | | | | |
| 1.114 | 1.3 | | | | | |
| 1.115 | 3.5 | | | | | |
| 1.116 | 2.6 | | | | | |
| 1.117 | 0.44 | | | | | |
| 1.118 | 9.7 | | | | | |
| 1.119 | 2.9 | | | | | |
| 2.2 | 0.39 | | | | | |
| 2.4 | | 11 | | | | |
| 2.13 | 1.69 | 3.6 | 6.0 | | | |
| 2.14 | | 9.3 | >30 | | | |

TABLE 5

In vitro enzyme inhibition

| Compound No. | DNA-PK IC$_{50}$ (µM) |
|---|---|
| 3.1 | >10 |
| 3.2 | >10 |
| 3.3 | 0.0018 |

The invention claimed is:

1. A compound of Formula III, IV, V or VI, or a stereoisomer, mixture of stereoisomers, isotopically enriched analog or pharmaceutically acceptable salt thereof:

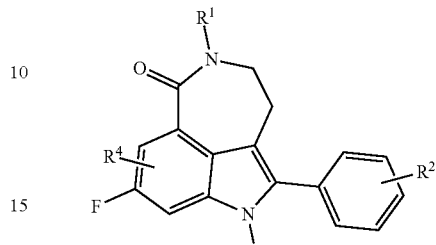

III

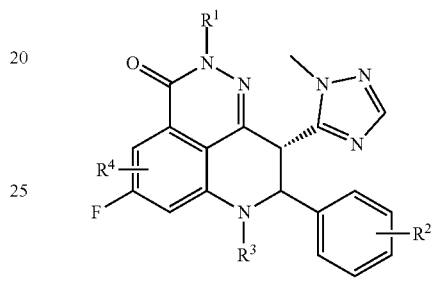

IV

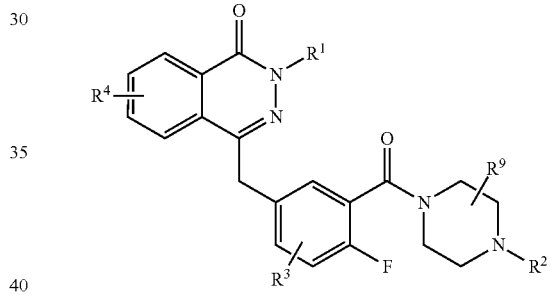

V

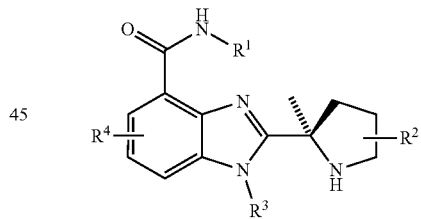

VI wherein:
each R$^1$, R$^2$, R$^3$ and R$^4$ is independently -L-(B)$_m$, hydrogen, C$_{1-12}$ alkyl, C$_{2-12}$ alkenyl, C$_{2-12}$ alkynyl, C$_{3-10}$ cycloalkyl, heterocyclyl, aryl, heteroaryl, —C(=O)R$^5$, —C(=O)OR$^5$, —C(=O)NR$^5$R$^6$, —S(=O)$_{1-2}$R$^5$, —S(=O)$_{1-2}$NR$^5$R$^6$, —NR$^5$S(=O)$_{1-2}$R$^6$ or —C=NOR$^5$, wherein each alkyl, alkenyl, alkynyl, cycloalkyl, heterocyclyl, aryl and heteroaryl of R$^1$, R$^2$, R$^3$ and R$^4$ are independently optionally substituted with one or more R$^{10}$ as valency permits;

m is 1, 2, or 3;

each L is independently a covalent bond or a linking moiety;

wherein the linking moiety is of the formula:

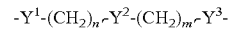

wherein:

each of $Y^1$, $Y^2$, and $Y^3$ are independently a bond, $-NR^{11}-$, $-O-$, $-S(O)_{0-2}-$, $-NR^{11}C(O)-$, $-C(O)NR^{11}-$, $-NR^{11}S(O)_2-$, $-S(O)_2NR^{11}-$, $-CR^{12}=N-NR^{11}-$, $-NR^{11}-N=CR^{12}$, $C(O)-$, $C_{6-20}$ arylene, $C_{3-12}$ heteroarylene, $C_{3-10}$ cycloalkylene or heterocycloalkylene having from 1 to 9 carbon atoms; wherein each arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently hydrogen, $C_{1-4}$ alkyl, $C_{1-4}$ haloalkyl, aryl, heteroaryl, cycloalkyl or heterocyclyl;

each $R^{12}$ is independently hydrogen, $C_{1-4}$ alkyl, $C_{1-4}$ haloalkyl, aryl, heteroaryl, cycloalkyl or heterocyclyl; and n' and m' are each independently 0, 1, 2, 3, 4, 5, 6, 7, or 8;

each B is

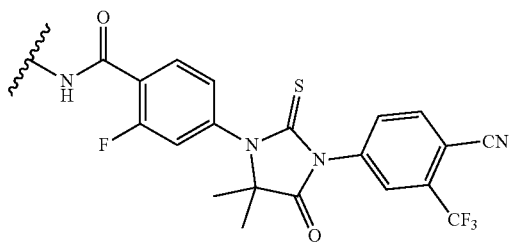

each $R^{10}$ is independently halo, cyano, nitro, $-OR^7$, $-SR^7$, $-SF_5$, $-NR^7R^8$, $C_{1-12}$ alkyl, $C_{2-12}$ alkenyl, $C_{2-12}$ alkynyl, $C_{3-10}$ cycloalkyl, heterocyclyl, aryl, heteroaryl, $-C(=O)R^7$, $-C(=O)OR^7$, $-OC(=O)OR^7$, $-OC(=O)R^7$, $-C(=O)NR^7R^8$, $-OC(=O)NR^7R^8$, $-NR^7C(=O)NR^7R^8$, $-S(=O)_{1-2}R^7$, $-S(=O)_{1-2}NR^7R^8$, $-NR^7S(=O)_{1-2}R^8$, $-NR^7S(=O)_{1-2}NR^7R^8$, $-NR^7C(=O)R^8$, $-NR^7C(=O)OR^8$ or $-C=NOR^7$, wherein each alkyl, alkenyl, alkynyl, cycloalkyl, heterocyclyl, aryl and heteroaryl of $R^{10}$ are independently optionally substituted with one or more halo or $C_{1-12}$ alkyl optionally substituted by oxo, halo, hydroxyl or amino as valency permits; and each $R^5$ and $R^6$ is independently hydrogen, deuterium, $C_{1-12}$ alkyl or $C_{3-12}$ cycloalkyl, optionally substituted with oxo, halo, hydroxyl or amino as valency permits; or $R^5$ and $R^6$ are taken together with the atoms to which they are attached to form heterocyclyl optionally substituted by halo or $C_{1-12}$ alkyl optionally substituted by oxo, halo, hydroxyl or amino;

each $R^7$ and $R^8$ is independently hydrogen, deuterium or $C_{1-12}$ alkyl optionally substituted with oxo, halo, hydroxyl or amino as valency permits; or $R^7$ and $R^8$ are taken together with the atoms to which they are attached to form heterocyclyl optionally substituted by halo or $C_{1-12}$ alkyl optionally substituted by oxo, halo, hydroxyl or amino; and $R^9$ is hydrogen or $R^2$;

provided that at least one $R^1$, $R^2$, $R^3$ and $R^4$ is $-L-(B)_m$.

2. A compound of Formula IIIB, IVA, VB or VIA, or a stereoisomer, mixture of stereoisomers, isotopically enriched analog or pharmaceutically acceptable salt thereof:

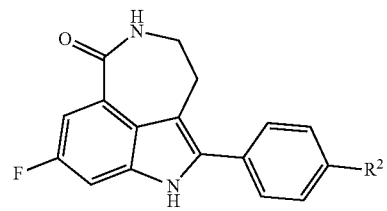
IIIB

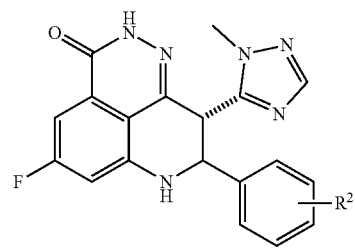
IVA

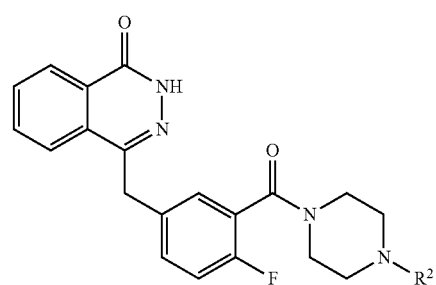
VB

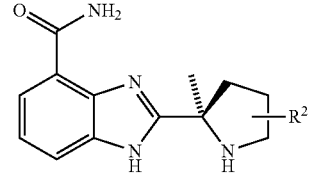
VIA wherein:

$R^2$ is $-L-(B)_m$;

m is 1, 2, or 3;

L is a covalent bond or a linking moiety;

wherein the linking moiety is of the formula:

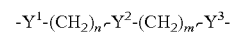

wherein:

each of $Y^1$, $Y^2$, and $Y^3$ are independently a bond, $-NR^{11}-$, $-O-$, $-S(O)_{0-2}-$, $-NR^{11}C(O)-$, $-C(O)NR^{11}-$, $-NR^{11}S(O)_2-$, $-S(O)_2NR^{11}-$, $-CR^{12}=N-NR^{11}-$, $-NR^{11}-N=CR^{12}$, $-C(O)-$, $C_{6-20}$ arylene, $C_{3-12}$ heteroarylene, $C_{3-10}$ cycloalkylene or heterocycloalkylene having from 1 to 9 carbon atoms; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{11}$ is independently hydrogen, $C_{1-4}$ alkyl, $C_{1-4}$ haloalkyl, aryl, heteroaryl, cycloalkyl or heterocyclyl;

each $R^{12}$ is independently hydrogen, $C_{1-4}$ alkyl, $C_{1-4}$ haloalkyl, aryl, heteroaryl, cycloalkyl or heterocyclyl; and n' and m' are each independently 0, 1, 2, 3, 4, 5, 6, 7, or 8; and each B is

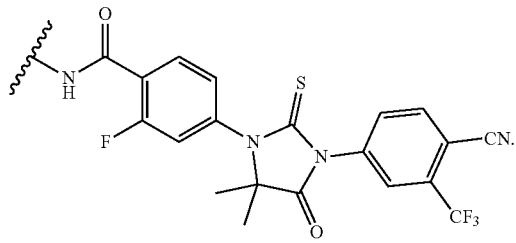

3. The compound of claim 1, or a stereoisomer, mixture of stereoisomers, isotopically enriched analog, or pharmaceutically acceptable salt thereof, wherein at least one linking moiety comprises a hydrazone linkage.

4. A method of treating an androgen receptor overexpressing cancer, comprising administering an effective amount of a compound of claim 1, or a stereoisomer, mixture of stereoisomers, isotopically enriched analog, or pharmaceutically acceptable salt thereof to an individual in need thereof.

5. The method of claim 4, wherein the cancer is prostate, breast, triple negative breast cancer, bladder, or liver cancer.

6. The compound of claim 2, or a stereoisomer, mixture of stereoisomers, isotopically enriched analog, or pharmaceutically acceptable salt thereof, wherein the compound is a compound of Formula IIIB.

7. The compound of claim 2, or a stereoisomer, mixture of stereoisomers, isotopically enriched analog, or pharmaceutically acceptable salt thereof, wherein the compound is a compound of Formula IVA.

8. The compound of claim 2, or a stereoisomer, mixture of stereoisomers, isotopically enriched analog, or pharmaceutically acceptable salt thereof, wherein the compound is a compound of Formula VB.

9. The compound of claim 2, or a stereoisomer, mixture of stereoisomers, isotopically enriched analog, or pharmaceutically acceptable salt thereof, wherein the compound is a compound of Formula VIA.

10. A compound selected from the group consisting of:

| No. | Structure |
| --- | --- |
| 1.1 | 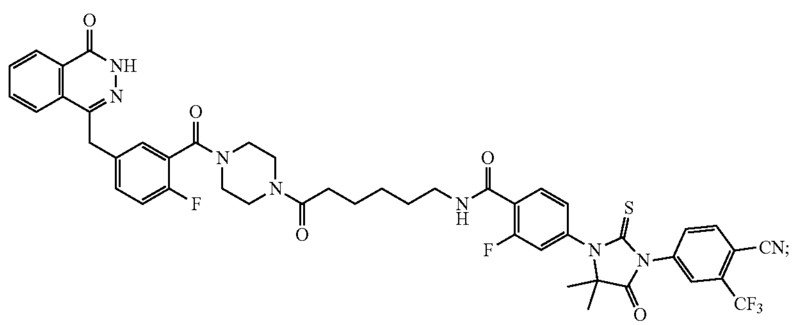 [SMILES: CC1(C)C(=O)N(c2ccc(C#N)c(C(F)(F)F)c2)C(=S)N1c1ccc(C(=O)NCCCCCC(=O)N2CCN(C(=O)c3cc(Cc4n[nH]c(=O)c5ccccc45)ccc3F)CC2)c(F)c1] |
| 1.3 | 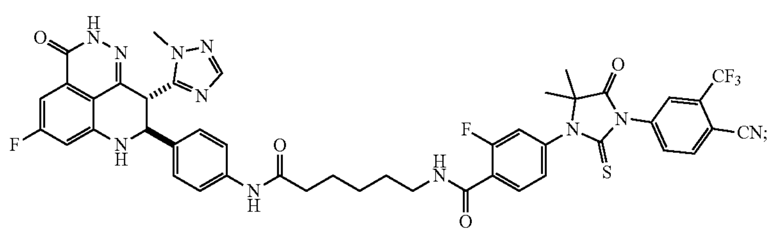 [SMILES: Cn1ncnc1[C@H]1c2n[nH]c(=O)c3cc(F)cc(c23)N[C@@H]1c1ccc(NC(=O)CCCCCNC(=O)c2ccc(N3C(=S)N(c4ccc(C#N)c(C(F)(F)F)c4)C(=O)C3(C)C)cc2F)cc1] |
| ent. 1.3 | 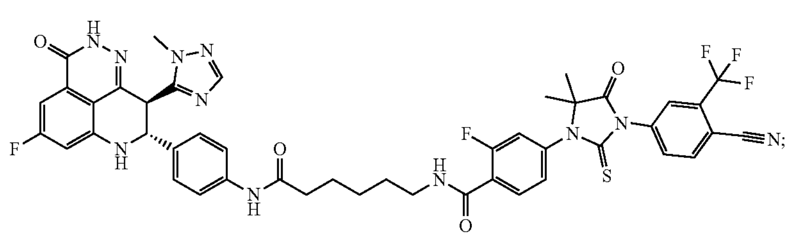 [SMILES: Cn1ncnc1[C@@H]1c2n[nH]c(=O)c3cc(F)cc(c23)N[C@H]1c1ccc(NC(=O)CCCCCNC(=O)c2ccc(N3C(=S)N(c4ccc(C#N)c(C(F)(F)F)c4)C(=O)C3(C)C)cc2F)cc1] |

-continued

| No. | Structure |
|---|---|
| 1.5 | 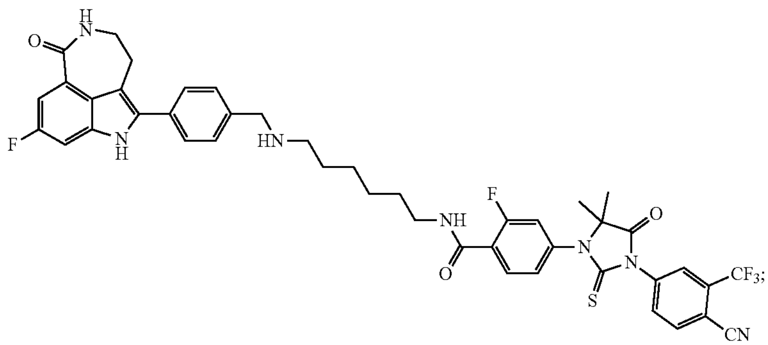 [SMILES: CC1(C)C(=O)N(c2ccc(C#N)c(C(F)(F)F)c2)C(=S)N1c1ccc(C(=O)NCCCCCCNCc2ccc(-c3[nH]c4cc(F)cc5c4c3CCNC5=O)cc2)c(F)c1] |
| 1.15 | 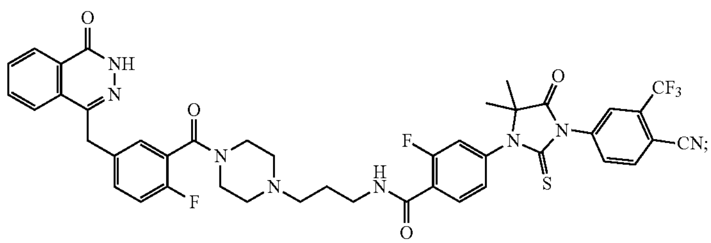 [SMILES: CC1(C)C(=O)N(c2ccc(C#N)c(C(F)(F)F)c2)C(=S)N1c1ccc(C(=O)NCCCN2CCN(C(=O)c3cc(Cc4n[nH]c(=O)c5ccccc45)ccc3F)CC2)c(F)c1] |
| 1.16 | 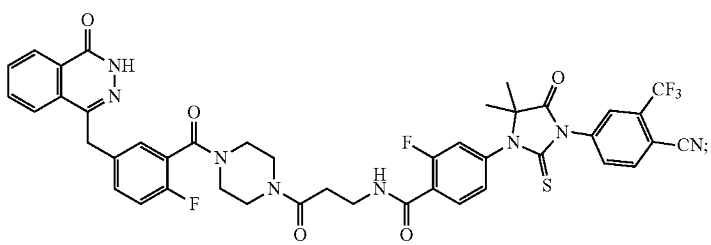 [SMILES: CC1(C)C(=O)N(c2ccc(C#N)c(C(F)(F)F)c2)C(=S)N1c1ccc(C(=O)NCCC(=O)N2CCN(C(=O)c3cc(Cc4n[nH]c(=O)c5ccccc45)ccc3F)CC2)c(F)c1] |
| 1.17 | 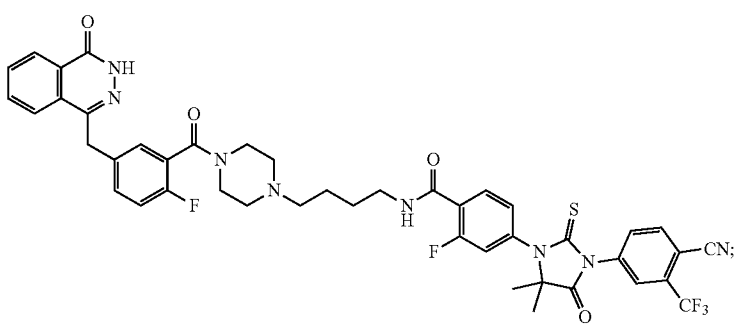 [SMILES: CC1(C)C(=O)N(c2ccc(C#N)c(C(F)(F)F)c2)C(=S)N1c1ccc(C(=O)NCCCCN2CCN(C(=O)c3cc(Cc4n[nH]c(=O)c5ccccc45)ccc3F)CC2)c(F)c1] |
| 1.18 | 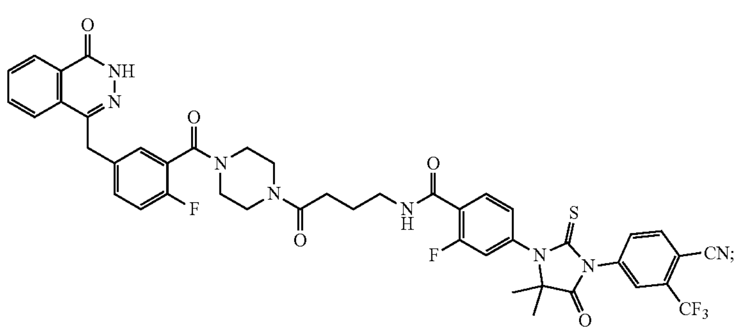 [SMILES: CC1(C)C(=O)N(c2ccc(C#N)c(C(F)(F)F)c2)C(=S)N1c1ccc(C(=O)NCCCC(=O)N2CCN(C(=O)c3cc(Cc4n[nH]c(=O)c5ccccc45)ccc3F)CC2)c(F)c1] |

-continued
| No. | Structure |
|---|---|
| 1.19 | 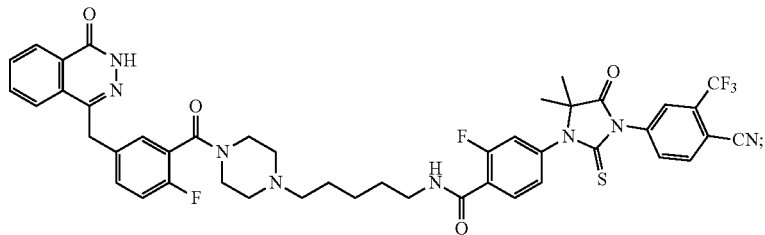 [SMILES: CC1(C)C(=O)N(c2ccc(C#N)c(C(F)(F)F)c2)C(=S)N1c1ccc(C(=O)NCCCCCN2CCN(C(=O)c3cc(Cc4n[nH]c(=O)c5ccccc45)ccc3F)CC2)c(F)c1] |
| 1.20 | 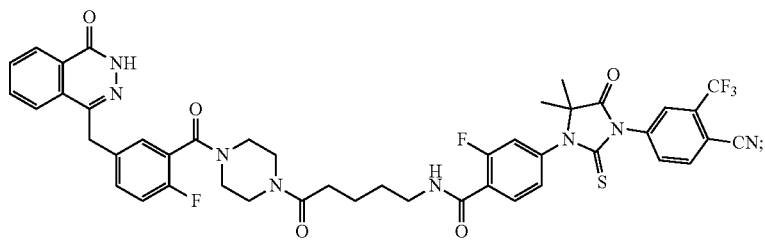 [SMILES: CC1(C)C(=O)N(c2ccc(C#N)c(C(F)(F)F)c2)C(=S)N1c1ccc(C(=O)NCCCCC(=O)N2CCN(C(=O)c3cc(Cc4n[nH]c(=O)c5ccccc45)ccc3F)CC2)c(F)c1] |
| 1.21 | 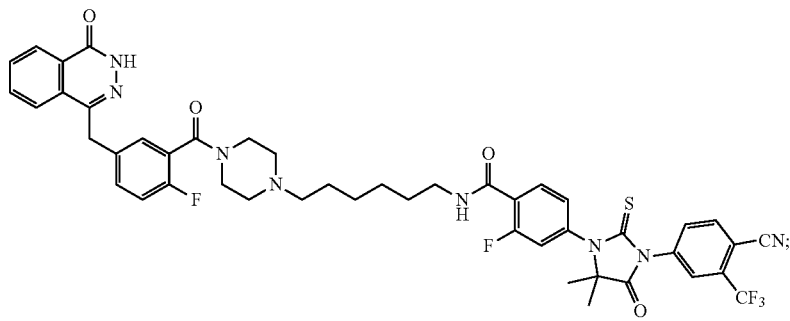 [SMILES: CC1(C)C(=O)N(c2ccc(C#N)c(C(F)(F)F)c2)C(=S)N1c1ccc(C(=O)NCCCCCCN2CCN(C(=O)c3cc(Cc4n[nH]c(=O)c5ccccc45)ccc3F)CC2)c(F)c1] |
| 1.22 | 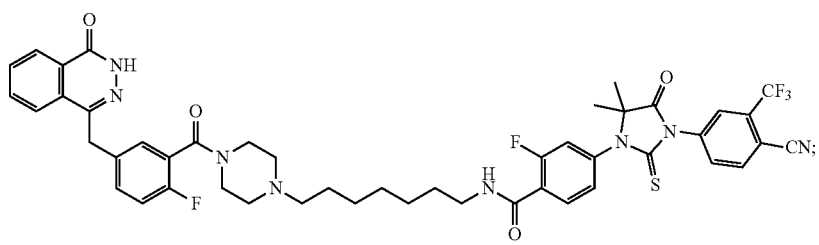 [SMILES: CC1(C)C(=O)N(c2ccc(C#N)c(C(F)(F)F)c2)C(=S)N1c1ccc(C(=O)NCCCCCCCN2CCN(C(=O)c3cc(Cc4n[nH]c(=O)c5ccccc45)ccc3F)CC2)c(F)c1] |
| 1.23 | 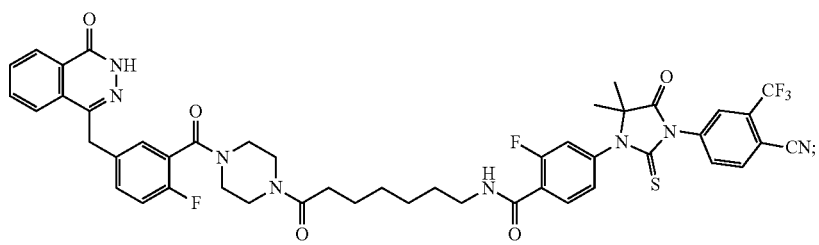 [SMILES: CC1(C)C(=O)N(c2ccc(C#N)c(C(F)(F)F)c2)C(=S)N1c1ccc(C(=O)NCCCCCCC(=O)N2CCN(C(=O)c3cc(Cc4n[nH]c(=O)c5ccccc45)ccc3F)CC2)c(F)c1] |

| No. | Structure |
|---|---|
| 1.34 | 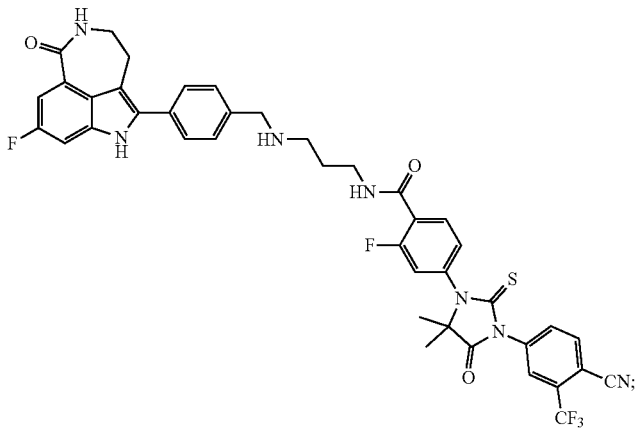 [SMILES: CC1(C)C(=O)N(c2ccc(C#N)c(C(F)(F)F)c2)C(=S)N1c1ccc(C(=O)NCCCNCc2ccc(-c3[nH]c4cc(F)cc5c4c3CCNC5=O)cc2)c(F)c1] |
| 1.35 | 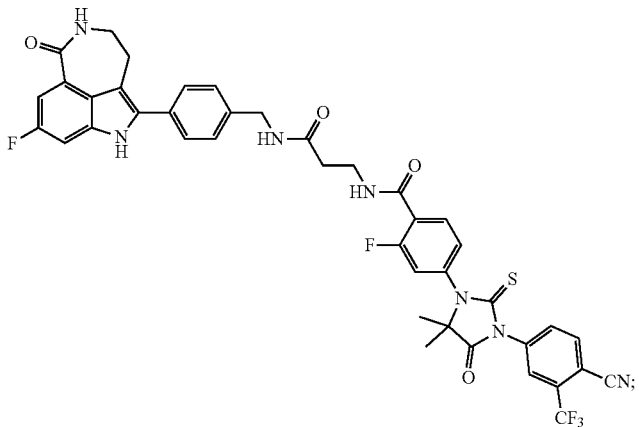 [SMILES: CC1(C)C(=O)N(c2ccc(C#N)c(C(F)(F)F)c2)C(=S)N1c1ccc(C(=O)NCCC(=O)NCc2ccc(-c3[nH]c4cc(F)cc5c4c3CCNC5=O)cc2)c(F)c1] |
| 1.36 | 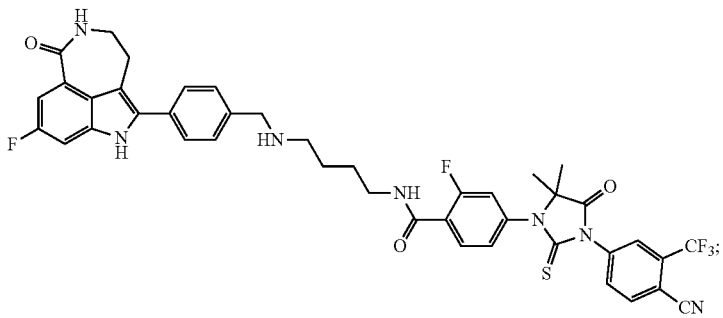 [SMILES: CC1(C)C(=O)N(c2ccc(C#N)c(C(F)(F)F)c2)C(=S)N1c1ccc(C(=O)NCCCCNCc2ccc(-c3[nH]c4cc(F)cc5c4c3CCNC5=O)cc2)c(F)c1] |
| 1.37 | 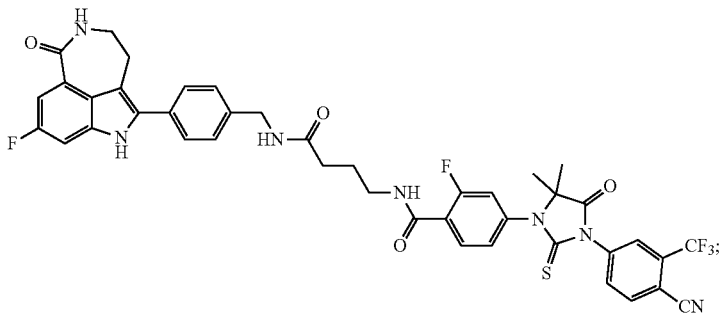 [SMILES: CC1(C)C(=O)N(c2ccc(C#N)c(C(F)(F)F)c2)C(=S)N1c1ccc(C(=O)NCCCC(=O)NCc2ccc(-c3[nH]c4cc(F)cc5c4c3CCNC5=O)cc2)c(F)c1] |

| No. | Structure |
|---|---|
| 1.38 | 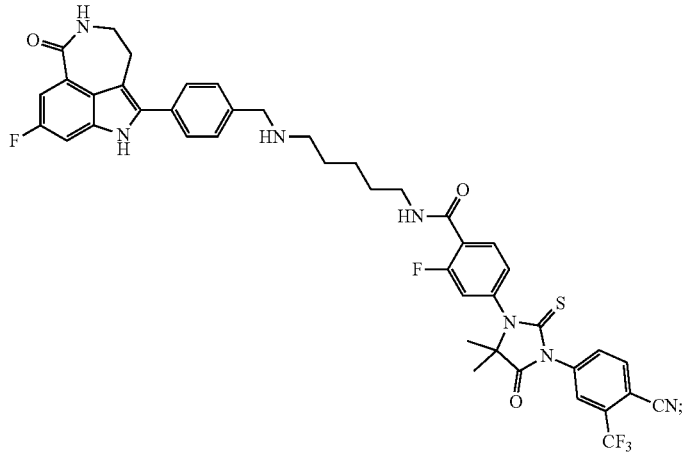 [SMILES: CC1(C)C(=O)N(c2ccc(C#N)c(C(F)(F)F)c2)C(=S)N1c1ccc(C(=O)NCCCCCNCc2ccc(-c3[nH]c4cc(F)cc5c4c3CCNC5=O)cc2)c(F)c1] |
| 1.39 | 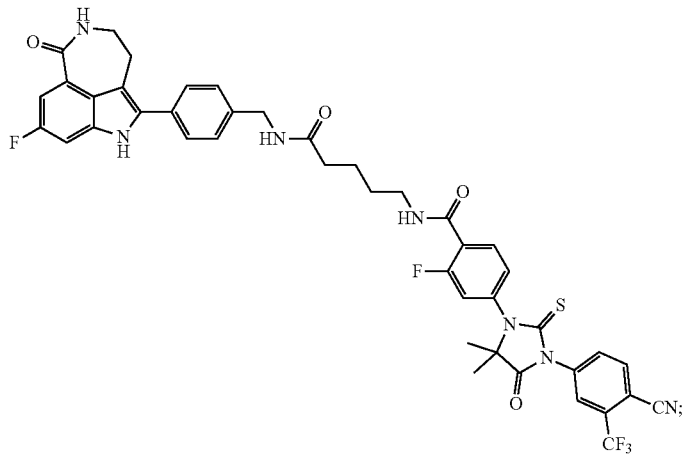 [SMILES: CC1(C)C(=O)N(c2ccc(C#N)c(C(F)(F)F)c2)C(=S)N1c1ccc(C(=O)NCCCCC(=O)NCc2ccc(-c3[nH]c4cc(F)cc5c4c3CCNC5=O)cc2)c(F)c1] |
| 1.40 | 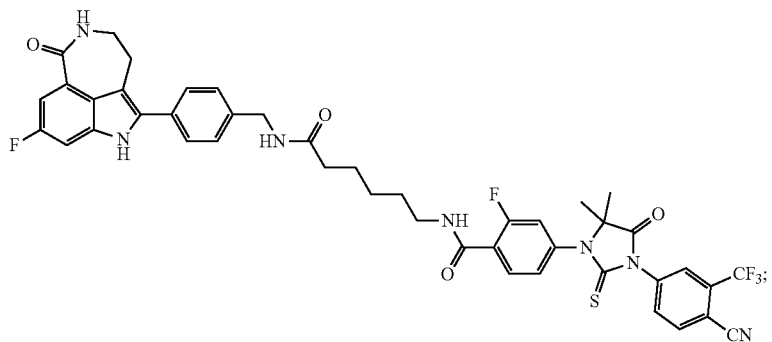 [SMILES: CC1(C)C(=O)N(c2ccc(C#N)c(C(F)(F)F)c2)C(=S)N1c1ccc(C(=O)NCCCCCC(=O)NCc2ccc(-c3[nH]c4cc(F)cc5c4c3CCNC5=O)cc2)c(F)c1] |

| No. | Structure |
|---|---|
| 1.41 | 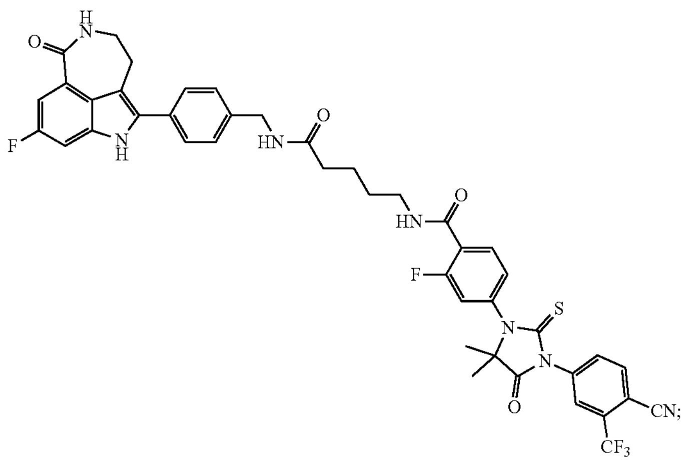 [SMILES: CC1(C)C(=O)N(c2ccc(C#N)c(C(F)(F)F)c2)C(=S)N1c1ccc(C(=O)NCCCCC(=O)NCc2ccc(-c3[nH]c4cc(F)cc5c4c3CCNC5=O)cc2)c(F)c1] |
| 1.42 | 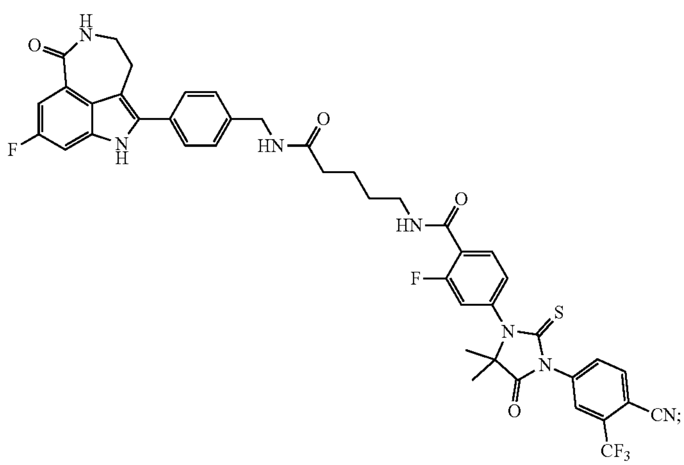 [SMILES: CC1(C)C(=O)N(c2ccc(C#N)c(C(F)(F)F)c2)C(=S)N1c1ccc(C(=O)NCCCCC(=O)NCc2ccc(-c3[nH]c4cc(F)cc5c4c3CCNC5=O)cc2)c(F)c1] |
| 1.52 | 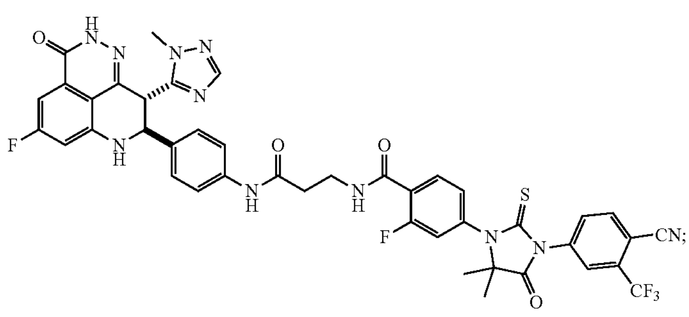 |
| 1.53 | 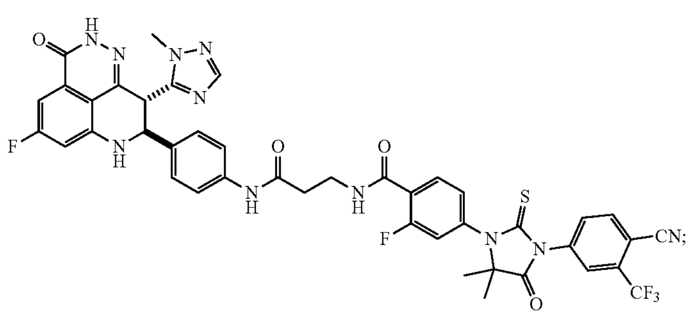 |

| No. | Structure |
|---|---|
| 1.54 | (chemical structure) |
| 1.55 | (chemical structure) |
| 1.56 | (chemical structure) |
| 1.57 | (chemical structure) |
| 1.58 | (chemical structure) |
| 1.59 | (chemical structure) |

| No. | Structure |
|---|---|
| 1.60 | 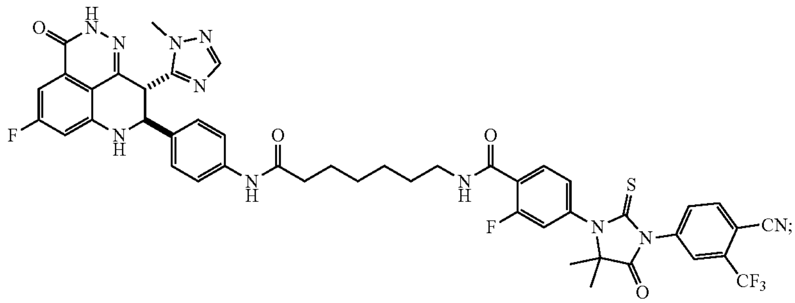 |
| 1.88 | 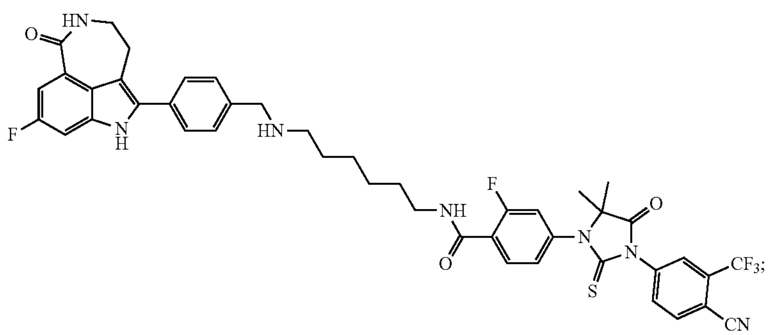 [SMILES: CC1(C)C(=O)N(c2ccc(C#N)c(C(F)(F)F)c2)C(=S)N1c1ccc(C(=O)NCCCCCCNCc2ccc(-c3[nH]c4cc(F)cc5c4c3CCNC5=O)cc2)c(F)c1] |
| 1.89 | 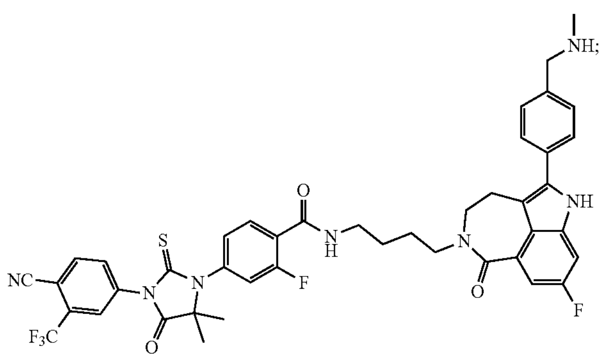 |
| 1.93 | | or a pharmaceutically acceptable salt thereof.

11. The compound of claim 10, or a pharmaceutically acceptable salt thereof, wherein the compound is

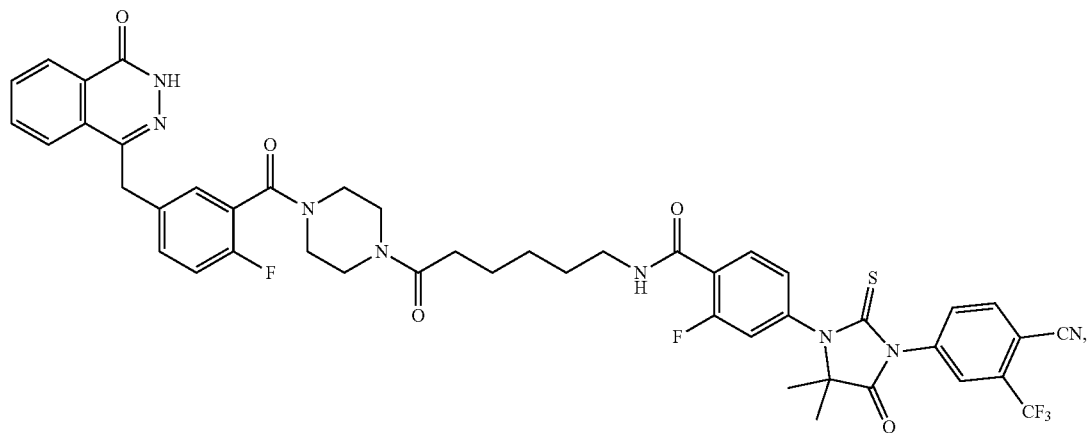 [SMILES: CC1(C)C(=O)N(c2ccc(C#N)c(C(F)(F)F)c2)C(=S)N1c1ccc(C(=O)NCCCCCC(=O)N2CCN(C(=O)c3cc(Cc4n[nH]c(=O)c5ccccc45)ccc3F)CC2)c(F)c1]

or a pharmaceutically acceptable thereof.

12. A pharmaceutical composition comprising a compound of claim 1, 2, 10, or 11, or a stereoisomer, mixture of stereoisomers, isotopically enriched analog, or pharmaceutically acceptable salt thereof, and a pharmaceutically acceptable excipient.

* * * * *